United States Patent
Wu et al.

(10) Patent No.: US 10,800,768 B2
(45) Date of Patent: *Oct. 13, 2020

(54) HETEROCYCLIC COMPOUNDS AS IMMUNOMODULATORS

(71) Applicant: Incyte Corporation, Wilmington, DE (US)

(72) Inventors: Liangxing Wu, Wilmington, DE (US); Jingwei Li, Westfield, NJ (US); Wenqing Yao, Chadds Ford, PA (US); Chao Qi, Newark, DE (US); Ding-Quan Qian, Newark, DE (US); Fenglei Zhang, Berwyn, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/373,150

(22) Filed: Apr. 2, 2019

(65) Prior Publication Data

US 2019/0225601 A1    Jul. 25, 2019

Related U.S. Application Data

(63) Continuation of application No. 15/850,170, filed on Dec. 21, 2017, now Pat. No. 10,308,644.

(60) Provisional application No. 62/438,009, filed on Dec. 22, 2016, provisional application No. 62/487,336, filed on Apr. 19, 2017, provisional application No. 62/551,033, filed on Aug. 28, 2017.

(51) Int. Cl.
| | |
|---|---|
| *A61K 31/4375* | (2006.01) |
| *C07D 413/14* | (2006.01) |
| *C07D 471/04* | (2006.01) |
| *A61P 37/02* | (2006.01) |
| *C07D 498/04* | (2006.01) |
| *C07D 513/04* | (2006.01) |
| *C07D 487/04* | (2006.01) |
| *C07D 413/06* | (2006.01) |
| *C07D 413/12* | (2006.01) |
| *A61P 37/00* | (2006.01) |

(52) U.S. Cl.
CPC ........ *C07D 413/14* (2013.01); *A61K 31/4375* (2013.01); *A61P 37/00* (2018.01); *A61P 37/02* (2018.01); *C07D 413/06* (2013.01); *C07D 413/12* (2013.01); *C07D 471/04* (2013.01); *C07D 487/04* (2013.01); *C07D 498/04* (2013.01); *C07D 513/04* (2013.01)

(58) Field of Classification Search
None
See application file for complete search history.

(56) References Cited

U.S. PATENT DOCUMENTS

| | | |
|---|---|---|
| 3,272,781 A | 9/1966 | Goodrow |
| 4,208,328 A | 6/1980 | Lavallee et al. |
| 4,789,711 A | 12/1988 | Monnier et al. |
| 5,077,164 A | 12/1991 | Ueda et al. |
| 6,114,497 A | 9/2000 | Tada et al. |
| 6,297,351 B1 | 10/2001 | Murayama et al. |
| 6,372,907 B1 | 4/2002 | Lee et al. |
| 6,521,618 B2 | 2/2003 | Boschelli |
| 6,867,200 B1 | 3/2005 | Allen et al. |
| 7,320,989 B2 | 1/2008 | Anderson et al. |
| 8,541,424 B2 | 9/2013 | DeGoey et al. |
| 8,993,604 B2 | 3/2015 | Byrd et al. |
| 9,163,017 B2 | 10/2015 | DeGoey et al. |
| 9,540,322 B2 | 1/2017 | Jorgensen et al. |
| 9,643,922 B2 | 5/2017 | Jorgensen et al. |
| 10,017,520 B2 | 7/2018 | Koehler et al. |
| 10,202,343 B2 | 2/2019 | Jorgensen et al. |
| 10,308,644 B2 | 6/2019 | Wu et al. |
| 2002/0082266 A1 | 6/2002 | Gallant et al. |
| 2003/0134843 A1 | 7/2003 | Lubisch et al. |
| 2004/0058938 A1 | 3/2004 | Cullmann et al. |
| 2004/0063963 A1 | 4/2004 | Ueno et al. |

(Continued)

FOREIGN PATENT DOCUMENTS

| | | |
|---|---|---|
| CA | 2355249 | 6/2000 |
| CL | 2018001531 | 7/2018 |

(Continued)

OTHER PUBLICATIONS

Abdellaoui et al., "Palladium-catalyzed non-directed C-H bond acylation of difluorobenzenes and dichlorobenzenes bearing benzoxazole or benzothiazole," Catalysis Communications, 2015, 71:13-16.

Arkin et al., "Small-Molecule Inhibitors of Protein-Protein Interactions: Progressing toward the Reality," Chemistry & Biology, Sep. 2014, 21:1102-1114.

Arkin et al., "Small-Molecule Inhibitors of Protein-Protein Interactions: Progressing Towards the Dream," Nature Reviews, Apr. 2004, 3:301-317.

(Continued)

*Primary Examiner* — Samantha L Shterengarts
(74) *Attorney, Agent, or Firm* — Fish & Richardson P.C.

(57) ABSTRACT

Disclosed are compounds of Formula (I), methods of using the compounds as immunomodulators, and pharmaceutical compositions comprising such compounds. The compounds are useful in treating, preventing or ameliorating diseases or disorders such as cancer or infections.

(I)

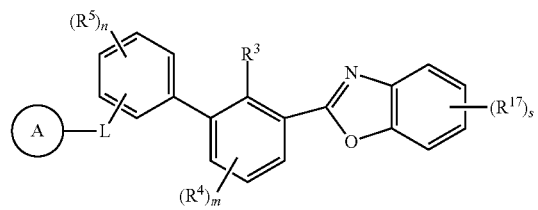

18 Claims, No Drawings

(56) References Cited

U.S. PATENT DOCUMENTS

| | | |
|---|---|---|
| 2004/0082635 A1 | 4/2004 | Hashimoto et al. |
| 2004/0186114 A1 | 9/2004 | Cirillo et al. |
| 2004/0214040 A1 | 10/2004 | Lee et al. |
| 2005/0187230 A1 | 8/2005 | Ding et al. |
| 2005/0245536 A1 | 11/2005 | Hao et al. |
| 2005/0260126 A1 | 11/2005 | Kudo et al. |
| 2005/0288295 A1 | 12/2005 | Currie et al. |
| 2006/0004010 A1 | 1/2006 | Habashita |
| 2006/0089362 A1 | 4/2006 | Seno et al. |
| 2006/0178367 A1 | 8/2006 | Currie et al. |
| 2006/0229337 A1 | 10/2006 | Brittelli et al. |
| 2006/0270686 A1 | 11/2006 | Kelly |
| 2007/0099938 A1 | 5/2007 | Ohmoto et al. |
| 2007/0191395 A1 | 8/2007 | Kawakami et al. |
| 2008/0139557 A1 | 6/2008 | Blomgren et al. |
| 2008/0153834 A1 | 6/2008 | Blomgren et al. |
| 2008/0280891 A1 | 11/2008 | Kelly et al. |
| 2009/0253735 A1 | 10/2009 | Almario-Garcia et al. |
| 2009/0281075 A1 | 11/2009 | Roughton et al. |
| 2009/0281120 A1 | 11/2009 | Nakai et al. |
| 2009/0304821 A1 | 12/2009 | Notoya et al. |
| 2010/0155712 A1 | 6/2010 | Kitamura |
| 2010/0160292 A1 | 6/2010 | Whitney et al. |
| 2010/0249151 A1 | 9/2010 | Klein et al. |
| 2010/0267775 A1 | 10/2010 | Negoro et al. |
| 2010/0267778 A1 | 10/2010 | Kusuda et al. |
| 2010/0273832 A1 | 10/2010 | Jung et al. |
| 2010/0292227 A1 | 11/2010 | Yoakim et al. |
| 2011/0053915 A1 | 3/2011 | Ivaschenko et al. |
| 2011/0062858 A1 | 3/2011 | Yersin et al. |
| 2011/0065699 A1 | 3/2011 | De Peretti et al. |
| 2011/0065700 A1 | 3/2011 | De Peretti et al. |
| 2011/0065745 A1 | 3/2011 | De Peretti et al. |
| 2011/0124640 A1 | 5/2011 | Liu et al. |
| 2011/0294781 A1 | 12/2011 | Yamamoto et al. |
| 2011/0301145 A1 | 12/2011 | Barbosa, Jr. et al. |
| 2012/0058996 A1 | 3/2012 | Liu et al. |
| 2012/0295884 A1 | 11/2012 | Altmann et al. |
| 2012/0323002 A1 | 12/2012 | Yamamoto et al. |
| 2012/0328569 A1 | 12/2012 | McComas et al. |
| 2013/0096118 A1 | 4/2013 | Liu et al. |
| 2013/0131063 A1 | 5/2013 | Castro et al. |
| 2013/0203741 A1 | 8/2013 | Suzuki et al. |
| 2013/0203747 A1 | 8/2013 | Yoakim et al. |
| 2013/0203754 A1 | 8/2013 | Yang et al. |
| 2013/0253011 A1 | 9/2013 | Jung et al. |
| 2014/0058097 A1 | 2/2014 | Kobayashi et al. |
| 2014/0088117 A1 | 3/2014 | Burch et al. |
| 2014/0128382 A1 | 5/2014 | Wu et al. |
| 2014/0243306 A1 | 8/2014 | Heng et al. |
| 2014/0275058 A1 | 9/2014 | Minatti et al. |
| 2014/0288094 A1 | 9/2014 | Bennett et al. |
| 2014/0378447 A1 | 12/2014 | Okano et al. |
| 2015/0005279 A1 | 1/2015 | Bonafoux et al. |
| 2015/0011751 A1 | 1/2015 | Kawakami et al. |
| 2015/0073024 A1 | 3/2015 | Sasikumar et al. |
| 2015/0181880 A1 | 7/2015 | Takahashi |
| 2015/0210680 A1 | 7/2015 | Kobayashi et al. |
| 2015/0232478 A1 | 8/2015 | Ishida et al. |
| 2015/0239868 A1 | 8/2015 | Pais et al. |
| 2015/0252011 A1 | 9/2015 | Minatti et al. |
| 2015/0258505 A1 | 9/2015 | Hironaka et al. |
| 2015/0291549 A1 | 10/2015 | Chupak et al. |
| 2015/0299227 A1 | 10/2015 | Wolkenberg et al. |
| 2015/0307465 A1 | 10/2015 | Scott et al. |
| 2015/0376172 A1 | 12/2015 | Guba et al. |
| 2016/0015690 A1 | 1/2016 | Babaoglu et al. |
| 2016/0046648 A1 | 2/2016 | Petrukhin et al. |
| 2016/0130251 A1 | 5/2016 | Graupe et al. |
| 2016/0229816 A1 | 8/2016 | Sato et al. |
| 2017/0107216 A1 | 4/2017 | Wu et al. |
| 2017/0145025 A1 | 5/2017 | Li et al. |
| 2017/0174671 A1 | 6/2017 | Wu et al. |
| 2017/0174679 A1 | 6/2017 | Lajkiewicz et al. |
| 2017/0320875 A1 | 11/2017 | Li et al. |
| 2017/0342060 A1 | 11/2017 | Lu et al. |
| 2017/0362253 A1 | 12/2017 | Xiao et al. |
| 2018/0016260 A1 | 1/2018 | Yu et al. |
| 2018/0057486 A1 | 3/2018 | Wu et al. |
| 2018/0177784 A1 | 6/2018 | Wu et al. |
| 2018/0177870 A1 | 6/2018 | Liu et al. |
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0273519 A1 | 9/2018 | Wu et al. |
| 2019/0040082 A1 | 2/2019 | Xiao et al. |
| 2019/0062345 A1 | 2/2019 | Xiao et al. |
| 2019/0071439 A1 | 3/2019 | Li et al. |
| 2019/0144439 A1 | 5/2019 | Wu et al. |
| 2019/0202824 A1 | 7/2019 | Wu et al. |
| 2019/0270706 A1 | 9/2019 | Jorgensen et al. |
| 2019/0300524 A1 | 10/2019 | Wu et al. |
| 2019/0345170 A1 | 11/2019 | Wu et al. |

FOREIGN PATENT DOCUMENTS

| | | |
|---|---|---|
| CL | 2018003734 | 2/2019 |
| CL | 2018003697 | 5/2019 |
| CN | 101891895 | 11/2010 |
| CN | 103933036 | 7/2014 |
| CN | 104045552 | 9/2014 |
| CN | 104211726 | 12/2014 |
| EP | 0644460 | 3/1995 |
| EP | 1505068 | 2/2005 |
| EP | 1942105 | 7/2008 |
| EP | 2233474 | 9/2010 |
| EP | 2402345 | 1/2012 |
| EP | 2871179 | 5/2015 |
| EP | 2824099 | 1/2018 |
| FR | 1425700 | 1/1966 |
| JP | H 10316853 | 12/1998 |
| JP | 2000128986 | 5/2000 |
| JP | 2000128987 | 5/2000 |
| JP | 2000212281 | 8/2000 |
| JP | 2001114893 | 4/2001 |
| JP | 2001163975 | 6/2001 |
| JP | 3461397 | 10/2003 |
| JP | 2003287634 | 10/2003 |
| JP | 2004059761 | 2/2004 |
| JP | 2004294556 | 10/2004 |
| JP | 2005002330 | 1/2005 |
| JP | 2005248082 | 9/2005 |
| JP | 2005290301 | 10/2005 |
| JP | 2006-290883 A | 10/2006 |
| JP | 2008218327 | 9/2008 |
| JP | 2010202530 | 9/2010 |
| JP | 2013084945 | 5/2013 |
| JP | 2015155397 | 8/2015 |
| JP | 2015193612 | 11/2015 |
| JP | 2016135778 | 7/2016 |
| KR | 1715090 | 3/2015 |
| KR | 1717601 | 12/2015 |
| KR | 1653560 | 2/2016 |
| WO | WO 98/27108 | 6/1998 |
| WO | WO 1999/018096 | 4/1999 |
| WO | WO 99/44992 A1 | 9/1999 |
| WO | WO 00/35886 | 6/2000 |
| WO | WO 2001/047883 | 7/2001 |
| WO | WO 01/74815 | 10/2001 |
| WO | WO 2002/000196 | 1/2002 |
| WO | WO 02/14321 | 2/2002 |
| WO | WO 02/48147 | 6/2002 |
| WO | WO 02/066477 | 8/2002 |
| WO | WO 02/071827 | 9/2002 |
| WO | WO 02/078700 | 10/2002 |
| WO | WO 02/083672 | 10/2002 |
| WO | WO 02/088124 | 11/2002 |
| WO | WO 03/022845 | 3/2003 |
| WO | WO 03/031587 | 4/2003 |
| WO | WO 2004/006906 | 1/2004 |
| WO | WO 2004/033454 | 4/2004 |
| WO | WO 2004/035588 | 4/2004 |
| WO | WO 2004/085385 | 10/2004 |

(56) References Cited

FOREIGN PATENT DOCUMENTS

| | | |
|---|---|---|
| WO | WO 2005/000833 | 1/2005 |
| WO | WO 2005/014543 | 2/2005 |
| WO | WO 2005/023761 | 3/2005 |
| WO | WO 2005/034869 | 4/2005 |
| WO | WO 2005/063710 | 7/2005 |
| WO | WO 2005/077948 | 8/2005 |
| WO | WO 2005/079802 | 9/2005 |
| WO | WO 2005/080316 | 9/2005 |
| WO | WO 2005/086808 | 9/2005 |
| WO | WO 2005/086904 | 9/2005 |
| WO | WO 2005/097751 | 10/2005 |
| WO | WO 2005/103022 | 11/2005 |
| WO | WO 2005/105798 | 11/2005 |
| WO | WO 2006/050803 | 5/2006 |
| WO | WO 2006/053121 | 5/2006 |
| WO | WO 2006/094235 | 9/2006 |
| WO | WO 2006/125101 | 11/2006 |
| WO | WO 2007/004954 | 1/2007 |
| WO | WO 2007/034282 | 3/2007 |
| WO | WO 2007/067711 | 6/2007 |
| WO | WO 2007/069565 | 6/2007 |
| WO | WO 2007/096764 | 8/2007 |
| WO | WO 2007/113226 | 10/2007 |
| WO | WO 2007/146712 | 12/2007 |
| WO | WO 2008/011560 | 1/2008 |
| WO | WO 2008/027812 | 3/2008 |
| WO | WO 2008/033854 | 3/2008 |
| WO | WO 2008/033857 | 3/2008 |
| WO | WO 2008/033858 | 3/2008 |
| WO | WO 2008/062182 | 5/2008 |
| WO | WO 2008/104077 | 9/2008 |
| WO | WO 2008/104278 | 9/2008 |
| WO | WO 2008/104279 | 9/2008 |
| WO | WO 2008/118122 | 10/2008 |
| WO | WO 2008/134553 | 11/2008 |
| WO | WO 2008/141249 | 11/2008 |
| WO | WO 2009/027733 | 3/2009 |
| WO | WO 2009/038759 | 3/2009 |
| WO | WO 2009/039397 | 3/2009 |
| WO | WO 2009/059162 | 5/2009 |
| WO | WO 2009/062059 | 5/2009 |
| WO | WO 2009/077197 | 6/2009 |
| WO | WO 2009/079683 | 7/2009 |
| WO | WO 2009/106539 | 9/2009 |
| WO | WO 2009/123986 | 10/2009 |
| WO | WO 2009/143156 | 11/2009 |
| WO | WO 2009/146358 | 12/2009 |
| WO | WO 2010/011837 | 1/2010 |
| WO | WO 2010/029950 | 3/2010 |
| WO | WO 2010/056875 | 5/2010 |
| WO | WO 2010/064020 | 6/2010 |
| WO | WO 2010/071885 | 6/2010 |
| WO | WO 2010/075376 | 7/2010 |
| WO | WO 2010/104306 | 9/2010 |
| WO | WO 2010/115736 | 10/2010 |
| WO | WO 2010/119264 | 10/2010 |
| WO | WO 2011/002635 | 1/2011 |
| WO | WO 2011/008709 | 1/2011 |
| WO | WO 2011/018170 | 2/2011 |
| WO | WO 2011/044181 | 4/2011 |
| WO | WO 2011/047129 | 4/2011 |
| WO | WO 2011/047319 | 4/2011 |
| WO | WO 2011/050245 | 4/2011 |
| WO | WO 2011/082400 | 7/2011 |
| WO | WO 2011/097607 | 8/2011 |
| WO | WO 2011/113606 | 9/2011 |
| WO | WO 2011/117264 | 9/2011 |
| WO | WO 2011/140202 | 11/2011 |
| WO | WO 2012/016133 | 2/2012 |
| WO | WO 2012/033735 | 3/2012 |
| WO | WO 2012/034363 | 3/2012 |
| WO | WO 2012/047856 | 4/2012 |
| WO | WO 2012/052730 | 4/2012 |
| WO | WO 2012/052745 | 4/2012 |
| WO | WO 2012/068406 | 5/2012 |
| WO | WO 2012/080376 | 6/2012 |
| WO | WO 2012/088411 | 6/2012 |
| WO | WO 2012/100342 | 8/2012 |
| WO | WO 2012/125886 | 9/2012 |
| WO | WO 2012/129562 | 9/2012 |
| WO | WO 2012/139425 | 10/2012 |
| WO | WO 2012/159565 | 11/2012 |
| WO | WO 2012/166951 | 12/2012 |
| WO | WO 2012/168733 | 12/2012 |
| WO | WO 2012/175991 | 12/2012 |
| WO | WO 2013/008095 | 1/2013 |
| WO | WO 2013/033901 | 3/2013 |
| WO | WO 2013/040528 | 3/2013 |
| WO | WO 2013/057650 | 4/2013 |
| WO | WO 2013/059594 | 4/2013 |
| WO | WO 2013/120040 | 8/2013 |
| WO | WO 2013/134113 | 9/2013 |
| WO | WO 2013/157021 | 10/2013 |
| WO | WO 2013/163404 | 10/2013 |
| WO | WO 2014/009295 | 1/2014 |
| WO | WO 2014/009296 | 1/2014 |
| WO | WO 2014/017087 | 1/2014 |
| WO | WO 2014/039595 | 3/2014 |
| WO | WO 2014/061693 | 4/2014 |
| WO | WO 2014/081878 | 5/2014 |
| WO | WO 2014/113388 | 7/2014 |
| WO | WO 2014/114532 | 7/2014 |
| WO | WO 2014/133046 | 9/2014 |
| WO | WO 2014/138484 | 9/2014 |
| WO | WO 2014/138791 | 9/2014 |
| WO | WO 2014/152536 | 9/2014 |
| WO | WO 2014/159959 | 10/2014 |
| WO | WO 2014/181287 | 11/2014 |
| WO | WO 2015/000715 | 1/2015 |
| WO | WO 2015/013635 | 1/2015 |
| WO | WO 2015/018940 | 2/2015 |
| WO | WO 2015/033299 | 3/2015 |
| WO | WO 2015/033301 | 3/2015 |
| WO | WO 2015/034820 | 3/2015 |
| WO | WO 2015/036927 | 3/2015 |
| WO | WO 2015/086499 | 6/2015 |
| WO | WO 2015/086502 | 6/2015 |
| WO | WO 2015/086512 | 6/2015 |
| WO | WO 2015/095337 | 6/2015 |
| WO | WO 2015/101622 | 7/2015 |
| WO | WO 2015/120364 | 8/2015 |
| WO | WO 2015/150097 | 10/2015 |
| WO | WO 2015/160641 | 10/2015 |
| WO | WO 2015/197028 | 12/2015 |
| WO | WO 2016/044604 | 3/2016 |
| WO | WO 2016/094688 | 6/2016 |
| WO | WO 2016/116525 | 7/2016 |
| WO | WO 2016/118404 | 7/2016 |
| WO | WO 2016/156282 | 10/2016 |
| WO | WO 2017/035405 | 3/2017 |
| WO | WO 2017/066227 | 4/2017 |
| WO | WO 2017/070089 | 4/2017 |
| WO | WO 2017/070320 | 4/2017 |
| WO | WO 2017/087777 | 5/2017 |
| WO | WO 2017/106634 | 6/2017 |
| WO | WO 2017/108569 | 6/2017 |
| WO | WO 2017/109041 | 6/2017 |
| WO | WO 2017/112617 | 6/2017 |
| WO | WO 2017/112730 | 6/2017 |
| WO | WO 2017/192961 | 11/2017 |
| WO | WO 2017/205464 | 11/2017 |
| WO | WO 2017/222976 | 12/2017 |
| WO | WO 2018/013789 | 1/2018 |
| WO | WO 2018/026971 | 2/2018 |
| WO | WO 2018/044783 | 3/2018 |
| WO | WO 2018/045084 | 3/2018 |
| WO | WO 2016/057500 | 4/2018 |
| WO | WO 2018/116259 | 6/2018 |
| WO | WO 2018/119036 | 6/2018 |
| WO | WO 2018/119221 | 6/2018 |
| WO | WO 2018/119224 | 6/2018 |
| WO | WO 2018/119236 | 6/2018 |
| WO | WO 2018/119263 | 6/2018 |
| WO | WO 2018/119266 | 6/2018 |

(56) References Cited

FOREIGN PATENT DOCUMENTS

| WO | WO 2018/119286 | 6/2018 |
|---|---|---|
| WO | WO 2018/195321 | 10/2018 |
| WO | WO 2019/023575 | 1/2019 |
| WO | WO 2019/032547 | 2/2019 |
| WO | WO 2019/034172 | 2/2019 |
| WO | WO 2019/191707 | 10/2019 |
| WO | WO 2019/192506 | 10/2019 |
| WO | WO 2019/204609 | 10/2019 |

OTHER PUBLICATIONS

Atzrodt et al., The Renaissance of H/D Exchange, Angew Chem Int Ed., 2007, 7744-7765.
Barakat, "Do We Need Small Molecule Inhibitors for the Immune Checkpoints?" J. Pharma. Care Health Sys., 2014, 1(4):1000e119.
Bather et al, "Restoring function in exhausted CD8 T cells during chronic viral infection," Nature, Feb. 2006, 439:682-687.
Berg, "Modulation of Protein-Protein Interactions with Small Organic Molecules," Angew. Chem. Int. Ed., 2003, 42:2462-2481.
Berge et al., "Pharmaceutical Salts," J. Pharm. Sci., Jan. 1977, 66(1):1-19.
Blank et al, "PD-L1/B7H-1 Inhibits the Effector Phase of Tumor Rejection by T Cell Receptor (TCR) Transgenic CD8+ T Cells," Cancer Res., Feb. 2004, 64(3):1140-5.
Blom et al., "Optimizing Preparative LC-MS Configurations and Methods for Parallel Synthesis Purification", J. Combi. Chem., 2003, 5:670-83.
Blom et al., "Preparative LC-MS Purification: Improved Compound Specific Method Optimization", J. Combi. Chem., Nov. 2004, 6:874-883.
Blom, "Two-Pump at Column Dilution Configuration for Preparative LC-MS", K. Blom, J. Combi. Chem., 2002, 4:295-301.
Bross et al., "Radiation damage to 2-(2'-hydroxyphenyl)benzothiazoles," Radiation Physics and Chemistry, Jul. 1992, 41:379-387.
Carter et al, "PD-1:PD-L inhibitory pathway affects both CD4+ and CD8+ T cells and is overcome by IL-2," Eur. J. Immunol., 2002, 32(3):634-643.
Chang et al., "Blocking of the PD-1/PD-L1 Interaction by a d-Peptide Antagonist for Cancer Immunotherapy," Angew. Chem. Int. Ed., 2015, 127(40):11926-11930.
Chang et al., "Blocking of the PD-1/PD-L1 Interaction by a d-Peptide Antagonist for Cancer Immunotherapy: Supporting Information" Angew. Chem. Int. Ed., 2015, 26 pages.
Chen et al., "Anti-PD-1/PD-L1 therapy of human cancer: past, present, and future," J. Clin. Invest., Sep. 2015, 125(9):3384-3391.
Cheng et al., "Recent Advances in Small Molecule Based Cancer Immunotherapy," Euro. Journ. of Med. Chem., 2018, 157:582-598.
Cheng et al., "Structure and Interactions of the Human Programmed Cell Death 1 Receptor," J. Bio. Chem., Apr. 2013, 288(17):11771-11785.
Chilean Office Action in Chilean Application No. 201801685, dated Aug. 20, 2019, 18 pages.
Curis, "Overview and Path for Growth," Aurigene Strategic Collaboration, Jan. 21, 2015, 13 slides.
Database Accession No. 1590700-72-3 abstract, Apr. 27, 2014, 1 page.
Database Accession No. 1581556-71-9 abstract, Apr. 8, 2014, 1 page.
Database Accession No. 1580823-55-7 abstract, Apr. 6, 2014, 1 page.
Database Accession No. 1568738-04-4 abstract, Mar. 14, 2014, 1 page.
Database accession No. 1478989-52-4 abstract, Nov. 22, 2013, 1 page.
Database accession No. 2013:447446 abstract, 2013, 1 page.
Differding, "AUNP-12—A Novel Peptide Therapeutic Targeting PD-1 Immune Checkpoint Pathway for Cancer Immunotherapy—Structure Activity Relationships & Peptide / Peptidomimetic Analogs," Feb. 26, 2014, 12 pages.
Dolan et al., "PD-1 Pathway Inhibitors: Changing the Landscape of Cancer Immunotherapy," Cancer Control, Jul. 2014, 21(3):231-237.
Domling et al., "Programmed Death-1: Therapeutic Success after More than 100 Years of Cancer Immunotherapy," Angew. Chem. Int. Ed., 2014, 53:2283-2288.
FDA Report, "22 Case Studies Where Phase 2 and Phase 3 Trials Had Divergent Results," U.S. Food and Drug Administration, Jan. 2017, 44 pages.
Francisco et al., "The PD-1 Pathway in Tolerance and Autoimmunity," Immunol. Rev., Jul. 2010, 236:219-242.
Freeman et al, "Engagement of the Pd-1 Immunoinhibinny Receptor by a Novel B7 Family Member Leads to Negative Regulation of Lymphocyte Activation," J. Exp. Med., Oct. 2000, 192(7):1027-34.
Freeman, "Structures of PD-1 with its ligands. Sideways and dancing cheek to cheek," PNAS, Jul. 2008, 105(30):10275-10276.
Goswami et al., "A turn on ESIPT probe for rapid and mtiometric fluorogenic detection of homocysteine and cysteine in water with live cell-imaging," Tetrahedron Letters, 2014, 55(2):490-494.
Greenwald et al, "The B7 Family Revisited," Annu. Rev. Immunol., 2005, 23:515-548.
Huang et al, "The prognostic significance of PD-L1 in bladder cancer," Oncol. Rep., 2015, 33:3075-3084.
HuGEMM™ and HuCELL™ Models, "FactSheet," CrownBio, Oct. 2016, 8 pages.
International Preliminary Report on Patentability in International Application No. PCT/US2016/057487, dated May 3, 2018, 7 pages.
International Preliminary Report on Patentability in International Application No. PCT/US2016/062730, dated May 31, 2018, 7 pages.
International Preliminary Report on Patentability in International Application No. PCT/US2016/067155, dated Jun. 19, 2018, 10 pages.
International Preliminary Report on Patentability in International Application No. PCT/US2016/067925, dated Jun. 26, 2018, 8 pages.
International Preliminary Report on Patentability in International Application No. PCT/US2017/031242, dated Nov. 6, 2018, 7 pages.
International Preliminary Report on Patentability in International Application No. PCT/US2017/034173, dated Nov. 27, 2018, 8 pages.
International Preliminary Report on Patentability in International Application No. PCT/US2017/038120, dated Dec. 25, 2018, 6 pages.
International Preliminary Report on Patentability in International Application No. PCT/US2017/041899, dated Jan. 15, 2019, 7 pages.
International Preliminary Report on Patentability in International Application No. PCT/US2017/048880, dated Mar. 5, 2019, 9 pages.
International Preliminary Report on Patentability in International Application No. PCT/US2017/067904, dated Jun. 25, 2019, 7 pages.
International Preliminary Report on Patentability in International Application No. PCT/US2017/067951, dated Jun. 25, 2019, 8 pages.
International Preliminary Report on Patentability in International Application No. PCT/US2017/067880, dated Jun. 25, 2019, 7 pages.
International Preliminary Report on Patentability in International Application No. PCT/US2017/067984, dated Jun. 25, 2019, 7 pages.
International Preliminary Report on Patentability in International Application No. PCT/US2017/067946, dated Jun. 25, 2019, 9 pages.
International Preliminary Report on Patentability in International Application No. PCT/US2017/067886, dated Jun. 25, 2019, 9 pages.
International Search Report and Written Opinion in International Application No. PCT/US2016/057487, dated Dec. 8, 2016, 11 pages.
International Search Report and Written Opinion in International Application No. PCT/US2016/062730, dated Feb. 9, 2017, 12 pages.

(56) References Cited

OTHER PUBLICATIONS

International Search Report and Written Opinion in International Application No. PCT/US2016/067925, dated Mar. 27, 2017, 13 pages.
International Search Report and Written Opinion in International Application No. PCT/US2016/067155, dated Apr. 24, 2017, 26 pages.
International Search Report and Written Opinion in International Application No. PCT/US2017/031242, dated Jun. 20, 2017, 22 pages.
International Search Report and Written Opinion in International Application No. PCT/US2017/034173, dated Aug. 8, 2017, 15 pages.
International Search Report and Written Opinion in International Application No. PCT/US2017/041899, dated Sep. 5, 2017, 12 pages.
International Search Report and Written Opinion in International Application No. PCT/US2017/038120, dated Aug. 1, 2017, 14 pages.
International Search Report and Written Opinion in International Application No. PCT/US2017/067904, dated Mar. 22, 2018, 14 pages.
International Search Report and Written Opinion in International Application No. PCT/US2017/067880, dated Mar. 21, 2018, 13 pages.
International Search Report and Written Opinion in International Application No. PCT/US2017/067984, dated Mar. 22, 2018, 14 pages.
International Search Report and Written Opinion in International Application No. PCT/US2017/067886, dated Mar. 23, 2018, 24 pages.
International Search Report and Written Opinion in International Application No. PCT/US2017/067946, dated May 22, 2018, 16 Pages.
International Search Report and Written Opinion in International Application No. PCT/US2017/067951, dated Mar. 27, 2018, 15 pages.
International Search Report and Written Opinion in International Application No. PCT/US2017/048880, dated Oct. 23, 2017, 15 pages.
International Search Report and Written Opinion in International Application No. PCT/US2019/031728, dated Jun. 25, 2019, 12 pages.
International Search Report and Written Opinion in International Application No. PCT/US2019/025036, dated Jul. 3, 2019, 12 pages.
Iwai et al, "Involvement of PD-L1 on tumor cells in the escape from host immune system and tumor immunotherapy by PD-L1 blockade," PNAS, Sep. 2002, 99(19):12293-12297.
Keir et al., "PD-1 and Its Ligands in Tolerance and Immunity," Annu Rev. Immunol., 2008, 26:677-704.
Kerekes et al., "Aurora kinase inhibitors based on the imidazo[1,2-a]pyrazine core: fluorine and deuterium incorporation improve oral absorption and exposure," J. Med. Chem., 2011, 54(1):201-210.
Komiyama et al, "IL-17 Plays an Important Role in the Development of Experimental Autoimmune Encephalomyelitis," J. Immunol., Jul. 2006, 177:566-73.
Latchman et al, "PD-L2 is a second ligand for PD-1 and inhibits T cell activation," Nat. Immunol., Mar. 2001, 2(3):261-268.
Lazar-Molnar et al., "Crystal structure of the complex between programmed death-1 (PD-1) and its ligand PD-L2," PNAS, Jul. 2008, 105(30):10483-10488.
Li et al., "A Mini-Review for Cancer Immunotherapy: Molecular Understanding of PD-1/PD-L1 Pathway & Translational Blockade of Immune Checkpoints," Int. J. Mol. Soc., 2016, 17:1151, 22 pages.
Li et al., "Analysis of Receptor Tyrosine Kinase Internalization Using Flow Cytometry," Methods Mol. Biol., 2008, 457:305-317.
Li et al., "Discovery of peptide inhibitors targeting human programmed death 1 (PD-1) receptor," Oncotarget, Aug. 2016, 7(40):64967-64976.
Lin et al., "The PD-1/PD-L1 complex resembles the antigen-binding Fv domains of antibodies and T cell receptors," PNAS, Feb. 2008, 105(8):3011-3016.
Lipson et al., "From Discovery to Development: Blocking PD-1 and its Ligands," The Melanoma Letter, A Publication of the Skin Cancer Foundation, vol. 31, Summer 2013, 6 pages.
Liu et al., "Development of amino- and dimethylcarbamate-substituted resorcinol as programmed cell death-1 (Pd-1) inhibitor," European Journal of Pharmaceutical Sciences, 88:50-58.
Mahoney et al., "The Next Immune-Checkpoint Inhibitors:PD-1/PD-L1 Blockade in Melanoma," Clin. Therapeutics, Nov. 2015, 37(4):761-782.
Nero et al., "Oncogenic protein interfaces: small molecules, big challenges," Nature Reviews, Apr. 2014, 14:248-262.
Nishimura et al, "Autoimmune Dilated Cardiomyopathy in PD-1 Receptor-Deficient Mice," Science, Jan. 2001, 291:319-322.
Nishimura et al, "Development of Lupus-like Autoimmune Diseases by Disruption of the PD-1 Gene Encoding an ITIM Motif-Carrying Immunoreceptor," Immunity, Aug. 1999, 11:141-151.
Nishimura et al., "PD-1: an inhibitory immunoreceptor involved in peripheral tolerance," Trends in Immunology, May 2001, 22(5):265-268.
Nishino et al., "Copper-Mediated C-H/C-H Biaryl Coupling of Benzoic Acid Derivatives and 1,3-Azoles," Angew. Chem. Int. Ed., 2013, 52:4457-4461.
Okazaki and Honjo, "The PD-1-PD-L pathway in immunological tolerance," Trends Immunol., Apr. 2006, 4:195-201.
Okazaki et al., "A rheostat for immune responses: the unique properties of PD-1 and their advantages for clinical application," Nature Immunology, Dec. 2013, 14(12):1212-1218.
Pardoll, "The blockade of immune checkpoints in cancer immunotherapy," Nature, Apr. 2012, 12:252-264.
Parry et al, "CTLA-4 and PD-1 Receptors Inhibit T-Cell Activation by Distinct Mechanisms," Mol. Cell. Biol., Nov. 2005, 25(21):9543-9553.
Pascolutti et al., "Structure and Dynamics of PD-L1 and an Ultra-High-Affinity PD-1 Receptor Mutant," Structure, Oct. 2016, 24:1719-1728.
Paulini et al., "Orthogonal Multipolar Interactions in Structural Chemistry and Biology," Angew. Chem. Int. Ed., 2005, 44:1788-1805.
Postow et al, "Immune Checkpoint Blockade in Cancer Therapy," J. Clinical Oncology, Jun. 2015, 33(17):1974-1982.
Press Release Archive, "Boehringer Ingelheim and Yale University collaborate to investigate novel immunotherapy targets across several therapeutic areas," Boehringer Ingelheim, Jan. 13, 2015, 2 pages.
Sabatier et al, "Prognostic and predictive value of PDL1 expression in breast cancer," Oncotarget, Mar. 2015, 6(7):5449-5464.
Sharpe et al, "The function of programmed cell death 1 and its ligands in regulating autoimmunity and infection," Nat. Immunol., Mar. 2007 8(3):239-245.
Sharpe et al., "The B7-CD28 Superfamily," Nature Reviews, Feb. 2002, 2:116-126.
STN Search Report dated Apr. 14 2016, 79 pages.
STN Search Report dated Apr. 29, 2016, 69 pages.
STN Search Report dated Aug. 30, 2016, 4 pages.
STN Search Report dated Jun. 6, 2016, 115 pages.
STN Search Report dated Sep. 2, 2016, 115 pages.
Search Report, dated May 1, 2016, 12 pages.
Storz, "Intellectual property issues of immune checkpoint inhibitors," mAbs, Jan. 2016, 8(1):10-26.
Thiel et al., "Small-Molecule Stabilization of Protein—Protein Interactions: An Underestimated Concept in Drug Discovery?" Angew. Chem. Int. Ed., 2012, 51:2012-2018.
Velcheti et al., "Programmed death-1/programmed death-1 ligand axis as a therapeutic target in oncology: current insights," Journal of Receptor Ligand and Channel Research, Dec. 2014, 8(23): 1-7.
Wang et al, "The prognostic value of PD-L1 expression for non-small cell lung cancer patients: A meta-analysis," Eur. J. Surg. Oncol., 2015, 41:450-456.

(56) References Cited

OTHER PUBLICATIONS

Wang et al., "A binuclear Zn(II)—Zn(II) complex from a 2-hydroxybenzohydrazide-derived Schiff base for selective detection of pyrophosphate," Dalton Transactions, Oct. 2014, 43(37):14142-14146.

Wang et al., "Molecular Modeling and Functional Mapping of B7-H1 and B7-DC Uncouple Costimulatory Function from PD-1 Interaction," J. Exp. Med., Apr. 2013, 197(3):1083-1091.

Wei et al., "Strength of PD-1 signaling differentially affects T-cell effector functions," PNAS, Apr. 2013, E2480-E2489.

Weinmann, "Cancer Immunotherapy: Selected Targets and Small-Molecule Modulators," Chem. Med. Chem., 2016, 11:450-466.

Wells et al., "Reaching for high-hanging fruit in drug discovery at protein-protein interfaces," Nature, Dec. 2007, 450:1001-1009.

Wu et al., "Targeting the BACE1 Active Site Flap Leads to a Potent Inhibitor That Elicits Robust Brain Aβ Reduction in Rodents," ACS Medicinal Chemistry Letters, 2016, 7(3):271-276.

www.medscape.com [online]. "The 'Family Business' Behind the Flurry of PD-1 Inhibitors," Sep. 10, 2014. [Retrieved on Jan. 29, 2015]. Retrieved from the Internet: URL<http://www.medscape.com/viewarticle/831448_print>. 3 pages.

Xu et al., "Design, synthesis and biological evaluation of deuterated nintedanib for improving pharmacokinetic properties," J. Label. Compd. RadioPharm., Jun. 15, 2015, 58(7):308-312.

Yin et al., "Strategies for Targeting Protein-Protein Interactions With Synthetic Agents," Angew. Chem. Int. Ed., 2005, 44:4130-4163.

Young et al., "Discovery of highly potent and selective Bruton's tyrosine kinase inhibitors: Pyridazinone analogs with improved metabolic stability," Bioorganic & Medicinal Chemistry Letters, 2016, 26(2):575-579.

Young et al., "Potent and selective Bruton's tyrosine kinase inhibitors: Discovery of GDC-0834," Bmioorganic & Medicinal Chemistry Letters , 2015, 25(6):1333-1337.

Zarganes-Tzitzikas, "Inhibitors of programmed cell death 1 (PD-1): a patent review (2010-2015)," Expert Opinion on Therapeutic Patents, Sep. 19, 2016, 26(9):973-977.

Zak et al., "Structural basis for small molecule targeting of the programmed death ligand 1 (PD-L1)," Oncotarget, 2016, 7(21):30323-30335.

Zak et al., "Structural basis for small molecule targeting of the programmed death ligand 1 (PD-L1): Supplementary Material" Oncotarget, Apr. 2016, 19 pages.

Zak et al., "Structure of the Complex of Human Programmed Death 1, PD-1, and Its Ligand PD-L1: with Supplemental Information," Structure, Dec. 2015, 23:2341-2348.

Zhan et al., "From monoclonal antibodies to small molecules: the development of inhibitors targeting the PD-1/PD-L1 pathway," Drug Discovery Today, Apr. 2016, 10 pages.

Zhang et al., "Structural and Functional Analysis of the Costimulatory Receptor Programmed Death-1,"399' Immunity, Mar. 2004, 20:337-347.

European Communication in European Application No. 16805690.1, dated Jul. 10, 2018, 6 pages.

Ahmed et al., "Enantioselective Polymerization of Epoxides Using Biaryl-Linked Bimetallic Cobalt Catalysts: A Mechanistic Study," J. Am. Chem. Soc., 2013, 135(50):18901-18911.

Amaya et al., "Synthesis of three-dimensionally arranged bisbiphenol ligand on hexaaryl benzene scaffold and its application for cross-pinacol coupling reaction," Tetrahedron Letters, 2011, 52(35):4567-4569.

Anyika et al.,"Point-to-Axial Chirality Transfer—A New Probe for "Sensing" the Absolute Configurations of Monoamines," J. Am. Chem. Soc., 2014, 136(2):550-553.

Artz et al., "Host-guest complexation. 28. Hemispherands with four self-organizing units," J. Am. Chem. Soc., 1984, 106(7):2160-2171.

Bentley et al., "Antenna Biphenols: Development of Extended Wavelength Chiroptical Reporters," J. Org. Chem., 2016, 81(3):1185-1191.

Buisman et al., "Chiral Cooperativity in Diastereomeric Diphosphite Ligands. Effects on the Rhodium-Catalyzed Enantioselective Hydroformylation of Styrene," Organometallics, 1997, 16(13):2929-2939.

Cheng et al., "Synthetic connections to the aromatic directed metalation reaction. Iterative ortho metalation-cross coupling tactics for the construction of polyphenyls," Tetrahedron Letters, 1978, 28(43):5097-5098.

Chilean Office Action in Chilean Application No. 201803701, dated Nov. 22, 2019, 18 pages.

Clayden et al., "Conformational Preference and Remote (1,10) Stereocontrol in Biphenyl-2,2'- dicarboxamides," Org. Lett., 2001, 3(26):4133-4136.

Cram et al., "Host-guest complexation. 32. Spherands composed of cyclic urea and anisyl units," J. Am. Chem. Soc., 1984, 106(23):7150-7167.

Cram et al., "Host-guest complexation. 29. Expanded hemispherands," J. Am. Chem. Soc., 1984, 106(11):6386-3292.

Cram et al., "Host-guest complexation. 26. Cavitands composed of fluorobenzene units bonded in their 2,6-positions to form macrocycles," J. Am. Chem. Soc., 1984, 106(3):695-701.

Cram et al., "Spherand hosts containing cyclic urea units," J. Am. Chem. Soc., 1982, 104(24):6828-6830.

De Lucca et al., "Small Molecule Reversible Inhibitors of Bruton's Tyrosine Kinase (BTK): Structure-Activity Relationships Leading to the Identification of 7-(2-Hydroxypropan-2-yl)-4-[2-methyl-3-(4-oxo-3,4-dihydroquinazolin-3-yl)phenyl]-9H-carbazole-1-carboxamide (BMS-935177)," Journal of Medicinal Chemistry, 2016, 59(17):7915-7935.

Dhanunjayarao et al., "Synthesis and Optical Properties of Salicylaldimine-Based Diboron Complexes," Eur J Inorg Chem., 2014, 3:539-545.

Ecuador Opposition in Ecuador Application No. SENADI-2019-3773, dated Oct. 10, 2019, 29 pages.

Escarcega-Bobadilla et al., "A Recyclable Trinuclear Bifunctional Catalyst Derived from a Tetraoxo Bis-Zn(salphen) Metalloligand," Chemistry—A European Journal, 2013, 19(8):2641-2648.

Escarcega-Bobadilla et al., "Metal-directed assembly of chiral bis-Zn(II) Schiff base structures," Dalton Transactions, 2012, 41(32):9766-9772.

Escarcega-Bobadilla et al., "Versatile Switching in Substrate Topicity: Supramolecular Chirality Induction in Di- and Trinuclear Host Complexes," Chemistry—A European Journal, 2012:8(22):6805-6810.

Eurasian Office Action in Eurasian Application No. 201990074/28, dated Oct. 3, 2019, 5 pages.

European Communication in European Application No. 16805690.1, dated Jan. 22, 2020, 5 pages.

European Communication in European Application No. 17743174.9, dated Jan. 31, 2020, 5 pages.

Fabris et al., "Central to Axial Transfer of Chirality in Menthone or Camphor-Derived 2,2'- Biphenols," J. Org. Chem., 1997, 62(21):7156-7164.

Freindorf, M., "Vibronic couplings in an excited state of hydrogen bond dimeric systems," Acta Physica Polonica, 1990, A78(6):825-839.

Gong et al., "Rhodium(I)-catalyzed regiospecific dimerization of aromatic acids: two direct C—H bond activations in water," Angewandte Chemie, 2015, 54(19):5718-5721.

Green et al., "Synthesis and investigation of the configurational stability of some dimethylammonium borate salts," J. Chem. Soc., Perkin Trans. 1, 2000, 24:4403-4408.

Han et al., "Synthesis of binuclear phenoxyimino organoaluminum complexes and their use as the catalyst precursors for efficient ring-opening polymerisation of E-caprolactone," Dalton Transactions, 2013, 41:12346-12353.

Helgeson et al., "Host-guest complexation. 66. 18-Membered-ring spherands containing five anisyl groups," J. Am. Chem. Soc., 1993, 1115(24):11506-11511.

Hu et al., "Syntheses and Ethylene Polymerization Behavior of Supported Salicylaldimine-Based Neutral Nickel(II) Catalysts," Organometallics, 2007, 26(10):2609-2615.

(56) References Cited

OTHER PUBLICATIONS

Hu et al., "Synthesis and Ethylene Polymerization Activity of a Novel, Highly Active Single-Component Binuclear Neutral Nickel(II) Catalyst," Organometallics, 2005, 24(11):2628-2632.
Hu et al., "Novel highly active binuclear neutral nickel and palladium complexes as precatalysts for norbornene polymerization," Journal of Molecular Catalysis A: Chemical 253, 2006, 155-164.
Huddle et al., "Reactions of alkyl-lithium compounds with aryl halides ," J Chem Soc., Perkin I, 1980, 12:2617-2625.
Israeli Office Action in Israeli Application No. 259,406, dated Mar. 11, 2020, 10 pages.
Jiang et al., "Self-immobilizing binuclear neutral nickel catalyst for ethylene polymerization: Synthesis and catalytic studies," J. Mol. Cat., 2013, 380:139-143.
Kayal et al., "3,3'-Bis(triphenylsilyl)biphenoxide as a Sterically Hindered Ligand on Fe(II), Fe(III), and Cr(II)," Inorg. Chem., 2002, 41(2):321-330.
Koch et al., "Nucleophilic reactions of pyridines and imidazoles with vinyl and aromatic halides," J. Org. Chem., 1993, 58(6):1409-1414.
Legon'kova et al., "Interaction of o,o-dihalo o'-hydroxy azo compounds with metallic copper. II. Preparation of oligomeric azo compounds from monoazo compounds," Mosk Khim-Tekhnol Inst im Mendeleeva., 1968, 11(11):1281-1284 Machine Translation.
Legon'kova et al., "Interaction of o,o-dihalogeno o-hydroxy azo compounds with metallic copper," Trudy Instituta—Moskovskii Khimiko-Tekhnologicheskii Institut imeni D. I. Mendeleeva, 1965, 48:120-125 Machine Translation.
Lehtonen et al., "Comparison of quaternary methyl-, ethyl- and butylammonium hydroxides as alkylating reagents in pyrolysis-GC/MS studies of aquatic fulvic acid," Journal of Analytical and Applied Pyrolysis, 2003, 68-69:315-329.
Li et al., "Asymmetric Alternating Copolymerization of Meso-epoxides and Cyclic Anhydrides: Efficient Access to Enantiopure Polyesters," J. Am. Chem. Soc., 2016, 138(36):11493-11496.
Li et al., "A 3D Mesomeric Supramolecular Structure of a Cu(II) Coordination Polymer with 1,1'-Biphenyl-2,2',3,3'-tetracarboxylic Acid and 5,5'-Dimethyl-2,2'-bipyridine Ligands," J Inorg and Organomet Poly Mat., 2012, 22(6):1320-1324.
Liu et al., "Asymmetric Copolymerization of CO2 with meso-Epoxides Mediated by Dinuclear Cobalt(III) Complexes: Unprecedented Enantioselectivity and Activity," Angewandte Chemie, 2013, 52(44):11594-11598.
Maier et al., "Effects of the stationary phase and the solvent on the stereodynamics of biphep ligands quantified by dynamic three-column HPLC," Angewante Chemie, 2012, 51(12):2985-2988.
Manecke et al., "Preparation and properties of monomeric and polymeric Schiff bases derived from salicylaldehyde and 2,5-dihydroxyterephthalaldehyde. II. Electrical conductivity," Makromolekulare Chemie, 1972, 160:111-126 English Abstract.
Manecke et al., "Preparation and properties of chelate-forming monomeric and polymeric Schiff bases derived from salicylaldehyde and 2,5-dihydroxyterephthalaldehyde. I," Makromolekulare Chemie, 1970, 133:61-82 English Abstract.
Mochida et al., "Rhodium-Catalyzed Regioselective Olefination Directed by a Carboxylic Group," J. Org. Chem, 2011, 76(9):3024-3033.
Moneta et al., "Boron templated synthesis of macrocyclic hosts containing convergent hydroxy or methoxy groups," Bulletin de la Societe Chimique de France, 1988, 6:995-1004 (English Abstract).
Nallasivam et al., "Development of Unimolecular Tetrakis(piperidin-4-ol) as a Ligand for Suzuki-Miyaura Cross-Coupling Reactions: Synthesis of Incrustoporin and Preclamol," Eur. J. Org. Chem., 2015(16):3558-3567.
Normand et al., "Dinuclear vs. mononuclear complexes: accelerated, metal-dependent ring-opening polymerization of lactide," Chem. Commun., 2013, 49(99):11692-11694.
Paek et al., "Facile syntheses and multi-orthofunctionalizations of tertiary benzamides," Bulletin of the Korean Chemical Society, 1993, 14(6):732-739.

Paek et al., "Chiral host. Attempted synthesis using McMurray reaction as a final ring closure method," Bulletin of the Korean Chemical Society, 1989, 10(6):572-577.
Parsons et al., "Directed ortho metalation reactions. Expedient synthesis of 3,3'-disubstituted 1,1'-bi-(2-phenols) (BIPOLS)," Tetrahedron Letters, 1994, 35(41):7537-7540.
Pearson et al., "The formation of complexes alkylammonium salts. Part 5. Chiral 3126 between aza-derivatives of crown ethers and primary macrocyclic diamines," J. Chem. Soc., Perkin I, 1979, 12:3113-3126.
Pfeiffer et al., "Inner complex salts of the aldimine and azo series," Journal fuer Praktische Chemie, 1937, 149:217-296 Machine Translation.
Pierre et al., "Synthesis of a new macrobicyclic siderophoric host molecule with six converging phenolate groups," Angewandte Chemie, 1991, 103(1):75-76 Machine Translation.
Puehlhofer et al., "SASAPOS cascades of perfluorinated aromatic carboxylic acids: low-temperature decarboxylation triggered by electrostatic effects of polycationic ligand sets," Eur. J. Org. Chem., 2004, 5:1002-1007.
Punniyamurthy et al., "Enantiomerically pure bicyclo[3.3.1]nona-2,6-diene as the sole source of enantioselectivity in BIPHEP-Rh asymmetric hydrogenation," Chem. Comm., 2008, 41:5092-5094.
Sharma et al., "Palladium-Catalyzed Decarboxylative Acylation of O-Phenyl Carbamates with Alpha-Oxocarboxylic Acids at Room Temperature," Advanced Synthesis & Catalysis, 2013, 355(4):667-672.
STN Search Report dated May 24, 2016, 92 pages.
STN Search Report dated Sep. 12, 2016, 4 pages.
STN Search Report dated Jun. 16, 2016, 8 pages.
STN Search Report dated Sep. 12, 2016, 17 pages.
STN Search Report dated Jul. 12, 2016, 4 pages.
STN Search Report dated Aug. 19, 2016, 23 pages.
STN Search Report dated Dec. 15, 2016, 4 pages.
STN Search Report dated Dec. 19, 2016, 11 pages.
STN Search Report dated Dec. 16, 2016, 25 pages.
STN Search Report dated Dec. 16, 2016, 4 pages.
STN Search Report dated Dec. 20, 2016, 117 pages.
STN Search Report dated Sep. 27, 2017, 4 pages.
STN Search Report dated Mar. 27, 2018, 4 pages.
STN Search Report dated Apr. 30, 2018, 8 pages.
Sorrell et al., "3,3'-Disubstituted 2,2'-biphenols. Synthesis of nonplanar, tetradentate chelating ligands," J. Org. Chem., 1985, 50(26):5765-5769.
Sumrit et al., "Aluminum complexes containing salicylbenzoxazole ligands and their application in the ring-opening polymerization of rac-lactide and ε-caprolactone," Dalton Transactions (2016), 45(22), 9250-9266.
Tang et al., "Facile synthesis of enantioenriched phenol-sulfoxides and their aluminum complexes," Org Biomol Chem., 2016, 14(24):5580-5585.
Tucker et al., "Host-guest complexation. 52. Bridged and chiral hemispherands," J. Org. Chem., 1989, 54(23):5460-5482.
Unrau et al., "Directed ortho metalation. regiospecific routes to functionalized Suzuki cross coupling connections. Convenient m- and p-teraryls and m-quinquemyls," Tetrahedron Letters, 1992, 33(20):2773-2776.
Weiss et al., "Electrostatics and color: Massive electrostatic perturbation of chromophores by ion cluster ligands," J. Am. Chem. Soc., 2007, 129(3):547-553.
Weiss et al., "Electrostatic activation of SNAr-reactivity by sulfonylonio substituents," Zeitschrift fuer Naturforschung, 2001, 56(12):1360-1368 English Abstract.
Weiss et al., "First-ever per(onio) substitution of benzene: the role of the counterion," Angewandte Chemie, 1995, 34(12):1319-1321.
Weiss et al., "Massive electrostatic effects on heteropolar C—C disconnections: Transforming a phenyl anion into a potent leaving group," Eur. J. Org. Chem., 2005, 16:3530-3535.
Weiss et al., "Poly-onio substituted quinones as strong electron acceptors," Angewandte Chemie International Edition, 1986, 25(10):925-926.

(56) References Cited

OTHER PUBLICATIONS

Weiss et al., "SASAPOS, not Sisyphus: highly efficient 20-step one-pot synthesis of a discrete organic-inorganic ion cluster with a porphyrin core," Angewandte Chemie International Edition, 2002, 41(20):3815-3817.

Weiss et al., "Syntheses and Reactions of Polycationically Substituted Azido- and Diazidobenzenes," Eur. J. Org. Chem., Nov. 2007, 31:5270-5276.

Xiong et al., "Biaryl-Bridged Salalen Ligands and Their Application in Titanium-Catalyzed Asymmetric Epoxidation of Olefins with Aqueous H2O2," Eur. J. Org. Chem., 2011, 23:4289-4292.

Xu et al., "Quantitative structure-activity relationship study on BTK inhibitors by modified multivariate adaptive regression spline and CoMSIA methods," SAR QSAR Environ Res., 2015, 26(4):279-300.

Zang et al., "Four 2D metal-organic networks incorporating Cd-cluster SUBs: hydrothermal synthesis, structures and photoluminescent properties," CrystEngComm, 2009, 11(1):122-129.

Zhang et al., "Electrospray mass spectrum of a per(onio)-substituted benzene: retention of Coulombic charge upon collisionally activated decomposition," J Am Soc. Mass. Spectrom., 1998, 9(1):15-20.

Zhang et al., "Non-symmetrical diarylcarboxylic acids via rhodium(I)-catalyzed regiospecific cross-dehydrogenation coupling of aromatic acids: twofold direct C—H bond activations in water," RSC Advances, 2016, 6(64):91617-91620.

Zhang et al., "Biaryl-Based Macrocyclic and Polymeric Chiral (Salophen)Ni(II) Complexes: Synthesis and Spectroscopic Study," J. Org. Chem., 2001, 66(2):481-487.

Zhao et al., "Design, synthesis and organocatalysis of 2,2'-biphenol-based prolinamide organocatalysts in the asymmetric direct aldol reaction in water," Synlett, 2013, 24(20):2743-2747.

Chilean Office Action in Chilean Application No. 201901744, dated Apr. 14, 2020, 19 pages.

HETEROCYCLIC COMPOUNDS AS IMMUNOMODULATORS

FIELD OF THE INVENTION

The present application is concerned with pharmaceutically active compounds. The disclosure provides compounds as well as their compositions and methods of use. The compounds modulate PD-1/PD-L1 protein/protein interaction and are useful in the treatment of various diseases including infectious diseases and cancer.

BACKGROUND OF THE INVENTION

The immune system plays an important role in controlling and eradicating diseases such as cancer. However, cancer cells often develop strategies to evade or to suppress the immune system in order to favor their growth. One such mechanism is altering the expression of costimulatory and co-inhibitory molecules expressed on immune cells (Postow et al, J. Clinical Oncology 2015, 1-9). Blocking the signaling of an inhibitory immune checkpoint, such as PD-1, has proven to be a promising and effective treatment modality.

Programmed cell death-1 (PD-1), also known as CD279, is a cell surface receptor expressed on activated T cells, natural killer T cells, B cells, and macrophages (Greenwald et al, Annu. Rev. Immunol 2005, 23:515-548; Okazaki and Honjo, Trends Immunol 2006, (4):195-201). It functions as an intrinsic negative feedback system to prevent the activation of T-cells, which in turn reduces autoimmunity and promotes self-tolerance. In addition, PD-1 is also known to play a critical role in the suppression of antigen-specific T cell response in diseases like cancer and viral infection (Sharpe et al, *Nat Immunol* 2007 8, 239-245; Postow et al, J. Clinical Oncol 2015, 1-9).

The structure of PD-1 consists of an extracellular immunoglobulin variable-like domain followed by a transmembrane region and an intracellular domain (Parry et al, Mol Cell Biol 2005, 9543-9553). The intracellular domain contains two phosphorylation sites located in an immunoreceptor tyrosine-based inhibitory motif and an immunoreceptor tyrosine-based switch motif, which suggests that PD-1 negatively regulates T cell receptor-mediated signals. PD-1 has two ligands, PD-L1 and PD-L2 (Parry et al, Mol Cell Biol 2005, 9543-9553; Latchman et al, Nat Immunol 2001, 2, 261-268), and they differ in their expression patterns. PD-L1 protein is upregulated on macrophages and dendritic cells in response to lipopolysaccharide and GM-CSF treatment, and on T cells and B cells upon T cell receptor and B cell receptor signaling. PD-L1 is also highly expressed on almost all tumor cells, and the expression is further increased after IFN-γ treatment (Iwai et al, PNAS 2002, 99(19):12293-7; Blank et al, Cancer Res 2004, 64(3):1140-5). In fact, tumor PD-L1 expression status has been shown to be prognostic in multiple tumor types (Wang et al, Eur J Surg Oncol 2015; Huang et al, Oncol Rep 2015; Sabatier et al, Oncotarget 2015, 6(7): 5449-5464). PD-L2 expression, in contrast, is more restricted and is expressed mainly by dendritic cells (Nakae et al, J Immunol 2006, 177:566-73). Ligation of PD-1 with its ligands PD-L1 and PD-L2 on T cells delivers a signal that inhibits IL-2 and IFN-γ production, as well as cell proliferation induced upon T cell receptor activation (Carter et al, Eur J Immunol 2002, 32(3):634-43; Freeman et al, J Exp Med 2000, 192(7): 1027-34). The mechanism involves recruitment of SHP-2 or SHP-1 phosphatases to inhibit T cell receptor signaling such as Syk and Lck phosphorylation (Sharpe et al, Nat Immunol 2007, 8, 239-245). Activation of the PD-1 signaling axis also attenuates PKC-θ activation loop phosphorylation, which is necessary for the activation of NF-κB and AP1 pathways, and for cytokine production such as IL-2, IFN-γ and TNF (Sharpe et al, Nat Immunol 2007, 8, 239-245; Carter et al, Eur J Immunol 2002, 32(3):634-43; Freeman et al, J Exp Med 2000, 192(7):1027-34).

Several lines of evidence from preclinical animal studies indicate that PD-1 and its ligands negatively regulate immune responses. PD-1-deficient mice have been shown to develop lupus-like glomerulonephritis and dilated cardiomyopathy (Nishimura et al, Immunity 1999, 11:141-151; Nishimura et al, Science 2001, 291:319-322). Using an LCMV model of chronic infection, it has been shown that PD-1/PD-L1 interaction inhibits activation, expansion and acquisition of effector functions of virus-specific CD8 T cells (Barber et al, Nature 2006, 439, 682-7). Together, these data support the development of a therapeutic approach to block the PD-1-mediated inhibitory signaling cascade in order to augment or "rescue" T cell response. Accordingly, there is a need for new compounds that block PD-1/PD-L1 protein/protein interaction.

SUMMARY

The present disclosure provides, inter alia, a compound of Formula (I):

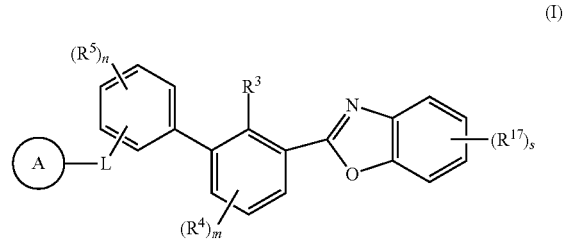

(I)

or a pharmaceutically acceptable salt or a stereoisomer thereof, wherein constituent variables are defined herein. The present disclosure further provides a pharmaceutical composition comprising a compound disclosed herein, or a pharmaceutically acceptable salt or a stereoisomer thereof, and one or more pharmaceutically acceptable excipient or carrier.

The present disclosure further provides methods of inhibiting PD-1/PD-L1 interaction, said method comprising administering to a patient a compound disclosed herein, or a pharmaceutically acceptable salt or a stereoisomer thereof.

The present disclosure further provides methods of treating a disease or disorder associated with inhibition of PD-1/PD-L1 interaction, said method comprising administering to a patient in need thereof a therapeutically effective amount of a compound of disclosed herein, or a pharmaceutically acceptable salt or a stereoisomer thereof.

The present disclosure further provides methods of enhancing, stimulating and/or increasing the immune response in a patient, said method comprising administering to the patient in need thereof a therapeutically effective amount of a compound disclosed herein, or a pharmaceutically acceptable salt or a stereoisomer thereof.

DETAILED DESCRIPTION

I. Compounds

The present disclosure provides, inter alia, compounds of Formula (I):

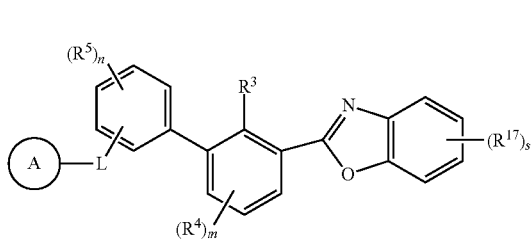

(I)

or a pharmaceutically acceptable salt or a stereoisomer thereof, wherein:

ring A is 5- to 14-membered heteroaryl, 4- to 14-membered heterocycloalkyl, $C_{6-10}$ aryl or $C_{3-14}$ cycloalkyl, wherein the 5- to 14-membered heteroaryl and 4- to 14-membered heterocycloalkyl each has 1-4 heteroatoms as ring members selected from B, P, N, O and S, wherein the P, N or S atom as ring members is optionally oxidized and one or more carbon atoms as ring members are each optionally replaced by a carbonyl group; and wherein ring A is optionally substituted with 1, 2, 3, 4 or 5 $R^6$ substituents;

L is a bond, —C(O)$NR^{13}$—, —$NR^{13}$C(O)—, —C(=S)$NR^{13}$—, —$NR^{13}$C(=S)—, —C(=$NR^{13}$)$NR^{13}$—, —$NR^{13}$C(=$NR^{13}$)—, —C(=$NOR^{13}$)$NR^{13}$—, —$NR^{13}$C(=$NOR^{13}$)—, —C(=NCN)$NR^{13}$—, —$NR^{13}$C(=NCN)—, O, —$(CR^{14}R^{15})_q$—, —$(CR^{14}R^{15})_q$—O—, —O$(CR^{14}R^{15})_q$—, —$NR^{13}$—, —$(CR^{14}R^{15})_q$—$NR^{13}$—, —$NR^{13}$—$(CR^{14}R^{15})_q$—, —CH=CH—, —C≡C—, —SO$_2NR^{13}$—, —$NR^{13}$SO$_2$—, —$NR^{13}$SO$_2NR^{13}$—, —$NR^{13}$C(O)O—, —OC(O)$NR^{13}$— or —$NR^{13}$C(O)$NR^{13}$—;

$R^3$ is methyl, halo, CN or $C_{1-4}$ haloalkyl;

$R^4$ is $C_{1-4}$ alkyl, $C_{1-4}$ alkoxy, $C_{1-4}$ haloalkyl, $C_{1-4}$ haloalkoxy, CN, halo, OH, —COOH, NH$_2$, —NHC$_{1-4}$ alkyl or —N(C$_{1-4}$ alkyl)$_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, NH$_2$, —NHC$_{1-4}$ alkyl or —N(C$_{1-4}$ alkyl)$_2$;

$R^6$ and $R^{17}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, NO$_2$, OR$^a$, SR$^a$, NHOR$^a$, C(O)R$^a$, C(O)NR$^a$R$^a$, C(O)OR$^a$, C(O)NR$^a$S(O)$_2$R$^a$, OC(O)R$^a$, OC(O)NR$^a$R$^a$, NHR$^a$, NR$^a$R$^a$, NR$^a$C(O)R$^a$, NR$^a$C(=NR$^a$)R$^a$, NR$^a$C(O)OR$^a$, NR$^a$C(O)NR$^a$R$^a$, C(=NR$^a$)R$^a$, C(=NOH)R$^a$, C(=NOH)NR$^a$R$^a$, C(=NCN)NR$^a$R$^a$, NR$^a$C(=NCN)NR$^a$R$^a$, C(=NR$^a$)NR$^a$R$^a$, NR$^a$C(=NR$^a$)NR$^a$R$^a$, NR$^a$S(O)R$^a$, NR$^a$S(O)R$^a$, NR$^a$S(O)$_2$R$^a$, S(O)R$^a$, S(O)NR$^a$R$^a$, S(O)$_2$R$^a$, S(O)$_2$NR$^a$C(O)R$^a$, —P(O)R$^a$R$^a$, —P(O)(OR$^a$)(OR$^a$), —B(OH)$_2$, —B(OR$^a$)$_2$ and S(O)$_2$NR$^a$R$^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^6$ and $R^{17}$ are each optionally substituted with 1, 2, 3, 4 or 5 independently selected $R^b$ substituents;

or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, NH$_2$, —NHC$_{1-4}$ alkyl and —N(C$_{1-4}$ alkyl)$_2$;

$R^{14}$ and $R^{15}$ are each independently selected from H, halo, CN, OH, —COOH, $C_{1-4}$ alkyl, $C_{1-4}$ alkoxy, —NHC$_{1-4}$ alkyl, —N(C$_{1-4}$ alkyl)$_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5-, 6- or 7-membered heterocycloalkyl, each of which is optionally substituted with 1 or 2 independently selected $R^q$ substituents;

each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^a$ are each optionally substituted with 1, 2, 3, 4, or 5 independently selected $R^d$ substituents;

each $R^d$ is independently selected from $C_{1-6}$ alkyl, $C_{1-6}$ haloalkyl, halo, $C_{6-10}$ aryl, 5-10 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, NH$_2$, NHOR$^e$, OR$^e$, SR$^e$, C(O)R$^e$, C(O)NR$^e$R$^e$, C(O)OR$^e$, C(O)NR$^e$S(O)$_2$R$^e$, OC(O)R$^e$, OC(O)NR$^e$R$^e$, NHR$^e$, NR$^e$R$^e$, NR$^e$C(O)R$^e$, NR$^e$C(=NR$^e$)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, S(O)$_2$NR$^e$C(O)R$^e$, NR$^e$S(O)$_2$R$^e$, NR$^e$S(O)$_2$NR$^e$R$^e$, —P(O)R$^e$R$^e$, —P(O)(OR$^e$)(OR$^e$), —B(OH)$_2$, —B(OR$^e$)$_2$ and S(O)$_2$NR$^e$R$^e$, wherein the $C_{1-6}$ alkyl, $C_{1-6}$ haloalkyl, $C_{6-10}$ aryl, 5-14 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $C(O)NR^cS(O)_2R^c$, $OC(O)R^c$, $OC(O)NR^cR^c$, $C(=NOH)R^c$, $C(=NOH)NR^c$, $C(=NCN)NR^cR^c$, $NR^cC(=NCN)NR^cR^c$, $C(=NR^c)NR^cR^c$, $NR^cC(=NR^c)NR^cR^c$, $NHR^c$, $NR^cR^c$, $NR^cC(O)R^c$, $NR^cC(=NR^c)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, $S(O)_2NR^cC(O)R^c$, —$P(O)R^cR^c$, —$P(O)(OR^c)(OR^c)$, —$B(OH)_2$, —$B(OR^c)_2$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2 or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 independently selected $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $C(O)NR^gS(O)_2R^g$, $OC(O)R^g$, $OC(O)NR^gR^g$, $NHR^g$, $NR^gR^g$, $NR^gC(O)R^g$, $NR^gC(=NR^g)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R$, $S(O)_2NR^gC(O)R^g$, $NR^gS(O)_2R^g$, $NR^gS(O)_2NR^gR^g$, —$P(O)R^gR^g$, —$P(O)(OR^g)(OR^g)$, —$B(OH)_2$, —$B(OR^g)_2$ and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 independently selected $R^n$ substituents;

each $R^n$ is substituents independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^o$, $OR^o$, $SR^o$, $C(O)R^o$, $C(O)NR^oR^o$, $C(O)OR^o$, $C(O)NR^oS(O)_2R^o$, $OC(O)R^o$, $OC(O)NR^oR^o$, $NHR^o$, $NR^oR^o$, $NR^oC(O)R^o$, $NR^oC(=NR^o)R^o$, $NR^oC(O)NR^oR^o$, $NR^oC(O)OR^o$, $C(=NR)NR^oR^o$, $NR^oC(=NR)NR^oR^o$, $S(O)R^o$, $S(O)NR^oR^o$, $S(O)_2R^o$, $S(O)_2NR^oC(O)R$, $NR^oS(O)_2R^o$, $NR^oS(O)_2NR^oR^o$, —$P(O)R^oR^o$, —$P(O)(OR^o)(OR^o)$, —$B(OH)_2$, —$B(OR^o)_2$ and $S(O)_2NR^oR^o$, wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^n$ are each optionally substituted with 1, 2 or 3 independently selected $R^q$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1, 2, or 3 independently selected $R^p$ substituents;

each $R^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^r$, $OR^r$, $SR^r$, $C(O)R^r$, $C(O)NR^rR^r$, $C(O)OR^r$, $C(O)NR^rS(O)_2R^r$, $OC(O)R^r$, $OC(O)NR^rR^r$, $NHR^r$, $NR^rR^r$, $NR^rC(O)R^r$, $NR^rC(=NR^r)R^r$, $NR^rC(O)NR^rR^r$, $NR^rC(O)OR^r$, $C(=NR^r)NR^rR^r$, $NR^rC(=NR^r)NR^rR^r$, $NR^rC(=NOH)NR^rR^r$, $NR^rC(=NCN)NR^rR^r$, $S(O)R^r$, $S(O)NR^rR^r$, $S(O)_2R^r$, $S(O)_2NR^rC(O)R^r$, $NR^rS(O)_2R^r$, $NR^rS(O)_2NR^rR^r$, —$P(O)R^rR^r$, —$P(O)(OR^r)(OR^r)$, —$B(OH)_2$, —$B(OR^r)_2$ and $S(O)_2NR^rR^r$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^p$ is optionally substituted with 1, 2 or 3 independently selected $R^q$ substituents;

or any two $R^a$ substituents together with the boron, phosphorus or nitrogen atom to which they are attached form a 4-, 5-, 6-, 7-, 8-, 9- or 10-membered heterocycloalkyl group optionally substituted with 1, 2 or 3 independently selected $R^h$ substituents;

each $R^h$ is independently selected from $C_{1-6}$ alkyl, $C_{3-10}$ cycloalkyl, 4-10 membered heterocycloalkyl, $C_{6-10}$ aryl, 5-10 membered heteroaryl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $C_{1-6}$ haloalkyl, $C_{1-6}$ haloalkoxy, $C_{2-6}$ alkenyl, $C_{2-6}$ alkynyl, halo, CN, $OR^i$, $SR^i$, $NHOR^i$, $C(O)R^i$, $C(O)NR^iR^i$, $C(O)OR^i$, $C(O)NR^iS(O)_2R^i$, $OC(O)R^i$, $OC(O)NR^iR^i$, $NHR^i$, $NR^iR^i$, $NR^iC(O)R^i$, $NR^iC(=NR^i)R^i$, $NR^iC(O)NR^iR^i$, $NR^iC(O)OR^i$, $C(=NR^i)NR^iR^i$, $NR^iC(=NR)NR^iR^i$, $S(O)R^i$, $S(O)NR^iR^i$, $S(O)_2R^i$, $S(O)_2NR^iC(O)R^i$, $NR^iS(O)_2R^i$, $NR^iS(O)_2NR^iR^i$, —$P(O)R^iR^i$, —$P(O)(OR^i)(OR^i)$, —$B(OH)_2$, —$B(OR^i)_2$ and $S(O)_2NR^iR^i$, wherein the $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{6-10}$ aryl-$C_{1-4}$ alkyl-, $C_{3-10}$ cycloalkyl-$C_{1-4}$ alkyl-, (5-10 membered heteroaryl)-

$C_{1-4}$ alkyl-, (4-10 membered heterocycloalkyl)-$C_{1-4}$ alkyl- of $R^h$ are each further optionally substituted by 1, 2, or 3 independently selected $R^j$ substituents;

each $R^j$ is independently selected from $C_{3-6}$ cycloalkyl, $C_{6-10}$ aryl, 5 or 6-membered heteroaryl, 4-7 membered heterocycloalkyl, $C_{2-4}$ alkenyl, $C_{2-4}$ alkynyl, halo, $C_{1-4}$ alkyl, $C_{1-4}$ haloalkyl, $C_{1-4}$ haloalkoxy, CN, $NHOR^k$, $OR^k$, $SR^k$, $C(O)R^k$, $C(O)NR^kR^k$, $C(O)OR^k$, $C(O)NR^kS(O)_2R^k$, $OC(O)R^k$, $OC(O)NR^kR^k$, $NHR^k$, $NR^kR^k$, $NR^kC(O)R^k$, $NR^kC(=NR^k)R^k$, $NR^kC(O)NR^kR^k$, $NR^kC(O)OR^k$, $C(=NR^k)NR^kR^k$, $NR^kC(=NR^k)NR^kR^k$, $S(O)R^k$, $S(O)NR^kR^k$, $S(O)_2R^k$, $S(O)_2NR^kC(O)R^k$, $NR^kS(O)_2R^k$, $NR^kS(O)_2NR^kR^k$, —$P(O)R^kR^k$, —$P(O)(OR^k)(OR^k)$, —$B(OH)_2$, —$B(OR^k)_2$ and $S(O)_2NR^kR^k$, wherein the $C_{1-4}$ alkyl, $C_{3-6}$ cycloalkyl, $C_{6-10}$ aryl, 5- or 6-membered heteroaryl, 4-7 membered heterocycloalkyl, $C_{2-4}$ alkenyl, $C_{2-4}$ alkynyl, $C_{1-4}$ haloalkyl, and $C_{1-4}$ haloalkoxy of $R^j$ are each optionally substituted with 1, 2 or 3 independently selected $R^q$ substituents;

or two $R^h$ groups attached to the same carbon atom of the 4- to 10-membered heterocycloalkyl taken together with the carbon atom to which they are attached form a $C_{3-6}$ cycloalkyl or 4- to 6-membered heterocycloalkyl having 1-2 heteroatoms as ring members selected from O, N or S;

or any two $R^c$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^e$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^g$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^i$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents, or 1, 2, or 3 independently selected $R^q$ substituents;

or any two $R^k$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents, or 1, 2, or 3 independently selected $R^q$ substituents;

or any two $R^o$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^r$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

each $R^i$, $R^k$, $R^o$ or $R^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of $R^i$, $R^k$, $R^o$ or $R^r$ are each optionally substituted with 1, 2 or 3 independently selected $R^q$ substituents;

each $R^q$ is independently selected from halo, OH, CN, —COOH, $NH_2$, —NH—$C_{1-6}$ alkyl, —$N(C_{1-6}$ alkyl$)_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with 1, 2 or 3 substituents independently selected from halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

each subscript q is independently an integer of 1, 2, 3 or 4; and the subscript s is an integer of 1, 2, 3 or 4.

In some embodiments, the present disclosure provides compounds of Formula (I), or a pharmaceutically acceptable salt or a stereoisomer thereof, wherein:

ring A is 5- to 14-membered heteroaryl, 4- to 14-membered heterocycloalkyl, $C_{6-10}$ aryl or $C_{3-14}$ cycloalkyl, wherein the 5- to 14-membered heteroaryl and 4- to 14-membered heterocycloalkyl each has 1-4 heteroatoms as ring members selected from B, P, N, O and S, wherein the P, N or S atom as ring members is optionally oxidized and one or more carbon atoms as ring members are each optionally replaced by a carbonyl group; and wherein ring A is optionally substituted with 1, 2, 3, 4 or 5 $R^6$ substituents;

L is a bond, —$C(O)NR^{13}$—, —$NR^{13}C(O)$—, O, —$(CR^4R^5)$—, —$(CR^{14}R^{15})_q$—O—, —$O(CR^{14}R^{15})_q$—, —$NR^{13}$, —$(CR^{14}R^{15})_q$—$NR^{13}$—, —$NR^{13}$—$(CR^{14}R^{15})_q$—, —CH=CH—, —C≡C—, —$SO_2NR^{13}$—, —$NR^{13}SO_2$—, —$NR^{13}SO_2NR^{13}$—, —$NR^{13}C(O)O$—, —$OC(O)NR^{13}$— or —$NR^{13}C(O)NR^{13}$—;

$R^3$ is methyl, halo, CN or $C_{1-4}$ haloalkyl; $R^4$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$;

$R^6$ and $R^{17}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, —$P(O)R^aR^a$, —$P(O)(OR^a)(OR^a)$, —$B(OH)_2$, —$B(OR^a)_2$ and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^6$ and $R^{17}$ are each optionally substituted with 1, 2, 3, 4 or 5 independently selected $R^b$ substituents;

or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl and —$N(C_{1-4}$ alkyl$)_2$;

$R^{14}$ and $R^{15}$ are each independently selected from H, halo, CN, OH, —COOH, $C_{1-4}$ alkyl, $C_{1-4}$ alkoxy, —$NHC_{1-4}$ alkyl, —$N(C_{1-4}$ alkyl$)_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_1$-4 alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5-, 6- or 7-membered heterocycloalkyl, each of which is optionally substituted with 1 or 2 independently selected $R^q$ substituents;

each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^a$ are each optionally substituted with 1, 2, 3, 4, or 5 independently selected $R^d$ substituents;

each $R^d$ is independently selected from $C_{1-6}$ alkyl, $C_{1-6}$ haloalkyl, halo, $C_{6-10}$ aryl, 5-10 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, —$P(O)R^eR^e$, —$P(O)(OR^e)(OR^e)$, —$B(OH)_2$, —$B(OR^e)_2$ and $S(O)_2NR^eR^e$, wherein the $C_{1-6}$ alkyl, $C_{1-6}$ haloalkyl, $C_{6-10}$ aryl, 5-14 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NOH)R^c$, $C(=NOH)NR^c$, $C(=NCN)NR^cR^c$, $NR^cC(=NCN)NR^cR^c$, $C(=NR^c)NR^cR^c$, $NR^cC(=NR)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, —$P(O)R^cR^c$, —$P(O)(OR^c)(OR^c)$, —$B(OH)_2$, —$B(OR^c)_2$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2 or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 independently selected $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R$, $NR^gS(O)_2R^g$, $NR^gS(O)_2NR^gR^g$, —$P(O)R^gR^g$, —$P(O)(OR^g)(OR^g)$, —$B(OH)_2$, —$B(OR^g)_2$ and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 independently selected $R^n$ substituents;

each $R^n$ is substituents independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR)NR^oR^o$, $NR^oC(=NR)NR^oR^o$, $S(O)R^o$, $S(O)NR^oR^o$, $S(O)_2R^o$, $NR^oS(O)_2R$, $NR^oS(O)_2NR^oR^o$, —$P(O)R^oR^o$, —$P(O)(OR^o)(OR^o)$, —$B(OH)_2$, —$B(OR^o)_2$ and $S(O)_2NR^oR^o$, wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^n$ are each optionally substituted with 1, 2 or 3 independently selected $R^q$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1, 2, or 3 independently selected $R^p$ substituents;

each $R^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, NHOR$^r$, OR$^r$, SR$^r$, C(O)R$^r$, C(O)NR$'$R$^r$, C(O)OR$^r$, OC(O)R$^r$, OC(O)NR$'$R$^r$, NHR$^r$, NR$'$R$^r$, NR$'$C(O)R$^r$, NR$'$C(O)NR$'$R$^r$, NR$'$C(O)OR$^r$, C(=NR$^r$)NR$'$R$^r$, NR$'$C(=NR$^r$)NR$'$R$^r$, NR$'$C(=NOH)NR$'$R$^r$, NR$'$C(=NCN)NR$'$R$^r$, S(O)R$^r$, S(O)NR$'$R$^r$, S(O)$_2$R$^r$, NR$'$S(O)$_2$R$^r$, NR$'$S(O)$_2$NR$'$R$^r$, —P(O)R$'$R$^r$, —P(O)(OR$^r$)(OR$^r$), —B(OH)$_2$, —B(OR$^r$)$_2$ and S(O)$_2$NR$'$R$^r$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^p$ is optionally substituted with 1, 2 or 3 independently selected $R^q$ substituents;

or any two $R^a$ substituents together with the boron, phosphorus or nitrogen atom to which they are attached form a 4-, 5-, 6-, 7-, 8-, 9- or 10-membered heterocycloalkyl group optionally substituted with 1, 2 or 3 independently selected $R^h$ substituents;

each $R^h$ is independently selected from $C_{1-6}$ alkyl, $C_{3-10}$ cycloalkyl, 4-10 membered heterocycloalkyl, $C_{6-10}$ aryl, 5-10 membered heteroaryl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $C_{1-6}$ haloalkyl, $C_{1-6}$ haloalkoxy, $C_{2-6}$ alkenyl, $C_{2-6}$ alkynyl, halo, CN, OR$^i$, SR$^i$, NHOR$^i$, C(O)R$^i$, C(O)NR$^i$R$^i$, C(O)OR$^{11}$, OC(O)R$^i$, OC(O)NR$^i$R$^i$, NHR$^i$, NR$^i$R$^i$, NR$^i$C(O)R$^i$, NR$^i$C(O)NR$^i$R$^i$, NR$^i$C(O)OR$^i$, C(=NR$^i$)NR$^i$R$^i$, NR$^i$C(=NR$^i$)NR$^i$R$^i$, S(O)R$^i$, S(O)NR$^i$R$^i$, S(O)$_2$R$^i$, NR$^i$S(O)$_2$R$^i$, NR$^i$S(O)$_2$NR$^i$R$^i$, —P(O)R$^i$R$^i$, —P(O)(OR$^i$)(OR$^i$), —B(OH)$_2$, —B(OR$^i$)$_2$ and S(O)$_2$NR$^i$R$^i$, wherein the $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl- of $R^h$ are each further optionally substituted by 1, 2, or 3 independently selected $R^j$ substituents;

each $R^j$ is independently selected from $C_{3-6}$ cycloalkyl, $C_{6-10}$ aryl, 5 or 6-membered heteroaryl, 4-7 membered heterocycloalkyl, $C_{2-4}$ alkenyl, $C_{2-4}$ alkynyl, halo, $C_{1-4}$ alkyl, $C_{1-4}$ haloalkyl, $C_{1-4}$ haloalkoxy, CN, NHOR$^k$, OR$^k$, SR$^k$, C(O)R$^k$, C(O)NR$^k$R$^k$, C(O)OR$^k$, OC(O)R$^k$, OC(O)NR$^k$R$^k$, NHR$^k$, NR$^k$R$^k$, NR$^k$C(O)R$^k$, NR$^k$C(O)NR$^k$R$^k$, NR$^k$C(O)OR$^k$, C(=NR$^k$)NR$^k$R$^k$, NR$^k$C(=NR$^k$)NR$^k$R$^k$, S(O)R$^k$, S(O)NR$^k$R$^k$, S(O)$_2$R$^k$, NR$^k$S(O)$_2$R$^k$, NR$^k$S(O)$_2$NR$^k$R$^k$, —P(O)R$^k$R$^k$, —P(O)(OR$^k$)(OR$^k$), —B(OH)$_2$, —B(OR$^k$)$_2$ and S(O)$_2$NR$^k$R$^k$, wherein the $C_{1-4}$ alkyl, $C_{3-6}$ cycloalkyl, $C_{6-10}$ aryl, 5- or 6-membered heteroaryl, 4-7 membered heterocycloalkyl, $C_{2-4}$ alkenyl, $C_{2-4}$ alkynyl, $C_{1-4}$ haloalkyl, and $C_{1-4}$ haloalkoxy of $R^j$ are each optionally substituted with 1, 2 or 3 independently selected $R^q$ substituents;

or two $R^h$ groups attached to the same carbon atom of the 4- to 10-membered heterocycloalkyl taken together with the carbon atom to which they are attached form a $C_{3-6}$ cycloalkyl or 4- to 6-membered heterocycloalkyl having 1-2 heteroatoms as ring members selected from O, N or S;

or any two $R^e$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^e$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^g$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^i$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents, or 1, 2, or 3 independently selected $R^q$ substituents;

or any two $R^k$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents, or 1, 2, or 3 independently selected $R^q$ substituents;

or any two $R^o$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^r$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

each $R^i$, $R^k$, $R^o$ or $R^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of $R^i$, $R^k$, $R^o$ or $R^r$ are each optionally substituted with 1, 2 or 3 independently selected $R^q$ substituents;

each $R^q$ is independently selected from halo, OH, CN, —COOH, NH$_2$, —NH—$C_{1-6}$ alkyl, —N($C_{1-6}$ alkyl)$_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with 1, 2 or 3 substituents independently selected from halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;
the subscript n is an integer of 0, 1, 2 or 3;
each subscript q is independently an integer of 1, 2, 3 or 4; and
the subscript s is an integer of 1, 2, 3 or 4.

In some embodiments, the present disclosure provides compounds of Formula (I), or a pharmaceutically acceptable salt or a stereoisomer thereof, wherein:

ring A is 5- to 14-membered heteroaryl, 4- to 14-membered heterocycloalkyl, $C_{6-10}$ aryl or $C_{3-14}$ cycloalkyl, wherein the 5- to 14-membered heteroaryl and 4- to 14-membered heterocycloalkyl each has 1-4 heteroatoms as ring members selected from B, P, N, O and S, wherein the P, N or S atom as ring members is optionally oxidized and one or more carbon atoms as ring members are each optionally replaced by a carbonyl group; and wherein ring A is optionally substituted with 1, 2, 3, 4 or 5 $R^6$ substituents;

L is a bond, —C(O)$NR^{13}$—, —$NR^{13}$C(O)—, O, —$(CR^{14}R^{15})_q$—, —$(CR^{14}R^{15})_q$—O—, —O$(CR^{14}R^{15})_q$—, —$NR^{13}$—, —$(CR^{14}R^{15})_q$—$NR^{13}$—, —$NR^{13}$—$(CR^{14}R^{15})_q$—, —CH═CH—, —C≡C—, —$SO_2NR^{13}$—, —$NR^{13}SO_2$—, —$NR^{13}SO_2NR^{13}$—, —$NR^{13}C(O)O$—, —$OC(O)NR^{13}$— or —$NR^{13}C(O)NR^{13}$—;

$R^3$ is methyl, halo, CN or $C_{1-4}$ haloalkyl;

$R^4$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$;

$R^6$ and $R^{17}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, C(═$NR^a$)$R^a$, C(═NOH)$R^a$, C(═NOH)$NR^a$, C(═NCN)$NR^aR^a$, $NR^aC$(═NCN)$NR^aR^a$, C(═$NR^a$)$NR^aR^a$, $NR^aC$(═$NR^a$)$NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, —$P(O)R^aR^a$, —$P(O)(OR^a)(OR^a)$, —$B(OH)_2$, —$B(OR^a)_2$ and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^6$ and $R^{17}$ are each optionally substituted with 1, 2, 3, 4 or 5 independently selected $R^b$ substituents;

or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl and —$N(C_{1-4}$ alkyl$)_2$;

$R^{14}$ and $R^{15}$ are each independently selected from H, halo, CN, OH, —COOH, $C_{1-4}$ alkyl, $C_{1-4}$ alkoxy, —$NHC_{1-4}$ alkyl, —$N(C_{1-4}$ alkyl$)_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5-, 6- or 7-membered heterocycloalkyl, each of which is optionally substituted with 1 or 2 independently selected $R^q$ substituents;

each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^a$ are each optionally substituted with 1, 2, 3, 4, or 5 independently selected $R^d$ substituents;

each $R^d$ is independently selected from $C_{1-6}$ alkyl, $C_{1-6}$ haloalkyl, halo, $C_{6-10}$ aryl, 5-10 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, C(═$NR^e$)$NR^eR^e$, $NR^eC$(═$NR^e$)$NR^eR^e$, $NR^eC$(═NOH)$NR^eR^e$, $NR^eC$(═NCN)$NR^eR^e$, $S(O)R^e$, $S(O)NR^eR^e$, $S(O)_2R^e$, $NR^eS(O)_2R^e$, $NR^eS(O)_2NR^eR^e$, —$P(O)R^eR^e$, —$P(O)(OR^e)(OR^e)$, —$B(OH)_2$, —$B(OR^e)_2$ and $S(O)_2NR^eR^e$, wherein the $C_{1-6}$ alkyl, $C_{1-6}$ haloalkyl, $C_{6-10}$ aryl, 5-14 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, C(═NOH)$R^c$, C(═NOH)$NR^c$, C(═NCN)$NR^cR^c$, $NR^cC$(═NCN)$NR^cR^c$, C(═$NR^c$)$NR^cR^c$, $NR^cC$(═$NR^c$)$NR^cR^c$, $NHR^c$, $NR^cR^c$, $NR^cC(O)R^c$, $NR^cC(O)OR^c$, $NR^cC(O)$ NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$, —P(O)R$^c$R$^c$, —P(O)(OR$^c$)(OR$^c$), —B(OH)$_2$, —B(OR$^c$)$_2$ and S(O)$_2$NR$^c$R$^c$; wherein the C$_{1-6}$ alkyl, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^b$ are each further optionally substituted with 1, 2 or 3 independently selected R$^d$ substituents;

each R$^e$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^e$ are each optionally substituted with 1, 2, 3, 4, or 5 independently selected R$^f$ substituents;

each R$^f$ is independently selected from C$_{1-4}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, halo, CN, NHOR$^g$, OR$^g$, SR$^g$, C(O)R$^g$, C(O)NR$^g$R$^g$, C(O)OR$^g$, OC(O)R$^g$, OC(O)NR$^g$R$^g$, NHR$^g$, NR$^g$R$^g$, NR$^g$C(O)R$^g$, NR$^g$C(O)NR$^g$R$^g$, NR$^g$C(O)OR$^g$, C(=NR$^g$)NR$^g$R$^g$, NR$^g$C(=NR$^g$)NR$^g$R$^g$, S(O)R$^g$, S(O)NR$^g$R$^g$, S(O)$_2$R, NR$^g$S(O)$_2$R$^g$, NR$^g$S(O)$_2$NR$^g$R$^g$, —P(O)R$^g$R$^g$, —P(O)(OR$^g$)(OR$^g$), —B(OH)$_2$, —B(OR$^g$)$_2$ and S(O)$_2$NR$^g$R$^g$; wherein the C$_{1-4}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- of R$^f$ are each optionally substituted with 1, 2, 3, 4, or 5 independently selected R$^n$ substituents;

each R$^n$ is substituents independently selected from C$_{1-4}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, halo, CN, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR)NR$^o$R$^o$, NR$^o$C(=NR)NR$^o$R$^o$, S(O)R$^o$, S(O)NR$^o$R$^o$, S(O)$_2$R$^o$, NR$^o$S(O)$_2$R, NR$^o$S(O)$_2$NR$^o$R$^o$, —P(O)R$^o$R$^o$, —P(O)(OR$^o$)(OR$^o$), —B(OH)$_2$, —B(OR$^o$)$_2$ and S(O)$_2$NR$^o$R$^o$, wherein the C$_{1-4}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- of R$^n$ are each optionally substituted with 1, 2 or 3 independently selected R$^q$ substituents;

each R$^g$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^g$ are each optionally substituted with 1, 2, or 3 independently selected R$^p$ substituents;

each R$^p$ is independently selected from C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, halo, CN, NHOR$^r$, OR$^r$, SR$^r$, C(O)R$^r$, C(O)NR$^r$R$^r$, C(O)OR$^r$, OC(O)R$^r$, OC(O)NR$^r$R$^r$, NHR$^r$, NR$^r$R$^r$, NR$^r$C(O)R$^r$, NR$^r$C(O)NR$^r$R$^r$, NR$^r$C(O)OR$^r$, C(=NR$^r$)NR$^r$R$^r$, NR$^r$C(=NR$^r$)NR$^r$R$^r$, NR$^r$C(=NOH)NR$^r$R$^r$, NR$^r$C(=NCN)NR$^r$R$^r$, S(O)R$^r$, S(O)NR$^r$R$^r$, S(O)$_2$R$^r$, NR$^r$S(O)$_2$R$^r$, NR$^r$S(O)$_2$NR$^r$R$^r$, —P(O)R$^r$R$^r$, —P(O)(OR$^r$)(OR$^r$), —B(OH)$_2$, —B(OR$^r$)$_2$ and S(O)$_2$NR$^r$R$^r$, wherein the C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^p$ is optionally substituted with 1, 2 or 3 independently selected R$^q$ substituents;

or any two R$^a$ substituents together with the boron, phosphorus or nitrogen atom to which they are attached form a 4-, 5-, 6-, 7-, 8-, 9- or 10-membered heterocycloalkyl group optionally substituted with 1, 2 or 3 independently selected R$^h$ substituents;

each R$^h$ is independently selected from C$_{1-6}$ alkyl, C$_{3-10}$ cycloalkyl, 4-10 membered heterocycloalkyl, C$_{6-10}$ aryl, 5-10 membered heteroaryl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, C$_{1-6}$ haloalkyl, C$_{1-6}$ haloalkoxy, C$_{2-6}$ alkenyl, C$_{2-6}$ alkynyl, halo, CN, OR$^i$, SR$^i$, NHOR$^i$, C(O)R$^i$, C(O)NR$^i$R$^i$, C(O)OR$^i$, OC(O)R$^i$, OC(O)NR$^i$R$^i$, NHR$^i$, NR$^i$R$^i$, NR$^i$C(O)R$^i$, NR$^i$C(O)NR$^i$R$^i$, NR$^i$C(O)OR$^i$, C(=NR$^i$)NR$^i$R$^i$, NR$^i$C(=NR$^i$)NR$^i$R$^i$, S(O)R$^i$, S(O)NR$^i$R$^i$, S(O)$_2$R$^i$, NR$^i$S(O)$_2$R$^i$, NR$^i$S(O)$_2$NR$^i$R$^i$, —P(O)R$^i$R$^i$, —P(O)(OR$^i$)(OR$^i$), —B(OH)$_2$, —B(OR$^i$)$_2$ and S(O)$_2$NR$^i$R$^i$, wherein the C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl- of R$^h$ are each further optionally substituted by 1, 2, or 3 independently selected R$^j$ substituents;

each R$^j$ is independently selected from C$_{3-6}$ cycloalkyl, C$_{6-10}$ aryl, 5 or 6-membered heteroaryl, 4-7 membered heterocycloalkyl, C$_{2-4}$ alkenyl, C$_{2-4}$ alkynyl, halo, C$_{1-4}$ alkyl, C$_{1-4}$ haloalkyl, C$_{1-4}$ haloalkoxy, CN, NHOR$^k$, OR$^k$, SR$^k$, C(O)R$^k$, C(O)NR$^k$R$^k$, C(O)OR$^k$, OC(O)R$^k$, OC(O)NR$^k$R$^k$, NHR$^k$, NR$^k$R$^k$, NR$^k$C(O)R$^k$, NR$^k$C(O)NR$^k$R$^k$, NR$^k$C(O)OR$^k$, C(=NR$^k$)NR$^k$R$^k$, NR$^k$C(=NR$^k$)NR$^k$R$^k$, S(O)R$^k$, S(O)NR$^k$R$^k$, S(O)$_2$R$^k$, NR$^k$S(O)$_2$R$^k$, NR$^k$S(O)$_2$NR$^k$R$^k$, —P(O)R$^k$R$^k$, —P(O)(OR$^k$)(OR$^k$), —B(OH)$_2$, —B(OR$^k$)$_2$ and S(O)$_2$NR$^k$R$^k$, wherein the C$_{1-4}$ alkyl, C$_{3-6}$ cycloalkyl, C$_{6-10}$ aryl, 5- or 6-membered heteroaryl, 4-7 membered heterocycloalkyl, C$_{2-4}$ alkenyl, C$_{2-4}$ alkynyl, C$_{1-4}$ haloalkyl, and C$_{1-4}$ haloalkoxy of R$^j$ are each optionally substituted with 1, 2 or 3 independently selected R$^q$ substituents;

or two R$^h$ groups attached to the same carbon atom of the 4- to 10-membered heterocycloalkyl taken together with the carbon atom to which they are attached form a C$_{3-6}$ cycloalkyl or 4- to 6-membered heterocycloalkyl having 1-2 heteroatoms as ring members selected from O, N or S;

or any two $R^c$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^e$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^g$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^i$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^q$ substituents;

or any two $R^k$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^q$ substituents;

or any two $R^o$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^r$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

each $R^i$, $R^k$, $R^o$ or $R^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of $R^i$, $R^k$, $R^o$ or $R^r$ are each optionally substituted with 1, 2 or 3 independently selected $R^q$ substituents;

each $R^q$ is independently selected from halo, OH, CN, —COOH, $NH_2$, —NH—$C_{1-6}$ alkyl, —N($C_{1-6}$ alky)$_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with 1, 2 or 3 substituents independently selected from halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

each subscript q is independently an integer of 1, 2, 3 or 4; and the subscript s is an integer of 1, 2, 3 or 4.

In some embodiments, provided herein is a compound of Formula (I), or a pharmaceutically acceptable salt or a stereoisomer thereof, wherein:

ring A is 5- to 14-membered heteroaryl, 4- to 14-membered heterocycloalkyl, $C_{6-10}$ aryl or $C_{3-14}$ cycloalkyl, wherein the 5- to 14-membered heteroaryl and 4- to 14-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, 3, 4 or 5 $R^6$ substituents;

L is a bond, —C(O)$NR^{13}$—, —$NR^{13}$C(O)—, O, —$(CR^{14}R^{15})_q$—, —$(CR^{14}R^{15})_q$—O—, —O$(CR^{14}R^{15})_q$—, —$NR^{13}$—, $(CR^{14}R^{15})_q$—$NR^{13}$—, —$NR^{13}$—$(CR^{14}R^{15})_q$—, —CH=CH—, —C≡C—, —$SO_2NR^{13}$, —$NR^{13}SO_2$—, —$NR^{13}SO_2NR^{13}$—, —$NR^{13}$C(O)O—, —OC(O)$NR^{13}$— or —$NR^{13}$C(O)$NR^{13}$—;

$R^3$ is methyl, halo, CN or $C_{1-4}$ haloalkyl;

$R^4$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl)$_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl)$_2$;

$R^6$ and $R^{17}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^6$ and $R^{17}$ are each optionally substituted with 1, 2, 3, 4 or 5 independently selected $R^b$ substituents;

or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl and —N($C_{1-4}$ alkyl)$_2$;

$R^{14}$ and $R^{15}$ are each independently selected from H, halo, CN, OH, —COOH, $C_{1-4}$ alkyl, $C_{1-4}$ alkoxy, —$NHC_{1-4}$ alkyl, —N($C_{1-4}$ alkyl)$_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5-, 6- or 7-membered heterocycloalkyl, each of which is optionally substituted with 1 or 2 independently selected $R^q$ substituents;

each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl- wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^a$ are each optionally substituted with 1, 2, 3, 4, or 5 independently selected $R^d$ substituents;

each $R^d$ is independently selected from $C_{1-6}$ alkyl, $C_{1-6}$ haloalkyl, halo, $C_{6-10}$ aryl, 5-10 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, wherein the $C_{1-6}$ alkyl, $C_{1-6}$ haloalkyl, $C_{6-10}$ aryl, 5-14 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NOH)R^c$, $C(=NOH)NR^c$, $C(=NCN)NR^cR^c$, $NR^cC(=NCN)NR^cR^c$, $C(=NR^c)NR^cR^c$, $NR^cC(=NR)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2 or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 independently selected $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R$, $NR^gS(O)_2R^g$, $NR^gS(O)_2NR^gR^g$, and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 independently selected $R^n$ substituents;

each $R^n$ is substituents independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR)NR^oR^o$, $NR^oC(=NR)NR^oR^o$, $S(O)R^o$, $S(O)NR^oR^o$, $S(O)_2R^o$, $NR^oS(O)_2R$, $NR^oS(O)_2NR^oR^o$, and $S(O)_2NR^oR^o$, wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^n$ are each optionally substituted with 1, 2 or 3 independently selected $R^q$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1, 2, or 3 independently selected $R^p$ substituents;

each $R^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^r$, $OR^r$, $SR^r$, $C(O)R^r$, $C(O)NR^rR^r$, $C(O)OR^r$, $OC(O)R^r$, $OC(O)NR^rR^r$, $NHR^r$, $NR^rR^r$, $NR^rC(O)R^r$, $NR^rC(O)NR^rR^r$, $NR^rC$ (O)OR$^r$, C(=NR$^r$)NR$^r$R$^r$, NR$^r$C(=NR$^r$)NR$^r$R$^r$, NR$^r$C(=NOH)NR$^r$R$^r$, NR$^r$C(=NCN)NR$^r$R$^r$, S(O)R$^r$, S(O)NR$^r$R$^r$, S(O)$_2$R$^r$, NR$^r$S(O)$_2$R$^r$, NR$^r$S(O)$_2$NR$^r$R$^r$ and S(O)$_2$NR$^r$R$^r$, wherein the C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^p$ is optionally substituted with 1, 2 or 3 independently selected R$^q$ substituents;

or any two R$^a$ substituents together with the nitrogen atom to which they are attached form a 4-, 5-, 6-, 7-, 8-, 9- or 10-membered heterocycloalkyl group optionally substituted with 1, 2 or 3 independently selected R$^h$ substituents;

each R$^h$ is independently selected from C$_{1-6}$ alkyl, C$_{3-10}$ cycloalkyl, 4-10 membered heterocycloalkyl, C$_{6-10}$ aryl, 5-10 membered heteroaryl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, C$_{1-6}$ haloalkyl, C$_{1-6}$ haloalkoxy, C$_{2-6}$ alkenyl, C$_{2-6}$ alkynyl, halo, CN, OR$^i$, SR$^i$, NHOR$^i$, C(O)R$^i$, C(O)NR$^i$R$^i$, C(O)OR$^i$, OC(O)R$^i$, OC(O)NR$^i$R$^i$, NHR$^i$, NR$^i$R$^i$, NR$^i$C(O)R$^i$, NR$^i$C(O)NR$^i$R$^i$, NR$^i$C(O)OR$^i$, C(=NR$^i$)NR$^i$R$^i$, NR$^i$C(=NR$^i$)NR$^i$R$^i$, S(O)R$^i$, S(O)NR$^i$R$^i$, S(O)$_2$R$^i$, NR$^i$S(O)$_2$R$^i$, NR$^i$S(O)$_2$NR$^i$R$^i$, and S(O)$_2$NR$^i$R$^i$, wherein the C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl- of R$^h$ are each further optionally substituted by 1, 2, or 3 independently selected R$^j$ substituents;

each R$^j$ is independently selected from C$_{3-6}$ cycloalkyl, C$_{6-10}$ aryl, 5 or 6-membered heteroaryl, 4-7 membered heterocycloalkyl, C$_{2-4}$ alkenyl, C$_{2-4}$ alkynyl, halo, C$_{1-4}$ alkyl, C$_{1-4}$ haloalkyl, C$_{1-4}$ haloalkoxy, CN, NHOR$^k$, OR$^k$, SR$^k$, C(O)R$^k$, C(O)NR$^k$R$^k$, C(O)OR$^k$, OC(O)R$^k$, OC(O)NR$^k$R$^k$, NHR$^k$, NR$^k$R$^k$, NR$^k$C(O)R$^k$, NR$^k$C(O)NR$^k$R$^k$, NR$^k$C(O)OR$^k$, C(=NR$^k$)NR$^k$R$^k$, NR$^k$C(=NR$^k$)NR$^k$R$^k$, S(O)R$^k$, S(O)NR$^k$R$^k$, S(O)$_2$R$^k$, NR$^k$S(O)$_2$R$^k$, NR$^k$S(O)$_2$NR$^k$R$^k$, and S(O)$_2$NR$^k$R$^k$, wherein the C$_{1-4}$ alkyl, C$_{3-6}$ cycloalkyl, C$_{6-10}$ aryl, 5- or 6-membered heteroaryl, 4-7 membered heterocycloalkyl, C$_{2-4}$ alkenyl, C$_{2-4}$ alkynyl, C$_{1-4}$ haloalkyl, and C$_{1-4}$ haloalkoxy of R$^j$ are each optionally substituted with 1, 2 or 3 independently selected R$^q$ substituents;

or two R$^h$ groups attached to the same carbon atom of the 4- to 10-membered heterocycloalkyl taken together with the carbon atom to which they are attached form a C$_{3-6}$ cycloalkyl or 4- to 6-membered heterocycloalkyl having 1-2 heteroatoms as ring members selected from O, N or S;

or any two R$^c$ substituents together with the nitrogen atom to which they are attached form a 4-, 5-, 6-, 7-, 8-, 9- or 10-membered heterocycloalkyl group optionally substituted with 1, 2, or 3 independently selected R$^h$ substituents;

or any two R$^e$ substituents together with the nitrogen atom to which they are attached form a 4-, 5-, 6-, 7-, 8-, 9- or 10-membered heterocycloalkyl group optionally substituted with 1, 2, or 3 independently selected R$^h$ substituents;

or any two R$^g$ substituents together with the nitrogen atom to which they are attached form a 4-, 5-, 6-, 7-, 8-, 9- or 10-membered heterocycloalkyl group optionally substituted with 1, 2, or 3 independently selected R$^h$ substituents;

or any two R$^i$ substituents together with the nitrogen atom to which they are attached form a 4-, 5-, 6-, 7-, 8-, 9- or 10-membered heterocycloalkyl group optionally substituted with 1, 2, or 3 independently selected R$^h$ substituents, or 1, 2 or 3 independently selected R$^q$ substituents;

or any two R$^k$ substituents together with the nitrogen atom to which they are attached form a 4-, 5-, 6-, 7-, 8-, 9- or 10-membered heterocycloalkyl group optionally substituted with 1, 2, or 3 independently selected R$^h$ substituents, or 1, 2 or 3 independently selected R$^q$ substituents;

or any two R$^o$ substituents together with the nitrogen atom to which they are attached form a 4-, 5-, 6-, 7-, 8-, 9- or 10-membered heterocycloalkyl group optionally substituted with 1, 2, or 3 independently selected R$^h$ substituents;

or any two R$^r$ substituents together with the nitrogen atom to which they are attached form a 4-, 5-, 6-, 7-, 8-, 9- or 10-membered heterocycloalkyl group optionally substituted with 1, 2, or 3 independently selected R$^h$ substituents;

each R$^i$, R$^k$, R$^o$ or R$^r$ is independently selected from H, C$_{1-4}$ alkyl, C$_{3-6}$ cycloalkyl, C$_{6-10}$ aryl, 5 or 6-membered heteroaryl, 4-7 membered heterocycloalkyl, C$_{1-6}$ haloalkyl, C$_{1-6}$ haloalkoxy, C$_{2-4}$ alkenyl, and C$_{2-4}$ alkynyl, wherein the C$_{1-4}$ alkyl, C$_{3-6}$ cycloalkyl, C$_{6-10}$ aryl, 5 or 6-membered heteroaryl, 4-7 membered heterocycloalkyl, C$_{2-4}$ alkenyl, and C$_{2-4}$ alkynyl of R$^i$, R$^k$, R$^o$ or R$^r$ are each optionally substituted with 1, 2 or 3 independently selected R$^q$ substituents;

each R$^q$ is independently selected from halo, OH, CN, —COOH, NH$_2$, —NH—C$_{1-6}$ alkyl, —N(C$_{1-6}$ alky)$_2$, C$_{1-6}$ alkyl, C$_{1-6}$ alkoxy, C$_{1-6}$ alkylthio, C$_{1-6}$ haloalkyl, C$_{1-6}$ haloalkoxy, phenyl, 5-6 membered heteroaryl, 4-6 membered heterocycloalkyl and C$_{3-6}$ cycloalkyl, wherein the C$_{1-6}$ alkyl, phenyl, C$_{3-6}$ cycloalkyl, 4-6 membered heterocycloalkyl, and 5-6 membered heteroaryl of R$^q$ are each optionally substituted with 1, 2 or 3 substituents independently selected from halo, OH, CN, —COOH, NH$_2$, C$_{1-4}$ alkyl, C$_{1-4}$ alkoxy, C$_{1-4}$ haloalkyl, C$_{1-4}$ haloalkoxy, phenyl, C$_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

each subscript q is independently an integer of 1, 2, 3 or 4; and the subscript s is an integer of 1, 2, 3 or 4.

In some embodiments, the present disclosure provides compounds of Formula (I), or a pharmaceutically acceptable salt or a stereoisomer thereof, wherein:

ring A is 5- to 14-membered heteroaryl, 4- to 14-membered heterocycloalkyl, C$_{6-10}$ aryl or C$_{3-14}$ cycloalkyl, wherein the 5- to 14-membered heteroaryl and 4- to 14-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, 3, 4 or 5 R$^6$ substituents;

L is a bond, —C(O)NR$^{13}$—, —NR$^{13}$C(O)—, O, —(CR$^4$R$^5$)—, —(CR$^{14}$R$^{15}$)$_q$—O—, —O(CR$^{14}$R$^{15}$)$_q$—, —NR$^{13}$—, —(CR$^{14}$R$^{15}$)$_q$—NR$^{13}$—, —NR$^{13}$—(CR$^{14}$R$^{15}$)$_q$—, —CH=CH—, —C≡C—, —SO$_2$NR$^{13}$—, —NR$^{13}$SO$_2$—, —NR$^{13}$SO$_2$NR$^{13}$—, —NR$^{13}$C(O)O—, —OC(O)NR$^{13}$— or —NR$^{13}$C(O)NR$^{13}$—;

R$^3$ is methyl, halo, CN or C$_{1-4}$ haloalkyl;

R$^4$ is C$_{1-4}$ alkyl, C$_{1-4}$ alkoxy, C$_{1-4}$ haloalkyl, C$_{1-4}$ haloalkoxy, CN, halo, OH, —COOH, NH$_2$, —NHC$_{1-4}$ alkyl or —N(C$_{1-4}$ alkyl)$_2$;

R$^5$ is C$_{1-4}$ alkyl, C$_{1-4}$ alkoxy, C$_{1-4}$ haloalkyl, C$_{1-4}$ haloalkoxy, CN, halo, OH, —COOH, NH$_2$, —NHC$_{1-4}$ alkyl or —N(C$_{1-4}$ alkyl)$_2$;

R$^6$ and R$^{17}$ are each independently selected from H, halo, C$_{1-6}$ alkyl, C$_{2-6}$ alkenyl, C$_{2-6}$ alkynyl, C$_{1-6}$ haloalkyl, C$_{1-6}$ haloalkoxy, C$_{6-10}$ aryl, C$_{3-14}$ cycloalkyl, 5-14 membered heteroaryl, 4-14 membered heterocycloalkyl, C$_{6-10}$ aryl-C$_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^6$ and $R^{17}$ are each optionally substituted with 1, 2, 3, 4 or 5 independently selected $R^b$ substituents;

or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl and —$N(C_{1-4}$ alkyl$)_2$;

$R^{14}$ and $R^{15}$ are each independently selected from H, halo, CN, OH, —COOH, $C_{1-4}$ alkyl, $C_{1-4}$ alkoxy, —$NHC_{1-4}$ alkyl, —$N(C_{1-4}$ alkyl$)_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_1$-4 alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5-, 6- or 7-membered heterocycloalkyl, each of which is optionally substituted with 1 or 2 independently selected $R^q$ substituents;

each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^a$ are each optionally substituted with 1, 2, 3, 4, or 5 independently selected $R^d$ substituents;

each $R^d$ is independently selected from $C_{1-6}$ alkyl, $C_{1-6}$ haloalkyl, halo, $C_{6-10}$ aryl, 5-10 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, wherein the $C_{1-6}$ alkyl, $C_{1-6}$ haloalkyl, $C_{6-10}$ aryl, 5-14 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NOH)R^c$, $C(=NOH)NR^c$, $C(=NCN)NR^cR^c$, $NR^cC(=NCN)NR^cR^c$, $C(=NR^c)NR^cR^c$, $NR^cC(=NR^c)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2 or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 independently selected $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R$, $NR^gS(O)_2R^g$, $NR^gS(O)_2NR^gR^g$, and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 independently selected $R^n$ substituents;

each $R^n$ is substituents independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR)NR$^o$R$^o$, NR$^o$C(=NR)NR$^o$R$^o$, S(O)R$^o$, S(O)NR$^o$R$^o$, S(O)$_2$R$^o$, NR$^o$S(O)$_2$R, NR$^o$S(O)$_2$NR$^o$R$^o$, and S(O)$_2$NR$^o$R$^o$, wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^n$ are each optionally substituted with 1, 2 or 3 independently selected $R^q$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1, 2, or 3 independently selected $R^p$ substituents;

each $R^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, NHOR$^r$, OR$^r$, SR$^r$, C(O)R$^r$, C(O)NR$'$R$^r$, C(O)OR$^r$, OC(O)R$^r$, OC(O)NR$'$R$^r$, NHR$^r$, NR$'$R$^r$, NR$'$C(O)R$^r$, NR$'$C(O)NR$'$R$^r$, NR$'$C(O)OR$^r$, C(=NR$^r$)NR$'$R$^r$, NR$'$C(=NR$^r$)NR$'$R$^r$, NR$'$C(=NOH)NR$'$R$^r$, NR$'$C(=NCN)NR$'$R$^r$, S(O)R$^r$, S(O)NR$'$R$^r$, S(O)$_2$R$^r$, NR$'$S(O)$_2$R$^r$, NR$'$S(O)$_2$NR$'$R$^r$ and S(O)$_2$NR$'$R$^r$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^p$ is optionally substituted with 1, 2 or 3 independently selected $R^q$ substituents;

or any two $R^a$ substituents together with the nitrogen atom to which they are attached form a 4-, 5-, 6-, 7-, 8-, 9- or 10-membered heterocycloalkyl group optionally substituted with 1, 2 or 3 independently selected $R^h$ substituents;

each $R^h$ is independently selected from $C_{1-6}$ alkyl, $C_{3-10}$ cycloalkyl, 4-10 membered heterocycloalkyl, $C_{6-10}$ aryl, 5-10 membered heteroaryl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $C_{1-6}$ haloalkyl, $C_{1-6}$ haloalkoxy, $C_{2-6}$ alkenyl, $C_{2-6}$ alkynyl, halo, CN, OR$^i$, SR$^i$, NHOR$^i$, C(O)R$^i$, C(O)NR$'$R$^i$, C(O)OR$^i$, OC(O)R$^i$, OC(O)NR$'$R$^i$, NHR$^i$, NR$'$R$^i$, NR$'$C(O)R$^i$, NR$'$C(O)NR$'$R$^i$, NR$'$C(O)OR$^i$, C(=NR$^i$)NR$'$R$^i$, NR$'$C(=NR$^i$)NR$'$R$^i$, S(O)R$^i$, S(O)NR$'$R$^i$, S(O)$_2$R$^i$, NR$'$S(O)$_2$R$^i$, NR$'$S(O)$_2$NR$'$R$^i$, and S(O)$_2$NR$'$R$^i$, wherein the $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{6-10}$ aryl-$C_1$-4 alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl- of $R^h$ are each further optionally substituted by 1, 2, or 3 independently selected $R^j$ substituents;

each $R^j$ is independently selected from $C_{3-6}$ cycloalkyl, $C_{6-10}$ aryl, 5 or 6-membered heteroaryl, 4-7 membered heterocycloalkyl, $C_{2-4}$ alkenyl, $C_{2-4}$ alkynyl, halo, $C_{1-4}$ alkyl, $C_{1-4}$ haloalkyl, $C_{1-4}$ haloalkoxy, CN, NHOR$^k$, OR$^k$, SR$^k$, C(O)R$^k$, C(O)NR$^k$R$^k$, C(O)OR$^k$, OC(O)R$^k$, OC(O)NR$^k$R$^k$, NHR$^k$, NR$^k$R$^k$, NR$^k$C(O)R$^k$, NR$^k$C(O)NR$^k$R$^k$, NR$^k$C(O)OR$^k$, C(=NR$^k$)NR$^k$R$^k$, NR$^k$C(=NR$^k$)NR$^k$R$^k$, S(O)R$^k$, S(O)NR$^k$R$^k$, S(O)$_2$R$^k$, NR$^k$S(O)$_2$R$^k$, NR$^k$S(O)$_2$NR$^k$R$^k$, and S(O)$_2$NR$^k$R$^k$, wherein the $C_{1-4}$ alkyl, $C_{3-6}$ cycloalkyl, $C_{6-10}$ aryl, 5- or 6-membered heteroaryl, 4-7 membered heterocycloalkyl, $C_{2-4}$ alkenyl, $C_{2-4}$ alkynyl, $C_{1-4}$ haloalkyl, and $C_{1-4}$ haloalkoxy of $R^j$ are each optionally substituted with 1, 2 or 3 independently selected $R^q$ substituents;

or two $R^h$ groups attached to the same carbon atom of the 4- to 10-membered heterocycloalkyl taken together with the carbon atom to which they are attached form a $C_{3-6}$ cycloalkyl or 4- to 6-membered heterocyloalkyl having 1-2 heteroatoms as ring members selected from O, N or S;

or any two $R^c$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^e$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^g$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^i$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^k$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^o$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^r$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

each $R^i$, $R^k$, $R^o$ or $R^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of $R^i$, $R^k$, $R^o$ or $R^r$ are each optionally substituted with 1, 2 or 3 independently selected $R^q$ substituents;

each $R^q$ is independently selected from halo, OH, CN, —COOH, NH$_2$, —NH—$C_{1-6}$ alkyl, —N($C_{1-6}$ alky)$_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with 1, 2 or 3 substituents independently selected from halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;
the subscript n is an integer of 0, 1, 2 or 3;
each subscript q is independently an integer of 1, 2, 3 or 4; and the subscript s is an integer of 1, 2, 3 or 4.

In some embodiments, the present disclosure provides, compounds of Formula (I), or a pharmaceutically acceptable salt or a stereoisomer thereof, wherein:

ring A is 5- to 14-membered heteroaryl, 4- to 14-membered heterocycloalkyl, $C_{6-10}$ aryl or $C_{3-14}$ cycloalkyl, wherein the 5- to 14-membered heteroaryl and 4- to 14-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, 3, 4 or 5 $R^6$ substituents;

L is a bond, —C(O)$NR^{13}$—, —$NR^{13}$C(O)—, O, —($CR^{14}R^{15}$)$_q$—, —($CR^{14}R^{15}$)$_q$—O—, —O($CR^{14}R^{15}$)$_q$—, —$NR^{13}$—, —($CR^{14}R^{15}$)$_q$—$NR^{13}$—, —$NR^{13}$—($CR^{14}R^{15}$)$_q$—, —CH=CH—, —C≡C—, —$SO_2NR^{13}$—, —$NR^{13}SO_2$—, —$NR^{13}SO_2NR^{13}$—, —$NR^{13}$C(O)O—, —OC(O)$NR^{13}$— or —$NR^{13}$C(O)$NR^{13}$—;

$R^3$ is methyl, halo, CN or $C_{1-4}$ haloalkyl;

$R^4$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl)$_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl)$_2$;

$R^6$ and $R^{17}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, C(=$NR^a$)$R^a$, C(=NOH)$R^a$, C(=NOH)$NR^a$, C(=NCN)$NR^aR^a$, $NR^aC$(=NCN)$NR^aR^a$, C(=$NR^a$)$NR^aR^a$, $NR^aC$(=$NR^a$)$NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^6$ and $R^{17}$ are each optionally substituted with 1, 2, 3, 4 or 5 independently selected $R^b$ substituents;

or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl and —N($C_{1-4}$ alkyl)$_2$;

$R^{14}$ and $R^{15}$ are each independently selected from H, halo, CN, OH, —COOH, $C_{1-4}$ alkyl, $C_{1-4}$ alkoxy, —$NHC_{1-4}$ alkyl, —N($C_{1-4}$ alkyl)$_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_1$-4 alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5-, 6- or 7-membered heterocycloalkyl, each of which is optionally substituted with 1 or 2 independently selected $R^q$ substituents;

each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^a$ are each optionally substituted with 1, 2, 3, 4, or 5 independently selected $R^d$ substituents;

each $R^d$ is independently selected from $C_{1-6}$ alkyl, $C_{1-6}$ haloalkyl, halo, $C_{6-10}$ aryl, 5-10 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, C(=$NR^e$)$NR^eR^e$, $NR^eC$(=$NR^e$)$NR^eR^e$, $NR^eC$(=NOH)$NR^eR^e$, $NR^eC$(=NCN)$NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, wherein the $C_{1-6}$ alkyl, $C_{1-6}$ haloalkyl, $C_{6-10}$ aryl, 5-14 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, C(=NOH)$R^c$, C(=NOH)$NR^c$, C(=NCN)$NR^cR^c$, $NR^cC$ (=NCN)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ and S(O)$_2$NR$^c$R$^c$; wherein the C$_{1-6}$ alkyl, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^b$ are each further optionally substituted with 1, 2 or 3 independently selected R$^d$ substituents;

each R$^e$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^e$ are each optionally substituted with 1, 2, 3, 4, or 5 independently selected R$^f$ substituents;

each R$^f$ is independently selected from C$_{1-4}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, halo, CN, NHOR$^g$, OR$^g$, SR$^g$, C(O)R$^g$, C(O)NR$^g$R$^g$, C(O)OR, OC(O)R$^g$, OC(O)NR$^g$R$^g$, NHR$^g$, NR$^g$R$^g$, NR$^g$C(O)R$^g$, NR$^g$C(O)NR$^g$R$^g$, NR$^g$C(O)OR$^g$, C(=NR$^g$)NR$^g$R$^g$, NR$^g$C(=NR$^g$)NR$^g$R$^g$, S(O)R$^g$, S(O)NR$^g$R$^g$, S(O)$_2$R, NR$^g$S(O)$_2$R$^g$, NR$^g$S(O)$_2$NR$^g$R$^g$, and S(O)$_2$NR$^g$R$^g$; wherein the C$_{1-4}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- of R$^f$ are each optionally substituted with 1, 2, 3, 4, or 5 independently selected R$^n$ substituents;

each R$^n$ is substituents independently selected from C$_{1-4}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, halo, CN, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR)NR$^o$R$^o$, NR$^o$C(=NR)NR$^o$R$^o$, S(O)R$^o$, S(O)NR$^o$R$^o$, S(O)$_2$R$^o$, NR$^o$S(O)$_2$R, NR$^o$S(O)$_2$NR$^o$R$^o$, and S(O)$_2$NR$^o$R$^o$, wherein the C$_{1-4}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- of R$^n$ are each optionally substituted with 1, 2 or 3 independently selected R$^q$ substituents;

each R$^g$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^g$ are each optionally substituted with 1, 2, or 3 independently selected R$^p$ substituents;

each R$^p$ is independently selected from C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, halo, CN, NHOR$^r$, OR$^r$, SR$^r$, C(O)R$^r$, C(O)NR'R$^r$, C(O)OR$^r$, OC(O)R$^r$, OC(O)NR'R$^r$, NHR$^r$, NR'R$^r$, NR'C(O)R$^r$, NR'C(O)NR'R$^r$, NR'C(O)OR$^r$, C(=NR')NR'R$^r$, NR'C(=NR')NR'R$^r$, NR'C(=NOH)NR'R$^r$, NR'C(=NCN)NR'R$^r$, S(O)R$^r$, S(O)NR'R$^r$, S(O)$_2$R$^r$, NR'S(O)$_2$R$^r$, NR'S(O)$_2$NR'R$^r$ and S(O)$_2$NR'R$^r$, wherein the C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^p$ is optionally substituted with 1, 2 or 3 independently selected R$^q$ substituents;

or any two R$^a$ substituents together with the nitrogen atom to which they are attached form a 4-, 5-, 6-, 7-, 8-, 9- or 10-membered heterocycloalkyl group optionally substituted with 1, 2 or 3 independently selected R$^h$ substituents;

each R$^h$ is independently selected from C$_{1-6}$ alkyl, C$_{3-10}$ cycloalkyl, 4-10 membered heterocycloalkyl, C$_{6-10}$ aryl, 5-10 membered heteroaryl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, C$_{1-6}$ haloalkyl, C$_{1-6}$ haloalkoxy, C$_{2-6}$ alkenyl, C$_{2-6}$ alkynyl, halo, CN, OR$^i$, SR$^i$, NHOR$^i$, C(O)R$^i$, C(O)NR'R$^i$, C(O)OR$^i$, OC(O)R$^i$, OC(O)NR'R$^i$, NHR$^i$, NR'R$^i$, NR'C(O)R$^i$, NR'C(O)NR'R$^i$, NR'C(O)OR$^i$, C(=NR')NR'R$^i$, NR'C(=NR') NR'R$^i$, S(O)R$^i$, S(O)NR'R$^i$, S(O)$_2$R$^i$, NR'S(O)$_2$R$^i$, NR'S(O)$_2$NR'R$^i$, and S(O)$_2$NR'R$^i$, wherein the C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl- of R$^h$ are each further optionally substituted by 1, 2, or 3 independently selected R$^j$ substituents;

each R$^j$ is independently selected from C$_{3-6}$ cycloalkyl, C$_{6-10}$ aryl, 5 or 6-membered heteroaryl, 4-7 membered heterocycloalkyl, C$_{2-4}$ alkenyl, C$_{2-4}$ alkynyl, halo, C$_{1-4}$ alkyl, C$_{1-4}$ haloalkyl, C$_{1-4}$ haloalkoxy, CN, NHOR$^k$, OR$^k$, SR$^k$, C(O)R$^k$, C(O)NR$^k$R$^k$, C(O)OR$^k$, OC(O)R$^k$, OC(O)NR$^k$R$^k$, NHR$^k$, NR$^k$R$^k$, NR$^k$C(O)R$^k$, NR$^k$C(O)NR$^k$R$^k$, NR$^k$C(O)OR$^k$, C(=NR$^k$)NR$^k$R$^k$, NR$^k$C(=NR$^k$)NR$^k$R$^k$, S(O)R$^k$, S(O)NR$^k$R$^k$, S(O)$_2$R$^k$, NR$^k$S(O)$_2$R$^k$, NR$^k$S(O)$_2$NR$^k$R$^k$, and S(O)$_2$NR$^k$R$^k$, wherein the C$_{1-4}$ alkyl, C$_{3-6}$ cycloalkyl, C$_{6-10}$ aryl, 5- or 6-membered heteroaryl, 4-7 membered heterocycloalkyl, C$_{2-4}$ alkenyl, C$_{2-4}$ alkynyl, C$_{1-4}$ haloalkyl, and C$_{1-4}$ haloalkoxy of R$^j$ are each optionally substituted with 1, 2 or 3 independently selected R$^q$ substituents;

or two R$^h$ groups attached to the same carbon atom of the 4- to 10-membered heterocycloalkyl taken together with the carbon atom to which they are attached form a C$_{3-6}$ cycloalkyl or 4- to 6-membered heterocycloalkyl having 1-2 heteroatoms as ring members selected from O, N or S;

or any two R$^c$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^e$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^g$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^i$ substituents together with the nitrogen atom to which they are attached form a 4-, 5-, 6-, 7-, 8-, 9- or 10-membered heterocycloalkyl group optionally substituted with 1, 2, or 3 independently selected $R^q$ substituents;

or any two $R^k$ substituents together with the nitrogen atom to which they are attached form a 4-, 5-, 6-, 7-, 8-, 9- or 10-membered heterocycloalkyl group optionally substituted with 1, 2, or 3 independently selected $R^q$ substituents;

or any two $R^o$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^r$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

each $R^i$, $R^k$, $R^o$ or $R^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of R, $R^k$, $R^o$ or $R^r$ are each optionally substituted with 1, 2 or 3 independently selected $R^q$ substituents;

each $R^q$ is independently selected from halo, OH, CN, —COOH, $NH_2$, —NH—$C_{1-6}$ alkyl, —N($C_{1-6}$ alky)$_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with 1, 2 or 3 substituents independently selected from halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

each subscript q is independently an integer of 1, 2, 3 or 4; and the subscript s is an integer of 1, 2, 3 or 4.

In some embodiments, the present disclosure provides a compound of Formula (I), or a pharmaceutically acceptable salt or a stereoisomer thereof, wherein:

ring A is 5- to 14-membered heteroaryl, 4- to 14-membered heterocycloalkyl, $C_{6-10}$ aryl or $C_{3-14}$ cycloalkyl, wherein the 5- to 14-membered heteroaryl and 4- to 14-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, 3, 4 or 5 independently selected $R^6$ substituents;

L is a bond, —C(O)NR$^{13}$—, —NR$^{13}$C(O)—, O, —(CR$^{14}$R$^{15}$)$_q$—, (CR$^{14}$R$^{15}$)$_q$—O—, —O(CR$^{14}$R$^{15}$)$_q$—, —NR$^{13}$—, —(CR$^{14}$R$^{15}$)$_q$—NR$^{13}$—, —NR$^{13}$—(CR$^{14}$R$^{15}$)$_q$—, —CH=CH—, —C≡C—, —SO$_2$NR$^{13}$, —NR$^{13}$SO$_2$—, —NR$^{13}$SO$_2$NR$^{13}$—, —NR$^{13}$C(O)O—, —OC(O)NR$^{13}$— or —NR$^{13}$C(O)NR$^{13}$—;

$R^3$ is methyl, halo, CN or $C_{1-4}$ haloalkyl;

$R^4$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —NH$C_{1-4}$ alkyl or —N($C_{1-4}$ alkyl)$_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —NH$C_{1-4}$ alkyl or —N($C_{1-4}$ alkyl)$_2$;

$R^6$ and $R^{17}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NOH)R^a$, $C(=NOH)NR^a$, $C(=NR^a)NR^aR^a$, $NR^aC(=NR^a)NR^aR^a$, $C(=NCN)NR^aR^a$, $NR^aC(=NCN)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^6$ and $R^{17}$ are each optionally substituted with 1, 2, 3, 4 or 5 independently selected $R^b$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —NH$C_{1-4}$ alkyl and —N($C_{1-4}$ alkyl)$_2$;

$R^{14}$ and $R^{15}$ are each independently selected from H, halo, CN, OH, —COOH, $C_{1-4}$ alkyl, $C_{1-4}$ alkoxy, —NH$C_{1-4}$ alkyl, —N($C_{1-4}$ alkyl)$_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5-, 6- or 7-membered heterocycloalkyl, each of which is optionally substituted with 1 or 2 $R^q$ substituents;

each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^a$ are each optionally substituted with 1, 2, 3, 4, or 5 independently selected $R^d$ substituents;

each $R^d$ is independently selected from $C_{1-6}$ alkyl, $C_{1-6}$ haloalkyl, halo, $C_{6-10}$ aryl, 5-10 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-

C$_{1-4}$ alkyl-, CN, NH$_2$, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, and S(O)$_2$NR$^e$R$^e$, wherein the C$_{1-6}$ alkyl, C$_1$-6 haloalkyl, C$_{6-10}$ aryl, 5-14 membered heteroaryl, C$_{3-14}$ cycloalkyl, 4-14 membered heterocycloalkyl, C$_{6-10}$ aryl-C$_{1-4}$ alkyl-, C$_{3-14}$ cycloalkyl-C$_{1-4}$ alkyl-, (5-14 membered heteroaryl)-C$_{1-4}$ alkyl-, and (4-14 membered heterocycloalkyl)-C$_{1-4}$ alkyl- of R$^d$ are each optionally substituted with 1, 2, or 3 independently selected R$^q$ substituents;

each R$^e$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein the C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^e$ are each optionally substituted with 1, 2 or 3 independently selected R$^q$ substituents;

each R$^b$ substituent is independently selected from halo, C$_{1-6}$ alkyl, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, CN, OH, NH$_2$, NO$_2$, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NOH)R$^c$, C(=NR$^c$)NR$^c$R$^c$, NR$^c$C(=NR$^c$)NR$^c$R$^c$, C(=NCN)NR$^c$R$^c$, NR$^c$C(=NCN)NR$^c$R$^c$, NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ and S(O)$_2$NR$^c$R$^c$; wherein the C$_{1-6}$ alkyl, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^b$ are each further optionally substituted with 1, 2 or 3 independently selected R$^d$ substituents;

each R$^c$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^c$ are each optionally substituted with 1, 2, 3, 4, or 5 independently selected R$^d$ substituents;

or any two R$^a$ substituents together with the nitrogen atom to which they are attached form a 4-, 5-, 6-, 7-, 8-, 9- or 10-membered heterocycloalkyl group optionally substituted with 1, 2 or 3 independently selected R$^h$ substituents;

or any two R$^c$ substituents together with the nitrogen atom to which they are attached form a 4-, 5-, 6-, 7-, 8-, 9- or 10-membered heterocycloalkyl group optionally substituted with 1, 2, or 3 independently selected R$^h$ substituents;

or any two R$^e$ substituents together with the nitrogen atom to which they are attached form a 4-, 5-, 6-, 7-, 8-, 9- or 10-membered heterocycloalkyl group optionally substituted with 1, 2, or 3 independently selected R$^h$ substituents;

each R$^h$ is independently selected from C$_{1-6}$ alkyl, C$_{3-10}$ cycloalkyl, 4-10 membered heterocycloalkyl, C$_{6-10}$ aryl, 5-10 membered heteroaryl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, C$_{1-6}$ haloalkyl, C$_{1-6}$ haloalkoxy, C$_{2-6}$ alkenyl, C$_{2-6}$ alkynyl, halo, CN, OR$^i$, SR$^i$, NHOR$^i$, C(O)R$^i$, C(O)NR$^i$R$^i$, C(O)OR$^i$, OC(O)R$^i$, OC(O)NR$^i$R$^i$, NHR$^i$, NR$^i$R$^i$, NR$^i$C(O)R$^i$, NR$^i$C(O)NR$^i$R$^i$, NR$^i$C(O)OR$^i$, C(=NR$^i$)NR$^i$R$^i$, NR$^i$C(=NR$^i$) NR$^i$R$^i$, S(O)R$^i$, S(O)NR$^i$R$^i$, S(O)$_2$R$^i$, NR$^i$S(O)$_2$R$^i$, NR$^i$S(O)$_2$ NR$^i$R$^i$, and S(O)$_2$NR$^i$R$^i$, wherein the C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl- of R$^h$ are each further optionally substituted by 1, 2, or 3 independently selected R$^j$ substituents;

each R$^j$ is independently selected from C$_{3-6}$ cycloalkyl, C$_{6-10}$ aryl, 5 or 6-membered heteroaryl, 4-7 membered heterocycloalkyl, C$_{2-4}$ alkenyl, C$_{2-4}$ alkynyl, halo, C$_{1-4}$ alkyl, C$_{1-4}$ haloalkyl, C$_{1-4}$ haloalkoxy, CN, NHOR$^k$, OR$^k$, SR$^k$, C(O)R$^k$, C(O)NR$^k$R$^k$, C(O)OR$^k$, OC(O)R$^k$, OC(O)NR$^k$R$^k$, NHR$^k$, NR$^k$R$^k$, NR$^k$C(O)R$^k$, NR$^k$C(O)NR$^k$R$^k$, NR$^k$C(O) OR$^k$, C(=NR$^k$)NR$^k$R$^k$, NR$^k$C(=NR$^k$)NR$^k$R$^k$, S(O)R$^k$, S(O) NR$^k$R$^k$, S(O)$_2$R$^k$, NR$^k$S(O)$_2$R$^k$, NR$^k$S(O)$_2$NR$^k$R$^k$, and S(O)$_2$ NR$^k$R$^k$, wherein the C$_{1-4}$ alkyl, C$_{3-6}$ cycloalkyl, C$_{6-10}$ aryl, 5- or 6-membered heteroaryl, 4-7 membered heterocycloalkyl, C$_{2-4}$ alkenyl, C$_{2-4}$ alkynyl, C$_{1-4}$ haloalkyl, and C$_{1-4}$ haloalkoxy of R are each optionally substituted with 1, 2 or 3 independently selected R$^q$ substituents;

each of R$^i$ and R$^k$ is independently selected from H, C$_{1-4}$ alkyl, C$_{3-6}$ cycloalkyl, C$_{6-10}$ aryl, 5 or 6-membered heteroaryl, 4-7 membered heterocycloalkyl, C$_{1-6}$ haloalkyl, C$_{1-6}$ haloalkoxy, C$_2$-4 alkenyl, and C$_{2-4}$ alkynyl, wherein the C$_{1-4}$ alkyl, C$_{3-6}$ cycloalkyl, C$_{6-10}$ aryl, 5 or 6-membered heteroaryl, 4-7 membered heterocycloalkyl, C$_{2-4}$ alkenyl, and C$_{2-4}$ alkynyl of R$^i$ or R$^k$ are each optionally substituted with 1, 2 or 3 independently selected R$^q$ substituents;

each R$^q$ is independently selected from halo, OH, CN, —COOH, NH$_2$, —NH—C$_{1-6}$ alkyl, —N(C$_{1-6}$ alky)$_2$, C$_{1-6}$ alkyl, C$_{1-6}$ alkoxy, C$_{1-6}$ alkylthio, C$_{1-6}$ haloalkyl, C$_{1-6}$ haloalkoxy, phenyl, 5-6 membered heteroaryl, 4-6 membered heterocycloalkyl and C$_{3-6}$ cycloalkyl, wherein the C$_{1-6}$ alkyl, phenyl, C$_{3-6}$ cycloalkyl, 4-6 membered heterocycloalkyl, and 5-6 membered heteroaryl of R$^q$ are each optionally substituted with 1, 2 or 3 substituents selected from halo, OH, CN, —COOH, NH$_2$, C$_{1-4}$ alkyl, C$_{1-4}$ alkoxy, C$_{1-4}$ haloalkyl, C$_{1-4}$ haloalkoxy, phenyl, C$_{3-10}$ cycloalkyl, 5-6 membered heteroaryl and 4-6 membered heterocycloalkyl;

the subscript m is an integer of 0, 1, 2 or 3;
the subscript n is an integer of 0, 1, 2 or 3;
each subscript q is independently an integer of 1, 2, 3 or 4; and
the subscript s is an integer of 1, 2, 3 or 4.

In some embodiments, provided herein is a compound of Formula (I), or a pharmaceutically acceptable salt or a stereoisomer thereof, wherein:

ring A is 5- to 10-membered heteroaryl, 4- to 11-membered heterocycloalkyl, C$_{6-10}$ aryl or C$_{3-10}$ cycloalkyl, wherein the 5- to 10-membered heteroaryl and 4- to 11-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, 3, 4 or 5 $R^6$ substituents;

L is a bond, —C(O)NR$^{13}$—, —NR$^{13}$C(O)—, O, —(CR$^{14}$R$^{15}$)$_q$, —(CR$^{14}$R$^{15}$)$_q$—O—, —O(CR$^{14}$R$^{15}$)$_q$—, —NR$^{13}$—, —(CR$^{14}$R$^{15}$)$_q$—NR$^{13}$—, —NR$^{13}$—(CR$^{14}$R$^{15}$)$_q$—, —CH=CH—, —C≡C—, —SO$_2$NR$^{13}$—, —NR$^{13}$SO$_2$—, —NR$^{13}$C(O)O— or —NR$^{13}$C(O)NR$^{13}$—;

$R^3$ is methyl, halo, CN or $C_{1-4}$ haloalkyl;

$R^4$ is $C_{1-4}$ alkyl, $C_{1-4}$ alkoxy, $C_{1-4}$ haloalkyl, $C_{1-4}$ haloalkoxy, CN, halo, OH, —COOH, NH$_2$, —NHC$_{1-4}$ alkyl or —N(C$_{1-4}$ alkyl)$_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, NH$_2$, —NHC$_{1-4}$ alkyl or —N(C$_{1-4}$ alkyl)$_2$;

$R^6$ and $R^{17}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, and S(O)$_2$NR$^a$R$^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-10 membered heterocycloalkyl)-$C_{1-4}$ alkyl- of $R^6$ and $R^{17}$ are each optionally substituted with 1, 2, 3, 4 or 5 $R^b$ substituents;

or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, NH$_2$, —NHC$_{1-4}$ alkyl and —N(C$_{1-4}$ alkyl)$_2$;

$R^{14}$ and $R^{15}$ are each independently selected from H, halo, CN, OH, —COOH, $C_{1-4}$ alkyl, $C_{1-4}$ alkoxy, —NHC$_{1-4}$ alkyl, —N(C$_{1-4}$ alkyl)$_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5- or 6-membered heterocycloalkyl, each of which is optionally substituted with 1 or 2 $R^q$ substituents;

each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^a$ are each optionally substituted with 1, 2, 3, 4, or 5 $R^d$ substituents;

each $R^d$ is independently selected from $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, NH$_2$, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, and S(O)$_2$NR$^e$R$^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, NH$_2$, NO$_2$, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ and S(O)$_2$NR$^c$R$^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2 or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, NHOR$^g$, OR$^g$, SR$^g$, C(O)R$^g$, C(O)NR$^g$R$^g$, C(O)OR$^g$, OC(O)R$^g$, OC(O)NR$^g$R$^g$, NHR$^g$, NR$^g$R$^g$, NR$^g$C(O)R$^g$, NR$^g$C(O)NR$^g$R$^g$, NR$^g$C(O)OR$^g$, C(=NR$^g$)NR$^g$R$^g$, NR$^g$C(=NR$^g$)NR$^g$R$^g$, S(O)R$^g$, S(O)NR$^g$R$^g$, S(O)$_2$R, NR$^g$S(O)$_2$R$^g$, NR$^g$S(O)$_2$NR$^g$R$^g$, and S(O)$_2$NR$^g$R$^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 $R^n$ substituents;

each $R^n$ is substituents independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR)NR$^o$R$^o$, NR$^o$C(=NR)NR$^o$R$^o$, S(O)R$^o$, S(O)NR$^o$R$^o$, S(O)$_2$R$^o$, NR$^o$S(O)$_2$R, NR$^o$S(O)$_2$NR$^o$R$^o$, and S(O)$_2$NR$^o$R$^o$, wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^n$ are each optionally substituted with 1, 2 or 3 independently selected $R^q$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_6$-10 aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1, 2, or 3 $R^p$ substituents;

each $R^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, NHOR$^r$, OR$^r$, SR$^r$, C(O)R$^r$, C(O)NR$'$R$^r$, C(O)OR$^r$, OC(O)R$^r$, OC(O)NR$'$R$^r$, NHR$^r$, NR$'$R$^r$, NR$'$C(O)R$^r$, NR$'$C(O)NR$'$R$^r$, NR$'$C(O)OR$^r$, C(=NR$^r$)NR$'$R$^r$, NR$'$C(=NR$^r$)NR$'$R$^r$, NR$'$C(=NOH)NR$'$R$^r$, NR$''$C(=NCN)NR$'$R$^r$, S(O)R$^r$, S(O)NR$'$R$^r$, S(O)$_2$R$^r$, NR$''$S(O)$_2$R$^r$, NR$''$S(O)$_2$NR$'$R$^r$ and S(O)$_2$NR$'$R$^r$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^p$ is optionally substituted with 1, 2 or 3 $R^q$ substituents;

or any two $R^a$ substituents together with the nitrogen atom to which they are attached form a 4-, 5-, 6-, 7-, 8-, 9- or 10-membered heterocycloalkyl group optionally substituted with 1, 2 or 3 $R^h$ substituents;

each $R^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{1-6}$ haloalkoxy, $C_{2-6}$ alkenyl, $C_{2-6}$ alkynyl, halo, CN, OR$^i$, SR$^i$, NHOR$^i$, C(O)R$^i$, C(O)NR$'$R$^i$, C(O)OR$^i$, OC(O)R$^i$, OC(O)NR$'$R$^i$, NHR$^i$, NR$'$R$^i$, NR$'$C(O)R$^i$, NR$'$C(O)NR$'$R$^i$, NR$'$C(O)OR$^i$, C(=NR$^i$)NR$'$R$^i$, NR$'$C(=NR$^i$)NR$'$R$^i$, S(O)R$^i$, S(O)NR$'$R$^i$, S(O)$_2$R$^i$, NR$^1$S(O)$_2$R$^i$, NR$'$S(O)$_2$ NR$'$R$^i$, and S(O)$_2$NR$'$R$^i$, wherein the $C_{1-6}$ alkyl, $C_{2-6}$ alkenyl, $C_{2-6}$ alkynyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of $R^h$ are each further optionally substituted by 1, 2, or 3 $R^j$ substituents;

each $R^j$ is independently selected from $C_{3-6}$ cycloalkyl, $C_{6-10}$ aryl, 5 or 6-membered heteroaryl, 4-7 membered heterocycloalkyl, $C_{2-4}$ alkenyl, $C_{2-4}$ alkynyl, halo, $C_{1-4}$ alkyl, $C_{1-4}$ haloalkyl, CN, NHOR$^k$, OR$^k$, SR$^k$, C(O)R$^k$, C(O)NR$^k$R$^k$, C(O)OR$^k$, OC(O)R$^k$, OC(O)NR$^k$R$^k$, NHR$^k$, NR$^k$R$^k$, NR$^k$C(O)R$^k$, NR$^k$C(O)NR$^k$R$^k$, NR$^k$C(O)OR$^k$, C(=NR$^k$)NR$^k$R$^k$, NR$^k$C(=NR$^k$)NR$^k$R$^k$, S(O)R$^k$, S(O)NR$^k$R$^k$, S(O)$_2$R$^k$, NR$^k$S(O)$_2$R$^k$, NR$^k$S(O)$_2$NR$^k$R$^k$, and S(O)$_2$NR$^k$R$^k$, wherein the $C_{1-4}$ alkyl, $C_{3-6}$ cycloalkyl, $C_{6-10}$ aryl, 5- or 6-membered heteroaryl, 4-6 membered heterocycloalkyl, $C_{2-4}$ alkenyl, $C_{2-4}$ alkynyl, $C_{1-4}$ haloalkyl, and $C_{1-4}$ haloalkoxy of $R^j$ are each optionally substituted with 1, 2 or 3 independently selected $R^q$ substituents;

or two $R^h$ groups attached to the same carbon atom of the 4- to 10-membered heterocycloalkyl taken together with the carbon atom to which they are attached form a $C_{3-6}$ cycloalkyl or 4- to 6-membered heterocycloalkyl having 1-2 heteroatoms as ring members selected from O, N or S;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

or any two $R^e$ substituents together with the nitrogen atom to which they are attached form a 4-, 5-, 6-, or 7-membered heterocycloalkyl group optionally substituted with 1, 2, or 3 independently selected $R^h$ substituents;

or any two $R^g$ substituents together with the nitrogen atom to which they are attached form a 4-, 5-, 6-, or 7-membered heterocycloalkyl group optionally substituted with 1, 2, or 3 independently selected $R^h$ substituents;

or any two $R^i$ substituents together with the nitrogen atom to which they are attached form a 4-, 5-, 6-, or 7-membered heterocycloalkyl group optionally substituted with 1, 2, or 3 independently selected $R^h$ substituents, or 1, 2 or 3 independently selected $R^q$ substituents;

or any two $R^k$ substituents together with the nitrogen atom to which they are attached form a 4-, 5-, 6-, or 7-membered heterocycloalkyl group optionally substituted with 1, 2, or 3 independently selected $R^h$, or 1, 2 or 3 independently selected $R^q$ substituents substituents;

or any two $R^o$ substituents together with the nitrogen atom to which they are attached form a 4-, 5-, 6-, or 7-membered heterocycloalkyl group optionally substituted with 1, 2, or 3 independently selected $R^h$ substituents;

or any two $R^r$ substituents together with the nitrogen atom to which they are attached form a 4-, 5-, 6-, or 7-membered heterocycloalkyl group optionally substituted with 1, 2, or 3 independently selected $R^h$ substituents;

each $R^i$, $R^k$, $R^o$ or $R^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of $R^i$, $R^k$, $R^o$ or $R^r$ are each optionally substituted with 1, 2 or 3 $R^q$ substituents;

each $R^q$ is independently selected from halo, OH, CN, —COOH, $NH_2$, —NH—$C_{1-6}$ alkyl, —N($C_{1-6}$ alky)$_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with 1, 2 or 3 substituents selected from halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

each subscript q is independently an integer of 1, 2, 3 or 4; and the subscript s is an integer of 1, 2, 3 or 4.

In some embodiments, provided herein is a compound of Formula (I): or a pharmaceutically acceptable salt or a stereoisomer thereof, wherein:

ring A is 5- to 10-membered heteroaryl, 4- to 11-membered heterocycloalkyl, $C_{6-10}$ aryl or $C_{3-10}$ cycloalkyl, wherein the 5- to 10-membered heteroaryl and 4- to 11-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, 3, 4 or 5 $R^6$ substituents;

L is a bond, —C(O)$NR^{13}$—, —$NR^{13}$C(O)—, O, —($CR^{14}R^{15}$)$_q$, —($CR^{14}R^{15}$)$_q$—O—, —O($CR^{14}R^{15}$)$_q$—, —$NR^{13}$—, —($CR^{14}R^{15}$)$_q$—$NR^{13}$—, —$NR^{13}$—($CR^{14}R^{15}$)$_q$—, —CH═CH—, —C≡C—, —$SO_2NR^{13}$—, $NR^{13}SO_2$, —$NR^{13}$C(O)O— or —$NR^{13}$C(O)$NR^{13}$—;

$R^3$ is methyl, halo, CN or $C_{1-4}$ haloalkyl;

$R^4$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl)$_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl)$_2$;

$R^6$ and $R^{17}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, C(O)$R^a$, C(O)$NR^aR^a$, C(O)$OR^a$, OC(O)$R^a$, OC(O)$NR^aR^a$, $NHR^a$, $NR^aR^a$, $NR^aC(O)R^a$, $NR^aC(O)OR^a$, $NR^aC(O)NR^aR^a$, C(═$NR^a$)$R^a$, C(═$NR^a$)$NR^aR^a$, $NR^aC$(═$NR^a$)$NR^aR^a$, $NR^aS(O)R^a$, $NR^aS(O)_2R^a$, $NR^aS(O)_2NR^aR^a$, S(O)$R^a$, S(O)$NR^aR^a$, S(O)$_2R^a$, and S(O)$_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-10 membered heterocycloalkyl)-$C_{1-4}$ alkyl- of $R^6$ are each optionally substituted with 1, 2, 3, 4 or 5 $R^b$ substituents;

or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl and —N($C_{1-4}$ alkyl)$_2$;

$R^{14}$ and $R^{15}$ are each independently selected from H, halo, CN, OH, —COOH, $C_{1-4}$ alkyl, $C_{1-4}$ alkoxy, —$NHC_{1-4}$ alkyl, —N($C_{1-4}$ alkyl)$_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_1$-4 alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5- or 6-membered heterocycloalkyl, each of which is optionally substituted with 1 or 2 $R^q$ substituents;

each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^a$ are each optionally substituted with 1, 2, 3, 4, or 5 $R^d$ substituents;

each $R^d$ is independently selected from $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NH_2$, $NHOR^e$, $OR^e$, $SR^e$, C(O)$R^e$, C(O)$NR^eR^e$, C(O)$OR^e$, OC(O)$R^e$, OC(O)$NR^eR^e$, $NHR^e$, $NR^eR^e$, $NR^eC(O)R^e$, $NR^eC(O)NR^eR^e$, $NR^eC(O)OR^e$, C(═$NR^e$)$NR^eR^e$, $NR^eC$(═$NR^e$)$NR^eR^e$, $NR^eC$(═NOH)$NR^eR^e$, $NR^eC$(═NCN)$NR^eR^e$, S(O)$R^e$, S(O)$NR^eR^e$, S(O)$_2R^e$, $NR^eS(O)_2R^e$, $NR^eS(O)_2NR^eR^e$, and S(O)$_2NR^eR^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR)NR^cR^c$, $NR^cC(=NR)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2 or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R$, $NR^gS(O)_2R^g$, $NR^gS(O)_2NR^gR^g$, and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 $R^n$ substituents;

each $R^n$ is substituents independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^o$-$C(O)NR^oR^o$, $NR^oC(O)OR^o$, $C(=NR)NR^oR^o$, $NR^oC(=NR)NR^oR^o$, $S(O)R^o$, $S(O)NR^oR^o$, $S(O)_2R^o$, $NR^oS(O)_2R$, $NR^oS(O)_2NR^oR^o$, and $S(O)_2NR^oR^o$, wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^n$ are each optionally substituted with 1, 2 or 3 independently selected $R^q$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1, 2, or 3 $R^p$ substituents;

each $R^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^r$, $OR^r$, $SR^r$, $C(O)R^r$, $C(O)NR'R^r$, $C(O)OR^r$, $OC(O)R^r$, $OC(O)NR'R^r$, $NHR^r$, $NR'R^r$, $NR'C(O)R^r$, $NR'C(O)NR'R^r$, $NR'C(O)OR^r$, $C(=NR')NR'R^r$, $NR'C(=NR')NR'R^r$, $NR'C(=NOH)NR'R^r$, $NR'C(=NCN)NR'R^r$, $S(O)R^r$, $S(O)NR'R^r$, $S(O)_2R^r$, $NR'S(O)_2R^r$, $NR'S(O)_2NR'R^r$ and $S(O)_2NR'R^r$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^p$ is optionally substituted with 1, 2 or 3 $R^q$ substituents;

or any two $R^a$ substituents together with the nitrogen atom to which they are attached form a 4-, 5-, 6-, 7-, 8-, 9- or 10-membered heterocycloalkyl group optionally substituted with 1, 2 or 3 $R^h$ substituents;

each $R^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{1-6}$ haloalkoxy, $C_{2-6}$ alkenyl, $C_{2-6}$ alkynyl, halo, CN, $OR^i$, $SR^i$, $NHOR^i$, $C(O)R^i$, $C(O)NR^iR^i$, $C(O)OR^i$, $OC(O)R^i$, $OC(O)NR^iR^i$, $NHR^i$, $NR^iR^i$, $NR^iC(O)R^i$, $NR^iC(O)NR^iR^i$, $NR^iC(O)OR^i$, $C(=NR^i)NR^iR^i$, $NR^iC(=NR^i)NR^iR^i$, $S(O)R^i$, $S(O)NR^iR^i$, $S(O)_2R^i$, $NR^iS(O)_2R^i$, $NR^iS(O)_2NR^iR^i$, and $S(O)_2NR^iR^i$, wherein the $C_{1-6}$ alkyl, $C_{2-6}$ alkenyl, $C_{2-6}$ alkynyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of $R^h$ are each further optionally substituted by 1, 2, or 3 $R^j$ substituents;

each $R^j$ is independently selected from $C_{3-6}$ cycloalkyl, $C_{6-10}$ aryl, 5 or 6-membered heteroaryl, 4-7 membered heterocycloalkyl, $C_{2-4}$ alkenyl, $C_{2-4}$ alkynyl, halo, $C_{1-4}$ alkyl, $C_{1-4}$ haloalkyl, CN, $NHOR^k$, $OR^k$, $SR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $NR^kC(O)NR^kR^k$, $NR^kC(O)OR^k$, $C(=NR^k)NR^kR^k$, $NR^kC(=NR^k)NR^kR^k$, $S(O)R^k$, $S(O)NR^kR^k$, $S(O)_2R^k$, $NR^kS(O)_2R^k$, $NR^kS(O)_2NR^kR^k$, and $S(O)_2NR^kR^k$, wherein the $C_{1-4}$ alkyl, $C_{3-6}$ cycloalkyl, $C_{6-10}$ aryl, 5- or 6-membered heteroaryl, 4-6 membered heterocycloalkyl, $C_{2-4}$ alkenyl, $C_{2-4}$ alkynyl, $C_{1-4}$ haloalkyl, and $C_{1-4}$ haloalkoxy of $R^j$ are each optionally substituted with 1, 2 or 3 independently selected $R^q$ substituents;

or two $R^h$ groups attached to the same carbon atom of the 4- to 10-membered heterocycloalkyl taken together with the carbon atom to which they are attached form a $C_{3-6}$ cycloalkyl or 4- to 6-membered heterocycloalkyl having 1-2 heteroatoms as ring members selected from O, N or S;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

or any two $R^e$ substituents together with the nitrogen atom to which they are attached form a 4-, 5-, 6-, or 7-membered heterocycloalkyl group optionally substituted with 1, 2, or 3 independently selected $R^h$ substituents;

or any two $R^g$ substituents together with the nitrogen atom to which they are attached form a 4-, 5-, 6-, or 7-membered heterocycloalkyl group optionally substituted with 1, 2, or 3 independently selected $R^h$ substituents;

or any two $R^i$ substituents together with the nitrogen atom to which they are attached form a 4-, 5-, 6-, or 7-membered heterocycloalkyl group optionally substituted with 1, 2, or 3 independently selected $R^h$ substituents, or 1, 2 or 3 independently selected $R^q$ substituents;

or any two $R^k$ substituents together with the nitrogen atom to which they are attached form a 4-, 5-, 6-, or 7-membered heterocycloalkyl group optionally substituted with 1, 2, or 3 independently selected $R^h$ substituents, or 1, 2 or 3 independently selected $R^q$ substituents;

or any two $R^o$ substituents together with the nitrogen atom to which they are attached form a 4-, 5-, 6-, or 7-membered heterocycloalkyl group optionally substituted with 1, 2, or 3 independently selected $R^h$ substituents;

or any two $R^r$ substituents together with the nitrogen atom to which they are attached form a 4-, 5-, 6-, or 7-membered heterocycloalkyl group optionally substituted with 1, 2, or 3 independently selected $R^h$ substituents;

each $R^i$, $R^k$, $R^o$ or $R^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of $R^i$, $R^k$, $R^o$ or $R^p$ are each optionally substituted with 1, 2 or 3 $R^q$ substituents;

each $R^q$ is independently selected from halo, OH, CN, —COOH, $NH_2$, —NH—$C_{1-6}$ alkyl, —N($C_{1-6}$ alky)$_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocloalkyl, and 5-6 membered heteroaryl of $R^q$ are each optionally substituted with 1, 2 or 3 substituents selected from halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;
the subscript n is an integer of 0, 1, 2 or 3;
the subscript p is an integer of 1, 2, 3 or 4;
each subscript q is independently an integer of 1, 2, 3 or 4; and
the subscript s is an integer of 1, 2, 3 or 4.

In some embodiments, any two $R^i$ substituents together with the nitrogen atom to which they are attached form a 4-, 5-, 6-, 7-, 8-, 9- or 10-membered heterocycloalkyl group optionally substituted with 1, 2, or 3 independently selected $R^q$ substituents;

or any two $R^k$ substituents together with the nitrogen atom to which they are attached form a 4-, 5-, 6-, 7-, 8-, 9- or 10-membered heterocycloalkyl group optionally substituted with 1, 2, or 3 independently selected $R^q$ substituents.

In some embodiments, provided herein is a compound having Formula (I), or a pharmaceutically acceptable salt or a stereoisomer thereof, wherein (1) when L is —C(O)NH—, ring A is not 4,5,6,7-tetrahydro-1H-imidazo[4,5-c]pyridin-2-yl; (2) when L is a bond, ring A is not [1,2,4]triazolo[1,5-a]pyridin-2-yl; (3) when L is —NH—, ring A is not 1,7-naphthyridin-8-yl or pyrido[3,2-d]pyrimidin-4-yl; and (4) when L is —C(O)NH—, ring A is not 2-pyridyl.

In some embodiments, provided herein is a compound having Formula (I), or a pharmaceutically acceptable salt or a stereoisomer thereof, wherein (1) when L is —C(O)NH—, ring A is not 4,5,6,7-tetrahydro-1H-imidazo[4,5-c]pyridin-2-yl; (2) when L is a bond, ring A is not [1,2,4]triazolo[1,5-a]pyridin-2-yl; (3) when L is —NH—, ring A is not 1,7-naphthyridin-8-yl or pyrido[3,2-d]pyrimidin-4-yl; or (4) when L is —C(O)NH—, ring A is not 2-pyridyl.

In some embodiments, provided herein is a compound having Formula (Ia):

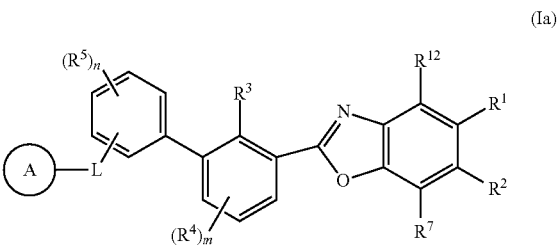

(Ia)

or a pharmaceutically acceptable salt or a stereoisomer thereof, wherein:

one of $R^1$ and $R^2$ is —$(CR^8R^9)_p$—$NR^{10}R^{11}$ and the other is H, $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl)$_2$, wherein the $C_{1-4}$ alkyl and $C_{1-4}$ alkoxy of $R^1$ or $R^2$ is optionally substituted with 1 or 2 substituents independently selected from $C_{1-4}$ alkoxy, $C_{1-4}$ haloalkyl, $C_{1-4}$ haloalkoxy, CN, halo, OH, —COOH, —C(O)$NH_2$, $NH_2$, —$NHC_{1-4}$ alkyl and —$N(C_{1-4}$ alkyl)$_2$;

$R^7$ is H, $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl)$_2$, wherein the $C_{1-4}$ alkyl and $C_{1-4}$ alkoxy are each optionally substituted with 1 or 2 substituents independently selected from CN, halo or —C(O)$NH_2$;

$R^8$ and $R^9$ are each independently selected from H, halo, CN, OH, —COOH, $C_{1-4}$ alkyl, $C_1$-4 alkoxy, —$NHC_{1-4}$ alkyl, —$N(C_{1-4}$ alkyl)$_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^8$ or $R^9$ are each optionally substituted with 1, 2 or 3 independently selected $R^q$ substituents;

or $R^8$ and $R^9$ taken together with the carbon atom to which they are attached form 3-, 4-, 5- or 6-membered cycloalkyl or 4-, 5-, 6- or 7-membered heterocycloalkyl, each of which is optionally substituted with 1 or 2 $R^q$ substituents;

or $R^8$ and $R^{10}$ taken together with the atoms to which they are attached form 4-, 5-, 6- or 7-membered heterocycloalkyl, having zero to one additional heteroatoms as ring members selected from O, N or S, wherein the 4-, 5-, 6- or 7-membered heterocycloalkyl formed by $R^8$ and $R^{10}$ are each optionally substituted with 1 or 2 $R^q$ substituents;

$R^{10}$ and $R^{11}$ are each independently selected from H, $C_{1-6}$ alkyl, $C_{1-6}$ haloalkyl, $C_{3-6}$ cycloalkyl, $C_{6-10}$ aryl, 5-10 membered heteroaryl, 4-10 membered heterocycloalkyl, $C_{6-10}$ aryl-$C_{1-4}$ alkyl-, $C_{3-6}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, —C(O)$R^g$, —C(O)O$R^g$, —C(O)N$R^g R^g$, —SO$_2 R^g$ and —SO$_2$N$R^g R^g$, wherein the $C_{1-6}$ alkyl, $C_{1-6}$ haloalkyl, $C_{3-6}$ cycloalkyl, $C_{6-10}$ aryl, 5-10 membered heteroaryl, 4-10 membered heterocycloalkyl, $C_{6-10}$ aryl-$C_{1-4}$ alkyl-, $C_{3-6}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^{10}$ or $R^{11}$ are each optionally substituted with 1, 2, or 3 independently selected $R^d$ substituents;

or $R^{10}$ and $R^{11}$ taken together with the nitrogen atom to which they are attached form 4-, 5-, 6-, 7-, 8-, 9-, 10-, or 11-membered heterocycloalkyl, wherein the 4-11 membered heterocycloalkyl is each optionally substituted with 1, 2 or 3 $R^f$ substituents; and $R^{12}$ is H, $C_{1-4}$ alkyl, $C_{1-4}$ alkoxy, $C_{1-4}$ haloalkyl, $C_{1-4}$ haloalkoxy, CN, halo, OH, —COOH, NH$_2$, —NH$C_{1-4}$ alkyl or —N($C_{1-4}$ alkyl)$_2$. In some embodiments, the subscript p is 1, 2, 3 or 4.

In some embodiments, provided herein is a compound of Formula (Ia), or a pharmaceutically acceptable salt or a stereoisomer thereof, wherein:

one of $R^1$ and $R^2$ is —(C$R^8 R^9$)$_p$—N$R^{10} R^{11}$ and the other is H, $C_{1-4}$ alkyl, $C_{1-4}$ alkoxy, $C_{1-4}$ haloalkyl, $C_{1-4}$ haloalkoxy, CN, halo, OH, —COOH, NH$_2$, —NH$C_{1-4}$ alkyl or —N($C_{1-4}$ alkyl)$_2$, wherein the $C_{1-4}$ alkyl and $C_{1-4}$ alkoxy of $R^1$ or $R^2$ is optionally substituted with 1 or 2 substituents independently selected from $C_{1-4}$ alkoxy, $C_{1-4}$ haloalkyl, $C_{1-4}$ haloalkoxy, CN, halo, OH, —COOH, —C(O)NH$_2$, NH$_2$, —NH$C_{1-4}$ alkyl and —N($C_{1-4}$ alkyl)$_2$;

$R^7$ is H, $C_{1-4}$ alkyl, $C_{1-4}$ alkoxy, $C_{1-4}$ haloalkyl, $C_{1-4}$ haloalkoxy, CN, halo, OH, —COOH, NH$_2$, —NH$C_{1-4}$ alkyl or —N($C_{1-4}$ alkyl)$_2$, wherein the $C_{1-4}$ alkyl and $C_{1-4}$ alkoxy are each optionally substituted with 1 or 2 substituents independently selected from CN, halo or —C(O)NH$_2$; $R^8$ and $R^9$ are each independently selected from H, halo, CN, OH, —COOH, $C_{1-4}$ alkyl, $C_1$-4 alkoxy, —NH$C_{1-4}$ alkyl, —N($C_{1-4}$ alkyl)$_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^8$ or $R^9$ are each optionally substituted with 1, 2 or 3 independently selected $R^q$ substituents;

or $R^8$ and $R^9$ taken together with the carbon atom to which they are attached form 3-, 4-, 5- or 6-membered cycloalkyl or 4-, 5-, 6- or 7-membered heterocycloalkyl, each of which is optionally substituted with 1 or 2 $R^q$ substituents;

or $R^8$ and $R^{10}$ taken together with the atoms to which they are attached form 4-, 5-, 6- or 7-membered heterocycloalkyl, having zero to one additional heteroatoms as ring members selected from O, N or S, wherein the 4-, 5-, 6- or 7-membered heterocycloalkyl formed by $R^8$ and $R^{10}$ are each optionally substituted with 1 or 2 $R^q$ substituents;

$R^{10}$ and $R^{11}$ are each independently selected from H, $C_{1-6}$ alkyl, $C_{1-6}$ haloalkyl, $C_{3-6}$ cycloalkyl, $C_{6-10}$ aryl, 5-10 membered heteroaryl, 4-10 membered heterocycloalkyl, $C_{6-10}$ aryl-$C_1$-4 alkyl-, $C_{3-6}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, —C(O)$R^g$, —C(O)O$R^g$, —C(O)N$R^g R^g$, —SO$_2 R$ and —SO$_2$N$R^g R^g$, wherein the $C_{1-6}$ alkyl, $C_{1-6}$ haloalkyl, $C_{3-6}$ cycloalkyl, $C_{6-10}$ aryl, 5-10 membered heteroaryl, 4-10 membered heterocycloalkyl, $C_{6-10}$ aryl-$C_{1-4}$ alkyl-, $C_{3-6}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^{10}$ or $R^{11}$ are each optionally substituted with 1, 2, or 3 independently selected $R^d$ substituents;

or $R^{10}$ and $R^{11}$ taken together with the nitrogen atom to which they are attached form 4-, 5-, 6-, 7-, 8-, 9-, 10-, or 11-membered heterocycloalkyl, wherein the 4-11 membered heterocycloalkyl is each optionally substituted with 1, 2 or 3 $R^f$ substituents;

$R^{12}$ is H, $C_{1-4}$ alkyl, $C_{1-4}$ alkoxy, $C_{1-4}$ haloalkyl, $C_{1-4}$ haloalkoxy, CN, halo, OH, —COOH, NH$_2$, —NH$C_{1-4}$ alkyl or —N($C_{1-4}$ alkyl)$_2$; and the subscript p is an integer of 1, 2, 3 or 4

In some embodiments, provided herein is a compound having Formula (II):

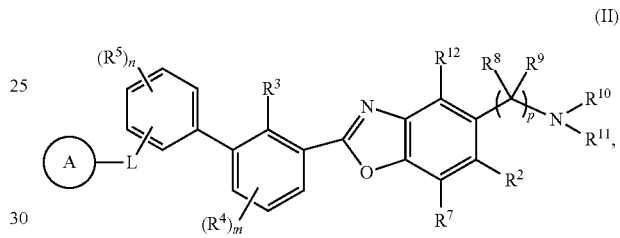

(II)

or a pharmaceutically acceptable salt or a stereoisomer thereof.

In some embodiments, provided herein is a compound having Formula (IIa):

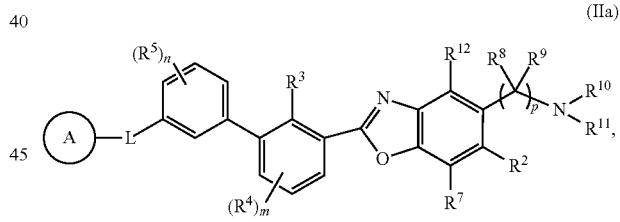

(IIa)

or a pharmaceutically acceptable salt or a stereoisomer thereof.

In some embodiments, provided herein is a compound having Formula (IIb):

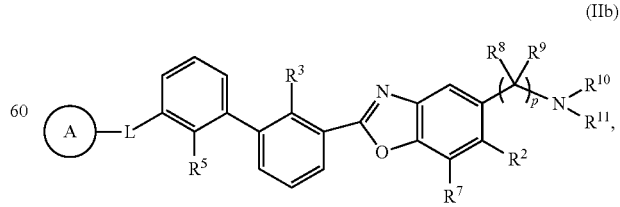

(IIb)

or a pharmaceutically acceptable salt or a stereoisomer thereof.

In some embodiments, provided herein is a compound having Formula (IIb-1):

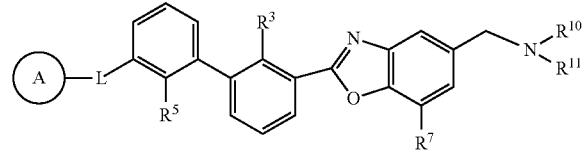

(IIb-1)

or a pharmaceutically acceptable salt or a stereoisomer thereof, wherein:

ring A is 5- to 10-membered heteroaryl, 4- to 11-membered heterocycloalkyl or $C_{6-10}$ aryl, wherein the 5- to 10-membered heteroaryl and 4- to 11-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2 or 3 $R^6$ substituents; and L is a bond, —C(O)NH—, —NH— or —OCH$_2$—, wherein the carbonyl group in the —C(O)NH— linkage or the oxygen atom in the —OCH$_2$— linkage is attached to ring A.

In some embodiments, provided herein is a compound having Formula (IIc):

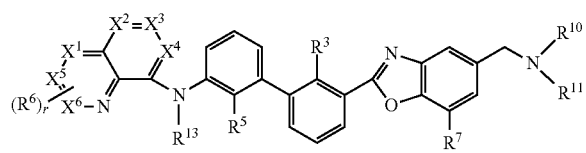

(IIc)

or a pharmaceutically acceptable salt or a stereoisomer thereof, wherein:

$X^1$, $X^2$, $X^3$, $X^4$, $X^5$ and $X^6$ are each independently N or CH, with the proviso that $X^1$, $X^5$ and $X^6$ are not simultaneously N;

$R^{13}$ is H or $C_{1-4}$ alkyl; and the subscript r is an integer of 1, 2 or 3.

In some embodiments, provided herein is a compound having Formula (IIc-1):

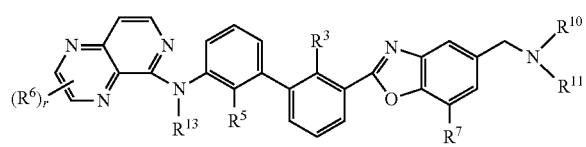

(IIc-1)

or a pharmaceutically acceptable salt or a stereoisomer thereof, wherein the subscript r is an integer of 1, 2 or 3.

In some embodiments, provided herein is a compound having Formula (IIc-2):

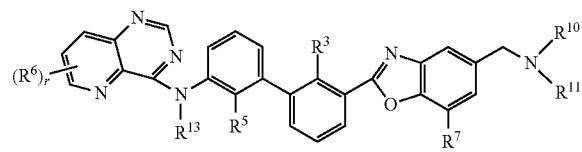

(IIc-2)

or a pharmaceutically acceptable salt or a stereoisomer thereof, wherein the subscript r is an integer of 1, 2 or 3.

In some embodiments, provided herein is a compound having Formula (IIc-3):

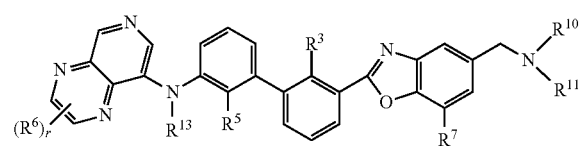

(IIc-3)

or a pharmaceutically acceptable salt or a stereoisomer thereof, wherein $R^{13}$ is H or $C_{1-4}$ alkyl; and the subscript r is an integer of 1, 2 or 3.

In some embodiments, provided herein is a compound having Formula (IIc-4):

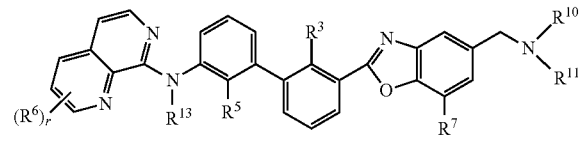

(IIc-4)

or a pharmaceutically acceptable salt or a stereoisomer thereof, wherein the subscript r is an integer of 1, 2 or 3.

In some embodiments, provided herein is a compound having Formula (IId):

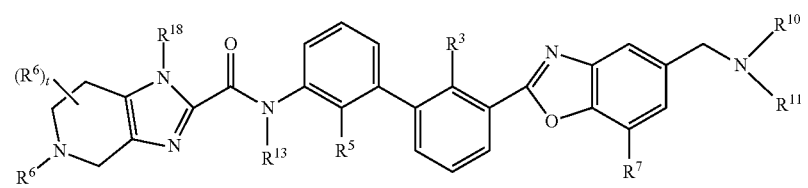

(IId)

or a pharmaceutically acceptable salt or a stereoisomer thereof, wherein:

$R^{13}$ is H or $C_{1-4}$ alkyl;

$R^{18}$ is H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^{18}$ are each optionally substituted with 1, 2, or 3 $R^b$ substituents; and the subscript t is an integer of 0, 1 or 2.

In some embodiments, $R^{13}$ is H.

In some embodiments, provided herein is a compound having Formula (IIe):

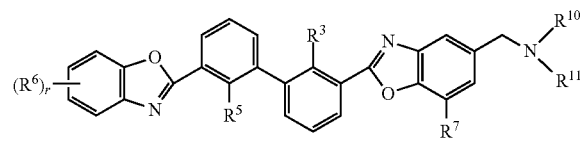
(IIe)

or a pharmaceutically acceptable salt or a stereoisomer thereof, wherein the subscript r is an integer of 1, 2 or 3.

In some embodiments, provided herein is a compound having Formula (IIf):

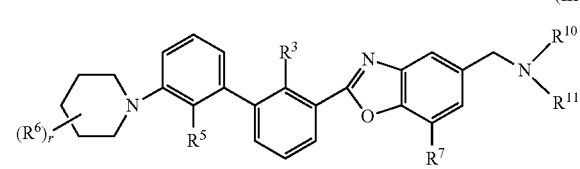
(IIf)

or a pharmaceutically acceptable salt or a stereoisomer thereof, wherein the subscript r is an integer of 1, 2 or 3.

In some embodiments, provided herein is a compound having Formula (IIf-1):

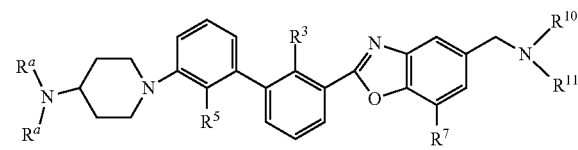
(IIf-1)

or a pharmaceutically acceptable salt or a stereoisomer thereof.

In some embodiments, provided herein is a compound having Formula (IIg):

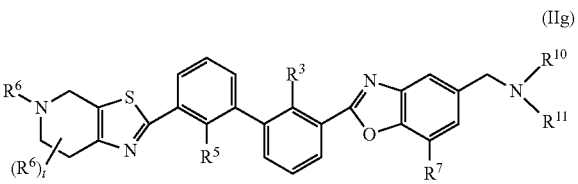
(IIg)

or a pharmaceutically acceptable salt or a stereoisomer thereof, wherein the subscript t is an integer of 0, 1 or 2.

In some embodiments, provided herein is a compound having Formula (IIh):

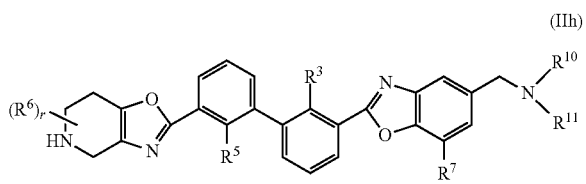
(IIh)

or a pharmaceutically acceptable salt or a stereoisomer thereof, wherein the subscript r is an integer of 1, 2 or 3.

In some embodiments, provided herein is a compound having Formula (IIj):

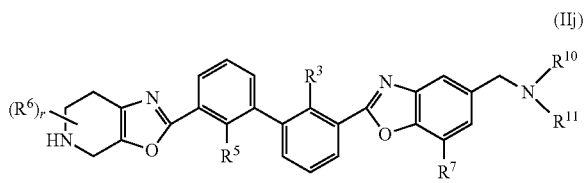
(IIj)

or a pharmaceutically acceptable salt or a stereoisomer thereof, wherein the subscript r is an integer of 1, 2 or 3.

In some embodiments, provided herein is a compound having Formula (IIk):

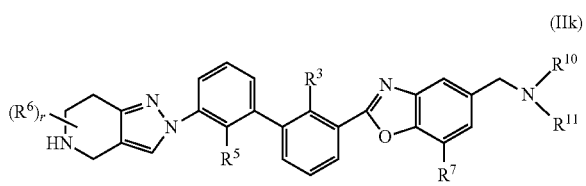
(IIk)

or a pharmaceutically acceptable salt or a stereoisomer thereof, wherein the subscript r is an integer of 1, 2 or 3.

In some embodiments, provided herein is a compound having Formula (IIm):

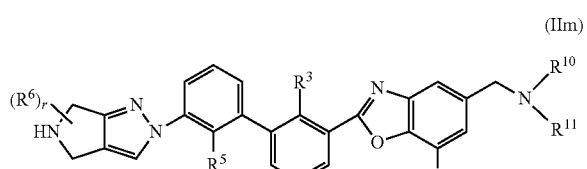
(IIm)

or a pharmaceutically acceptable salt or a stereoisomer thereof, wherein the subscript r is an integer of 1, 2 or 3.

In some embodiments, provided herein is a compound having Formula (IIn):

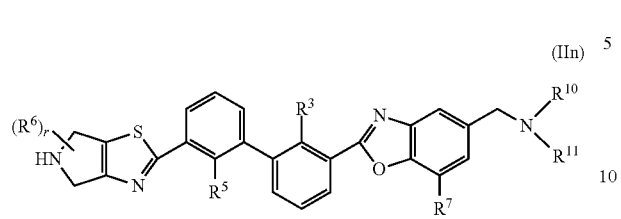

(IIn)

or a pharmaceutically acceptable salt or a stereoisomer thereof, wherein the subscript r is an integer of 1, 2 or 3.

In some embodiments, provided herein is a compound having Formula (IIo):

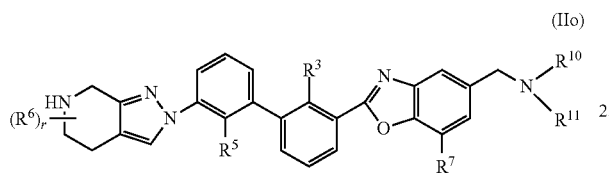

(IIo)

or a pharmaceutically acceptable salt or a stereoisomer thereof, wherein the subscript r is an integer of 1, 2 or 3.

In some embodiments, provided herein is a compound having Formula (IIp):

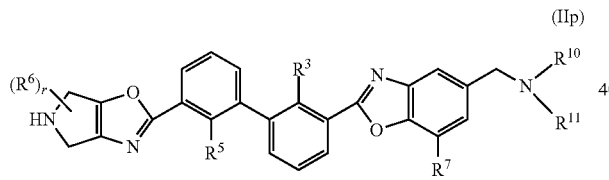

(IIp)

or a pharmaceutically acceptable salt or a stereoisomer thereof, wherein the subscript r is an integer of 1, 2 or 3.

In some embodiments, provided herein is a compound having Formula (III):

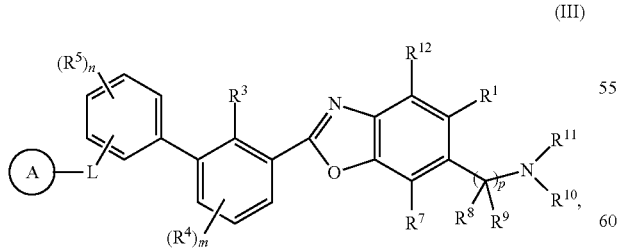

(III)

or a pharmaceutically acceptable salt or a stereoisomer thereof.

In some embodiments, provided herein is a compound having Formula (IIIa):

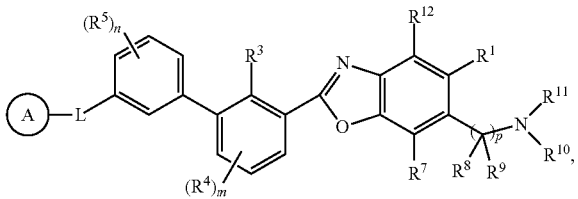

(IIIa)

or a pharmaceutically acceptable salt or a stereoisomer thereof.

In some embodiments, provided herein is a compound having Formula (IIIb):

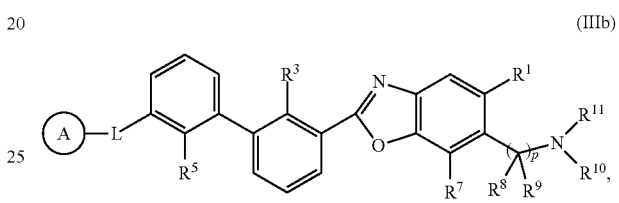

(IIIb)

or a pharmaceutically acceptable salt or a stereoisomer thereof.

In some embodiments, provided herein are compounds having Formula (IV):

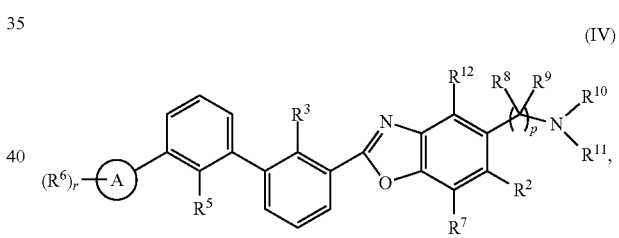

(IV)

or a pharmaceutically acceptable salt or a stereoisomer thereof, wherein the subscript r is 1, 2, 3, 4 or 5.

In one embodiment, ring A is pyridyl, for example, 2-pyridyl. In some embodiments, the subscript n is 0, 1 or 2 and each $R^5$ is independently $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$. In certain instances, $R^5$ is halo or $C_{1-4}$ alkyl. In some embodiments, the subscript m is 0. In some embodiments, the subscript r is 1 or 2. In some embodiments, $R^{12}$ is H, $C_{1-4}$ alkyl, $C_{1-4}$ alkoxy, $C_{1-4}$ haloalkyl, $C_{1-4}$ haloalkoxy, CN, halo, —COOH, $NH_2$, —$NHC_{1-4}$ alkyl or —$N(C_{1-4}$ alkyl$)_2$. In one embodiment, $R^2$ is H. In some embodiments, the subscript p is 1 and $R^8$ and $R^9$ are each H. In one embodiment, $R^{10}$ is H. In some embodiments, $R^8$ and $R^{10}$ taken together form 4- to 6-membered heterocycloalkyl, optionally substituted with 1 or 2 $R^q$ substituents. In some embodiments, $R^{10}$ and $R^{11}$ taken together form 4- to 6-membered heterocycloalkyl, optionally substituted with 1 or 2 $R^q$ substituents.

In some embodiments, provided herein are compounds having Formula (V):

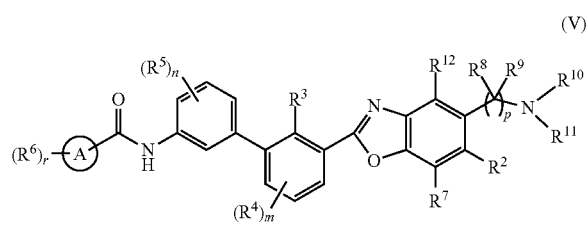

(V)

or a pharmaceutically acceptable salt or a stereoisomer thereof, wherein the subscript r is 1, 2, 3, 4 or 5, the other variables of Formula (V) are as defined in any embodiment disclosed herein. In some embodiments, the subscript r is 1 or 2.

In some embodiments, provided herein are compounds having Formula (VI):

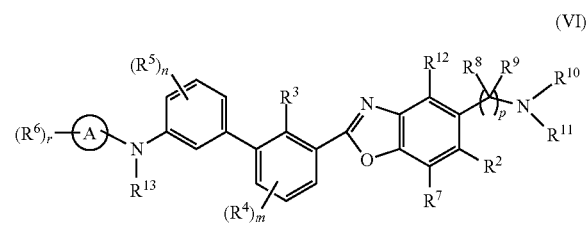

(VI)

or a pharmaceutically acceptable salt or a stereoisomer thereof, wherein the subscript r is 1, 2, 3, 4 or 5, the other variables of Formula (VI) are as defined in any embodiment disclosed herein. In some embodiments, the subscript r is 1 or 2.

In some embodiments, provided herein are compounds having Formula (VIIa) or (VIIb):

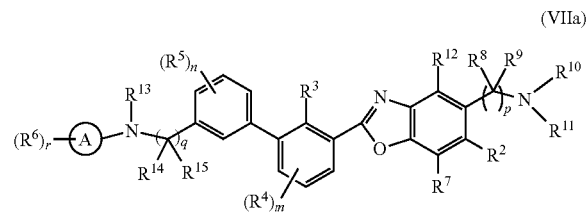

(VIIa)

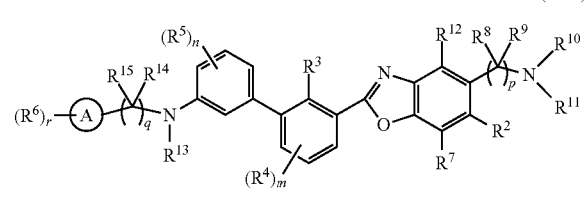

(VIIb)

or a pharmaceutically acceptable salt or a stereoisomer thereof, wherein the subscript r is 1, 2, 3, 4 or 5, the other variables of Formula (VIIa) or (VIIb) are as defined in any embodiment disclosed herein. In some embodiments, the subscript r is 1 or 2.

In some embodiments, provided herein are compounds having Formula (VIIIa) or (VIIIb):

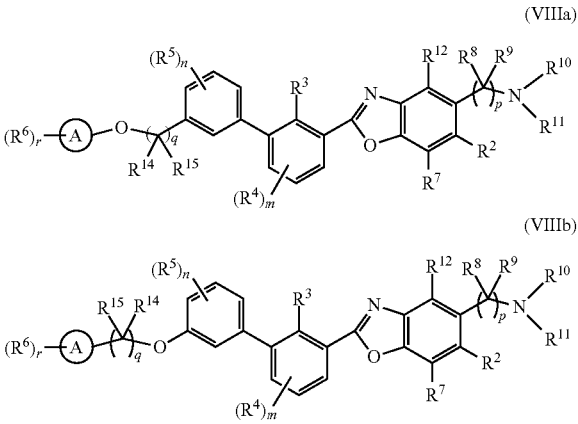

(VIIIa)

(VIIIb)

or a pharmaceutically acceptable salt or a stereoisomer thereof, wherein the subscript r is 1, 2, 3, 4 or 5, the other variables of Formula (VIIIa) or (VIIIb) are as defined in any embodiment disclosed herein. In some embodiments, the subscript r is 1 or 2.

In some embodiments, ring A is 5- to 14-membered heteroaryl, 4- to 14-membered heterocycloalkyl, or $C_{6-10}$ aryl, wherein the 5- to 14-membered heteroaryl and 4- to 14-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, or 3 $R^6$ substituents. In some embodiments, ring A is 5- to 14-membered heteroaryl or 4- to 14-membered heterocycloalkyl, wherein the 5- to 14-membered heteroaryl and 4- to 14-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, or 3 $R^6$ substituents. In some embodiments, ring A is 5- to 14-membered heteroaryl, wherein the 5- to 14-membered heteroaryl has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, or 3 $R^6$ substituents. In some embodiments, ring A is 4- to 14-membered heterocycloalkyl, wherein the 4- to 14-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, or 3 $R^6$ substituents. In some embodiments, ring A is $C_{6-10}$ aryl is optionally substituted with 1, 2, or 3 $R^6$ substituents.

In some embodiments, ring A is selected from:

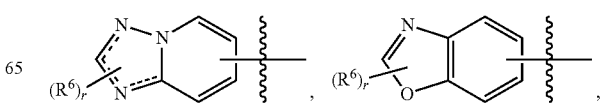

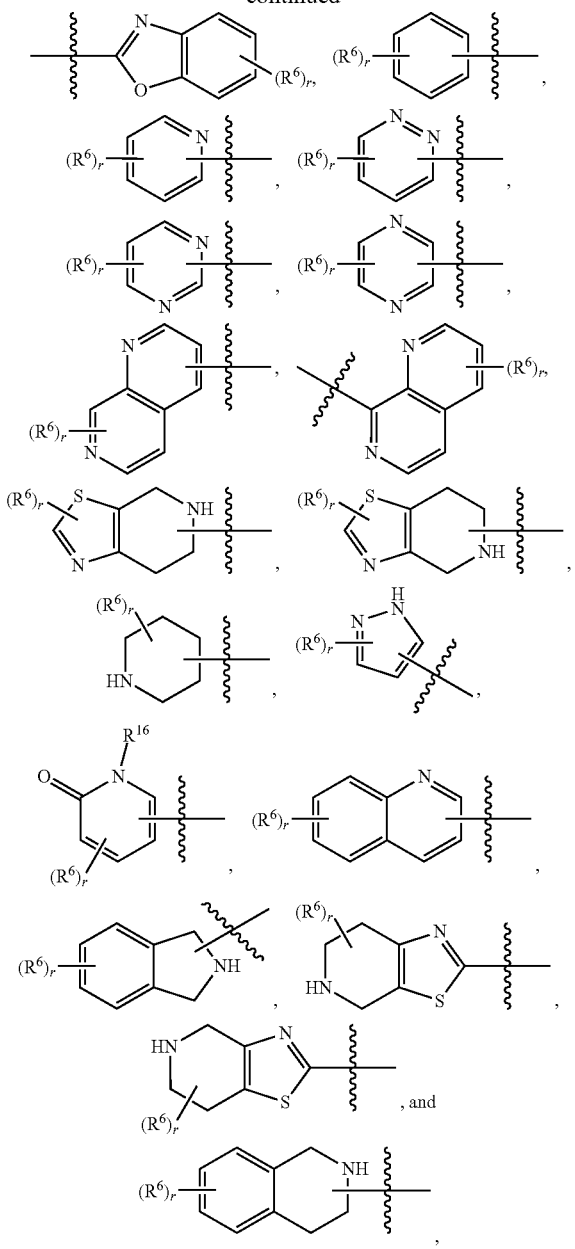

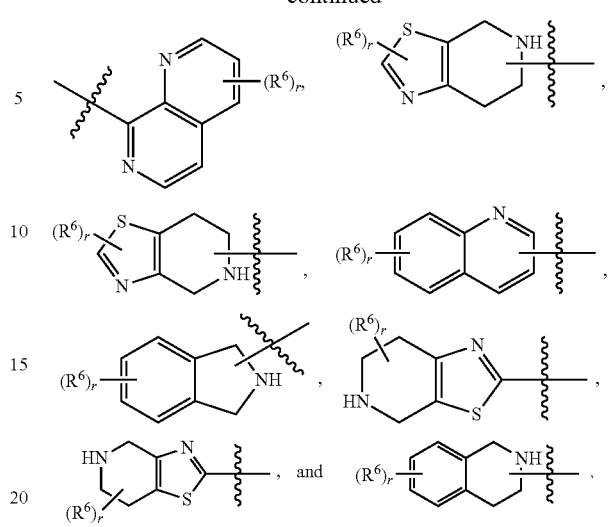

wherein each subscript r is an integer of 1, 2, 3, 4 or 5; $R^{16}$ is $C_{1-6}$ alkyl; and the wavy line indicates the point of attachment to L.

In some embodiments, ring A is selected from:

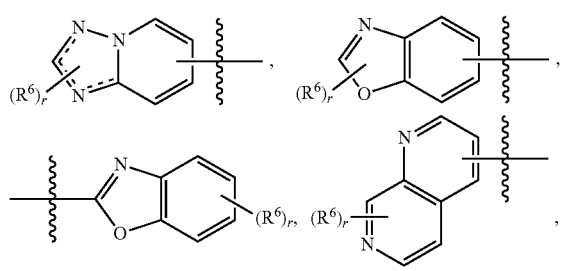

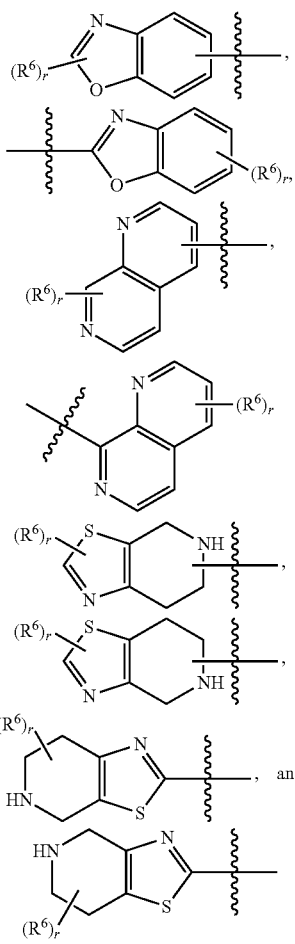

wherein each subscript r is an integer of 1, 2, 3, 4 or 5; and the wavy line indicates the point of attachment to L.

In some embodiments, ring A is selected from:

wherein each subscript r is an integer of 1, 2, 3, 4 or 5; and the wavy line indicates the point of attachment to L.

In some embodiments, ring A is selected from:

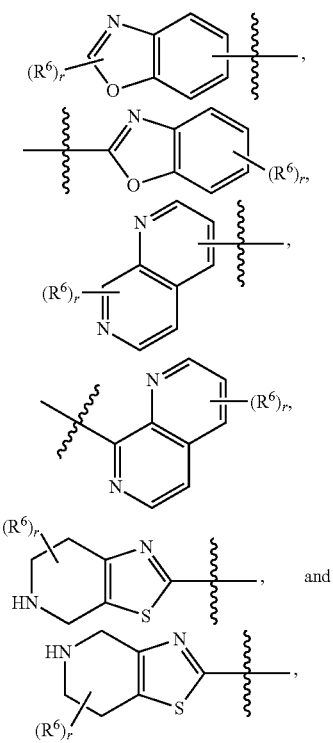

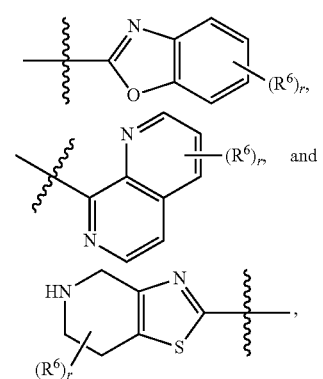

wherein each subscript r is an integer of 1, 2, 3, 4 or 5; and the wavy line indicates the point of attachment to L.

In some embodiments, ring A is selected from:

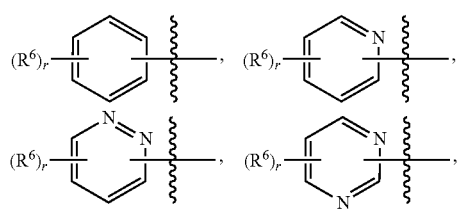

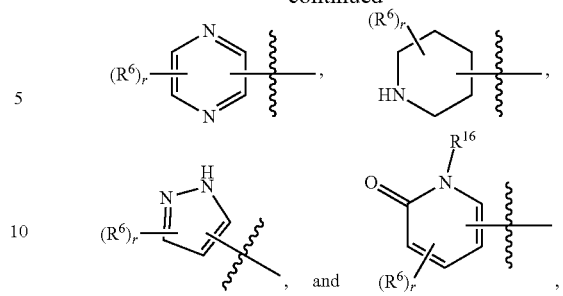

wherein each subscript r is an integer of 1, 2, 3, 4 or 5; $R^{16}$ is $C_{1-6}$ alkyl; and the wavy line indicates the point of attachment to L.

In some embodiments, ring A is selected from:

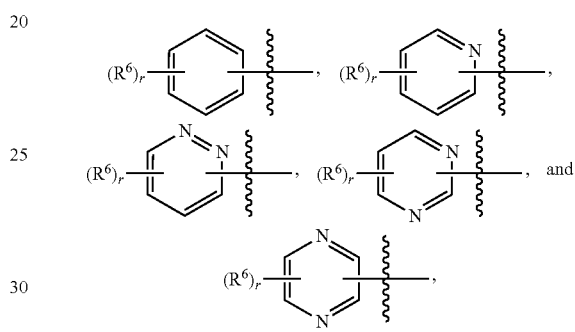

wherein each subscript r is an integer of 1, 2, 3, 4 or 5; and the wavy line indicates the point of attachment to L.

In some embodiments, ring A is selected from:

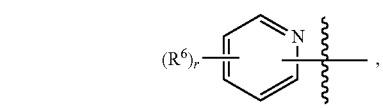

wherein each subscript r is an integer of 1, 2, 3, 4 or 5; and the wavy line indicates the point of attachment to L.

In some embodiments, ring A is selected from:

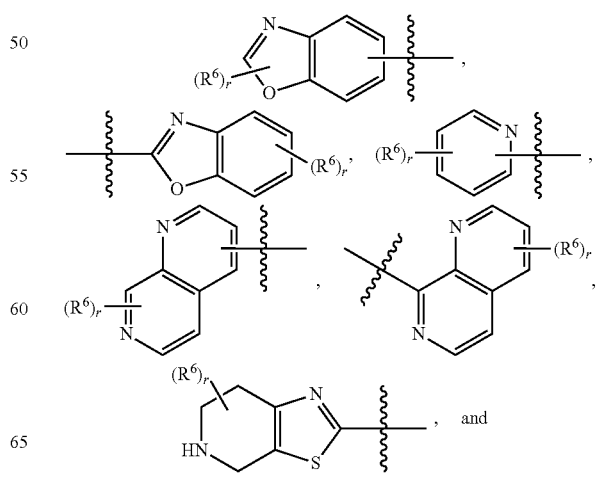

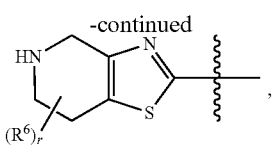

wherein each subscript r is an integer of 1, 2, 3, 4 or 5; and the wavy line indicates the point of attachment to L.

In some embodiments, ring A is selected from:

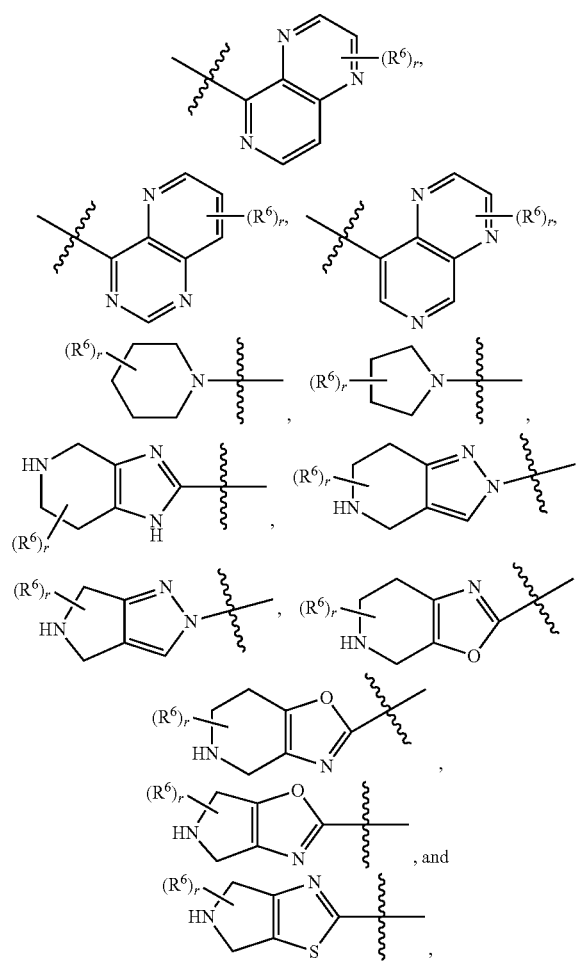

wherein the subscript r is an integer of 1, 2, 3, 4 or 5, and the wavy line indicates the point of attachment to L.

In some embodiments, ring A is selected from:

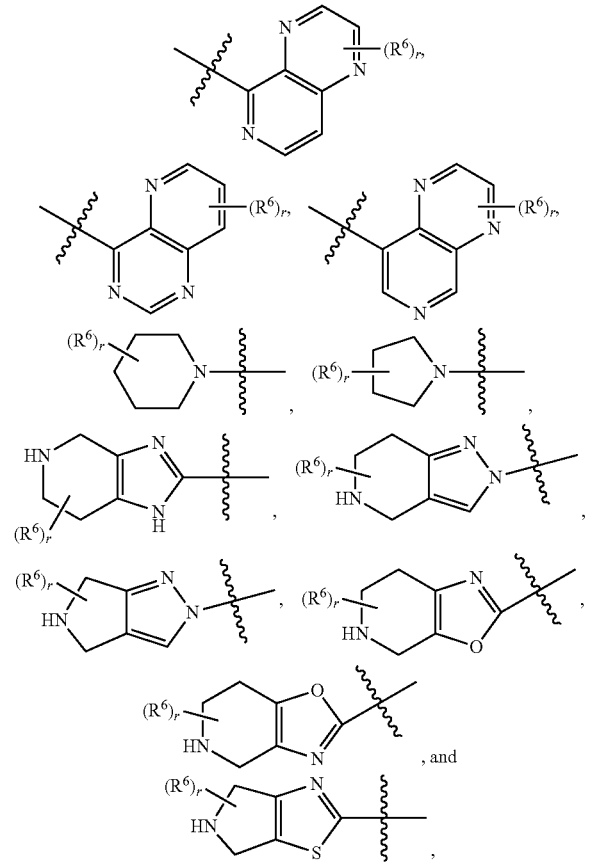

wherein the subscript r is an integer of 1, 2, 3, 4 or 5, and the wavy line indicates the point of attachment to L.

In some embodiments, ring A is 2-pyridyl, optionally substituted with 1, 2, 3, or 4 independently selected $R^6$ substituents.

In some embodiments, ring A is selected from:

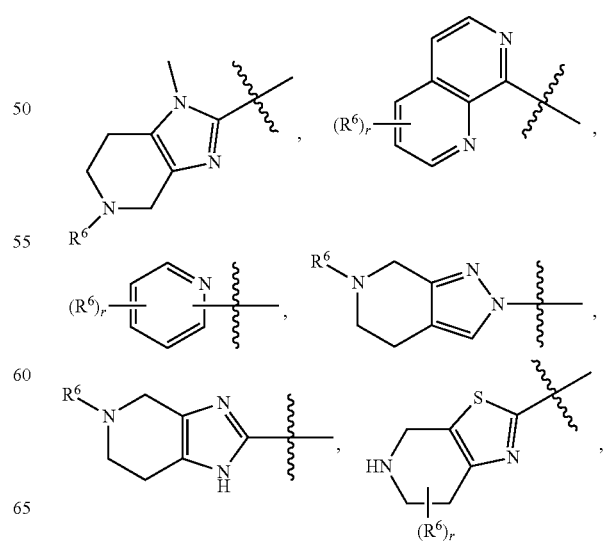

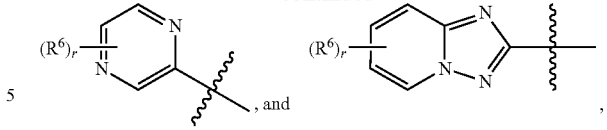

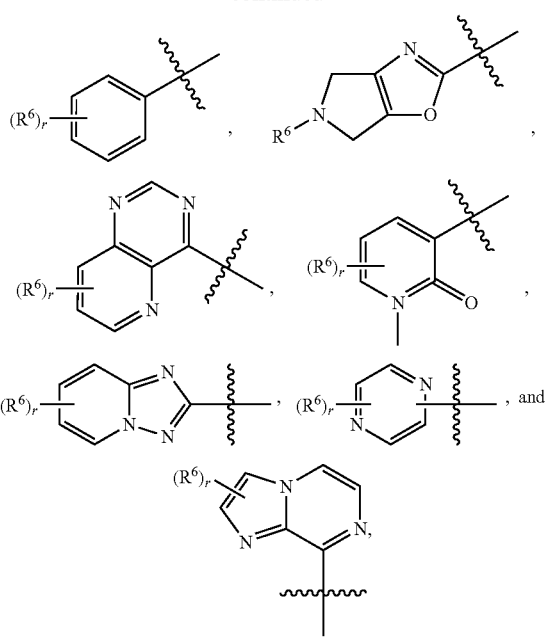

wherein the subscript r is an integer of 1, 2 or 3.

In some embodiments, ring A is selected from:

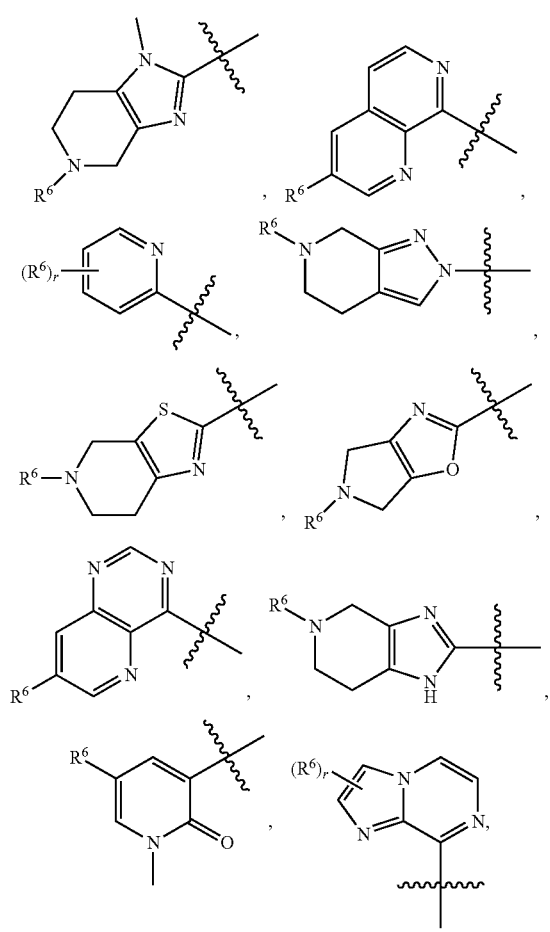

wherein the subscript r is an integer of 1, 2 or 3.

In some embodiments, L is a bond, —C(O)NR$^{13}$—, —NR$^{13}$C(O)—, O, —(CR$^{14}$R$^{15}$)$_q$—, —(CR$^{14}$R$^{15}$)$_q$—O—, —O(CR$^{14}$R$^{15}$)$_q$—, —NR$^{13}$—, —(CR$^{14}$R$^{15}$)$_q$—NR$^{13}$—, or —NR$^{13}$—(CR$^{14}$R$^{15}$)$_q$—, wherein the subscript q is 1, 2 or 3.

In some embodiments, L is a bond, —C(O)NR$^{13}$—, —NR$^{13}$C(O)—, —(CR$^{14}$R$^{15}$)$_q$—O—, —O(CR$^{14}$R$^{15}$)$_q$—, or —NR$^{13}$—, wherein the subscript q is 1, 2 or 3.

In some embodiments, L is a bond, —C(O)NR$^{13}$—, —NR$^{13}$C(O)—, or —NR$^{13}$. In some embodiments, L is a bond, —C(O)NR$^{13}$—, or —NR$^{13}$—;

In some embodiments, L is a bond, —NH—, —CH═CH— or —C(O)NH—, wherein the carbonyl group in the —C(O)NH— linkage is attached to ring A.

In some embodiments, L is a bond, —NR$^{13}$—, —(CR$^{14}$R$^{15}$)$_q$O—, —O(CR$^{14}$R$^{15}$)$_q$—, —(CR$^{14}$R$^{15}$)$_q$NR$^{13}$— or —NR$^{13}$—(CR$^{14}$R$^{15}$)$_q$—, wherein the subscript q is 1, 2 or 3. In certain instances, R$^{14}$ and R$^{15}$ are each independently H or C$_{1-4}$ alkyl. In other instances, R$^{14}$ and R$^{15}$ taken together form C$_{3-6}$ cycloalkyl or 4-6-membered heterocycloalkyl, each of which is optionally substituted with 1 or 2 R$^q$ substituents.

In some embodiments, L is a bond.

In some embodiments, L is —NR$^{13}$. In certain instances, R$^{13}$ is H or C$_{1-4}$ alkyl.

In some embodiments, L is —CH$_2$O— or —OCH$_2$—.

In some embodiments, L is —NR$^{13}$CH$_2$— or —CH$_2$NR$^{13}$. In certain instances, R$^{13}$ is H or C$_{1-4}$ alkyl.

In some embodiments, L is —C(O)NH—. In some embodiments, L is —NH—.

In some embodiments, the subscript m is an integer of 0 or 1. In some embodiments, the subscript m is 0.

In some embodiments, R$^5$ is C$_{1-4}$ alkyl, C$_{1-4}$ alkoxy, C$_{1-4}$ haloalkyl, C$_{1-4}$ haloalkoxy, CN, halo, or OH. In some embodiments, R$^5$ is C$_{1-4}$ alkyl, C$_{1-4}$ alkoxy, halo, or OH. In some embodiments, R$^5$ is C$_{1-4}$ alkyl or halo. In some embodiments, R$^5$ is C$_{1-4}$ alkyl. In some embodiments, R$^5$ is halo. In some embodiments, the subscript n is 1 and R$^5$ is halo or C$_{1-4}$ alkyl.

In some embodiments, R$^3$ is methyl, halo, or CN. In some embodiments, R$^3$ is methyl, CN or Cl. In some embodiments, R$^3$ is methyl. In some embodiments, R$^3$ is CN. In some embodiments, R$^3$ is Cl.

In some embodiments, R$^3$ and R$^5$ are each independently halo, methyl or CN.

In some embodiments, R$^7$ is CN or halo.

In some embodiments, R$^{12}$ is H, C$_{1-4}$ alkyl, C$_{1-4}$ alkoxy, C$_{1-4}$ haloalkyl, C$_{1-4}$ haloalkoxy, CN, halo, or OH, wherein the C$_{1-4}$ alkyl and C$_{1-4}$ alkoxy of R$^{12}$ are each optionally substituted with phenyl, C$_{3-6}$ cycloalkyl, 5-6-membered heteroaryl or 4-6-membered heterocycloalkyl. In some embodiments, R$^{12}$ is H, C$_{1-4}$ alkyl, C$_{1-4}$ alkoxy, or halo. In some embodiments, R$^{12}$ is H, halo, CN, C$_{1-4}$ alkyl or C$_{1-4}$ alkoxy. In some embodiments, R$^{12}$ is H or C$_{1-4}$ alkyl. In some embodiments, R$^{12}$ is H.

In some embodiments, R$^6$ and R$^{17}$ are each independently selected from H, halo, C$_{1-6}$ alkyl, C$_{2-6}$ alkenyl, C$_{2-6}$ alkynyl, C$_{1-6}$ haloalkyl, C$_{1-6}$ haloalkoxy, C$_{6-10}$ aryl, C$_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, and $NR^aC(O)OR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_1$-4 alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^6$ and $R^{17}$ are each optionally substituted with 1, 2, 3, 4 or 5 independently selected $R^b$ substituents.

In some embodiments, $R^6$ and $R^{17}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $OR^a$, $C(O)R^a$, $C(O)NR^aR^a$, $C(O)OR^a$, $NHR^a$, $NR^aR^a$, $NR^aC(O)R^a$, and $NR^aC(O)OR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^6$ and $R^{17}$ are each optionally substituted with 1, 2, or 3 independently selected $R^b$ substituents.

In some embodiments, $R^6$ and $R^{17}$ are each independently selected from H, halo, $C_{1-6}$ alkyl, 4-14 membered heterocycloalkyl, (4-14 membered heterocycloalkyl)-$C_{1-4}$ alkyl-, CN, $OR^a$, and $C(O)R^a$, wherein the $C_{1-6}$ alkyl, 4-14 membered heterocycloalkyl, and (4-14 membered heterocycloalkyl)-$C_{1-4}$ alkyl- of $R^6$ and $R^{17}$ are each optionally substituted with 1 or 2 independently selected $R^b$ substituents.

In some embodiments, $R^6$ is H, $C_{1-6}$ alkyl, 2-hydroxyethyl, 1-(2-hydroxyethyl)azetidin-3-yl, pyrrolidin-2-yl, 3-(dimethylamino)propanoyl, 1-methylpyrrolidine-2-carbonyl, 2-(4-methylpiperazin-1-yl)acetyl, 2-(isopropylamino)acetyl, 2-((R)-3-hydroxypyrrolidin-1-yl)acetyl, 2-((S)-3-hydroxypyrrolidin-1-yl)acetyl, 2-(3-hydroxypyrrolidin-1-yl)acetyl, 2-(azetidin-1-yl)acetyl, 2-(ethyl(methyl)amino)acetyl, 2-((S)-3-hydroxy-3-methylpyrrolidin-1-yl)acetyl, 2-((R)-3-hydroxy-3-methylpyrrolidin-1-yl)acetyl, (S)-(1-methylpyrrolidin-2-yl)methanoyl, 2-(3-hydroxyazetidin-1-yl)acetyl, 2-((R)-3-hydroxyazetidin-1-yl)acetyl, 2-((S)-3-hydroxyazetidin-1-yl)acetyl, 2-(3-hydroxy-3-methylazetidin-1-yl)acetyl, 2-((R)-3-hydroxy-3-methylazetidin-1-yl)acetyl, 2-((S)-3-hydroxy-3-methylazetidin-1-yl)acetyl, 2-(azetidin-1-yl)acetyl, pyrrolidin-1-ylmethyl, azetidin-1-ylmethyl, 3-hydroxyazetidin-1-yl)methyl, (R)-3-hydroxyazetidin-1-yl)methyl, (S)-3-hydroxyazetidin-1-yl)methyl, 2-(3-hydroxy-3-methylpyrrolidin-1-yl)methyl, 2-((S)-3-hydroxy-3-methylpyrrolidin-1-yl)methyl, 2-((R)-3-hydroxy-3-methylpyrrolidin-1-yl)methyl, 1-((R)-3-hydroxypyrrolidin-1-yl)ethyl, (((S)-2-hydroxypropyl)amino) methyl, (((R)-2-hydroxypropyl)amino)methyl, ((−2-hydroxypropyl)amino)methyl, (2-hydroxyethyl)amino) methyl, (3-carboxypyrrolidin-1-yl)methyl, (R)-(3-carboxypyrrolidin-1-yl)methyl, (S)-(3-carboxypyrrolidin-1-yl)methyl, (3-hydroxypyrrolidin-1-yl)methyl, (R)-(3-hydroxypyrrolidin-1-yl)methyl, (S)-(3-hydroxypyrrolidin-1-yl)methyl, (2-hydroxyethylamino)methyl, (2-hydroxy-2-methylpropylamino)methyl, 2-(dimethylamino)ethanoyl, 2-(3-carboxyazetidin-1-yl)ethanoyl, (R)-2-(3-carboxyazetidin-1-yl)ethanoyl, (S)-2-(3-carboxyazetidin-1-yl)ethanoyl, 2-(2-carboxypiperidin-1-yl)ethanoyl, (R)-2-(2-carboxypiperidin-1-yl)ethanoyl, (S)-2-(2-carboxypiperidin-1-yl)ethanoyl, 2-(3-carboxypyrrolidin-1-yl)ethanoyl, (S)-2-(3-carboxypyrrolidin-1-yl)ethanoyl, (R)-2-(3-carboxypyrrolidin-1-yl)ethanoyl, (5-cyanopyridin-3-yl)methoxy, halo or CN.

In some embodiments, $R^6$ is 2-(3-hydroxypyrrolidin-1-yl) ethyl, (R)-2-(3-hydroxypyrrolidin-1-yl)ethyl, (S)-2-(3-hydroxypyrrolidin-1-yl)ethyl, 4,5-dihydro-1H-imidazol-2-yl, (S)-(1-hydroxybutan-2-ylamino)methyl, (S)-(1-hydroxybutan-2-ylamino)methyl, (1-hydroxybutan-2-ylamino)methyl, (S)-(1-hydroxypropan-2-ylamino)methyl, (R)-(1-hydroxypropan-2-ylamino)methyl, (1-hydroxypropan-2-ylamino) methyl, (methylamino)methyl, (1-hydroxy-2-methylpropan-2-ylamino)methyl, (1-hydroxycyclopropyl)methylamino) methyl, (4-carboxypiperidin-1-yl)methyl, (R)-(3-carboxy-3-methylpyrrolidin-1-yl)methyl, (S)-(3-carboxy-3-methylpyrrolidin-1-yl)methyl, (3-carboxy-3-methylpyrrolidin-1-yl)methyl, 2-(isopropyl(methyl)amino)acetyl, 2-(ethyl (methyl)amino)acetyl, 2-((cyclopropylmethyl)(methyl) amino)acetyl, 2-(4-ethylpiperazin-1-yl)acetyl, 2-(4-methylpiperazin-1-yl)acetyl, 2-((2-hydroxyethyl)(methyl) amino)acetyl, 2-(((R)-1-hydroxypropan-2-yl)(methyl) amino)acetyl, 2-(((S)-1-hydroxypropan-2-yl)(methyl) amino)acetyl, 2-((−1-hydroxypropan-2-yl)(methyl)amino) acetyl, (4-boronophenyl)methyl, 2-(methyl(methyl)amino) acetyl, 2-(4-hydroxypiperidin-1-yl)acetyl, 2-(5-methyl-2,5-diazabicyclo[2.2.1]heptan-2-yl)acetyl, (4-carboxycyclohexyl)methyl, trans-(4-carboxycyclohexyl)methyl, cis-(4-carboxycyclohexyl)methyl, (3-carboxybicyclo[1.1.1]pentan-1-yl)methyl, 3-carboxy-3-methylcyclobutyl, 4-carboxycycloheptanyl, 2-(4-carboxycyclohexan-1-yl)ethyl, (4-carboxycyclohexan-1-yl)methyl, (4-carbo- xybicyclo[2.2.1] heptan-1-yl)methyl or (4-carboxy-4-methylcyclohexyl) methyl.

In some embodiments, $R^7H$, is $C_{1-4}$ alkyl, $C_{1-4}$ alkoxy, $C_{1-4}$ haloalkyl, $C_{1-4}$ haloalkoxy, CN, halo, or OH, wherein the $C_{1-4}$ alkyl and $C_{1-4}$ alkoxy are each optionally substituted with 1 or 2 substituents independently selected from CN, halo or $—C(O)NH_2$. In some embodiments, $R^7$ is H, $C_{1-4}$ alkyl, $C_{1-4}$ alkoxy, $C_{1-4}$ haloalkyl, $C_{1-4}$ haloalkoxy, CN, or halo, wherein the $C_{1-4}$ alkyl and $C_{1-4}$ alkoxy are each optionally substituted with 1 or 2 substituents independently selected from CN or halo. In some embodiments, $R^7$ is H, halo, CN, $C_{1-4}$ alkyl, $C_{1-4}$ alkoxy or $C_{1-4}$ haloalkoxy, wherein the $C_{1-4}$ alkyl and $C_{1-4}$ alkoxy of $R^7$ are each optionally substituted with CN. In some embodiments, $R^7$ is H, halo, CN, $C_{1-4}$ alkyl, $C_{1-4}$ alkoxy or $C_{1-4}$ haloalkoxy. In some embodiments, $R^7$ is halo. In some embodiments, $R^7$ is H.

In some embodiments, one of $R^1$ and $R^2$ is $—(CR^8 R^9)_p—NR^{10}R^{11}$ and the other is H, $C_{1-4}$ alkyl, $C_{1-4}$ alkoxy, $C_{1-4}$ haloalkyl, $C_{1-4}$ haloalkoxy, CN, halo, or OH, wherein the $C_{1-4}$ alkyl and $C_{1-4}$ alkoxy of $R^1$ or $R^2$ is optionally substituted with 1 or 2 substituents independently selected from $C_{1-4}$ alkoxy, $C_{1-4}$ haloalkyl, $C_{1-4}$ haloalkoxy, CN, halo, and OH. In some embodiments, one of $R^1$ and $R^2$ is $—(CR^8R^9)_p—NR^{10}R^{11}$ and the other is H, $C_{1-4}$ alkyl or $C_{1-4}$ alkoxy, wherein the $C_{1-4}$ alkyl and $C_{1-4}$ alkoxy of $R^1$ or $R^2$ is optionally substituted with 1 or 2 substituents independently selected from $C_{1-4}$ alkoxy, $C_{1-4}$ haloalkyl, $C_{1-4}$ haloalkoxy, and CN.

In some embodiments, $R^2$ is cyanomethoxy.

In some embodiments, $R^1$ is cyanomethoxy.

In some embodiments, the subscript p is 1, 2, or 3. In some embodiments, the subscript p is 1 or 2. In some embodiments, the subscript p is 1.

In some embodiments, $R^8$ and $R^9$ are each independently selected from H, halo, CN, OH, —COOH, $C_{1-4}$ alkyl, $C_{1-4}$ alkoxy, —NHC$_{1-4}$ alkyl, —N(C$_{1-4}$ alkyl)$_2$, $C_{1-4}$ haloalkyl, and $C_{1-4}$ haloalkoxy. In some embodiments, $R^8$ and $R^9$ are each independently selected from H, halo, CN, OH, $C_{1-4}$ alkyl, $C_{1-4}$ alkoxy, $C_{1-4}$ haloalkyl, and $C_{1-4}$ haloalkoxy. In some embodiments, $R^8$ and $R^9$ are each independently selected from H, halo, $C_{1-4}$ alkyl and $C_{1-4}$ alkoxy. In some embodiments, $R^8$ is H. In some embodiments, $R^9$ is H. In some embodiments, $R^8$ and $R^9$ are each H.

In some embodiments, $R^{10}$ is selected from H, $C_{1-6}$ alkyl, and $C_{1-6}$ haloalkyl. In some embodiments, $R^{10}$ is selected from H and $C_{1-6}$ alkyl. In some embodiments, $R^{10}$ is H.

In some embodiments, $R^{11}$ is selected from H, $C_{1-6}$ alkyl, $C_{1-6}$ haloalkyl, —C(O)R$^g$, —C(O)OR$^g$, —C(O)NR$^g$R$^g$, —SO$_2$R$^g$ and —SO$_2$NR$^g$R$^g$, wherein the $C_{1-6}$ alkyl and $C_{1-6}$ haloalkyl of $R^{11}$ are each optionally substituted with 1 or 2 independently selected R$^f$ substituents. In some embodiments, R" is selected from H and $C_{1-6}$ alkyl optionally substituted with 1 or 2 independently selected R$^f$ substituents. In some embodiments, R" is 2-hydroxyethyl, 2-carboxyethyl, [1-(hydroxymethyl)cyclopropyl]methyl, [1-(hydroxymethyl)cyclobutyl]methyl or 2-(dimethylamino)-2-oxo-ethyl.

In some embodiments, —NR$^{10}$R$^{11}$ is (2-hydroxyethyl)amino, (2-carboxyethyl)amino, 2-carboxy-1-piperidinyl, 2-oxooxazolidin-3-yl, [1-(hydroxymethyl)cyclopropyl]methylamino, [1-(hydroxymethyl)cyclobutyl]methylamino, 3-carboxypyrrolidin-1-yl, (R)-3-carboxypyrrolidin-1-yl, (S)-3-carboxypyrrolidin-1-yl, (S)-2-carboxypyrrolidin-1-yl, (R)-2-carboxypyrrolidin-1-yl, 2-carboxypyrrolidin-1-yl, (1-carboxyethyl)amino, (R)-(1-carboxyethyl)amino, (S)-(1-carboxyethyl)amino, 3-methyl-3-carboxypyrrolidin-1-yl, 4-carboxypiperidin-1-yl, (S)-4-carboxypiperidin-1-yl, (R)-4-carboxypiperidin-1-yl, 3-carboxy-azetidin-1-yl, (R)-3-carboxy-azetidin-1-yl, (S)-3-carboxy-azetidin-1-yl, (2-hydroxyethyl)(methyl)amino, [2-(dimethylamino)-2-oxo-ethyl]amino, (R)-3-methyl-3-carboxypyrrolidin-1-yl, (S)-3-methyl-3-carboxypyrrolidin-1-yl, (1-carboxyethyl)amino, (4-carboxycyclohexyl)amino, 3-(methylaminocarbonyl)pyrrolidin-1-yl, (R)-3-(methylaminocarbonyl)pyrrolidin-1-yl, (S)-3-(methylaminocarbonyl)pyrrolidin-1-yl, 3-(2-hydroxyethylaminocarbonyl)pyrrolidin-1-yl, (R)-3-(2-hydroxyethylaminocarbonyl)pyrrolidin-1-yl, (S)-3-(2-hydroxyethylaminocarbonyl)pyrrolidin-1-yl, 2-(methylcarbonylamino)ethylamino, 3-(2-hydroxyethylcarbonylamino)pyrrolidin-1-yl, (R)-3-(2-hydroxyethylcarbonylamino)pyrrolidin-1-yl, (S)-3-(2-hydroxyethylcarbonylamino)pyrrolidin-1-yl, (R)-3-hydroxypyrrolidin-1-yl, (S)-3-hydroxypyrrolidin-1-yl, or 3-hydroxypyrrolidin-1-yl In some embodiments, —NR$^{10}$R$^{11}$ is (2-hydroxyethyl)amino, (2-carboxyethyl)amino, 2-carboxy-1-piperidinyl, 2-oxooxazolidin-3-yl, [1-(hydroxymethyl)cyclopropyl]methylamino, [1-(hydroxymethyl)cyclobutyl]methylamino, 3-carboxypyrrolidin-1-yl, (S)-2-carboxypyrrolidin-1-yl, (S)-3-methyl-3-carboxypyrrolidin-1-yl, 4-carboxypiperidin-1-yl, 3-carboxy-azetidin-1l-yl, (2-hydroxyethyl)(methyl)amino, [2-(dimethylamino)-2-oxo-ethyl]amino, (R)-3-methyl-3-carboxypyrrolidin-1-yl, (1-carboxyethyl)amino, (4-carboxycyclohexyl)amino, 3-(methylaminocarbonyl)pyrrolidin-1-yl, 3-(2-hydroxyethylaminocarbonyl)pyrrolidin-1-yl, 2-(methylcarbonylamino)ethylamino, 3-(2-hydroxyethylcarbonylamino)pyrrolidin-1-yl, or 3-hydroxypyrrolidin-1-yl.

In some embodiments, —NR$^{10}$R$^{11}$ is (2-hydroxyethyl)amino, (2-carboxyethyl)amino, 2-carboxy-1-piperidinyl, 2-oxooxazolidin-3-yl, [1-(hydroxymethyl)cyclopropyl]methylamino, [1-(hydroxymethyl)cyclobutyl]methylamino, 3-carboxypyrrolidin-1-yl, (S)-2-carboxypyrrolidin-1-yl, (S)-3-methyl-3-carboxypyrrolidin-1-yl, 4-carboxypiperidin-1-yl, 3-carboxy-azetidin-1l-yl, (2-hydroxyethyl)(methyl)amino or [2-(dimethylamino)-2-oxo-ethyl]amino.

In some embodiments, —NR$^{10}$R$^{11}$ is (2-hydroxyethyl)amino, (2-carboxyethyl)amino, 2-carboxy-1-piperidinyl, 2-oxooxazolidin-3-yl, [1-(hydroxymethyl)cyclopropyl]methylamino, [1-(hydroxymethyl)cyclobutyl]methylamino or [2-(dimethylamino)-2-oxo-ethyl]amino.

In some embodiments, —NR$^{10}$R$^{11}$ is 5-carboxy-2-azabicyclo[2.2.1]heptan-2-yl, 4-carboxy-2-azbicyclo[2.1.1]hexan-2-yl, 6-carboxy-2-azaspiro[3.3]heptan-2-yl, 3-carboxy-3-methoxymethylpyrrolidin-1-yl, (R)-3-carboxy-3-methoxymethylpyrrolidin-1-yl, (S)-3-carboxy-3-methoxymethylpyrrolidin-1-yl, 4-carboxy-2-azabicyclo[2.1.1]hexan-2-yl, 3-methanesulfamoylpyrrolidin-1-yl, 5-carboxy-2-azabicyclo[2.2.1]heptan-2-yl, 5-hydroxy-2-azabicyclo[2.2.1]heptan-2-yl, pyrrolidin-1-yl, (1R,3S)-3-carboxycyclopentan-1-ylamino, (1R,3R)-3-carboxycyclopentan-1-ylamino, (1S,3 S)-3-carboxycyclopentan-1-ylamino, (1S,3R)-3-carboxycyclopentan-1-ylamino, (1R,2R)-2-carboxycyclopentan-1-ylamino, (1 S, 2S)-2-carboxycyclopentan-1-ylamino, (1R,2S)-2-carboxycyclopentan-1-ylamino, (1 S, 2R)-2-carboxycyclopentan-1-ylamino, trans-3-carboxycyclobutan-1-ylamino, cis-3-carboxycyclobutan-1-ylamino, trans-4-(carboxymethyl)cyclohexan-1-ylamino, cis-4-(carboxymethyl)cyclohexan-1-ylamino, 4-carboxybicyclo[2.2.1]heptan-1-ylamino, (R)-2-hydroxypropylamino, (S)-2-hydroxypropylamino, (R)-3-hydroxy-propan-2-ylamino or (S)-3-hydroxy-propan-2-ylamino.

In some embodiments, $R^{14}$ and $R^{15}$ are each independently selected from H, halo, CN, OH, —COOH, $C_{1-4}$ alkyl, $C_{1-4}$ alkoxy, —NHC$_{1-4}$ alkyl, —N(C$_{1-4}$ alkyl)$_2$, $C_{1-4}$ haloalkyl, and $C_{1-4}$ haloalkoxy. In some embodiments, $R^{14}$ and $R^{15}$ are each independently selected from H, halo, CN, OH, —COOH, and $C_{1-4}$ alkyl. In some embodiments, $R^{14}$ and $R^{15}$ are each independently selected from H and $C_{1-4}$ alkyl. In some embodiments, $R^{14}$ and $R^{15}$ are H.

In some embodiments, each R$^a$ is independently selected from H, CN, $C_{1-6}$ alkyl, $C_{1-4}$ haloalkyl, $C_{2-6}$ alkenyl, $C_{2-6}$ alkynyl, 5-14 membered heteroaryl, 4-14 membered heterocycloalkyl, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, 5-14 membered heteroaryl, 4-14 membered heterocycloalkyl, (5-14 membered heteroaryl)-$C_{1-4}$ alkyl- and (4-14 membered heterocycloalkyl)-$C_{1-4}$ alkyl- of R$^a$ are each optionally substituted with 1, 2, or 3 independently selected R$^d$ substituents. In some embodiments, each R$^a$ is independently selected from H, $C_{1-6}$ alkyl, 4-14 membered heterocycloalkyl, (5-14 membered heteroaryl)-$C_{1-4}$ alkyl-, and (4-14 membered heterocycloalkyl)-$C_{1-4}$ alkyl-, wherein the $C_{1-6}$ alkyl, 4-14 membered heterocycloalkyl, (5-14 membered heteroaryl)-$C_{1-4}$ alkyl- and (4-14 membered heterocycloalkyl)-$C_{1-4}$ alkyl- of R$^a$ are each optionally substituted with 1 or 2 independently selected R$^d$ substituents.

In some embodiments, each R$^d$ is independently selected from $C_{1-6}$ alkyl, $C_{1-6}$ haloalkyl, halo, 5-10 membered heteroaryl, 4-14 membered heterocycloalkyl, (5-14 membered heteroaryl)-$C_{1-4}$ alkyl-, (4-14 membered heterocycloalkyl)-$C_{1-4}$ alkyl-, CN, NH$_2$, OR$^e$, C(O)R$^e$, C(O)NR$^e$R$^e$, C(O)OR$^e$, NHR$^e$, NR$^e$R$^e$, NR$^e$C(O)R$^e$, NR$^e$C(O)NR$^e$R$^e$, and NR$^e$C(O)OR$^e$, wherein the $C_{1-6}$ alkyl, $C_{1-6}$ haloalkyl, 5-14 membered heteroaryl, 4-14 membered heterocycloalkyl, (5-14 membered heteroaryl)-$C_{1-4}$ alkyl-, and (4-14 membered heterocycloalkyl)-$C_{1-4}$ alkyl- of R$^d$ are each optionally substituted with 1, 2, or 3 independently selected $R^f$ substituents. In some embodiments, each $R^d$ is independently selected from $C_{1-6}$ alkyl, 4-14 membered heterocycloalkyl, (4-14 membered heterocycloalkyl)-$C_{1-4}$ alkyl-, CN, $NH_2$, $OR^e$, $C(O)$ $OR^e$, $NHR^e$, and $NR^eR^e$, wherein the $C_{1-6}$ alkyl, 4-14 membered heterocycloalkyl, and (4-14 membered heterocycloalkyl)-$C_{1-4}$ alkyl- of $R^d$ are each optionally substituted with 1, 2, or 3 independently selected $R^f$ substituents.

In some embodiments, each $R^e$ is independently selected from H, $C_{1-6}$ alkyl, $C_{1-6}$ haloalkyl, $C_{2-6}$ alkenyl, and $C_{2-6}$ alkynyl. In some embodiments, each $R^e$ is independently selected from H and $C_{1-6}$ alkyl.

In some embodiments, each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, CN, OH, $NH_2$, $OR^c$, $C(O)R^c$, $C(O)NR^cR^c$, $C(O)OR^c$, $NHR^c$, $NR^cR^c$, $NR^cC(O)R^c$, and $NR^cC(O)OR^c$; wherein the $C_{1-6}$ alkyl, $C_{1-6}$ haloalkyl, $C_{1-6}$ haloalkoxy, $C_{2-6}$ alkenyl, and $C_{2-6}$ alkynyl of $R^b$ are each further optionally substituted with 1, 2 or 3 independently selected $R^d$ substituents. In some embodiments, each $R^b$ substituent is independently selected from halo, $C_{1-6}$ alkyl, OH, $NH_2$, $OR^c$, $C(O)R^c$, $C(O)NR^cR^c$, $C(O)OR^c$, $NHR^c$, and $NR^cR^c$; wherein the $C_{1-6}$ alkyl of $R^b$ is further optionally substituted with 1 or 2 independently selected $R^d$ substituents. In some embodiments, each $R^b$ substituent is independently selected from $C_{1-6}$ alkyl, OH, $NH_2$, $OR^c$, $C(O)NR^cR^c$, $C(O)OR^c$, $NHR^c$, and $NR^cR^c$; wherein the $C_{1-6}$ alkyl of $R^b$ is further optionally substituted with 1 or 2 independently selected $R^d$ substituents.

In some embodiments, each $R^c$ is independently selected from H, $C_{1-6}$ alkyl, $C_{1-4}$ haloalkyl, $C_{2-6}$ alkenyl, $C_{2-6}$ alkynyl, $C_{3-10}$ cycloalkyl, and 4-10 membered heterocycloalkyl, wherein the $C_{1-6}$ alkyl, $C_{2-6}$ alkenyl, $C_{2-6}$ alkynyl, $C_{3-10}$ cycloalkyl, and 4-10 membered heterocycloalkyl of $R^c$ are each optionally substituted with 1, 2, or 3 independently selected $R^f$ substituents. In some embodiments, each $R^c$ is independently selected from H, $C_{1-6}$ alkyl, and $C_{3-10}$ cycloalkyl, wherein the $C_{1-6}$ alkyl and $C_{3-10}$ cycloalkyl of $R^c$ are each optionally substituted with 1 or 2 independently selected $R^f$ substituents.

In some embodiments, each $R^f$ is independently selected from $C_{1-4}$ alkyl, $C_{1-4}$ haloalkyl, $C_{2-6}$ alkenyl, $C_{2-6}$ alkynyl, halo, CN, $OR^g$, $C(O)R^g$, $C(O)NR^gR^g$, $C(O)OR^g$, $NHR^g$, $NR^gR^g$, and $NR^gC(O)R^g$. In some embodiments, each $R^f$ is independently selected from $C_{1-4}$ alkyl, $OR^g$, $C(O)OR$, and $NR^c(O)R$. In some embodiments, each $R^g$ is independently selected from H, $C_{1-6}$ alkyl, $C_{1-4}$ haloalkyl, $C_{2-6}$ alkenyl, and $C_{2-6}$ alkynyl. In some embodiments, each $R^g$ is independently selected from H and $C_{1-6}$ alkyl.

In some embodiments, the subscript m is an integer of 0, 1, or 2. In some embodiments, the subscript m is an integer of 0 or 1. In some embodiments, the subscript m is an integer of 0.

In some embodiments, the subscript n is an integer of 0, 1 or 2. In some embodiments, the subscript n is an integer of 0 or 1. In some embodiments, the subscript n is an integer of 0. In some embodiments, the subscript n is an integer of 1.

In some embodiments, each subscript q is independently an integer of 1, 2, or 3. In some embodiments, each subscript q is independently an integer of 1 or 2. In some embodiments, each subscript q is independently an integer of 1. In some embodiments, each subscript q is independently an integer of 2.

In some embodiments, the subscript s is an integer of 1, 2, or 3. In some embodiments, the subscript s is an integer of 1 or 2. In some embodiments, the subscript s is an integer of 1. In some embodiments, the subscript s is an integer of 2.

In some embodiments, provided herein is a compound of Formula (I) or (Ia), or a pharmaceutically acceptable salt or a stereoisomer thereof, wherein:

ring A is 5- to 10-membered heteroaryl or 4- to 11-membered heterocycloalkyl, wherein the 5- to 10-membered heteroaryl and 4- to 11-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, or 3 $R^6$ substituents;

L is a bond, $-C(O)NR^{13}-$, $-NR^{13}C(O)-$, O, or $-NR^{13}-$;

one of $R^1$ and $R^2$ is $-(CR^8R^9)_p-NR^{10}R^{11}$ and the other is H, $C_{1-4}$ alkyl, $C_{1-4}$ alkoxy, $C_{1-4}$ haloalkyl, $C_{1-4}$ haloalkoxy, CN, halo, or OH, wherein the $C_{1-4}$ alkyl and $C_{1-4}$ alkoxy of $R^1$ or $R^2$ is optionally substituted with 1 or 2 substituents independently selected from $C_{1-4}$ alkoxy, $C_{1-4}$ haloalkyl, $C_{1-4}$ haloalkoxy, CN, halo, OH, $NH_2$, $-NHC_{1-4}$ alkyl and $-N(C_{1-4}$ alkyl$)_2$;

$R^3$ is methyl or halo;

$R^4$ is $C_{1-4}$ alkyl, $C_{1-4}$ alkoxy, $C_{1-4}$ haloalkyl, $C_{1-4}$ haloalkoxy, CN, halo, or OH;

$R^5$ is $C_{1-4}$ alkyl, $C_{1-4}$ alkoxy, $C_{1-4}$ haloalkyl, $C_{1-4}$ haloalkoxy, CN, halo, or OH;

each $R^6$ is independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, CN, $OR^a$, $C(O)R^a$, $C(O)NR^aR^a$, $C(O)OR^a$, $NHR^a$, $NR^aR^a$, and $NR^aC(O)R^a$, wherein the $C_{1-6}$ alkyl, $C_{2-6}$ alkenyl, and $C_{2-6}$ alkynyl of $R^6$ are each optionally substituted with 1 or 2 $R^b$ substituents;

$R^7$ is H, $C_{1-4}$ alkyl, $C_{1-4}$ alkoxy, $C_{1-4}$ haloalkyl, $C_{1-4}$ haloalkoxy, CN, halo, or OH;

$R^8$ and $R^9$ are each independently selected from H, halo, CN, OH, $-COOH$, $C_{1-4}$ alkyl, $C_{1-4}$ alkoxy, $-NHC_{1-4}$ alkyl, $-N(C_{1-4}$ alkyl$)_2$, $C_{1-4}$ haloalkyl, and $C_{1-4}$ haloalkoxy;

$R^{10}$ and $R^{11}$ are each independently selected from H, $C_{1-6}$ alkyl, $C_{1-6}$ haloalkyl, $-C(O)R^g$, $-C(O)OR^g$, and $-C(O)NR^gR^g$, wherein the $C_{1-6}$ alkyl and $C_{1-6}$ haloalkyl of $R^{10}$ or $R^{11}$ are each optionally substituted with 1, 2 or 3 independently selected $R^f$ substituents;

or $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1 or 2 $R^h$ substituents;

$R^{12}$ is H, $C_{1-4}$ alkyl, $C_{1-4}$ alkoxy, $C_{1-4}$ haloalkyl, $C_{1-4}$ haloalkoxy, CN, halo, or OH;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, or OH;

each $R^a$ is independently selected from H, CN, $C_{1-6}$ alkyl, $C_{1-4}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^a$ are each optionally substituted with 1 or 2 $R^d$ substituents;

each $R^d$ is independently selected from $C_{1-6}$ alkyl, $C_{1-6}$ haloalkyl, halo, CN, $NH_2$, $OR^e$, $C(O)R^e$, $C(O)NR^eR^e$, $C(O)OR^e$, $NHR^e$, $NR^eR^e$, and $NR^eC(O)R^e$;

each $R^e$ is independently selected from H, $C_{1-6}$ alkyl, $C_{1-6}$ haloalkyl, $C_{2-6}$ alkenyl, and $C_{2-6}$ alkynyl;

each $R^b$ substituent is independently selected from halo, $C_{1-6}$ alkyl, $C_{1-6}$ haloalkyl, $C_{1-6}$ haloalkoxy, 5-10 membered heteroaryl, 4-10 membered heterocycloalkyl, (5-10 membered heteroaryl)-$C_{1-4}$ alkyl-, (4-10 membered heterocycloalkyl)-$C_{1-4}$ alkyl-, CN, OH, $NH_2$, $OR^c$, $C(O)R^c$, $C(O)NR^cR^c$, $C(O)OR^c$, $NHR^c$, $NR^cR^c$, and $NR^cC(O)R^c$; wherein the $C_{1-4}$ alkyl, $C_{1-4}$ haloalkyl, $C_{1-4}$ haloalkoxy, 5-10 membered heteroaryl, 4-10 membered heterocycloalkyl, (5-10 membered heteroaryl)-$C_{1-4}$ alkyl- and (4-10 membered heterocycloalkyl)-$C_{1-4}$ alkyl- of $R^b$ are each further optionally substituted with 1 or 2 independently selected $R^d$ substituents;

each $R^c$ is independently selected from H, $C_{1-6}$ alkyl, $C_{1-4}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^c$ are each optionally substituted with 1, 2, or 3 $R^f$ substituents;

each $R^f$ is independently selected from $C_{1-4}$ alkyl, $C_{1-4}$ haloalkyl, $C_{2-6}$ alkenyl, $C_{2-6}$ alkynyl, halo, CN, $OR^g$, $C(O)R^g$, $C(O)NR^gR^g$, $C(O)OR^g$, $NHR^g$, $NR^gR^g$, and $NR^cC(O)R^g$;

each $R^g$ is independently selected from H, $C_{1-6}$ alkyl, $C_{1-4}$ haloalkyl, $C_{2-6}$ alkenyl, and $C_{2-6}$ alkynyl;

each $R^h$ is independently selected from $C_{1-6}$ alkyl, $C_{1-6}$ haloalkyl, $C_{1-6}$ haloalkoxy, $C_{2-6}$ alkenyl, $C_{2-6}$ alkynyl, halo, CN, $OR^i$, $C(O)R^i$, $C(O)NR^iR^i$, $C(O)OR^i$, $NHR^i$, $NR^iR^i$, and $NR^iC(O)R^i$;

each $R^i$ is independently selected from H, $C_{1-4}$ alkyl, $C_{1-6}$ haloalkyl, $C_{1-6}$ haloalkoxy, $C_{2-4}$ alkenyl, and $C_{2-4}$ alkynyl;

the subscript m is an integer of 0, 1 or 2;
the subscript n is an integer of 0, 1, or 2; and
the subscript p is an integer of 1, 2, or 3.

In some embodiments, provided herein is a compound of Formula (I) or (Ia), or a pharmaceutically acceptable salt or a stereoisomer thereof, wherein:

ring A is 5- to 10-membered heteroaryl or 4- to 11-membered heterocycloalkyl, wherein the 5- to 10-membered heteroaryl and 4- to 11-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1 or 2 $R^6$ substituents;

L is a bond, $-C(O)NR^{13}-$, $-NR^{13}C(O)-$, or $-NR^{13}-$;

one of $R^1$ and $R^2$ is $-(CR^8R^9)_p-NR^{10}R^{11}$ and the other is H, $C_{1-4}$ alkyl, or $C_{1-4}$ alkoxy, wherein the $C_{1-4}$ alkyl and $C_{1-4}$ alkoxy of $R^1$ or $R^2$ is optionally substituted with 1 or 2 substituents independently selected from $C_{1-4}$ alkoxy, CN, halo, OH, and $NH_2$;

$R^3$ is methyl or halo;

$R^4$ is $C_{1-4}$ alkyl, $C_{1-4}$ alkoxy, CN, halo, or OH;

$R^5$ is $C_{1-4}$ alkyl, $C_{1-4}$ alkoxy, CN, halo, or OH;

each $R^6$ is independently selected from H, halo, $C_{1-6}$ alkyl, $C_{2-6}$ alkenyl, $C_{2-6}$ alkynyl, CN, and $OR^a$, wherein the $C_{1-6}$ alkyl, $C_{2-6}$ alkenyl, and $C_{2-6}$ alkynyl of $R^6$ are each optionally substituted with 1 or 2 $R^b$ substituents;

$R^7$ is H, $C_{1-4}$ alkyl, $C_{1-4}$ alkoxy, CN, halo, or OH;

$R^8$ and $R^9$ are each independently selected from H, halo, CN, OH, and $C_{1-4}$ alkyl;

$R^{10}$ and $R^{11}$ are each independently selected from H, $C_{1-6}$ alkyl, and $C_{1-6}$ haloalkyl, wherein the $C_{1-6}$ alkyl and $C_{1-6}$ haloalkyl of $R^{10}$ or $R^{11}$ are each optionally substituted with 1, 2 or 3 independently selected $R^f$ substituents;

or $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1 or 2 $R^h$ substituents;

$R^{12}$ is H or $C_{1-4}$ alkyl;

each $R^{13}$ is independently H or $C_{1-6}$ alkyl;

each $R^a$ is independently selected from H and $C_{1-6}$ alkyl optionally substituted with 1 or 2 $R^d$ substituents;

each $R^d$ is independently selected from $C_{1-6}$ alkyl, $C_{1-6}$ haloalkyl, halo, CN, and $C(O)OR^e$; each $R^e$ is independently selected from H and $C_{1-6}$ alkyl;

each $R^b$ substituent is independently selected from halo, $C_{1-6}$ alkyl, 5-10 membered heteroaryl, 4-10 membered heterocycloalkyl, CN, OH, $NH_2$, $NHR^c$, $NR^cR^c$, and $NR^cC(O)R^c$; wherein the $C_{1-4}$ alkyl, 5-10 membered heteroaryl, and 4-10 membered heterocycloalkyl of $R^b$ are each further optionally substituted with 1 or 2 independently selected $R^d$ substituents;

each $R^c$ is independently selected from H and $C_{1-6}$ alkyl optionally substituted with 1, 2, or 3 $R^f$ substituents;

each $R^f$ is independently selected from $C_{1-4}$ alkyl, halo, CN, $OR^g$, $C(O)R^g$, $C(O)NR^gR^g$, and $C(O)OR^g$;

each $R^g$ is independently selected from H and $C_{1-6}$ alkyl;

each $R^h$ is independently selected from $C_{1-6}$ alkyl, $C_{2-6}$ alkenyl, $C_{2-6}$ alkynyl, halo, $OR^i$, $C(O)R^i$, $C(O)NR^iR^i$, and $C(O)OR^i$;

each $R^i$ is independently selected from H and $C_{1-4}$ alkyl;

the subscript m is an integer of 0 or 1;
the subscript n is an integer of 0 or 1; and
the subscript p is an integer of 1 or 2.

In some embodiments, provided herein is a compound of Formula (I) or (Ia), or a pharmaceutically acceptable salt or a stereoisomer thereof, wherein:

ring A is 5- to 10-membered heteroaryl or 4- to 11-membered heterocycloalkyl, wherein the 5- to 10-membered heteroaryl and 4- to 11-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, or 3 $R^6$ substituents;

L is a bond, $-C(O)NR^{13}-$, $-NR^{13}C(O)-$, O, or $-NR^{13}-$;

one of $R^1$ and $R^2$ is $-(CR^8R^9)_p-NR^{10}R^{11}$ and the other is H, $C_{1-4}$ alkyl, $C_{1-4}$ alkoxy, $C_{1-4}$ haloalkyl, $C_{1-4}$ haloalkoxy, CN, halo, or OH, wherein the $C_{1-4}$ alkyl and $C_{1-4}$ alkoxy of $R^1$ or $R^2$ is optionally substituted with 1 or 2 substituents independently selected from $C_{1-4}$ alkoxy, $C_{1-4}$ haloalkyl, $C_{1-4}$ haloalkoxy, CN, halo, OH, $NH_2$, $-NHC_{1-4}$ alkyl and $-N(C_{1-4}$ alkyl$)_2$;

$R^3$ is methyl or halo;

$R^4$ is $C_{1-4}$ alkyl, $C_{1-4}$ alkoxy, $C_{1-4}$ haloalkyl, $C_{1-4}$ haloalkoxy, CN, halo, or OH;

$R^5$ is $C_{1-4}$ alkyl, $C_{1-4}$ alkoxy, $C_{1-4}$ haloalkyl, $C_{1-4}$ haloalkoxy, CN, halo, or OH;

each $R^6$ is independently selected from H, halo, $C_{1-6}$ alkyl, $C_{2-6}$ alkenyl, $C_{2-6}$ alkynyl, $C_{3-10}$ cycloalkyl, $C_{1-6}$ haloalkyl, $C_{1-6}$ haloalkoxy, CN, $OR^a$, $C(O)R^a$, $C(O)NR^aR^a$, $C(O)OR^a$, $NHR^a$, $NR^aR^a$, and $NR^aC(O)R^a$, wherein the $C_{1-6}$ alkyl, $C_{2-6}$ alkenyl, $C_{2-6}$ alkynyl, and $C_{3-10}$ cycloalkyl of $R^6$ are each optionally substituted with 1 or 2 $R^b$ substituents;

$R^7$ is H, $C_{1-4}$ alkyl, $C_{1-4}$ alkoxy, $C_{1-4}$ haloalkyl, $C_{1-4}$ haloalkoxy, CN, halo, or OH;

$R^8$ and $R^9$ are each independently selected from H, halo, CN, OH, $-COOH$, $C_{1-4}$ alkyl, $C_1$-4 alkoxy, $-NHC_{1-4}$ alkyl, $-N(C_{1-4}$ alkyl$)_2$, $C_{1-4}$ haloalkyl, and $C_{1-4}$ haloalkoxy;

$R^{10}$ and $R^{11}$ are each independently selected from H, $C_{1-6}$ alkyl, $C_{1-6}$ haloalkyl, $-C(O)R^g$, $-C(O)OR^g$, and $-C(O)NR^gR^g$, wherein the $C_{1-6}$ alkyl and $C_{1-6}$ haloalkyl of $R^{10}$ or $R^{11}$ are each optionally substituted with 1, 2 or 3 independently selected $R^f$ substituents;

or $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1 or 2 $R^h$ substituents;

$R^{12}$ is H, $C_{1-4}$ alkyl, $C_{1-4}$ alkoxy, $C_{1-4}$ haloalkyl, $C_{1-4}$ haloalkoxy, CN, halo, or OH; each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, or OH;

each $R^a$ is independently selected from H, CN, $C_{1-6}$ alkyl, $C_{1-4}$ haloalkyl, $C_{2-6}$ alkenyl, $C_{2-6}$ alkynyl, and $C_{3-10}$ cycloalkyl, wherein the $C_{1-6}$ alkyl, $C_{2-6}$ alkenyl, $C_{2-6}$ alkynyl, and $C_{3-10}$ cycloalkyl of $R^a$ are each optionally substituted with 1 or 2 $R^d$ substituents;

each $R^d$ is independently selected from $C_{1-6}$ alkyl, $C_{3-10}$ cycloalkyl, $C_{1-6}$ haloalkyl, halo, CN, $NH_2$, $OR^e$, $C(O)R^e$, $C(O)NR^eR^e$, $C(O)OR^e$, $NHR^e$, $NR^eR^e$, and $NR^eC(O)R^e$, wherein the $C_{1-6}$ alkyl and $C_{3-10}$ cycloalkyl of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, and $C_{2-6}$ alkynyl;

each $R^b$ substituent is independently selected from halo, $C_{1-6}$ alkyl, $C_{1-6}$ haloalkyl, $C_{1-6}$ haloalkoxy, $C_{3-10}$ cycloalkyl, 5-10 membered heteroaryl, 4-10 membered heterocycloalkyl, (5-10 membered heteroaryl)-$C_{1-4}$ alkyl-, (4-10 membered heterocycloalkyl)-$C_{1-4}$ alkyl-, CN, OH, $NH_2$, $OR^c$, $C(O)R^c$, $C(O)NR^cR^c$, $C(O)OR^c$, $NHR^c$, $NR^cR^c$, and $NR^cC(O)R^c$; wherein the $C_{1-4}$ alkyl, $C_{1-4}$ haloalkyl, $C_{1-4}$ haloalkoxy, $C_{3-10}$ cycloalkyl, 5-10 membered heteroaryl, 4-10 membered heterocycloalkyl, (5-10 membered heteroaryl)-$C_{1-4}$ alkyl- and (4-10 membered heterocycloalkyl)-$C_{1-4}$ alkyl- of $R^b$ are each further optionally substituted with 1 or 2 independently selected $R^d$ substituents;

each $R^c$ is independently selected from H, $C_{1-6}$ alkyl, $C_{1-4}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^c$ are each optionally substituted with 1, 2, or 3 $R^f$ substituents;

each $R^f$ is independently selected from $C_{1-4}$ alkyl, $C_{1-4}$ haloalkyl, $C_{2-6}$ alkenyl, $C_{2-6}$ alkynyl, halo, CN, $OR^g$, $C(O)R$, $C(O)NR^gR^g$, $C(O)OR$, $NHR^g$, $NR^gR^g$, and $NR^c(O)R^g$; each $R^g$ is independently selected from H, $C_{1-6}$ alkyl, $C_{1-4}$ haloalkyl, $C_{2-6}$ alkenyl, and $C_{2-6}$ alkynyl;

each $R^h$ is independently selected from $C_{1-6}$ alkyl, $C_{1-6}$ haloalkyl, $C_{1-6}$ haloalkoxy, $C_{2-6}$ alkenyl, $C_{2-6}$ alkynyl, halo, CN, $OR^i$, $C(O)R^i$, $C(O)NR^iR^i$, $C(O)OR^i$, $NHR^i$, $NR^iR^i$, and $NR^iC(O)R^i$;

each $R^i$ is independently selected from H, $C_{1-4}$ alkyl, $C_{1-6}$ haloalkyl, $C_{1-6}$ haloalkoxy, $C_{2-4}$ alkenyl, and $C_{2-4}$ alkynyl;

the subscript m is an integer of 0, 1 or 2;
the subscript n is an integer of 0, 1, or 2; and
the subscript p is an integer of 1, 2, or 3.

In some embodiments, provided herein is a compound of Formula (I) or (Ia), or a pharmaceutically acceptable salt or a stereoisomer thereof, wherein:

ring A is 5- to 10-membered heteroaryl or 4- to 11-membered heterocycloalkyl, wherein the 5- to 10-membered heteroaryl and 4- to 11-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1 or 2 $R^6$ substituents;

L is a bond, $-C(O)NR^{13}-$, $-NR^{13}C(O)-$, or $-NR^{13}-$;

one of $R^1$ and $R^2$ is $-(CR^8R^9)_p-NR^{10}R^{11}$ and the other is H, $C_{1-4}$ alkyl, or $C_{1-4}$ alkoxy, wherein the $C_{1-4}$ alkyl and $C_{1-4}$ alkoxy of $R^1$ or $R^2$ is optionally substituted with 1 or 2 substituents independently selected from $C_{1-4}$ alkoxy, CN, halo, OH, and $NH_2$;

$R^3$ is methyl or halo;
$R^4$ is $C_{1-4}$ alkyl, $C_{1-4}$ alkoxy, CN, halo, or OH;
$R^5$ is $C_{1-4}$ alkyl, $C_{1-4}$ alkoxy, CN, halo, or OH;

each $R^6$ is independently selected from H, halo, $C_{1-6}$ alkyl, $C_{2-6}$ alkenyl, $C_{2-6}$ alkynyl, CN, $OR^a$, $NHR^a$, $NR^aR^a$, and $C_{3-10}$ cycloalkyl, wherein the $C_{1-6}$ alkyl, $C_{2-6}$ alkenyl, $C_{2-6}$ alkynyl, and $C_{3-10}$ cycloalkyl of $R^6$ are each optionally substituted with 1 or 2 $R^b$ substituents;

$R^7$ is H, $C_{1-4}$ alkyl, $C_{1-4}$ alkoxy, CN, halo, or OH;

$R^8$ and $R^9$ are each independently selected from H, halo, CN, OH, and $C_{1-4}$ alkyl;

$R^{10}$ and $R^{11}$ are each independently selected from H, $C_{1-6}$ alkyl, and $C_{1-6}$ haloalkyl, wherein the $C_{1-6}$ alkyl and $C_{1-6}$ haloalkyl of $R^{10}$ or $R^{11}$ are each optionally substituted with 1, 2 or 3 independently selected $R^f$ substituents;

or $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1 or 2 $R^h$ substituents;

$R^{12}$ is H or $C_{1-4}$ alkyl;
each $R^{13}$ is independently H or $C_{1-6}$ alkyl;

each $R^a$ is independently selected from H, $C_{1-6}$ alkyl, and $C_{3-10}$ cycloalkyl optionally substituted with 1 or 2 $R^d$ substituents;

each $R^d$ is independently selected from $C_{1-6}$ alkyl, $C_{3-10}$ cycloalkyl, $C_{1-6}$ haloalkyl, halo, CN, $OR^e$ and $C(O)OR^e$, wherein the $C_{1-6}$ alkyl and $C_{3-10}$ cycloalkyl of $R^d$ are each optionally substituted with 1, 2, or 3 independently selected $R^f$ substituents;

each $R^e$ is independently selected from H and $C_{1-6}$ alkyl;

each $R^b$ substituent is independently selected from halo, $C_{1-6}$ alkyl, $C_{3-10}$ cycloalkyl, 5-10 membered heteroaryl, 4-10 membered heterocycloalkyl, CN, OH, $NH_2$, $NHR^c$, $NR^cR^c$, and $NR^cC(O)R^c$; wherein the $C_{1-4}$ alkyl, $C_{3-10}$ cycloalkyl, 5-10 membered heteroaryl, and 4-10 membered heterocycloalkyl of $R^b$ are each further optionally substituted with 1 or 2 independently selected $R^d$ substituents;

each $R^c$ is independently selected from H and $C_{1-6}$ alkyl optionally substituted with 1, 2, or 3 $R^f$ substituents;

each $R^f$ is independently selected from $C_{1-4}$ alkyl, halo, CN, $OR^g$, $C(O)R^g$, $C(O)NR^gR^g$, and $C(O)OR^g$;

each $R^g$ is independently selected from H and $C_{1-6}$ alkyl;

each $R^h$ is independently selected from $C_{1-6}$ alkyl, $C_{2-6}$ alkenyl, $C_{2-6}$ alkynyl, halo, $OR^i$, $C(O)R^i$, $C(O)NR^iR^i$, and $C(O)OR^i$;

each $R^i$ is independently selected from H and $C_{1-4}$ alkyl;
the subscript m is an integer of 0 or 1;
the subscript n is an integer of 0 or 1; and
the subscript p is an integer of 1 or 2.

In some embodiments, provided herein is a compound of Formula (I) or (Ia), or a pharmaceutically acceptable salt or a stereoisomer thereof, wherein:

ring A is 5- to 10-membered heteroaryl, 4- to 11-membered heterocycloalkyl, or $C_{6-10}$ aryl, wherein the 5- to 10-membered heteroaryl and 4- to 11-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2 or 3 $R^6$ substituents;

L is a bond, —C(O)NR$^{13}$—, —NR$^{13}$C(O)—, —(CR$^{14}$R$^{15}$)$_q$—O—, —O(CR$^{14}$R$^{15}$)$_q$—, or —NR$^{13}$—; one of R$^1$ and R$^2$ is —(CR$^8$R$^9$)$_p$—NR$^{10}$R$^{11}$ and the other is H, C$_{1-4}$ alkyl, or C$_{1-4}$ alkoxy, wherein the C$_{1-4}$ alkyl and C$_{1-4}$ alkoxy of R$^1$ or R$^2$ is optionally substituted with 1 or 2 substituents independently selected from C$_{1-4}$ alkoxy, CN, halo, OH, and NH$_2$;

R$^3$ is methyl or halo;

R$^4$ is C$_{1-4}$ alkyl, C$_{1-4}$ alkoxy, CN, halo, or OH;

R$^5$ is C$_{1-4}$ alkyl, C$_{1-4}$ alkoxy, CN, halo, or OH;

each R$^6$ is independently selected from H, halo, C$_{1-6}$ alkyl, C$_{2-6}$ alkenyl, C$_{2-6}$ alkynyl, CN, OR$^a$, NHR$^a$, NR$^a$R$^a$, C$_{3-10}$ cycloalkyl, 4-14 membered heterocycloalkyl, (4-14 membered heterocycloalkyl)-C$_{1-4}$ alkyl-, CN, OR$^a$, and C(O)R$^a$, wherein the C$_{1-6}$ alkyl, C$_{2-6}$ alkenyl, C$_{2-6}$ alkynyl, C$_{3-10}$ cycloalkyl, 4-14 membered heterocycloalkyl, and (4-14 membered heterocycloalkyl)-C$_{1-4}$ alkyl- of R$^6$ are each optionally substituted with 1 or 2 R$^b$ substituents;

each R$^{13}$ is independently H or C$_{1-6}$ alkyl;

R$^{14}$ and R$^{15}$ are each independently selected from H and C$_{1-4}$ alkyl;

R$^7$ is H, C$_{1-4}$ alkyl, C$_{1-4}$ alkoxy, CN, halo, or OH;

R$^8$ and R$^9$ are each independently selected from H, halo, CN, OH, and C$_{1-4}$ alkyl;

R$^{10}$ and R$^{11}$ are each independently selected from H, C$_{1-6}$ alkyl, and C$_{1-6}$ haloalkyl, wherein the C$_{1-6}$ alkyl and C$_{1-6}$ haloalkyl of R$^{10}$ or R$^{11}$ are each optionally substituted with 1, 2 or 3 independently selected R$^f$ substituents;

or R$^{10}$ and R$^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1 or 2 R$^h$ substituents;

R$^{12}$ is H or C$_{1-4}$ alkyl;

each R$^{13}$ is independently H or C$_{1-6}$ alkyl;

each R$^a$ is independently selected from H, C$_{1-6}$ alkyl, C$_{3-10}$ cycloalkyl, 4-14 membered heterocycloalkyl, (5-14 membered heteroaryl)-C$_{1-4}$ alkyl-, and (4-14 membered heterocycloalkyl)-C$_{1-4}$ alkyl-, wherein C$_{1-6}$ alkyl, C$_{3-10}$ cycloalkyl, 4-14 membered heterocycloalkyl, (5-14 membered heteroaryl)-C$_{1-4}$ alkyl- and (4-14 membered heterocycloalkyl)-C$_{1-4}$ alkyl- of R$^a$ are each optionally substituted with 1 or 2 independently selected R$^d$ substituents;

each R$^d$ is independently selected from C$_{1-6}$ alkyl, C$_{3-10}$ cycloalkyl, 4-14 membered heterocycloalkyl, C$_{1-6}$ haloalkyl, halo, CN, OR$^e$, C(O)OR$^e$, NHR$^e$, and NR$^e$R$^e$, wherein the C$_{1-6}$ alkyl, C$_{3-10}$ cycloalkyl, and 4-14 membered heterocycloalkyl of R$^d$ are each optionally substituted with 1, 2, or 3 independently selected R$^f$ substituents;

each R$^e$ is independently selected from H and C$_{1-6}$ alkyl;

each R$^b$ substituent is independently selected from halo, C$_{1-6}$ alkyl, C$_{3-10}$ cycloalkyl, 5-10 membered heteroaryl, 4-10 membered heterocycloalkyl, CN, OH, OR$^c$, C(O)NR$^c$R$^c$, C(O)OR$^c$, NH$_2$, NHR$^c$, NR$^c$R$^c$, and NR$^c$C(O)R$^c$; wherein the C$_{1-4}$ alkyl, C$_{3-10}$ cycloalkyl, 5-10 membered heteroaryl, and 4-10 membered heterocycloalkyl of R$^b$ are each further optionally substituted with 1 or 2 independently selected R$^d$ substituents;

each R$^c$ is independently selected from H, C$_{1-6}$ alkyl, and C$_{3-10}$ cycloalkyl, wherein C$_{1-6}$ alkyl and C$_{3-10}$ cycloalkyl are each optionally substituted with 1, 2, or 3 R$^f$ substituents;

each R$^f$ is independently selected from C$_{1-4}$ alkyl, halo, CN, OR$^g$, C(O)R$^g$, C(O)NR$^g$R$^g$, C(O)OR$^9$, and NR$^g$C(O)R$^g$;

each R$^g$ is independently selected from H and C$_{1-6}$ alkyl;

each R$^h$ is independently selected from C$_{1-6}$ alkyl, C$_{2-6}$ alkenyl, C$_{2-6}$ alkynyl, halo, OR, C(O)R$^i$, C(O)NR$^i$R$^i$, and C(O)OR$^i$;

each R$^i$ is independently selected from H and C$_{1-4}$ alkyl;

the subscript m is an integer of 0 or 1;

the subscript n is an integer of 0 or 1; and the subscript p is an integer of 1 or 2.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "C$_{1-6}$ alkyl" is specifically intended to individually disclose (without limitation) methyl, ethyl, C$_3$ alkyl, C$_4$ alkyl, C$_5$ alkyl and C$_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR (CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "C$_{n-m}$" indicates a range which includes the endpoints, wherein n and m are integers and indicate the number of carbons. Examples include C$_{1-4}$, C$_{1-6}$ and the like.

The term "alkyl" employed alone or in combination with other terms, refers to a saturated hydrocarbon group that may be straight-chained or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The term "amino" refers to a group of formula —$NH_2$.

The term "carbamyl" refers to a group of formula —C(O)$NH_2$.

The term "carbonyl", employed alone or in combination with other terms, refers to a —C(=O)— group, which also may be written as C(O).

The term "cyano" or "nitrile" refers to a group of formula —C≡N, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to $\{2(n \text{ to } m)+1\}$ halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "sulfido" refers to a sulfur atom as a divalent substituent, forming a thiocarbonyl group (C=S) when attached to carbon.

The term "aromatic" refers to a carbocycle or heterocycle having one or more polyunsaturated rings having aromatic character (i.e., having (4n+2) delocalized $\pi$ (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, indanyl, indenyl and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl. In some embodiments, the aryl group is naphthyl.

The term "heteroatom" used herein is meant to include boron, phosphorus, sulfur, oxygen and nitrogen.

The term "heteroaryl" or "heteroaromatic," employed alone or in combination with other terms, refers to a monocyclic or polycyclic aromatic heterocycle having at least one heteroatom ring member selected from boron, phosphorus, sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-14, or 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, benzothiophenyl, benzofuranyl, benzisoxazolyl, imidazo[1,2-b]thiazolyl, purinyl, and the like.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6, 7, 8, 9, 10, 11, 12, 13, or 14 ring-forming carbons ($C_{3-14}$). In some embodiments, the cycloalkyl group has 3 to 14 members, 3 to 10 members, 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from boron, nitrogen, sulfur oxygen and phosphorus, and which has 4-14 ring members, 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic or polycyclic (e.g., having two or three fused or bridged rings) ring systems or spirorcycles. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or $S(O)_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include azetidinyl, azepanyl, dihydrobenzofuranyl, dihydrofuranyl, dihydropyranyl, morpholino, 3-oxa-9-azaspiro[5.5]undecanyl, 1-oxa-8-azaspiro[4.5]decanyl, piperidinyl, piperazinyl, oxopiperazinyl, pyranyl, pyrrolidinyl, quinuclidinyl, tetrahydrofuranyl, tetrahydropyranyl, 1,2,3,4-tetrahydroquinolinyl, tropanyl, 4,5,6,7-tetrahydrothiazolo[5,4-c]pyridinyl, and thiomorpholino.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art.

The term, "compound," as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

II. Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of formula (I) can be prepared, e.g., using a process as illustrated in Schemes 1-4.

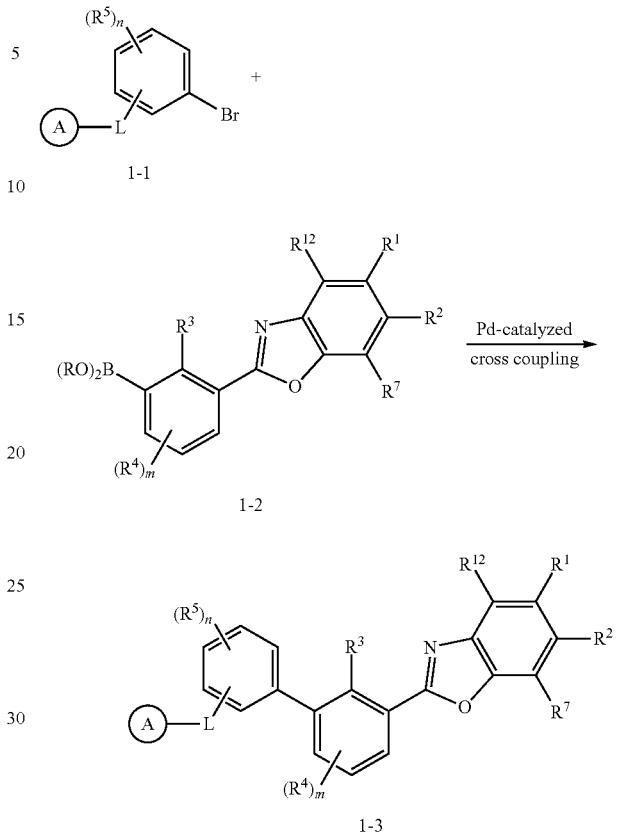

Scheme 1

The compounds of Formula 1-3 can be prepared according to Scheme 1. Aryl bromides 1-1 can react with boronates 1-2 under standard Suzuki coupling condition (e.g., in the presence of a palladium catalyst and a suitable base) to give the benzo[d]oxazol-2-yl substituted biaryl compounds 1-3.

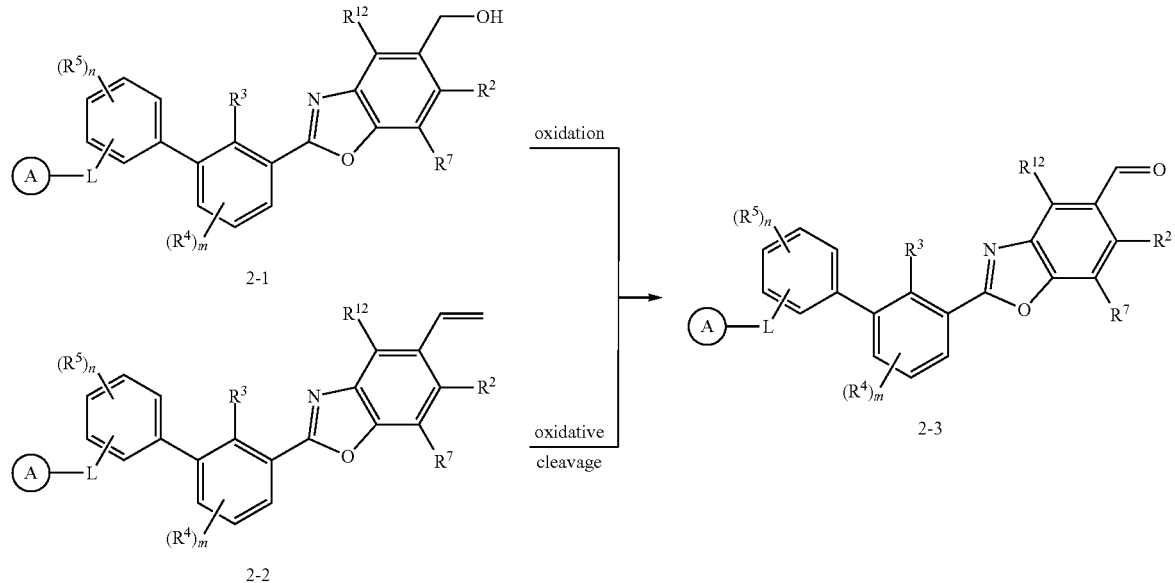

Scheme 2

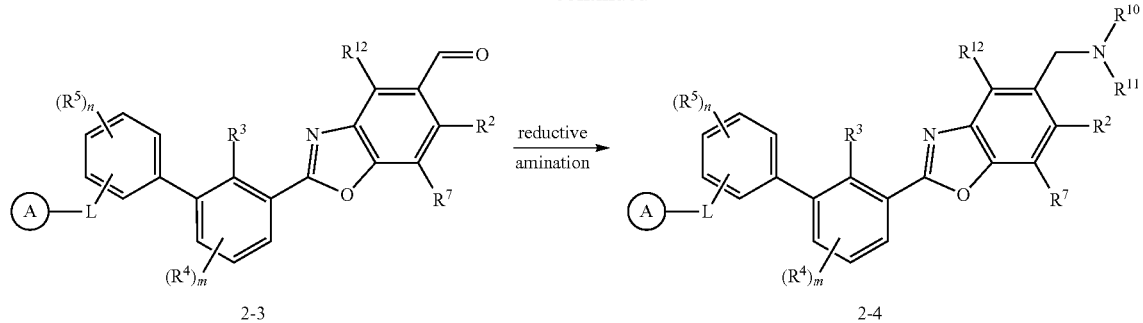

The benzo[d]oxazol-2-yl substituted biaryl compounds of Formula 2-3 can be prepared according to Scheme 2, starting from compounds of formula 2-1 or 2-2 which can be prepared according to procedures as described in Scheme 1. Briefly, the benzylic alcohols 2-1 can be transformed to the corresponding aldehydes 2-3 by oxidation (e.g., Dess-Martin periodinane as oxidant). The vinyl group in compounds 2-2 can be oxidatively cleaved by $NaIO_4$ in the presence of catalytic amount of $OsO_4$ or its equivalents to form aldehydes 2-3. Then the aldehydes 2-3 react with amines of formula $HNR^{10}R^{11}$ under standard reductive amination conditions (e.g., sodium triacetoxyborohydride or sodium cyanoborohydride as reducing reagents) to generate compounds of formula 2-4.

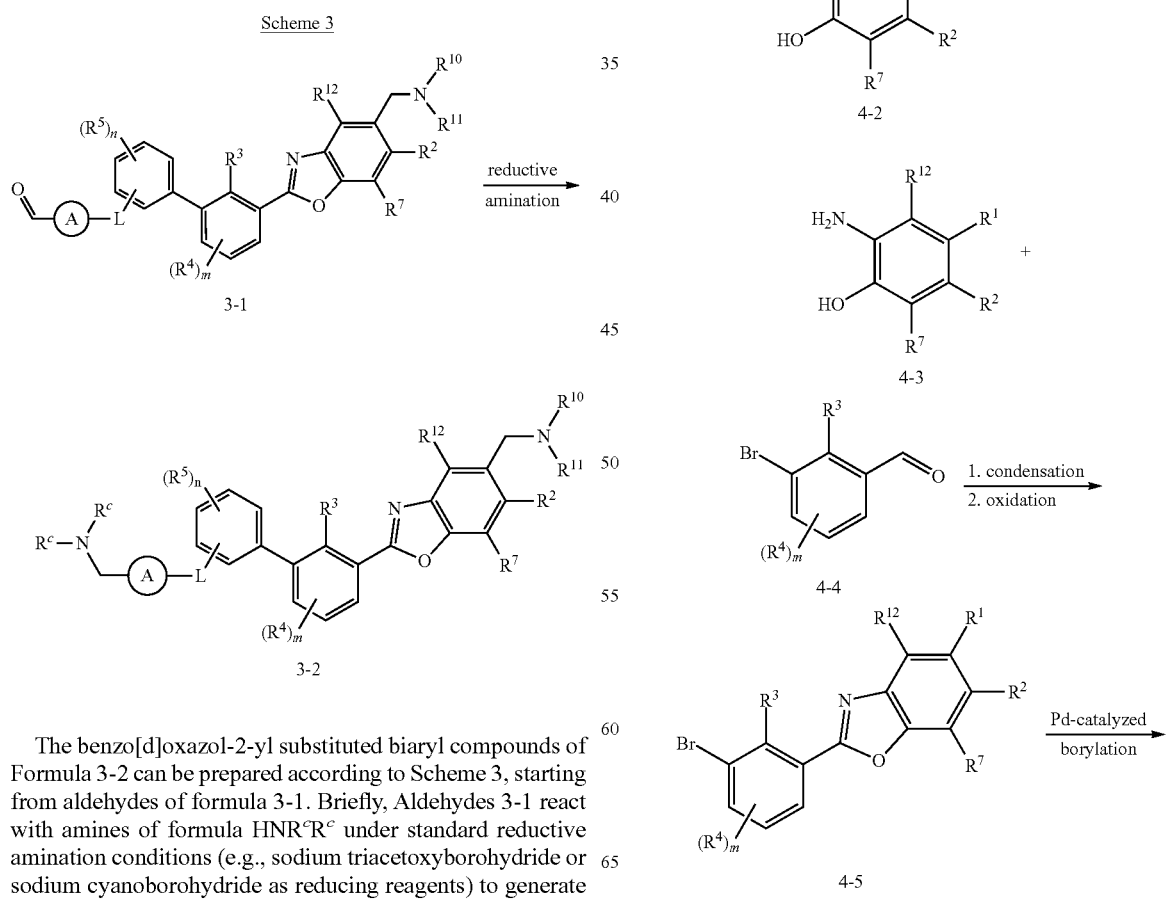

The benzo[d]oxazol-2-yl substituted biaryl compounds of Formula 3-2 can be prepared according to Scheme 3, starting from aldehydes of formula 3-1. Briefly, Aldehydes 3-1 react with amines of formula $HNR^cR^c$ under standard reductive amination conditions (e.g., sodium triacetoxyborohydride or sodium cyanoborohydride as reducing reagents) to generate compounds of formula 3-2.

-continued

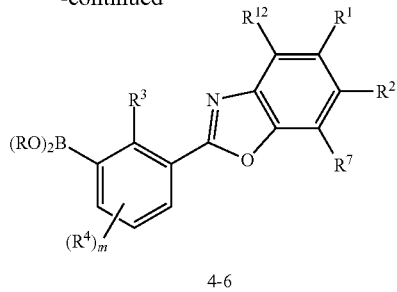

4-6

The benzo[d]oxazol-2-yl substituted aryl boronates of Formula 4-6 can be prepared according to Scheme 4, starting from phenols of formula 4-1. Briefly, Phenols 4-1 can be nitrated to nitro compounds 4-2 under standard nitration condition (e.g., nitric acid as nitrating reagent in the presence of acetic acid). The nitro compounds are reduced to anilines 4-3 either through Pd/C catalyzed hydrogenation or by iron powder in acetic acid. The anilines 4-3 condense with aldehydes 4-4 in absolute ethanol to afford dihydrobenzo[d]oxazole intermediates, which can be oxidized by dichlorodicyanoquinone to form benzo[d]oxazoles 4-5. The bromo group of benzo[d]oxazoles 4-5 can be converted to the boronic esters 4-6 under standard conditions [e.g., in the presence of bis(pinacolato)diboron and a palladium catalyst, such as, tetrakis(triphenylphosphine) palladium(0), palladium(II) acetate].

III. Uses of the Compounds

Compounds of the present disclosure can inhibit the activity of PD-1/PD-L1 protein/protein interaction and, thus, are useful in treating diseases and disorders associated with activity of PD-1 and the diseases and disorders associated with PD-L1 including its interaction with other proteins such as PD-1 and B7-1 (CD80). In certain embodiments, the compounds of the present disclosure, or pharmaceutically acceptable salts or stereoisomers thereof, are useful for therapeutic administration to enhance, stimulate and/or increase immunity in cancer, chronic infection or sepsis, including enhancement of response to vaccination. In some embodiments, the present disclosure provides a method for inhibiting the PD-1/PD-L1 protein/protein interaction. The method includes administering to an individual or a patient a compound of Formula (I) or of any of the formulas as described herein, or of a compound as recited in any of the claims and described herein, or a pharmaceutically acceptable salt or a stereoisomer thereof. The compounds of the present disclosure can be used alone, in combination with other agents or therapies or as an adjuvant or neoadjuvant for the treatment of diseases or disorders, including cancer or infection diseases. For the uses described herein, any of the compounds of the disclosure, including any of the embodiments thereof, may be used.

The compounds of the present disclosure inhibit the PD-1/PD-L1 protein/protein interaction, resulting in a PD-1 pathway blockade. The blockade of PD-1 can enhance the immune response to cancerous cells and infectious diseases in mammals, including humans. In some embodiments, the present disclosure provides treatment of an individual or a patient in vivo using a compound of Formula (I) or a salt or stereoisomer thereof such that growth of cancerous tumors is inhibited. A compound of Formula (I) or of any of the formulas as described herein, or a compound as recited in any of the claims and described herein, or a salt or stereoisomer thereof, can be used to inhibit the growth of cancerous tumors. Alternatively, a compound of Formula (I) or of any of the formulas as described herein, or a compound as recited in any of the claims and described herein, or a salt or stereoisomer thereof, can be used in conjunction with other agents or standard cancer treatments, as described below. In one embodiment, the present disclosure provides a method for inhibiting growth of tumor cells in vitro. The method includes contacting the tumor cells in vitro with a compound of Formula (I) or of any of the formulas as described herein, or of a compound as recited in any of the claims and described herein, or of a salt or stereoisomer thereof. In another embodiment, the present disclosure provides a method for inhibiting growth of tumor cells in an individual or a patient. The method includes administering to the individual or patient in need thereof a therapeutically effective amount of a compound of Formula (I) or of any of the formulas as described herein, or of a compound as recited in any of the claims and described herein, or a salt or a stereoisomer thereof.

In some embodiments, provided herein is a method for treating cancer. The method includes administering to a patient in need thereof, a therapeutically effective amount of a compound of Formula (I) or any of the formulas as described herein, a compound as recited in any of the claims and described herein, or a salt thereof. Examples of cancers include those whose growth may be inhibited using compounds of the disclosure and cancers typically responsive to immunotherapy.

In some embodiments, the present disclosure provides a method of enhancing, stimulating and/or increasing the immune response in a patient. The method includes administering to the patient in need thereof a therapeutically effective amount of a compound of Formula (I) or any of the formulas as described herein, a compound or composition as recited in any of the claims and described herein, or a salt thereof.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers, especially metastatic cancers that express PD-L1.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, colon cancer, lung cancer (e.g. non-small cell lung cancer and small cell lung cancer), squamous cell head and neck cancer, urothelial cancer (e.g. bladder) and cancers with high microsatellite instability (MSI$^{high}$). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, cancers that are treatable using the compounds of the present disclosure include, but are not limited to, cholangiocarcinoma, bile duct cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, the compounds of the present disclosure can be used to treat sickle cell disease and sickle cell anemia.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

PD-1 pathway blockade with compounds of the present disclosure can also be used for treating infections such as viral, bacteria, fungus and parasite infections. The present disclosure provides a method for treating infections such as viral infections. The method includes administering to a patient in need thereof, a therapeutically effective amount of a compound of Formula (I) or any of the formulas as described herein, a compound as recited in any of the claims and described herein, a salt thereof. Examples of viruses causing infections treatable by methods of the present disclosure include, but are not limit to, human immunodeficiency virus, human papillomavirus, influenza, hepatitis A, B, C or D viruses, adenovirus, poxvirus, herpes simplex viruses, human cytomegalovirus, severe acute respiratory syndrome virus, ebola virus, and measles virus. In some embodiments, viruses causing infections treatable by methods of the present disclosure include, but are not limit to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, comovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

The present disclosure provides a method for treating bacterial infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic bacteria causing infections treatable by methods of the disclosure include *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

The present disclosure provides a method for treating fungus infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic fungi causing infections treatable by methods of the disclosure include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

The present disclosure provides a method for treating parasite infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

It is believed that compounds of Formula (I), or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors or one or more therapies for the treatment of diseases, such as cancer or infections. Examples of diseases and indications treatable with combination therapies include those as described herein. Examples of cancers include solid tumors and liquid tumors, such as blood cancers. Examples of infections include viral infections, bacterial infections, fungus infections or parasite infections. For example, the compounds of the present disclosure can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, PI3K (alpha, beta, gamma, delta), CSFIR, KIT, FLK-II, KDR/FLK-1, FLK-4, fit-1, FGFR1, FGFR2, FGFR3, FGFR4, c-Met, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat, NLG919, or BMS-986205), an LSD1 inhibitor (e.g., INCB59872 and INCB60003), a TDO inhibitor, a PI3K-delta inhibitor (e.g., INCB50797 and INCB50465), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer), an adenosine receptor antagonist (e.g., A2a/A2b receptor antagonist), an HPK1 inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), a poly ADP ribose polymerase (PARP) inhibitor such as rucaparib, olaparib, niraparib, veliparib, or talazoparib, an arginase inhibitor (INCB01158), and an adenosine receptor antagonist or combinations thereof.

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olaparib, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib and zoledronate.

Other anti-cancer agent(s) include antibody therapeutics such as trastuzumab (Herceptin), antibodies to costimulatory molecules such as CTLA-4 (e.g., ipilimumab), 4-1BB (e.g., urelumab, utomilumab), antibodies to PD-1 and PD-L1, or antibodies to cytokines (IL-10, TGF-β, etc.). Examples of antibodies to PD-1 and/or PD-L1 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

Compounds of the present disclosure can be used in combination with one or more immune checkpoint inhibitors for the treatment of diseases, such as cancer or infections. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab or pembrolizumab. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab.

In some embodiments, the inhibitor of an immune checkpoint molecule is an inhibitor of LAG3, e.g., an anti-LAG3 antibody. In some embodiments, the anti-LAG3 antibody is BMS-986016, LAG525 or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

The compounds of the present disclosure can further be used in combination with one or more anti-inflammatory agents, steroids, immunosuppressants or therapeutic antibodies.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, *Giardia*, Malaria, *Leishmania, Staphylococcus aureus, Pseudomonas Aeruginosa*.

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, comovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

Pathogenic parasites causing infections treatable by methods of the disclosure include, but are not limited to, *Entamoeba histolytica, Balantidium coli*, Naegleriafowleri, *Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma* gondi, and *Nippostrongylus brasiliensis*.

When more than one pharmaceutical agent is administered to a patient, they can be administered simultaneously, separately, sequentially, or in combination (e.g., for more than two agents).

IV. Formulation, Dosage Forms and Administration

When employed as pharmaceuticals, the compounds of the present disclosure can be administered in the form of pharmaceutical compositions. Thus the present disclosure provides a composition comprising a compound of Formula (I) or any of the formulas as described herein, a compound as recited in any of the claims and described herein, or a pharmaceutically acceptable salt thereof, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel KOOLV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

V. Labeled Compounds and Assay Methods

The compounds of the present disclosure can further be useful in investigations of biological processes in normal and abnormal tissues. Thus, another aspect of the present invention relates to labeled compounds of the invention (radio-labeled, fluorescent-labeled, etc.) that would be useful not only in imaging techniques but also in assays, both in vitro and in vivo, for localizing and quantitating PD-1 or PD-L1 protein in tissue samples, including human, and for identifying PD-L1 ligands by inhibition binding of a labeled compound. Accordingly, the present invention includes PD-1/PD-L1 binding assays that contain such labeled compounds.

The present invention further includes isotopically-substituted compounds of the disclosure. An "isotopically-substituted" compound is a compound of the invention where one or more atoms are replaced or substituted by an atom having the same atomic number but a different atomic mass or mass number, e.g., a different atomic mass or mass number from the atomic mass or mass number typically found in nature (i.e., naturally occurring). It is to be understood that a "radio-labeled" compound is a compound that has incorporated at least one isotope that is radioactive (e.g., radionuclide). Suitable radionuclides that may be incorporated in compounds of the present invention include but are not limited to $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro PD-L1 protein labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}$, $^{123}I$, $^{124}I$, $^{131}I$, $^{75}Br$, $^{76}Br$ or $^{77}Br$ will generally be most useful.

In some embodiments the radionuclide is selected from the group consisting of $^3H$, $^{14}C$, $^{125}I$, $^{35}S$ and $^{82}Br$. Synthetic methods for incorporating radio-isotopes into organic compounds are known in the art.

Specifically, a labeled compound of the invention can be used in a screening assay to identify and/or evaluate compounds. For example, a newly synthesized or identified compound (i.e., test compound) which is labeled can be evaluated for its ability to bind a PD-L1 protein by monitoring its concentration variation when contacting with the PD-L1 protein, through tracking of the labeling. For example, a test compound (labeled) can be evaluated for its ability to reduce binding of another compound which is known to bind to a PD-L1 protein (i.e., standard compound). Accordingly, the ability of a test compound to compete with the standard compound for binding to the PD-L1 protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

VI. Kits

The present disclosure also includes pharmaceutical kits useful, e.g., in the treatment or prevention of diseases or disorders associated with the activity of PD-L1 including its interaction with other proteins such as PD-1 and B7-1 (CD80), such as cancer or infections, which include one or more containers containing a pharmaceutical composition comprising a therapeutically effective amount of a compound of Formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of PD-1/PD-L1 protein/protein interaction according to at least one assay described herein.

EXAMPLES

Experimental procedures for compounds of the invention are provided below. Open Access Preparative LCMS Purification of some of the compounds prepared was performed on Waters mass directed fractionation systems. The basic equipment setup, protocols and control software for the operation of these systems have been described in detail in literature. See, e.g., Blom, "Two-Pump At Column Dilution Configuration for Preparative LC-MS", K. Blom, *J. Combi. Chem.*, 2002, 4, 295-301; Blom et al., "Optimizing Preparative LC-MS Configurations and Methods for Parallel Synthesis Purification", *J. Combi. Chem.*, 2003, 5, 670-83; and Blom et al., "Preparative LC-MS Purification: Improved Compound Specific Method Optimization", *J. Combi. Chem.*, 2004, 6, 874-883.

Example 1

(S)-1-((7-chloro-2-(2'-chloro-3'-(5-(((2-hydroxyethyl)amino)methyl)picolinamido)-2-methyl-[1,1'-biphenyl]-3-yl)benzo[d]oxazol-5-yl)methyl)piperidine-2-carboxylic acid

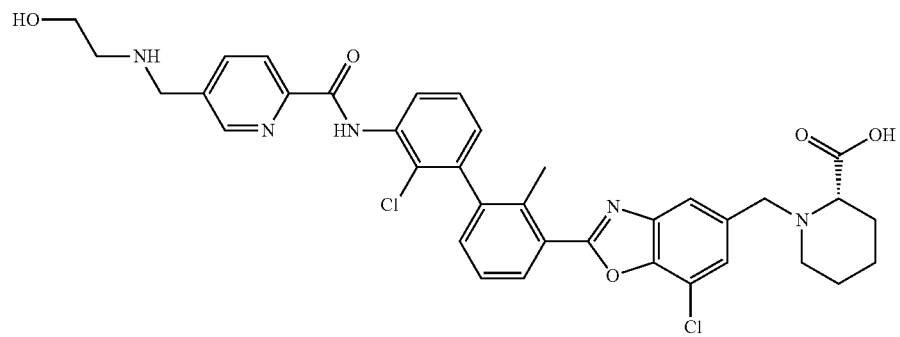 [SMILES: Cc1c(-c2nc3cc(CN4CCCC[C@H]4C(=O)O)cc(Cl)c3o2)cccc1-c1cccc(NC(=O)c2ccc(CNCCO)cn2)c1Cl]

Step 1: methyl 3-chloro-4-hydroxy-5-nitrobenzoate

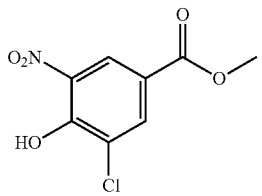

To a solution of methyl 3-chloro-4-hydroxybenzoate (Alfa Aesar, # A512389: 10.0 g, 53.6 mmol) in acetic acid (20.0 mL, 352 mmol) was added a mixture of acetic acid (20.0 mL, 352 mmol) and nitric acid (4.72 mL, 112 mmol) dropwise at 0° C. Then the ice bath was removed and the thick mixture was stirred at room temperature for 2 hrs. Then an equal volume of water was added to the reaction suspension at 0° C. The mixture was filtered and washed with cold water. A yellow solid was obtained as desired product without further purification. LC-MS calculated for $C_8H_7ClNO_5$ (M+H)$^+$: m/z=232.0; found 232.0.

Step 2: methyl 3-amino-5-chloro-4-hydroxybenzoate

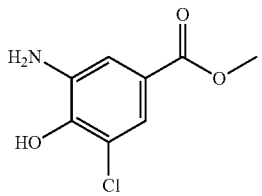

Methyl 3-chloro-4-hydroxy-5-nitrobenzoate (2.08 g, 8.98 mmol) was hydrogenated under ambient pressure of hydrogen using palladium on carbon (10 wt %, 0.57 g, 0.539 mmol) in ethyl acetate (15 mL) for 1 h. The resulting suspension was filtered through a pad of Celite and washed with EtOAc and the solvent was removed under reduced pressure to give a crude product, which was purified by column chromatography (eluting with MeOH/DCM 0%-10%). LC-MS calculated for $C_8H_9ClNO_3$ (M+H)$^+$: m/z=202.0; found 202.0.

Step 3: methyl 2-(3-bromo-2-methylphenyl)-7-chlorobenzo[d]oxazole-5-carboxylate

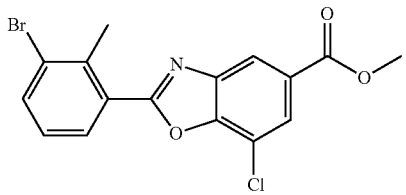 [SMILES: COC(=O)c1cc(Cl)c2oc(-c3cccc(Br)c3C)nc2c1]

A mixture of methyl 3-amino-5-chloro-4-hydroxybenzoate (1.04 g, 5.16 mmol), 3-bromo-2-methylbenzaldehyde (AstaTech, #52940: 0.98 g, 4.92 mmol) in EtOH (25 ml) was placed in a vial and stirred at room temperature for 1 h. The mixture was then concentrated. The residue was redissovled in methylene chloride (25 mL) and dichlorodicyanoquinone (1.12 g, 4.92 mmol) was added. The mixture was stirred at room temperature for 30 min. The reaction was diluted with methylene chloride and washed with an aqueous $Na_2S_2O_3$ solution and $NaHCO_3$ solution. The organic phase was dried over $MgSO_4$, filtered and the filtrate was concentrated. The crude residue was used directly without further purification. LC-MS calculated for $C_{16}H_{12}BrClNO_3$ (M+H)$^+$: m/z=380.0, 382.0; found 379.9, 381.9.

Step 4: (2-(3-bromo-2-methylphenyl)-7-chlorobenzo[d]oxazol-5-yl)methanol

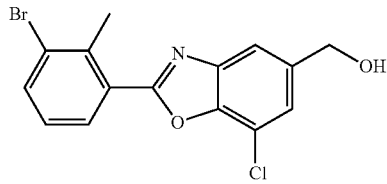 [SMILES: Cc1c(Br)cccc1-c1nc2cc(CO)cc(Cl)c2o1]

To a solution of methyl 2-(3-bromo-2-methylphenyl)-7-chlorobenzo[d]oxazole-5-carboxylate (395.0 mg, 1.04 mmol) in DCM (10.0 ml) was added diisobutylaluminum hydride in DCM (1.0 M, 2.08 ml, 2.08 mmol) dropwise at −78 OC. The mixture was slowly warmed up to 0° C. Then the mixture was quenched with EtOAc and DCM, followed by aqueous Rochell's salt solution. The mixture was stirred vigorously at room temperature for 1 h. The organic phase was separated and dried over $MgSO_4$ before filtering through a short pad of Celite to remove solids. The filtrate was concentrated and purified by column chromatography (eluting with 0-5% MeOH/DCM) to give the desired product. LC-MS calculated for $C_{15}H_{12}BrClNO_2$ (M+H)$^+$: m/z=352.0, 354.0; found 352.0, 354.0.

Step 5: (7-chloro-2-(2-methyl-3-(4,4,5,5-tetramethyl-1,3,2-dioxaborolan-2-yl)phenyl)benzo[d]oxazol-5-yl)methanol

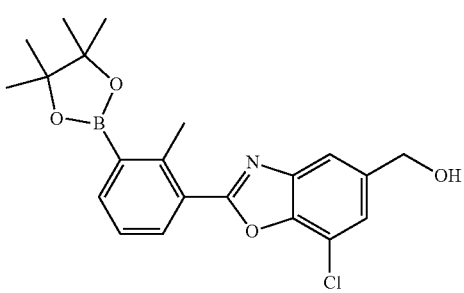 [SMILES: Cc1c(B2OC(C)(C)C(C)(C)O2)cccc1-c1nc2cc(CO)cc(Cl)c2o1]

A mixture of (2-(3-bromo-2-methylphenyl)-7-chlorobenzo[d]oxazol-5-yl)methanol (113 mg, 0.322 mmol), bis(pinacolato)diboron (98 mg, 0.386 mmol), dichloro[1,1'-bis(diphenylphosphino)ferrocene]palladium (II) dichloromethane adduct (26.3 mg, 0.032 mmol) and anhydrous potassium acetate (79 mg, 0.804 mmol) in 1,4-dioxane (3.5 mL) was purged with nitrogen and stirred at 110° C. for 2 h. The crude was diluted with DCM, and then filtered through Celite. The filtrate was concentrated. The residue was purified by flash chromatography (eluting with EtOAc/Hexanes, 0-40%). LC-MS calculated for $C_{21}H_{24}BClNO_4$ (M+H)$^+$: m/z=400.2; found 400.2.

Step 6: N-(3-bromo-2-chlorophenyl)-5-(dimethoxymethyl)picolinamide

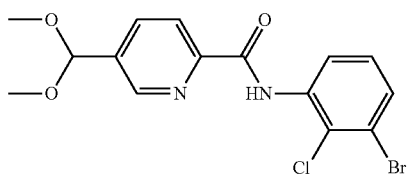 [SMILES: COC(OC)c1ccc(C(=O)Nc2cccc(Br)c2Cl)nc1]

To a solution of 3-bromo-2-chloroaniline (345 mg, 1.67 mmol) and methyl 5-(dimethoxymethyl)picolinate (388 mg, 1.84 mmol) in THF (10 ml) was added potassium tert-butoxide in THF (1.0 M, 3.34 ml, 3.34 mmol) at room temperature, the mixture was stirred at this temperature for 2 hrs. Water was then added to quench the reaction. The mixture was extracted with DCM three times. The organic phases were combined, dried over MgSO$_4$, filtered and the filtrate was concentrated. The residue was used directly without further purification. LC-MS calculated for $C_{15}H_{15}BrClN_2O_3$(M+H)$^+$: m/z=385.0; found 385.0.

Step 7: N-(2-chloro-3'-(7-chloro-5-(hydroxymethyl)benzo[d]oxazol-2-yl)-2'-methyl-[1,1'-biphenyl]-3-yl)-5-(dimethoxymethyl)picolinamide

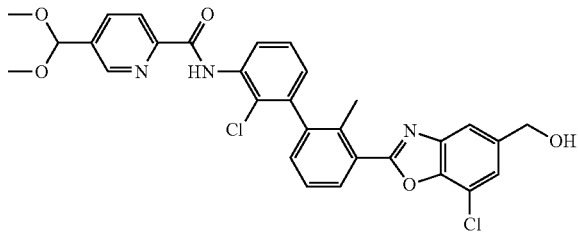 [SMILES: COC(OC)c1ccc(C(=O)Nc2cccc(-c3cccc(-c4nc5cc(CO)cc(Cl)c5o4)c3C)c2Cl)nc1]

A mixture of N-(3-bromo-2-chlorophenyl)-5-(dimethoxymethyl)picolinamide (156 mg, 0.404 mmol), (7-chloro-2-(2-methyl-3-(4,4,5,5-tetramethyl-1,3,2-dioxaborolan-2-yl)phenyl)benzo[d]oxazol-5-yl)methanol (125 mg, 0.312 mmol), bis(dicyclohexylphosphino)ferrocene] palladium(II) (23.6 mg, 0.031 mmol) and cesium fluoride (119 mg, 0.780 mmol) in a mixed water (300 µL) and 1,4-dioxane (1500 µlL was purged with N$_2$ and then stirred at 100° C. for 3 hrs. The reaction was cooled to room temperature and then diluted with EtOAc and water. The aqueous phase was extracted with EtOAc. The organic phase was dried over MgSO$_4$, filtered and the filtrate was concentrated under reduced pressure. The crude material was purified by flash chromatography on a silica gel (eluting with MeOH/DCM, 0-10%) to give the desired product. LC-MS calculated for $C_{30}H_{26}Cl_2N_3O_5$ (M+H)$^+$: m/z=578.1; found 578.1.

Step 8: N-(2-chloro-3'-(7-chloro-5-formylbenzo[d]oxazol-2-yl)-2'-methyl-[1,1'-biphenyl]-3-yl)-5-(dimethoxymethyl)picolinamide

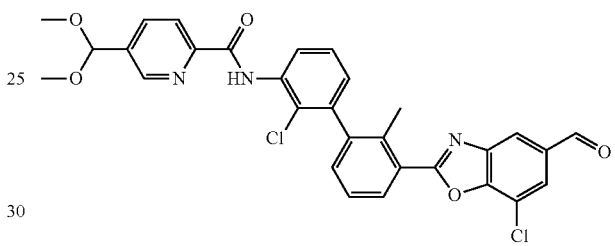

To N-(2-chloro-3'-(7-chloro-5-(hydroxymethyl)benzo[d]oxazol-2-yl)-2'-methyl-[1,1'-biphenyl]-3-yl)-5-(dimethoxymethyl)picolinamide (189 mg, 0.327 mmol) and sodium bicarbonate (220 mg, 2.61 mmol) in DCM (2 mL) was added Dess-Martin periodinane (0.115 ml, 0.327 mmol) in one portion at rt and the resulting mixture was stirred at room temperature for 20 min. The reaction was quenched by NaHCO$_3$ and Na$_2$S$_2$O$_3$ solution, extracted with DCM. The organic phase was dried over MgSO$_4$, filtered and the filtrate was concentrated. The residue was used directly without further purification. LC-MS calculated for $C_{30}H_{24}Cl_2N_3O_5$ (M+H)$^+$: m/z=576.1; found 576.1.

Step 9: (S)-1-((7-chloro-2-(2'-chloro-3'-(5-(dimethoxymethyl)picolinamido)-2-methyl-[1,1'-biphenyl]-3-yl)benzo[d]oxazol-5-yl)methyl)piperidine-2-carboxylic acid

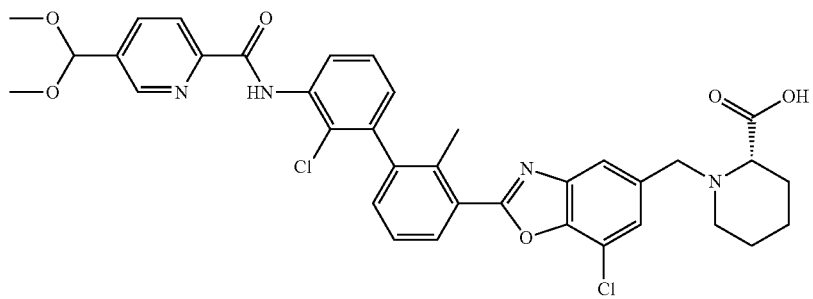 [SMILES: COC(OC)c1ccc(C(=O)Nc2cccc(-c3cccc(-c4nc5cc(CN6CCCC[C@H]6C(=O)O)cc(Cl)c5o4)c3C)c2Cl)nc1]

A mixture of N-(2-chloro-3'-(7-chloro-5-formylbenzo[d]oxazol-2-yl)-2'-methyl-[1,1'-biphenyl]-3-yl)-5-(dimethoxymethyl)picolinamide (65.1 mg, 0.113 mmol) and (S)-piperidine-2-carboxylic acid (58.3 mg, 0.452 mmol) in DCM (1129 µL) was stirred at room temperature for 2 hrs. Then sodium triacetoxyborohydride (71.8 mg, 0.339 mmol) and acetic acid (19.40 µl, 0.339 mmol) was added. The mixture was further stirred at room temperature for 1 h. The reaction was diluted with DCM and quenched by NH$_3$—H$_2$O. The organic layer was dried over MgSO$_4$, and concentrated and purified by column chromatography (eluting with DCM/MeOH, 0-15%). LC-MS calculated for $C_{36}H_{35}Cl_2N_4O_6$ (M+H)$^+$: m/z=689.2; found 689.4.

Step 10: (S)-1-((7-chloro-2-(2'-chloro-3'-(5-formylpicolinamido)-2-methyl-[1,1'-biphenyl]-3-yl)benzo[d]oxazol-5-yl)methyl)piperidine-2-carboxylic acid

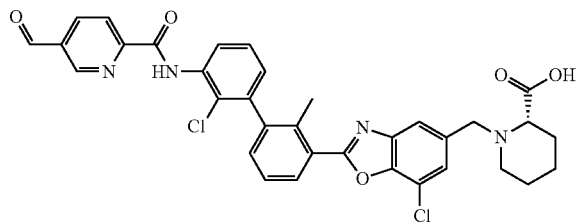 [SMILES: Cc1c(-c2nc3cc(CN4CCCC[C@H]4C(=O)O)cc(Cl)c3o2)cccc1-c1cccc(NC(=O)c2ccc(C=O)cn2)c1Cl]

To a solution of (S)-1-((7-chloro-2-(2'-chloro-3'-(5-(dimethoxymethyl)picolinamido)-2-methyl-[1,1'-biphenyl]-3-yl)benzo[d]oxazol-5-yl)methyl)piperidine-2-carboxylic acid (35 mg, 0.051 mmol) in DCM (400 µL) was added TFA (117 µL, 1.51 mmol) at room temperature. Then the mixture was stirred at room temperature for 1 h. The mixture was concentrated under vacuum before being redissovled with DCM, quenched by aqueous NaHCO$_3$ solution. The organic phase was dried over MgSO$_4$, filtered and the filtrate was concentrated. The crude product was used directly in the next step. LC-MS calculated for $C_{34}H_{29}Cl_2N_4O_5$ (M+H)$^+$: m/z=643.2; found 643.4.

Step 11: (S)-1-((7-chloro-2-(2'-chloro-3'-(5-(((2-hydroxyethyl)amino)methyl)picolinamido)-2-methyl-[1,1'-biphenyl]-3-yl)benzo[d]oxazol-5-yl)methyl)piperidine-2-carboxylic acid A mixture of (S)-1-((7-chloro-2-(2'-chloro-3'-(5-formylpicolinamido)-2-methyl-[1,1'-biphenyl]-3-yl)benzo[d]oxazol-5-yl)methyl)piperidine-2-carboxylic acid (31.1 mg, 0.048 mmol) and 2-aminoethan-1-ol (11.8 mg, 0.19 mmol) in DCM (0.5 mL) was stirred at room temperature for 2 h. Then sodium triacetoxyborohydride (30.7 mg, 0.14 mmol) and acetic acid (8 µL, 0.14 mmol) was added. The mixture was further stirred at room temperature for 1 h. The reaction was diluted with MeOH and then purified by prep-HPLC (pH=2, acetonitrile/water+TFA) to give the desired product as TFA salt. LC-MS calculated for $C_{36}H_{36}Cl_2N_5O_5$ (M+H)$^+$: m/z=688.2; found 688.1.

Example 2

(S)-1-((7-chloro-2-(2'-chloro-3'-(5-(((S)-3-hydroxypyrrolidin-1-yl)methyl)picolinamido)-2-methyl-[1,1'-biphenyl]-3-yl)benzo[d]oxazol-5-yl)methyl)piperidine-2-carboxylic acid

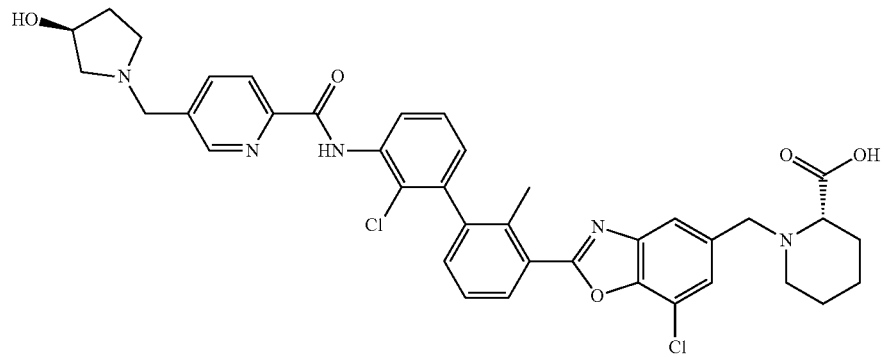 [SMILES: Cc1c(-c2nc3cc(CN4CCCC[C@H]4C(=O)O)cc(Cl)c3o2)cccc1-c1cccc(NC(=O)c2ccc(CN3CC[C@H](O)C3)cn2)c1Cl]

This compound was prepared using similar procedures as described for Example 1 with (S)-pyrrolidin-3-ol replacing ethanolamine in Step 11. The reaction was diluted with MeOH and then purified by prep-HPLC (pH=10, acetonitrile/water+NH$_4$OH) to give the desired product. LC-MS calculated for $C_{38}H_{38}Cl_2N_5O_5$ (M+H)$^+$: m/z=714.2; found 714.2.

Example 3

(S)-1-((7-chloro-2-(3'-((3-(((2-hydroxyethyl)amino)methyl)-1,7-naphthyridin-8-yl)amino)-2,2'-dimethyl-[1,1'-biphenyl]-3-yl)benzo[d]oxazol-5-yl)methyl)piperidine-2-carboxylic acid

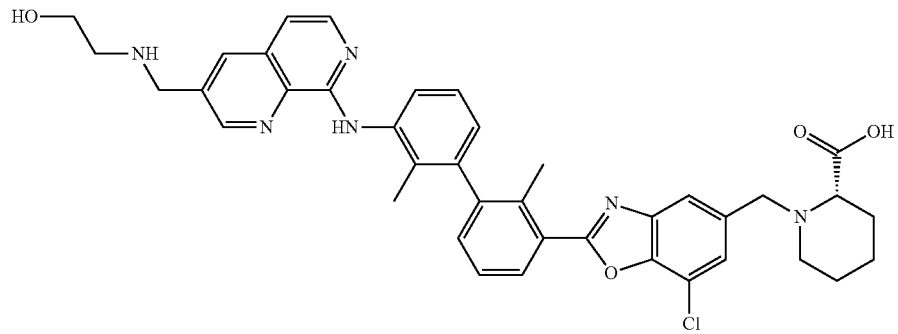 [SMILES: Cc1c(Nc2nccc3cc(CNCCO)cnc23)cccc1-c1cccc(-c2nc3cc(CN4CCCC[C@H]4C(=O)O)cc(Cl)c3o2)c1C]

Step 1: 8-chloro-3-vinyl-1,7-naphthyridine

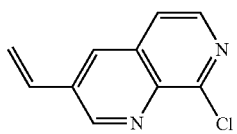

A mixture of 3-bromo-8-chloro-1,7-naphthyridine (389 mg, 1.60 mmol) (PharmaBlock, cat # PBLJ2743), 4,4,5,5-tetramethyl-2-vinyl-1,3,2-dioxaborolane (295 mg, 1.92 mmol), sodium carbonate (423 mg, 3.99 mmol) and bis(dicyclohexylphosphino)ferrocene]palladium(II) (60.4 mg, 0.080 mmol) in t-butanol (3.2 mL) and water (3.2 mL) was degassed and sealed. It was stirred at 110° C. for 2 h. The reaction mixture was cooled then extracted with ethyl acetate. The combined organic layers were washed with brine, dried over MgSO$_4$, filtered and concentrated under reduced pressure. The crude residue was used directly in the next step without further purification. LC-MS calculated for $C_{10}H_8ClN_2$ (M+H)$^+$: m/z=191.0; found 191.0.

Step 2: N-(3-bromo-2-methylphenyl)-3-vinyl-1,7-naphthyridin-8-amine

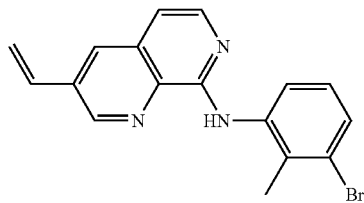

A mixture of 3-bromo-2-methylaniline (139 mg, 0.74 mmol), 8-chloro-3-vinyl-1,7-naphthyridine (142 mg, 0.74 mmol) and HCl in dioxane (4.0 M, 186 μL, 0.74 mmol) in t-butanol (3.7 mL) was heated at 130° C. for 2 h. The reaction was then cooled to room temperature and diluted with DCM. The reaction was quenched by aqueous NaHCO$_3$ solution, extracted with DCM. The organic phase was dried over MgSO$_4$, filtered and the filtrate was concentrated. The residue was used directly for next step. LC-MS calculated for $C_{17}H_{15}BrN_3$ (M+H)$^+$: m/z=340.0, 342.0; found 340.1, 342.1.

Step 3: (7-chloro-2-(2,2'-dimethyl-3'-((3-vinyl-1,7-naphthyridin-8-yl)amino)-[1,1'-biphenyl]-3-yl)benzo[d]oxazol-5-yl)methanol

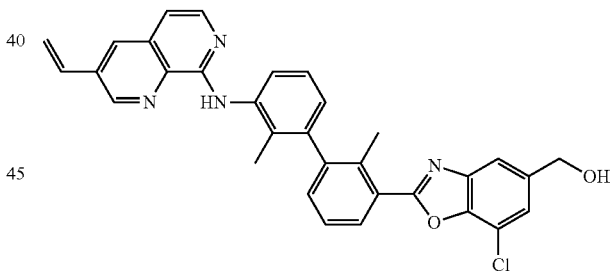

A mixture of N-(3-bromo-2-methylphenyl)-3-vinyl-1,7-naphthyridin-8-amine (81 mg, 0.24 mmol), (7-chloro-2-(2-methyl-3-(4,4,5,5-tetramethyl-1,3,2-dioxaborolan-2-yl)phenyl)benzo[d]oxazol-5-yl)methanol (95 mg, 0.24 mmol), chloro(2-dicyclohexylphosphino-2',4',6'-triisopropyl-1,1'-biphenyl)[2-(2'-amino-1,1'-biphenyl)]palladium(II) (18.7 mg, 0.024 mmol) and potassium phosphate (126 mg, 0.60 mmol) in a mixed water (400 μl) and 1,4-dioxane (2.0 mL) was purged with N$_2$ and then stirred at 70° C. for 1 h. The reaction was cooled to room temperature. The reaction mixture was diluted with ethyl acetate and then washed with H$_2$O. The organic layer was dried over MgSO$_4$, filtered and concentrated to give a crude residue, which was purified by flash chromatography (eluting with MeOH/DCM, 0-10%). LC-MS calculated for $C_{32}H_{26}ClN_4O_2$ (M+H)$^+$: m/z=533.2; found 533.2.

Step 4: 7-chloro-2-(2,2'-dimethyl-3'-((3-vinyl-1,7-naphthyridin-8-yl)amino)-[1,1'-biphenyl]-3-yl)benzo[d]oxazole-5-carbaldehyde

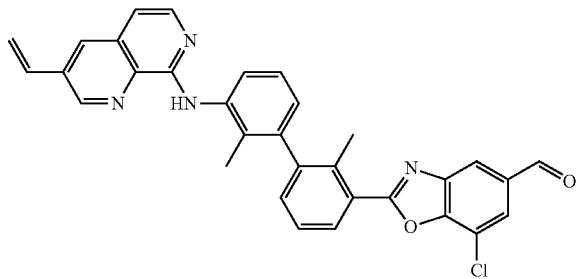 [SMILES: C=Cc1cnc2c(Nc3cccc(-c4cccc(-c5nc6cc(C=O)cc(Cl)c6o5)c4C)c3C)nccc2c1]

This compound was prepared using similar procedures as described for Example 1 with (7-chloro-2-(2,2'-dimethyl-3'-((3-vinyl-1,7-naphthyridin-8-yl)amino)-[1,1'-biphenyl]-3-yl)benzo[d]oxazol-5-yl)methanol replacing N-(2-chloro-3'-(7-chloro-5-(hydroxymethyl)benzo[d]oxazol-2-yl)-2'-methyl-[1,1'-biphenyl]-3-yl)-5-(dimethoxymethyl)picolinamide in Step 8. LC-MS calculated for $C_{32}H_{24}ClN_4O_2(M+H)^+$: m/z=531.2; found 531.2.

Step 5: (S)-1-((7-chloro-2-(2,2'-dimethyl-3'-((3-vinyl-1,7-naphthyridin-8-yl)amino)-[1,1'-biphenyl]-3-yl)benzo[d]oxazol-5-yl)methyl)piperidine-2-carboxylic acid

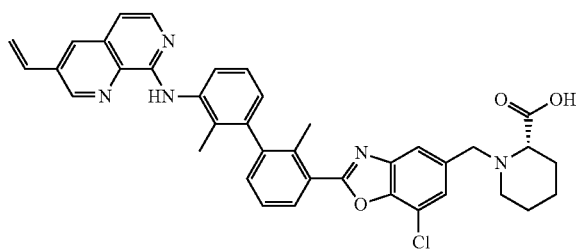 [SMILES: C=Cc1cnc2c(Nc3cccc(-c4cccc(-c5nc6cc(CN7CCCC[C@H]7C(=O)O)cc(Cl)c6o5)c4C)c3C)nccc2c1]

This compound was prepared using similar procedures as described for Example 1 with 7-chloro-2-(2,2'-dimethyl-3'-((3-vinyl-1,7-naphthyridin-8-yl)amino)-[1,1'-biphenyl]-3-yl)benzo[d]oxazole-5-carbaldehyde replacing N-(2-chloro-3'-(7-chloro-5-formylbenzo[d]oxazol-2-yl)-2'-methyl-[1,1'-biphenyl]-3-yl)-5-(dimethoxymethyl)picolinamide in Step 9. LC-MS calculated for $C_{38}H_{35}ClN_5O_3(M+H)^+$: m/z=644.2; found 644.2.

Step 6: (S)-1-((7-chloro-2-(3'-((3-formyl-1,7-naphthyridin-8-yl)amino)-2,2'-dimethyl-[1,1'-biphenyl]-3-yl)benzo[d]oxazol-5-yl)methyl)piperidine-2-carboxylic acid

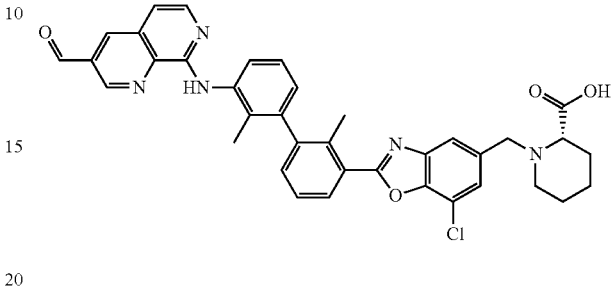

A vial was charged with (S)-1-((7-chloro-2-(2,2'-dimethyl-3'-((3-vinyl-1,7-naphthyridin-8-yl)amino)-[1,1'-biphenyl]-3-yl)benzo[d]oxazol-5-yl)methyl)piperidine-2-carboxylic acid (11 mg, 0.017 mmol), a stir bar, 1,4-dioxane (128 μL) and water (42 μL). To this suspension was added osmium tetroxide (4% w/w in water, 6.7 μl, 0.85 mmol). The reaction was stirred for 5 min then sodium periodate (18.2 mg, 0.085 mmol) was added. After stirring at room temperature for 1 h, the reaction was quenched with a saturated aqueous solution of sodium thiosulfate. The mixture was then extracted with ethyl acetate, and the combined organic layers were separated, washed with brine, dried over $Na_2SO_4$, filtered, and concentrated in vacuo. The crude residue was used directly. LC-MS calculated for $C_{37}H_{33}ClN_5O_4(M+H)^+$: m/z=646.2; found 646.2.

Step 7: (S)-1-((7-chloro-2-(3'-((3-(((2-hydroxyethyl)amino)methyl)-1,7-naphthyridin-8-yl)amino)-2,2'-dimethyl-[1,1'-biphenyl]-3-yl)benzo[d]oxazol-5-yl)methyl)piperidine-2-carboxylic acid This compound was prepared using similar procedures as described for Example 1 with (S)-1-((7-chloro-2-(3'-((3-formyl-1,7-naphthyridin-8-yl)amino)-2,2'-dimethyl-[1,1'-biphenyl]-3-yl)benzo[d]oxazol-5-yl)methyl)piperidine-2-carboxylic acid (product from Step 6) replacing (S)-1-((7-chloro-2-(2'-chloro-3'-(5-formylpicolinamido)-2-methyl-[1,1'-biphenyl]-3-yl)benzo[d]oxazol-5-yl)methyl)piperidine-2-carboxylic acid in Step 11. The mixture was dissolved in MeOH then purified by prep-HPLC (pH=2, acetonitrile/water+TFA) to give the desired product as TFA salt. LC-MS calculated for $C_{39}H_{40}ClN_6O_4(M+H)^+$: m/z=691.3; found 691.3.

Example 4

(S)-1-((7-chloro-2-(3'-((3-(((2-hydroxy-2-methylpropyl)amino)methyl)-1,7-naphthyridin-8-yl)amino)-2,2'-dimethyl-[1,1'-biphenyl]-3-yl)benzo[d]oxazol-5-yl)methyl)piperidine-2-carboxylic acid

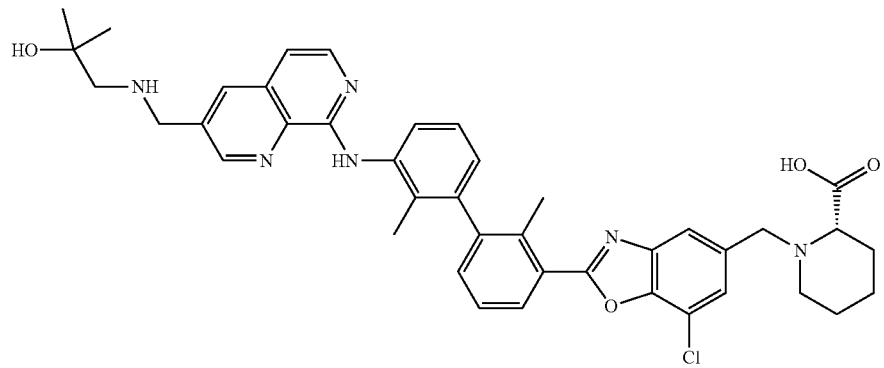 [SMILES: Cc1c(Nc2nccc3cc(CNCC(C)(C)O)cnc23)cccc1-c1cccc(-c2nc3cc(CN4CCCC[C@H]4C(=O)O)cc(Cl)c3o2)c1C]

This compound was prepared using similar procedures as described for Example 3 with 1-amino-2-methylpropan-2-ol replacing ethanolamine in Step 7. The reaction was diluted with MeOH and then purified by prep-HPLC (pH=10, acetonitrile/water+NH$_4$OH) to give the desired product. LC-MS calculated for C$_{41}$H$_{44}$ClN$_6$O$_4$(M+H)$^+$: m/z=719.3; found 719.2.

Example 5

(S)-1-((7-chloro-2-(3'-((3-(((S)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)piperidine-2-carboxylic acid

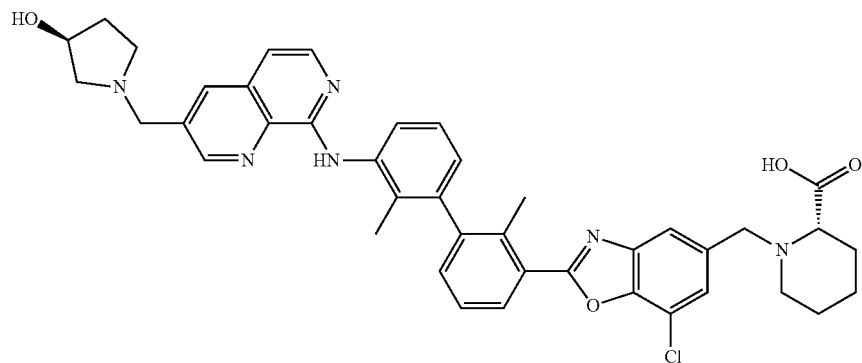 [SMILES: Cc1c(Nc2nccc3cc(CN4CC[C@H](O)C4)cnc23)cccc1-c1cccc(-c2nc3cc(CN4CCCC[C@H]4C(=O)O)cc(Cl)c3o2)c1C]

This compound was prepared using similar procedures as described for Example 3 with (S)-pyrrolidin-3-ol replacing ethanolamine in Step 7. The reaction was diluted with MeOH and then purified by prep-HPLC (pH=10, acetonitrile/water+NH$_4$OH) to give the desired product. LC-MS calculated for C$_{41}$H$_{42}$ClN$_6$O$_4$(M+H)$^+$: m/z=717.3; found 717.2.

Example 6

3-(((7-chloro-2-(3'-((3-(((2-hydroxyethyl)amino)methyl)-1,7-naphthyridin-8-yl)amino)-2,2'-dimethyl-[1,1'-biphenyl]-3-yl)benzo[d]oxazol-5-yl)methyl)amino)propanoic acid

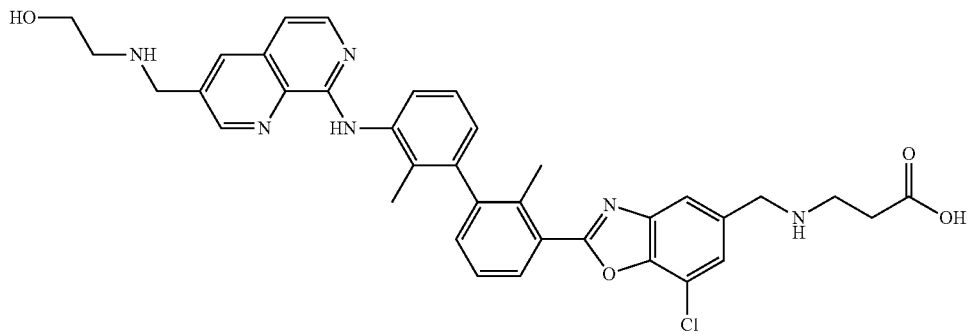 [SMILES: Cc1c(Nc2nccc3cc(CNCCO)cnc23)cccc1-c1cccc(-c2nc3cc(CNCCC(=O)O)cc(Cl)c3o2)c1C]

Step 1: methyl 3-(((7-chloro-2-(2,2'-dimethyl-3'-((3-vinyl-1,7-naphthyridin-8-yl)amino)-[1,1'-biphenyl]-3-yl)benzo[d]oxazol-5-yl)methyl)amino)propanoate

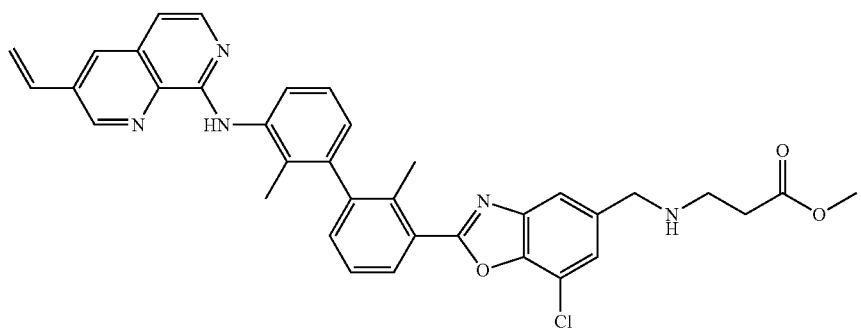 [SMILES: C=Cc1cnc2c(Nc3cccc(-c4cccc(-c5nc6cc(CNCCC(=O)OC)cc(Cl)c6o5)c4C)c3C)nccc2c1]

This compound was prepared using similar procedures as described for Example 1 with 7-chloro-2-(2,2'-dimethyl-3'-((3-vinyl-1,7-naphthyridin-8-yl)amino)-[1,1'-biphenyl]-3-yl)benzo[d]oxazole-5-carbaldehyde (product from Step 4 in Example 3) replacing N-(2-chloro-3'-(7-chloro-5-formylbenzo[d]oxazol-2-yl)-2'-methyl-[1,1'-biphenyl]-3-yl)-5-(dimethoxymethyl)picolinamide and methyl 3-aminopropanoate hydrochloride salt replacing (S)-piperidine-2-carboxylic acid in Step 9. LC-MS calculated for $C_{36}H_{33}ClN_5O_3$ $(M+H)^+$: m/z=618.2; found 618.2.

Step 2: methyl 3-(((7-chloro-2-(3'-((3-formyl-1,7-naphthyridin-8-yl)amino)-2,2'-dimethyl-[1,1'-biphenyl]-3-yl)benzo[d]oxazol-5-yl)methyl)amino)propanoate

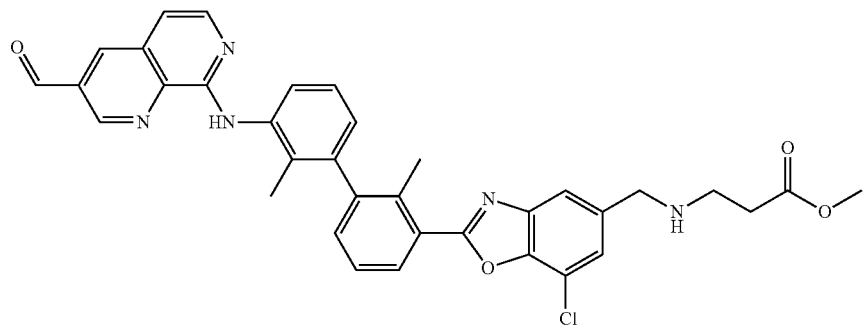 [SMILES: COC(=O)CCNCc1cc(Cl)c2oc(-c3cccc(-c4cccc(Nc5nccc6cc(C=O)cnc56)c4C)c3C)nc2c1]

This compound was prepared using similar procedures as described for Example 3 with methyl 3-(((7-chloro-2-(2,2'-dimethyl-3'-((3-vinyl-1,7-naphthyridin-8-yl)amino)-[1,1'-biphenyl]-3-yl)benzo[d]oxazol-5-yl)methyl)amino)propanoate (product from Step 1) replacing (S)-1-((7-chloro-2-(2, 2'-dimethyl-3'-((3-vinyl-1,7-naphthyridin-8-yl)amino)-[1, 1'-biphenyl]-3-yl)benzo[d]oxazol-5-yl)methyl)piperidine-2-carboxylic acid in Step 6. LC-MS calculated for $C_{35}H_{31}ClN_5O_4(M+H)^+$: m/z=620.2; found 620.2.

Step 3: methyl 3-(((7-chloro-2-(3'-((3-(((2-hydroxyethyl)amino)methyl)-1,7-naphthyridin-8-yl)amino)-2,2'-dimethyl-[1,1'-biphenyl]-3-yl)benzo[d]oxazol-5-yl)methyl)amino)propanoate

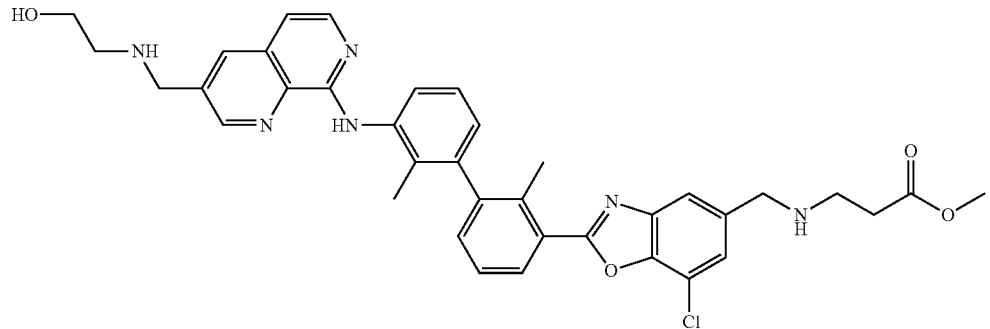 [SMILES: COC(=O)CCNCc1cc(Cl)c2oc(-c3cccc(-c4cccc(Nc5nccc6cc(CNCCO)cnc56)c4C)c3C)nc2c1]

This compound was prepared using similar procedures as described for Example 3 with methyl 3-(((7-chloro-2-(3'-((3-formyl-1,7-naphthyridin-8-yl)amino)-2,2'-dimethyl-[1, 1'-biphenyl]-3-yl)benzo[d]oxazol-5-yl)methyl)amino)propanoate replacing (S)-1-((7-chloro-2-(3'-((3-formyl-1,7-naphthyridin-8-yl)amino)-2,2'-dimethyl-[1,1'-biphenyl]-3-yl)benzo[d]oxazol-5-yl)methyl)piperidine-2-carboxylic acid in Step 7. The reaction was diluted with DCM and quenched by $NH_3$—$H_2O$. The organic layer was dried over $MgSO_4$, filtered and the filtrate was concentrated. The residue was purified by column chromatography (eluting with DCM/MeOH, 0-10%). LC-MS calculated for $C_{37}H_{38}ClN_6O_4$ $(M+H)^+$: m/z=665.3; found 665.3.

Step 4: 3-(((7-chloro-2-(3'-((3-(((2-hydroxyethyl)amino)methyl)-1,7-naphthyridin-8-yl)amino)-2,2'-dimethyl-[1,1'-biphenyl]-3-yl)benzo[d]oxazol-5-yl)methyl)amino)propanoic acid To a solution of methyl 3-(((7-chloro-2-(3'-((3-(((2-hydroxyethyl)amino)methyl)-1,7-naphthyridin-8-yl)amino)-2, 2'-dimethyl-[1,1'-biphenyl]-3-yl)benzo[d]oxazol-5-yl)methyl)amino)propanoate (10.0 mg, 0.015 mmol) in a mixture of water (63 μL), THF (125 μL) and MeOH (63 μL) was added lithium hydroxide (3.6 mg, 0.15 mmol). The reaction was stirred at room temperature for 2 h. The reaction was diluted with MeOH and then purified by prep-HPLC (pH=2, acetonitrile/water+TFA) to give the desired product as TFA salt. LC-MS calculated for $C_{36}H_{36}ClN_6O_4(M+H)^+$: m/z=651.2; found 651.2.

Example 7

(2S,2'S)-1,1'-(((2,2'-dimethyl-[1,1'-biphenyl]-3,3'-diyl)bis(6-(cyanomethoxy)benzo[d]oxazole-2,5-diyl))bis(methylene))bis(piperidine-2-carboxylic acid)

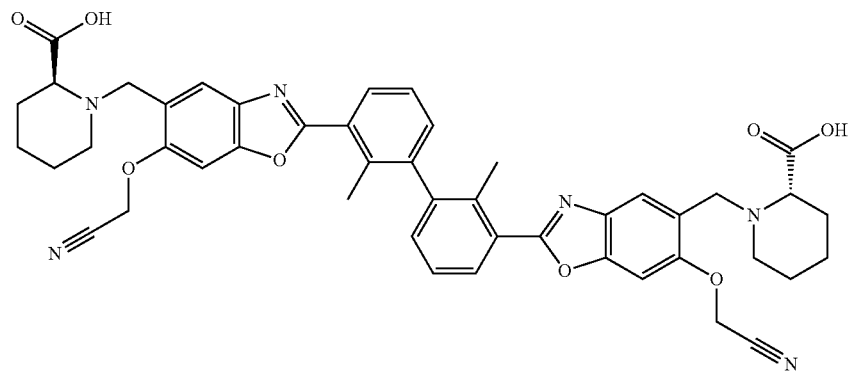 [SMILES: Cc1c(-c2nc3cc(CN4CCCC[C@H]4C(=O)O)c(OCC#N)cc3o2)cccc1-c1cccc(-c2nc3cc(CN4CCCC[C@H]4C(=O)O)c(OCC#N)cc3o2)c1C]

Step 1: methyl 2,4-dihydroxy-5-nitrobenzoate

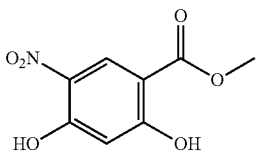

To a solution of methyl 2,4-dihydroxybenzoate (Aldrich, cat # M42505: 9.15 g, 54.4 mmol) in acetic anhydride (34 mL) and acetic acid (66 mL) was slowly added mixture of nitric acid (3.82 mL, 63.8 mmol) in acetic acid (30 mL) at 0° C. After addition, a light brown solution was formed. Then the mixture was stirred at room temperature for 30 min, after which a suspension had formed. Water (130 mL) was added, whereupon the mixture was aged for another 30 min without stirring. The precipitate was filtered, rinsed with small amount of water, and dried under vacuum to give crude product, which was used directly in the next step without further purification. LC-MS calculated for $C_8H_8NO_6$ (M+H)$^+$: m/z=214.0; found 214.0.

Step 2: methyl 5-amino-2,4-dihydroxybenzoate

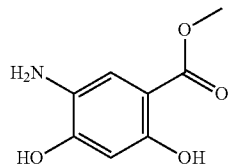

Methyl 2,4-dihydroxy-5-nitrobenzoate (592 mg, 2.78 mmol) was hydrogenated under ambient pressure of hydrogen using palladium on carbon (10 wt %, 300 mg, 0.28 mmol) in ethyl acetate (30 mL) for 3 h. The resulting suspension was filtered through a pad of Celite, washed with ethyl acetate and the solvent was removed under reduced pressure to give crude product, which was used directly without further purification. LC-MS calculated for $C_8H_{10}NO_4$ (M+H)$^+$: m/z=184.1; found 184.0.

Step 3: methyl 2-(3-bromo-2-methylphenyl)-6-hydroxybenzo[d]oxazole-5-carboxylate

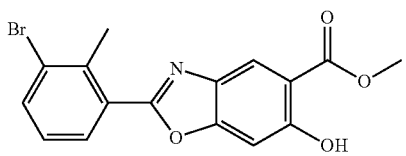 [SMILES: COC(=O)c1cc2nc(-c3cccc(Br)c3C)oc2cc1O]

This compound was prepared using similar procedures as described for Example 1 with methyl 5-amino-2,4-dihydroxybenzoate replacing methyl 3-amino-5-chloro-4-hydroxybenzoate in Step 3. LC-MS calculated for $C_{16}H_{13}BrNO_4$ (M+H)$^+$: m/z=362.0, 364.0; found 362.0, 364.0.

Step 4: 2-(3-bromo-2-methylphenyl)-5-(hydroxymethyl)benzo[d]oxazol-6-ol

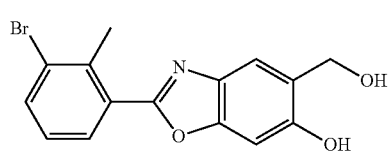 [SMILES: Cc1c(Br)cccc1-c1nc2cc(CO)c(O)cc2o1]

This compound was prepared using similar procedures as described for Example 1 with methyl 2-(3-bromo-2-methylphenyl)-6-hydroxy-2,3-dihydrobenzo[d]oxazole-5-carboxylate replacing methyl 2-(3-bromo-2-methylphenyl)-7-chlorobenzo[d]oxazole-5-carboxylate in Step 4. LC-MS calculated for $C_{15}H_{13}BrNO_3$ (M+H)$^+$: m/z=334.0, 336.0; found 334.0, 336.0.

Step 5: 2-((2-(3-bromo-2-methylphenyl)-5-(hydroxymethyl)benzo[d]oxazol-6-yl)oxy)acetonitrile

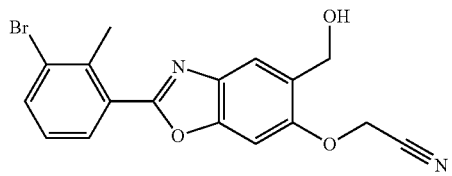 [SMILES: Cc1c(Br)cccc1-c1nc2cc(CO)c(OCC#N)cc2o1]

To a solution of 2-bromoacetonitrile (219 mg, 1.82 mmol) and 2-(3-bromo-2-methylphenyl)-5-(hydroxymethyl)benzo[d]oxazol-6-ol (406.6 mg, 1.22 mmol) in DMF (2.5 mL) was added potassium carbonate (336 mg, 2.43 mmol). The mixture was heated up to 60° C. for 1 h. The reaction was then cooled to room temperature and diluted with EtOAc, quenched with water. After extraction, the organic phase was dried over MgSO$_4$, filtered and the filtrate was concentrated. The residue was used directly without further purification. LC-MS calculated for $C_{17}H_{14}BrN_2O_3$(M+H)$^+$: m/z=373.0, 375.0; found 373.0, 375.0.

Step 6: 2-((5-(hydroxymethyl)-2-(2-methyl-3-(4,4,5,5-tetramethyl-1,3,2-dioxaborolan-2-yl)phenyl)benzo[d]oxazol-6-yl)oxy)acetonitrile

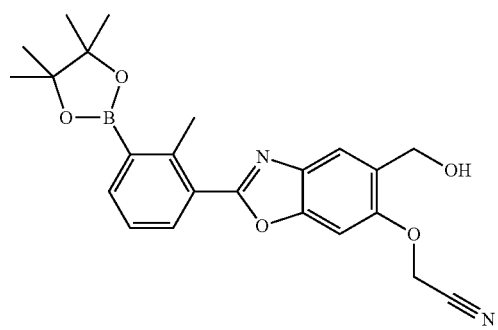 [SMILES: Cc1c(B2OC(C)(C)C(C)(C)O2)cccc1-c1nc2cc(CO)c(OCC#N)cc2o1]

This compound was prepared using similar procedures as described for Example 1 with 2-((2-(3-bromo-2-methylphenyl)-5-(hydroxymethyl)benzo[d]oxazol-6-yl)oxy)acetonitrile replacing (2-(3-bromo-2-methylphenyl)-7-chlorobenzo[d]oxazol-5-yl)methanol in Step 5. LC-MS calculated for $C_{23}H_{26}BN_2O_5(M+H)^+$: m/z=421.2; found 421.2.

Step 7: 2,2'-(((2,2'-dimethyl-[1,1'-biphenyl]-3,3'-diyl)bis(5-(hydroxymethyl)benzo[d]oxazole-2,6-diyl))bis(oxy))diacetonitrile

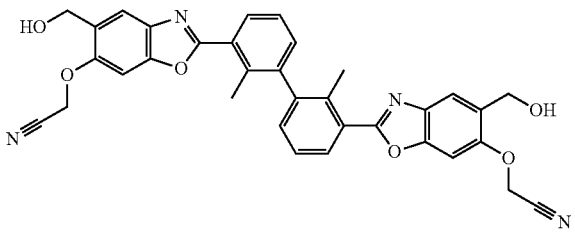 [SMILES: Cc1c(-c2nc3cc(CO)c(OCC#N)cc3o2)cccc1-c1cccc(-c2nc3cc(CO)c(OCC#N)cc3o2)c1C]

This compound was prepared using similar procedures as described for Example 1 with 2-((5-(hydroxymethyl)-2-(2-methyl-3-(4,4,5,5-tetramethyl-1,3,2-dioxaborolan-2-yl)phenyl)benzo[d]oxazol-6-yl)oxy)acetonitrile (product from Step 6) replacing (7-chloro-2-(2-methyl-3-(4,4,5,5-tetramethyl-1,3,2-dioxaborolan-2-yl)phenyl)benzo[d]oxazol-5-yl)methanol, 2-((2-(3-bromo-2-methylphenyl)-5-(hydroxymethyl)benzo[d]oxazol-6-yl)oxy)acetonitrile (product from Step 5) replacing N-(3-bromo-2-chlorophenyl)-5-(dimethoxymethyl)picolinamide and potassium carbonate replacing cesium fluoride in Step 7. LC-MS calculated for $C_{34}H_{27}N_4O_6$ $(M+H)^+$: m/z=587.2; found 587.2.

Step 8: 2,2'-(((2,2'-dimethyl-[1,1'-biphenyl]-3,3'-diyl)bis(5-formylbenzo[d]oxazole-2,6-diyl))bis(oxy))diacetonitrile

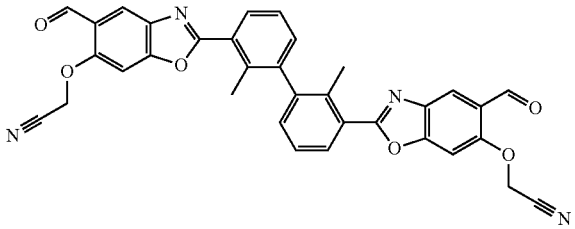 [SMILES: Cc1c(-c2nc3cc(C=O)c(OCC#N)cc3o2)cccc1-c1cccc(-c2nc3cc(C=O)c(OCC#N)cc3o2)c1C]

This compound was prepared using similar procedures as described for Example 1 with 2,2'-(((2,2'-dimethyl-[1,1'-biphenyl]-3,3'-diyl)bis(5-(hydroxymethyl)benzo[d]oxazole-2,6-diyl))bis(oxy))diacetonitrile replacing N-(2-chloro-3'-(7-chloro-5-(hydroxymethyl)benzo[d]oxazol-2-yl)-2'-methyl-[1,1'-biphenyl]-3-yl)-5-(dimethoxymethyl)picolinamide and two equivalents of Dess-Martin periodinane in Step 8. LC-MS calculated for $C_{34}H_{23}N_4O_6$ $(M+H)^+$: m/z=583.2; found 583.2.

Step 9: (2S,2'S)-1,1'-(((2,2'-dimethyl-[1,1'-biphenyl]-3,3'-diyl)bis(6-(cyanomethoxy)benzo[d]oxazole-2,5-diyl))bis(methylene))bis(piperidine-2-carboxylic acid)

This compound was prepared using similar procedures as described for Example 1 with 2,2'-(((2,2'-dimethyl-[1,1'-biphenyl]-3,3'-diyl)bis(5-formylbenzo[d]oxazole-2,6-diyl))bis(oxy))diacetonitrile (product from step 8) replacing N-(2-chloro-3'-(7-chloro-5-formylbenzo[d]oxazol-2-yl)-2'-methyl-[1,1'-biphenyl]-3-yl)-5-(dimethoxymethyl)picolinamide in Step 9. The reaction mixture was diluted with methanol and then purified by prep-HPLC (pH=10, acetonitrile/water+NH4OH) to give the desired product. LC-MS calculated for $C_{46}H_{45}N_6O_8$ $(M+H)^+$: m/z=809.3; found 809.2.

Example 8

(S)-1-((7-chloro-2-(2'-chloro-2-methyl-3'-(5-methyl-4,5,6,7-tetrahydrothiazolo[5,4-c]pyridine-2-carboxamido)-[1,1'-biphenyl]-3-yl)benzo[d]oxazol-5-yl)methyl)piperidine-2-carboxylic acid

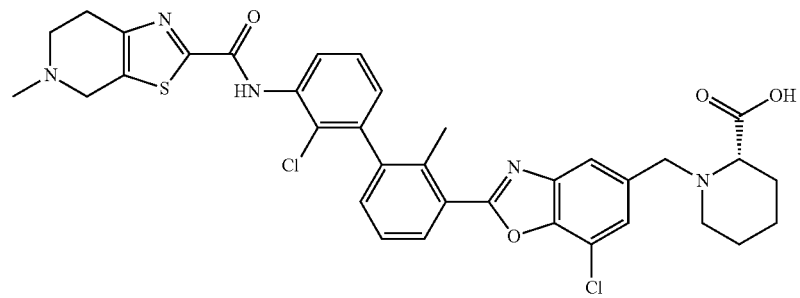 [SMILES: Cc1c(-c2nc3cc(CN4CCCC[C@H]4C(=O)O)cc(Cl)c3o2)cccc1-c1cccc(NC(=O)c2nc3c(s2)CN(C)CC3)c1Cl]

Step 1: N-(3-bromo-2-chlorophenyl)-4,5,6,7-tetrahydrothiazolo[5,4-c]pyridine-2-carboxamide

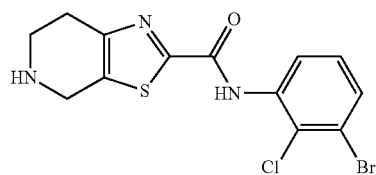 [SMILES: O=C(Nc1cccc(Br)c1Cl)c1nc2c(s1)CNCC2]

To a solution of 3-bromo-2-chloroaniline (174 mg, 0.84 mmol) and 5-(tert-butyl) 2-ethyl 6,7-dihydrothiazolo[5,4-c]pyridine-2,5(4H)-dicarboxylate (528 mg, 1.69 mmol) in THF (5.5 mL) was added potassium tert-butoxide in THF (1.0 M, 1.27 mL, 1.27 mmol) at −10° C. The mixture was stirred and slowly warmed up to 0° C. for 1 h. Water was then added to quench the reaction. The mixture was extracted with DCM. The organic phase was dried over MgSO₄ and concentrated. The residue was redissovled in DCM. The DCM solution was treated with TFA (0.19 mL, 2.52 mmol). The volatile was removed under reduced pressure after 1 h. The residue was used for next step directly. LC-MS calculated for $C_{13}H_{12}BrClN_3OS$ $(M+H)^+$: m/z=372.0; found 371.9.

Step 2: N-(3-bromo-2-chlorophenyl)-5-methyl-4,5,6,7-tetrahydrothiazolo[5,4-c]pyridine-2-carboxamide

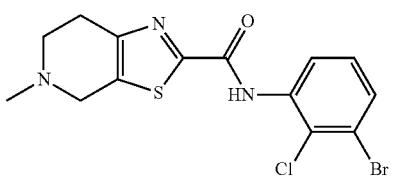 [SMILES: CN1CCc2nc(C(=O)Nc3cccc(Br)c3Cl)sc2C1]

A mixture of N-(3-bromo-2-chlorophenyl)-4,5,6,7-tetrahydrothiazolo[5,4-c]pyridine-2-carboxamide (61 mg, 0.16 mmol) and formaldehyde (37% in water, 66 mg, 0.82 mmol) in DCM (500 µL) was stirred at rt for 2 h. Then sodium triacetoxyborohydride (104 mg, 0.49 mmol) and acetic acid (28 µL, 0.49 mmol) was added. The mixture was further stirred at room temperature for 1 h. The reaction was quenched by NH₄OH, then extracted with DCM. The organic phase was dried over MgSO₄, filtered and the filtrate was concentrated. The residue was purified by column chromatography (eluting with MeOH/DCM, 0-10%). LC-MS calculated for $C_{14}H_{14}BrClN_3OS$ $(M+H)^+$: m/z=386.0/388.0; found 385.9/387.9.

Step 3: N-(2-chloro-3'-(7-chloro-5-(hydroxymethyl)benzo[d]oxazol-2-yl)-2'-methyl-[1,1'-biphenyl]-3-yl)-5-methyl-4,5,6,7-tetrahydrothiazolo[5,4-c]pyridine-2-carboxamide

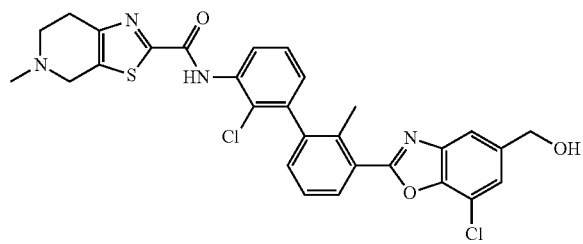 [SMILES: Cc1c(-c2nc3cc(CO)cc(Cl)c3o2)cccc1-c1cccc(NC(=O)c2nc3c(s2)CN(C)CC3)c1Cl]

This compound was prepared using similar procedures as described for Example 1 with N-(3-bromo-2-chlorophenyl)-5-methyl-4,5,6,7-tetrahydrothiazolo[5,4-c]pyridine-2-carboxamide (product from Step 2) replacing N-(3-bromo-2-chlorophenyl)-5-(dimethoxymethyl)picolinamide and chloro(2-dicyclohexylphosphino-2',4',6'-triisopropyl-1,1'-biphenyl)[2-(2'-amino-1,1'-biphenyl)]palladium(II) replacing bis(dicyclohexylphosphino)ferrocene]palladium(II) in Step 7. LC-MS calculated for $C_{29}H_{25}Cl_2N_4O_3S$ $(M+H)^+$: m/z=579.1; found 579.1.

Step 4: N-(2-chloro-3'-(7-chloro-5-formylbenzo[d]oxazol-2-yl)-2'-methyl-[1,1'-biphenyl]-3-yl)-5-methyl-4,5,6,7-tetrahydrothiazolo[5,4-c]pyridine-2-carboxamide

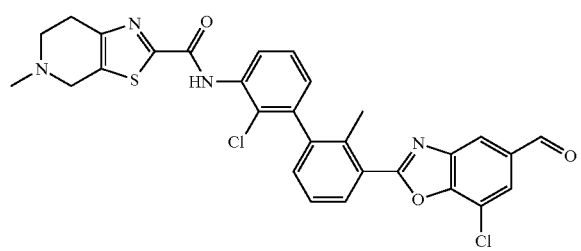 [SMILES: Cc1c(-c2nc3cc(C=O)cc(Cl)c3o2)cccc1-c1cccc(NC(=O)c2nc3c(s2)CN(C)CC3)c1Cl]

This compound was prepared using similar procedures as described for Example 1 with N-(2-chloro-3'-(7-chloro-5-(hydroxymethyl)benzo[d]oxazol-2-yl)-2'-methyl-[1,1'-biphenyl]-3-yl)-5-methyl-4,5,6,7-tetrahydrothiazolo[5,4-c]pyridine-2-carboxamide (product from step 3) replacing N-(2-chloro-3'-(7-chloro-5-(hydroxymethyl)benzo[d]oxazol-2-yl)-2'-methyl-[1,1'-biphenyl]-3-yl)-5-(dimethoxymethyl)picolinamide in Step 8. LC-MS calculated for $C_{29}H_{23}Cl_2N_4O_3S$ $(M+H)^+$: m/z=577.1; found 577.1.

Step 5: (S)-1-((7-chloro-2-(2'-chloro-2-methyl-3'-(5-methyl-4,5,6,7-tetrahydrothiazolo[5,4-c]pyridine-2-carboxamido)-[1,1'-biphenyl]-3-yl)benzo[d]oxazol-5-yl)methyl)piperidine-2-carboxylic acid This compound was prepared using similar procedures as described for Example 1 with N-(2-chloro-3'-(7-chloro-5-formylbenzo[d]oxazol-2-yl)-2'-methyl-[1,1'-biphenyl]-3-yl)-5-methyl-4,5,6,7-tetrahydrothiazolo[5,4-c]pyridine-2-carboxamide (product from step 4) replacing N-(2-chloro-3'-(7-chloro-5-formylbenzo[d]oxazol-2-yl)-2'-methyl-[1,1'-biphenyl]-3-yl)-5-(dimethoxymethyl)picolinamide in Step 9. The reaction mixture was diluted with MeOH and then purified by prep-HPLC (pH=10, acetonitrile/water+ NH₄OH) to give the desired product. LC-MS calculated for $C_{35}H_{34}Cl_2N_5O_4S$ $(M+H)^+$: m/z=690.2; found 690.2.

Example 9

N-(2-chloro-3'-(7-chloro-5-(((2-hydroxyethyl)amino)methyl)benzo[d]oxazol-2-yl)-2'-methyl-[1,1'-biphenyl]-3-yl)-5-methyl-4,5,6,7-tetrahydrothiazolo[5,4-c]pyridine-2-carboxamide

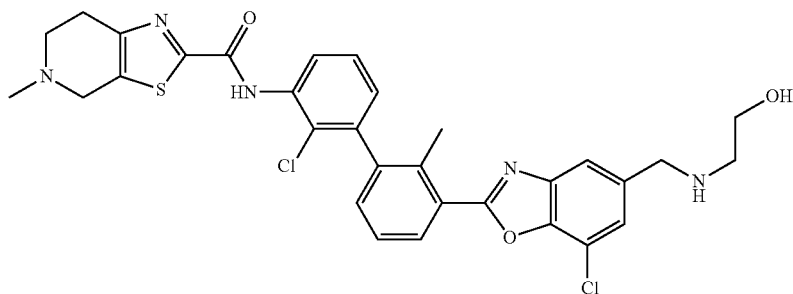 [SMILES: Cc1c(-c2nc3cc(CNCCO)cc(Cl)c3o2)cccc1-c1cccc(NC(=O)c2nc3c(s2)CN(C)CC3)c1Cl]

This compound was prepared using similar procedures as described for Example 1 with N-(2-chloro-3'-(7-chloro-5-formylbenzo[d]oxazol-2-yl)-2'-methyl-[1,1'-biphenyl]-3-yl)-5-methyl-4,5,6,7-tetrahydrothiazolo[5,4-c]pyridine-2-carboxamide (product from step 4) replacing (S)-1-((7-chloro-2-(2'-chloro-3'-(5-formylpicolinamido)-2-methyl-[1,1'-biphenyl]-3-yl)benzo[d]oxazol-5-yl)methyl)piperidine-2-carboxylic acid in Step 11. The reaction was diluted with MeOH and then purified by prep-HPLC (pH=10, acetonitrile/water+NH$_4$OH) to give the desired product. LC-MS calculated for C$_{31}$H$_{30}$Cl$_2$N$_5$O$_3$S (M+H)$^+$: m/z=622.1; found 622.2.

Example 10

(S)-1-((7-chloro-2-(3'-(7-chloro-5-(((S)-3-hydroxypyrrolidin-1-yl)methyl)benzo[d]oxazol-2-yl)-2,2'-dimethylbiphenyl-3-yl)benzo[d]oxazol-5-yl)methyl)pyrrolidine-3-carboxylic acid Step 1: 2-(3-bromo-2-methylphenyl)-7-chlorobenzo[d]oxazole-5-carbaldehyde

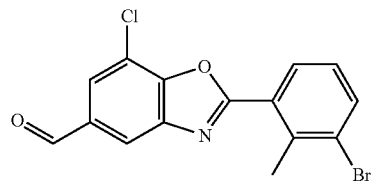

This compound was prepared using similar procedures as described for Example 1, Step 8 with (2-(3-bromo-2-methylphenyl)-7-chlorobenzo[d]oxazol-5-yl)methanol (Example 1, Step 4) replacing N-(2-chloro-3'-(7-chloro-5-(hydroxymethyl)benzo[d]oxazol-2-yl)-2'-methyl-[1,1'-biphenyl]-3-yl)-5-(dimethoxymethyl)picolinamide. LC-MS calculated for C$_{15}$H$_{10}$BrClNO$_2$ (M+H)$^+$: m/z=350.0; found 350.0.

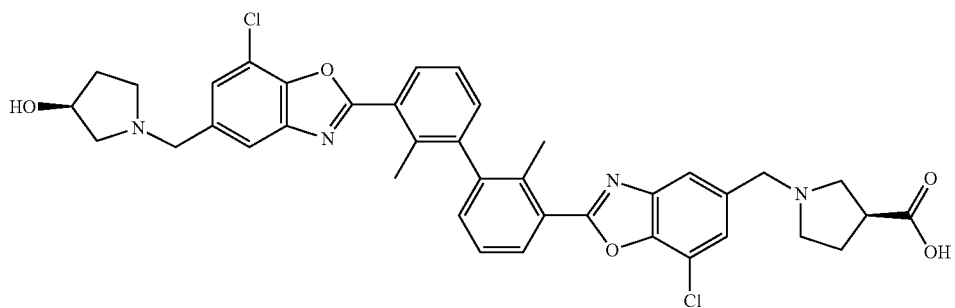 [SMILES: Cc1c(-c2nc3cc(CN4CC[C@H](O)C4)cc(Cl)c3o2)cccc1-c1cccc(-c2nc3cc(CN4CC[C@H](C(=O)O)C4)cc(Cl)c3o2)c1C]

Step 2: (S)-1-((2-(3-bromo-2-methylphenyl)-7-chlorobenzo[d]oxazol-5-yl)methyl)pyrrolidin-3-ol

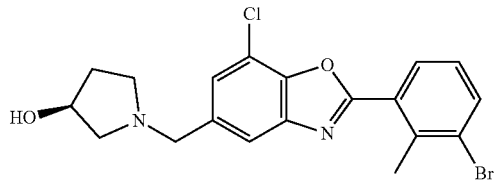 [SMILES: Cc1c(Br)cccc1-c1nc2cc(CN3CC[C@H](O)C3)cc(Cl)c2o1]

This compound was prepared using similar procedures as described for Example 1, Step 11 with (S)-pyrrolidin-3-ol replacing ethanolamine and 2-(3-bromo-2-methylphenyl)-7-chlorobenzo[d]oxazole-5-carbaldehyde replacing (S)-1-((7-chloro-2-(2'-chloro-3'-(5-formylpicolinamido)-2-methyl-[1,1'-biphenyl]-3-yl)benzo[d]oxazol-5-yl)methyl)piperidine-2-carboxylic acid. The reaction was quenched by NH$_4$OH aqueous solution and extracted with DCM. The organic phase was combined and dried over MgSO$_4$, then filtered. The filtrate was concentrated and purified by column chromatography (0-5% MeOH in DCM). LC-MS calculated for C$_{19}$H$_{19}$BrClN$_2$O$_2$ (M+H)$^+$: m/z=421.0; found 421.1.

Step 3: (S)-1-((7-chloro-2-(3'-(7-chloro-5-(hydroxymethyl)benzo[d]oxazol-2-yl)-2,2'-dimethylbiphenyl-3-yl)benzo[d]oxazol-5-yl)methyl)pyrrolidin-3-ol

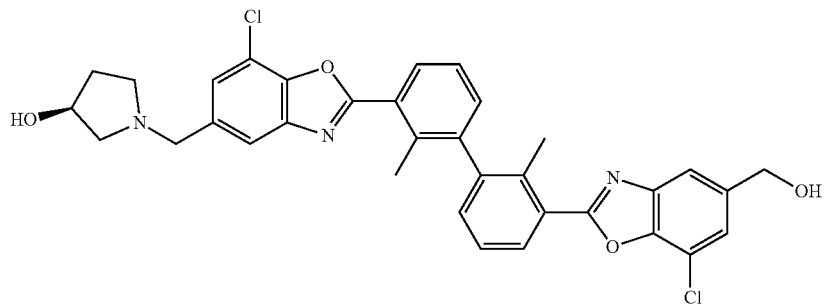 [SMILES: Cc1c(-c2nc3cc(CO)cc(Cl)c3o2)cccc1-c1cccc(-c2nc3cc(CN4CC[C@H](O)C4)cc(Cl)c3o2)c1C]

A mixture of (S)-1-((2-(3-bromo-2-methylphenyl)-7-chlorobenzo[d]oxazol-5-yl)methyl)pyrrolidin-3-ol (38 mg, 0.09 mmol), (7-chloro-2-(2-methyl-3-(4,4,5,5-tetramethyl-1,3,2-dioxaborolan-2-yl)phenyl)benzo[d]oxazol-5-yl)methanol (Example 1, Step 5: 39 mg, 0.10 mmol), sodium carbonate (24 mg, 0.22 mmol) and tetrakis(triphenylphosphine)palladium(0) (10 mg, 8.9 μmol) in a mixed water (150 μl) and 1,4-dioxane (750 μl) was purged with N$_2$ and then stirred at 100° C. for 2 h. The reaction mixture was cooled to room temperature, diluted with ethyl acetate and then washed with H$_2$O. The organic layer was dried MgSO$_4$, filtered and concentrated to give a crude residue, which was purified by flash chromatography on a silica gel column eluting with 0 to 10% MeOH/DCM to give the desired product. LC-MS calculated for C$_{34}$H$_{30}$Cl$_2$N$_3$O$_4$ (M+H)$^+$: m/z=614.2; found 614.2.

Step 4: (S)-7-chloro-2-(3'-(7-chloro-5-((3-hydroxypyrrolidin-1-yl)methyl)benzo[d]oxazol-2-yl)-2,2'-dimethylbiphenyl-3-yl)benzo[d]oxazole-5-carbaldehyde

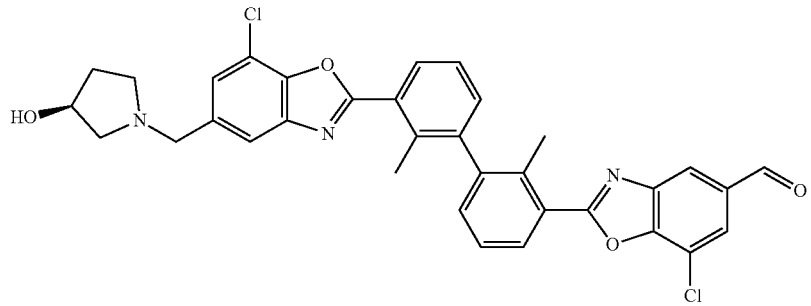 [SMILES: Cc1c(-c2nc3cc(C=O)cc(Cl)c3o2)cccc1-c1cccc(-c2nc3cc(CN4CC[C@H](O)C4)cc(Cl)c3o2)c1C]

A suspension of(S)-1-((7-chloro-2-(3'-(7-chloro-5-(hydroxymethyl)benzo[d]oxazol-2-yl)-2,2'-dimethyl-[1,1'-biphenyl]-3-yl)benzo[d]oxazol-5-yl)methyl)pyrrolidin-3-ol (31 mg, 0.050 mmol) and manganese dioxide (110 mg, 1.26 mmol) in DCM (500 µl) was stirred at 45° C. for 15 min. The reaction was filtered through a short pad of celite and then concentrated to yield a crude residue, which was used directly without further purification. LC-MS calculated for $C_{34}H_{28}Cl_2N_3O_4$ $(M+H)^+$: m/z=612.2; found 612.2.

Step 5. (S)-1-((7-chloro-2-(3'-(7-chloro-5-(((S)-3-hydroxypyrrolidin-1-yl)methyl)benzo[d]oxazol-2-yl)-2,2'-dimethylbiphenyl-3-yl)benzo[d]oxazol-5-yl)methyl)pyrrolidine-3-carboxylic acid This compound was prepared using similar procedures as described for Example 1, Step 9 with (S)-7-chloro-2-(3'-(7-chloro-5-((3-hydroxypyrrolidin-1-yl)methyl)benzo[d]oxazol-2-yl)-2,2'-dimethylbiphenyl-3-yl)benzo[d]oxazole-5-carbaldehyde (product from Step 4) replacing N-(2-chloro-3'-(7-chloro-5-formylbenzo[d]oxazol-2-yl)-2'-methyl-[1,1'-biphenyl]-3-yl)-5-(dimethoxymethyl)picolinamide and (S)-pyrrolidine-3-carboxylic acid replacing (S)-piperidine-2-carboxylic acid. The reaction mixture was diluted with MeOH and then purified by prep-HPLC (pH=10, acetonitrile/water+NH$_4$OH) to give the desired product. LC-MS calculated for $C_{39}H_{37}Cl_2N_4O_5$ $(M+H)^+$: m/z=711.2; found 711.2.

Example 11

(R)-1-((7-chloro-2-(2,2'-dimethyl-3'-(pyrido[4,3-b]pyrazin-5-ylamino)biphenyl-3-yl)benzo[d]oxazol-5-yl)methyl)pyrrolidine-3-carboxylic acid

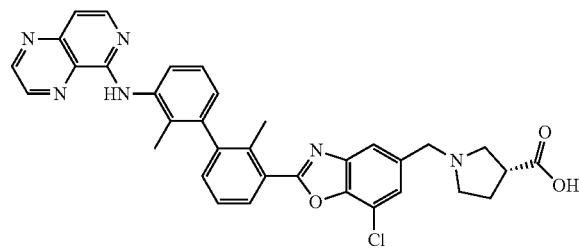 [SMILES: Cc1c(Nc2nccc3nccnc23)cccc1-c1cccc(-c2nc3cc(CN4CC[C@@H](C(=O)O)C4)cc(Cl)c3o2)c1C]

Step 1: N-(3-bromo-2-methylphenyl)pyrido[4,3-b]pyrazin-5-amine

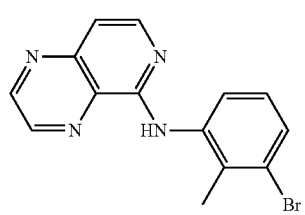 [SMILES: Cc1c(Br)cccc1Nc1nccc2nccnc12]

This compound was prepared using similar procedures as described for Example 3, Step 2 with 5-chloropyrido[4,3-b]pyrazine (Aurum Pharmatech, # C-1958) replacing 8-chloro-3-vinyl-1,7-naphthyridine. LC-MS calculated for $C_{14}H_{12}BrN_4$ $(M+H)^+$: m/z=315.0; found 315.0.

Step 2: (7-chloro-2-(2,2'-dimethyl-3'-(pyrido[4,3-b]pyrazin-5-ylamino)biphenyl-3-yl)benzo[d]oxazol-5-yl)methanol

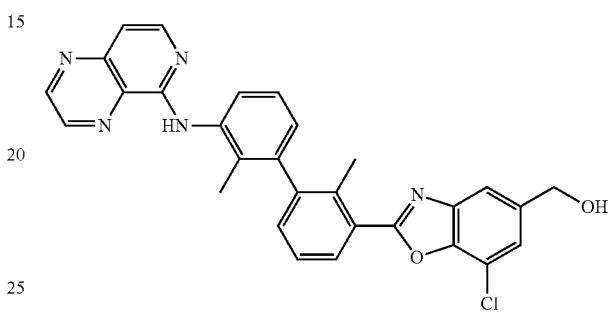

This compound was prepared using similar procedures as described for Example 10, Step 3 with N-(3-bromo-2-methylphenyl)pyrido[4,3-b]pyrazin-5-amine replacing (S)-1-((2-(3-bromo-2-methylphenyl)-7-chlorobenzo[d]oxazol-5-yl)methyl)pyrrolidin-3-ol. LC-MS calculated for $C_{29}H_{23}ClN_5O_2(M+H)^+$: m/z=508.2; found 508.2.

Step 3: 7-chloro-2-(2,2'-dimethyl-3'-(pyrido[4,3-b]pyrazin-5-ylamino)biphenyl-3-yl)benzo[d]oxazole-5-carbaldehyde

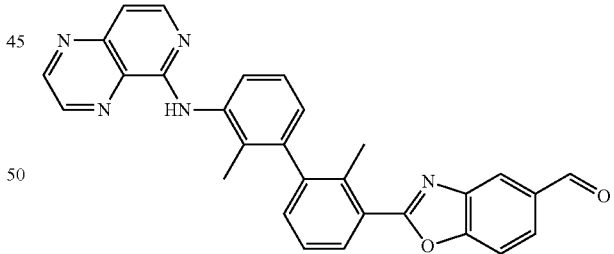

This compound was prepared using similar procedures as described for Example 10, Step 4 with (7-chloro-2-(2,2'-dimethyl-3'-(pyrido[4,3-b]pyrazin-5-ylamino)biphenyl-3-yl)benzo[d]oxazol-5-yl)methanol replacing (S)-1-((7-chloro-2-(3'-(7-chloro-5-(hydroxymethyl)benzo[d]oxazol-2-yl)-2,2'-dimethylbiphenyl-3-yl)benzo[d]oxazol-5-yl)methyl)pyrrolidin-3-ol. LC-MS calculated for $C_{29}H_{21}ClN_5O_2(M+H)^+$: m/z=506.1; found 506.2.

Step 4: (R)-1-((7-chloro-2-(2,2'-dimethyl-3'-(pyrido[4,3-b]pyrazin-5-ylamino)biphenyl-3-yl)benzo[d]oxazol-5-yl)methyl)pyrrolidine-3-carboxylic acid This compound was prepared using similar procedures as described for Example 1, Step 9 with 7-chloro-2-(2,2'-dimethyl-3'-(pyrido[4,3-b]pyrazin-5-ylamino)biphenyl-3-yl)benzo[d]oxazole-5-carbaldehyde (product from Step 3) replacing N-(2-chloro-3'-(7-chloro-5-formylbenzo[d]oxazol-2-yl)-2'-methyl-[1,1'-biphenyl]-3-yl)-5-(dimethoxymethyl)picolinamide and (R)-pyrrolidine-3-carboxylic acid replacing (S)-piperidine-2-carboxylic acid. The reaction was diluted with MeOH and then purified by prep-HPLC (pH=10, acetonitrile/water+NH$_4$OH) to give the desired product. LC-MS calculated for C$_{34}$H$_{30}$ClN$_6$O$_3$(M+H)$^+$: m/z=605.2; found 605.2.

Example 12

(R)-1-((7-cyano-2-(2,2'-dimethyl-3'-(pyrido[4,3-b]pyrazin-5-ylamino)biphenyl-3-yl)benzo[d]oxazol-5-yl)methyl)pyrrolidine-3-carboxylic acid

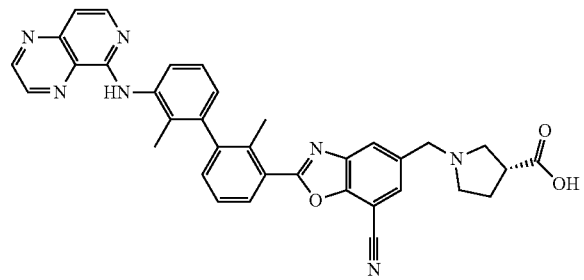 [SMILES: Cc1c(Nc2nccc3nccnc23)cccc1-c1cccc(-c2nc3cc(CN4CC[C@@H](C(=O)O)C4)cc(C#N)c3o2)c1C]

Step 1: 2-(2,2'-dimethyl-3'-(pyrido[4,3-b]pyrazin-5-ylamino)biphenyl-3-yl)-5-(hydroxymethyl)benzo[d]oxazole-7-carbonitrile

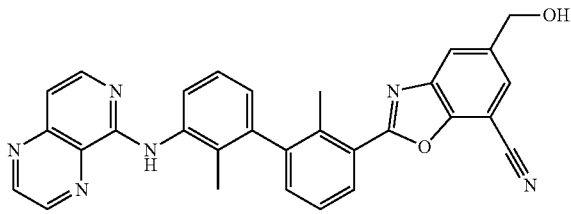 [SMILES: Cc1c(Nc2nccc3nccnc23)cccc1-c1cccc(-c2nc3cc(CO)cc(C#N)c3o2)c1C]

A mixture of (7-chloro-2-(2,2'-dimethyl-3'-(pyrido[3,4-b]pyrazin-5-ylamino)-[1,1'-biphenyl]-3-yl)benzo[d]oxazol-5-yl)methanol (Example 11, product from Step 2, 14.7 mg, 0.029 mmol), [(2-di-tert-butylphosphino-2',4',6'-triisopropyl-1,1'-biphenyl)-2-(2'-amino-1,1'-biphenyl)]palladium(II) methanesulfonate (2.3 mg, 2.9 µmol), potassium hexacyanoferrate(II) trihydrate (12.2 mg, 0.029 mmol) and potassium acetate (5.7 mg, 0.058 mmol) in a mixed 1,4-dioxane (250 µl) and water (250 µl) was stirred and heated at 100° C. for 2 h. After cooling to room temperature, the reaction mixture was diluted with EtOAc and water, extracted with EtOAc. The combined organic phase was dried over MgSO$_4$, and then filtered. The filtrate was concentrated. The crude material was purified by column chromatography (0-8% MeOH in DCM) to give the desired product. LC-MS calculated for C$_{30}$H$_{23}$N$_6$O$_2$ (M+H)$^+$: m/z=499.2; found 499.2.

Step 2: 2-(2,2'-dimethyl-3'-(pyrido[4,3-b]pyrazin-5-ylamino)biphenyl-3-yl)-5-formylbenzo[d]oxazole-7-carbonitrile

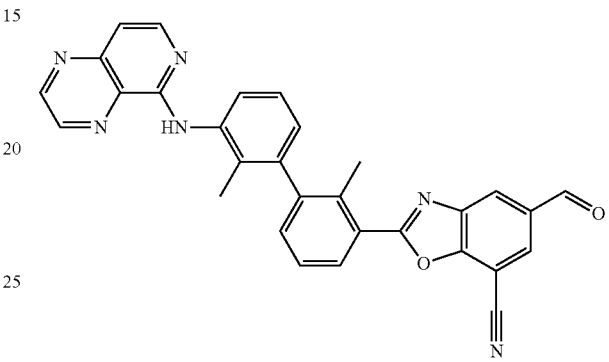

This compound was prepared using similar procedures as described for Example 10, Step 4 with 2-(2,2'-dimethyl-3'-(pyrido[4,3-b]pyrazin-5-ylamino)biphenyl-3-yl)-5-(hydroxymethyl)benzo[d]oxazole-7-carbonitrile replacing (S)-1-((7-chloro-2-(3'-(7-chloro-5-(hydroxymethyl)benzo[d]oxazol-2-yl)-2,2'-dimethylbiphenyl-3-yl)benzo[d]oxazol-5-yl)methyl)pyrrolidin-3-ol. LC-MS calculated for C$_{30}$H$_{21}$N$_6$O$_2$ (M+H)$^+$: m/z=497.2; found 497.2.

Step 3: (R)-1-((7-cyano-2-(2,2'-dimethyl-3'-(pyrido[4,3-b]pyrazin-5-ylamino)biphenyl-3-yl)benzo[d]oxazol-5-yl)methyl)pyrrolidine-3-carboxylic acid This compound was prepared using similar procedures as described for Example 1, Step 9 with 2-(2,2'-dimethyl-3'-(pyrido[4,3-b]pyrazin-5-ylamino)biphenyl-3-yl)-5-formylbenzo[d]oxazole-7-carbonitrile replacing N-(2-chloro-3'-(7-chloro-5-formylbenzo[d]oxazol-2-yl)-2'-methyl-[1,1'-biphenyl]-3-yl)-5-(dimethoxymethyl)picolinamide and (R)-pyrrolidine-3-carboxylic acid replacing (S)-piperidine-2-carboxylic acid. The reaction was diluted with MeOH and then purified by prep-HPLC (pH=2, acetonitrile/water+TFA) to give the desired product as the TFA salt. LC-MS calculated for C$_{35}$H$_{30}$N$_7$O$_3$ (M+H)$^+$: m/z=596.2; found 596.2. $^1$H NMR (600 MHz, 330K, CD$_3$CN, with T2 filter) δ 9.07 (d, J=1.8 Hz, 1H), 8.84 (d, J=1.9 Hz, 1H), 8.23 (dd, J=7.5, 1.4 Hz, 3H), 8.19 (d, J=6.3 Hz, 1H), 7.95 (d, J=1.5 Hz, 1H), 7.54 (t, J=7.8 Hz, 1H), 7.46 (dd, J=7.5, 1.4 Hz, 1H), 7.42 (t, J=7.8 Hz, 1H), 7.29 (d, J=6.2 Hz, 1H), 7.12-7.07 (m, 1H), 4.48 (d, J=1.6 Hz, 2H), 3.70-3.49 (m, 2H), 3.49-3.28 (m, 3H), 2.53 (s, 3H), 2.47-2.24 (m, 2H), 2.12 (s, 3H).

Example 13

(R)-1-((7-cyano-2-(2,2'-dimethyl-3'-(pyrido[3,2-d]pyrimidin-4-ylamino)biphenyl-3-yl)benzo[d]oxazol-5-yl)methyl)pyrrolidine-3-carboxylic acid

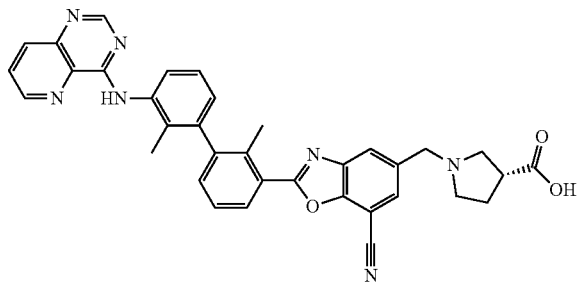 [SMILES: Cc1c(Nc2ncnc3cccnc23)cccc1-c1cccc(-c2nc3cc(CN4CC[C@@H](C(=O)O)C4)cc(C#N)c3o2)c1C]

Step 1: N-(3-bromo-2-methylphenyl)pyrido[3,2-d]pyrimidin-4-amine

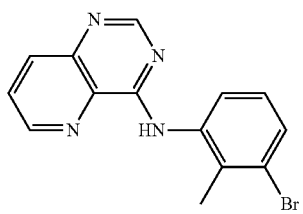 [SMILES: Cc1c(Br)cccc1Nc1ncnc2cccnc12]

This compound was prepared using similar procedures as described for Example 3, Step 2 with 4-chloropyrido[3,2-d]pyrimidine replacing 8-chloro-3-vinyl-1,7-naphthyridine. LC-MS calculated for $C_{14}H_{12}BrN_4$ (M+H)$^+$: m/z=315.0; found 315.0.

Step 2: (R)-1-((7-cyano-2-(2,2'-dimethyl-3'-(pyrido[3,2-d]pyrimidin-4-ylamino)biphenyl-3-yl)benzo[d]oxazol-5-yl)methyl)pyrrolidine-3-carboxylic acid This compound was prepared using similar procedures as described for Example 12 with N-(3-bromo-2-methylphenyl)pyrido[3,2-d]pyrimidin-4-amine replacing N-(3-bromo-2-methylphenyl)pyrido[4,3-b]pyrazin-5-amine. The reaction was diluted with MeOH and then purified by prep-HPLC (pH=2, acetonitrile/water+TFA) to give the desired product as TFA salt. LC-MS calculated for $C_{35}H_{30}N_7O_3$(M+H)$^+$: m/z=596.2; found 596.2.

Example 14

(R)-1-((2-(2'-chloro-2-methyl-3'-(pyrido[4,3-b]pyrazin-5-ylamino)biphenyl-3-yl)-7-cyanobenzo[d]oxazol-5-yl)methyl)pyrrolidine-3-carboxylic acid

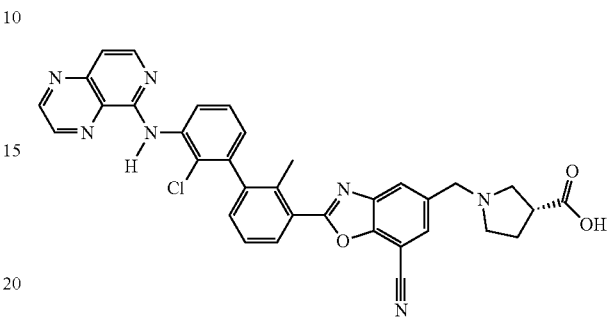

Step 1: N-(3-bromo-2-chlorophenyl)pyrido[4,3-b]pyrazin-5-amine

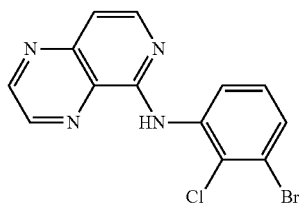 [SMILES: Clc1c(Br)cccc1Nc1nccc2nccnc12]

This compound was prepared using similar procedures as described for Example 3, Step 2 with 3-bromo-2-chloroaniline replacing 3-bromo-2-methylaniline and 5-chloropyrido[4,3-b]pyrazine replacing 8-chloro-3-vinyl-1,7-naphthyridine. LC-MS calculated for $C_{13}H_9BrClN_4$ (M+H)$^+$: m/z=335.0; found 335.0.

Step 2: (R)-1-((2-(2'-chloro-2-methyl-3'-(pyrido[4,3-b]pyrazin-5-ylamino)biphenyl-3-yl)-7-cyanobenzo[d]oxazol-5-yl)methyl)pyrrolidine-3-carboxylic acid This compound was prepared using similar procedures as described for Example 12 with N-(3-bromo-2-chlorophenyl)pyrido[4,3-b]pyrazin-5-amine replacing N-(3-bromo-2-methylphenyl)pyrido[4,3-b]pyrazin-5-amine. The reaction was diluted with MeOH and then purified by prep-HPLC (pH=2, acetonitrile/water+TFA) to give the desired product as TFA salt. LC-MS calculated for $C_{34}H_{27}ClN_7O_3$(M+H)$^+$: m/z=616.2; found 616.1.

Example 15

(R)-1-((2-(2'-chloro-2-methyl-3'-(pyrido[3,4-b]pyrazin-8-ylamino)biphenyl-3-yl)-7-cyanobenzo[d]oxazol-5-yl)methyl)pyrrolidine-3-carboxylic acid

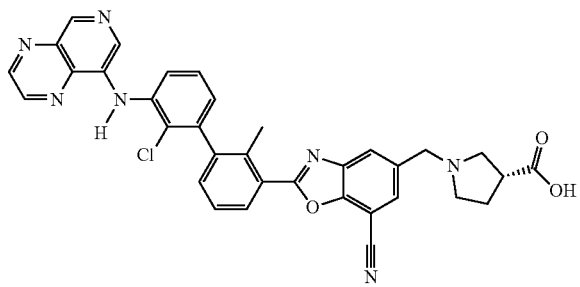 [SMILES: Cc1c(-c2nc3cc(CN4CC[C@@H](C(=O)O)C4)cc(C#N)c3o2)cccc1-c1cccc(Nc2cncc3nccnc23)c1Cl]

Step 1: (2-(3'-amino-2'-chloro-2-methylbiphenyl-3-yl)-7-chlorobenzo[d]oxazol-5-yl)methanol

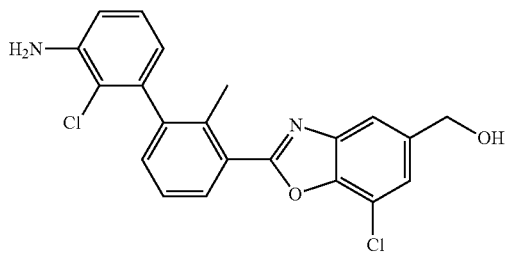 [SMILES: Cc1c(-c2nc3cc(CO)cc(Cl)c3o2)cccc1-c1cccc(N)c1Cl]

A mixture of 3-bromo-2-chloroaniline (222 mg, 1.08 mmol), (7-chloro-2-(2-methyl-3-(4,4,5,5-tetramethyl-1,3,2-dioxaborolan-2-yl)phenyl)benzo[d]oxazol-5-yl)methanol (535 mg, 0.977 mmol), sodium carbonate (259 mg, 2.44 mmol) and tetrakis(triphenylphosphine) palladium(0) (113 mg, 0.098 mmol) in a mixed water (1.6 ml) and 1,4-dioxane (8.1 ml) was purged with $N_2$ and then stirred at 100° C. for 1 h. The reaction mixture was cooled to room temperature, diluted with ethyl acetate and then washed with water. The organic layer was dried $MgSO_4$, and then filtered. The filtrate was concentrated to give a crude residue, which was purified by flash chromatography on a silica gel column eluting with 0 to 10% MeOH/DCM to give the desired product. LC-MS calculated for $C_{21}H_{17}Cl_2N_2O_2$ $(M+H)^+$: m/z=399.1; found 399.1.

Step 2: (7-chloro-2-(2'-chloro-2-methyl-3'-(pyrido[3,4-b]pyrazin-8-ylamino)biphenyl-3-yl)benzo[d]oxazol-5-yl)methanol

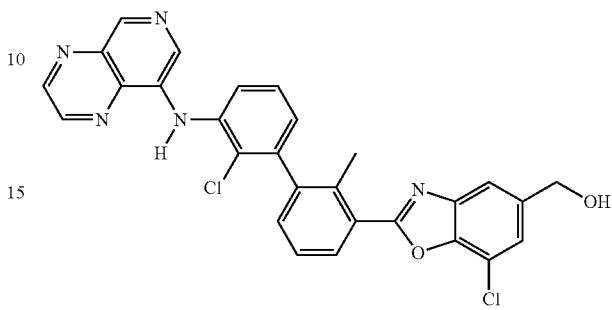

A vial equipped with a magnetic stir bar, was charged with (2-(3'-amino-2'-chloro-2-methyl-[1,1'-biphenyl]-3-yl)-7-chlorobenzo[d]oxazol-5-yl)methanol (31 mg, 0.078 mmol), 8-bromopyrido[3,4-b]pyrazine (33 mg, 0.16 mmol), sodium tert-butoxide (15 mg, 0.16 mmol), (±)-2,2'-bis(diphenylphosphino)-1,1'-binaphthalene (7.25 mg, 0.012 mmol) and tris(dibenzylideneacetone)dipalladium(0) (3.55 mg, 3.88 μmol). The mixture was bubbled by $N_2$ for 1 min before sealed. The reaction mixture was heated at 100° C. for 1 h. The solution was allowed to cool to room temperature, then quenched by the addition of 1M HCl (1 mL), diluted with EtOAc and poured into sat. $NaHCO_3$. After extracting with EtOAc three times, the combined organic layers were washed with brine, dried over $MgSO_4$, and then filtered. The filtrate was concentrated. The crude product was purified by flash column chromatography (0-10% MeOH in DCM) to give the desired product. LC-MS calculated for $C_{28}H_{20}Cl_2N_5O_2$ $(M+H)^+$: m/z=528.1; found 528.2.

Step 3: (R)-1-((2-(2'-chloro-2-methyl-3'-(pyrido[3,4-b]pyrazin-8-ylamino)biphenyl-3-yl)-7-cyanobenzo[d]oxazol-5-yl)methyl)pyrrolidine-3-carboxylic acid This compound was prepared using similar procedures as described for Example 12 with (7-chloro-2-(2'-chloro-2-methyl-3'-(pyrido[3,4-b]pyrazin-8-ylamino)biphenyl-3-yl)benzo[d]oxazol-5-yl)methanol replacing (7-chloro-2-(2,2'-dimethyl-3'-(pyrido[3,4-b]pyrazin-5-ylamino)-[1,1'-biphenyl]-3-yl)benzo[d]oxazol-5-yl)methanol in Step 1. The reaction mixture was diluted with MeOH and then purified by prep-HPLC (pH=2, acetonitrile/water+TFA) to give the desired product as TFA salt. LC-MS calculated for $C_{34}H_{27}ClN_7O_3$ $(M+H)^+$: m/z=616.2; found 616.2.

Example 16

(R)-1-((7-chloro-2-(3'-(3-(((S)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid

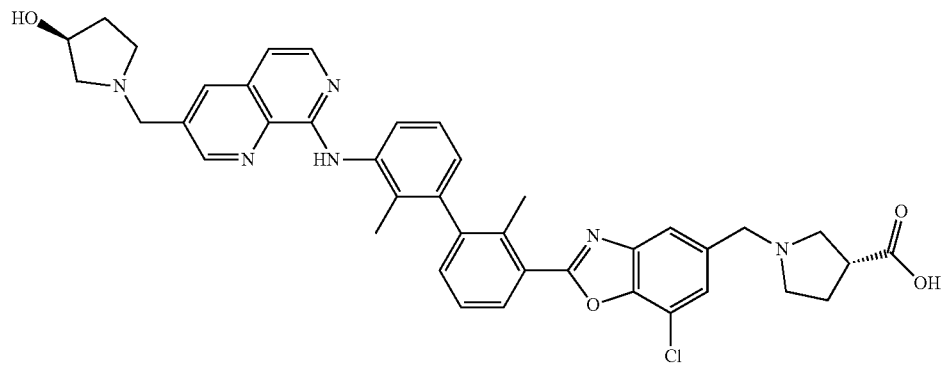

Step 1: 8-chloro-3-vinyl-1,7-naphthyridine

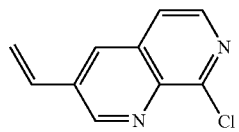

A mixture of 3-bromo-8-chloro-1,7-naphthyridine (PharmaBlock, cat # PBLJ2743: 1221 mg, 5.01 mmol), 4,4,5,5-tetramethyl-2-vinyl-1,3,2-dioxaborolane (927 mg, 6.02 mmol), sodium carbonate (1329 mg, 12.54 mmol) and tetrakis(triphenylphosphine)palladium(0) (290 mg, 0.25 mmol) in t-butanol (12 ml) and water (12 ml) was purged with nitrogen and sealed. It was stirred at 90° C. for 2 h. The reaction mixture was cooled to room temperature then extracted with ethyl acetate. The combined organic layers were washed with brine, dried over MgSO$_4$, filtered and concentrated under reduced pressure. The crude residue was used directly in the next step without further purification. LC-MS calculated for C$_{10}$H$_8$ClN$_2$ (M+H)$^+$: m/z=191.0; found 191.0.

Step 2: N-(3-bromo-2-methylphenyl)-3-vinyl-1,7-naphthyridin-8-amine

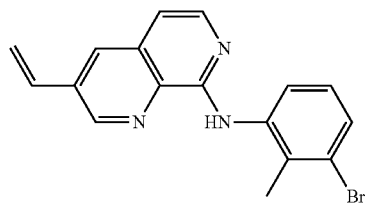

A mixture of 3-bromo-2-methylaniline (139 mg, 0.74 mmol), 8-chloro-3-vinyl-1,7-naphthyridine (142 mg, 0.74 mmol) and HCl in dioxane (4.0 M, 186 µL, 0.74 mmol) in t-butanol (3.7 mL) was heated at 130° C. for 2 h. The reaction mixture was then cooled to room temperature and diluted with DCM. The reaction was quenched by aqueous NaHCO$_3$ solution, extracted with DCM. The organic phase was dried over MgSO$_4$, filtered and the filtrate was concentrated. The residue was used directly for next step. LC-MS calculated for C$_{17}$H$_{15}$BrN$_3$ (M+H)$^+$: m/z=340.0; found 340.1.

Step 3: 8-(3-bromo-2-methylphenylamino)-1,7-naphthyridine-3-carbaldehyde

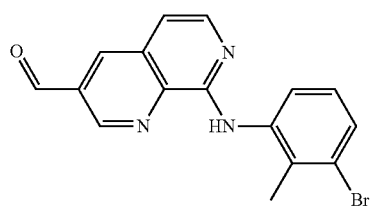 [SMILES: Cc1c(Br)cccc1Nc1nccc2cc(C=O)cnc12]

A vial was charged with N-(3-bromo-2-methylphenyl)-3-vinyl-1,7-naphthyridin-8-amine (281 mg, 0.826 mmol), a stir bar, 1,4-dioxane (6.2 ml) and water (2.0 ml). To this suspension was added osmium tetroxide (4% w/w in water, 324 µl, 0.041 mmol). The reaction was stirred for 5 min then sodium periodate (883 mg, 4.13 mmol) was added. After stirring at room temperature for 1 h, the reaction mixture was quenched with a saturated aqueous solution of sodium thiosulfate. The mixture was then extracted with ethyl acetate, and the combined organic layers were separated, washed with brine, dried over Na$_2$SO$_4$, filtered, and concentrated in vacuo. The crude residue was used directly in the next step without further purification. LC-MS calculated for C$_{16}$H$_{13}$BrN$_3$O (M+H)$^+$: m/z=342.0; found 342.0.

Step 4: (S)-1-((8-(3-bromo-2-methylphenylamino)-,1,7-naphthyridin-3-yl)methyl)pyrrolidin-3-ol

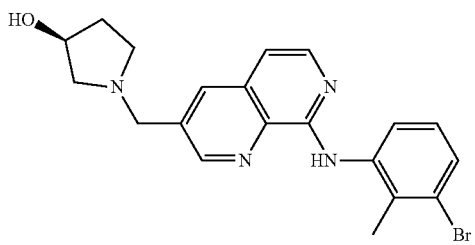 [SMILES: Cc1c(Br)cccc1Nc1nccc2cc(CN3CC[C@H](O)C3)cnc12]

A mixture of 8-((3-bromo-2-methylphenyl)amino)-1,7-naphthyridine-3-carbaldehyde (2.09 g, 6.11 mmol) and (S)-pyrrolidin-3-ol (1.06 g, 12.22 mmol) in DCM (30.5 ml) was stirred at room temperature for 0.5 h. Then sodium triacetoxyborohydride (1.94 g, 9.16 mmol) and acetic acid (0.52 ml, 9.16 mmol) were added. The mixture was further stirred at room temperature for 1 h. The reaction mixture was quenched by NH$_4$OH aqueous solution and extracted with DCM. The organic phase was combined and dried over MgSO$_4$, then filtered. The filtrate was concentrated and purified by column chromatography (0-8% MeOH in DCM) to give the desired product. LC-MS calculated for C$_{20}$H$_{22}$BrN$_4$O (M+H)$^+$: m/z=413.0; found 413.1.

Step 5: (S)-1-((8-(3'-(7-chloro-5-(hydroxymethyl)benzo[d]oxazol-2-yl)-2,2'-dimethylbiphenyl-3-ylamino)-1,7-naphthyridin-3-yl)methyl)pyrrolidin-3-ol

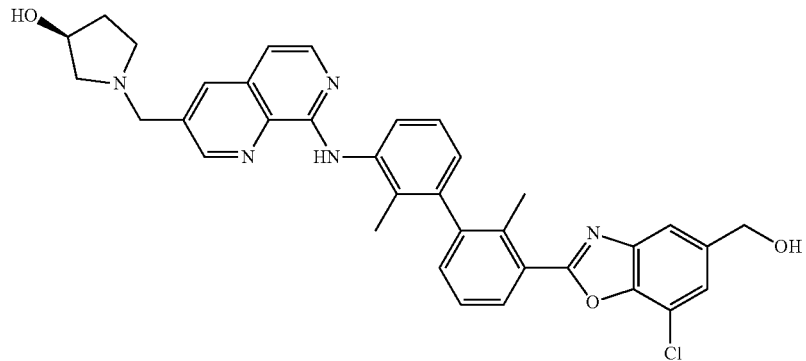

A mixture of (S)-1-((8-((3-bromo-2-methylphenyl)amino)-1,7-naphthyridin-3-yl)methyl)pyrrolidin-3-ol (462 mg, 1.12 mmol), (7-chloro-2-(2-methyl-3-(4,4,5,5-tetramethyl-1,3,2-dioxaborolan-2-yl)phenyl)benzo[d]oxazol-5-yl)methanol (673 mg, 1.23 mmol), sodium carbonate (296 mg, 2.79 mmol) and tetrakis(triphenylphosphine)palladium(0) (129 mg, 0.112 mmol) in water (1.9 mL) and 1,4-dioxane (9.3 mL) was purged with N$_2$ and then stirred at 100° C. for 4 h. The reaction mixture was cooled to room temperature, diluted with ethyl acetate and then washed with H$_2$O. The organic layer was dried MgSO$_4$ and filtered. The filtrate was concentrated to give a crude residue, which was purified by flash chromatography on a silica gel column eluting with 0 to 12% MeOH/DCM to give the desired product. LC-MS calculated for C$_{35}$H$_{33}$ClN$_5$O$_3$ (M+H)$^+$: m/z=606.2; found 606.4.

Step 6: (S)-7-chloro-2-(3'-(3-((3-hydroxypyrrolidin-1-yl)methyl)-1,7-naphthyridin-8-ylamino)-2,2'-dimethylbiphenyl-3-yl)benzo[d]oxazole-5-carbaldehyde

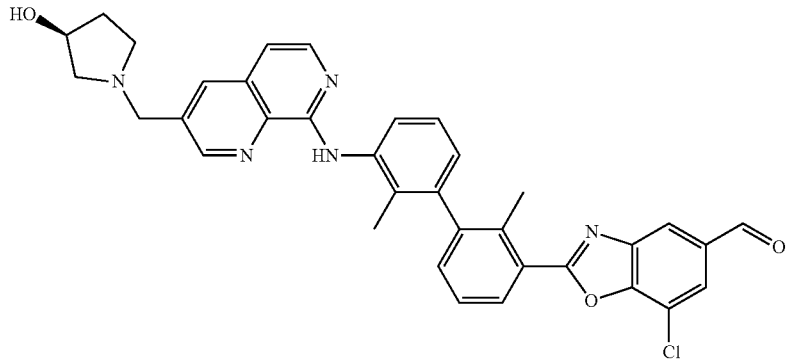 [SMILES: Cc1c(Nc2nccc3cc(CN4CC[C@H](O)C4)cnc23)cccc1-c1cccc(-c2nc3cc(C=O)cc(Cl)c3o2)c1C]

A suspension of (S)-1-((8-((3'-(7-chloro-5-(hydroxymethyl)benzo[d]oxazol-2-yl)-2,2'-dimethyl-[1,1'-biphenyl]-3-yl)amino)-1,7-naphthyridin-3-yl)methyl)pyrrolidin-3-ol (35 mg, 0.058 mmol) and manganese dioxide (100 mg, 1.16 mmol) in DCM (580 μl) was stirred at 45° C. for 15 min. The reaction mixture was cooled to room temperature, filtered through a short pad of celite and then concentrated to yield a crude residue, which was used directly without further purification. LC-MS calculated for $C_{35}H_{31}ClN_5O_3(M+H)^+$: m/z=604.2; found 604.4.

Step 7: (R)-1-((7-chloro-2-(3'-(3-(((S)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid A mixture of (S)-7-chloro-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazole-5-carbaldehyde (31 mg, 0.051 mmol), (R)-pyrrolidine-3-carboxylic acid (17.7 mg, 0.154 mmol) and triethylamine (21.5 μL, 0.154 mmol) in DCM (500 μL) was stirred at room temperature for 2 h. Then sodium triacetoxyborohydride (32.6 mg, 0.154 mmol) and acetic acid (8.81 μL, 0.154 mmol) were added. The mixture was further stirred at room temperature for 1 h. The reaction mixture was diluted with MeOH and then purified by prep-HPLC (pH=2, acetonitrile/water+TFA) to give the desired product as the TFA salt. LC-MS calculated for $C_{40}H_{40}ClN_6O_4(M+H)^+$: m/z=703.3; found 703.3. $^1$H NMR (400 MHz, 330K, $CD_3CN$) δ 9.11 (d, J=2.0 Hz, 1H), 8.52 (d, J=2.1 Hz, 1H), 8.19 (dd, J=7.9, 1.5 Hz, 1H), 7.93-7.78 (m, 3H), 7.66 (d, J=1.5 Hz, 1H), 7.57-7.41 (m, 3H), 7.29-7.18 (m, 2H), 4.63-4.55 (m, 3H), 4.44 (s, 2H), 3.58-3.34 (m, 9H), 2.53 (s, 3H), 2.45-2.28 (m, 3H), 2.10-2.05 (m, 4H).

Example 17

(S)-1-((7-chloro-2-(3'-(3-(((S)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid

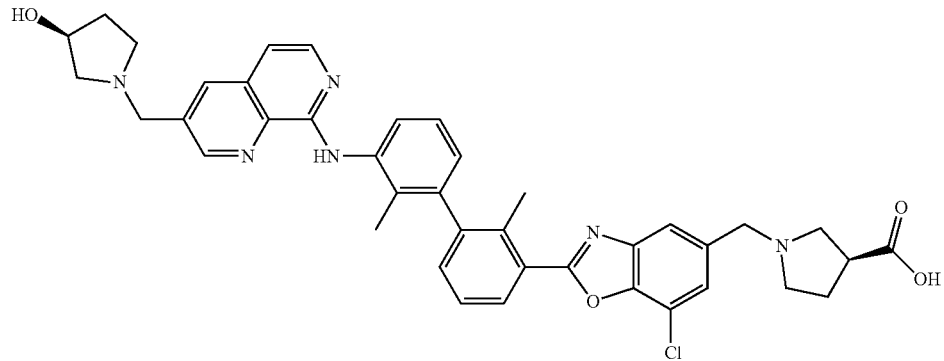 [SMILES: Cc1c(Nc2nccc3cc(CN4CC[C@H](O)C4)cnc23)cccc1-c1cccc(-c2nc3cc(CN4CC[C@H](C(=O)O)C4)cc(Cl)c3o2)c1C]

This compound was prepared using similar procedures as described for Example 16 with (S)-pyrrolidine-3-carboxylic acid replacing (R)-pyrrolidine-3-carboxylic acid in Step 7. The reaction was diluted with MeOH and then purified by prep-HPLC (pH=10, acetonitrile/water+$NH_4OH$) to give the desired product. LC-MS calculated for $C_{40}H_{40}ClN_6O_4$ $(M+H)^+$: m/z=703.3; found 703.3.

Example 18

(R)-1-((7-chloro-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid

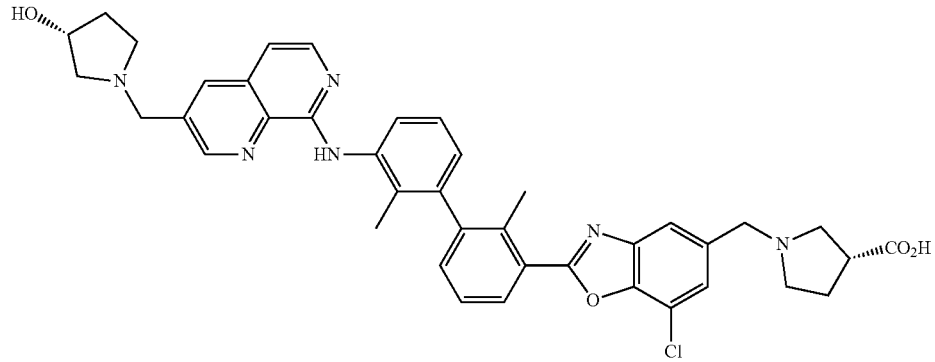 [SMILES: Cc1c(Nc2nccc3cc(CN4CC[C@@H](O)C4)cnc23)cccc1-c1cccc(-c2nc3cc(CN4CC[C@@H](C(=O)O)C4)cc(Cl)c3o2)c1C]

This compound was prepared using similar procedures as described for Example 16 with (R)-pyrrolidin-3-ol replacing (S)-pyrrolidin-3-ol in Step 4. For the last step, the reaction mixture was diluted with MeOH and then purified by prep-HPLC (pH=2, acetonitrile/water+TFA) to give the desired product as TFA salt. LC-MS calculated for $C_{40}H_{40}ClN_6O_4(M+H)^+$: m/z=703.3; found 703.3. $^1$H NMR (600 MHz, DMSO) δ 10.84-10.49 (m, 1H), 10.43-10.21 (m, 1H), 9.07 (s, 1H), 8.52 (s, 1H), 8.16 (dd, J=8.0, 1.4 Hz, 2H), 8.03 (d, J=1.5 Hz, 2H), 7.79 (d, J=1.4 Hz, 1H), 7.57 (t, J=7.7 Hz, 1H), 7.46 (dd, J=7.7, 1.4 Hz, 1H), 7.41 (t, J=7.8 Hz, 1H), 7.23 (d, J=5.9 Hz, 1H), 7.05 (s, 1H), 5.52 (br, 1H), 4.84-4.36 (m, 5H), 3.76-3.07 (m, 9H), 2.48 (s, 3H), 2.44-2.15 (m, 3H), 2.06 (s, 3H), 2.03-1.80 (m, 1H).

Example 19

(S)-1-((7-chloro-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid

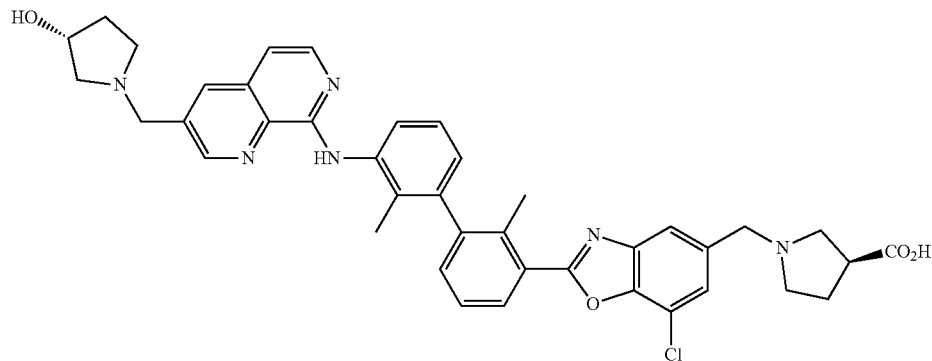 [SMILES: Cc1c(Nc2nccc3cc(CN4CC[C@@H](O)C4)cnc23)cccc1-c1cccc(-c2nc3cc(CN4CC[C@H](C(=O)O)C4)cc(Cl)c3o2)c1C]

This compound was prepared using similar procedures as described for Example 16 with (R)-pyrrolidin-3-ol replacing (S)-pyrrolidin-3-ol in Step 4 and (S)-pyrrolidine-3-carboxylic acid replacing (R)-pyrrolidine-3-carboxylic acid in the Step 7. For the last step, the reaction mixture was diluted with MeOH and then purified by prep-HPLC (pH=2, acetonitrile/water+TFA) to give the desired product as TFA salt. LC-MS calculated for $C_{40}H_{40}ClN_6O_4(M+H)^+$: m/z=703.3; found 703.3.

Example 20

(S)-3-((7-chloro-2-(3'-(3-((3-hydroxypyrrolidin-1-yl)methyl)-1,7-naphthyridin-8-ylamino)-2,2'-dimethylbiphenyl-3-yl)benzo[d]oxazol-5-yl)methylamino)propanoic acid

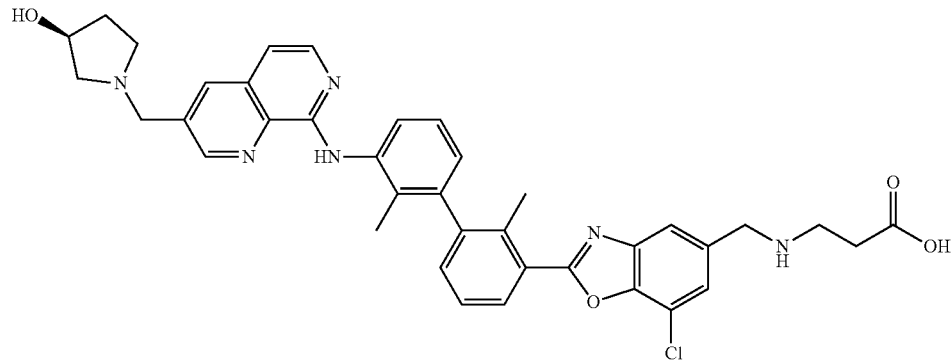 [SMILES: Cc1c(Nc2nccc3cc(CN4CC[C@H](O)C4)cnc23)cccc1-c1cccc(-c2nc3cc(CNCCC(=O)O)cc(Cl)c3o2)c1C]

This compound was prepared using similar procedures as described for Example 16 with 3-aminopropanoic acid replacing (R)-pyrrolidine-3-carboxylic acid in Step 7. The reaction mixture was diluted with MeOH and then purified by prep-HPLC (pH=10, acetonitrile/water+NH$_4$OH) to give the desired product. LC-MS calculated for $C_{38}H_{38}ClN_6O_4(M+H)^+$: m/z=677.3; found 677.3.

Example 21

(S)-3-(((7-chloro-2-(3'-(3-((3-hydroxypyrrolidin-1-yl)methyl)-1,7-naphthyridin-8-ylamino)-2,2'-dimethylbiphenyl-3-yl)benzo[d]oxazol-5-yl)methyl)(methyl)amino)propanoic acid

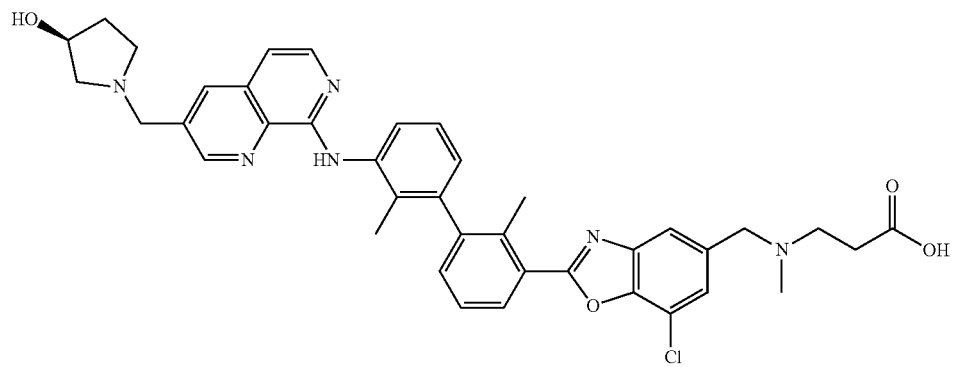 [SMILES: Cc1c(Nc2nccc3cc(CN4CC[C@H](O)C4)cnc23)cccc1-c1cccc(-c2nc3cc(CN(C)CCC(=O)O)cc(Cl)c3o2)c1C]

This compound was prepared using similar procedures as described for Example 16 with 3-(methylamino)propanoic acid replacing (R)-pyrrolidine-3-carboxylic acid in Step 7.

The reaction mixture was diluted with MeOH and then purified by prep-HPLC (pH=10, acetonitrile/water+NH$_4$OH) to give the desired product. LC-MS calculated for C$_{39}$H$_{40}$ClN$_6$O$_4$ (M+H)$^+$: m/z=691.3; found 691.2.

Example 22

(S)-1-((7-chloro-2-(3'-(3-((3-hydroxypyrrolidin-1-yl)methyl)-1,7-naphthyridin-8-ylamino)-2,2'-dimethylbiphenyl-3-yl)benzo[d]oxazol-5-yl)methyl)piperidine-4-carboxylic acid

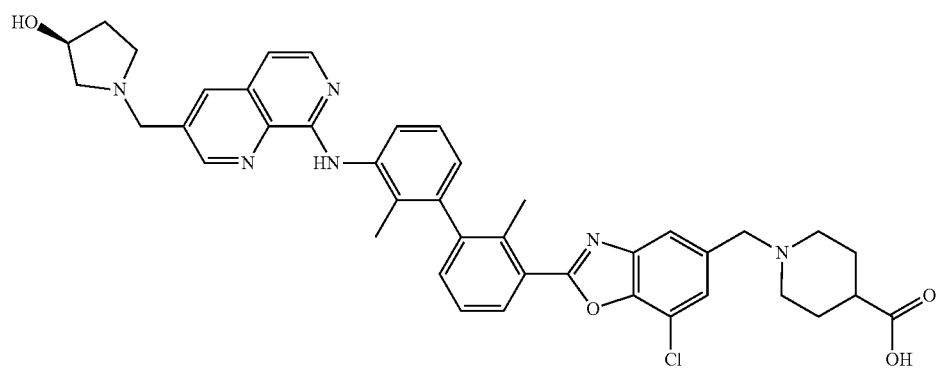 [SMILES: Cc1c(Nc2nccc3cc(CN4CC[C@H](O)C4)cnc23)cccc1-c1cccc(-c2nc3cc(CN4CCC(C(=O)O)CC4)cc(Cl)c3o2)c1C]

This compound was prepared using similar procedures as described for Example 16 with piperidine-4-carboxylic acid replacing (R)-pyrrolidine-3-carboxylic acid in Step 7. The reaction was diluted with MeOH and then purified by prep-HPLC (pH=10, acetonitrile/water+NH$_4$OH) to give the desired product. LC-MS calculated for C$_{41}$H$_{42}$ClN$_6$O$_4$ (M+H)$^+$: m/z=717.3; found 717.3.

Example 23

(S)-1-((7-chloro-2-(3'-(3-((3-hydroxypyrrolidin-1-yl)methyl)-1,7-naphthyridin-8-ylamino)-2,2'-dimethylbiphenyl-3-yl)benzo[d]oxazol-5-yl)methyl)azetidine-3-carboxylic acid

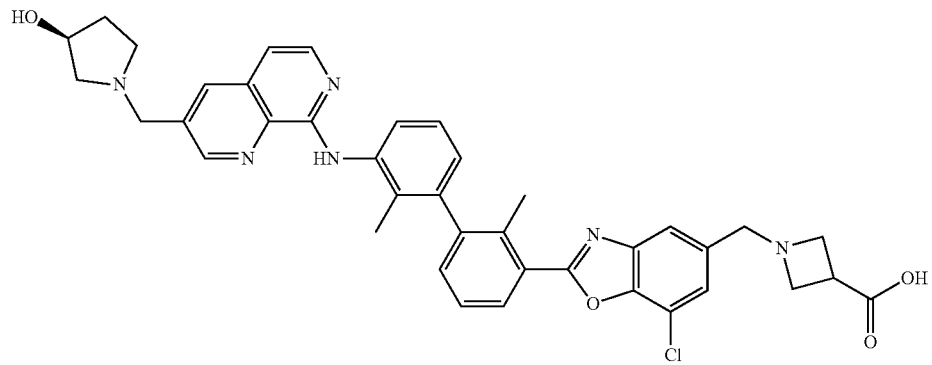 [SMILES: Cc1c(Nc2nccc3cc(CN4CC[C@H](O)C4)cnc23)cccc1-c1cccc(-c2nc3cc(CN4CC(C(=O)O)C4)cc(Cl)c3o2)c1C]

This compound was prepared using similar procedures as described for Example 16 with azetidine-3-carboxylic acid replacing (R)-pyrrolidine-3-carboxylic acid in Step 7. The reaction was diluted with MeOH and then purified by prep-HPLC (pH=10, acetonitrile/water+NH$_4$OH) to give the desired product. LC-MS calculated for $C_{39}H_{38}ClN_6O_4$ (M+H)$^+$: m/z=689.3; found 689.3.

Example 24

(R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid

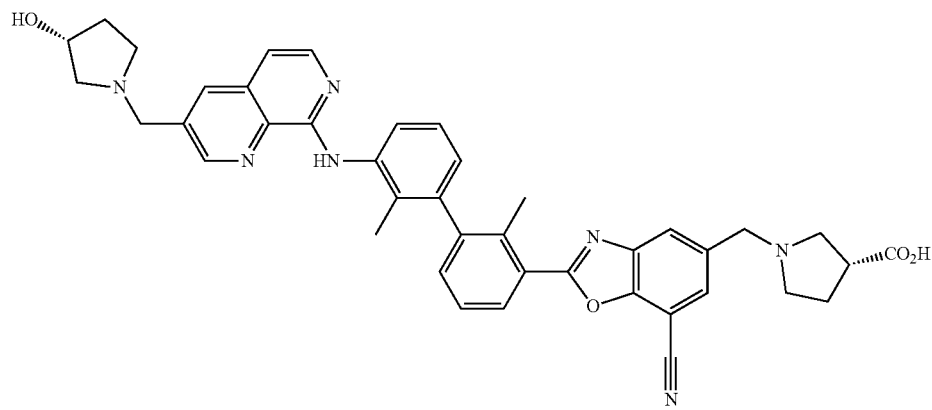 [SMILES: Cc1c(Nc2nccc3cc(CN4CC[C@@H](O)C4)cnc23)cccc1-c1cccc(-c2nc3cc(CN4CC[C@@H](C(=O)O)C4)cc(C#N)c3o2)c1C]

Step 1: (R)-1-((8-(3-bromo-2-methylphenylamino)-1,7-naphthyridin-3-yl)methyl)pyrrolidin-3-ol

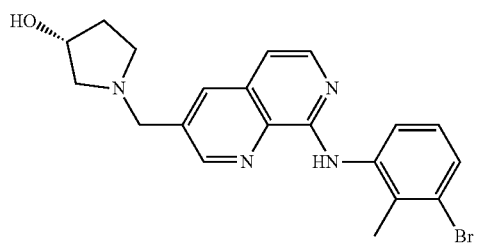 [SMILES: Cc1c(Br)cccc1Nc1nccc2cc(CN3CC[C@@H](O)C3)cnc12]

A mixture of 8-((3-bromo-2-methylphenyl)amino)-1,7-naphthyridine-3-carbaldehyde (Example 16, Step 3: 102 mg, 0.298 mmol) and (R)-pyrrolidin-3-ol (51.9 mg, 0.596 mmol) in DCM (1490 µl) was stirred at room temperature for 0.5 h. Then sodium triacetoxyborohydride (95 mg, 0.447 mmol) and acetic acid (25.0 µl, 0.447 mmol) were added. The mixture was further stirred at room temperature for 1 h. The reaction mixture was quenched by NH$_4$OH aqueous solution then extracted with DCM. The organic phase was combined and dried over MgSO$_4$, then filtered. The filtrate was concentrated and used directly in the next step without further purification. LC-MS calculated for $C_{20}H_{22}BrN_4O$ (M+H)$^+$: m/z=413.1; found 413.1.

Step 2: (R)-1-((8-(3'-(7-chloro-5-(hydroxymethyl)benzo[d]oxazol-2-yl)-2,2'-dimethylbiphenyl-3-ylamino)-1,7-naphthyridin-3-yl)methyl)pyrrolidin-3-ol

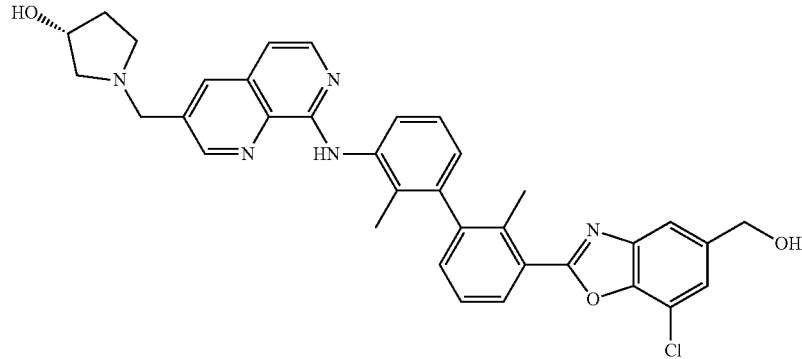 [SMILES: Cc1c(Nc2nccc3cc(CN4CC[C@@H](O)C4)cnc23)cccc1-c1cccc(-c2nc3cc(CO)cc(Cl)c3o2)c1C]

A mixture of (R)-1-((8-((3-bromo-2-methylphenyl)amino)-1,7-naphthyridin-3-yl)methyl)pyrrolidin-3-ol (419 mg, 1.01 mmol), (7-chloro-2-(2-methyl-3-(4,4,5,5-tetramethyl-1,3,2-dioxaborolan-2-yl)phenyl)benzo[d]oxazol-5-yl)methanol (Example 1, Step 5: 611 mg, 1.12 mmol), sodium carbonate (269 mg, 2.53 mmol) and tetrakis(triphenylphosphine)palladium(0) (117 mg, 0.101 mmol) in water (1.7 mL) and 1,4-dioxane (8.4 mL) was purged with $N_2$ and then stirred at 100° C. for 4 h. The reaction mixture was cooled to room temperature, diluted with ethyl acetate and then washed with $H_2O$. The organic layer was dried over $MgSO_4$ and filtered. The filtrate was concentrated to give a crude residue, which was purified by flash chromatography on a silica gel column eluting with 0 to 15% MeOH/DCM to give the desired product. LC-MS calculated for $C_{35}H_{33}ClN_5O_3$ $(M+H)^+$: m/z=606.2; found 606.4.

Step 3: (R)-5-(hydroxymethyl)-2-(3'-(3-((3-hydroxypyrrolidin-1-yl)methyl)-1,7-naphthyridin-8-ylamino)-2,2'-dimethylbiphenyl-3-yl)benzo[d]oxazole-7-carbonitrile

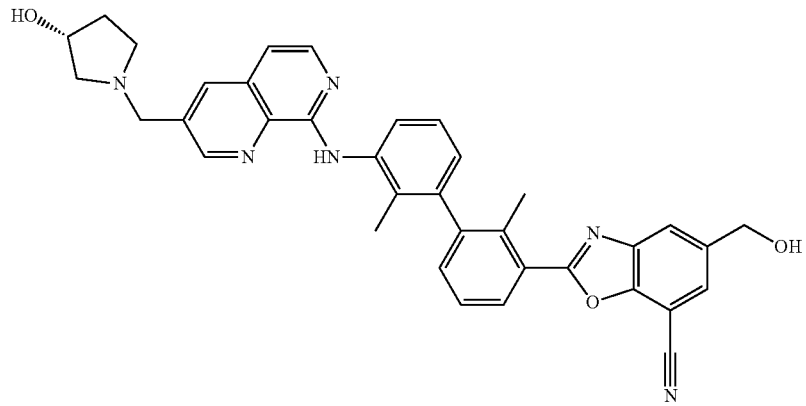 [SMILES: Cc1c(Nc2nccc3cc(CN4CC[C@@H](O)C4)cnc23)cccc1-c1cccc(-c2nc3cc(CO)cc(C#N)c3o2)c1C]

A mixture of (R)-1-((8-((3'-(7-chloro-5-(hydroxymethyl)benzo[d]oxazol-2-yl)-2,2'-dimethyl-[1,1'-biphenyl]-3-yl)amino)-1,7-naphthyridin-3-yl)methyl)pyrrolidin-3-ol (79 mg, 0.13 mmol), [(2-di-tert-butylphosphino-2',4',6'-triisopropyl-1,1'-biphenyl)-2-(2'-amino-1,1'-biphenyl)]palladium(II) methanesulfonate (10.4 mg, 0.013 mmol), potassium hexacyanoferrate(II) trihydrate (55.1 mg, 0.130 mmol) and potassium acetate (2.6 mg, 0.026 mmol) in 1,4-dioxane (650 µl) and water (650 µl) was stirred and heated at 100° C. for 4 h. After cooling to room temperature, the reaction mixture was diluted with EtOAc and water, extracted with EtOAc. The combined organic phase was dried over $MgSO_4$, and then filtered. The filtrate was concentrated. The crude material was purified by column chromatography (0-8% MeOH in DCM) to give the desired product. LC-MS calculated for $C_{36}H_{33}N_6O_3$ $(M+H)^+$: m/z=597.3; found 597.2.

Step 4: (R)-5-formyl-2-(3'-(3-((3-hydroxypyrrolidin-1-yl)methyl)-1,7-naphthyridin-8-ylamino)-2,2'-dimethylbiphenyl-3-yl)benzo[d]oxazole-7-carbonitrile

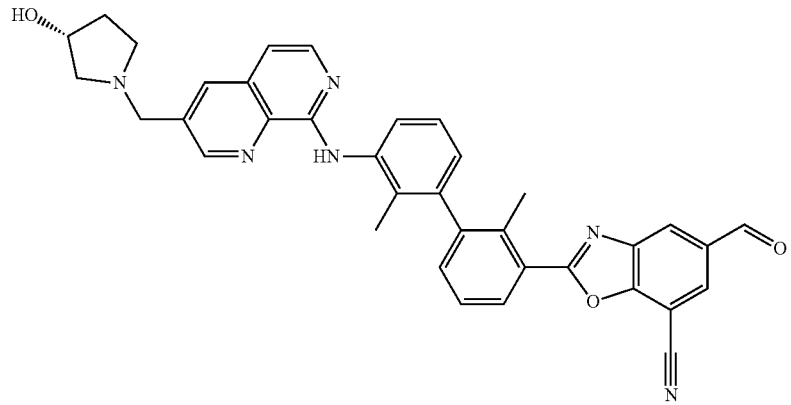 [SMILES: Cc1c(Nc2nccc3cc(CN4CC[C@@H](O)C4)cnc23)cccc1-c1cccc(-c2nc3cc(C=O)cc(C#N)c3o2)c1C]

A suspension of (R)-5-(hydroxymethyl)-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazole-7-carbonitrile (72 mg, 0.12 mmol) and manganese dioxide (231 mg, 2.65 mmol) in DCM (1.2 mL) was stirred at 45° C. for 25 min. The reaction mixture was cooled to room temperature, filtered through a short pad of celite and then concentrated to yield a crude residue, which was used directly in the next step without further purification. LC-MS calculated for $C_{36}H_{31}N_6O_3$ (M+H)$^+$: m/z=595.2; found 595.2.

Step 5: (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid A mixture of (R)-5-formyl-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazole-7-carbonitrile (72 mg, 0.12 mmol), (R)-pyrrolidine-3-carboxylic acid (27.9 mg, 0.242 mmol) and triethylamine (34 μl, 0.24 mmol) in DCM (800 μl) was stirred at room temperature for 2 h. Then sodium triacetoxyborohydride (38.5 mg, 0.182 mmol) and acetic acid (10.5 μl, 0.18 mmol) was added. The mixture was further stirred at room temperature for 1 h. The reaction mixture was diluted with MeOH and then purified by prep-HPLC (pH=2, acetonitrile/water+TFA) to give the desired product as TFA salt. LC-MS calculated for $C_{41}H_{40}N_7O_4$ (M+H)$^+$: m/z=694.3; found 694.3. $^1$H NMR (500 MHz, DMSO) δ 9.07 (s, 1H), 8.55-8.48 (m, 1H), 8.40 (d, J=1.5 Hz, 1H), 8.25-8.10 (m, 3H), 8.04 (d, J=5.8 Hz, 1H), 7.59 (t, J=7.7 Hz, 1H), 7.48 (dd, J=7.6, 1.4 Hz, 1H), 7.41 (t, J=7.8 Hz, 1H), 7.23 (d, J=6.0 Hz, 1H), 7.06 (d, J=7.3 Hz, 1H), 4.86-4.36 (m, 5H), 3.88-3.00 (m, 9H), 2.49 (s, 3H), 2.42-2.15 (m, 2H), 2.06 (s, 3H), 2.02-1.80 (m, 2H).

Example 25

(S)-1-((7-cyano-2-(3'-(3-(((S)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid

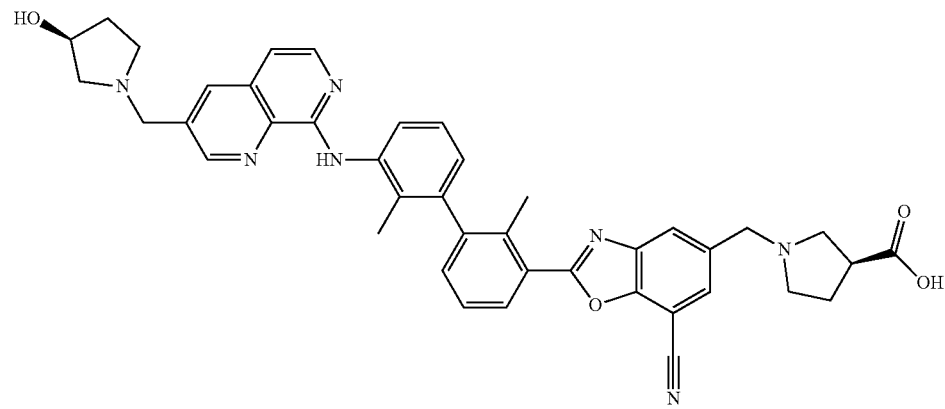 [SMILES: Cc1c(Nc2nccc3cc(CN4CC[C@H](O)C4)cnc23)cccc1-c1cccc(-c2nc3cc(CN4CC[C@H](C(=O)O)C4)cc(C#N)c3o2)c1C]

This compound was prepared similar procedures as described for Example 24 with (S)-pyrrolidin-3-ol replacing (R)-pyrrolidin-3-ol in Step 1 and (S)-pyrrolidine-3-carboxylic acid replacing (R)-pyrrolidine-3-carboxylic acid in Step 5. The reaction was diluted with MeOH and then purified by prep-HPLC (pH=2, acetonitrile/water+TFA) to give the desired product as TFA salt. LC-MS calculated for $C_{41}H_{40}N_7O_4$ (M+H)$^+$: m/z=694.3; found 694.3. $^1$H NMR (600 MHz, DMSO) δ 9.14 (s, 1H), 8.58 (s, 1H), 8.40 (d, J=1.6 Hz, 1H), 8.20 (dd, J=8.1, 1.3 Hz, 1H), 8.14 (d, J=1.6 Hz, 1H), 8.02-7.87 (m, 2H), 7.60 (t, J=7.7 Hz, 1H), 7.52-7.43 (m, 2H), 7.27 (d, J=6.5 Hz, 1H), 7.18 (d, J=7.2 Hz, 1H), 4.85-4.39 (m, 5H), 3.79-3.09 (m, 9H), 2.50 (s, 3H), 2.44-2.07 (m, 3H), 2.03 (s, 3H), 1.94-1.83 (m, 1H).

Example 26

(R)-1-((7-cyano-2-(3'-(3-(((S)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid

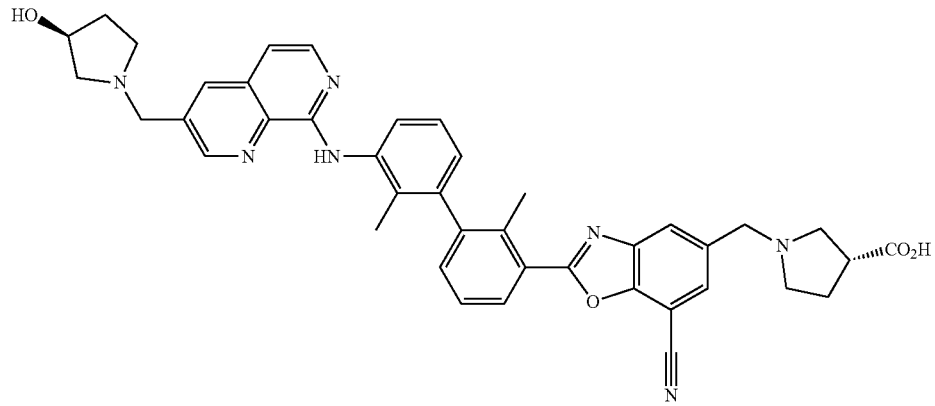 [SMILES: Cc1c(Nc2nccc3cc(CN4CC[C@H](O)C4)cnc23)cccc1-c1cccc(-c2nc3cc(CN4CC[C@@H](C(=O)O)C4)cc(C#N)c3o2)c1C]

This compound was prepared using similar procedures as described for Example 24 with (S)-pyrrolidin-3-ol replacing (R)-pyrrolidin-3-ol in Step 1. The reaction mixture was diluted with MeOH and then purified by prep-HPLC (pH=2, acetonitrile/water+TFA) to give the desired product as TFA salt. LC-MS calculated for $C_{41}H_{40}N_7O_4$ (M+H)$^+$: m/z=694.3; found 694.3. $^1$H NMR (500 MHz, DMSO) δ 9.13 (s, 1H), 8.57 (s, 1H), 8.42-8.35 (m, 1H), 8.19 (d, J=7.8 Hz, 1H), 8.13 (d, J=1.1 Hz, 1H), 8.03-7.86 (m, 2H), 7.58 (t, J=7.7 Hz, 1H), 7.46 (dd, J=14.9, 7.2 Hz, 2H), 7.26 (d, J=6.1 Hz, 1H), 7.16 (d, J=6.8 Hz, 1H), 4.81-4.40 (m, 5H), 3.79-3.07 (m, 9H), 2.49 (s, 3H), 2.28-1.87 (m, 4H), 2.02 (s, 3H).

Example 27

(S)-1-((7-cyano-2-(3'-(3-(((S)-3-hydroxypyrrolidin-1-yl)methyl)-1,7-naphthyridin-8-ylamino)-2,2'-dimethylbiphenyl-3-yl)benzo[d]oxazol-5-yl)methyl)piperidine-2-carboxylic acid

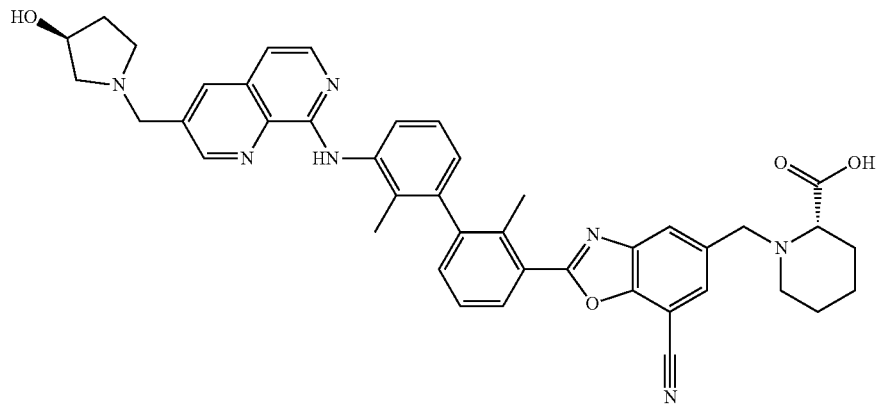 [SMILES: Cc1c(Nc2nccc3cc(CN4CC[C@H](O)C4)cnc23)cccc1-c1cccc(-c2nc3cc(CN4CCCC[C@H]4C(=O)O)cc(C#N)c3o2)c1C]

This compound was prepared using similar procedures as described for Example 24 with (S)-pyrrolidin-3-ol replacing (R)-pyrrolidin-3-ol in Step 1 and (S)-piperidine-2-carboxylic acid replacing (R)-pyrrolidine-3-carboxylic acid in Step 5. The reaction mixture was diluted with MeOH and then purified by prep-HPLC (pH=2, acetonitrile/water+TFA) to give the desired product as TFA salt. LC-MS calculated for $C_{42}H_{42}N_7O_4$ (M+H)⁺: m/z=708.3; found 708.3. ¹H NMR (600 MHz, DMSO) δ 9.10 (s, 1H), 8.54 (s, 1H), 8.30 (s, 1H), 8.20 (d, J=7.9 Hz, 1H), 8.04 (s, 2H), 7.95 (m, 1H), 7.59 (t, J=7.7 Hz, 1H), 7.48 (d, J=7.5 Hz, 1H), 7.44 (t, J=7.7 Hz, 1H), 7.25 (d, J=5.4 Hz, 1H), 7.14 (d, J=8.4 Hz, 1H), 4.81-4.57 (m, 3H), 4.55-4.28 (m, 2H), 4.03 (s, 1H), 3.73-2.96 (m, 6H), 2.49 (s, 3H), 2.36-2.12 (m, 2H), 2.03 (s, 3H), 1.99-1.43 (m, 6H).

Example 28

(S)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid

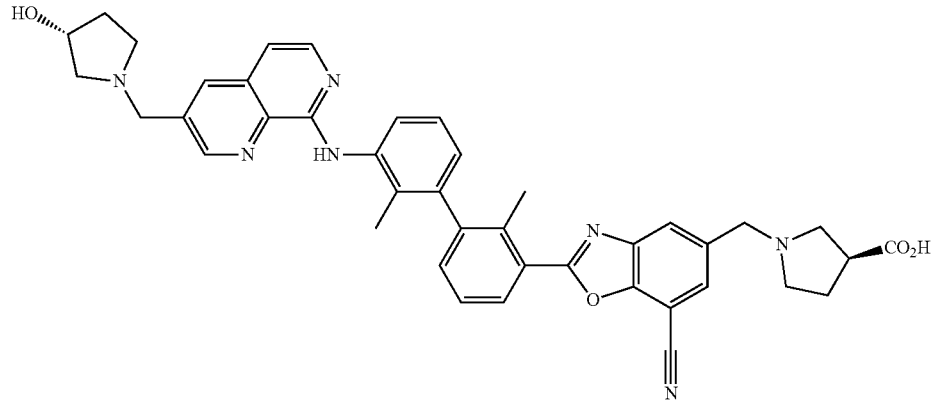 [SMILES: Cc1c(Nc2nccc3cc(CN4CC[C@@H](O)C4)cnc23)cccc1-c1cccc(-c2nc3cc(CN4CC[C@H](C(=O)O)C4)cc(C#N)c3o2)c1C]

This compound was prepared using similar procedures as described for Example 24 with (S)-pyrrolidine-3-carboxylic acid replacing (R)-pyrrolidine-3-carboxylic acid in Step 5. The reaction mixture was diluted with MeOH and then purified by prep-HPLC (pH=2, acetonitrile/water+TFA) to give the desired product as TFA salt. LC-MS calculated for $C_{41}H_{40}N_7O_4$ (M+H)⁺: m/z=694.3; found 694.3. ¹H NMR (500 MHz, DMSO) δ 9.09 (s, 1H), 8.53 (s, 1H), 8.40 (d, J=1.6 Hz, 1H), 8.20 (dd, J=8.0, 1.4 Hz, 1H), 8.17-8.06 (m, 2H), 8.01 (d, J=6.8 Hz, 1H), 7.59 (t, J=7.7 Hz, 1H), 7.48 (dd, J=7.7, 1.4 Hz, 1H), 7.43 (t, J=7.8 Hz, 1H), 7.24 (d, J=6.0 Hz, 1H), 7.09 (d, J=7.7 Hz, 1H), 4.82-4.37 (m, 5H), 3.77-3.06 (m, 9H), 2.50 (s, 3H), 2.43-1.82 (m, 4H), 2.06 (s, 3H).

Example 29

(R)-1-((7-chloro-2-(2'-chloro-3'-(3-(((S)-3-hydroxypyrrolidin-1-yl)methyl)-1,7-naphthyridin-8-ylamino)-2-methylbiphenyl-3-yl)benzo[d]oxazol-5-yl)methyl)pyrrolidine-3-carboxylic acid

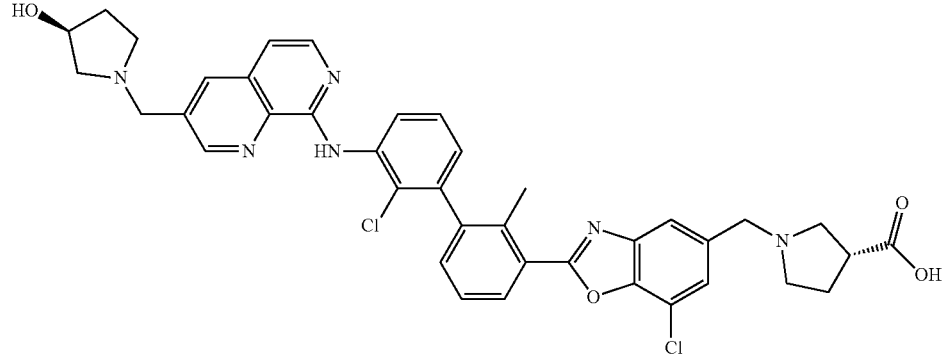 [SMILES: Cc1c(-c2nc3cc(CN4CC[C@@H](C(=O)O)C4)cc(Cl)c3o2)cccc1-c1cccc(Nc2nccc3cc(CN4CC[C@H](O)C4)cnc23)c1Cl]

Step 1: 8-chloro-3-vinyl-1,7-naphthyridine

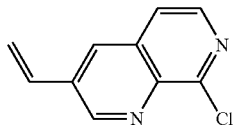

A mixture of 3-bromo-8-chloro-1,7-naphthyridine (PharmaBlock, cat # PBLJ2743: 770 mg, 3.16 mmol), 4,4,5,5-tetramethyl-2-vinyl-1,3,2-dioxaborolane (584 mg, 3.79 mmol), sodium carbonate (838 mg, 7.91 mmol) and tetrakis(triphenylphosphine)palladium(0) (183 mg, 0.158 mmol) in t-butanol (8 ml) and water (8 ml) was purged with nitrogen and sealed. It was stirred at 80° C. for 2 h. The reaction mixture was cooled then extracted with ethyl acetate. The combined organic layers were washed with brine, dried over MgSO$_4$, and filtered. The filtrate was concentrated under reduced pressure. The crude residue was used directly in the next step without further purification. LC-MS calculated for $C_{10}H_8ClN_2$ (M+H)$^+$: m/z=191.0; found 191.0.

Step 2: N-(3-bromo-2-chlorophenyl)-3-vinyl-1,7-naphthyridin-8-amine

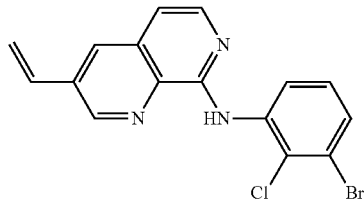 [SMILES: C=Cc1cnc2c(Nc3cccc(Br)c3Cl)nccc2c1]

A mixture of 3-bromo-2-chloroaniline (536 mg, 2.59 mmol), 8-chloro-3-vinyl-1,7-naphthyridine (471 mg, 2.47 mmol) and HCl in dioxane (618 μl, 2.47 mmol) in t-butanol (12.4 mL) was heated at 120° C. for 2 h. The reaction mixture was cooled to room temperature, diluted with DCM then quenched by aqueous NaHCO$_3$ solution and extracted with DCM. The organic phase was dried over MgSO$_4$, filtered and the filtrate was concentrated. The residue was used directly in the next step without further purification. LC-MS calculated for $C_{16}H_{12}BrClN_3$ (M+H)$^+$: m/z=360.0; found 360.0.

Step 3: 8-(3-bromo-2-chlorophenylamino)-1,7-naphthyridine-3-carbaldehyde

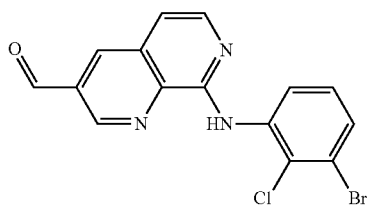 [SMILES: O=Cc1cnc2c(Nc3cccc(Br)c3Cl)nccc2c1]

To the solution of N-(3-bromo-2-chlorophenyl)-3-vinyl-1,7-naphthyridin-8-amine (135 mg, 0.374 mmol) in 1,4-dioxane (2.8 mL) and water (0.9 mL) was added osmium tetroxide (4% w/w in water, 147 μl, 0.019 mmol). The mixture was stirred at room temperature for 5 min then sodium periodate (400 mg, 1.872 mmol) was added. After stirring at room temperature for 1 h, the reaction mixture was quenched with a saturated aqueous solution of sodium thiosulfate. The mixture was then extracted with ethyl acetate, and the combined organic layers were separated, washed with brine, dried over Na$_2$SO$_4$, filtered, and concentrated in vacuo. The crude residue was used directly in the next step without further purification. LC-MS calculated for $C_{15}H_{10}BrClN_3O$ (M+H)$^+$: m/z=362.0; found 362.0.

Step 4: (S)-1-((8-(3-bromo-2-chlorophenylamino)-1,7-naphthyridin-3-yl)methyl)pyrrolidin-3-ol

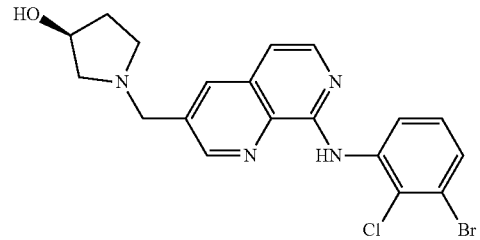

A mixture of 8-((3-bromo-2-chlorophenyl)amino)-1,7-naphthyridine-3-carbaldehyde (384 mg, 1.06 mmol) and (S)-pyrrolidin-3-ol (185 mg, 2.12 mmol) in DCM (5.3 mL) was stirred at room temperature for 0.5 h. Then sodium triacetoxyborohydride (337 mg, 1.59 mmol) and acetic acid (91 μl, 1.59 mmol) were added. The mixture was further stirred at room temperature for 1 h. The reaction mixture was quenched by NH$_4$OH aqueous solution and extracted with DCM. The organic phase was combined and dried over MgSO$_4$, then filtered. The filtrate was concentrated and the residue was purified by column chromatography on a silica gel column eluting with 0 to 8% MeOH/DCM to give the desired product. LC-MS calculated for $C_{19}H_{19}BrClN_4O$ (M+H)$^+$: m/z=433.0; found 433.0.

Step 5: (S)-1-((8-(2-chloro-3'-(7-chloro-5-(hydroxymethyl)benzo[d]oxazol-2-yl)-2'-methylbiphenyl-3-ylamino)-1,7-naphthyridin-3-yl)methyl)pyrrolidin-3-ol

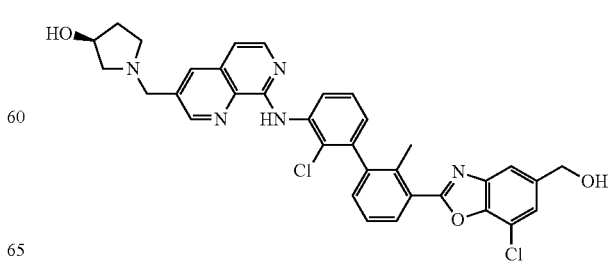

A mixture of (S)-1-((8-(3-bromo-2-chlorophenylamino)-1,7-naphthyridin-3-yl)methyl)pyrrolidin-3-ol (10.3 mg, 0.024 mmol), (7-chloro-2-(2-methyl-3-(4,4,5,5-tetramethyl-1,3,2-dioxaborolan-2-yl)phenyl)benzo[d]oxazol-5-yl)methanol (Example 1, Step 5: 9.5 mg, 0.024 mmol), sodium carbonate (6.30 mg, 0.059 mmol) and tetrakis(triphenylphosphine) palladium(0) (2.75 mg, 2.377 mmol) in water (40 μl) and 1,4-dioxane (200 μl) was purged with $N_2$ and then stirred at 100° C. for 1 h. The reaction mixture was cooled to room temperature, diluted with ethyl acetate and then washed with $H_2O$. The organic layer was dried $MgSO_4$ and filtered. The filtrate was concentrated to give a crude residue, which was purified by flash chromatography on a silica gel column eluting with 0 to 15% MeOH/DCM to give the desired product. LC-MS calculated for $C_{34}H_{30}Cl_2N_5O_3$ (M+H)$^+$: m/z=626.2; found 626.2.

Step 6: (S)-7-chloro-2-(2'-chloro-3'-(3-((3-hydroxypyrrolidin-1-yl)methyl)-1,7-naphthyridin-8-ylamino)-2-methylbiphenyl-3-yl)benzo[d]oxazole-5-carbaldehyde

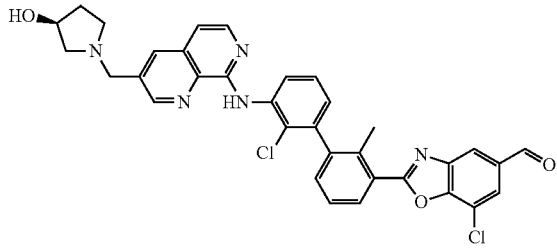 [SMILES: Cc1c(-c2nc3cc(C=O)cc(Cl)c3o2)cccc1-c1cccc(Nc2nccc3cc(CN4CC[C@H](O)C4)cnc23)c1Cl]

A suspension of (S)-1-((8-((2-chloro-3'-(7-chloro-5-(hydroxymethyl)benzo[d]oxazol-2-yl)-2'-methyl-[1,1'-biphenyl]-3-yl)amino)-1,7-naphthyridin-3-yl)methyl)pyrrolidin-3-ol (4.9 mg, 7.8 μmol) and manganese dioxide (17 mg, 0.20 mmol) in DCM (80 μl) was stirred at 45° C. for 15 min. The reaction mixture was filtered through a short pad of celite and then concentrated to yield a crude residue, which was used directly without further purification. LC-MS calculated for $C_{34}H_{28}Cl_2N_5O_3$ (M+H)$^+$: m/z=624.2; found 624.3.

Step 7: (R)-1-((7-chloro-2-(2'-chloro-3'-(3-(((S)-3-hydroxypyrrolidin-1-yl)methyl)-1,7-naphthyridin-8-ylamino)-2-methylbiphenyl-3-yl)benzo[d]oxazol-5-yl)methyl)pyrrolidine-3-carboxylic acid A mixture of (S)-7-chloro-2-(2'-chloro-3'-((3-((3-hydroxypyrrolidin-1-yl)methyl)-1,7-naphthyridin-8-yl)amino)-2-methyl-[1,1'-biphenyl]-3-yl)benzo[d]oxazole-5-carbaldehyde (4.5 mg, 7.2 mmol), triethylamine (3.0 μl, 0.022 mmol) and (R)-pyrrolidine-3-carboxylic acid (2.5 mg, 0.022 mmol) in DCM (75 μl) was stirred at rt for 2 h. Then sodium triacetoxyborohydride (4.5 mg, 0.022 mmol) and acetic acid (1.2 μl, 0.022 mmol) were added. The mixture was further stirred at rt for 1 h. The reaction was diluted with MeOH and then purified by prep-HPLC (pH=10, acetonitrile/water+ $NH_4OH$) to give the desired product. LC-MS calculated for $C_{39}H_{37}Cl_2N_6O_4$ (M+H)$^+$: m/z=723.2; found 723.2.

Example 30

(R)-1-((2-(2'-chloro-3'-(3-(((S)-3-hydroxypyrrolidin-1-yl)methyl)-1,7-naphthyridin-8-ylamino)-2-methylbiphenyl-3-yl)-7-cyanobenzo[d]oxazol-5-yl)methyl)pyrrolidine-3-carboxylic acid

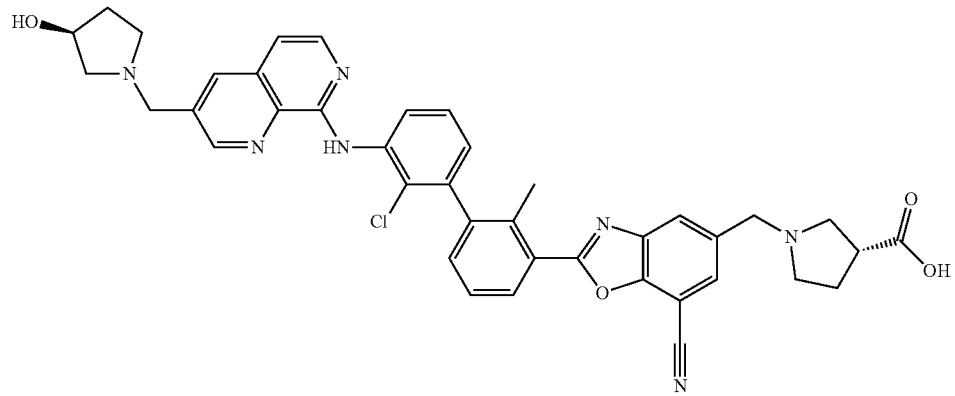 [SMILES: Cc1c(-c2nc3cc(CN4CC[C@@H](C(=O)O)C4)cc(C#N)c3o2)cccc1-c1cccc(Nc2nccc3cc(CN4CC[C@H](O)C4)cnc23)c1Cl]

Step 1: (S)-2-(2'-chloro-3'-(3-((3-hydroxypyrrolidin-1-yl)methyl)-1,7-naphthyridin-8-ylamino)-2-methylbiphenyl-3-yl)-5-(hydroxymethyl)benzo[d]oxazole-7-carbonitrile

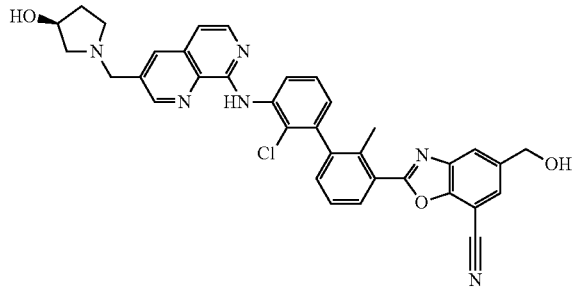 [SMILES: Cc1c(-c2nc3cc(CO)cc(C#N)c3o2)cccc1-c1cccc(Nc2nccc3cc(CN4CC[C@H](O)C4)cnc23)c1Cl]

A mixture of (S)-1-((8-((2-chloro-3'-(7-chloro-5-(hydroxymethyl)benzo[d]oxazol-2-yl)-2'-methyl-[1,1'-biphenyl]-3-yl)amino)-1,7-naphthyridin-3-yl)methyl)pyrrolidin-3-ol (Example 29, Step 5: 114 mg, 0.182 mmol), [(2-di-tert-butylphosphino-2',4',6'-triisopropyl-1,1'-biphenyl)-2-(2'-amino-1,1'-biphenyl)]palladium(II) methanesulfonate (14.4 mg, 0.018 mmol), potassium hexacyanoferrate(II) trihydrate (77 mg, 0.18 mmol) and potassium acetate (3.6 mg, 0.036 mmol) in 1,4-dioxane (910 µl) and water (910 µl) was stirred and heated at 100° C. for 1 h. After cooling to room temperature, the reaction mixture was diluted with EtOAc and water, extracted with EtOAc. The combined organic phase was dried over MgSO$_4$, and then filtered. The filtrate was concentrated. The crude material was purified by column chromatography (0-8% MeOH in DCM) to give the desired product. LC-MS calculated for C$_{35}$H$_{30}$ClN$_6$O$_3$(M+H)$^+$: m/z=617.2; found 617.4.

Step 2: (S)-2-(2'-chloro-3'-(3-((3-hydroxypyrrolidin-1-yl)methyl)-1,7-naphthyridin-8-ylamino)-2-methylbiphenyl-3-yl)-5-formylbenzo[d]oxazole-7-carbonitrile

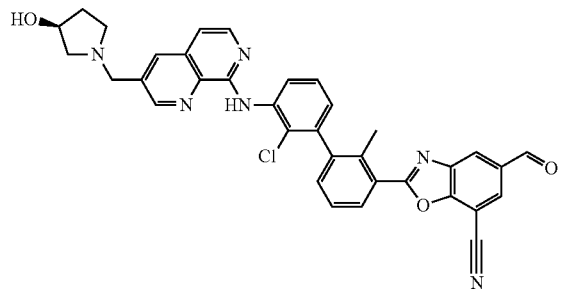 [SMILES: Cc1c(-c2nc3cc(C=O)cc(C#N)c3o2)cccc1-c1cccc(Nc2nccc3cc(CN4CC[C@H](O)C4)cnc23)c1Cl]

A suspension of (S)-2-(2'-chloro-3'-((3-((3-hydroxypyrrolidin-1-yl)methyl)-1,7-naphthyridin-8-yl)amino)-2-methyl-[1,1'-biphenyl]-3-yl)-5-(hydroxymethyl)benzo[d]oxazole-7-carbonitrile (64 mg, 0.104 mmol) and manganese dioxide (198 mg, 2.28 mmol) in DCM (1.0 mL) was stirred at 45° C. for 15 min. The reaction was filtered through a short pad of celite and then concentrated to yield a crude residue, which was used directly without further purification. LC-MS calculated for C$_{35}$H$_{28}$ClN$_6$O$_3$ (M+H)$^+$: m/z=615.2; found 615.2.

Step 3: (R)-1-((2-(2'-chloro-3'-(3-(((S)-3-hydroxypyrrolidin-1-yl)methyl)-1,7-naphthyridin-8-ylamino)-2-methylbiphenyl-3-yl)-7-cyanobenzo[d]oxazol-5-yl)methyl)pyrrolidine-3-carboxylic acid A mixture of (S)-2-(2'-chloro-3'-((3-((3-hydroxypyrrolidin-1-yl)methyl)-1,7-naphthyridin-8-yl)amino)-2-methyl-[1,1'-biphenyl]-3-yl)-5-formylbenzo[d]oxazole-7-carbonitrile (53.2 mg, 0.086 mmol), (R)-pyrrolidine-3-carboxylic acid (29.9 mg, 0.259 mmol) and triethylamine (36 µl, 0.259 mmol) in DCM (580 µl) was stirred at rt for 2 h. Then sodium triacetoxyborohydride (55.0 mg, 0.259 mmol) and acetic acid (14.8 µl, 0.259 mmol) were added. The mixture was further stirred at rt for 1 h. The reaction was diluted with MeOH and then purified by prep-HPLC (pH=2, acetonitrile/water+TFA) to give the desired product as TFA salt. LC-MS calculated for C$_{40}$H$_{37}$ClN$_7$O$_4$(M+H)$^+$: m/z=714.3; found 714.3. $^1$H NMR (600 MHz, DMSO) δ 10.00 (s, 1H), 9.12-9.06 (m, 1H), 9.05-9.01 (m, 1H), 8.57 (s, 1H), 8.40 (d, J=1.6 Hz, 1H), 8.30-8.19 (m, 2H), 8.14 (d, J=1.6 Hz, 1H), 7.62 (t, J=7.7 Hz, 1H), 7.59-7.52 (m, 2H), 7.44-7.34 (m, 1H), 7.11 (dd, J=7.7, 1.5 Hz, 1H), 4.82-4.36 (m, 5H), 3.73-3.07 (m, 9H), 2.51 (s, 3H), 2.44-1.82 (m, 4H).

Example 31

(R)-1-((2-(2'-chloro-2-methyl-3'-(3-((2-oxooxazolidin-3-yl)methyl)-1,7-naphthyridin-8-ylamino)biphenyl-3-yl)-7-cyanobenzo[d]oxazol-5-yl)methyl)pyrrolidine-3-carboxylic acid

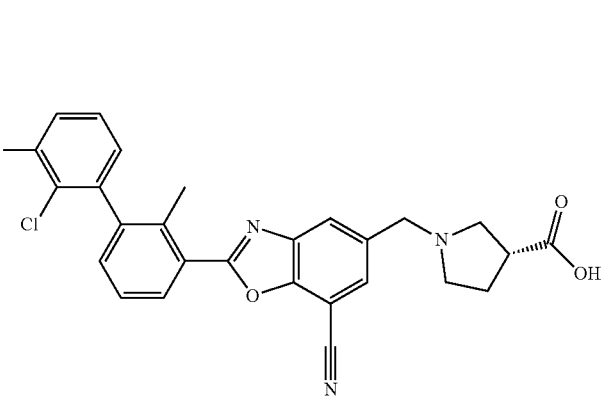

Step 1: 2-((8-(3-bromo-2-chlorophenylamino)-1,7-naphthyridin-3-yl)methylamino)ethanol

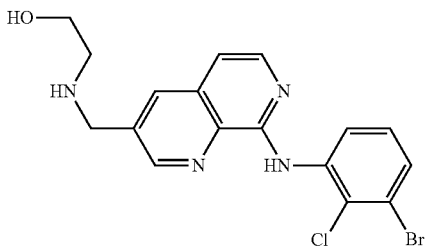 [SMILES: OCCNCc1cnc2c(Nc3cccc(Br)c3Cl)nccc2c1]

This compound was prepared using similar procedures as described for Example 29 with 2-aminoethanol replacing (S)-pyrrolidin-3-ol in Step 4. LC-MS calculated for $C_{17}H_{17}BrClN_4O$ (M+H)$^+$: m/z=407.0; found 407.0.

Step 2: 3-((8-(3-bromo-2-chlorophenylamino)-1,7-naphthyridin-3-yl)methyl)oxazolidin-2-one

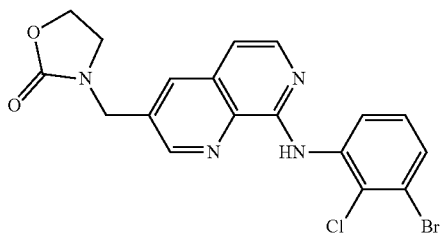 [SMILES: O=C1OCCN1Cc1cnc2c(Nc3cccc(Br)c3Cl)nccc2c1]

To a solution of 2-(((8-((3-bromo-2-chlorophenyl)amino)-1,7-naphthyridin-3-yl)methyl)amino)ethan-1-ol (30 mg, 0.075 mmol) and 1,8-diazabicyclo[5.4.0]undec-7-ene (17.8 μl, 0.12 mmol) in DCM (750 μl) was added 1,1'-carbonyldiimidazole (15.7 mg, 0.10 mmol). The mixture was stirred at room temperature for 30 min. The reaction was concentrated and purified by column chromatography (0-5% MeOH in DCM). LC-MS calculated for $C_{18}H_{15}BrClN_4O_2$ (M+H)$^+$: m/z=433.0; found 433.1.

Step 3: (R)-1-((2-(2'-chloro-2-methyl-3'-(3-((2-oxooxazolidin-3-yl)methyl)-1,7-naphthyridin-8-ylamino)biphenyl-3-yl)-7-cyanobenzo[d]oxazol-5-yl)methyl)pyrrolidine-3-carboxylic acid This compound was prepared using similar procedures as described for Example 24, Step 2-5 with 3-((8-(3-bromo-2-chlorophenylamino)-1,7-naphthyridin-3-yl)methyl)oxazolidin-2-one replacing (R)-1-((8-(3-bromo-2-methylphenylamino)-1,7-naphthyridin-3-yl)methyl)pyrrolidin-3-ol in Step 2. The reaction was diluted with MeOH and then purified by prep-HPLC (pH=2, acetonitrile/water+TFA) to give the desired product as TFA salt. LC-MS calculated for $C_{39}H_{33}ClN_7O_5$(M+H)$^+$: m/z=714.2; found 714.2.

Example 32

(S)-1-((7-chloro-2-(2'-chloro-3'-(3-(((S)-3-hydroxypyrrolidin-1-yl)methyl)-1,7-naphthyridin-8-ylamino)-2-methylbiphenyl-3-yl)benzo[d]oxazol-5-yl)methyl)pyrrolidine-3-carboxylic acid

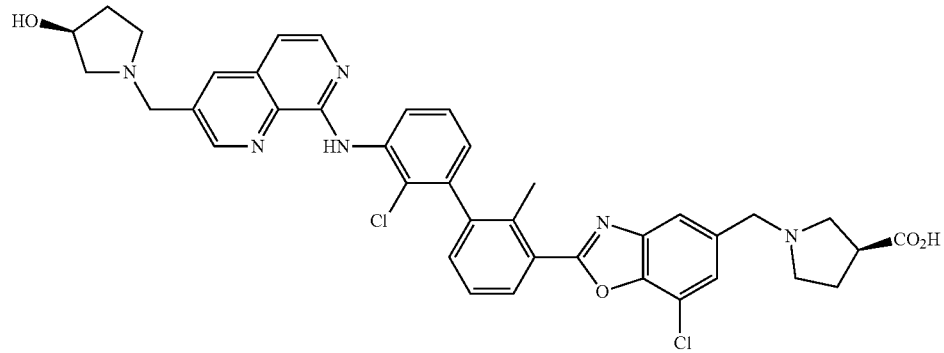 [SMILES: Cc1c(-c2nc3cc(CN4CC[C@H](C(=O)O)C4)cc(Cl)c3o2)cccc1-c1cccc(Nc2nccc3cc(CN4CC[C@H](O)C4)cnc23)c1Cl]

This compound was prepared using similar procedures as described for Example 29 with (S)-pyrrolidine-3-carboxylic acid replacing (R)-pyrrolidine-3-carboxylic acid in Step 7. The reaction was diluted with MeOH and then purified by prep-HPLC (pH=2, acetonitrile/water+TFA) to give the desired product as TFA salt. LC-MS calculated for $C_{39}H_{37}Cl_2N_6O_4$ (M+H)$^+$: m/z=723.2; found 723.2.

Example 33

(S)-1-((2-(2'-chloro-3'-(3-(((S)-3-hydroxypyrrolidin-1-yl)methyl)-1,7-naphthyridin-8-ylamino)-2-methyl-biphenyl-3-yl)-7-cyanobenzo[d]oxazol-5-yl)methyl)pyrrolidine-3-carboxylic acid

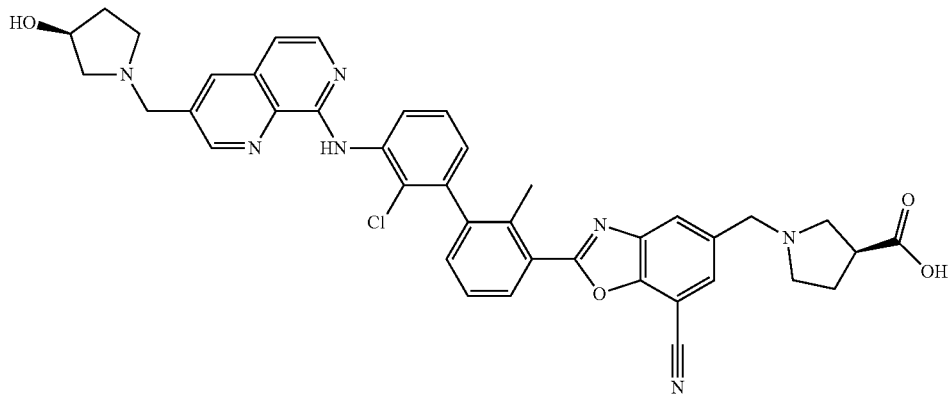 [SMILES: Cc1c(-c2nc3cc(CN4CC[C@H](C(=O)O)C4)cc(C#N)c3o2)cccc1-c1cccc(Nc2nccc3cc(CN4CC[C@H](O)C4)cnc23)c1Cl]

This compound was prepared using similar procedures as described for Example 30 with (S)-pyrrolidine-3-carboxylic acid replacing (R)-pyrrolidine-3-carboxylic acid in Step 3. For the last step, the reaction was diluted with MeOH and then purified by prep-HPLC (pH=2, acetonitrile/water+TFA) to give the desired product as TFA salt. LC-MS calculated for $C_{40}H_{37}ClN_7O_4(M+H)^+$: m/z=714.3; found 714.3.

Example 34

(R)-1-((2-(2'-chloro-3'-(3-(((S)-3-hydroxypyrrolidin-1-yl)methyl)-1,7-naphthyridin-8-ylamino)-2-methyl-biphenyl-3-yl)-7-cyanobenzo[d]oxazol-5-yl)methyl)-3-methylpyrrolidine-3-carboxylic acid

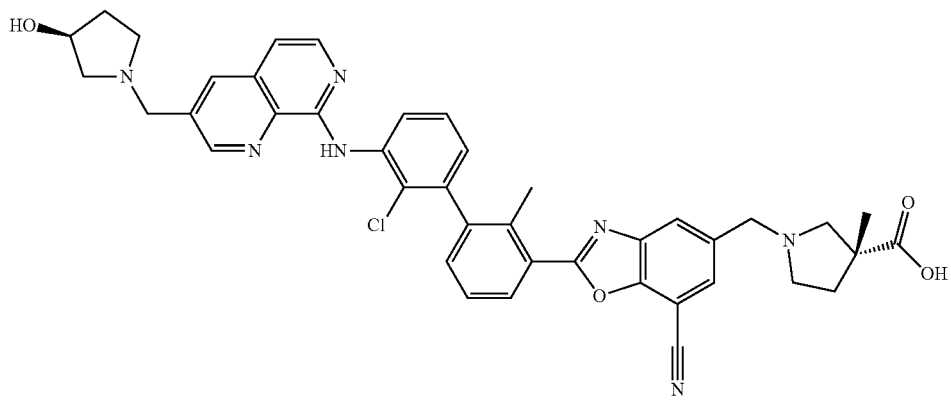 [SMILES: Cc1c(-c2nc3cc(CN4CC[C@@](C)(C(=O)O)C4)cc(C#N)c3o2)cccc1-c1cccc(Nc2nccc3cc(CN4CC[C@H](O)C4)cnc23)c1Cl]

This compound was prepared using similar procedures as described for Example 30 with (R)-3-methylpyrrolidine-3-carboxylic acid (J&W Pharmlab, #75R0495) replacing (R)-pyrrolidine-3-carboxylic acid in Step 3. For the last step, the reaction was diluted with MeOH and then purified by prep-HPLC (pH=2, acetonitrile/water+TFA) to give the desired product as TFA salt. LC-MS calculated for $C_{41}H_{39}ClN_7O_4(M+H)^+$: m/z=728.3; found 728.3.

Example 35

(S)-1-((7-cyano-2-(3'-(3-(((S)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-2-carboxylic acid

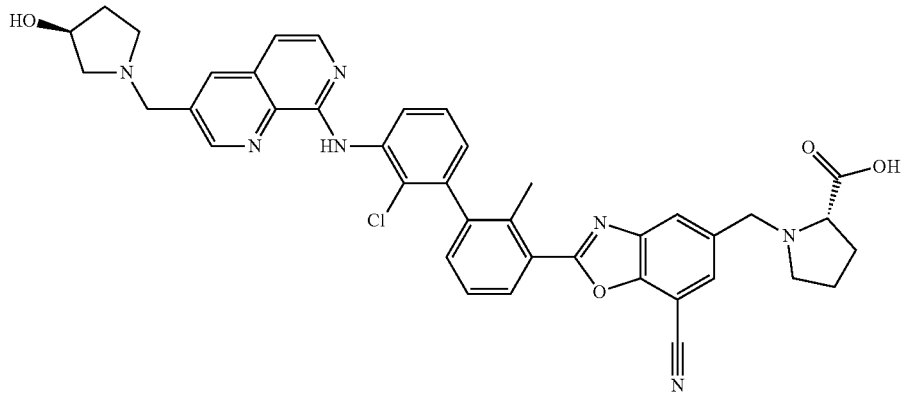 [SMILES: Cc1c(-c2nc3cc(CN4CCC[C@H]4C(=O)O)cc(C#N)c3o2)cccc1-c1cccc(Nc2nccc3cc(CN4CC[C@H](O)C4)cnc23)c1Cl]

This compound was prepared using similar procedures as described for Example 24 with (S)-pyrrolidin-3-ol replacing (R)-pyrrolidin-3-ol in Step 1 and (S)-pyrrolidine-2-carboxylic acid replacing (R)-pyrrolidine-3-carboxylic acid in Step 5. The reaction was diluted with MeOH and then purified by prep-HPLC (pH=10, acetonitrile/water+NH$_4$OH) to give the desired product. LC-MS calculated for C$_{41}$H$_{40}$N$_7$O$_4$ (M+H)$^+$: m/z=694.3; found 694.3.

Example 36

(S)-1-((7-cyano-2-(3'-(1,5-dimethyl-4,5,6,7-tetrahydro-1H-imidazo[4,5-c]pyridine-2-carboxamido)-2,2'-dimethylbiphenyl-3-yl)benzo[d]oxazol-5-yl)methyl)pyrrolidine-3-carboxylic acid

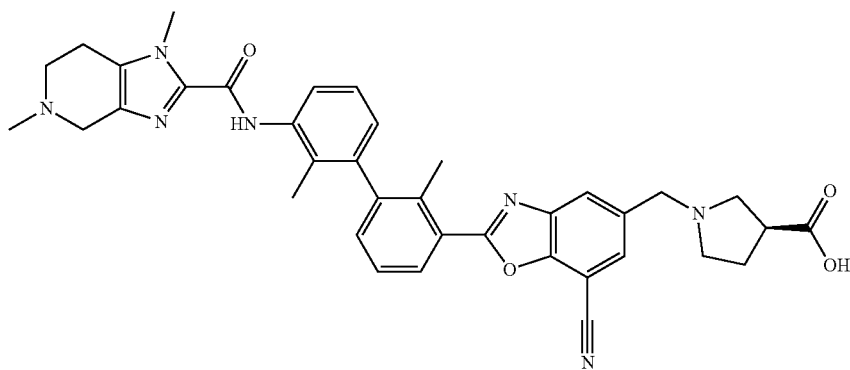 [SMILES: Cc1c(NC(=O)c2nc3c(n2C)CCN(C)C3)cccc1-c1cccc(-c2nc3cc(CN4CC[C@H](C(=O)O)C4)cc(C#N)c3o2)c1C]

Step 1: tert-butyl 1-methyl-1,4,6,7-tetrahydro-5H-imidazo[4,5-c]pyridine-5-carboxylate

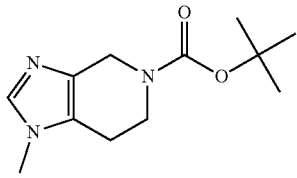 [SMILES: Cn1cnc2c1CCN(C(=O)OC(C)(C)C)C2]

A solution of 1-methyl-4,5,6,7-tetrahydro-1H-imidazo[4,5-c]pyridine (Accela, cat # SY032476: 2.0 g, 14.58 mmol), (Boc)$_2$O (3.38 mL, 14.58 mmol) in dichloromethane (60 mL) was stirred at room temperature for 1 h. The reaction was quenched with saturated aqueous NaHCO$_3$ solution, and extracted with ethyl acetate. The combined organic layers were washed with brine, dried over Na$_2$SO$_4$, filtered, and concentrated under reduced pressure. The crude product was used for next step without further purification. LCMS calculated for C$_{12}$H$_{20}$N$_3$O$_2$(M+H)$^+$: m/z=238.2; found 238.2.

Step 2: 5-tert-butyl 2-methyl 1-methyl-6,7-dihydro-1H-imidazo[4,5-c]pyridine-2,5(4H)-dicarboxylate

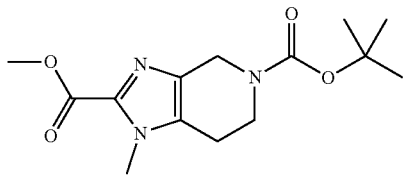 [SMILES: COC(=O)c1nc2c(n1C)CCN(C(=O)OC(C)(C)C)C2]

n-Butyllithium in hexanes (2.5 M, 7.00 mL, 17.49 mmol) was added to a cold (−78° C.) solution of the crude product from Step 1 in tetrahydrofuran (60.0 mL). The reaction mixture was stirred at −78° C. for 10 min prior to the addition of methyl chloroformate (1.7 mL, 21.9 mmol). After being stirred at −78° C. for 30 min, the reaction was then quenched with saturated aqueous NaHCO$_3$ solution, and extracted with ethyl acetate, dried over Na$_2$SO$_4$, filtered, and concentrated under reduced pressure. The residue was purified by flash chromatography on a silica gel column eluting with 0 to 100% ethyl acetate in hexanes to afford the desired product. LCMS calculated for C$_{14}$H$_{22}$N$_3$O$_4$ (M+H)$^+$: m/z=296.2; found 296.3.

Step 3: tert-butyl 2-(3-bromo-2-methylphenylcarbamoyl)-1-methyl-6,7-dihydro-1H-imidazo[4,5-c]pyridine-5(4H)-carboxylate

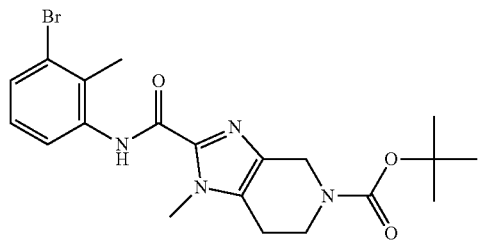 [SMILES: Cc1c(Br)cccc1NC(=O)c1nc2c(n1C)CCN(C(=O)OC(C)(C)C)C2]

Potassium tert-butoxide in THF (1.0 M, 3.39 mL, 3.39 mmol) was added to a solution of 5-tert-butyl 2-methyl 1-methyl-6,7-dihydro-1H-imidazo[4,5-c]pyridine-2,5(4H)-dicarboxylate (500 mg, 1.69 mmol) and 3-bromo-2-methylaniline (1.69 mmol) in tetrahydrofuran (12.0 mL). After being stirred at room temperature for 1 h, the reaction mixture was quenched with water, and extracted with ethyl acetate. The combined organic layers were washed with brine, dried over Na$_2$SO$_4$, filtered, and concentrated under reduced pressure. The residue was purified by flash chromatography on a silica gel column eluting with 50% ethyl acetate in hexanes to afford the desired product (720 mg, 95%). LCMS calculated for C$_{20}$H$_{26}$BrN$_4$O$_3$(M+H)$^+$: m/z=449.1; found 449.1.

Step 4: tert-butyl 2-(3'-(7-chloro-5-(hydroxymethyl)benzo[d]oxazol-2-yl)-2,2'-dimethylbiphenyl-3-ylcarbamoyl)-1-methyl-6,7-dihydro-1H-imidazo[4,5-c]pyridine-5(4H)-carboxylate

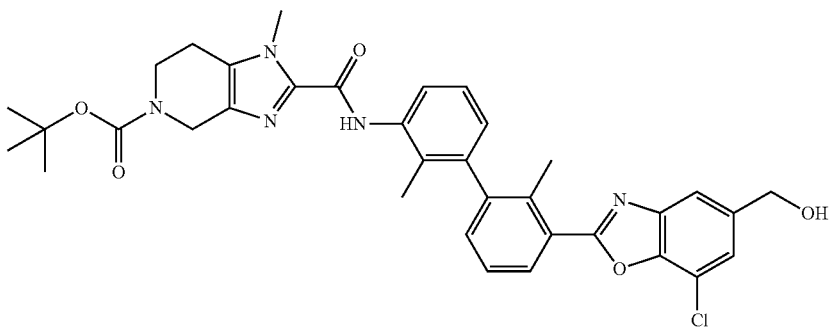 [SMILES: Cc1c(NC(=O)c2nc3c(n2C)CCN(C(=O)OC(C)(C)C)C3)cccc1-c1cccc(-c2nc3cc(CO)cc(Cl)c3o2)c1C]

A mixture of tert-butyl 2-((3-bromo-2-methylphenyl)carbamoyl)-1-methyl-1,4,6,7-tetrahydro-5H-imidazo[4,5-c]pyridine-5-carboxylate (400 mg, 0.89 mmol), (7-chloro-2-(2-methyl-3-(4,4,5,5-tetramethyl-1,3,2-dioxaborolan-2-yl)phenyl)benzo[d]oxazol-5-yl)methanol (Example 1, Step 5: 356 mg, 0.89 mmol), tetrakis(triphenylphosphine)palladium (0) (103 mg, 0.089 mmol) and sodium carbonate (236 mg, 2.23 mmol) in water (1.5 mL) and 1,4-dioxane (7.5 mL) was purged with nitrogen and then stirred at 100° C. for 3 h. After being cooled to room temperature, the reaction mixture was extracted with ethyl acetate. The combined organic layers were washed with brine, dried over Na$_2$SO$_4$, filtered and concentrated under reduced pressure. The residue was purified by flash chromatography on a silica gel column eluting with 0 to 50% ethyl acetate in hexanes to afford the desired product (350 mg, 61%). LC-MS calculated for C$_{35}$H$_{37}$ClN$_5$O$_5$(M+H)$^+$: m/z=642.3; found 642.3.

Step 5: tert-butyl 2-(3'-(7-cyano-5-(hydroxymethyl)benzo[d]oxazol-2-yl)-2,2'-dimethylbiphenyl-3-ylcarbamoyl)-1-methyl-6,7-dihydro-1H-imidazo[4,5-c]pyridine-5(4H)-carboxylate

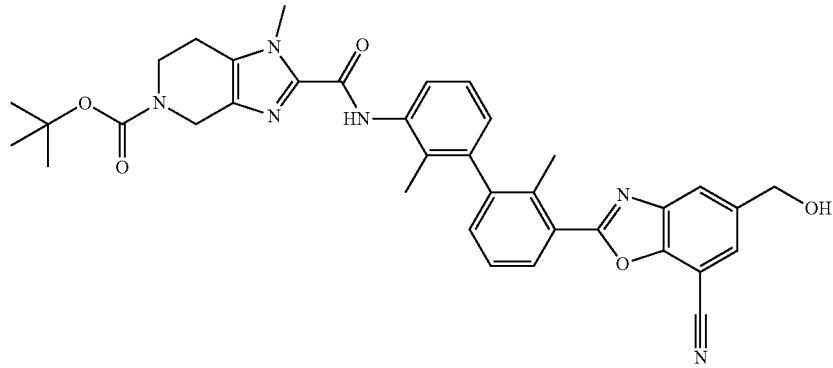 [SMILES: Cc1c(NC(=O)c2nc3c(n2C)CCN(C(=O)OC(C)(C)C)C3)cccc1-c1cccc(-c2nc3cc(CO)cc(C#N)c3o2)c1C]

A mixture of tert-butyl 2-((3'-(7-chloro-5-(hydroxymethyl)benzo[d]oxazol-2-yl)-2,2'-dimethyl-[1,1'-biphenyl]-3-yl)carbamoyl)-1-methyl-1,4,6,7-tetrahydro-5H-imidazo[4,5-c]pyridine-5-carboxylate (350 mg, 0.545 mmol), [(2-di-tert-butylphosphino-2',4',6'-triisopropyl-1,1'-biphenyl)-2-(2'-amino-1,1'-biphenyl)]palladium(II) methanesulfonate (43.3 mg, 0.055 mmol), potassium hexacyanoferrate(II) trihydrate (230 mg, 0.545 mmol) and potassium acetate (10.70 mg, 0.109 mmol) in 1,4-dioxane (4.5 mL) and water (4.5 mL) was purged with nitrogen and then stirred at 100° C. for 1 h. After being cooled to rt, the reaction was extracted with ethyl acetate. The combined organic phases was dried over Na$_2$SO$_4$ and concentrated under reduced pressure. The crude was used directly for next step without further purification. LC-MS calculated for C$_{36}$H$_{37}$N$_6$O$_5$ (M+H)$^+$: m/z=633.4; found 633.3.

Step 6: tert-butyl 2-(3'-(7-cyano-5-formylbenzo[d]oxazol-2-yl)-2,2'-dimethylbiphenyl-3-ylcarbamoyl)-1-methyl-6,7-dihydro-1H-imidazo[4,5-c]pyridine-5(4H)-carboxylate

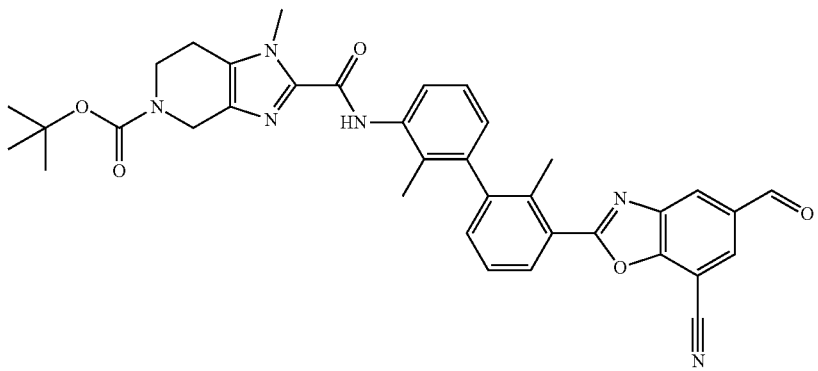 [SMILES: Cc1c(NC(=O)c2nc3c(n2C)CCN(C(=O)OC(C)(C)C)C3)cccc1-c1cccc(-c2nc3cc(C=O)cc(C#N)c3o2)c1C]

A suspension of tert-butyl 2-((3'-(7-cyano-5-(hydroxymethyl)benzo[d]oxazol-2-yl)-2,2'-dimethyl-[1,1'-biphenyl]-3-yl)carbamoyl)-1-methyl-1,4,6,7-tetrahydro-5H-imidazo[4,5-c]pyridine-5-carboxylate (345 mg, 0.545 mmol) and manganese dioxide (948 mg, 10.91 mmol) in dichloromethane (5.0 mL) was stirred at 45° C. for 30 min. The reaction was filtered through a short pad of celite and then concentrated to yield a crude residue, which was used directly without further purification. LC-MS calculated for C$_{36}$H$_{35}$N$_6$O$_5$ (M+H)$^+$: m/z=631.3; found 631.3.

Step 7: (S)-1-((7-cyano-2-(2,2'-dimethyl-3'-(1-methyl-4,5,6,7-tetrahydro-1H-imidazo[4,5-c]pyridine-2-carboxamido)biphenyl-3-yl)benzo[d]oxazol-5-yl)methyl)pyrrolidine-3-carboxylic acid

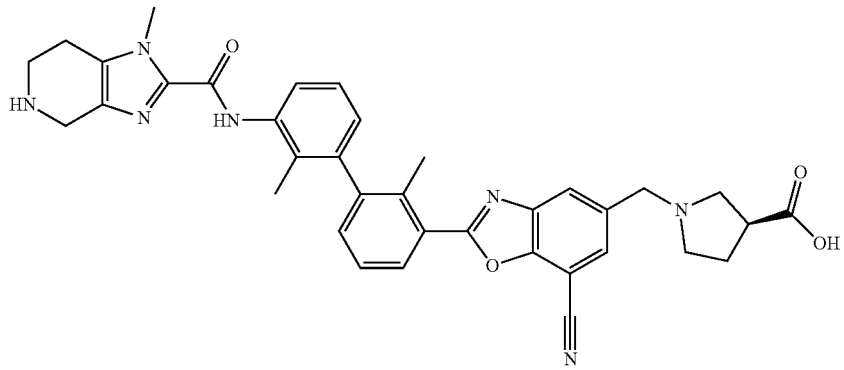 [SMILES: Cc1c(NC(=O)c2nc3c(n2C)CCNC3)cccc1-c1cccc(-c2nc3cc(CN4CC[C@H](C(=O)O)C4)cc(C#N)c3o2)c1C]

A mixture of tert-butyl 2-((3'-(7-cyano-5-formylbenzo[d]oxazol-2-yl)-2,2'-dimethyl-[1,1'-biphenyl]-3-yl)carbamoyl)-1-methyl-1,4,6,7-tetrahydro-5H-imidazo[4,5-c]pyridine-5-carboxylate (200 mg, 0.317 mmol) and (S)-pyrrolidine-3-carboxylic acid (110 mg, 0.951 mmol) in dichloromethane (3.0 mL) was stirred at room temperature for 2 h. Then sodium triacetoxyborohydride (202 mg, 0.951 mmol) and acetic acid (54.5 µl, 0.951 mmol) was added. After being stirred at 50° C. for 1 h, 2 N HCl in water (0.2 mL) was added, and the reaction was stirred at room temperature for 1 h. The reaction mixture was concentrated, and purified via pH 2 preparative HPLC (MeCN/water with TFA) to give the desired product as TFA salt. LC-MS calculated for $C_{36}H_{36}N_7O_4$ (M+H)$^+$: m/z=630.3; found 630.4.

Step 8: (S)-1-((7-cyano-2-(3'-(1,5-dimethyl-4,5,6,7-tetrahydro-1H-imidazo[4,5-c]pyridine-2-carboxamido)-2,2'-dimethylbiphenyl-3-yl)benzo[d]oxazol-5-yl)methyl)pyrrolidine-3-carboxylic acid Sodium triacetoxyborohydride (32.7 mg, 0.154 mmol) was added to a solution of (S)-1-((7-cyano-2-(2,2'-dimethyl-3'-(1-methyl-4,5,6,7-tetrahydro-1H-imidazo[4,5-c]pyridine-2-carboxamido)-[1,1'-biphenyl]-3-yl)benzo[d]oxazol-5-yl)methyl)pyrrolidine-3-carboxylic acid, 3TFA (50 mg, 0.051 mmol) and 37 wt. % formaldehyde in water (38.3 µL, 0.515 mmol) in THF (0.5 mL). The reaction mixture was stirred at room temperature for 1 h, then diluted with MeOH, and purified via pH 2 preparative HPLC (MeCN/water with TFA) to give the desired product as TFA salt. $^1$H NMR (400 MHz, CD$_3$CN) δ 9.24 (s, 1H), 8.27-8.22 (m, 2H), 7.98-7.95 (m, 1H), 7.54 (dd, J=7.7, 7.7 Hz, 1H), 7.43 (dd, J=7.7, 1.4 Hz, 1H), 7.37 (dd, J=7.7, 7.7 Hz, 1H), 7.07 (dd, J=7.7, 1.4 Hz, 1H), 4.49 (d, J=13.5 Hz, 1H), 4.45 (d, J=13.5 Hz, 1H), 4.30-4.15 (m, 2H), 3.98 (s, 3H), 3.67-3.45 (m, 4H), 3.44-3.26 (m, 3H), 3.11-3.00 (m, 2H), 2.96 (s, 3H), 2.50 (s, 3H), 2.43-2.20 (m, 2H), 2.06 (s, 3H). LC-MS calculated for $C_{37}H_{38}N_7O_4$ (M+H)$^+$: m/z=644.3; found 644.3.

Example 37

(S)-1-((7-cyano-2-(3'-(5-ethyl-1-methyl-4,5,6,7-tetrahydro-1H-imidazo[4,5-c]pyridine-2-carboxamido)-2,2'-dimethylbiphenyl-3-yl)benzo[d]oxazol-5-yl)methyl)pyrrolidine-3-carboxylic acid

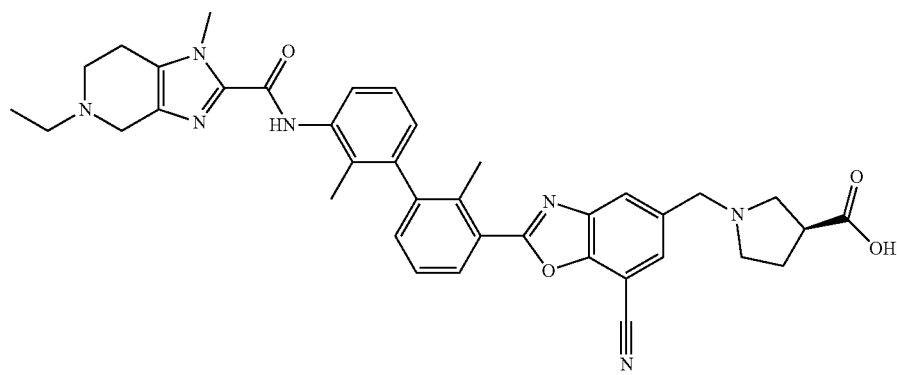 [SMILES: CCN1CCc2c(nc(C(=O)Nc3cccc(-c4cccc(-c5nc6cc(CN7CC[C@H](C(=O)O)C7)cc(C#N)c6o5)c4C)c3C)n2C)C1]

Sodium triacetoxyborohydride (6.54 mg, 0.031 mmol) were added to a solution of (S)-1-((7-cyano-2-(2,2'-dimethyl-3'-(1-methyl-4,5,6,7-tetrahydro-1H-imidazo[4,5-c]pyridine-2-carboxamido)-[1,1'-biphenyl]-3-yl)benzo[d]oxazol-5-yl)methyl)pyrrolidine-3-carboxylic acid, 3TFA (Example 36, Step 7; 10 mg, 10.29 µmol) and acetaldehyde (1.360 mg, 0.031 mmol) in THF (0.5 mL). The reaction was stirred at room temperature for 1 h, then diluted with MeOH, and purified via pH 2 preparative HPLC (MeCN/water with TFA) to give the desired product as TFA salt. LC-MS calculated for $C_{38}H_{40}N_7O_4$ (M+H)$^+$: m/z=658.3; found 658.4.

Example 38

(S)-1-((7-cyano-2-(3'-(5-isopropyl-1-methyl-4,5,6,7-tetrahydro-1H-imidazo[4,5-c]pyridine-2-carboxamido)-2,2'-dimethylbiphenyl-3-yl)benzo[d]oxazol-5-yl)methyl)pyrrolidine-3-carboxylic acid

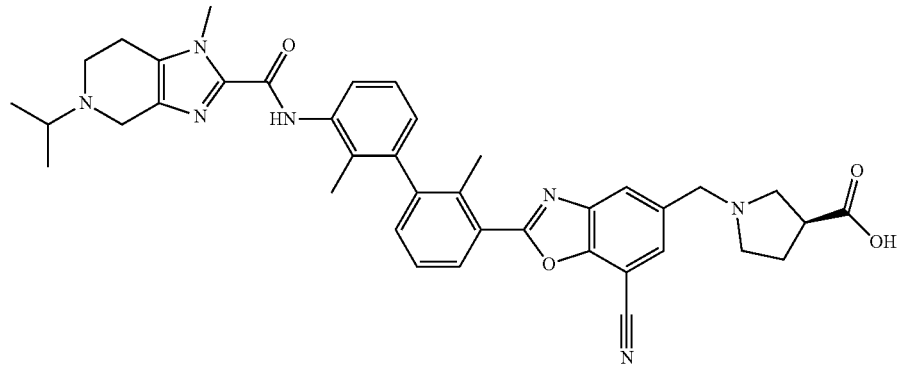 [SMILES: Cc1c(NC(=O)c2nc3c(n2C)CCN(C(C)C)C3)cccc1-c1cccc(-c2nc3cc(CN4CC[C@H](C(=O)O)C4)cc(C#N)c3o2)c1C]

A suspension of (S)-1-((7-cyano-2-(2,2'-dimethyl-3'-(1-methyl-4,5,6,7-tetrahydro-1H-imidazo[4,5-c]pyridine-2-carboxamido)-[1,1'-biphenyl]-3-yl)benzo[d]oxazol-5-yl)methyl)pyrrolidine-3-carboxylic acid, 3TFA (Example 36, Step 7; 10 mg, 10.27 µmol), 2-iodopropane (5.24 mg, 0.031 mmol), and potassium carbonate (7.1 mg, 0.051 mmol) in DMF (0.1 mL) was stirred at 90° C. for 1 h. The reaction was diluted with MeOH, and purified via pH 2 preparative HPLC (MeCN/water with TFA) to give the desired product as TFA salt. LC-MS calculated for $C_{39}H_{42}N_7O_4$ (M+H)$^+$: m/z= 672.3; found 672.3.

Example 39

(S)-1-((7-cyano-2-(3'-(5-cyclopropyl-1-methyl-4,5,6,7-tetrahydro-1H-imidazo[4,5-c]pyridine-2-carboxamido)-2,2'-dimethylbiphenyl-3-yl)benzo[d]oxazol-5-yl)methyl)pyrrolidine-3-carboxylic acid

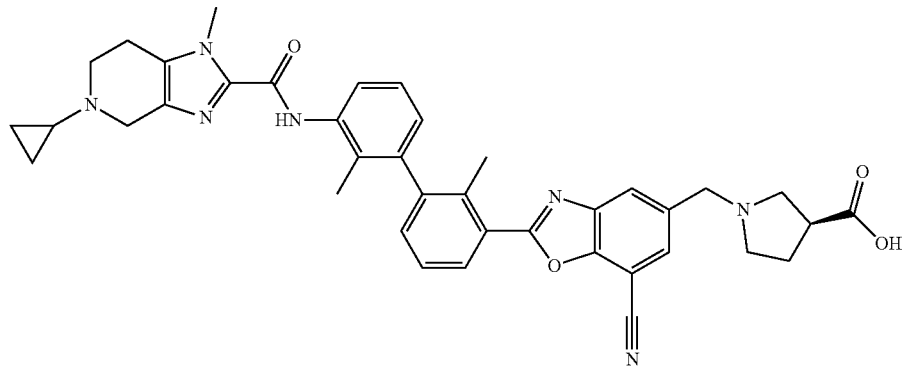 [SMILES: Cc1c(NC(=O)c2nc3c(n2C)CCN(C2CC2)C3)cccc1-c1cccc(-c2nc3cc(CN4CC[C@H](C(=O)O)C4)cc(C#N)c3o2)c1C]

A suspension of (S)-1-((7-cyano-2-(2,2'-dimethyl-3'-(1-methyl-4,5,6,7-tetrahydro-1H-imidazo[4,5-c]pyridine-2-carboxamido)-[1,1'-biphenyl]-3-yl)benzo[d]oxazol-5-yl)methyl)pyrrolidine-3-carboxylic acid, 3TFA (Example 36, Step 7; 10 mg, 10.27 μmol), bromocyclopropane (12.42 mg, 0.103 mmol), potassium iodide (5.11 mg, 0.031 mmol) and potassium carbonate (7.1 mg, 0.051 mmol) in DMF (50 μL) was stirred at 90° C. for 5 h. The reaction was diluted with MeOH, and purified via pH 2 preparative HPLC (MeCN/water with TFA) to give the desired product as TFA salt. LC-MS calculated for $C_{39}H_{40}N_7O_4$ $(M+H)^+$: m/z=670.3; found 670.4.

Example 40

(S)-1-((7-cyano-2-(3'-(5-(3,3-difluorocyclobutyl)-1-methyl-4,5,6,7-tetrahydro-1H-imidazo[4,5-c]pyridine-2-carboxamido)-2,2'-dimethylbiphenyl-3-yl)benzo[d]oxazol-5-yl)methyl)pyrrolidine-3-carboxylic acid

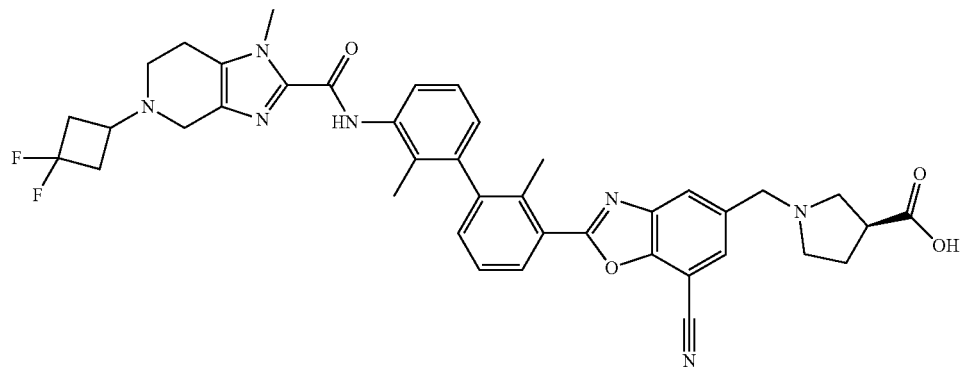 [SMILES: Cc1c(NC(=O)c2nc3c(n2C)CCN(C2CC(F)(F)C2)C3)cccc1-c1cccc(-c2nc3cc(CN4CC[C@H](C(=O)O)C4)cc(C#N)c3o2)c1C]

A suspension of (S)-1-((7-cyano-2-(2,2'-dimethyl-3'-(1-methyl-4,5,6,7-tetrahydro-1H-imidazo[4,5-c]pyridine-2-carboxamido)-[1,1'-biphenyl]-3-yl)benzo[d]oxazol-5-yl)methyl)pyrrolidine-3-carboxylic acid, 3TFA (Example 36, Step 7; 10 mg, 10.27 μmol), 3-bromo-1,1-difluorocyclobutane (5.27 mg, 0.031 mmol), potassium iodide (5.11 mg, 0.031 mmol) and potassium carbonate (7.10 mg, 0.051 mmol) in DMF (0.2 mL) was stirred at 90° C. for 1 h. The reaction was diluted with MeOH, and purified via pH 2 preparative HPLC (MeCN/water with TFA) to give the desired product as TFA salt. LC-MS calculated for $C_{40}H_{40}F_2N_7O_4$ $(M+H)^+$: m/z=720.3; found 720.4.

Example 41

(S)-1-((7-cyano-2-(3'-(5-((S)-2-hydroxypropyl)-1-methyl-4,5,6,7-tetrahydro-1H-imidazo[4,5-c]pyridine-2-carboxamido)-2,2'-dimethylbiphenyl-3-yl)benzo[d]oxazol-5-yl)methyl)pyrrolidine-3-carboxylic acid

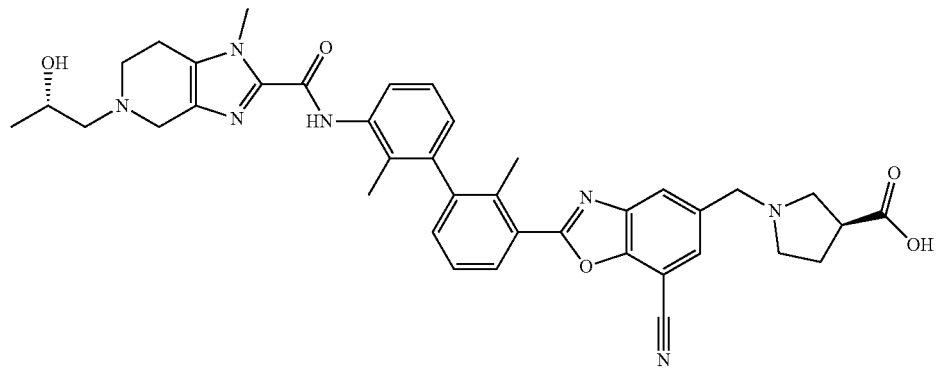 [SMILES: Cc1c(NC(=O)c2nc3c(n2C)CCN(C[C@H](C)O)C3)cccc1-c1cccc(-c2nc3cc(CN4CC[C@H](C(=O)O)C4)cc(C#N)c3o2)c1C]

A solution of(S)-1-((7-cyano-2-(2,2'-dimethyl-3'-(1-methyl-4,5,6,7-tetrahydro-1H-imidazo[4,5-c]pyridine-2-carboxamido)-[1,1'-biphenyl]-3-yl)benzo[d]oxazol-5-yl)methyl)pyrrolidine-3-carboxylic acid, 3TFA (Example 36, Step 7; 10 mg, 10.29 μmol), (S)-2-((tert-butyldimethylsilyl)oxy)propanal (5.81 mg, 0.031 mmol) and Hünig's base (5.39 μL, 0.031 mmol) in THF (0.2 mL) was stirred at room temperature for 1 h. Sodium triacetoxyborohydride (6.54 mg, 0.031 mmol) was added. After being stirred at room temperature for 2 h, 2 N HCl solution in water (0.2 mL) was added, and the reaction was stirred at 50° C. for 30 min. The reaction mixture was diluted with MeOH, and purified via pH 2 preparative HPLC (MeCN/water with TFA) to give the desired product as TFA salt. LC-MS calculated for $C_{39}H_{42}N_7O_5$ $(M+H)^+$: m/z=688.3; found 688.4.

Example 42

3-(((7-chloro-2-(3'-(1,5-dimethyl-4,5,6,7-tetrahydro-1H-imidazo[4,5-c]pyridine-2-carboxamido)-2,2'-dimethylbiphenyl-3-yl)benzo[d]oxazol-5-yl)methyl)(methyl)amino) propanoic acid

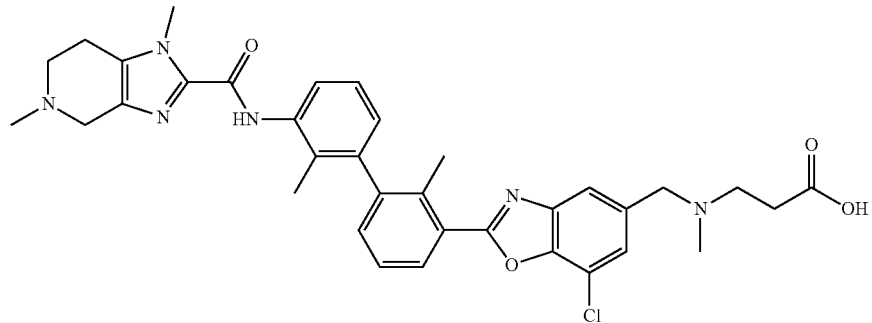 [SMILES: Cc1c(NC(=O)c2nc3c(n2C)CCN(C)C3)cccc1-c1cccc(-c2nc3cc(CN(C)CCC(=O)O)cc(Cl)c3o2)c1C]

Step 1: N-(3'-(7-chloro-5-(hydroxymethyl)benzo[d]oxazol-2-yl)-2,2'-dimethylbiphenyl-3-yl)-1-methyl-4,5,6,7-tetrahydro-1H-imidazo[4,5-c]pyridine-2-carboxamide

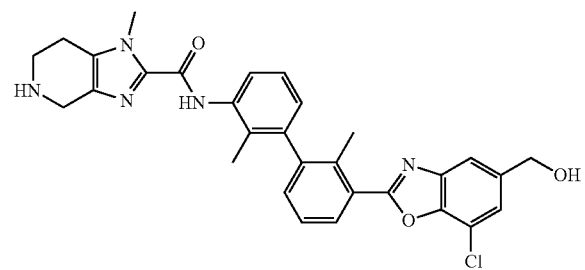 [SMILES: Cc1c(NC(=O)c2nc3c(n2C)CCNC3)cccc1-c1cccc(-c2nc3cc(CO)cc(Cl)c3o2)c1C]

To a solution of tert-butyl 2-((3'-(7-chloro-5-(hydroxymethyl)benzo[d]oxazol-2-yl)-2,2'-dimethyl-[1,1'-biphenyl]-3-yl)carbamoyl)-1-methyl-1,4,6,7-tetrahydro-5H-imidazo[4,5-c]pyridine-5-carboxylate (Example 36, Step 4; 121 mg, 0.188 mmol) in DCM (1.9 ml) was slowly added trifluoroacetic acid (360 μl, 4.7 mmol) at room temperature. The mixture was stirred at this temperature for 1 h. Then the mixture was concentrated and redissovled in DCM, washed by sat. NaHCO₃ aq. solution, water. The organic phase was dried over MgSO₄, and then filtered. The filtrate was concentrated to give a crude material, which was used directly for next step. LC-MS calculated for $C_{30}H_{29}ClN_5O_3(M+H)^+$: m/z=542.2; found 542.2.

Step 2: N-(3'-(7-chloro-5-(hydroxymethyl)benzo[d]oxazol-2-yl)-2,2'-dimethylbiphenyl-3-yl)-1,5-dimethyl-4,5,6,7-tetrahydro-1H-imidazo[4,5-c]pyridine-2-carboxamide

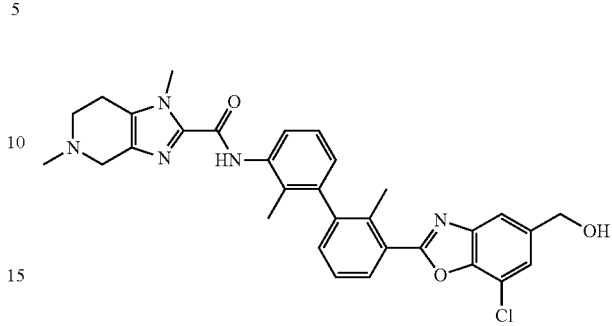

A mixture of N-(3'-(7-chloro-5-(hydroxymethyl)benzo[d]oxazol-2-yl)-2,2'-dimethylbiphenyl-3-yl)-1-methyl-4,5,6,7-tetrahydro-1H-imidazo[4,5-c]pyridine-2-carboxamide and paraformaldehyde (8.5 mg, 0.28 mmol) in DCM (1.9 mL) was stirred at room temperature for 2 h. Then sodium triacetoxyborohydride (60 mg, 0.28 mmol) and acetic acid (16.0 μl, 0.28 mmol) was added. The mixture was further stirred at room temperature for 1 h. The reaction was quenched by aq. NH₄OH solution and extracted with DCM. The organic phase was dried over MgSO₄, and then filtered. The filtrate was concentrated and the crude material was used directly for next step. LC-MS calculated for $C_{31}H_{31}ClN_5O_3(M+H)^+$: m/z=556.2; found 556.3.

Step 3: N-(3'-(7-chloro-5-formylbenzo[d]oxazol-2-yl)-2,2'-dimethylbiphenyl-3-yl)-1,5-dimethyl-4,5,6,7-tetrahydro-1H-imidazo[4,5-c]pyridine-2-carboxamide

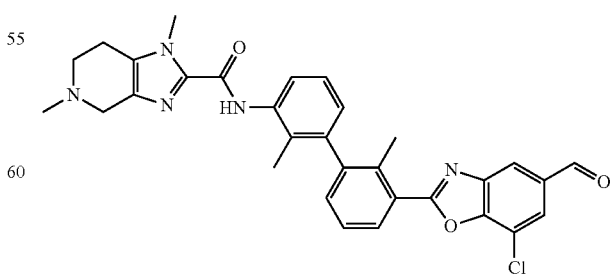

This compound was prepared using similar procedures as described for Example 36, Step 6 with N-(3'-(7-chloro-5-

(hydroxymethyl)benzo[d]oxazol-2-yl)-2,2'-dimethylbiphenyl-3-yl)-1,5-dimethyl-4,5,6,7-tetrahydro-1H-imidazo[4,5-c]pyridine-2-carboxamide replacing tert-butyl 2-((3'-(7-cyano-5-(hydroxymethyl)benzo[d]oxazol-2-yl)-2,2'-dimethyl-[1,1'-biphenyl]-3-yl)carbamoyl)-1-methyl-1,4,6,7-tetrahydro-5H-imidazo[4,5-c]pyridine-5-carboxylate. LC-MS calculated for $C_{31}H_{29}ClN_5O_3$ $(M+H)^+$: m/z=554.2; found 554.3.

Step 4: 3-(((7-chloro-2-(3'-(1,5-dimethyl-4,5,6,7-tetrahydro-1H-imidazo[4,5-c]pyridine-2-carboxamido)-2,2'-dimethylbiphenyl-3-yl)benzo[d]oxazol-5-yl)methyl)(methyl)amino) propanoic acid This compound was prepared using similar procedures as described for Example 36, Step 7 with 3-(methylamino)propanoic acid replacing (S)-pyrrolidine-3-carboxylic acid. The reaction was diluted with MeOH and then purified by prep-HPLC (pH=10, acetonitrile/water+NH$_4$OH) to give the desired product. LC-MS calculated for $C_{35}H_{38}ClN_6O_4$ $(M+H)^+$: m/z=641.3; found 641.3.

Example 43

(R)-1-((7-chloro-2-(2'-chloro-2-methyl-3'-(4-(methylamino)piperidin-1-yl)biphenyl-3-yl)benzo[d]oxazol-5-yl)methyl)pyrrolidine-3-carboxylic acid

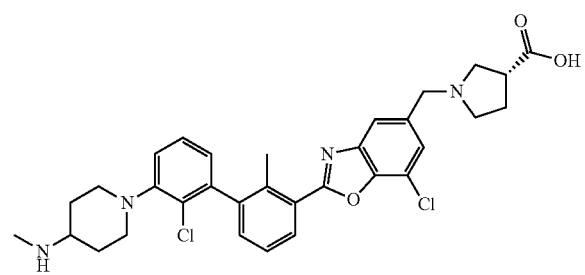 [SMILES: CNC1CCN(c2cccc(-c3cccc(-c4nc5cc(CN6CC[C@@H](C(=O)O)C6)cc(Cl)c5o4)c3C)c2Cl)CC1]

Step 1: 8-(3-bromo-2-chlorophenyl)-1,4-dioxa-8-azaspiro[4.5]decane

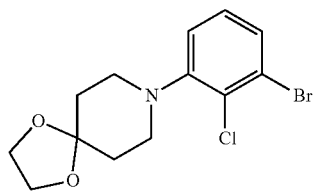 [SMILES: Clc1c(Br)cccc1N1CCC2(CC1)OCCO2]

A mixture of 1,3-dibromo-2-chlorobenzene (2.20 g, 8.80 mmol), 1,4-dioxa-8-azaspiro[4.5]decane (1.260 g, 8.80 mmol), palladium(II) acetate (0.20 g, 0.88 mmol), (+)-2,2'-bis(diphenylphosphino)-1,1'-binaphthyl (0.55 g, 0.88 mmol), and cesium carbonate (7.17 g, 22.01 mmol) in 1,4-dioxane (30 mL) was placed in a vial and stirred at 90° C. for 12 hrs. The mixture was filtered through a pad of Celite and washed with EtOAc and the solvent was removed under reduced pressure to give a crude product, which was purified by column chromatography (eluting with EtOAc/Hexanes 0%-100%). LC-MS calculated for $C_{13}H_{16}BrClNO_2$ $(M+H)^+$: m/z=332.0; found 332.1.

Step 2: (7-chloro-2-(2'-chloro-2-methyl-3'-(1,4-dioxa-8-azaspiro[4.5]decan-8-yl)biphenyl-3-yl)benzo[d]oxazol-5-yl)methanol

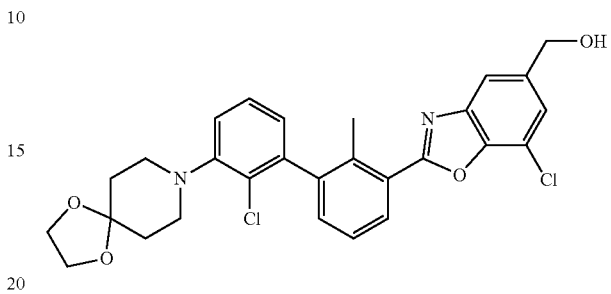

A mixture of 8-(3-bromo-2-chlorophenyl)-1,4-dioxa-8-azaspiro[4.5]decane (83 mg, 0.25 mmol), (7-chloro-2-(2-methyl-3-(4,4,5,5-tetramethyl-1,3,2-dioxaborolan-2-yl)phenyl)benzo[d]oxazol-5-yl)methanol (Example 1, Step 5; 100 mg, 0.250 mmol), sodium carbonate (53.0 mg, 0.500 mmol), and tetrakis(triphenylphosphine)palladium (29 mg, 0.025 mmol) in a mixed water (500 µL) and 1,4-dioxane (4500 µL) was purged with N$_2$ and then stirred at 100° C. for 3 hrs. The reaction was cooled to room temperature and then diluted with EtOAc and water. The aqueous phase was extracted with EtOAc. The organic phase was dried over MgSO$_4$, filtered and the filtrate was concentrated under reduced pressure. The crude material was purified by flash chromatography on a silica gel (eluting with EtOAc/Hexanes, 0-100%) to give the desired product. LC-MS calculated for $C_{28}H_{27}Cl_2N_2O_4$ $(M+H)^+$: m/z=525.1; found 525.1.

Step 3: 1-(2-chloro-3'-(7-chloro-5-(hydroxymethyl)benzo[d]oxazol-2-yl)-2'-methylbiphenyl-3-yl)piperidin-4-one

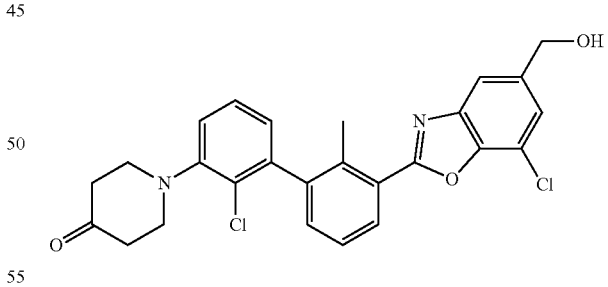

To a solution of (7-chloro-2-(2'-chloro-2-methyl-3'-(1,4-dioxa-8-azaspiro[4.5]decan-8-yl)biphenyl-3-yl)benzo[d]oxazol-5-yl)methanol (320 mg, 0.67 mmol) in acetone (5 mL) was added 5 mL of 1N HCl at room temperature, the mixture was stirred at 45° C. for 3 hrs. Solid NaHCO$_3$ was then added to quench the reaction. The mixture was extracted with EtOAc for three times. The organic phases were combined, dried over MgSO$_4$, filtered and the filtrate was concentrated. The residue was used directly without further purification. LC-MS calculated for $C_{26}H_{23}Cl_2N_2O_3$ $(M+H)^+$: m/z=481.1; found 481.1.

Step 4: (7-chloro-2-(2'-chloro-2-methyl-3'-(4-(methylamino)piperidin-1-yl)biphenyl-3-yl)benzo[d]oxazol-5-yl)methanol

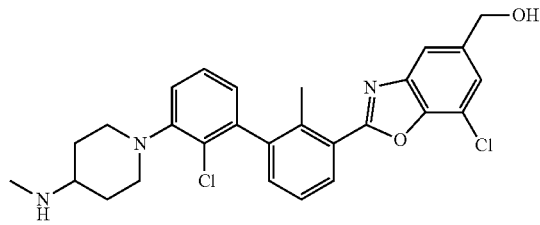 [SMILES: CNC1CCN(c2cccc(-c3cccc(-c4nc5cc(CO)cc(Cl)c5o4)c3C)c2Cl)CC1]

A mixture of 1-(2-chloro-3'-(7-chloro-5-(hydroxymethyl)benzo[d]oxazol-2-yl)-2'-methylbiphenyl-3-yl)piperidin-4-one (31 mg, 0.06 mmol) and methylamine THF solution (60 µL, 0.13 mmol) in DCM (500 µL) was stirred at room temperature for 2 hrs. Then sodium triacetoxyborohydride (27 mg, 0.13 mmol) was added. The mixture was further stirred at room temperature for 3 hrs. The reaction was diluted with MeOH and concentrated and purified by column chromatography (eluting with MeOH/DCM, 0-50%). LC-MS calculated for $C_{27}H_{28}Cl_2N_3O_2$ (M+H)$^+$: m/z=496.1; found 496.2.

Step 5: 7-chloro-2-(2'-chloro-2-methyl-3'-(4-(methylamino)piperidin-1-yl)biphenyl-3-yl)benzo[d]oxazole-5-carbaldehyde

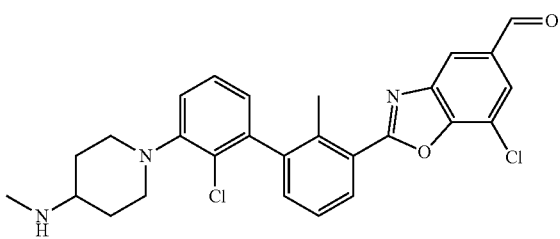 [SMILES: CNC1CCN(c2cccc(-c3cccc(-c4nc5cc(C=O)cc(Cl)c5o4)c3C)c2Cl)CC1]

To (7-chloro-2-(2'-chloro-2-methyl-3'-(4-(methylamino)piperidin-1-yl)biphenyl-3-yl)benzo[d]oxazol-5-yl)methanol (20 mg, 0.05 mmol) in DCM (2 mL) was added MnO$_2$ (79 mg, 0.91 mmol) in one portion at rt, and the resulting mixture was stirred at 45° C. for 20 min. The reaction was filtered and the filtrate was concentrated. The residue was used directly without further purification. LC-MS calculated for $C_{27}H_{26}Cl_2N_3O_2$ (M+H)$^+$: m/z=494.1; found 494.2.

Step 6: (R)-1-((7-chloro-2-(2'-chloro-2-methyl-3'-(4-(methylamino)piperidin-1-yl)biphenyl-3-yl)benzo[d]oxazol-5-yl)methyl)pyrrolidine-3-carboxylic acid

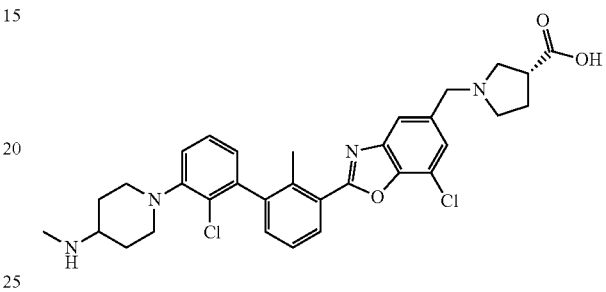

A mixture of 7-chloro-2-(2'-chloro-2-methyl-3'-(4-(methylamino)piperidin-1-yl)biphenyl-3-yl)benzo[d]oxazole-5-carbaldehyde (10.1 mg, 0.02 mmol), triethylamine (5.41 µl, 0.039 mmol) and (R)-pyrrolidine-3-carboxylic acid (4.47 mg, 0.039 mmol) in DCM (1129 µL) was stirred at room temperature for 2 hrs. Then sodium triacetoxyborohydride (8.23 mg, 0.039 mmol) and acetic acid (3.33 µl, 0.058 mmol) was added. The mixture was further stirred at room temperature for 1 h. The reaction was diluted with MeOH and then purified by prep-HPLC (pH=2, acetonitrile/water+TFA) to give the desired product as TFA salt. LC-MS calculated for $C_{32}H_{35}Cl_2N_4O_3$ (M+H)$^+$: m/z=593.2; found 593.3.

Example 44

(R)-1-((7-chloro-2-(2'-chloro-3'-(4-(cyclopropylamino)piperidin-1-yl)-2-methylbiphenyl-3-yl)benzo[d]oxazol-5-yl)methyl)pyrrolidine-3-carboxylic acid

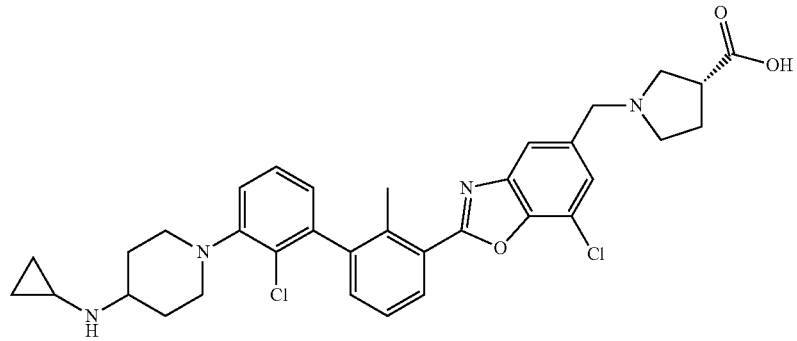 [SMILES: Cc1c(-c2nc3cc(CN4CC[C@@H](C(=O)O)C4)cc(Cl)c3o2)cccc1-c1cccc(N2CCC(NC3CC3)CC2)c1Cl]

This compound was prepared using similar procedures as described for Example 43 with cyclopropanamine replacing methylamine in Step 4. The reaction mixture was diluted with MeOH and then purified by prep-HPLC (pH=2, acetonitrile/water+TFA) to give the desired product as TFA salt. LC-MS calculated for $C_{34}H_{37}Cl_2N_4O_3$ (M+H)$^+$: m/z=619.2; found 619.2.

Example 45

(R)-1-((7-chloro-2-(2'-chloro-3'-(4-((1s,3s)-3-hydroxycyclobutylamino)piperidin-1-yl)-2-methylbiphenyl-3-yl)benzo[d]oxazol-5-yl)methyl)pyrrolidine-3-carboxylic acid

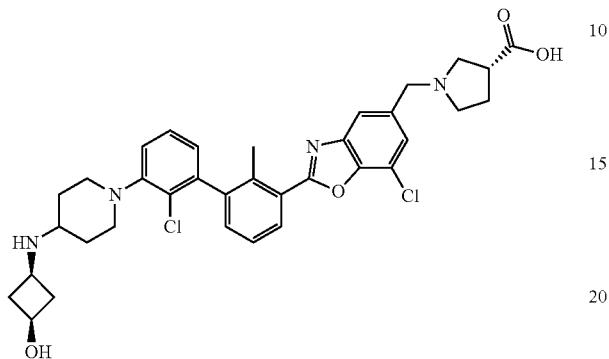

This compound was prepared using similar procedures as described for Example 43 with cis-3-aminocyclobutanol replacing methylamine in Step 4. The reaction mixture was diluted with MeOH and then purified by prep-HPLC (pH=2, acetonitrile/water+TFA) to give the desired product as TFA salt. LC-MS calculated for $C_{35}H_{39}Cl_2N_4O_4$ $(M+H)^+$: m/z=649.2; found 649.2.

Example 46

(R)-1-((7-chloro-2-(2'-chloro-3'-(4-((1-(hydroxymethyl)cyclobutyl)methylamino)piperidin-1-yl)-2-methylbiphenyl-3-yl)benzo[d]oxazol-5-yl)methyl)pyrrolidine-3-carboxylic acid

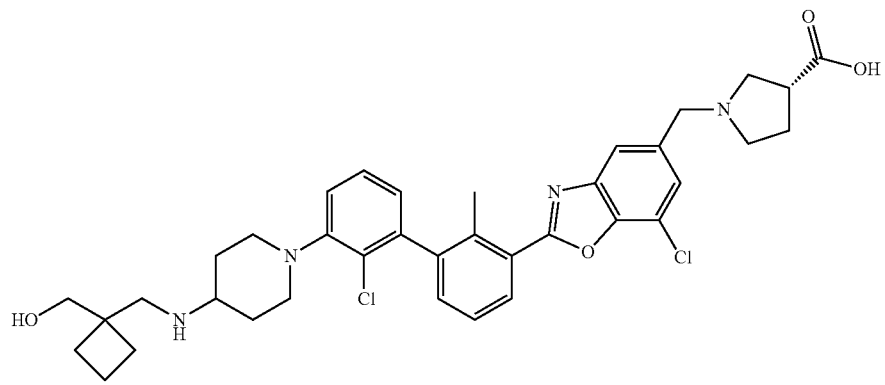 [SMILES: Cc1c(-c2nc3cc(CN4CC[C@@H](C(=O)O)C4)cc(Cl)c3o2)cccc1-c1cccc(N2CCC(NCC3(CO)CCC3)CC2)c1Cl]

This compound was prepared using similar procedures as described for Example 43 with (1-(aminomethyl)cyclobutyl)methanol replacing methylamine in Step 4. The reaction mixture was diluted with MeOH and then purified by prep-HPLC (pH=2, acetonitrile/water+TFA) to give the desired product as TFA salt. LC-MS calculated for $C_{37}H_{43}Cl_2N_4O_4$ $(M+H)^+$: m/z=677.2; found 677.2.

Example 47

(R)-1-((2-(2'-chloro-3'-(4-((1s,3s)-3-hydroxycyclobutylamino)piperidin-1-yl)-2-methylbiphenyl-3-yl)-7-cyanobenzo[d]oxazol-5-yl)methyl)pyrrolidine-3-carboxylic acid

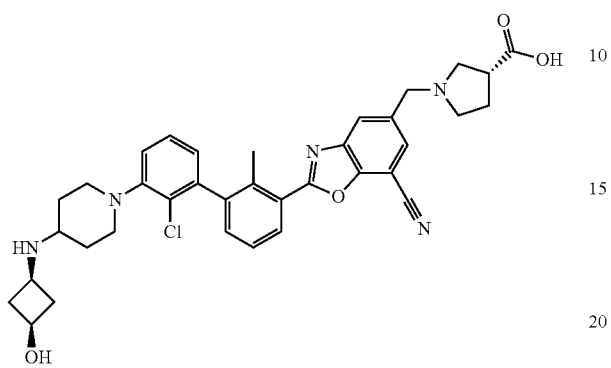

Step 1: 2-(2'-chloro-2-methyl-3'-(1,4-dioxa-8-azaspiro[4.5]decan-8-yl)biphenyl-3-yl)-5-(hydroxymethyl)benzo[d]oxazole-7-carbonitrile

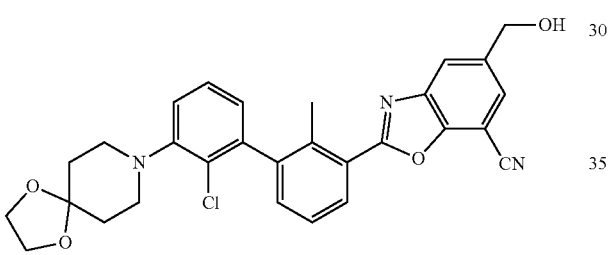

A mixture of (7-chloro-2-(2'-chloro-2-methyl-3'-(1,4-dioxa-8-azaspiro[4.5]decan-8-yl)-[1,1'-biphenyl]-3-yl)benzo[d]oxazol-5-yl)methanol (Example 43, step 2: 94 mg, 0.179 mmol), [(2-di-tert-butylphosphino-2',4',6'-triisopropyl-1,1'-biphenyl)-2-(2'-amino-1,1'-biphenyl)]palladium(II) methanesulfonate (14.21 mg, 0.018 mmol), potassium hexacyanoferrate(II) trihydrate (113 mg, 0.268 mmol) and potassium acetate (8.78 mg, 0.089 mmol) in 1,4-dioxane (2 ml)/water (2 ml) was stirred and heated at 100° C. for 1 h. After cooling to rt, the reaction was diluted with EtOAc and water, extracted with EtOAc. The combined organic phase was dried over MgSO$_4$ and concentrated. The crude material was used directly in the next step. LC-MS calculated for C$_{29}$H$_{27}$ClN$_3$O$_4$(M+H)$^+$: m/z=516.2; found 516.2.

Step 2: (R)-1-((2-(2'-chloro-3'-(4-((s, 3s)-3-hydroxycyclobulylamino)piperidin-1-yl)-2-methylbiphenyl-3-yl)-7-cyanobenzo[d]oxazol-5-yl)methyl)pyrrolidine-3-carboxylic acid This compound was prepared using similar procedures as described for Example 43 with 2-(2'-chloro-2-methyl-3'-(1,4-dioxa-8-azaspiro[4.5]decan-8-yl)biphenyl-3-yl)-5-(hydroxymethyl)benzo[d]oxazole-7-carbonitrile replacing (7-chloro-2-(2'-chloro-2-methyl-3'-(1,4-dioxa-8-azaspiro[4.5]decan-8-yl)biphenyl-3-yl)benzo[d]oxazol-5-yl)methanol in Step 3 and cis-3-aminocyclobutanol replacing methylamine in Step 4. The reaction mixture was purified by prep-HPLC (pH=2, acetonitrile/water+TFA) to give the desired product as TFA salt. LC-MS calculated for C$_{36}$H$_{39}$ClN$_5$O$_4$(M+H)$^+$: m/z=640.3; found 640.2.

Example 48

(R)-1-((2-(2'-chloro-3'-(4-(ethyl(2-hydroxyethyl)amino)piperidin-1-yl)-2-methylbiphenyl-3-yl)-7-cyanobenzo[d]oxazol-5-yl)methyl)pyrrolidine-3-carboxylic acid

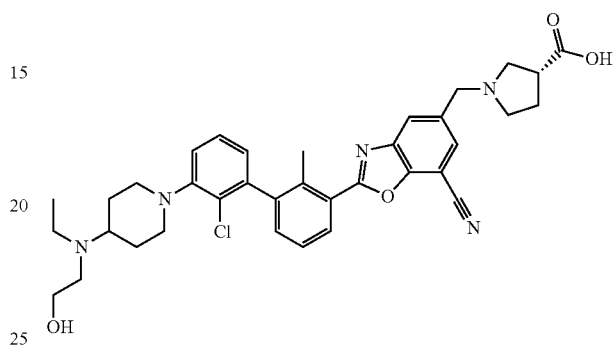

This compound was prepared using similar procedures as described for Example 47 with 2-(ethylamino)ethanol replacing cis-3-aminocyclobutanol. It was purified by prep-HPLC (pH=2, acetonitrile/water+TFA) to give the desired product as TFA salt. LC-MS calculated for C$_{36}$H$_{41}$ClN$_5$O$_4$ (M+H)$^+$: m/z=642.3; found 642.2.

Example 49

(R)-1-((2-(2'-chloro-3'-(4-(ethyl((1s,3s)-3-hydroxycyclobutyl)amino)piperidin-1-yl)-2-methylbiphenyl-3-yl)-7-cyanobenzo[d]oxazol-5-yl)methyl)pyrrolidine-3-carboxylic acid

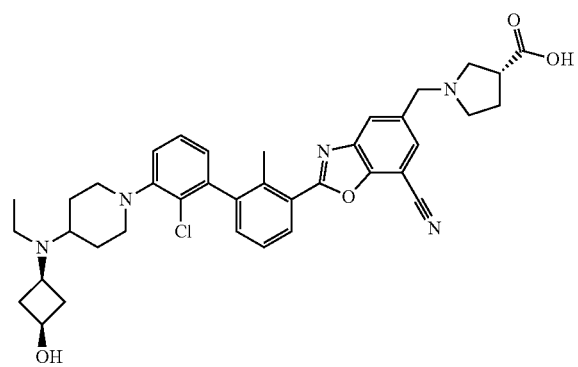 [SMILES: CCN(C1CCN(c2cccc(-c3cccc(-c4nc5cc(CN6CC[C@@H](C(=O)O)C6)cc(C#N)c5o4)c3C)c2Cl)CC1)[C@H]1C[C@@H](O)C1]

To a solution of (R)-1-((2-(2'-chloro-3'-(4-((1s,3s)-3-hydroxycyclobutylamino)piperidin-1-yl)-2-methylbiphenyl-3-yl)-7-cyanobenzo[d]oxazol-5-yl)methyl)pyrrolidine-3-carboxylic acid (Example 47; 11 mg, 0.016 mmol) and acetaldehyde (3.44 mg, 0.078 mmol) in DCM (500 µL) was stirred at room temperature for 2 hrs. Then sodium triacetoxyborohydride (6.62 mg, 0.031 mmol) was added. The mixture was further stirred at room temperature for 3 hrs. The reaction was diluted with MeOH and then purified by prep-HPLC (pH=2, acetonitrile/water+TFA) to give the desired product as TFA salt. LC-MS calculated for C$_{38}$H$_{43}$ClN$_5$O$_4$(M+H)$^+$: m/z=668.3; found 668.3.

Example 50

(S)-1-((2-(2'-chloro-3'-(1,5-dimethyl-4,5,6,7-tetra-hydro-1H-imidazo[4,5-c]pyridine-2-carboxamido)-2-methylbiphenyl-3-yl)-7-cyanobenzo[d]oxazol-5-yl)methyl)pyrrolidine-3-carboxylic acid

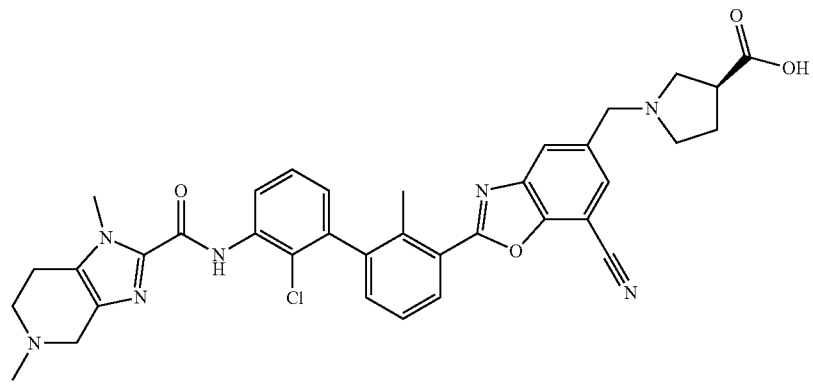 [SMILES: Cc1c(-c2nc3cc(CN4CC[C@H](C(=O)O)C4)cc(C#N)c3o2)cccc1-c1cccc(NC(=O)c2nc3c(n2C)CCN(C)C3)c1Cl]

Step 1: tert-butyl 2-(3-bromo-2-chlorophenylcarbamoyl)-1-methyl-6,7-dihydro-1H-imidazo[4,5-c]pyridine-5(4H)-carboxylate

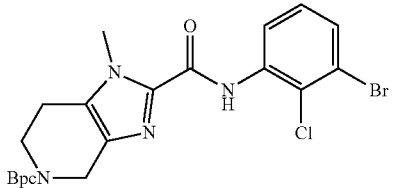

Potassium tert-butoxide in THF (1.0 M, 3.39 mL, 3.39 mmol) was added to a solution of 5-tert-butyl 2-methyl 1-methyl-6,7-dihydro-1H-imidazo[4,5-c]pyridine-2,5(4H)-dicarboxylate (Example 36, Step 2: 500 mg, 1.69 mmol) and 3-bromo-2-chloroaniline (350.0 mg, 1.69 mmol) in tetrahydrofuran (12.0 mL). After stirred at room temperature for 1 h, the reaction mixture was quenched with water, and extracted with ethyl acetate. The combined organic layers were washed with brine, dried over Na$_2$SO$_4$, filtered, and concentrated under reduced pressure. The residue was purified by flash chromatography on a silica gel column eluting with 50% ethyl acetate in hexanes to afford the desired product. LCMS calculated for C$_{19}$H$_{23}$BrClN$_4$O$_3$(M+H)$^+$: m/z=469.1; found 469.1.

Step 2: N-(3-bromo-2-chlorophenyl)-1,5-dimethyl-4,5,6,7-tetrahydro-1H-imidazo[4,5-c]pyridine-2-carboxamide

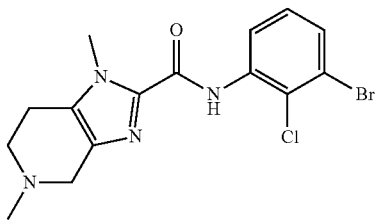 [SMILES: CN1CCc2c(nc(C(=O)Nc3cccc(Br)c3Cl)n2C)C1]

To a solution of tert-butyl 2-((3-bromo-2-chlorophenyl)carbamoyl)-1-methyl-1,4,6,7-tetrahydro-5H-imidazo[4,5-c]pyridine-5-carboxylate (160 mg, 0.341 mmol) in DCM (3 mL) was added trifluoroacetic acid (0.5 mL). The solution was stirred at r.t. for 1 h. then concentrate to dryness. The residue was dissolved in DCM (2.0 mL) and ACN (1 mL) then formaldehyde (37 wt % in water, 0.2 mL) was added. The resulting mixture was stirred at r.t. for 10 min, then sodium triacetoxyborohydride (217 mg, 1.022 mmol) was added. The reaction mixture was continued to stir at r.t. overnight. The reaction was quenched with sat. NH$_4$Cl solution, extracted with EtOAc. The combined organic phase was dried over Na$_2$SO$_4$, filtered and concentrated under reduced pressure to afford the desired product, which was used directly in the next step without further purification. LC-MS calculated for C$_{15}$H$_{17}$BrClN$_4$O (M+H)$^+$: m/z=383.0; found 383.0.

Step 3: N-(2-chloro-3'-(7-chloro-5-(hydroxymethyl)benzo[d/oxazol-2-yl)-2'-methylbiphenyl-3-yl)-1,5-dimethyl-4,5,6,7-tetrahydro-]H-imidazo[4,5-c]pyridine-2-carboxamide

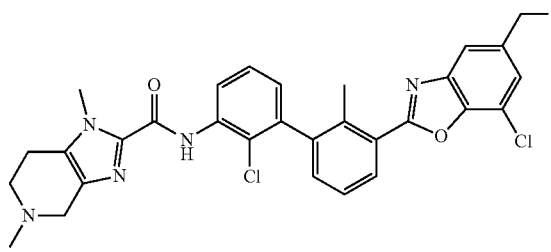

A mixture of N-(3-bromo-2-chlorophenyl)-1,5-dimethyl-4,5,6,7-tetrahydro-1H-imidazo[4,5-c]pyridine-2-carboxamide (150 mg, 0.391 mmol), (7-chloro-2-(2-methyl-3-(4,4,5,5-tetramethyl-1,3,2-dioxaborolan-2-yl)phenyl)benzo[d]oxazol-5-yl)methanol (Example 1, Step 5: 188 mg, 0.469 mmol), and dichloro[1,1'-bis(dicyclohexylphosphino)ferrocene]palladium(II) (17.7 mg, 0.023 mmol) in t-BuOH (5 ml) was added cesium carbonate (255 mg, 0.782 mmol) and a few drops of water. The reaction mixture was purged with nitrogen and then stirred at 100° C. for 5 hrs. After being cooled to room temperature, the reaction mixture was extracted with ethyl acetate. The combined organic layers were washed with brine, dried over $Na_2SO_4$, filtered and concentrated under reduced pressure. The residue was purified by flash chromatography on a silica gel column eluting with 0 to 10% methanol in DCM to afford the desired product. LC-MS calculated for $C_{30}H_{28}Cl_2N_5O_3$ $(M+H)^+$: m/z=576.2; found 576.1.

Step 4: N-(2-chloro-3'-(7-cyano-5-(hydroxymethyl)benzo[d]oxazol-2-yl)-2'-methylbiphenyl-3-yl)-1,5-dimethyl-4,5,6,7-tetrahydro-H-imidazo[4,5-c]pyridine-2-carboxamide

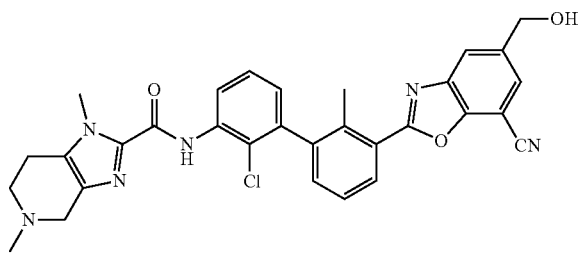 [SMILES: Cc1c(-c2nc3cc(CO)cc(C#N)c3o2)cccc1-c1cccc(NC(=O)c2nc3c(n2C)CCN(C)C3)c1Cl]

A mixture of N-(2-chloro-3'-(7-chloro-5-(hydroxymethyl)benzo[d]oxazol-2-yl)-2'-methyl-[1,1'-biphenyl]-3-yl)-1,5-dimethyl-4,5,6,7-tetrahydro-1H-imidazo[4,5-c]pyridine-2-carboxamide (140 mg, 0.24 mmol), [(2-di-tert-butylphosphino-2',4',6'-triisopropyl-1,1'-biphenyl)-2-(2'-amino-1,1'-biphenyl)]palladium(II) methanesulfonate (tBuXPhos Pd G3, 19.3 mg, 0.024 mmol), potassium hexacyanoferrate (II) trihydrate (103 mg, 0.24 mmol) and potassium acetate (4.8 mg, 0.049 mmol) in 1,4-dioxane (3.0 mL)/water (3.0 mL) was purged with nitrogen and then stirred at 100° C. for 1 h. After being cooled to room temperature, the reaction was extracted with ethyl acetate. The combined organic phases was dried over $Na_2SO_4$ and concentrated under reduced pressure. The crude was used directly in the next step without further purification. LC-MS calculated for $C_{31}H_{28}ClN_6O_3(M+H)^+$: m/z=567.2; found 567.2.

Step 5: N-(2-chloro-3'-(7-cyano-5-formylbenzo[d]oxazol-2-yl)-2'-methylbiphenyl-3-yl)-1,5-dimethyl-4,5,6,7-tetrahydro-1H-imidazo[4,5-c]pyridine-2-carboxamide

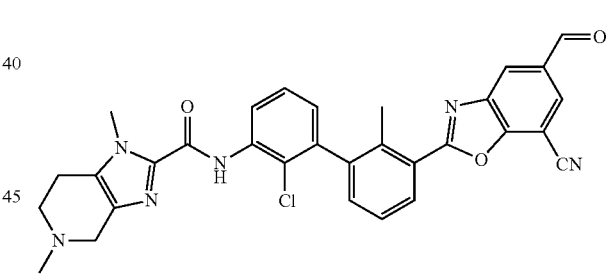

To a stirred solution of N-(2-chloro-3'-(7-cyano-5-(hydroxymethyl)benzo[d]oxazol-2-yl)-2'-methyl-[1,1'-biphenyl]-3-yl)-1,5-dimethyl-4,5,6,7-tetrahydro-1H-imidazo[4,5-c]pyridine-2-carboxamide (140.0 mg, 0.247 mmol) in DCM (3.0 ml) was added sodium bicarbonate (207 mg, 2.47 mmol) and dess-martin periodinane (157 mg, 0.370 mmol). The resulted mixture was stirred at rt for 2 hrs, then filtered. The filtrate was concentrated under reduced pressure. The residue was used in the next step directly without further purification. LC-MS calculated for $C_{31}H_{26}ClN_6O_3(M+H)^+$: m/z=565.2; found 565.1.

Step 6: (S)-1-((2-(2'-chloro-3'-(1,5-dimethyl-4,5,6,7-tetrahydro-1H-imidazo[4,5-c]pyridine-2-carboxamido)-2-methylbiphenyl-3-yl)-7-cyanobenzo[d]oxazol-5-yl)methyl)pyrrolidine-3-carboxylic acid To a solution of N-(2-chloro-3'-(7-cyano-5-formylbenzo[d]oxazol-2-yl)-2'-methyl-[1,1'-biphenyl]-3-yl)-1,5-dimethyl-4,5,6,7-tetrahydro-1H-imidazo[4,5-c]pyridine-2-carboxamide (65 mg, 0.115 mmol) in DCM (1 ml) was added (S)-pyrrolidine-3-carboxylic acid (66.2 mg, 0.575 mmol) and DIEA (0.161 ml, 0.920 mmol). The mixture was stirred at r.t. for 60 min, then sodium triacetoxyborohydride (73.1 mg, 0.345 mmol) was added. The resulting mixture was stirred at r.t. overnight then concentrated. The residue was purified via prep-HPLC (pH=2, MeCN/water with TFA) to give the desired product as the TFA salt. LC-MS calculated for $C_{36}H_{35}ClN_7O_4(M+H)^+$: m/z=664.2; found 664.2.

Example 51

(S)-1-((7-cyano-2-(3'-(1,5-dimethyl-4,5,6,7-tetrahydro-1H-imidazo[4,5-c]pyridine-2-carboxamido)-2'-fluoro-2-methylbiphenyl-3-yl)benzo[d]oxazol-5-yl)methyl)pyrrolidine-3-carboxylic acid

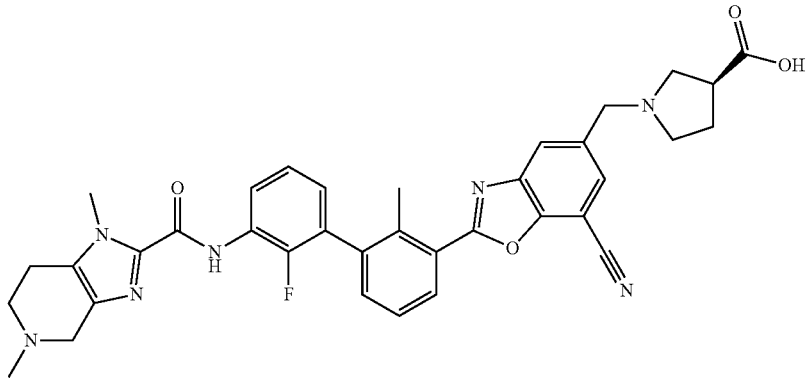 [SMILES: Cc1c(-c2nc3cc(CN4CC[C@H](C(=O)O)C4)cc(C#N)c3o2)cccc1-c1cccc(NC(=O)c2nc3c(n2C)CCN(C)C3)c1F]

This compound was prepared using similar procedure as described for Example 50 with 3-bromo-2-fluoroaniline replacing 3-bromo-2-chloroaniline in Step 1. It was purified via pH 2 preparative HPLC (MeCN/water with TFA) to give the desired product as its TFA salt. LC-MS calculated for $C_{36}H_{35}FN_7O_4(M+H)^+$: m/z=648.2; found 648.3.

Example 52

(S)-1-((2-(2'-chloro-3'-(1,5-dimethyl-4,5,6,7-tetrahydro-1H-imidazo[4,5-c]pyridine-2-carboxamido)-2-methylbiphenyl-3-yl)-7-cyanobenzo[d]oxazol-5-yl)methyl)piperidine-2-carboxylic acid

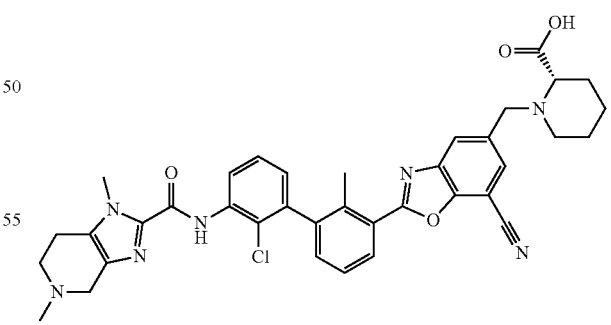

This compound was prepared using similar procedure as described for Example 50 with (S)-piperidine-2-carboxylic acid replacing (S)-pyrrolidine-3-carboxylic acid in Step 6. It was purified via pH 2 preparative HPLC (MeCN/water with TFA) to give the desired product as its TFA salt. LC-MS calculated for $C_{37}H_{37}ClN_7O_4(M+H)^+$: m/z=678.3; found 678.2.

Example 53

(R)-1-((2-(2'-chloro-3'-(1,5-dimethyl-4,5,6,7-tetrahydro-1H-imidazo[4,5-c]pyridine-2-carboxamido)-2-methylbiphenyl-3-yl)-7-cyanobenzo[d]oxazol-5-yl)methyl)pyrrolidine-3-carboxylic acid

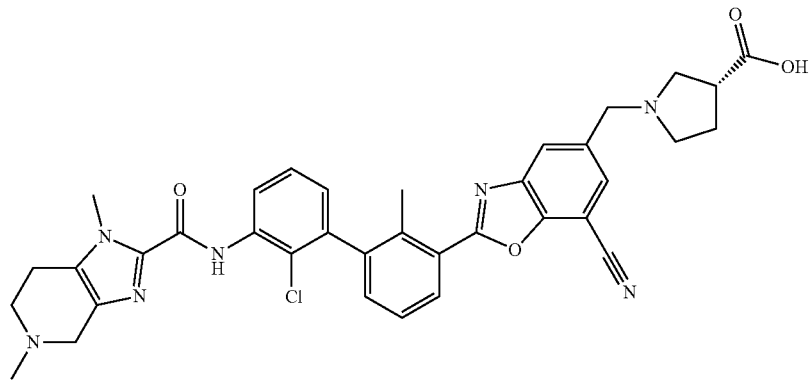

This compound was prepared using similar procedure as described for Example 50 with (R)-pyrrolidine-3-carboxylic acid replacing (S)-pyrrolidine-3-carboxylic acid in Step 6. It was purified via pH 2 preparative HPLC (MeCN/water with TFA) to give the desired product as its TFA salt. LC-MS calculated for $C_{36}H_{35}ClN_7O_4(M+H)^+$: m/z=664.2; found 664.2.

Example 54

(S)-1-((2-(2'-chloro-2-methyl-3'-(5-methyl-4,5,6,7-tetrahydro-2H-pyrazolo[4,3-c]pyridin-2-yl)biphenyl-3-yl)-7-cyanobenzo[d]oxazol-5-yl)methyl)pyrrolidine-3-carboxylic acid

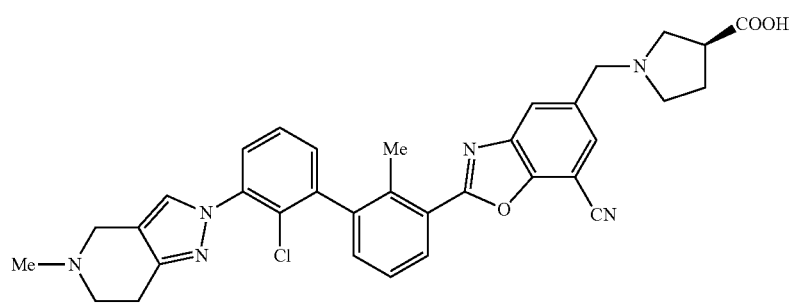 [SMILES: Cc1c(-c2nc3cc(CN4CC[C@H](C(=O)O)C4)cc(C#N)c3o2)cccc1-c1cccc(-n2cc3c(n2)CCN(C)C3)c1Cl]

Step 1: tert-butyl 2-(3-bromo-2-chlorophenyl)-6,7-dihydro-2H-pyrazolo[4,3-c]pyridine-5(4H)-carboxylate

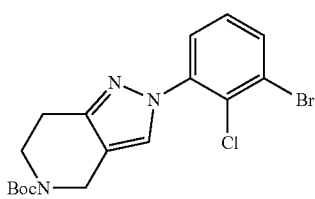 [SMILES: CC(C)(C)OC(=O)N1CCc2nn(-c3cccc(Br)c3Cl)cc2C1]

A mixture of tert-butyl 1,4,6,7-tetrahydro-5H-pyrazolo[4,3-c]pyridine-5-carboxylate (150 mg, 0.672 mmol; Astatech, cat # SC2911), potassium phosphate tribasic (428 mg, 2.015 mmol), 1,3-dibromo-2-chlorobenzene (363 mg, 1.344 mmol), and copper(I) iodide (12.79 mg, 0.067 mmol) was degassed and backfilled with $N_2$ three times. To the mixture was added trans-N,N'-dimethylcyclohexane-1,2-diamine (42.4 μl, 0.134 mmol) and toluene (2.2 mL). Then the mixture was allowed to stir at 110° C. overnight. The mixture was cooled to room temperature, filtered and concentrated. The residue was purified on silica gel column eluting with 0-80% EtOAc in Hexanes to give desired product. LC-MS calculated for $C_{17}H_{20}BrClN_3O_2(M+H)^+$: m/z=414.0; found 414.0.

Step 2: 5-(hydroxymethyl)-2-(2-methyl-3-(4,4,5,5-tetramethyl-1,3,2-dioxaborolan-2-yl)phenyl)benzo[d]oxazole-7-carbonitrile

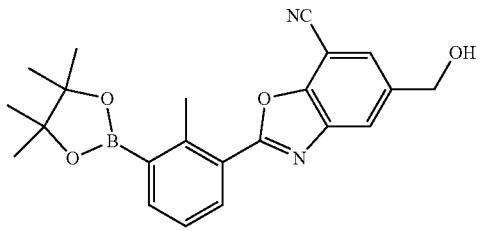 [SMILES: Cc1c(B2OC(C)(C)C(C)(C)O2)cccc1-c1nc2cc(CO)cc(C#N)c2o1]

A mixture of (7-chloro-2-(2-methyl-3-(4,4,5,5-tetramethyl-1,3,2-dioxaborolan-2-yl)phenyl)benzo[d]oxazol-5-yl)methanol (Example 1, Step 5: 40 mg, 0.100 mmol), [(2-di-tert-butylphosphino-2',4',6'-triisopropyl-1,1'-biphenyl)-2-(2'-amino-1,1'-biphenyl)]palladium(II) methanesulfonate (15.89 mg, 0.020 mmol), potassium hexacyanoferrate(II) trihydrate (42.3 mg, 0.100 mmol) and potassium acetate (3.93 mg, 0.040 mmol) in 1,4-dioxane (0.5 mL) and water (0.5 mL) was purged with $N_2$ and heated at 100° C. for 1 h. After cooling to room temperature, the reaction mixture was used directly in next step without further purification. LC-MS calculated for $C_{22}H_{24}BN_2O_4(M+H)^+$: m/z=391.2; found: 391.2.

Step 3: tert-butyl 2-(2-chloro-3'-(7-cyano-5-(hydroxymethyl)benzo[d]oxazol-2-yl)-2'-methylbiphenyl-3-yl)-6,7-dihydro-2H-pyrazolo[4,3-c]pyridine-5(4H)-carboxylate

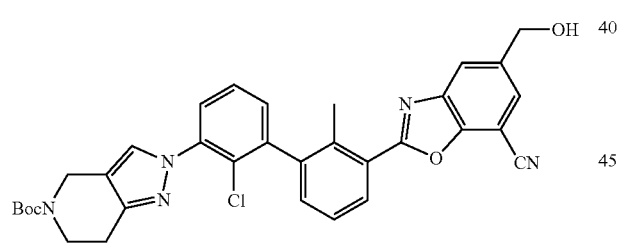

(1,1'-Bis(diphenylphosphino)ferrocene)-dichloropalladium(II) (7.32 mg, 10.00 μmol) was added to a mixture of 5-(hydroxymethyl)-2-(2-methyl-3-(4,4,5,5-tetramethyl-1,3,2-dioxaborolan-2-yl)phenyl)benzo[d]oxazole-7-carbonitrile (0.039 g, 0.100 mmol), tert-butyl 2-(3-bromo-2-chlorophenyl)-2,4,6,7-tetrahydro-5H-pyrazolo[4,3-c]pyridine-5-carboxylate (0.041 g, 0.10 mmol) and sodium carbonate (0.021 g, 0.200 mmol) in 1,4-dioxane (0.278 ml) and water (0.056 ml). The mixture was purged with $N_2$ and heated at 90° C. for 2 h. The mixture was concentrated and diluted with EtOAc and washed with water. The organic layer was dried over $Na_2SO_4$ and concentrated under reduce pressure. The residue was used in next step without further purification. LC-MS calculated for $C_{33}H_{31}ClN_5O_4(M+H)^+$: m/z=596.2; found 596.3.

Step 4: tert-butyl 2-(2-chloro-3'-(7-cyano-5-formyl-benzo[d]oxazol-2-yl)-2'-methylbiphenyl-3-yl)-6,7-dihydro-2H-pyrazolo[4,3-c]pyridine-5(4H)-carboxylate

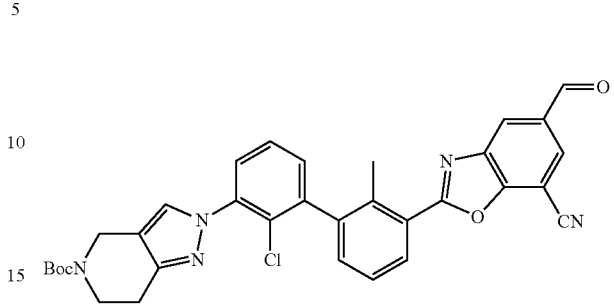

Dess-Martin periodinane (0.064 g, 0.150 mmol) was added to a DCM (0.33 mL) solution of tert-butyl 2-(2-chloro-3'-(7-cyano-5-(hydroxymethyl)benzo[d]oxazol-2-yl)-2'-methyl-[1,1'-biphenyl]-3-yl)-2,4,6,7-tetrahydro-5H-pyrazolo[4,3-c]pyridine-5-carboxylate (0.060 g, 0.1 mmol) and sodium bicarbonate (0.025 g, 0.300 mmol) at room temperature. After 1 h, the mixture was concentrated and purified by silica gel column eluting with 0 to 80% EtOAc in hexanes. LC-MS calculated for $C_{33}H_{29}ClN_5O_4(M+H)^+$: m/z=594.2; found 594.2.

Step 5: (S)-1-((2-(3'-(5-(tert-butoxycarbonyl)-4,5,6,7-tetrahydro-2H-pyrazolo[4,3-c]pyridin-2-yl)-2'-chloro-2-methylbiphenyl-3-yl)-7-cyanobenzo[d]oxazol-5-yl)methyl)pyrrolidine-3-carboxylic acid

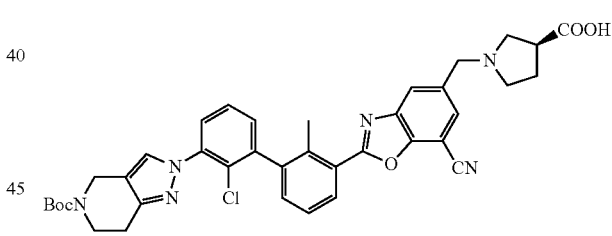

A mixture of tert-butyl 2-(2-chloro-3'-(7-cyano-5-formyl-benzo[d]oxazol-2-yl)-2'-methyl-[1,1'-biphenyl]-3-yl)-2,4,6,7-tetrahydro-5H-pyrazolo[4,3-c]pyridine-5-carboxylate (15 mg, 0.025 mmol) and (S)-pyrrolidine-3-carboxylic acid (5.81 mg, 0.050 mmol), hunig's base (8.82 μl, 0.050 mmol) in DCM (252 μl) was allowed to stir at room temperature for 2 h. Then sodium triacetoxyborohydride (8.03 mg, 0.038 mmol) was added to the mixture. The resulting mixture was stirred at room temperature for 1 h then it was diluted with DCM and washed with water and back extracted with DCM/iPrOH. The organic layers were combined and dried over sodium sulfate and concentrated and the residue was used in next step without further purification. LC-MS calculated for $C_{38}H_{38}ClN_6O_5(M+H)^+$: m/z=693.3; found 693.3.

Step 6: (S)-1-((2-(2'-chloro-2-methyl-3'-(4,5,6,7-tetrahydro-2H-pyrazolo[4,3-c]pyridin-2-yl)biphenyl-3-yl)-7-cyanobenzo[d]oxazol-5-yl)methyl)pyrrolidine-3-carboxylic acid

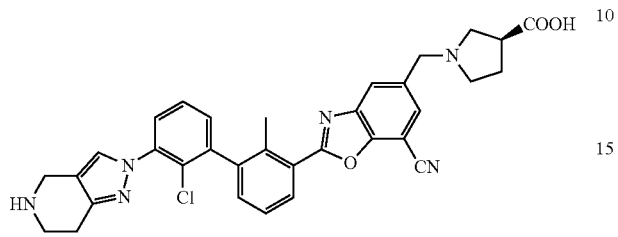

TFA (0.5 mL) was added to a DCM (1 mL) solution of (S)-1-((2-(3'-(5-(tert-butoxycarbonyl)-4,5,6,7-tetrahydro-2H-pyrazolo[4,3-c]pyridin-2-yl)-2'-chloro-2-methylbiphenyl-3-yl)-7-cyanobenzo[d]oxazol-5-yl)methyl)pyrrolidine-3-carboxylic acid (14 mg, 0.025 mmol) at room temperature. After 1 h, the mixture was concentrated and used in next step without further purification. LC-MS calculated for $C_{33}H_{30}ClN_6O_3(M+H)^+$: m/z=593.2; found 593.1.

Step 7: (S)-1-((2-(2'-chloro-2-methyl-3'-(5-methyl-4,5,6,7-tetrahydro-2H-pyrazolo[4,3-c]pyridin-2-yl)biphenyl-3-yl)-7-cyanobenzo[d]oxazol-5-yl)methyl)pyrrolidine-3-carboxylic acid

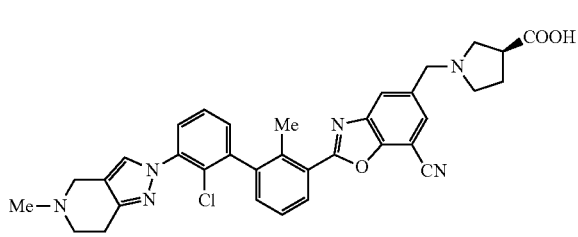 [SMILES: Cc1c(-c2nc3cc(CN4CC[C@H](C(=O)O)C4)cc(C#N)c3o2)cccc1-c1cccc(-n2cc3c(n2)CCN(C)C3)c1Cl]

A mixture of (S)-1-((2-(2'-chloro-2-methyl-3'-(4,5,6,7-tetrahydro-2H-pyrazolo[4,3-c]pyridin-2-yl)-[1,1'-biphenyl]-3-yl)-7-cyanobenzo[d]oxazol-5-yl)methyl)pyrrolidine-3-carboxylic acid (10 mg, 0.017 mmol) and formaldehyde 37% w/w in water (1.013 mg, 0.034 mmol) in DCM (169 µl) was allowed to stir for 2 h. Then sodium triacetoxyborohydride (7.0 mg, 0.034 mmol) was added to the mixture. After 2 h, the mixture was concentrated and diluted with MeOH and then purified by prep-HPLC (pH=2, acetonitrile/water+TFA) to give the desired product as TFA salt. LC-MS calculated for $C_{34}H_{32}ClN_6O_3(M+H)^+$: m/z=607.2; found 607.3.

Example 55

(R)-1-((2-(2'-chloro-2-methyl-3'-(5-methyl-5,6-dihydropyrrolo[3,4-c]pyrazol-2(4H)-yl)biphenyl-3-yl)-7-cyanobenzo[d]oxazol-5-yl)methyl)pyrrolidine-3-carboxylic acid

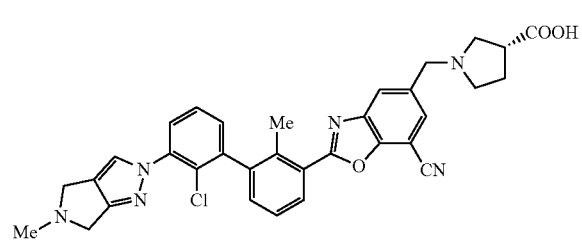 [SMILES: Cc1c(-c2nc3cc(CN4CC[C@@H](C(=O)O)C4)cc(C#N)c3o2)cccc1-c1cccc(-n2cc3c(n2)CN(C)C3)c1Cl]

Step 1: (R)-1-((2-(2'-chloro-3'-(5,6-dihydropyrrolo[3,4-c]pyrazol-2(4H)-yl)-2-methylbiphenyl-3-yl)-7-cyanobenzo[d]oxazol-5-yl)methyl)pyrrolidine-3-carboxylic acid

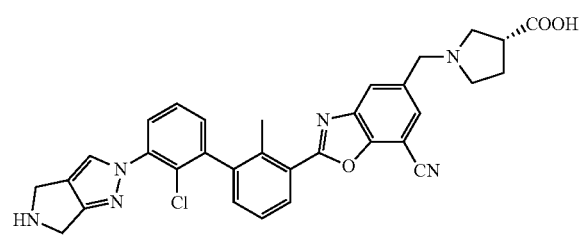 [SMILES: Cc1c(-c2nc3cc(CN4CC[C@@H](C(=O)O)C4)cc(C#N)c3o2)cccc1-c1cccc(-n2cc3c(n2)CNC3)c1Cl]

This compound was prepared using similar method in Example 54, Step 1-6 with tert-butyl 4,6-dihydropyrrolo[3,4-c]pyrazole-5(1H)-carboxylate (Astatech, cat #35882) replacing tert-butyl 1,4,6,7-tetrahydro-5H-pyrazolo[4,3-c]pyridine-5-carboxylate in Step 1 and with (R)-pyrrolidine-3-carboxylic acid replacing (S)-pyrrolidine-3-carboxylic acid in Step 5. LC-MS calculated for $C_{32}H_{28}ClN_6O_3(M+H)^+$: m/z=579.2; found 579.1.

Step 2: (R)-1-((2-(2'-chloro-2-methyl-3'-(5-methyl-5,6-dihydropyrrolo[3,4-c]pyrazol-2(4H)-yl)biphenyl-3-yl)-7-cyanobenzo[d]oxazol-5-yl)methyl)pyrrolidine-3-carboxylic acid This compound was prepared using similar method in Example 54, Step 7 with (R)-1-((2-(2'-chloro-3'-(5,6-dihydropyrrolo[3,4-c]pyrazol-2(4H)-yl)-2-methylbiphenyl-3-yl)-7-cyanobenzo[d]oxazol-5-yl)methyl)pyrrolidine-3-carboxylic acid replacing (S)-1-((2-(2'-chloro-2-methyl-3'-(4,5,6,7-tetrahydro-2H-pyrazolo[4,3-c]pyridin-2-yl)-[1,1'-biphenyl]-3-yl)-7-cyanobenzo[d]oxazol-5-yl)methyl)pyrrolidine-3-carboxylic acid. It was purified by prep-HPLC (pH=2, acetonitrile/water+TFA) to give the desired product as TFA salt. LC-MS calculated for $C_{33}H_{30}ClN_6O_3(M+H)^+$: m/z=593.2; found 593.2.

Example 56

(R)-1-((2-(2'-chloro-3'-(5-isopropyl-5,6-dihydropyr-rolo[3,4-c]pyrazol-2(4H)-yl)-2-methylbiphenyl-3-yl)-7-cyanobenzo[d]oxazol-5-yl)methyl)pyrrolidine-3-carboxylic acid

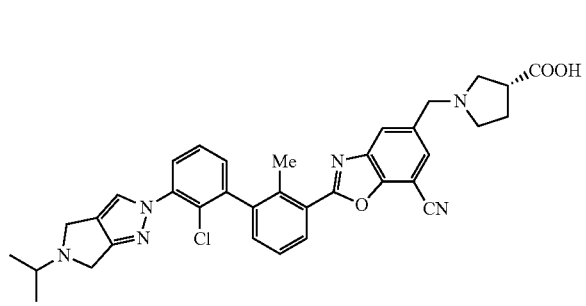 [SMILES: Cc1c(-c2nc3cc(CN4CC[C@@H](C(=O)O)C4)cc(C#N)c3o2)cccc1-c1cccc(-n2cc3c(n2)CN(C(C)C)C3)c1Cl]

This compound was prepared using similar method in Example 55 with acetone replacing formaldehyde in Step 2. It was purified by prep-HPLC (pH=2, acetonitrile/water+TFA) to give the desired product as TFA salt. LC-MS calculated for $C_{35}H_{34}ClN_6O_3(M+H)^+$: m/z=621.2; found 621.2.

Example 57

(R)-1-((2-(2'-chloro-2-methyl-3'-(6-methyl-4,5,6,7-tetrahydro-2H-pyrazolo[3,4-c]pyridin-2-yl)biphenyl-3-yl)-7-cyanobenzo[d]oxazol-5-yl)methyl)pyrrolidine-3-carboxylic acid

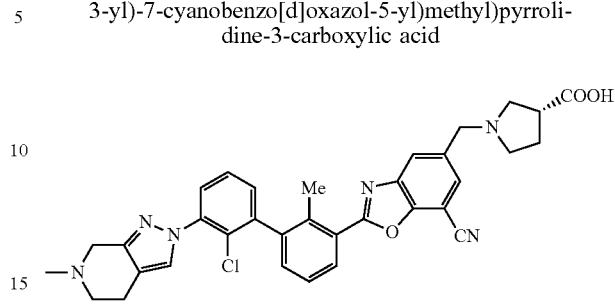

This compound was prepared using similar method in Example 54 with tert-butyl 1,4,5,7-tetrahydro-6H-pyrazolo[3,4-c]pyridine-6-carboxylate (Astatech, cat #79248) replacing tert-butyl 1,4,6,7-tetrahydro-5H-pyrazolo[4,3-c]pyridine-5-carboxylate in Step 1. It was purified by prep-HPLC (pH=2, acetonitrile/water+TFA) to give the desired product as TFA salt. LC-MS calculated for $C_{34}H_{32}ClN_6O_3$ $(M+H)^+$: m/z=607.3; found 607.3.

Example 58

(R)-1-((2-(2'-chloro-3'-(6-ethyl-4,5,6,7-tetrahydro-2H-pyrazolo[3,4-c]pyridin-2-yl)-2-methylbiphenyl-3-yl)-7-cyanobenzo[d]oxazol-5-yl)methyl)pyrrolidine-3-carboxylic acid

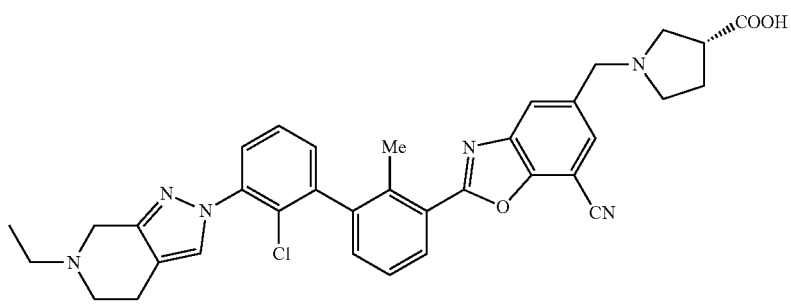 [SMILES: CCN1CCc2cn(-c3cccc(-c4cccc(-c5nc6cc(CN7CC[C@@H](C(=O)O)C7)cc(C#N)c6o5)c4C)c3Cl)nc2C1]

This compound was prepared using similar method in Example 57 with acetaldehyde replacing formaldehyde. It was purified by prep-HPLC (pH=2, acetonitrile/water+TFA) to give the desired product as TFA salt. LC-MS calculated for $C_{35}H_{34}ClN_6O_3(M+H)^+$: m/z=621.2; found 621.2.

Example 59

(R)-1-((7-chloro-2-(3'-(5-isopropyl-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid

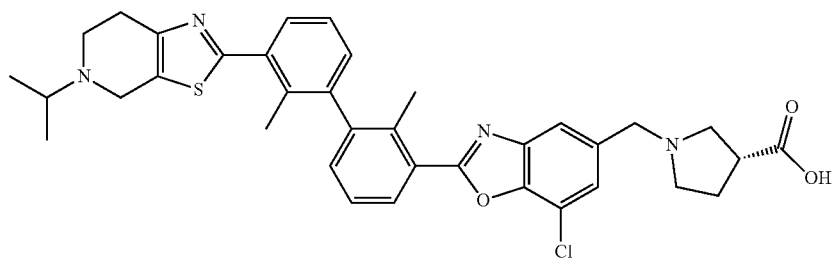 [SMILES: Cc1c(-c2nc3cc(CN4CC[C@@H](C(=O)O)C4)cc(Cl)c3o2)cccc1-c1cccc(-c2nc3c(s2)CN(C(C)C)CC3)c1C]

Step 1: (2-(3'-bromo-2,2'-dimethyl-[1,1'-biphenyl]-3-yl)-7-chlorobenzo[d]oxazol-5-yl)methanol

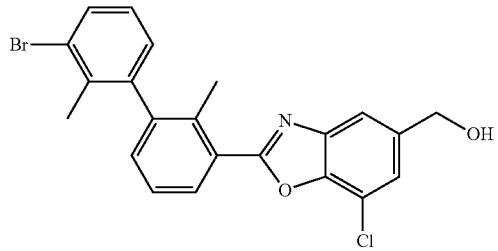 [SMILES: Cc1c(Br)cccc1-c1cccc(-c2nc3cc(CO)cc(Cl)c3o2)c1C]

To a solution of (7-chloro-2-(2-methyl-3-(4,4,5,5-tetramethyl-1,3,2-dioxaborolan-2-yl)phenyl)benzo[d]oxazol-5-yl)methanol (Example 1, Step 5: 11.3 g, 28.4 mmol) and 1,3-dibromo-2-methylbenzene (14.17 g, 56.7 mmol) in $H_2O$ (30 mL) and 1,4-dioxane (120 ml) was added $Na_2CO_3$ (6.01 g, 56.7 mmol) and $PdCl_2(dppf)-CH_2Cl_2$ adduct (2.316 g, 2.84 mmol). The resulted mixture was stirred in a closed vial flushed with nitrogen at 100° C. for 1.5 h. The reaction mixture was concentrated, followed by extraction with dichloromethane (25 mL×3). The combined organic layers were dried $Na_2SO_4$, filtered and concentrated. The crude product was added to a silica gel column and was eluted with ethyl acetate/dichloromethane from 0% to 40% to give (2-(3'-bromo-2,2'-dimethyl-[1,1'-biphenyl]-3-yl)-7-chlorobenzo[d]oxazol-5-yl)methanol (10.2 g, 23.0 mmol, 81% yield). LC-MS calculated for $C_{22}H_{18}BrClNO_2$ $(M+H)^+$: m/z=442.0; found 442.1.

Step 2: (7-chloro-2-(2,2'-dimethyl-3'-(4,4,5,5-tetramethyl-1,3,2-dioxaborolan-2-yl)-[1,1'-biphenyl]-3-yl)benzo[d]oxazol-5-yl)methanol

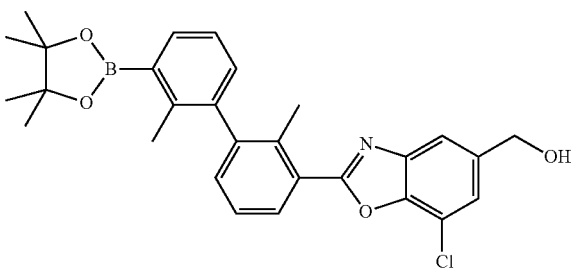 [SMILES: Cc1c(B2OC(C)(C)C(C)(C)O2)cccc1-c1cccc(-c2nc3cc(CO)cc(Cl)c3o2)c1C]

(2-(3'-bromo-2,2'-dimethyl-[1,1'-biphenyl]-3-yl)-7-chlorobenzo[d]oxazol-5-yl)methanol (6.52 g, 14.7 mmol) was dissolved in dioxane (14.7 mL) to give a pale yellow solution. $B_2Pin_2$ (4.49 g, 17.7 mmol), potassium acetate (2.89 g, 29.5 mmol) and $PdCl_2(dppf)-CH_2Cl_2$ adduct (1.20 g, 1.47 mmol) were added to the reaction mixture. The reaction mixture was heated to 100° C. After 12 h, saturated $NaHCO_3$ (25 mL) was added to the reaction mixture followed by extraction with dichloromethane (25 mL×3). The combined organic layers were dried $Na_2SO_4$, filtered and concentrated. The crude product was added to a silica gel column and was eluted with ethyl acetate/hexane from 0% to 60% to give (7-chloro-2-(2,2'-dimethyl-3'-(4,4,5,5-tetramethyl-1,3,2-dioxaborolan-2-yl)-[1,1'-biphenyl]-3-yl)benzo[d]oxazol-5-yl)methanol (6.33 g, 12.9 mmol, 88% yield) as a yellow foam. LC-MS calculated for $C_{28}H_{30}BClNO_4$ $(M+H)^+$: m/z=490.2; found 490.1.

Step 3: tert-butyl 2-(3'-(7-chloro-5-(hydroxymethyl)benzo[d]oxazol-2-yl)-2,2'-dimethyl-[1,1'-biphenyl]-3-yl)-6,7-dihydrothiazolo[5,4-c]pyridine-5(4H)-carboxylate

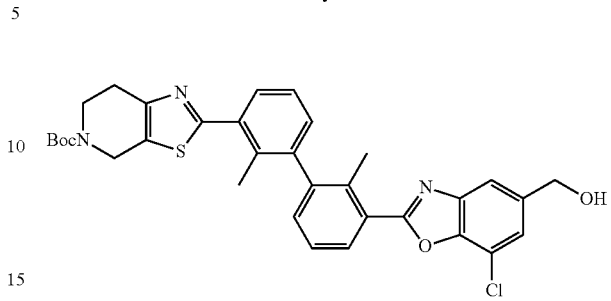

(7-chloro-2-(2,2'-dimethyl-3'-(4,4,5,5-tetramethyl-1,3,2-dioxaborolan-2-yl)-[1,1'-biphenyl]-3-yl)benzo[d]oxazol-5-yl)methanol (2.98 g, 6.08 mmol), tert-butyl 2-bromo-6,7-dihydrothiazolo[5,4-c]pyridine-5(4H)-carboxylate (AstaTech, cat # AB1021: 2.33 g, 7.29 mmol), $Na_2CO_3$ (1.29 g, 12.2 mmol) and $PdCl_2(dppf)-CH_2Cl_2$ adduct (496 mg, 0.608 mmol) in 1,4-dioxane (60 ml) and water (15 mL) were stirred in a closed vial flushed with nitrogen at 100° C. for 1 h. Saturated $NaHCO_3$ (50 mL) was added to the reaction mixture followed by extraction with dichloromethane (25 mL×4). The combined organic layers were dried $Na_2SO_4$, filtered and concentrated. The crude product was added to a silica gel column and was eluted with ethyl acetate/hexane from 0% to 60% to give tert-butyl 2-(3'-(7-chloro-5-(hydroxymethyl)benzo[d]oxazol-2-yl)-2,2'-dimethyl-[1,1'-biphenyl]-3-yl)-6,7-dihydrothiazolo[5,4-c]pyridine-5(4H)-carboxylate (1.80 g, 2.99 mmol, 49.2% yield) as a yellow oil. LC-MS calculated for $C_{33}H_{33}ClN_3O_4S$ $(M+H)^+$: m/z=602.2; found 602.1.

Step 4: tert-butyl 2-(3'-(7-chloro-5-formylbenzo[d]oxazol-2-yl)-2,2'-dimethyl-[1,1'-biphenyl]-3-yl)-6,7-dihydrothiazolo[5,4-c]pyridine-5(4H)-carboxylate

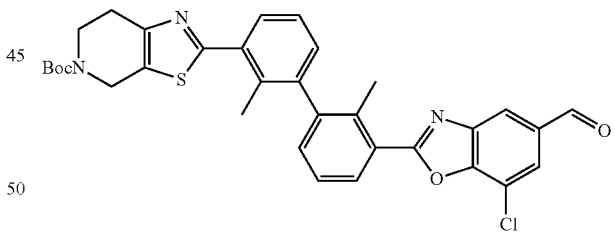

To a solution of tert-butyl 2-(3'-(7-chloro-5-(hydroxymethyl)benzo[d]oxazol-2-yl)-2,2'-dimethyl-[1,1'-biphenyl]-3-yl)-6,7-dihydrothiazolo[5,4-c]pyridine-5 (4H)-carboxylate (222 mg, 0.368 mmol) in DCM (3 mL) was added Dess-Martin periodinane (234 mg, 0.552 mmol). After 1 h, saturated $NaHCO_3$ (5 mL) was added to the reaction mixture followed by extraction with dichloromethane (5 mL×3). The combined organic layers were dried $Na_2SO_4$, filtered and concentrated. The crude product was added to a silica gel column and was eluted with ethyl acetate/hexane from 0% to 30% to give tert-butyl 2-(3'-(7-chloro-5-formylbenzo[d]oxazol-2-yl)-2,2'-dimethyl-[1,1'-biphenyl]-3-yl)-6,7-dihydrothiazolo[5,4-c]pyridine-5(4H)-carboxylate (143 mg, 0.238 mmol, 64.7% yield). LC-MS calculated for $C_{33}H_{31}ClN_3O_4S$ $(M+H)^+$: m/z=600.2; found 600.1.

Step 5: (R)-1-((2-(3'-(5-(tert-butoxycarbonyl)-4,5,6,7-tetrahydrothiazolo[5,4-c]pyridin-2-yl)-2,2'-dimethyl-[1,1'-biphenyl]-3-yl)-7-chlorobenzo[d]oxazol-5-yl)methyl)pyrrolidine-3-carboxylic acid

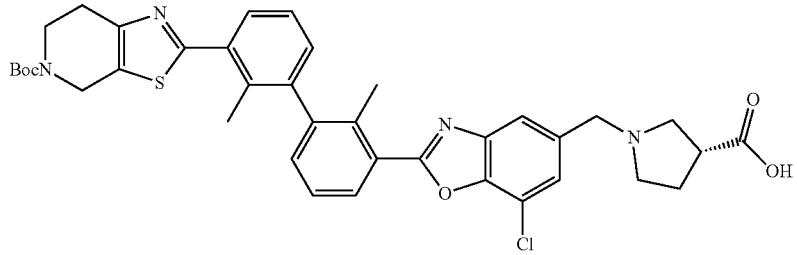 [SMILES: Cc1c(-c2nc3cc(CN4CC[C@@H](C(=O)O)C4)cc(Cl)c3o2)cccc1-c1cccc(-c2nc3c(s2)CN(C(=O)OC(C)(C)C)CC3)c1C]

To a solution of tert-butyl 2-(3'-(7-chloro-5-formylbenzo[d]oxazol-2-yl)-2,2'-dimethyl-[1,1'-biphenyl]-3-yl)-6,7-dihydrothiazolo[5,4-c]pyridine-5(4H)-carboxylate (70 mg, 0.117 mmol) in DMF (1.2 mL) was added (R)-pyrrolidine-3-carboxylic acid (40.2 mg, 0.350 mmol). After 1 h, sodium cyanoborohydride (15 mg, 0.233 mmol) was added to the reaction mixture. After 2 h, saturated NaHCO$_3$ (5 mL) was added followed by extraction with dichloromethane (5 mL×4). The combined organic layers were dried Na$_2$SO$_4$, filtered and concentrated. The crude product was used directly in the next step. LC-MS calculated for C$_{38}$H$_{40}$ClN$_4$O$_5$S (M+H)$^+$: m/z=699.2; found 699.3.

Step 6: (R)-1-((7-chloro-2-(2,2'-dimethyl-3'-(4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid

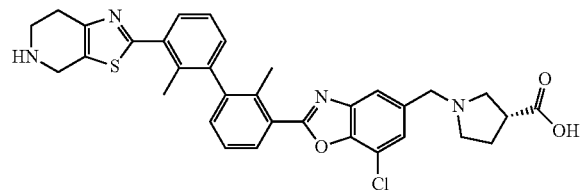

To a solution of (R)-1-((2-(3'-(5-(tert-butoxycarbonyl)-4,5,6,7-tetrahydrothiazolo[5,4-c]pyridin-2-yl)-2,2'-dimethyl-[1,1'-biphenyl]-3-yl)-7-chlorobenzo[d]oxazol-5-yl)methyl)pyrrolidine-3-carboxylic acid (82 mg, 0.117 mmol) in DCM (1 mL) was added TFA (0.5 mL). After 2 h, the reaction mixture was concentrated, and then the crude product was used directly in the next step. LC-MS calculated for C$_{33}$H$_{32}$ClN$_4$O$_3$S (M+H)$^+$: m/z=599.2; found 599.3.

Step 7: (R)-1-((7-chloro-2-(3'-(5-isopropyl-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid In a 1 dram vial (R)-1-((7-chloro-2-(2,2'-dimethyl-3'-(4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid (50 mg, 0.083 mmol) was dissolved in DCM (417 μl) to give a yellow solution. Acetone (30.6 μl, 0.417 mmol) and DIPEA (29.2 μl, 0.167 mmol) were added to the reaction mixture. After 1 h, sodium triacetoxyborohydride (88 mg, 0.417 mmol) was added to the reaction mixture. After 5 h, the reaction mixture was concentrated. The reaction mixture was diluted with MeOH then purified by prep-HPLC (pH=2, acetonitrile/water+TFA) to give the desired product as the TFA salt. LC-MS calculated for C$_{36}$H$_{38}$ClN$_4$O$_3$S (M+H)$^+$: m/z=641.2; found 641.3. $^1$H NMR (500 MHz, DMSO-d6) δ 8.16 (dd, J=7.9, 1.2 Hz, 1H), 8.02 (d, J=1.1 Hz, 1H), 7.78 (d, J=1.2 Hz, 1H), 7.67 (dd, J=7.8, 1.1 Hz, 1H), 7.56 (t, J=7.7 Hz, 1H), 7.46 (m, 2H), 7.32 (d, J=6.5 Hz, 1H), 4.77-4.68 (m, 2H), 4.54 (s, 2H), 3.85-3.12 (m, 10H), 2.43 (s, 3H), 2.18 (s, 3H), 2.05 (s, 2H), 1.36 (s, 3H), 1.35 (s, 3H).

Example 60

(R)-1-((7-chloro-2-(3'-(5-ethyl-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid

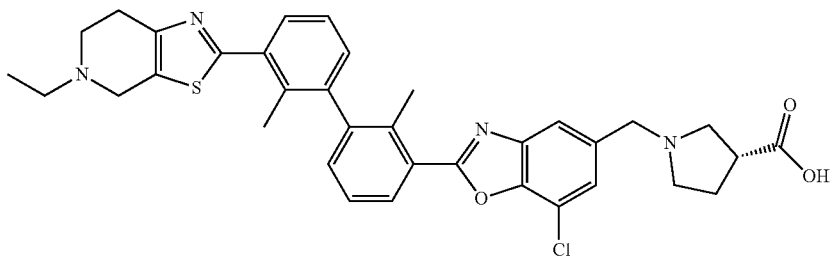

This compound was prepared using similar procedures as described for Example 59 with acetaldehyde replacing acetone in Step 7. The reaction mixture was diluted with MeOH then purified by prep-HPLC (pH=2, acetonitrile/water+TFA) to give the desired product as the TFA salt. LC-MS calculated for $C_{35}H_{36}ClN_4O_3S$ $(M+H)^+$: m/z=627.2; found 627.3.

Example 61

(R)-1-((7-chloro-2-(3'-(5-(2-hydroxyethyl)-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid

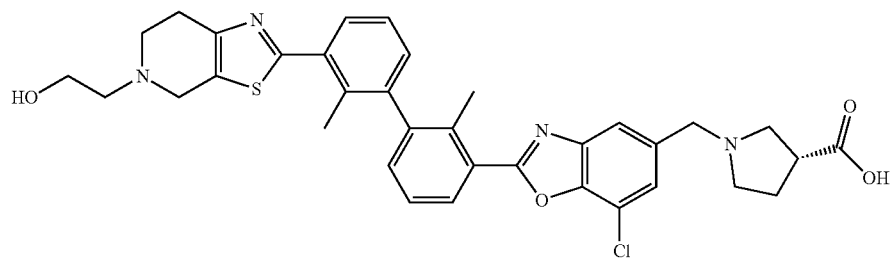

Step 1: (R)-1-((2-(3'-(5-(2-((tert-butyldimethylsilyl)oxy)ethyl)-4,5,6,7-tetrahydrothiazolo[5,4-c]pyridin-2-yl)-2,2'-dimethyl-[1,1'-biphenyl]-3-yl)-7-chlorobenzo[d]oxazol-5-yl)methyl)pyrrolidine-3-carboxylic acid

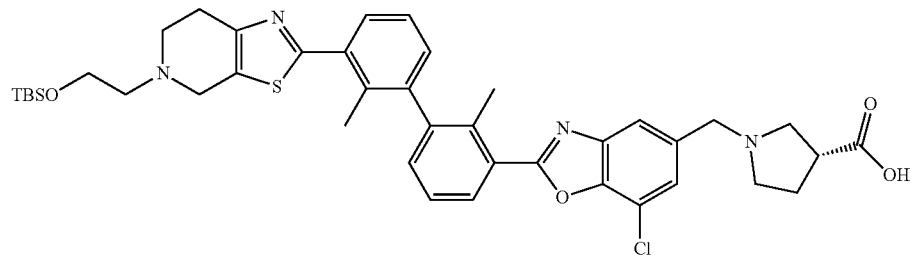 [SMILES: Cc1c(-c2nc3cc(CN4CC[C@@H](C(=O)O)C4)cc(Cl)c3o2)cccc1-c1cccc(-c2nc3c(s2)CN(CCO[Si](C)(C)C(C)(C)C)CC3)c1C]

This compound was prepared using similar procedures as described for Example 59 with (tert-Butyldimethylsilyloxy)acetaldehyde (Aldrich, cat #449458) replacing acetone in Step 7. The reaction mixture was concentrated, and then the crude product was used directly in the next step. LC-MS calculated for $C_{41}H_{50}ClN_4O_4SSi$ $(M+H)^+$: m/z=757.2; found 757.3.

Step 2: (R)-1-((7-chloro-2-(3'-(5-(2-hydroxyethyl)-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid (R)-1-((2-(3'-(5-(2-((tert-butyldimethylsilyl)oxy)ethyl)-4,5,6,7-tetrahydrothiazolo[5,4-c]pyridin-2-yl)-2,2'-dimethyl-[1,1'-biphenyl]-3-yl)-7-chlorobenzo[d]oxazol-5-yl)methyl)pyrrolidine-3-carboxylic acid (20 mg, 0.031 mmol) was dissolved in THF (1 mL), then treated with 1N HCl (0.1 mL). After 2 h, the reaction mixture was diluted with MeOH then purified by prep-HPLC (pH=2, acetonitrile/water+TFA) to give the desired product as the TFA salt. LC-MS calculated for $C_{35}H_{36}ClN_4O_4S$ $(M+H)^+$: m/z=643.2; found 643.2. $^1H$ NMR (500 MHz, DMSO-$d_6$) δ 10.37 (br, 1H), 8.16 (d, J=6.7 Hz, 1H), 8.02 (d, J=1.1 Hz, 1H), 7.78 (d, J=1.2 Hz, 1H), 7.69 (d, J=6.7 Hz, 1H), 7.56 (t, J=7.7 Hz, 1H), 7.48-7.42 (m, 2H), 7.32 (d, J=6.6 Hz, 1H), 4.88-4.33 (m, 2H), 4.53 (s, 2H), 3.83 (t, J=5.2 Hz, 2H), 3.68-2.99 (m, 13H), 2.42 (s, 3H), 2.19 (s, 3H).

Example 62

(3R)-1-((7-chloro-2-(3'-(5-(1-hydroxypropan-2-yl)-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid

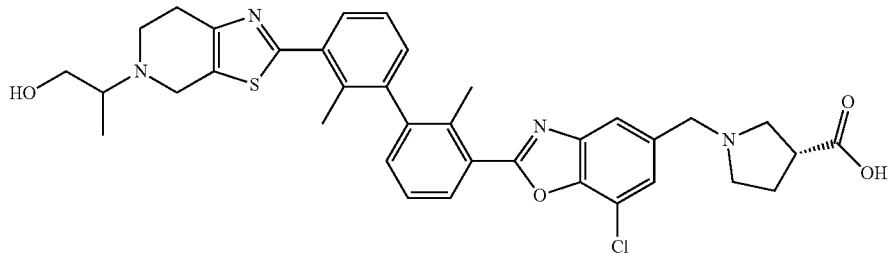 [SMILES: Cc1c(-c2nc3cc(CN4CC[C@@H](C(=O)O)C4)cc(Cl)c3o2)cccc1-c1cccc(-c2nc3c(s2)CN(C(C)CO)CC3)c1C]

Step 1: (3R)-1-((2-(3'-(5-(1-acetoxypropan-2-yl)-4,5,6,7-tetrahydrothiazolo[5,4-c]pyridin-2-yl)-2,2'-dimethyl-[1,1'-biphenyl]-3-yl)-7-chlorobenzo[d]oxazol-5-yl)methyl)pyrrolidine-3-carboxylic acid

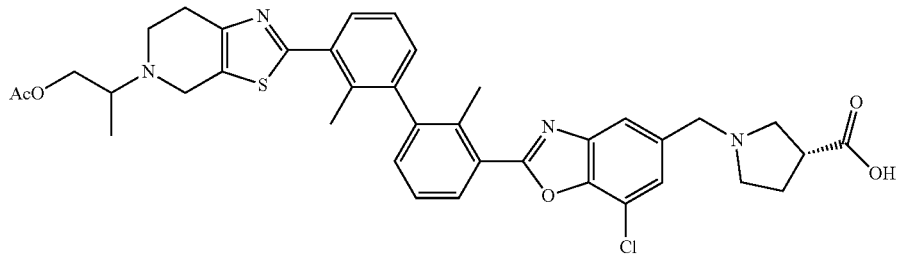 [SMILES: CC(=O)OCC(C)N1CCc2nc(-c3cccc(-c4cccc(-c5nc6cc(CN7CC[C@@H](C(=O)O)C7)cc(Cl)c6o5)c4C)c3C)sc2C1]

This compound was prepared using similar procedures as described for Example 59 with acetoxyacetone (Alfa Aesar, cat # H31346) replacing acetone in Step 7. The reaction mixture was concentrated, and then the crude product was used directly in the next step. LC-MS calculated for $C_{38}H_{40}ClN_4O_5S$ (M+H)$^+$: m/z=699.2; found 699.3.

Step 2: (3R)-1-((7-chloro-2-(3'-(5-(1-hydroxypropan-2-yl)-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid (3R)-1-((2-(3'-(5-(1-acetoxypropan-2-yl)-4,5,6,7-tetrahydrothiazolo[5,4-c]pyridin-2-yl)-2,2'-dimethyl-[1,1'-biphenyl]-3-yl)-7-chlorobenzo[d]oxazol-5-yl)methyl)pyrrolidine-3-carboxylic acid (20 mg, 0.031 mmol) was dissolved in dioxane (1 mL), then treated with 1N NaOH (0.1 mL). After 2 h, the reaction mixture was diluted with MeOH then purified by prep-HPLC (pH=2, acetonitrile/water+TFA) to give the desired product as the TFA salt. LC-MS calculated for $C_{36}H_{38}ClN_4O_4S$ (M+H)$^+$: m/z=657.2; found 657.2.

Example 63

(R)-1-((7-cyano-2-(3'-(5-isopropyl-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid

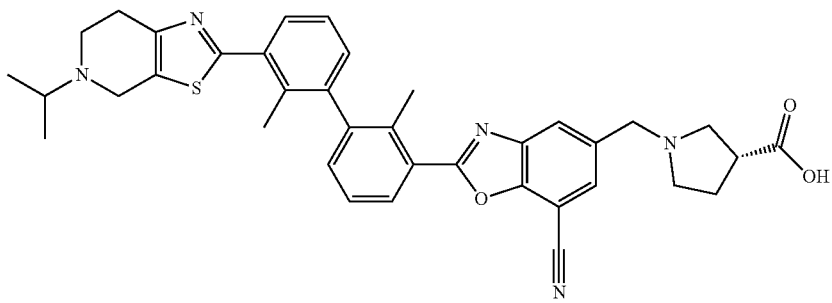 [SMILES: Cc1c(-c2nc3cc(CN4CC[C@@H](C(=O)O)C4)cc(C#N)c3o2)cccc1-c1cccc(-c2nc3c(s2)CN(C(C)C)CC3)c1C]

Step 1: tert-butyl 2-(3'-(7-cyano-5-(hydroxymethyl)benzo[d]oxazol-2-yl)-2,2'-dimethyl-[1,1'-biphenyl]-3-yl)-6,7-dihydrothiazolo[5,4-c]pyridine-5(4H)-carboxylate

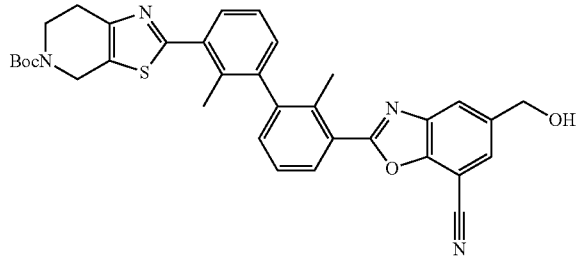 [SMILES: Cc1c(-c2nc3cc(CO)cc(C#N)c3o2)cccc1-c1cccc(-c2nc3c(s2)CN(C(=O)OC(C)(C)C)CC3)c1C]

In a 4 dram vial tert-butyl 2-(3'-(7-chloro-5-(hydroxymethyl)benzo[d]oxazol-2-yl)-2,2'-dimethyl-[1,1'-biphenyl]-3-yl)-6,7-dihydrothiazolo[5,4-c]pyridine-5(4H)-carboxylate (Example 59, Step 3; 900 mg, 1.50 mmol) and potassium ferrocyanide(II) hydrate (947 mg, 2.24 mmol) were dissolved in 1,4-dioxane (10 ml) and water (4.5 ml). Potassium acetate (367 mg, 3.74 mmol) and [(2-di-tert-butylphosphino-2',4',6'-triisopropyl-1,1'-biphenyl)-2-(2'-amino-1,1'-biphenyl)]palladium(II) methanesulfonate (119 mg, 0.15 mmol) were added to the reaction mixture. The reaction mixture was heated to 100° C. After 2 h, saturated NaHCO₃ (15 mL) was added to the reaction mixture followed by extraction with dichloromethane (10 mL×4). The combined organic layers were dried Na₂SO₄, filtered and concentrated. The crude product was added to a silica gel column and was eluted with ethyl acetate/hexane from 10% to 60% to give tert-butyl 2-(3'-(7-cyano-5-(hydroxymethyl)benzo[d]oxazol-2-yl)-2,2'-dimethyl-[1,1'-biphenyl]-3-yl)-6,7-dihydrothiazolo[5,4-c]pyridine-5(4H)-carboxylate (702 mg, 1.18 mmol, 79% yield) as a yellow oil. LC-MS calculated for $C_{34}H_{33}N_4O_4S$ (M+H)⁺: m/z=593.2; found 593.1.

Step 2: tert-butyl 2-(3'-(7-cyano-5-formylbenzo[d]oxazol-2-yl)-2,2'-dimethyl-[1,1'-biphenyl]-3-yl)-6,7-dihydrothiazolo[5,4-c]pyridine-5(4H)-carboxylate

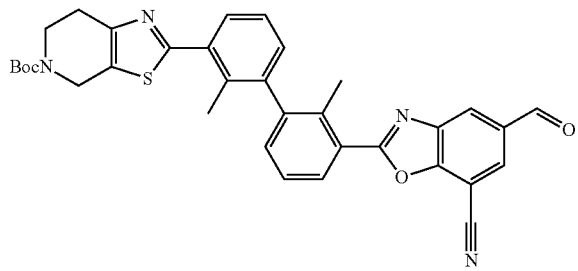 [SMILES: Cc1c(-c2nc3cc(C=O)cc(C#N)c3o2)cccc1-c1cccc(-c2nc3c(s2)CN(C(=O)OC(C)(C)C)CC3)c1C]

To a solution of tert-butyl 2-(3'-(7-cyano-5-(hydroxymethyl)benzo[d]oxazol-2-yl)-2,2'-dimethyl-[1,1'-biphenyl]-3-yl)-6,7-dihydrothiazolo[5,4-c]pyridine-5(4H)-carboxylate (150 mg, 0.253 mmol) in DCM (2 mL) was added Dess-Martin periodinane (161 mg, 0.380 mmol). After 1 h, saturated NaHCO₃ (5 mL) was added to the reaction mixture followed by extraction with dichloromethane (5 mL×3). The combined organic layers were dried Na₂SO₄, filtered and concentrated. The crude product was used for next step without further purification. LC-MS calculated for $C_{34}H_{31}N_4O_4S$ (M+H)⁺: m/z=591.2; found 591.3.

Step 3: (R)-1-((2-(3'-(5-(tert-butoxycarbonyl)-4,5,6,7-tetrahydrothiazolo[5,4-c]pyridin-2-yl)-2,2'-dimethyl-[1,1'-biphenyl]-3-yl)-7-cyanobenzo[d]oxazol-5-yl)methyl)pyrrolidine-3-carboxylic acid

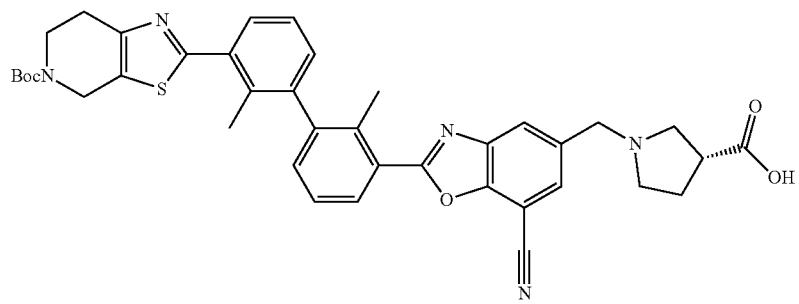 [SMILES: Cc1c(-c2nc3cc(CN4CC[C@@H](C(=O)O)C4)cc(C#N)c3o2)cccc1-c1cccc(-c2nc3c(s2)CN(C(=O)OC(C)(C)C)CC3)c1C]

To a solution of tert-butyl 2-(3'-(7-cyano-5-formylbenzo[d]oxazol-2-yl)-2,2'-dimethyl-[1,1'-biphenyl]-3-yl)-6,7-dihydrothiazolo[5,4-c]pyridine-5(4H)-carboxylate (150 mg, 0.253 mmol) and DIPEA (20 uL) in DCM (3 mL) was added (R)-pyrrolidine-3-carboxylic acid (116 mg, 1.01 mmol). After 1 h, sodium triacetoxyborohydride (268 mg, 1.26 mmol) was added to the reaction mixture. After 2 h, saturated NaHCO₃ (5 mL) was added followed by extraction with dichloromethane (5 mL×4). The combined organic layers were dried Na₂SO₄, filtered and concentrated. The crude product was used directly in the next step. LC-MS calculated for $C_{39}H_{40}N_5O_5S$ (M+H)⁺: m/z=690.2; found 690.3.

Step 4: (R)-1-((7-cyano-2-(2,2'-dimethyl-3'-(4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid

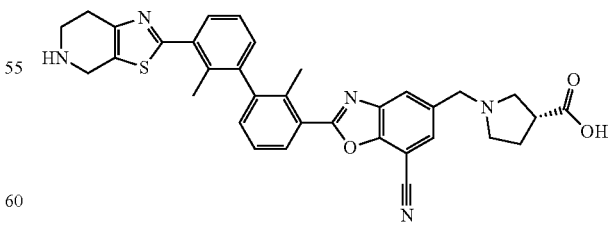

To a solution of (R)-1-((2-(3'-(5-(tert-butoxycarbonyl)-4,5,6,7-tetrahydrothiazolo[5,4-c]pyridin-2-yl)-2,2'-dimethyl-[1,1'-biphenyl]-3-yl)-7-cyanobenzo[d]oxazol-5-yl)methyl)pyrrolidine-3-carboxylic acid (175 mg, 0.253 mmol) was dissolved in DCM (2 mL) was added TFA (0.5 mL). After 2 h, the reaction mixture was concentrated, and then the crude product was used directly in the next step. LC-MS calculated for $C_{34}H_{32}N_5O_3S$ (M+H)⁺: m/z=590.2; found 590.3.

Step 5: (R)-1-((7-cyano-2-(3'-(5-isopropyl-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid In a 1 dram vial (R)-1-((7-cyano-2-(2,2'-dimethyl-3'-(4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid (50 mg, 0.083 mmol) was dissolved in DCM (500 μl) to give a yellow solution. Acetone (30.6 μl, 0.417 mmol) and DIPEA (29.2 μl, 0.167 mmol) were added to the reaction mixture. After 1 h, sodium triacetoxyborohydride (88 mg, 0.417 mmol) was added to the reaction mixture. After 5 h, the reaction mixture was concentrated. The reaction mixture was diluted with MeOH then purified by prep-HPLC (pH=2, acetonitrile/water+TFA) to give the desired product as the TFA salt. LC-MS calculated for $C_{37}H_{38}N_5O_3S$ (M+H)⁺: m/z=632.2; found 632.3. ¹H NMR (500 MHz, DMSO-d₆) δ 10.42 (br, 1H), 8.38 (d, J=1.3 Hz, 1H), 8.20 (dd, J=7.9, 1.2 Hz, 1H), 8.13 (d, J=1.4 Hz, 1H), 7.70-7.65 (m, 1H), 7.58 (t, J=7.7 Hz, 1H), 7.49-7.43 (m, 2H), 7.35-7.29 (m, 1H), 4.78-4.47 (m, 2H), 4.57 (s, 2H), 3.86-3.08 (m, 10H), 2.44 (s, 3H), 2.29-2.00 (m, 2H), 2.18 (s, 3H), 1.36 (s, 3H), 1.35 (s, 3H).

Example 64

(R)-1-((7-cyano-2-(3'-(5-(cyclopropylmethyl)-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid

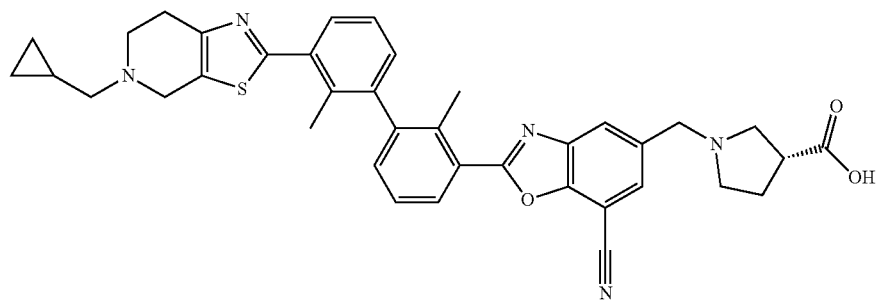 [SMILES: Cc1c(-c2nc3cc(CN4CC[C@@H](C(=O)O)C4)cc(C#N)c3o2)cccc1-c1cccc(-c2nc3c(s2)CN(CC2CC2)CC3)c1C]

This compound was prepared using similar procedures as described for Example 63 with cyclopropanecarbaldehyde replacing acetone in Step 5. The reaction mixture was diluted with MeOH then purified by prep-HPLC (pH=2, acetonitrile/water+TFA) to give the desired product as the TFA salt. LC-MS calculated for $C_{38}H_{38}N_5O_3S$ (M+H)⁺: m/z=644.2; found 644.3.

Example 65

(R)-1-((7-cyano-2-(3'-(5-(2-hydroxyethyl)-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid

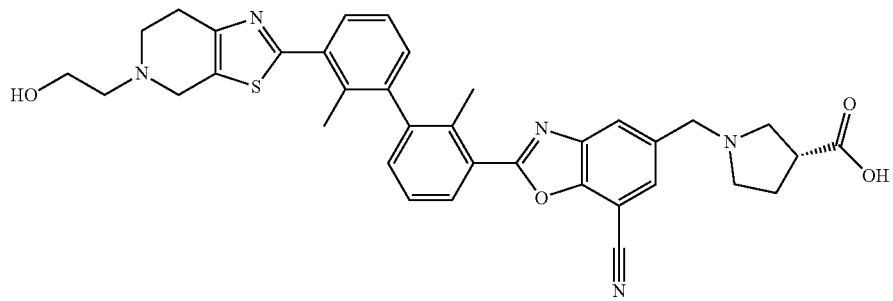 [SMILES: Cc1c(-c2nc3cc(CN4CC[C@@H](C(=O)O)C4)cc(C#N)c3o2)cccc1-c1cccc(-c2nc3c(s2)CN(CCO)CC3)c1C]

Step 1: (R)-1-((2-(3'-(5-(2-((tert-butyldimethylsilyl)oxy)ethyl)-4,5,6,7-tetrahydrothiazolo[5,4-c]pyridin-2-yl)-2,2'-dimethyl-[1,1'-biphenyl]-3-yl)-7-cyanobenzo[d]oxazol-5-yl)methyl)pyrrolidine-3-carboxylic acid

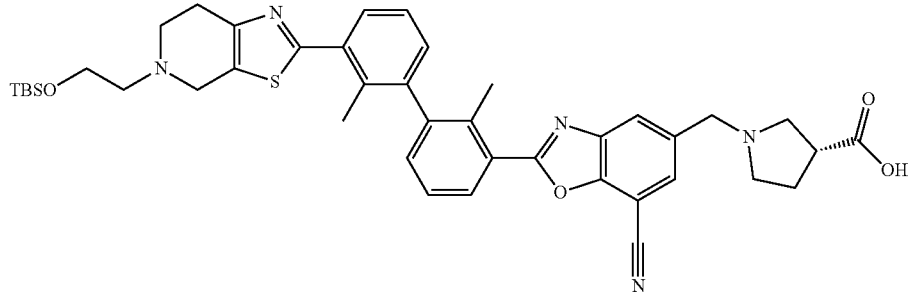 [SMILES: Cc1c(-c2nc3cc(CN4CC[C@@H](C(=O)O)C4)cc(C#N)c3o2)cccc1-c1cccc(-c2nc3c(s2)CN(CCO[Si](C)(C)C(C)(C)C)CC3)c1C]

This compound was prepared using similar procedures as described for Example 63 with (tert-butyldimethylsilyloxy)acetaldehyde (Aldrich, cat #449458) replacing acetone in Step 5. The reaction mixture was concentrated, and then the crude product was used directly in the next step. LC-MS calculated for $C_{42}H_{50}N_5O_4SSi$ (M+H)$^+$: m/z=748.2; found 748.3.

Step 2: (R)-1-((7-cyano-2-(3'-(5-(2-hydroxyethyl)-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid (R)-1-((2-(3'-(5-(2-((tert-butyldimethylsilyl)oxy)ethyl)-4,5,6,7-tetrahydrothiazolo[5,4-c]pyridin-2-yl)-2,2'-dimethyl-[1,1'-biphenyl]-3-yl)-7-cyanobenzo[d]oxazol-5-yl)methyl)pyrrolidine-3-carboxylic acid (20 mg, 0.031 mmol) was dissolved in THF (1 mL), then treated with 1N HCl (0.1 mL). After 2 h, the reaction mixture was diluted with MeOH then purified by prep-HPLC (pH=2, acetonitrile/water+TFA) to give the desired product as the TFA salt. LC-MS calculated for $C_{36}H_{36}N_5O_4S$ (M+H)$^+$: m/z=634.2; found 634.2. $^1$H NMR (500 MHz, DMSO-$d_6$) δ 10.41 (br, 1H), 8.39 (d, J=1.3 Hz, 1H), 8.21-8.18 (m, 1H), 8.12 (d, J=1.4 Hz, 1H), 7.72-7.67 (m, 1H), 7.58 (t, J=7.7 Hz, 1H), 7.51-7.42 (m, 2H), 7.32 (d, J=6.6 Hz, 1H), 4.86-4.45 (m, 2H), 4.57 (s, 2H), 3.83 (t, J=5.2 Hz, 2H), 3.71-3.07 (m, 11H), 2.43 (s, 3H), 2.40-2.00 (m, 5H).

Example 66

(3R)-1-((7-cyano-2-(3'-(5-(1-hydroxypropan-2-yl)-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid

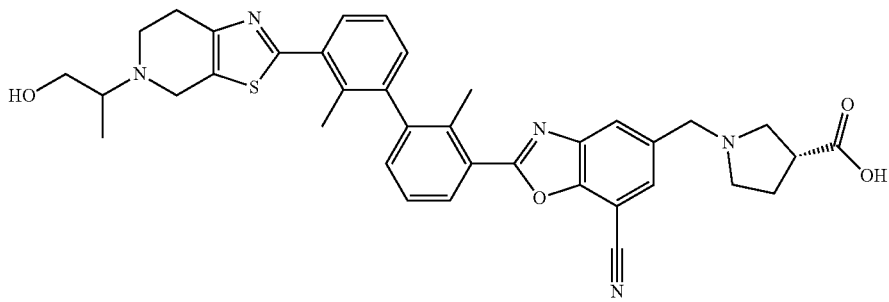 [SMILES: Cc1c(-c2nc3cc(CN4CC[C@@H](C(=O)O)C4)cc(C#N)c3o2)cccc1-c1cccc(-c2nc3c(s2)CN(C(C)CO)CC3)c1C]

Step 1: (3R)-1-((2-(3'-(5-(1-acetoxypropan-2-yl)-4,5,6,7-tetrahydrothiazolo[5,4-c]pyridin-2-yl)-2,2'-dimethyl-[1,1'-biphenyl]-3-yl)-7-cyanobenzo[d]oxazol-5-yl)methyl)pyrrolidine-3-carboxylic acid

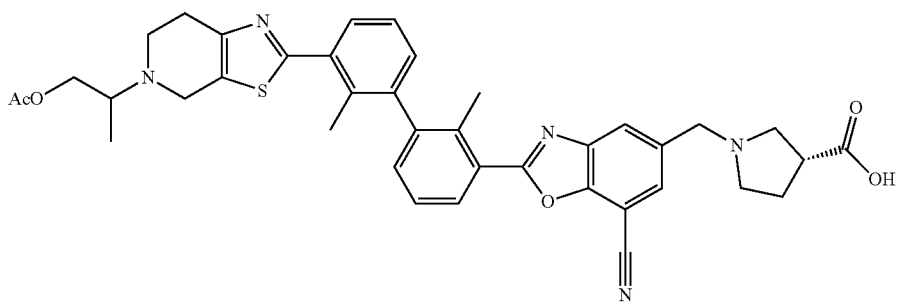 [SMILES: CC(=O)OCC(C)N1CCc2nc(-c3cccc(-c4cccc(-c5nc6cc(CN7CC[C@@H](C(=O)O)C7)cc(C#N)c6o5)c4C)c3C)sc2C1]

This compound was prepared using similar procedures as described for Example 63 with acetoxyacetone (Alfa Aesar, cat # H31346) replacing acetone in Step 5. The reaction mixture was concentrated, and then the crude product was used directly in the next step. LC-MS calculated for $C_{39}H_{40}N_5O_5S$ (M+H)$^+$: m/z=690.2; found 690.3.

Step 2: (3R)-1-((7-cyano-2-(3'-(5-(1-hydroxypropan-2-yl)-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid (3R)-1-((2-(3'-(5-(1-acetoxypropan-2-yl)-4,5,6,7-tetrahydrothiazolo[5,4-c]pyridin-2-yl)-2,2'-dimethyl-[1,1'-biphenyl]-3-yl)-7-cyanobenzo[d]oxazol-5-yl)methyl)pyrrolidine-3-carboxylic acid (20 mg, 0.031 mmol) was dissolved in dioxane (1 mL), then treated with 1N NaOH (0.1 mL). After 2 h, the reaction mixture was diluted with MeOH then purified by prep-HPLC (pH=2, acetonitrile/water+TFA) to give the desired product as the TFA salt. LC-MS calculated for $C_{37}H_{38}N_5O_4S$ (M+H)$^+$: m/z=648.2; found 648.2.

Example 67

(S)-1-((7-cyano-2-(3'-(5-(2-hydroxyethyl)-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid

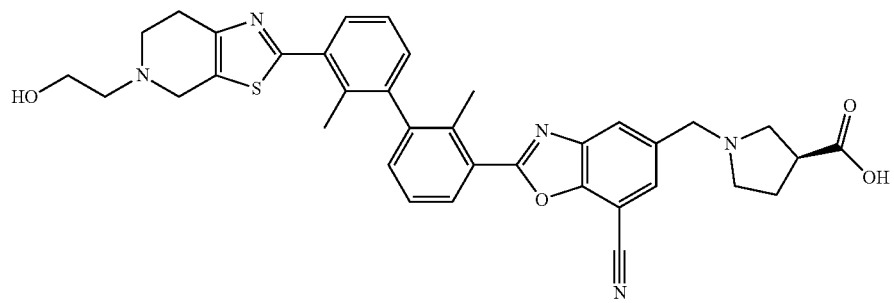 [SMILES: Cc1c(-c2nc3cc(CN4CC[C@H](C(=O)O)C4)cc(C#N)c3o2)cccc1-c1cccc(-c2nc3c(s2)CN(CCO)CC3)c1C]

Step: (S)-1-((2-(3'-(5-(tert-butoxycarbonyl)-4,5,6,7-tetrahydrothiazolo[5,4-c]pyridin-2-yl)-2,2'-dimethyl-[1,1'-biphenyl]-3-yl)-7-cyanobenzo[d]oxazol-5-yl)methyl)pyrrolidine-3-carboxylic acid

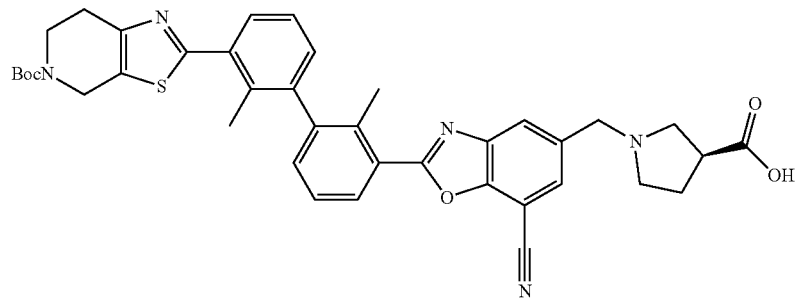 [SMILES: Cc1c(-c2nc3cc(CN4CC[C@H](C(=O)O)C4)cc(C#N)c3o2)cccc1-c1cccc(-c2nc3c(s2)CN(C(=O)OC(C)(C)C)CC3)c1C]

To a solution of tert-butyl 2-(3'-(7-cyano-5-formylbenzo[d]oxazol-2-yl)-2,2'-dimethyl-[1,1'-biphenyl]-3-yl)-6,7-dihydrothiazolo[5,4-c]pyridine-5 (4H)-carboxylate (Example 63, Step 2; 150 mg, 0.253 mmol) and DIPEA (20 uL) in DCM (3 mL) was added (S)-pyrrolidine-3-carboxylic acid (116 mg, 1.01 mmol). After 1 h, sodium triacetoxyborohydride (268 mg, 1.26 mmol) was added to the reaction mixture. After 2 h, saturated NaHCO$_3$(5 mL) was added followed by extraction with dichloromethane (5 mL×4). The combined organic layers were dried Na$_2$SO$_4$, filtered and concentrated. The crude product was used directly in the next step. LC-MS calculated for $C_{39}H_{40}N_5O_5S$ (M+H)$^+$: m/z=690.2; found 690.3.

Step 2: (S)-1-((7-cyano-2-(2,2'-dimethyl-3'-(4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid

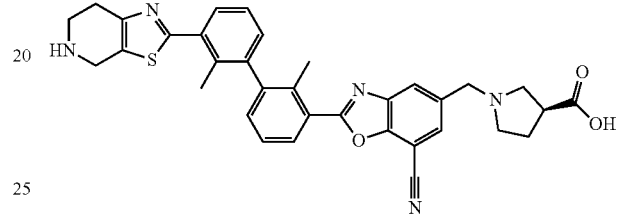

To a solution of (S)-1-((2-(3'-(5-(tert-butoxycarbonyl)-4,5,6,7-tetrahydrothiazolo[5,4-c]pyridin-2-yl)-2,2'-dimethyl-[1,1'-biphenyl]-3-yl)-7-cyanobenzo[d]oxazol-5-yl)methyl)pyrrolidine-3-carboxylic acid (175 mg, 0.253 mmol) was dissolved in DCM (2 mL) was added TFA (0.5 mL). After 2 h, the reaction mixture was concentrated, and then the crude product was used directly in the next step. LC-MS calculated for $C_{34}H_{32}N_5O_3S$ (M+H)$^+$: m/z=590.2; found 590.3.

Step 3: (S)-1-((2-(3'-(5-(2-((tert-butyldimethylsilyl)oxy)ethyl)-4,5,6,7-tetrahydrothiazolo[5,4-c]pyridin-2-yl)-2,2'-dimethyl-[1,1'-biphenyl]-3-yl)-7-cyanobenzo[d]oxazol-5-yl)methyl)pyrrolidine-3-carboxylic acid

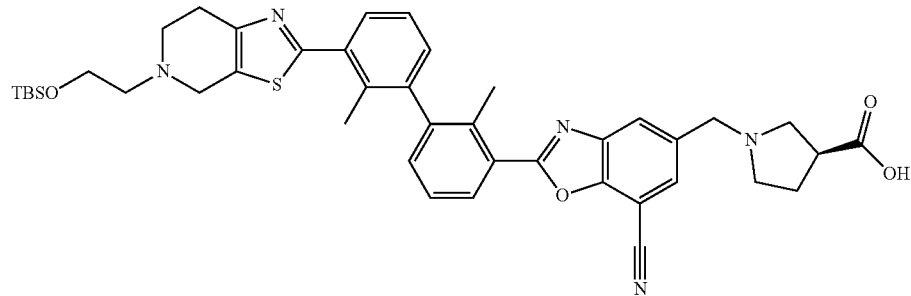 [SMILES: Cc1c(-c2nc3cc(CN4CC[C@H](C(=O)O)C4)cc(C#N)c3o2)cccc1-c1cccc(-c2nc3c(s2)CN(CCO[Si](C)(C)C(C)(C)C)CC3)c1C]

In a 1 dram vial (S)-1-((7-cyano-2-(2,2'-dimethyl-3'-(4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid (50 mg, 0.083 mmol) was dissolved in DCM (417 µl) to give a yellow solution. (tert-Butyldimethylsilyloxy)acetaldehyde (Aldrich, cat #449458: 30.6 µl, 0.417 mmol) and DIPEA (29.2 µl, 0.167 mmol) were added to the reaction mixture. After 1 h, sodium triacetoxyborohydride (88 mg, 0.417 mmol) was added to the reaction mixture. After 5 h, the reaction mixture was concentrated, and then the crude product was used directly in the next step. LC-MS calculated for $C_{42}H_{50}N_5O_4SSi$ (M+H)$^+$: m/z=748.3; found 748.3.

Step 4: (S)-1-((7-cyano-2-(3'-(5-(2-hydroxyethyl)-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid (S)-1-((2-(3'-(5-(2-((tert-butyldimethylsilyl)oxy)ethyl)-4,5,6,7-tetrahydrothiazolo[5,4-c]pyridin-2-yl)-2,2'-dimethyl-[1,1'-biphenyl]-3-yl)-7-cyanobenzo[d]oxazol-5-yl)methyl)pyrrolidine-3-carboxylic acid (20 mg, 0.031 mmol) was dissolved in THF (1 mL), then treated with 1N HCl (0.1 mL). After 2 h, the reaction mixture was diluted with MeOH then purified by prep-HPLC (pH=2, acetonitrile/water+TFA) to give the desired product as the TFA salt. LC-MS calculated for $C_{36}H_{36}N_5O_4S$ (M+H)$^+$: m/z=634.2; found 634.2.

Example 68

1-((7-cyano-2-(3'-(5-(2-hydroxyethyl)-4,5,6,7-tetrahydrothiazolo[5,4-c]pyridin-2-yl)-2,2'-dimethyl-[1,1'-biphenyl]-3-yl)benzo[d]oxazol-5-yl)methyl)azetidine-3-carboxylic acid

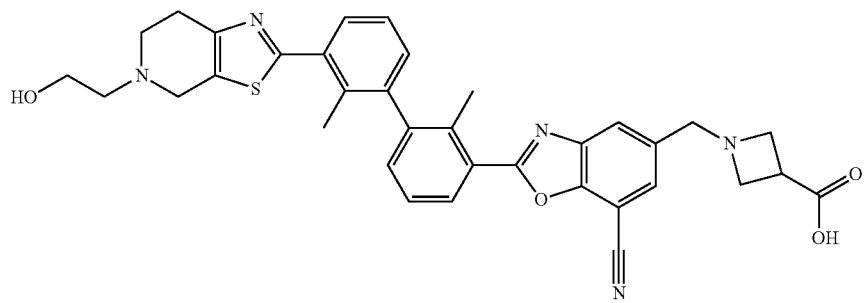 [SMILES: Cc1c(-c2nc3cc(CN4CC(C(=O)O)C4)cc(C#N)c3o2)cccc1-c1cccc(-c2nc3c(s2)CN(CCO)CC3)c1C]

Step 1: 1-((2-(3'-(5-(tert-butoxycarbonyl)-4,5,6,7-tetrahydrothiazolo[5,4-c]pyridin-2-yl)-2,2'-dimethyl-[1,1'-biphenyl]-3-yl)-7-cyanobenzo[d]oxazol-5-yl)methyl)azetidine-3-carboxylic acid

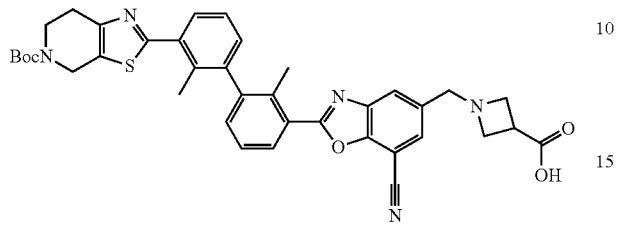

To a solution of tert-butyl 2-(3'-(7-cyano-5-formylbenzo[d]oxazol-2-yl)-2,2'-dimethyl-[1,1'-biphenyl]-3-yl)-6,7-dihydrothiazolo[5,4-c]pyridine-5 (4H)-carboxylate (Example 63, Step 2; 150 mg, 0.253 mmol) and DIPEA (20 uL) in DCM (3 mL) was added azetidine-3-carboxylic acid (116 mg, 1.01 mmol). After 1 h, sodium triacetoxyborohydride (268 mg, 1.26 mmol) was added to the reaction mixture. After 2 h, saturated NaHCO$_3$(5 mL) was added followed by extraction with dichloromethane (5 mL×4). The combined organic layers were dried Na$_2$SO$_4$, filtered and concentrated. The crude product was used directly in the next step. LC-MS calculated for $C_{38}H_{38}N_5O_5S$ (M+H)$^+$: m/z=676.2; found 676.3.

Step 2: 1-((7-cyano-2-(2,2'-dimethyl-3'-(4,5,6,7-tetrahydrothiazolo[5,4-c]pyridin-2-yl)-[1,1'-biphenyl]-3-yl)benzo[d]oxazol-5-yl)methyl)azetidine-3-carboxylic acid

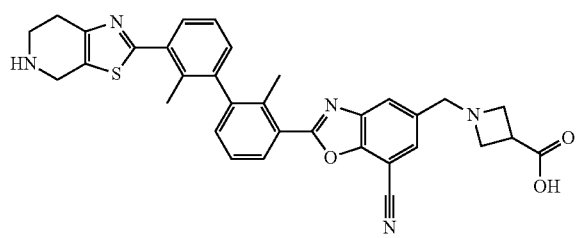 [SMILES: Cc1c(-c2nc3cc(CN4CC(C(=O)O)C4)cc(C#N)c3o2)cccc1-c1cccc(-c2nc3c(s2)CNCC3)c1C]

To a solution of 1-((2-(3'-(5-(tert-butoxycarbonyl)-4,5,6,7-tetrahydrothiazolo[5,4-c]pyridin-2-yl)-2,2'-dimethyl-[1,1'-biphenyl]-3-yl)-7-cyanobenzo[d]oxazol-5-yl)methyl)azetidine-3-carboxylic acid (175 mg, 0.253 mmol) was dissolved in DCM (2 mL) was added TFA (0.5 mL). After 2 h, the reaction mixture was concentrated, and then the crude product was used directly in the next step. LC-MS calculated for $C_{33}H_{30}N_5O_3S$ (M+H)$^+$: m/z=576.2; found 576.3.

Step 3: 1-((2-(3'-(5-(2-((tert-butyldimethylsilyl)oxy)ethyl)-4,5,6,7-tetrahydrothiazolo[5,4-c]pyridin-2-yl)-2,2'-dimethyl-[1,1'-biphenyl]-3-yl)-7-cyanobenzo[d]oxazol-5-yl)methyl)azetidine-3-carboxylic acid

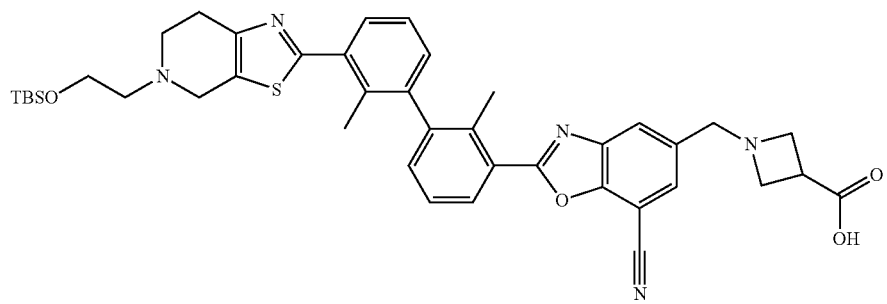 [SMILES: Cc1c(-c2nc3cc(CN4CC(C(=O)O)C4)cc(C#N)c3o2)cccc1-c1cccc(-c2nc3c(s2)CN(CCO[Si](C)(C)C(C)(C)C)CC3)c1C]

In a 1 dram vial 1-((7-cyano-2-(2,2'-dimethyl-3'-(4,5,6,7-tetrahydrothiazolo[5,4-c]pyridin-2-yl)-[1,1'-biphenyl]-3-yl)benzo[d]oxazol-5-yl)methyl)azetidine-3-carboxylic acid (50 mg, 0.083 mmol) was dissolved in DCM (417 µl) to give a yellow solution. (tert-Butyldimethylsilyloxy)acetaldehyde (Aldrich, cat #449458: 30.6 µl, 0.417 mmol) and DIPEA (29.2 µl, 0.167 mmol) were added to the reaction mixture. After 1 h, sodium triacetoxyborohydride (88 mg, 0.417 mmol) was added to the reaction mixture. After 5 h, the reaction mixture was concentrated, and then the crude product was used directly in the next step. LC-MS calculated for $C_{41}H_{48}N_5O_4SSi$ (M+H)$^+$: m/z=734.2; found 734.3.

Step 4: 1-((7-cyano-2-(3'-(5-(2-hydroxyethyl)-4,5,6,7-tetrahydrothiazolo[5,4-c]pyridin-2-yl)-2,2'-dimethyl-[1,1'-biphenyl]-3-yl)benzo[d]oxazol-5-yl)methyl)azetidine-3-carboxylic acid 1-((2-(3'-(5-(2-((tert-butyldimethylsilyl)oxy)ethyl)-4,5,6,7-tetrahydrothiazolo[5,4-c]pyridin-2-yl)-2,2'-dimethyl-[1,1'-biphenyl]-3-yl)-7-cyanobenzo[d]oxazol-5-yl)methyl)azetidine-3-carboxylic acid (20 mg, 0.031 mmol) was dissolved in THF (1 mL), then treated with 1N HCl (0.1 mL). After 2 h, the reaction mixture was diluted with MeOH then purified by prep-HPLC (pH=2, acetonitrile/water+TFA) to give the desired product as the TFA salt. LC-MS calculated for $C_{35}H_{34}N_5O_4S$ (M+H)$^+$: m/z=620.2; found 620.2.

Example 69

(R)-1-((2-(2-chloro-2'-methyl-3'-(4,5,6,7-tetrahydrothiazolo[5,4-c]pyridin-2-yl)-[1,1'-biphenyl]-3-yl)-7-cyanobenzo[d]oxazol-5-yl)methyl)pyrrolidine-3-carboxylic acid

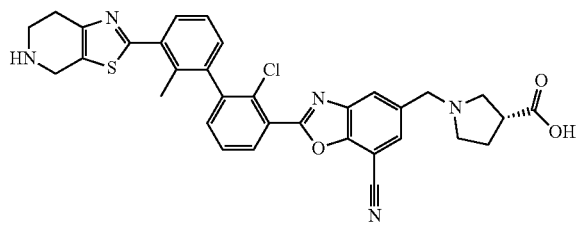

Step 1: 3-bromo-2-chlorobenzaldehyde

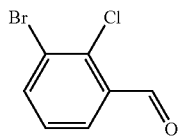

To a solution of (3-bromo-2-chlorophenyl)methanol (AstaTech, cat # CL8936: 2.20 g, 10 mmol) in DCM (50 mL) was added Dess-Martin periodinane (5.02 g, 12 mmol). After 1 h, saturated NaHCO$_3$(50 mL) was added to the reaction mixture followed by extraction with dichloromethane (25 mL×3). The combined organic layers were dried Na$_2$SO$_4$, filtered and concentrated. The crude product was added to a silica gel column and was eluted with 0 to 30% EtOAc/Hexanes to give the desired product (1.76 g, 80%). LC-MS calculated for C$_7$H$_5$BrClO (M+H)$^+$: m/z=220.9; found 221.0.

Step 2: methyl 2-(3-bromo-2-chlorophenyl)-7-chlorobenzo[d]oxazole-5-carboxylate

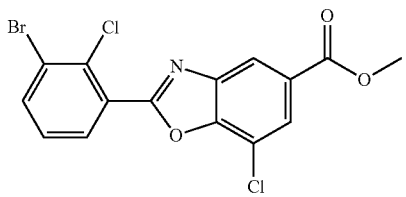 [SMILES: COC(=O)c1cc(Cl)c2oc(-c3cccc(Br)c3Cl)nc2c1]

A mixture of methyl 3-amino-5-chloro-4-hydroxybenzoate (Example 1, Step 2; 1.04 g, 5.16 mmol), 3-bromo-2-chlorobenzaldehyde (0.98 g, 4.92 mmol) in EtOH (25 ml) was placed in a vial and stirred at room temperature for 1 h. The mixture was then concentrated. The residue was redissovled in methylene chloride (25 mL) and dichlorodicyanoquinone (1.12 g, 4.92 mmol) was added. The mixture was stirred at room temperature for 30 min. The reaction was diluted with methylene chloride and washed with an aqueous Na$_2$S$_2$O$_3$ solution and NaHCO$_3$ solution. The organic phase was dried over MgSO$_4$, filtered and the filtrate was concentrated. The crude residue was used directly without further purification. LC-MS calculated for C$_{15}$H$_9$BrCl$_2$NO$_3$ (M+H)$^+$: m/z=401.9; found 401.9.

Step 3: (2-(3-bromo-2-chlorophenyl)-7-chlorobenzo[d]oxazol-5-yl)methanol

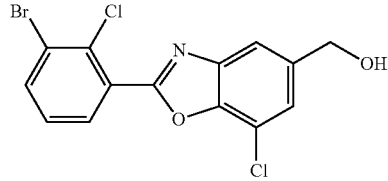 [SMILES: OCc1cc(Cl)c2oc(-c3cccc(Br)c3Cl)nc2c1]

To a solution of methyl 2-(3-bromo-2-chlorophenyl)-7-chlorobenzo[d]oxazole-5-carboxylate (0.030 g, 0.075 mmol) in THF (0.5 mL) was added DIBAL-H (0.187 ml, 0.187 mmol) at 0° C. After 1 h, saturated Rochelle's salt (2 mL) was added to the reaction mixture followed by extraction with ethyl acetate (5 mL×3). The combined organic layers were dried Na$_2$SO$_4$, filtered and concentrated. The organic layers were combined, dried over Na$_2$SO$_4$, concentrated, and purified by flash chromatography on a silica gel column eluting with 0 to 60% EtOAc/hexanes to give the desired product as a yellow solid. LC-MS calculated for C$_{14}$H$_9$BrCl$_2$NO$_2$ (M+H)$^+$: m/z=373.9; found 374.0.

Step 4: tert-butyl 2-(3-chloro-2-methylphenyl)-6,7-dihydro[1,3]thiazolo[5,4-c]pyridine-5(4H)-carboxylate

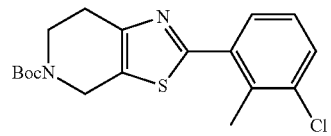 [SMILES: Cc1c(Cl)cccc1-c1nc2c(s1)CN(C(=O)OC(C)(C)C)CC2]

To a solution of (3-chloro-2-methylphenyl)boronic acid (Combi-blocks, cat # BB-2035: 64 mg, 0.38 mmol), tert-butyl 2-bromo-6,7-dihydro[1,3]thiazolo[5,4-c]pyridine-5(4H)-carboxylate (AstaTech, cat # AB1021: 100 mg, 0.31 mmol) and sodium carbonate (100 mg, 0.94 mmol) in tert-butyl alcohol (3.2 mL) and water (2 mL) was added Pd-127 (47 mg, 0.063 mmol). The resulting mixture was purged with N$_2$, then heated at 105° C. for 2 h. The reaction mixture was diluted with methylene chloride, washed with sat'd NaHCO$_3$, water and brine. The organic layer was dried over Na$_2$SO$_4$, filtered and concentrated. The residue was purified by flash chromatography on a silica gel column eluting with 0 to 40% ethyl acetate in hexanes to give the desired product (114 mg, 83%). LC-MS calculated for C$_{18}$H$_{22}$ClN$_2$O$_2$S (M+H)$^+$: m/z=365.1; found 365.2.

Step 5: tert-butyl 2-[2-methyl-3-(4,4,5,5-tetramethyl-1,3,2-dioxaborolan-2-yl)phenyl]-6,7-dihydro[1,3]thiazolo[5,4-c]pyridine-5(4H)-carboxylate

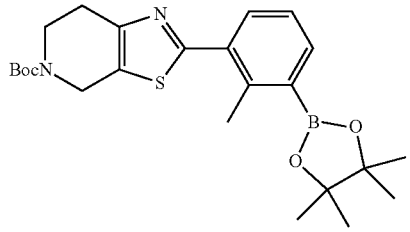 [SMILES: Cc1c(B2OC(C)(C)C(C)(C)O2)cccc1-c1nc2c(s1)CN(C(=O)OC(C)(C)C)CC2]

A mixture of tert-butyl 2-(3-chloro-2-methylphenyl)-6,7-dihydro[1,3]thiazolo[5,4-c]pyridine-5(4H)-carboxylate (95 mg, 0.26 mmol), 4,4,5,5,4',4',5',5'-octamethyl-[2,2']bi[[1,3,2]dioxaborolanyl] (200 mg, 0.78 mmol), palladium acetate (2.5 mg, 0.014 mmol), $K_3PO_4$ (170 mg, 0.78 mmol) and 2-(dicyclohexylphosphino)-2',6'-dimethoxy-1,1'-biphenyl (11 mg, 0.026 mmol) in 1,4-dioxane (1 mL) was degassed and stirred at r.t. for 3 d. The reaction mixture was diluted with methylene chloride, washed with sat'd $NaHCO_3$, water and brine. The organic layer was dried over $Na_2SO_4$, filtered and concentrated. The residue was purified by flash chromatography on a silica gel column eluting with 0 to 5% ethyl acetate in methylene chloride to give the desired product (108 mg, 90%). LC-MS calculated for $C_{24}H_{34}BN_2O_4S$ $(M+H)^+$: m/z=457.2; found 457.2.

Step 6: tert-butyl 2-(2'-chloro-3'-(7-chloro-5-(hydroxymethyl)benzo[d]oxazol-2-yl)-2-methyl-[1,1'-biphenyl]-3-yl)-6,7-dihydrothiazolo[5,4-c]pyridine-5(4H)-carboxylate

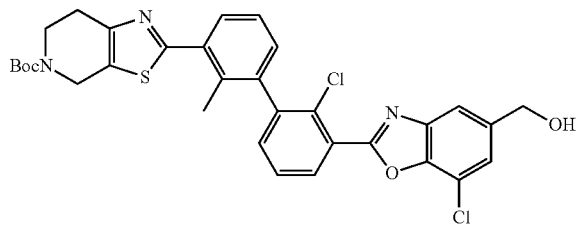 [SMILES: Cc1c(-c2nc3c(s2)CN(C(=O)OC(C)(C)C)CC3)cccc1-c1cccc(-c2nc3cc(CO)cc(Cl)c3o2)c1Cl]

In a nitrogen flushed 4 dram vial tert-butyl 2-(2-methyl-3-(4,4,5,5-tetramethyl-1,3,2-dioxaborolan-2-yl)phenyl)-6,7-dihydrothiazolo[5,4-c]pyridine-5(4H)-carboxylate (28 mg, 0.037 mmol) and (2-(3-bromo-2-chlorophenyl)-7-chlorobenzo[d]oxazol-5-yl)methanol (14 mg, 0.037 mmol) were dissolved in tBuOH (500 μl) and water (200 μl) to give a yellow solution. $Na_2CO_3$ (10 mg, 0.092 mmol) and Pd-127 (3 mg, 3.69 μmol) were added to the reaction mixture in one portion. The reaction mixture was heated to 90° C. After 1 h, the reaction mixture was cooled to r.t. Saturated $NaHCO_3$ (volume) was added to the reaction mixture followed by extraction with ethyl acetate (5 mL×3). The combined organic layers were dried over $Na_2SO_4$, filtered and concentrated. The crude product was used without further purification. LC-MS calculated for $C_{32}H_{30}Cl_2N_3O_4S$ $(M+H)^+$: m/z=622.1; found 622.1.

Step 7: tert-butyl 2-(2'-chloro-3'-(7-chloro-5-formylbenzo[d]oxazol-2-yl)-2-methyl-[1,1'-biphenyl]-3-yl)-6,7-dihydrothiazolo[5,4-c]pyridine-5(4H)-carboxylate

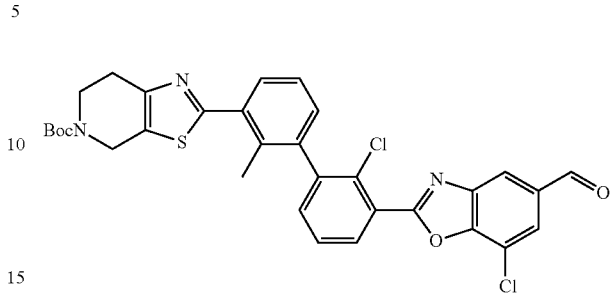

To a solution of tert-butyl 2-(2'-chloro-3'-(7-chloro-5-(hydroxymethyl)benzo[d]oxazol-2-yl)-2-methyl-[1,1'-biphenyl]-3-yl)-6,7-dihydrothiazolo[5,4-c]pyridine-5(4H)-carboxylate (23 mg, 0.037 mmol) in DCM (3 mL) was added Dess-Martin periodinane (23 mg, 0.055 mmol). After 1 h, saturated $NaHCO_3$(5 mL) was added to the reaction mixture followed by extraction with dichloromethane (5 mL×3). The combined organic layers were dried $Na_2SO_4$, filtered and concentrated. The crude product was added to a silica gel column and was eluted with ethyl acetate/hexane from 0% to 30% to give tert-butyl 2-(3'-(7-chloro-5-formylbenzo[d]oxazol-2-yl)-2,2'-dimethyl-[1,1'-biphenyl]-3-yl)-6,7-dihydrothiazolo[5,4-c]pyridine-5(4H)-carboxylate (14 mg, 0.024 mmol, 64.7% yield). LC-MS calculated for $C_{32}H_{28}Cl_2N_3O_4S$ $(M+H)^+$: m/z=620.2; found 620.1.

Step 8: (R)-1-((7-chloro-2-(2-chloro-2'-methyl-3'-(4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid

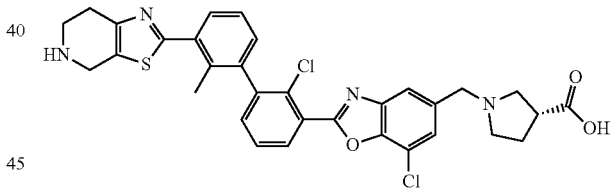

To a solution of tert-butyl 2-(2'-chloro-3'-(7-chloro-5-formylbenzo[d]oxazol-2-yl)-2-methyl-[1,1'-biphenyl]-3-yl)-6,7-dihydrothiazolo[5,4-c]pyridine-5(4H)-carboxylate (70 mg, 0.117 mmol) in DMF (1.2 mL) was added (R)-pyrrolidine-3-carboxylic acid (40.2 mg, 0.350 mmol). After 1 h, sodium cyanoborohydride (15 mg, 0.233 mmol) was added to the reaction mixture. After 2 h, the reaction mixture was diluted with DCM (1 mL) and treated with TFA (0.5 mL). After 2 h, the reaction mixture was diluted with MeOH then purified by prep-HPLC (pH=2, acetonitrile/water+TFA) to give the desired product as the TFA salt. LC-MS calculated for $C_{32}H_{29}Cl_2N_4O_3S$ $(M+H)^+$: m/z=619.2; found 619.3.

Step 9: (R)-1-((2-(2-chloro-2'-methyl-3'-(4,5,6,7-tetrahydrothiazolo[5,4-c]pyridin-2-yl)-[1,1'-biphenyl]-3-yl)-7-cyanobenzo[d]oxazol-5-ylmethyl)pyrrolidine-3-carboxylic acid In a 1 dram vial (R)-1-((7-chloro-2-(2-chloro-2'-methyl-3'-(4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid (5 mg, 8.07 µmol) and potassium ferrocyanide(II) hydrate (2.211 µl, 9.68 µmol) were dissolved in 1,4-dioxane (500 µl) and water (200 µl). Potassium acetate (8 mg, 50 µmol) and tBuXPhos Pd G3 (1.2 mg, 1.6 µmol) were added to the reaction mixture. The reaction mixture was heated to 100° C. After 2 h, the reaction mixture was diluted with MeOH then purified by prep-HPLC (pH=2, acetonitrile/water+TFA) to give the desired product as the TFA salt. LC-MS calculated for $C_{33}H_{29}ClN_5O_3S$ (M+H)$^+$: m/z=610.2; found 610.3.

Example 70

(R)-1-((7-chloro-2-(2,2'-dimethyl-3'-(4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid

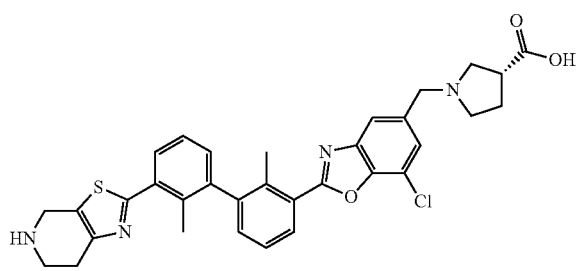 [SMILES: Cc1c(-c2nc3cc(CN4CC[C@@H](C(=O)O)C4)cc(Cl)c3o2)cccc1-c1cccc(-c2nc3c(s2)CNCC3)c1C]

Step 1: tert-butyl 2-(3'-(7-chloro-5-formylbenzo[d]oxazol-2-yl)-2,2'-dimethyl-[1,1'-biphenyl]-3-yl)-6,7-dihydrothiazolo[5,4-c]pyridine-5(4H)-carboxylate

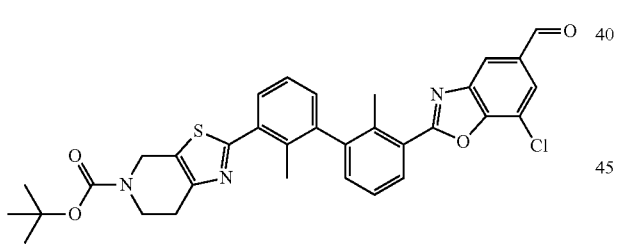

To a microwave vial was added tert-butyl 2-(2-methyl-3-(4,4,5,5-tetramethyl-1,3,2-dioxaborolan-2-yl)phenyl)-6,7-dihydrothiazolo[5,4-c]pyridine-5(4H)-carboxylate (Example 69, Step 5: 50 mg, 0.110 mmol), 2-(3-bromo-2-methylphenyl)-7-chlorobenzo[d]oxazole-5-carbaldehyde (Example 10, Step 1; 38.4 mg, 0.110 mmol), (1,1'-bis(diphenylphosphino)ferrocene)-dichloropalladium(II) (8.02 mg, 10.96 µmol), sodium carbonate (23.22 mg, 0.219 mmol), 1,4-dioxane (5.0 ml) and water (1.0 ml). The mixture was purged with $N_2$ and heated at 90° C. for 2 h. The reaction mixture was cooled to room temperature and then diluted with EtOAc and water. The aqueous phase was extracted with EtOAc. The organic phase was dried over MgSO$_4$, filtered and the filtrate was concentrated under reduced pressure. The crude material was purified by flash chromatography (eluting with EtOAc/Hexanes, 0-100%) to give the desired product (43 mg, 65%). LC-MS calculated for $C_{33}H_{31}ClN_3O_4S$ (M+H)$^+$: m/z=600.2; found 600.2.

Step 2: (R)-1-((7-chloro-2-(2,2'-dimethyl-3'-(4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid To a mixture of tert-butyl 2-(3'-(7-chloro-5-formylbenzo[d]oxazol-2-yl)-2,2'-dimethyl-[1,1'-biphenyl]-3-yl)-3a,6,7,7a-tetrahydrothiazolo[5,4-c]pyridine-5(4H)-carboxylate (22 mg, 0.037 mmol) (R)-pyrrolidine-3-carboxylic acid (4.2 mg, 0.037 mmol) in DCM (1.0 ml) was added sodium triacetoxyborohydride (7.7 mg, 0.037 mmol) at room temperature. After stirring at room temperature overnight, the reaction mixture was diluted with MeOH and then purified by prep-HPLC (pH=2, acetonitrile/water+TFA). After removing solvent, the residue was treated with 1:1 TFA/DCM (2 mL) for 1 h. The solvent was removed in vacuo. The residue was purified with prep LCMS (pH 2, acetonitrile/water+TFA) to give the desired product as TFA salt. LC-MS calculated for $C_{33}H_{32}ClN_4O_3S$ (M+H)$^+$: m/z=599.2; found 599.2. $^1$H NMR (500 MHz, DMSO) δ 8.14 (m, 1H), 7.73 (d, J=1.0 Hz, 1H), 7.65 (m, 1H), 7.58-7.48 (m, 2H), 7.42 (t, J=7.6 Hz, 2H), 7.30-7.24 (m, 1H), 3.97 (s, 2H), 3.72 (m, 2H), 3.04 (m, 2H), 2.95 (m, 1H), 2.79-2.62 (m, 4H), 2.60-2.48 (m, 2H), 2.43 (s, 3H), 2.19 (s, 3H), 1.98 (m, 2H).

Example 71

(R)-1-((7-chloro-2-(2,2'-dimethyl-3'-(5-methyl-4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid

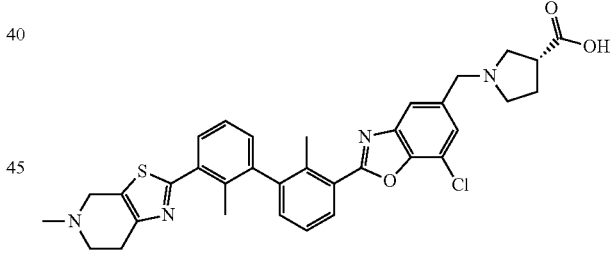

To a mixture of (R)-1-((7-chloro-2-(2,2'-dimethyl-3'-(4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid (Example 70; 20 mg, 0.033 mmol), paraformaldehyde (5.0 mg, 0.167 mmol) in $CH_2Cl_2$ (1.0 ml) was added sodium triacetoxyborohydride (14.1 mg, 0.067 mmol) and resultant mixture was stirred overnight. After removing solvent in vacuo, the mixture was diluted with MeOH and then purified by prep-HPLC (pH=2, acetonitrile/water+TFA) to give the desired product as TFA salt. LC-MS calculated for $C_{34}H_{34}ClN_4O_3S$ (M+H)$^+$: m/z=613.2; found 613.2. $^1$H NMR (500 MHz, DMSO) δ 8.18 (d, J=6.9 Hz, 1H), 8.03 (s, 1H), 7.79 (s, 1H), 7.71 (d, J=6.7 Hz, 1H), 7.58 (m, 1H), 7.47 (m, 2H), 7.33 (d, J=6.7 Hz, 1H), 4.52 (m, 4H), 3.64-3.20 (m, 8H), 3.17 (m, 1H), 2.99 (s, 3H), 2.42 (s, 3H), 2.38-2.05 (m, 2H), 2.21 (s, 3H).

Example 72

(R)-1-((7-cyano-2-(2,2'-dimethyl-3'-(4,5,6,7-tetrahydrothiazolo[5,4-c]pyridin-2-yl)biphenyl-3-yl)benzo[d]oxazol-5-yl)methyl)pyrrolidine-3-carboxylic acid

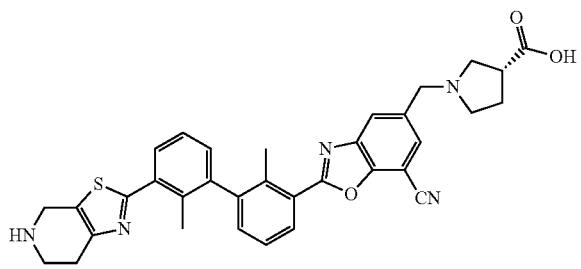

To a mixture of tert-butyl 2-(3'-(7-cyano-5-formylbenzo[d]oxazol-2-yl)-2,2'-dimethyl-[1,1'-biphenyl]-3-yl)-3a,6,7,7a-tetrahydrothiazolo[5,4-c]pyridine-5(4H)-carboxylate (Example 63, Step 2: 55 mg, 0.093 mmol), (R)-pyrrolidine-3-carboxylic acid (16.0 mg, 0.139 mmol) in $CH_2Cl_2$ (1.0 ml) was added sodium triacetoxyborohydride (19.7 mg, 0.093 mmol). After stirring at room temperature overnight, the reaction mixture was diluted with MeOH and then purified by prep-HPLC (pH=2, acetonitrile/water+TFA). After removing solvent, the residue was treated with 1:1 TFA/DCM (2 mL) for 1 h. The solvent was removed in vacuo. The residue was purified by prep LCMS (pH 2, acetonitrile/water+TFA) to give the desired product as TFA salt. LC-MS calculated for $C_{34}H_{32}N_5O_3S$ $(M+H)^+$: m/z=590.2; found 590.2. $^1$H NMR (600 MHz, DMSO) δ 8.42-8.39 (m, 1H), 8.24-8.19 (m, 1H), 8.14 (d, J=1.4 Hz, 1H), 7.76-7.67 (m, 1H), 7.64-7.56 (m, 1H), 7.51-7.44 (m, 2H), 7.33 (d, J=6.7 Hz, 1H), 4.64-4.53 (m, 4H), 3.66 (m, 2H), 3.55 (m, 2H), 3.51-3.44 (m, 3H), 3.27-3.21 (m, 2H), 3.10 (m, 2H), 2.45 (s, 3H), 2.20 (s, 3H).

Example 73

(R)-1-((7-cyano-2-(2,2'-dimethyl-3'-(5-methyl-4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid

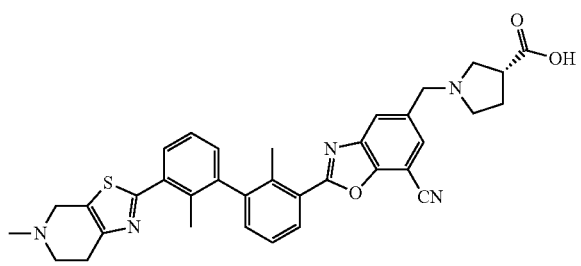 [SMILES: Cc1c(-c2nc3cc(CN4CC[C@@H](C(=O)O)C4)cc(C#N)c3o2)cccc1-c1cccc(-c2nc3c(s2)CN(C)CC3)c1C]

To a microwave vial was added (R)-1-((7-chloro-2-(2,2'-dimethyl-3'-(5-methyl-4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid (Example 71; 19 mg, 0.031 mmol), potassium ferrocyanide(II) hydrate (8.49 µl, 0.037 mmol), [(2-di-tert-butylphosphino-2',4',6'-triisopropyl-1,1'-biphenyl)-2-(2'-amino-1,1'-biphenyl)]palladium(II) methanesulfonate (2.462 mg, 3.10 µmol), potassium acetate (3.04 mg, 0.031 mmol), 1,4-dioxane (155 µl) and water (155 µl) The vial was capped and sparged with nitrogen. The reaction was heated to 100° C. for 3 hours. After cooling to room temperature, the reaction mixture was diluted with ethyl acetate and water, the aqueous phase was extracted with EtOAc. The organic phase was dried over $MgSO_4$, filtered and the filtrate was concentrated under reduced pressure. The crude material was purified by prep LCMS (pH 2, acetonitrile/water+TFA) to give the desired product as TFA salt. LC-MS calculated for $C_{35}H_{34}N_5O_3S$ $(M+H)^+$: m/z=604.2; found 604.2. $^1$H NMR (600 MHz, DMSO) δ 8.40 (d, J=1.3 Hz, 1H), 8.21 (m, 1H), 8.14 (d, J=1.4 Hz, 1H), 7.71 (m, 1H), 7.60 (m, 1H), 7.51-7.45 (m, 2H), 7.34 (m, 1H), 4.81-4.50 (m, 4H), 3.79-3.21 (m, 7H), 3.18 (m, 2H), 3.01 (s, 3H), 2.45 (s, 3H), 2.33-2.09 (m, 2H), 2.21 (s, 3H).

Example 74

(R)-1-((7-chloro-2-(2,2'-dimethyl-3'-(4,5,6,7-tetrahydrooxazolo[4,5-c]pyridin-2-yl)-[1,1'-biphenyl]-3-yl)benzo[d]oxazol-5-yl)methyl)pyrrolidine-3-carboxylic acid

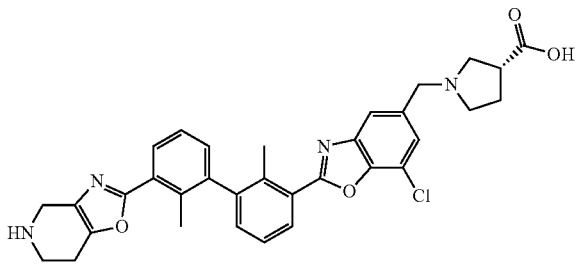

Step 1: Benzyl (3R,4R)-3-(3-bromo-2-methylbenzamido)-4-hydroxypiperidine-1-carboxylate

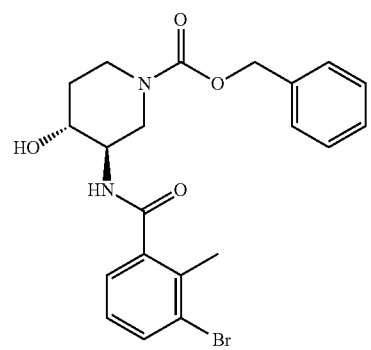 [SMILES: Cc1c(Br)cccc1C(=O)N[C@@H]1CN(C(=O)OCc2ccccc2)CC[C@H]1O]

A solution of 3-bromo-2-methylbenzoic acid (1.30 g, 6.05 mmol) and benzyl (3R,4R)-3-amino-4-hydroxypiperidine-1-carboxylate (1.513 g, 6.05 mmol) in DMF (30.2 ml) was added N,N, N,N'-tetramethyl-O-(7-azabenzotriazol-1-yl)uronium hexafluorophosphate (3.17 g, 8.34 mmol) and N,N-diisopropylethylamine (3.16 ml, 18.14 mmol). The reaction mixture was stirred at room temperature for 2 h. The reaction was diluted with DCM and water, the aqueous layer was extracted with DCM once. The combined organic layers were dried over Na$_2$SO$_4$, filtered and concentrated. The residue was purified with flash chromatography (eluting with 0-10% ethyl acetate/hexanes) to give the desired product (2.70 g, 100%). LC-MS calculated for C$_{21}$H$_{24}$BrN$_2$O$_4$ (M+H)$^+$: m/z=447.1; found 447.1.

Step 2: benzyl (R)-3-(3-bromo-2-methylbenzamido)-4-oxopiperidine-1-carboxylate

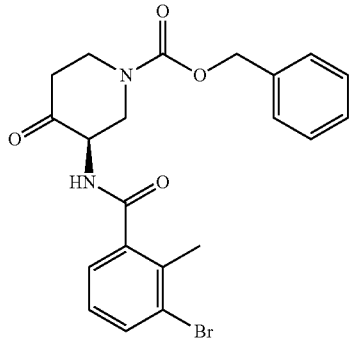 [SMILES: Cc1c(Br)cccc1C(=O)N[C@@H]1CN(C(=O)OCc2ccccc2)CCC1=O]

To a solution of benzyl (3R,4R)-3-(3-bromo-2-methylbenzamido)-4-hydroxypiperidine-1-carboxylate (2.70 g, 6.04 mmol) in DCM (20 ml) was added Dess-Martin periodinane (3.07 g, 7.24 mmol). The resulting mixture was stirred at room temperature for 2 h. The reaction mixture was diluted with Et$_2$O and 1 M NaOH. After stirring for 1 h, The organic layer was separated and dried over Na$_2$SO$_4$, filtered and concentrated. The crude was purified by flash chromatography (eluting with 0-10% ethyl acetate/hexanes) to give the desired product (1.84 g, 70%). LC-MS calculated for C$_{21}$H$_{22}$BrN$_2$O$_4$ (M+H)$^+$: m/z=445.1; found 445.1.

Step 3: benzyl 2-(3-bromo-2-methylphenyl)-6,7-dihydrooxazolo[4,5-c]pyridine-5(4H)-carboxylate

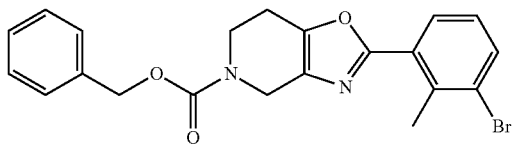 [SMILES: Cc1c(Br)cccc1-c1nc2c(o1)CCN(C(=O)OCc1ccccc1)C2]

To a solution of benzyl (R)-3-(3-bromo-2-methylbenzamido)-4-oxopiperidine-1-carboxylate (1.87 g, 4.20 mmol) in 1,4-dioxane (30 ml) was added POCl$_3$ (0.391 ml, 4.20 mmol). The resulting mixture was stirred at 110° C. for 3 h. After cooling to room temperature, the reaction mixture was diluted with saturated NaHCO$_3$ and ethyl acetate. The aqueous layer was extracted with ethyl acetate once. The combined organic layers were washed with brine, dried over Na$_2$SO$_4$, filtered and concentrated. The crude was purified by flash chromatography (eluting with 0-40% ethyl acetate/hexane) to give the desired product (1.22 g, 68%). LC-MS calculated for C$_{21}$H$_{20}$BrN$_2$O$_3$(M+H)$^+$: m/z=427.1; found 427.1.

Step 4: 2-(3-bromo-2-methylphenyl)-4,5,6,7-tetrahydrooxazolo[4,5-c]pyridine

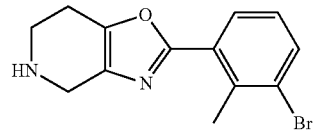 [SMILES: Cc1c(Br)cccc1-c1nc2c(o1)CCNC2]

To solution of benzyl 2-(3-bromo-2-methylphenyl)-6,7-dihydrooxazolo[4,5-c]pyridine-5(4H)-carboxylate (1.15 g, 2.69 mmol) in CH$_2$Cl$_2$ (10 ml) was added 1 M BBr$_3$ in DCM (5.38 ml, 5.38 mmol) at 0° C. After stirring at same temperature for 1 h, the reaction mixture was diluted DCM and saturated NaHCO$_3$ solution. The resultant precipitate was collected vial filtration and dried under vacuum to give the desired product as white solid (0.61 g, 77%). LC-MS calculated for C$_{13}$H$_{14}$BrN$_2$O (M+H)$^+$: m/z=293.0; found 293.0.

Step 5. (7-chloro-2-(2,2'-dimethyl-3'-(4,5,6,7-tetrahydrooxazolo[4,5-c]pyridin-2-yl)-[1,1'-biphenyl]-3-yl)benzo[d]oxazol-5-yl)methanol

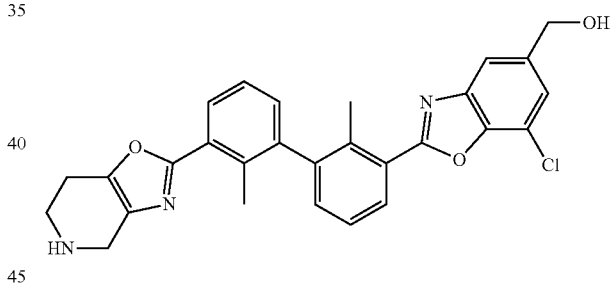

(1,1'-Bis(diphenylphosphino)ferrocene)-dichloropalladium(II) (127 mg, 0.174 mmol) was added to a mixture of 2-(3-bromo-2-methylphenyl)-4,5,6,7-tetrahydrooxazolo[4,5-c]pyridine (511 mg, 1.741 mmol), (7-chloro-2-(2-methyl-3-(4,4,5,5-tetramethyl-1,3,2-dioxaborolan-2-yl)phenyl)benzo[d]oxazol-5-yl)methanol (Example 1, Step 5; 696 mg, 1.741 mmol), sodium carbonate (369 mg, 3.48 mmol) in 1,4-dioxane (8.0 ml) and water (1.6 ml). The mixture was purged with N$_2$ and heated at 90° C. for 2 h. The mixture was diluted with ethyl acetate and water. The organic layer was separated and dried over Na$_2$SO$_4$, filtered and concentrated. The residue was purified by flash chromatography (eluting with 0-20% methanol in DCM) to give the desired product (0.72 g, 85%). LC-MS calculated for C$_{28}$H$_{25}$ClN$_3$O$_3$(M+H)$^+$: m/z=486.2; found 486.2.

Step 6. tert-butyl 2-(3'-(7-chloro-5-(hydroxymethyl) benzo[d]oxazol-2-yl)-2,2'-dimethyl-[1,1'-biphenyl]-3-yl)-6,7-dihydrooxazolo[4,5-c]pyridine-5(4H)-carboxylate

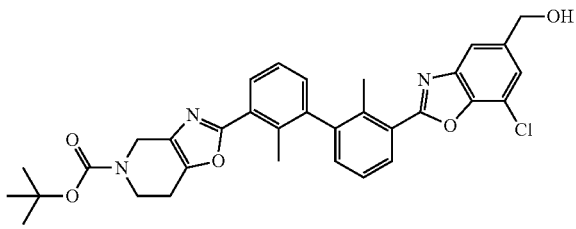 [SMILES: Cc1c(-c2nc3c(o2)CCN(C(=O)OC(C)(C)C)C3)cccc1-c1cccc(-c2nc3cc(CO)cc(Cl)c3o2)c1C]

To a solution of (7-chloro-2-(2,2'-dimethyl-3'-(4,5,6,7-tetrahydrooxazolo[4,5-c]pyridin-2-yl)-[1,1'-biphenyl]-3-yl)benzo[d]oxazol-5-yl)methanol (720 mg, 1.482 mmol) in methanol (10 ml) was added Boc-anhydride (0.344 ml, 1.482 mmol). The resulting mixture was stirred at rt for 2 h. The solvent was removed and residue was purified by flash chromatography (eluting with 0-60% ethyl acetate in hexanes) to give the desired product (0.71 g, 82%). LC-MS calculated for $C_{33}H_{33}ClN_3O_5(M+H)^+$: m/z=586.2; found 586.2.

Step 7. tert-butyl 2-(3'-(7-chloro-5-formylbenzo[d]oxazol-2-yl)-2,2'-dimethyl-[1,1'-biphenyl]-3-yl)-6,7-dihydrooxazolo[4,5-c]pyridine-5(4H)-carboxylate

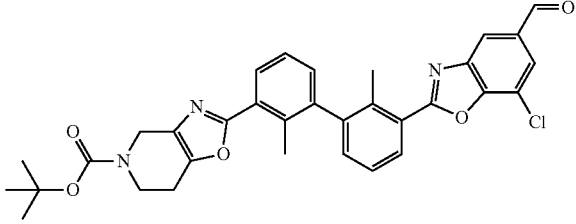

To a solution of tert-butyl 2-(3'-(7-chloro-5-(hydroxymethyl)benzo[d]oxazol-2-yl)-2,2'-dimethyl-[1,1'-biphenyl]-3-yl)-6,7-dihydrooxazolo[4,5-c]pyridine-5(4H)-carboxylate (710 mg, 1.211 mmol) in DCM (10 ml) was added Dess-Martin periodinane (617 mg, 1.454 mmol). The resulting mixture was stirred at rt for 2 h. The reaction mixture was diluted with $Et_2O$ and 1 M NaOH. After stirring for 1 h, the organic layer was separated and dried over $Na_2SO_4$, filtered and concentrated. The residue was purified by flash chromatography (eluting with 0-60% ethyl acetate in hexanes) to give the desired product (0.70 g, 99%). LC-MS calculated for $C_{33}H_{31}ClN_3O_5(M+H)^+$: m/z=584.2; found 584.2.

Step 8: (R)-1-((7-chloro-2-(2,2'-dimethyl-3'-(4,5,6,7-tetrahydrooxazolo[4,5-c]pyridin-2-yl)-[1,1'-biphenyl]-3-yl)benzo[d]oxazol-5-yl)methyl)pyrrolidine-3-carboxylic acid To a mixture of tert-butyl 2-(3'-(7-chloro-5-formylbenzo[d]oxazol-2-yl)-2,2'-dimethyl-[1,1'-biphenyl]-3-yl)-6,7-dihydrooxazolo[4,5-c]pyridine-5(4H)-carboxylate (360 mg, 0.616 mmol), (R)-pyrrolidine-3-carboxylic acid (71.0 mg, 0.616 mmol) and triethylamine (0.172 ml, 1.233 mmol) in $CH_2Cl_2$ (5.0 ml) was added sodium triacetoxyborohydride (131 mg, 0.616 mmol). After stirring at room temperature overnight, the reaction mixture was diluted with MeOH and then purified by prep-HPLC (pH=2, acetonitrile/water+TFA). After removing solvent, the residue was treated with 1:1 TFA/DCM (4 mL) for 1 h. The solvent was removed in vacuo. The residue was purified by prep LCMS (pH 2, acetonitrile/water+TFA) to give the desired product as TFA salt. LC-MS calculated for $C_{33}H_{32}ClN_4O_4(M+H)^+$: m/z=583.2; found 583.2. $^1$H NMR (500 MHz, DMSO) δ 8.18 (m, 1H), 8.03 (d, J=1.2 Hz, 1H), 7.95 (m, 1H), 7.79 (d, J=1.3 Hz, 1H), 7.58 (m, 1H), 7.54-7.43 (m, 2H), 7.36 (m, 1H), 4.55 (s, 2H), 4.48 (s, 2H), 3.66-3.15 (m, 7H), 2.90 (m, 2H), 2.42 (s, 3H), 2.33 (s, 3H), 2.20 (m, 2H).

Example 75

(R)-1-((7-cyano-2-(2,2'-dimethyl-3'-(4,5,6,7-tetrahydrooxazolo[4,5-c]pyridin-2-yl)-[1,1'-biphenyl]-3-yl)benzo[d]oxazol-5-yl)methyl)pyrrolidine-3-carboxylic acid

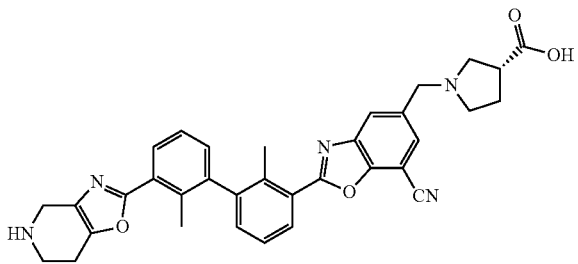 [SMILES: Cc1c(-c2nc3c(o2)CCNC3)cccc1-c1cccc(-c2nc3cc(CN4CC[C@@H](C(=O)O)C4)cc(C#N)c3o2)c1C]

In a microwave vial was combined (R)-1-((2-(3'-(5-(tert-butoxycarbonyl)-4,5,6,7-tetrahydrooxazolo[4,5-c]pyridin-2-yl)-2,2'-dimethyl-[1,1'-biphenyl]-3-yl)-7-chlorobenzo[d]oxazol-5-yl)methyl)pyrrolidine-3-carboxylic acid (Example 74; 6.0 mg, 8.78 mol), potassium ferrocyanide(II) hydrate (2.406 µl, 10.54 µmol), [(2-di-tert-butylphosphino-2',4',6'-triisopropyl-1,1'-biphenyl)-2-(2'-amino-1,1'-biphenyl)]palladium(II) methanesulfonate (0.698 mg, 0.878 µmol), potassium acetate (0.862 mg, 8.78 µmol), 1,4-dioxane (200 µl) and water (200 µl). The vial was capped and purged with nitrogen. The reaction was heated to 100° C. for 2 hours. After cooling to RT, the reaction mixture was diluted with methanol, passed through a syringe filter and purified by prep-HPLC (pH=2, acetonitrile/water+TFA). After removing solvent, the residue was treated with 1:1 TFA/DCM (4 mL) for 1 h. The solvent was removed in vacuo. The residue was purified by prep LCMS (pH 2, acetonitrile/water+TFA) to give the desired product as TFA salt. LC-MS calculated for $C_{34}H_{32}N_5O_4$ $(M+H)^+$: m/z=574.2; found 574.2.

Example 76

(S)-1-((7-chloro-2-(2,2'-dimethyl-3'-(4,5,6,7-tetrahydrooxazolo[4,5-c]pyridin-2-yl)-[1,1'-biphenyl]-3-yl)benzo[d]oxazol-5-yl)methyl)pyrrolidine-3-carboxylic acid

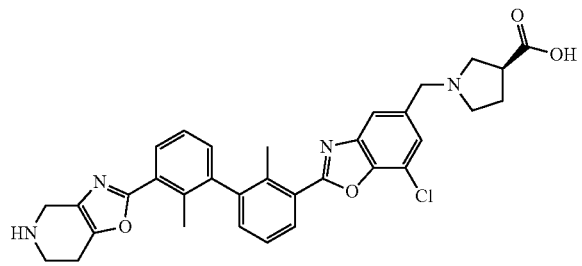 [SMILES: Cc1c(-c2nc3c(o2)CCNC3)cccc1-c1cccc(-c2nc3cc(CN4CC[C@H](C(=O)O)C4)cc(Cl)c3o2)c1C]

This compound was prepared using similar procedures as described for Example 74 with (S)-pyrrolidine-3-carboxylic acid replacing (R)-pyrrolidine-3-carboxylic acid in Step 8. LC-MS calculated for $C_{33}H_{32}ClN_4O_4(M+H)^+$: m/z=583.2; found 583.2.

Example 77

1-((7-chloro-2-(2,2'-dimethyl-3'-(4,5,6,7-tetrahydrooxazolo[4,5-c]pyridin-2-yl)-[1,1'-biphenyl]-3-yl)benzo[d]oxazol-5-yl)methyl)azetidine-3-carboxylic acid

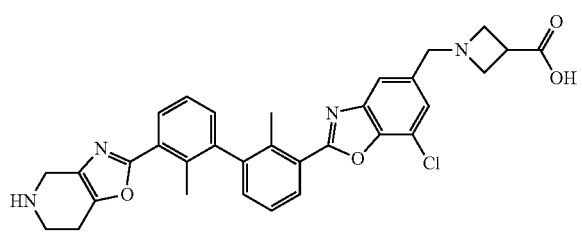 [SMILES: Cc1c(-c2nc3c(o2)CCNC3)cccc1-c1cccc(-c2nc3cc(CN4CC(C(=O)O)C4)cc(Cl)c3o2)c1C]

This compound was prepared using similar procedures as described for Example 74 with azetidine-3-carboxylic acid replacing (R)-pyrrolidine-3-carboxylic acid in Step 8. LC-MS calculated for $C_{32}H_{30}ClN_4O_4(M+H)^+$: m/z=569.2; found 569.2.

Example 78

(R)-1-((7-chloro-2-(2,2'-dimethyl-3'-(4,5,6,7-tetrahydrooxazolo[5,4-c]pyridin-2-yl)-[1,1'-biphenyl]-3-yl)benzo[d]oxazol-5-yl)methyl)pyrrolidine-3-carboxylic acid

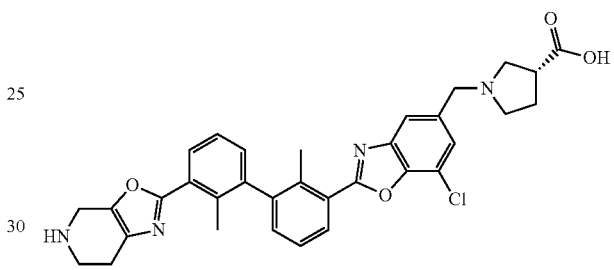

This compound was prepared using similar procedures as described for Example 74 with benzyl (3S,4S)-4-amino-3-hydroxypiperidine-1-carboxylate replacing benzyl (3R,4R)-3-amino-4-hydroxypiperidine-1-carboxylate in Step 1. LC-MS calculated for $C_{33}H_{32}ClN_4O_4$ $(M+H)^+$: m/z=583.2; found 583.2.

Example 79

(R)-1-((7-cyano-2-(2,2'-dimethyl-3'-(4,4,5-trimethyl-4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid

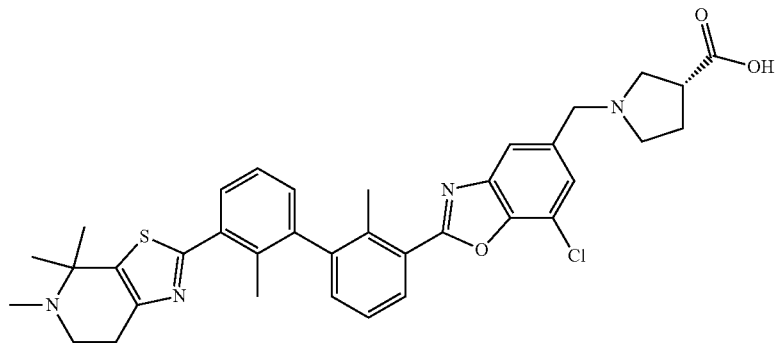 [SMILES: Cc1c(-c2nc3cc(CN4CC[C@@H](C(=O)O)C4)cc(Cl)c3o2)cccc1-c1cccc(-c2nc3c(s2)C(C)(C)N(C)CC3)c1C]

Step 1: 2-bromo-5-methyl-6,7-dihydrothiazolo[5,4-c]pyridin-4(5H)-one

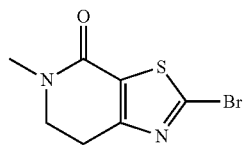

To solution of 2-bromo-6,7-dihydrothiazolo[5,4-c]pyridin-4(5H)-one (Ark Pharm, Inc, cat # AK-38786, 250 mg, 1.073 mmol) in tetrahydrofuran (3.0 mL) was added sodium hydride (60 wt % in mineral oil, 64.3 mg, 1.61 mmol) at 0° C. After stirring for 30 min, methyl iodide (0.134 mL, 2.145 mmol) was added to reaction mixture. The resultant mixture was stirred at rt overnight. The reaction was diluted with water and ethyl acetate. The organic layer was separated and concentrated. The residue was purified by flash chromatography (eluting with 0-40% ethyl acetate/hexanes) to give the desired product (254 mg, 96%). LC-MS calculated for $C_7H_8BrN_2OS$ (M+H)$^+$: m/z=247.0; found 246.9.

Step 2: 2-(3-chloro-2-methylphenyl)-5-methyl-6,7-dihydrothiazolo[5,4-c]pyridin-4 (5H)-one

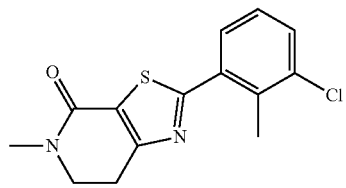 [SMILES: Cc1c(Cl)cccc1-c1nc2c(s1)C(=O)N(C)CC2]

To microwave vial was added (3-chloro-2-methylphenyl) boronic acid (175 mg, 1.03 mmol), 2-bromo-5-methyl-6,7-dihydrothiazolo[5,4-c]pyridin-4(5H)-one (254 mg, 1.03 mmol), (1,1'-bis(diphenylphosphino)ferrocene)-dichloropalladium(II) (75 mg, 0.10 mmol), sodium carbonate (218 mg, 2.05 mmol), 1,4-dioxane (6.5 ml) and water (1.300 ml). The mixture was purged with $N_2$ and heated at 90° C. for 2 h. The reaction mixture was diluted with ethyl acetate and water, the organic layer was separated, washed with brine, dried over $Na_2SO_4$, and filtered. The filtrate was concentrated and the residue was purified by flash chromatography (eluting with EtOAc/Hexanes 0-40%) to give the desired product (204 mg, 68%). LC-MS calculated for $C_{14}H_{14}ClN_2OS$ (M+H)$^+$: m/z=293.0; found 293.0.

Step 3: 2-(3-chloro-2-methylphenyl)-4,4,5-trimethyl-4,5,6,7-tetrahydrothiazolo[5,4-c]pyridine

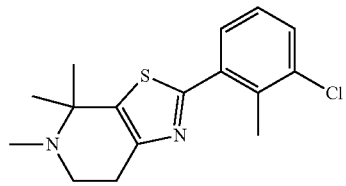 [SMILES: Cc1c(Cl)cccc1-c1nc2c(s1)C(C)(C)N(C)CC2]

To a solution of 2-(3-chloro-2-methylphenyl)-5-methyl-6,7-dihydrothiazolo[5,4-c]pyridin-4(5H)-one (204 mg, 0.697 mmol), 2,6-di-tert-butyl-4-methylpyridine (172 mg, 0.836 mmol) in DCM (6.0 ml) at −78° C. was added trifluoromethanesulfonic anhydride (0.141 ml, 0.836 mmol). After stirring at same temperature for 1 h, methylmagnesium bromide (3 M in ether 0.557 ml, 1.672 mmol) was added to reaction mixture and allowed to warm to room temperature over 3 h. The reaction mixture was diluted with DCM and saturated $NH_4Cl$ solution, the organic layer was separated and dried over $Na_2SO_4$, filtered and concentrated. The residue was purified by flash chromatography (eluting with 0-30% ethyl acetate/hexanes) to give the desired product (167 mg, 78%). LC-MS calculated for $C_{16}H_{20}ClN_2S$ (M+H)$^+$: m/z=307.1; found 307.1.

Step 4: 4,4,5-trimethyl-2-(2-methyl-3-(4,4,5,5-tetramethyl-1,3,2-dioxaborolan-2-yl)phenyl)-4,5,6,7-tetrahydrothiazolo[5,4-c]pyridine

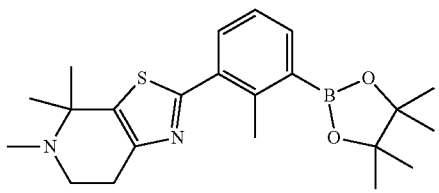

To a microwave vial was charged with 2-(3-chloro-2-methylphenyl)-4,4,5-trimethyl-4,5,6,7-tetrahydrothiazolo[5,4-c]pyridine (151 mg, 0.492 mmol), 4,4,4',4',5,5,5',5'-octamethyl-2,2'-bi(1,3,2-dioxaborolane) (125 mg, 0.492 mmol), tris(dibenzylideneacetone)dipalladium(0) (18.03 mg, 0.020 mmol), 2-dicyclohexylphosphino-2',4',6'-tri-isopropyl-1,1'-biphenyl (37.5 mg, 0.079 mmol) and potassium acetate (145 mg, 1.476 mmol). The vial was sealed and evacuated under high vacuum and refilled with nitrogen (this process was repeated three times). 1,4-dioxane (2 mL) was added. The mixture was stirred at 100° C. for 5 h. After cooling to room temperature, the mixture was diluted with ethyl acetate and filtered. The filtrate was concentrated in vacuo and the residue was purified by flash chromatography (eluting with 0-20% methanol in DCM) to give the desired product (160 mg, 82%). LC-MS calculated for $C_{22}H_{32}BN_2O_2S$ (M+H)$^+$: m/z=399.2; found 399.2.

Step 5: 7-chloro-2-(2,2'-dimethyl-3'-(4,4,5-trimethyl-4,5,6,7-tetrahydrothiazolo[5,4-c]pyridin-2-yl)-[1,1'-biphenyl]-3-yl)benzo[d]oxazole-5-carbaldehyde

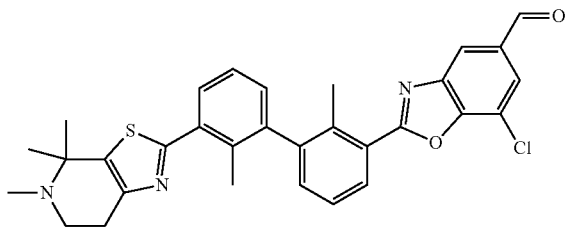 [SMILES: Cc1c(-c2nc3cc(C=O)cc(Cl)c3o2)cccc1-c1cccc(-c2nc3c(s2)C(C)(C)N(C)CC3)c1C]

To a microwave vial was charged with 4,4,5-trimethyl-2-(2-methyl-3-(4,4,5,5-tetramethyl-1,3,2-dioxaborolan-2-yl)phenyl)-4,5,6,7-tetrahydrothiazolo[5,4-c]pyridine (90 mg, 0.225 mmol), 2-(3-bromo-2-methylphenyl)-7-chlorobenzo[d]oxazole-5-carbaldehyde (Example 10, Step 1; 79 mg, 0.225 mmol), (1,1'-bis(diphenylphosphino)ferrocene)-dichloropalladium(II) (16.5 mg, 0.023 mmol), sodium carbonate (47.8 mg, 0.451 mmol) in 1,4-dioxane (2.0 ml) and water (0.400 ml). The mixture was purged with $N_2$ and heated at 90° C. for 2 h. The mixture was diluted with ethyl acetate and water, the organic layer was separated, dried over $Na_2SO_4$, filtered and concentrated. The residue was purified by flash chromatography (eluting with 0-20% methanol in DCM) to give the desired product (94 mg, 77%). LC-MS calculated for $C_{31}H_{29}ClN_3O_2S$ (M+H)$^+$: m/z=542.2; found 542.2.

Step 6: (R)-1-((7-chloro-2-(2,2'-dimethyl-3'-(4,4,5-trimethyl-4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid

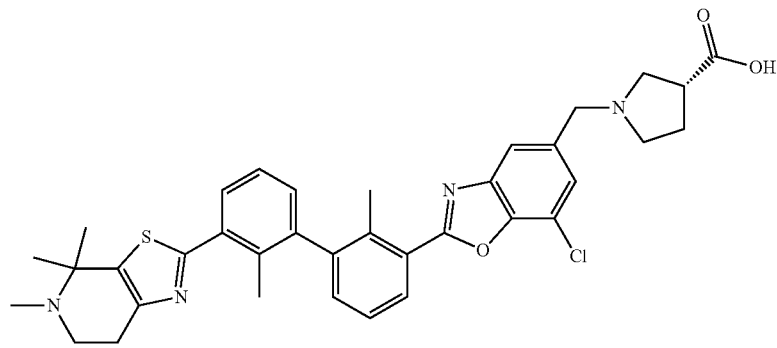 [SMILES: Cc1c(-c2nc3cc(CN4CC[C@@H](C(=O)O)C4)cc(Cl)c3o2)cccc1-c1cccc(-c2nc3c(s2)C(C)(C)N(C)CC3)c1C]

Sodium triacetoxyborohydride (12.5 mg, 0.059 mmol) was added to a mixture of 7-chloro-2-(2,2'-dimethyl-3'-(4,4,5-trimethyl-4,5,6,7-tetrahydrothiazolo[5,4-c]pyridin-2-yl)-[1,1'-biphenyl]-3-yl)benzo[d]oxazole-5-carbaldehyde (32 mg, 0.059 mmol), (R)-pyrrolidine-3-carboxylic acid (6.80 mg, 0.059 mmol) in DCM (1.0 ml) at room temperature. After stirring at rt overnight, The solvent was removed in vacuo and the residue was purified with prep LCMS (pH 2, acetonitrile/water+TFA) to give the desired product as TFA salt. LC-MS calculated for $C_{36}H_{38}ClN_4O_3S$ (M+H)$^+$: m/z=641.2; found 641.2.

Step 7: (R)-1-((7-cyano-2-(2,2'-dimethyl-3'-(4,4,5-trimethyl-4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid This compound was prepared using similar procedures as described for Example 73 with (R)-1-((7-chloro-2-(2,2'-dimethyl-3'-(4,4,5-trimethyl-4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid replacing (R)-1-((7-chloro-2-(2,2'-dimethyl-3'-(5-methyl-4,5,6,7-tetrahydrothiazolo[5,4-c]pyridin-2-yl)-[1,1'-biphenyl]-3-yl)benzo[d]oxazol-5-yl)methyl)pyrrolidine-3-carboxylic acid. LC-MS calculated for $C_{37}H_{38}N_5O_3S$ (M+H)$^+$: m/z=632.3; found 632.2.

Example 80

(R)-1-((7-cyano-2-(3'-(1,5-dimethyl-4,5,6,7-tetrahydro-1H-imidazo[4,5-c]pyridine-2-carboxamido)-2,2'-dimethylbiphenyl-3-yl)benzo[d]oxazol-5-yl)methyl)pyrrolidine-3-carboxylic acid

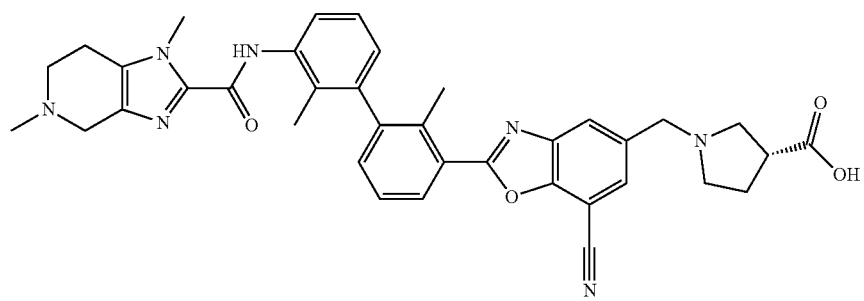 [SMILES: Cc1c(NC(=O)c2nc3c(n2C)CCN(C)C3)cccc1-c1cccc(-c2nc3cc(CN4CC[C@@H](C(=O)O)C4)cc(C#N)c3o2)c1C]

This compound was prepared using similar procedures as described for Example 36 with (R)-pyrrolidine-3-carboxylic acid replacing (S)-pyrrolidine-3-carboxylic acid in Step 7. The reaction was diluted with MeOH and then purified by prep-HPLC (pH=2, acetonitrile/water+TFA) to give the desired product as TFA salt. LC-MS calculated for $C_{37}H_{38}N_7O_4$ (M+H)$^+$: m/z=644.3; found 644.3.

Example 81

(S)-1-((7-chloro-2-(2'-chloro-3'-(3-(((R)-3-hydroxy-pyrrolidin-1-yl)methyl)-1,7-naphthyridin-8-ylamino)-2-methylbiphenyl-3-yl)benzo[d]oxazol-5-yl)methyl)pyrrolidine-3-carboxylic acid

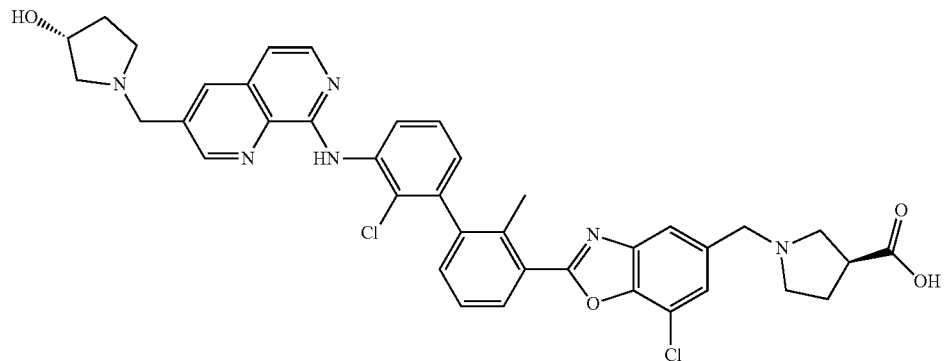 [SMILES: Cc1c(-c2nc3cc(CN4CC[C@H](C(=O)O)C4)cc(Cl)c3o2)cccc1-c1cccc(Nc2nccc3cc(CN4CC[C@@H](O)C4)cnc23)c1Cl]

This compound was prepared using similar procedures as described for Example 29 with (R)-pyrrolidin-3-ol replacing (S)-pyrrolidin-3-ol in Step 4 and (S)-pyrrolidine-3-carboxylic acid replacing (R)-pyrrolidine-3-carboxylic acid in Step 7. The reaction was diluted with MeOH and then purified by prep-HPLC (pH=10, acetonitrile/water+NH$_4$OH) to give the desired product. LC-MS calculated for $C_{39}H_{37}Cl_2N_6O_4$ (M+H)$^+$: m/z=723.2; found 723.2.

Example 82

(R)-1-((7-chloro-2-(2'-chloro-3'-(3-(((R)-3-hydroxy-pyrrolidin-1-yl)methyl)-1,7-naphthyridin-8-ylamino)-2-methylbiphenyl-3-yl)benzo[d]oxazol-5-yl)methyl)pyrrolidine-3-carboxylic acid

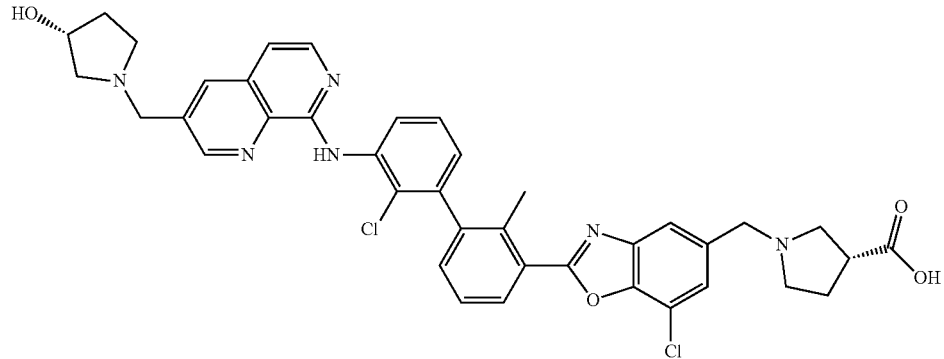 [SMILES: Cc1c(-c2nc3cc(CN4CC[C@@H](C(=O)O)C4)cc(Cl)c3o2)cccc1-c1cccc(Nc2nccc3cc(CN4CC[C@@H](O)C4)cnc23)c1Cl]

This compound was prepared using similar procedures as described for Example 29 with (R)-pyrrolidin-3-ol replacing (S)-pyrrolidin-3-ol in Step 4. The reaction was diluted with MeOH and then purified by prep-HPLC (pH=10, acetonitrile/water+NH$_4$OH) to give the desired product. LC-MS calculated for C$_{39}$H$_{37}$Cl$_2$N$_6$O$_4$ (M+H)$^+$: m/z=723.2; found 723.2.

Example 83

(S)-1-((2-(2'-chloro-3'-(3-(((R)-3-hydroxypyrrolidin-1-yl)methyl)-1,7-naphthyridin-8-ylamino)-2-methyl-biphenyl-3-yl)-7-cyanobenzo[d]oxazol-5-yl)methyl) pyrrolidine-3-carboxylic acid

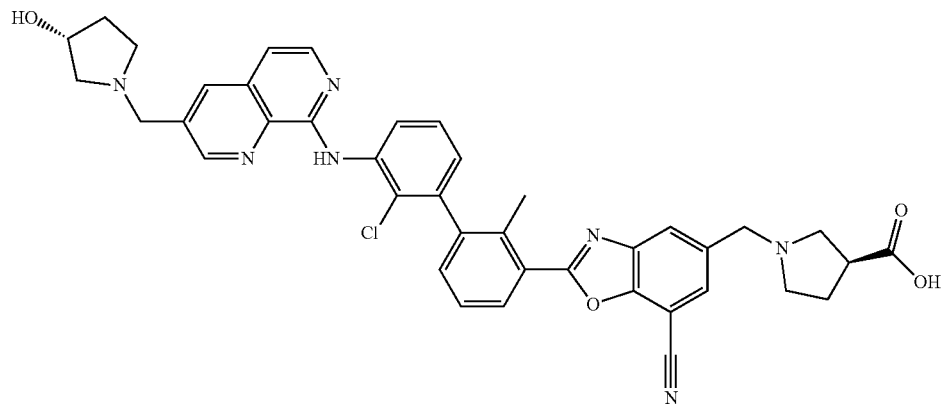 [SMILES: Cc1c(-c2nc3cc(CN4CC[C@H](C(=O)O)C4)cc(C#N)c3o2)cccc1-c1cccc(Nc2nccc3cc(CN4CC[C@@H](O)C4)cnc23)c1Cl]

This compound was prepared using similar procedures as described for Example 30 with (S)-pyrrolidine-3-carboxylic acid replacing (R)-pyrrolidine-3-carboxylic acid and (R)-pyrrolidin-3-ol replacing (S)-pyrrolidin-3-ol. The reaction was diluted with MeOH and then purified by prep-HPLC (pH=2, acetonitrile/water+TFA) to give the desired product as TFA salt. LC-MS calculated for C$_{40}$H$_{37}$ClN$_7$O$_4$(M+H)$^+$: m/z=714.3; found 714.3.

Example 84

(R)-1-((2-(2'-chloro-3'-(3-(((R)-3-hydroxypyrrolidin-1-yl)methyl)-1,7-naphthyridin-8-ylamino)-2-methyl-biphenyl-3-yl)-7-cyanobenzo[d]oxazol-5-yl)methyl) pyrrolidine-3-carboxylic acid

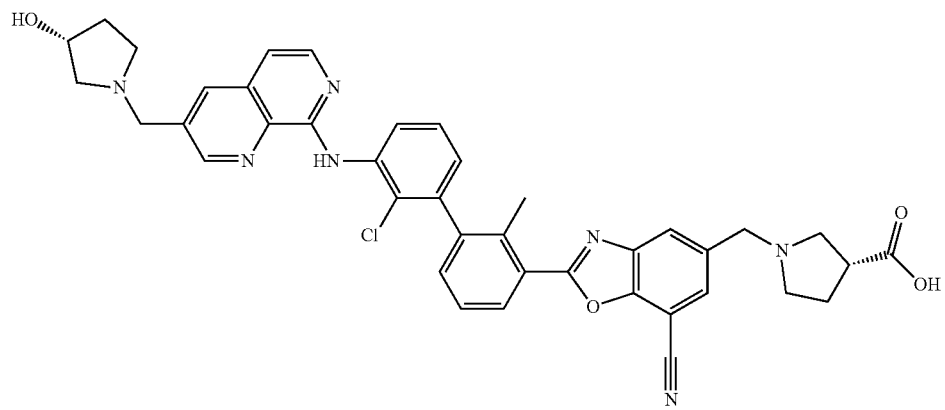 [SMILES: Cc1c(-c2nc3cc(CN4CC[C@@H](C(=O)O)C4)cc(C#N)c3o2)cccc1-c1cccc(Nc2nccc3cc(CN4CC[C@@H](O)C4)cnc23)c1Cl]

This compound was prepared using similar procedures as described for Example 30 with (R)-pyrrolidin-3-ol replacing (S)-pyrrolidin-3-ol. The reaction was diluted with MeOH and then purified by prep-HPLC (pH=2, acetonitrile/water+TFA) to give the desired product as TFA salt. LC-MS calculated for $C_{40}H_{37}ClN_7O_4(M+H)^+$: m/z=714.3; found 714.3.

Example 85

(R)-1-((7-cyano-2-(3'-(3-((3-hydroxypyrrolidin-1-yl)methyl)-1,7-naphthyridin-8-ylamino)-2,2'-dimethyl-biphenyl-3-yl)benzo[d]oxazol-5-yl)methyl)azetidine-3-carboxylic acid

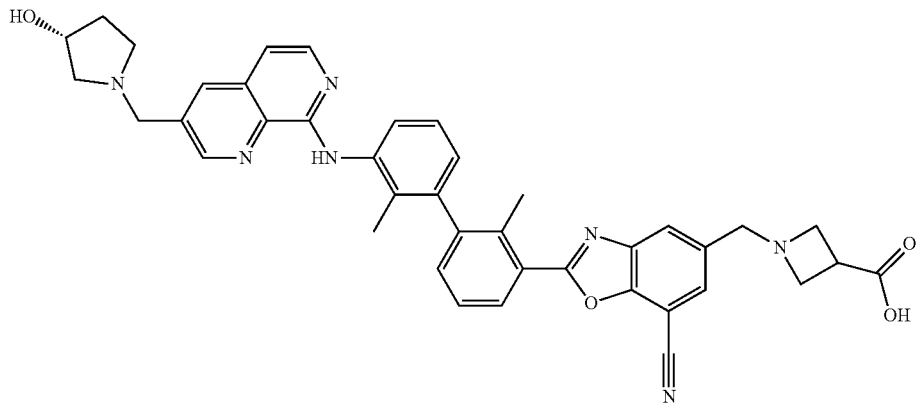 [SMILES: Cc1c(Nc2nccc3cc(CN4CC[C@@H](O)C4)cnc23)cccc1-c1cccc(-c2nc3cc(CN4CC(C(=O)O)C4)cc(C#N)c3o2)c1C]

This compound was prepared using similar procedures as described for Example 24 with azetidine-3-carboxylic acid replacing (R)-pyrrolidine-3-carboxylic acid in Step 5. The reaction mixture was diluted with MeOH and then purified by prep-HPLC (pH=10, acetonitrile/water+NH$_4$OH) to give the desired product. LC-MS calculated for $C_{40}H_{38}N_7O_4$ (M+H)$^+$: m/z=680.3; found 680.3.

Example 86

(R)-3-((7-cyano-2-(3'-(3-((3-hydroxypyrrolidin-1-yl)methyl)-1,7-naphthyridin-8-ylamino)-2,2'-dimethyl-biphenyl-3-yl)benzo[d]oxazol-5-yl)methylamino)-2,2-dimethylpropanoic acid

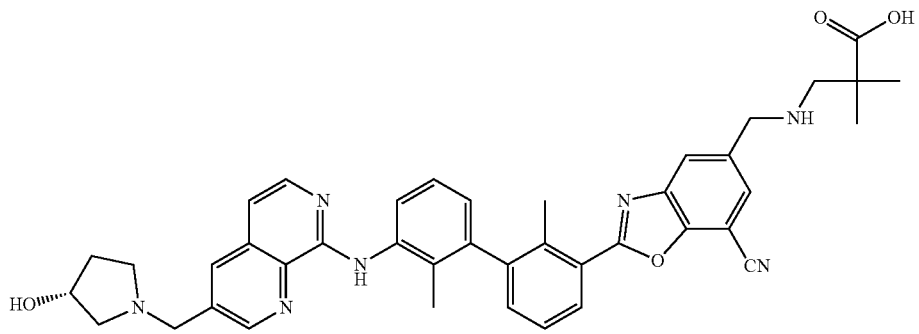 [SMILES: Cc1c(Nc2nccc3cc(CN4CC[C@@H](O)C4)cnc23)cccc1-c1cccc(-c2nc3cc(CNCC(C)(C)C(=O)O)cc(C#N)c3o2)c1C]

This compound was prepared using similar procedures as described for Example 24 with 3-amino-2,2-dimethylpropanoic acid replacing (R)-pyrrolidine-3-carboxylic acid in Step 5. The reaction mixture was diluted with MeOH and then purified by prep-HPLC (pH=10, acetonitrile/water+NH$_4$OH) to give the desired product. LC-MS calculated for $C_{41}H_{42}N_7O_4$ (M+H)$^+$: m/z=696.3; found 696.3.

Example 87

(R)-1-((2-(2'-chloro-3'-(6-isopropyl-4,5,6,7-tetrahydro-2H-pyrazolo[3,4-c]pyridin-2-yl)-2-methylbiphenyl-3-yl)-7-cyanobenzo[d]oxazol-5-yl)methyl)pyrrolidine-3-carboxylic acid

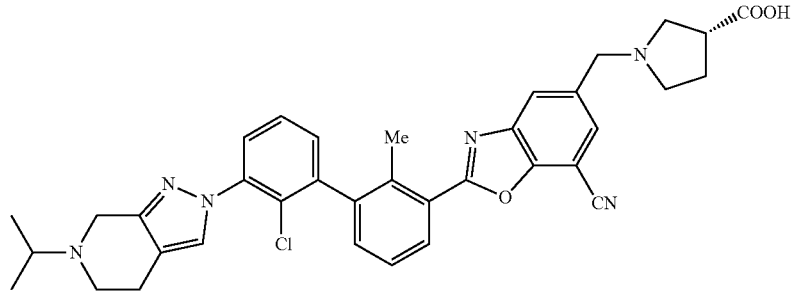 [SMILES: Cc1c(-c2nc3cc(CN4CC[C@@H](C(=O)O)C4)cc(C#N)c3o2)cccc1-c1cccc(-n2cc3c(n2)CN(C(C)C)CC3)c1Cl]

Step 1: (R)-1-((2-(2'-chloro-2-methyl-3'-(4,5,6,7-tetrahydro-2H-pyrazolo[3,4-c]pyridin-2-yl)biphenyl-3-yl)-7-cyanobenzo[d]oxazol-5-yl)methyl)pyrrolidine-3-carboxylic acid

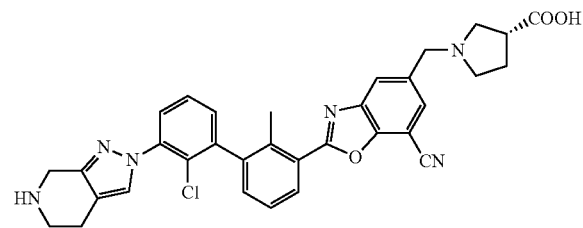 [SMILES: Cc1c(-c2nc3cc(CN4CC[C@@H](C(=O)O)C4)cc(C#N)c3o2)cccc1-c1cccc(-n2cc3c(n2)CNCC3)c1Cl]

This compound was prepared using similar method in Example 54, Step 1-6 with tert-butyl 1,4,5,7-tetrahydro-6H-pyrazolo[3,4-c]pyridine-6-carboxylate (Astatech, cat #79248) replacing tert-butyl 1,4,6,7-tetrahydro-5H-pyrazolo[4,3-c]pyridine-5-carboxylate in Step 1. The reaction mixture was concentrated and used in next step without further purification. LC-MS calculated for $C_{33}H_{30}ClN_6O_3(M+H)^+$: m/z=593.2; found 593.1.

Step 2: (R)-1-((2-(2'-chloro-3'-(6-isopropyl-4,5,6,7-tetrahydro-2H-pyrazolo[3,4-c]pyridin-2-yl)-2-methylbiphenyl-3-yl)-7-cyanobenzo[d]oxazol-5-yl)methyl)pyrrolidine-3-carboxylic acid A mixture of (R)-1-((2-(2'-chloro-2-methyl-3'-(4,5,6,7-tetrahydro-2H-pyrazolo[3,4-c]pyridin-2-yl)biphenyl-3-yl)-7-cyanobenzo[d]oxazol-5-yl)methyl)pyrrolidine-3-carboxylic acid (10 mg, 0.017 mmol) and acetone (2.4 µL, 0.034 mmol) in DCM (169 µl) was allowed to stir for 2 h. Then sodium triacetoxyborohydride (7.0 mg, 0.034 mmol) was added to the mixture. After 2 h, the mixture was concentrated and diluted with MeOH and then purified by prep-HPLC (pH=2, acetonitrile/water+TFA) to give the desired product as its TFA salt. LC-MS calculated for $C_{36}H_{36}ClN_6O_3(M+H)^+$: m/z=635.2; found 635.3. $^1H$ NMR (500 MHz, DMSO) δ 8.21 (d, J=6.7 Hz, 1H), 8.13 (s, 1H), 7.89 (s, 1H), 7.86 (s, 1H), 7.64-7.55 (m, 3H), 7.50 (d, J=6.4 Hz, 1H), 7.45 (dd, J=7.1, 2.1 Hz, 1H), 3.85-3.68 (m, 3H), 3.62 (s, 2H), 2.99-2.87 (m, 2H), 2.79-2.58 (m, 5H), 2.58-2.52 (m, 2H), 2.49 (s, 3H), 1.98 (q, J=7.1 Hz, 2H), 1.08 (d, J=6.6 Hz, 6H).

Example 88

(R)-1-((2-(2'-chloro-3'-(1,5-dimethyl-4,5,6,7-tetrahydro-1H-imidazo[4,5-c]pyridine-2-carboxamido)-2-methylbiphenyl-3-yl)-7-cyanobenzo[d]oxazol-5-yl)methyl)-3-methylpyrrolidine-3-carboxylic acid

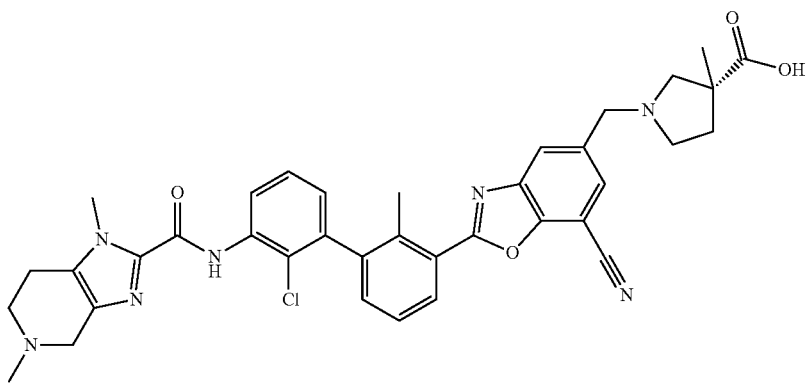 [SMILES: Cc1c(-c2nc3cc(CN4CC[C@@](C)(C(=O)O)C4)cc(C#N)c3o2)cccc1-c1cccc(NC(=O)c2nc3c(n2C)CCN(C)C3)c1Cl]

This compound was prepared using similar procedures as described for Example 50 with (R)-3-methylpyrrolidine-3-carboxylic acid replacing (S)-pyrrolidine-3-carboxylic acid in Step 6. The reaction was diluted with MeOH and then purified by prep-HPLC (pH=2, acetonitrile/water+TFA) to give the desired product as TFA salt. LC-MS calculated for $C_{37}H_{37}ClN_7O_4(M+H)^+$: m/z=678.3; found 678.3. $^1$H NMR (500 MHz, DMSO) δ 9.97 (s, 1H), 8.40 (d, J=1.2 Hz, 1H), 8.24 (dd, J=8.2, 1.3 Hz, 1H), 8.21 (d, J=7.0 Hz, 1H), 8.13 (d, J=1.2 Hz, 1H), 7.59 (t, J=7.7 Hz, 1H), 7.52 (t, J=7.9 Hz, 1H), 7.48 (d, J=6.8 Hz, 1H), 7.20 (dd, J=7.6, 1.4 Hz, 1H), 4.59 (s, 2H), 4.52-4.11 (m, 2H), 3.95 (s, 3H), 3.87-3.26 (m, 6H), 3.08-3.00 (m, 2H), 2.95 (s, 3H), 2.46 (s, 3H), 2.38-1.79 (m, 2H), 1.37 (s, 3H).

Example 89

1-((2-(2'-chloro-3'-(1,5-dimethyl-4,5,6,7-tetrahydro-1H-imidazo[4,5-c]pyridine-2-carboxamido)-2-methylbiphenyl-3-yl)-7-cyanobenzo[d]oxazol-5-yl)methyl)piperidine-4-carboxylic acid

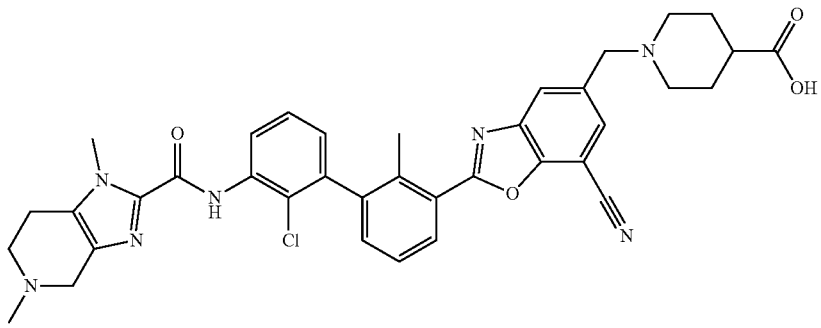 [SMILES: Cc1c(-c2nc3cc(CN4CCC(C(=O)O)CC4)cc(C#N)c3o2)cccc1-c1cccc(NC(=O)c2nc3c(n2C)CCN(C)C3)c1Cl]

This compound was prepared using similar procedures as described for Example 50 with piperidine-4-carboxylic acid replacing (S)-pyrrolidine-3-carboxylic acid in Step 6. The reaction was diluted with MeOH and then purified by prep-HPLC (pH=2, acetonitrile/water+TFA) to give the desired product as TFA salt. LC-MS calculated for $C_{37}H_{37}ClN_7O_4(M+H)^+$: m/z=678.3; found 678.3. $^1$H NMR (600 MHz, DMSO) δ 9.97 (s, 1H), 8.37 (s, 1H), 8.24 (dd, J=8.2, 1.5 Hz, 1H), 8.23-8.20 (m, 1H), 8.10 (s, 1H), 7.60 (t, J=7.7 Hz, 1H), 7.52 (t, J=7.9 Hz, 1H), 7.49 (dd, J=7.6, 1.0 Hz, 1H), 7.21 (dd, J=7.6, 1.5 Hz, 1H), 4.66-4.37 (m, 3H), 4.21 (s, 1H), 3.95 (s, 3H), 3.84-3.27 (m, 4H), 3.09-2.98 (m, 4H), 2.95 (s, 3H), 2.49 (m, 1H), 2.46 (s, 3H), 2.13-1.64 (m, 4H).

Example 90

(S)-2-((2-(2'-chloro-3'-(1,5-dimethyl-4,5,6,7-tetrahydro-1H-imidazo[4,5-c]pyridine-2-carboxamido)-2-methylbiphenyl-3-yl)-7-cyanobenzo[d]oxazol-5-yl)methylamino)propanoic acid

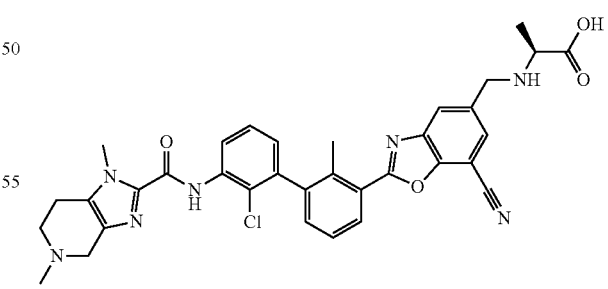

This compound was prepared using similar procedures as described for Example 50 with (S)-2-aminopropanoic acid replacing (S)-pyrrolidine-3-carboxylic acid in Step 6. The reaction was diluted with MeOH and then purified by prep-HPLC (pH=2, acetonitrile/water+TFA) to give the desired product as TFA salt. LC-MS calculated for $C_{34}H_{33}ClN_7O_4(M+H)^+$: m/z=638.2; found 638.2.

Example 91

(1R,4R)-4-((2-(2'-chloro-3'-(1,5-dimethyl-4,5,6,7-tetrahydro-1H-imidazo[4,5-c]pyridine-2-carboxamido)-2-methylbiphenyl-3-yl)-7-cyanobenzo[d]oxazol-5-yl)methylamino)cyclohexanecarboxylic acid

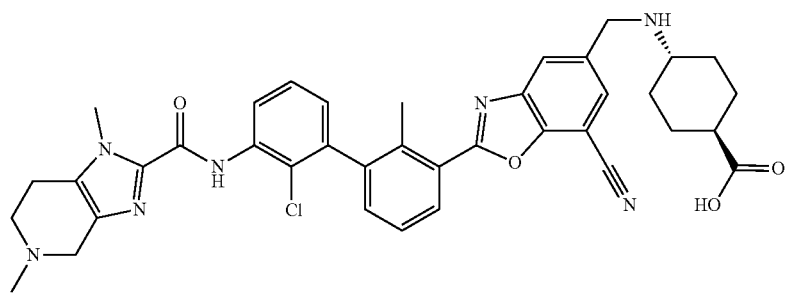 [SMILES: Cc1c(-c2nc3cc(CN[C@H]4CC[C@H](C(=O)O)CC4)cc(C#N)c3o2)cccc1-c1cccc(NC(=O)c2nc3c(n2C)CCN(C)C3)c1Cl]

This compound was prepared using similar procedures as described for Example 50 with (1R,4R)-4-aminocyclohexanecarboxylic acid replacing (S)-pyrrolidine-3-carboxylic acid in Step 6. The reaction was diluted with MeOH and then purified by prep-HPLC (pH=2, acetonitrile/water+TFA) to give the desired product as TFA salt. LC-MS calculated for $C_{38}H_{39}ClN_7O_4(M+H)^+$: m/z=692.3; found 692.3.

Example 92

(S)-1-((2-(2'-chloro-2-methyl-3'-(1-methyl-4,5,6,7-tetrahydro-1H-imidazo[4,5-c]pyridine-2-carboxamido)biphenyl-3-yl)-7-cyanobenzo[d]oxazol-5-yl)methyl)pyrrolidine-3-carboxylic acid

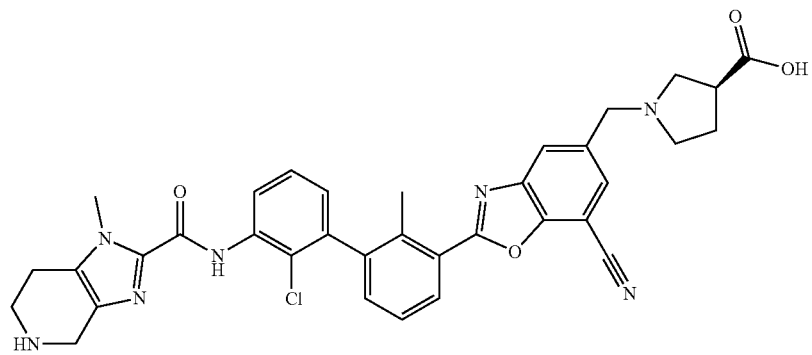 [SMILES: Cc1c(-c2nc3cc(CN4CC[C@H](C(=O)O)C4)cc(C#N)c3o2)cccc1-c1cccc(NC(=O)c2nc3c(n2C)CCNC3)c1Cl]

Step 1: tert-butyl 2-(2-chloro-3'-(7-chloro-5-(hydroxymethyl)benzo[d]oxazol-2-yl)-2'-methylbiphenyl-3-ylcarbamoyl)-1-methyl-6,7-dihydro-1H-imidazo[4,5-c]pyridine-5(4H)-carboxylate

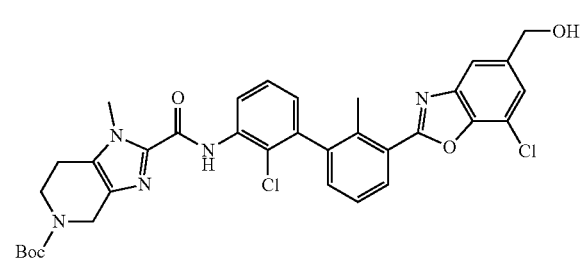 [SMILES: Cc1c(-c2nc3cc(CO)cc(Cl)c3o2)cccc1-c1cccc(NC(=O)c2nc3c(n2C)CCN(C(=O)OC(C)(C)C)C3)c1Cl]

A mixture of tert-butyl 2-(3-bromo-2-chlorophenylcarbamoyl)-1-methyl-6,7-dihydro-1H-imidazo[4,5-c]pyridine-5(4H)-carboxylate (Example 50, Step 1: 8.01 g, 17.03 mmol), (7-chloro-2-(2-methyl-3-(4,4,5,5-tetramethyl-1,3,2-dioxaborolan-2-yl)phenyl)benzo[d]oxazol-5-yl)methanol (Example 1, Step 5: 7.49 g, 18.73 mmol), and dichloro[1,1'-bis(dicyclohexylphosphino)ferrocene]palladium(II) (1.39 g, 1.70 mmol) in 1,4-dioxane (95 mL) and water (19 mL) was added sodium carbonate (3.61 g, 34.10 mmol). The reaction mixture was purged with nitrogen and then stirred at 100° C. for 36 hrs. After being cooled to room temperature, the reaction mixture was extracted with ethyl acetate. The combined organic layers were washed with brine, dried over $Na_2SO_4$, filtered and concentrated under reduced pressure. The residue was purified by flash chromatography on a silica gel column eluting with 0 to 70% EtOAc in hexanes to afford the desired product. LC-MS calculated for $C_{34}H_{34}Cl_2N_5O_5$ $(M+H)^+$: m/z=662.2; found 662.2.

Step 2: tert-butyl 2-(2-chloro-3'-(7-cyano-5-(hydroxymethyl)benzo[d]oxazol-2-yl)-2'-methylbiphenyl-3-ylcarbamoyl)-1-methyl-6,7-dihydro-1H-imidazo[4,5-c]pyridine-5(4H)-carboxylate

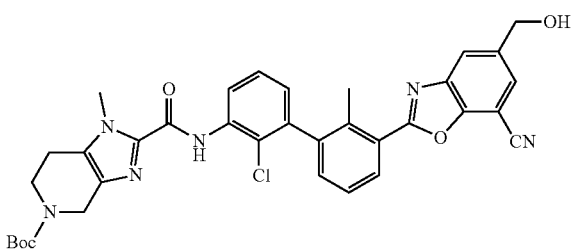 [SMILES: Cc1c(-c2nc3cc(CO)cc(C#N)c3o2)cccc1-c1cccc(NC(=O)c2nc3c(n2C)CCN(C(=O)OC(C)(C)C)C3)c1Cl]

A suspension of tert-butyl 2-(2-chloro-3'-(7-cyano-5-(hydroxymethyl)benzo[d]oxazol-2-yl)-2'-methylbiphenyl-3-ylcarbamoyl)-1-methyl-6,7-dihydro-1H-imidazo[4,5-c]pyridine-5(4H)-carboxylate (3.56 g, 6.28 mmol) and manganese dioxide (10.92 g, 126 mmol) in DCM (60 mL) was stirred at 45° C. for 3 hrs. The reaction was filtered through a short pad of celite and then concentrated to yield a crude residue, which was used directly without further purification. LC-MS calculated for $C_{35}H_{32}ClN_6O_5$ (M+H)⁺: m/z=651.2; found 651.2.

Step 4: (S)-1-((2-(3'-(5-(tert-butoxycarbonyl)-1-methyl-4,5,6,7-tetrahydro-1H-imidazo[4,5-c]pyridine-2-carboxamido)-2'-chloro-2-methylbiphenyl-3-yl)-7-cyanobenzo[d]oxazol-5-yl)methyl)pyrrolidine-3-carboxylic acid

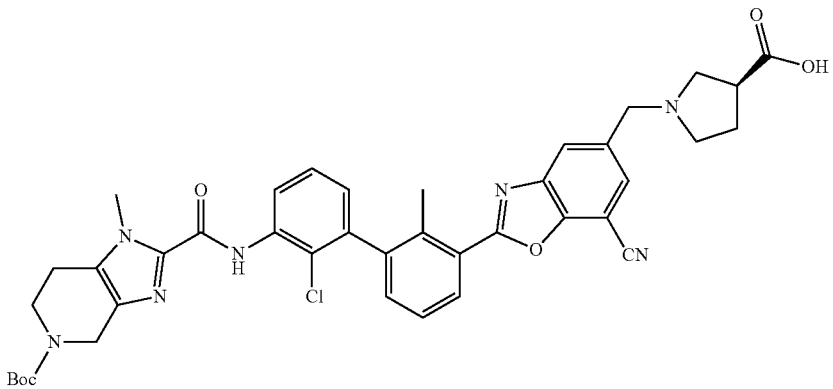

This compound was prepared using similar procedures as described for Example 12 with tert-butyl 2-(2-chloro-3'-(7-chloro-5-(hydroxymethyl)benzo[d]oxazol-2-yl)-2'-methylbiphenyl-3-ylcarbamoyl)-1-methyl-6,7-dihydro-1H-imidazo[4,5-c]pyridine-5 (4H)-carboxylate replacing (7-chloro-2-(2,2'-dimethyl-3'-(pyrido[3,4-b]pyrazin-5-ylamino)-[1,1'-biphenyl]-3-yl)benzo[d]oxazol-5-yl)methanol in Step 1. LC-MS calculated for $C_{35}H_{34}ClN_6O_5$ (M+H)⁺: m/z=653.2; found 653.2.

Step 3: tert-butyl 2-(2-chloro-3'-(7-cyano-5-formylbenzo[d]oxazol-2-yl)-2'-methylbiphenyl-3-ylcarbamoyl)-1-methyl-6,7-dihydro-1H-imidazo[4,5-c]pyridine-5(4H)-carboxylate

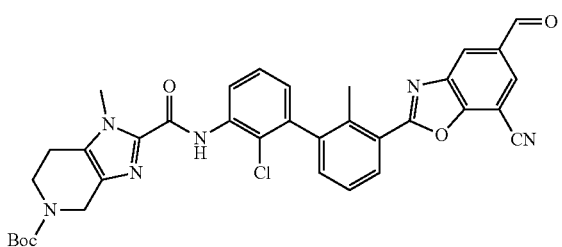 [SMILES: Cc1c(-c2nc3cc(C=O)cc(C#N)c3o2)cccc1-c1cccc(NC(=O)c2nc3c(n2C)CCN(C(=O)OC(C)(C)C)C3)c1Cl]

To a solution of tert-butyl 2-(2-chloro-3'-(7-cyano-5-formylbenzo[d]oxazol-2-yl)-2'-methylbiphenyl-3-ylcarbamoyl)-1-methyl-6,7-dihydro-1H-imidazo[4,5-c]pyridine-5 (4H)-carboxylate (100 mg, 0.153 mmol) in DCM (6 ml) was added (S)-pyrrolidine-3-carboxylic acid (26.5 mg, 0.230 mmol) and TEA (0.085 ml, 0.614 mmol). The mixture was stirred at r.t. for 60 min, then sodium triacetoxyborohydride (48.8 mg, 0.23 mmol) was added. The resulting mixture was stirred at r.t. overnight then concentrated. The residue was purified via prep-HPLC (pH=2, MeCN/water with TFA) to give the desired product as the TFA salt. LC-MS calculated for $C_{40}H_{41}ClN_7O_6$(M+H)⁺: m/z=750.3; found 750.3.

Step 5: (S)-1-((2-(2'-chloro-2-methyl-3'-(1-methyl-4,5,6,7-tetrahydro-1H-imidazo[4,5-c]pyridine-2-carboxamido)biphenyl-3-yl)-7-cyanobenzo[d]oxazol-5-yl)methyl)pyrrolidine-3-carboxylic acid To a solution of (S)-1-((2-(3'-(5-(tert-butoxycarbonyl)-1-methyl-4,5,6,7-tetrahydro-1H-imidazo[4,5-c]pyridine-2-carboxamido)-2'-chloro-2-methylbiphenyl-3-yl)-7-cyanobenzo[d]oxazol-5-yl)methyl)pyrrolidine-3-carboxylic acid (50 mg, 0.067 mmol) in DCM (1 mL) was added trifluoroacetic acid (1 mL) and MeOH (0.013 mL). The solution was stirred at r.t. for 1 h. then concentrate. The residue was purified via prep-HPLC (pH=2, MeCN/water with TFA) to give the desired product as the TFA salt. LC-MS calculated for $C_{35}H_{33}ClN_7O_4$(M+H)⁺: m/z=650.3; found 650.3.

Example 93

(S)-1-((2-(2'-chloro-3'-(5-(2-hydroxyethyl)-1-methyl-4,5,6,7-tetrahydro-1H-imidazo[4,5-c]pyridine-2-carboxamido)-2-methylbiphenyl-3-yl)-7-cyanobenzo[d]oxazol-5-yl)methyl)pyrrolidine-3-carboxylic acid

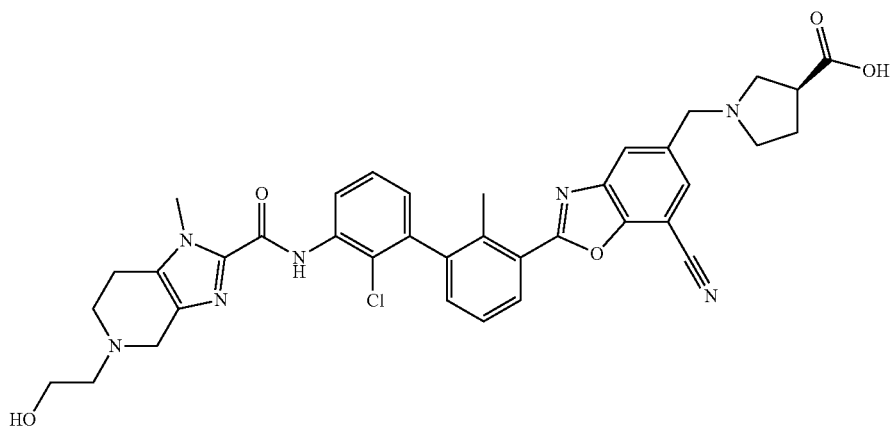 [SMILES: Cc1c(-c2nc3cc(CN4CC[C@H](C(=O)O)C4)cc(C#N)c3o2)cccc1-c1cccc(NC(=O)c2nc3c(n2C)CCN(CCO)C3)c1Cl]

To a solution of (S)-1-((2-(2'-chloro-2-methyl-3'-(1-methyl-4,5,6,7-tetrahydro-1H-imidazo[4,5-c]pyridine-2-carboxamido)biphenyl-3-yl)-7-cyanobenzo[d]oxazol-5-yl)methyl)pyrrolidine-3-carboxylic acid (Example 92, Step 5: 20 mg, 0.031 mmol) in DCM (0.5 ml) was added 2-(tert-butyldimethylsilyloxy)acetaldehyde (9.8 mg, 0.046 mmol). The mixture was stirred at r.t. for 60 min, then sodium triacetoxyborohydride (6.4 mg, 0.037 mmol) was added. After being stirred at room temperature for 2 hrs, 2 N HCl solution in water (0.2 mL) was added, and the reaction was stirred at 50° C. for 30 min. The reaction mixture was diluted with MeOH, and purified via pH 2 preparative HPLC (MeCN/water with TFA) to give the desired product as TFA salt. LC-MS calculated for $C_{37}H_{37}ClN_7O_5(M+H)^+$: m/z=694.3; found 694.3.

Example 94

(S)-1-((2-(2'-chloro-3'-(1,5-dimethyl-1,4,5,6-tetrahydropyrrolo[3,4-d]imidazole-2-carboxamido)-2-methylbiphenyl-3-yl)-7-cyanobenzo[d]oxazol-5-yl)methyl)pyrrolidine-3-carboxylic acid Step 1: 5-tert-butyl 2-ethyl 3a,4,6,6a-tetrahydropyrrolo[3,4-d]imidazole-2,5(1H)-dicarboxylate

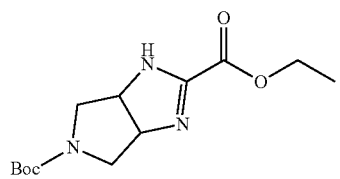

To a solution of cis-tert-butyl 3,4-diaminopyrrolidine-1-carboxylate (Pharmablock, cat # PB05568: 800 mg, 3.97 mmol) in HFIP (5 mL) was added ethyl 2-ethoxy-2-iminoacetate (577 mg, 3.97 mmol). The mixture was stirred at 50° C. for overnight before quenched by adding sat. NaCl solution. Then 1N HCl was added to adjust the pH to 1, which was then extracted with EtOAc for 3 times. The combined organic layers were washed with brine, dried over Na₂SO₄, filtered and concentrated under reduced pressure. The residue was purified by flash chromatography on a silica

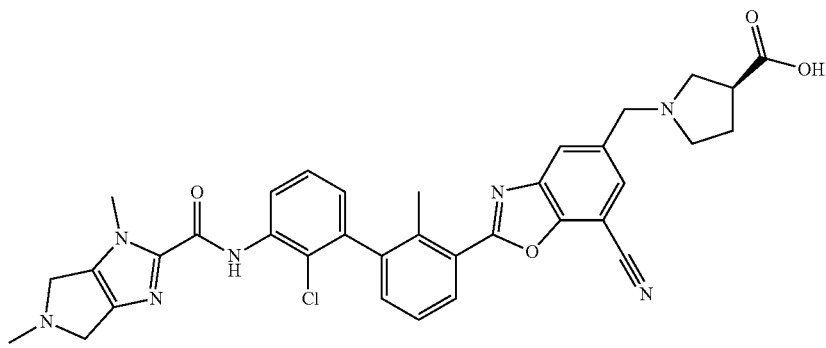 [SMILES: Cc1c(-c2nc3cc(CN4CC[C@H](C(=O)O)C4)cc(C#N)c3o2)cccc1-c1cccc(NC(=O)c2nc3c(n2C)CN(C)C3)c1Cl]

gel column eluting with 0 to 10% MeOH in DCM to afford the desired product. LC-MS calculated for $C_{13}H_{22}N_3O_4$ (M+H)$^+$: m/z=284.3; found 284.3.

Step 2: 5-tert-butyl 2-ethyl 1-methyl-4,6-dihydropyrrolo[3,4-d]imidazole-2,5(1H)-dicarboxylate

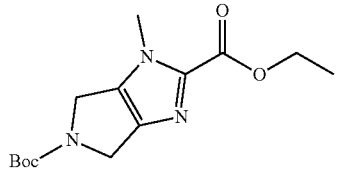 [SMILES: CCOC(=O)c1nc2c(n1C)CN(C(=O)OC(C)(C)C)C2]

To a solution of oxalyl chloride (0.13 mL, 1.48 mmol) in DCM (4 mL) was slowly added DMSO (0.21 mL, 2.96 mmol) for 30 mins. The resulting solution was added DCM solution of 5-tert-butyl 2-ethyl 3a,4,6,6a-tetrahydropyrrolo[3,4-d]imidazole-2,5(1H)-dicarboxylate (210 mg, 0.74 mmol) dropwise. After adding, the solution was stirred for 30 mins before DIEA (0.86 mL, 4.94 mmol) was added. The reaction mixture was warmed to r.t. over 2 hrs, which was then quenched by adding sat. NH$_4$Cl. The mixture was extracted with DCM for 3 times. The combined organic layers were washed with brine, dried over Na$_2$SO$_4$, filtered and concentrated under reduced pressure. The residue was dissolved in DMF (3 mL), K$_2$CO$_3$ (273 mg, 1.97 mmol) and methyl iodide (0.12 mL, 1.97 mmol) were added sequentially. The resulting mixture was stirred at r.t. overnight before 3 mL of water was added. The mixture was extracted with EtOAc for 3 times. The combined organic layers were washed with brine, dried over Na$_2$SO$_4$, filtered and concentrated under reduced pressure. The residue was purified by flash chromatography on a silica gel column eluting with 0 to 100% EtOAc in hexanes to afford the desired product. LC-MS calculated for $C_{14}H_{22}N_3O_4$ (M+H)$^+$: m/z=296.2; found 296.2.

Step 3: tert-butyl 2-(3-bromo-2-chlorophenylcarbamoyl)-1-methyl-4,6-dihydropyrrolo[3,4-d]imidazole-5(1H)-carboxylate

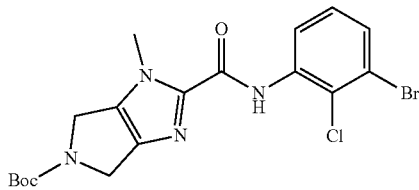 [SMILES: Cn1c(C(=O)Nc2cccc(Br)c2Cl)nc2c1CN(C(=O)OC(C)(C)C)C2]

Potassium tert-butoxide in THF (1.0 M, 2.13 mL) was added to a solution of 5-tert-butyl 2-ethyl 4,6-dihydropyrrolo[3,4-d]imidazole-2,5(1H)-dicarboxylate (400 mg, 1.42 mmol) and 3-bromo-2-chloroaniline (323 mg, 1.56 mmol) in THF (12.0 mL). After being stirred at room temperature for 1 h, the reaction mixture was quenched with water, and extracted with ethyl acetate. The combined organic layers were washed with brine, dried over Na$_2$SO$_4$, filtered, and concentrated under reduced pressure. The residue was purified by flash chromatography on a silica gel column eluting with 100% ethyl acetate in hexanes to afford the desired product. LCMS calculated for $C_{18}H_{21}BrClN_4O_3$(M+H)$^+$: m/z=457.0; found 457.0.

Step 4: tert-butyl 2-(2-chloro-3'-(7-chloro-5-(hydroxymethyl)benzo[d]oxazol-2-yl)-2'-methylbiphenyl-3-ylcarbamoyl)-1-methyl-4,6-dihydropyrrolo[3,4-d]imidazole-5(1H)-carboxylate

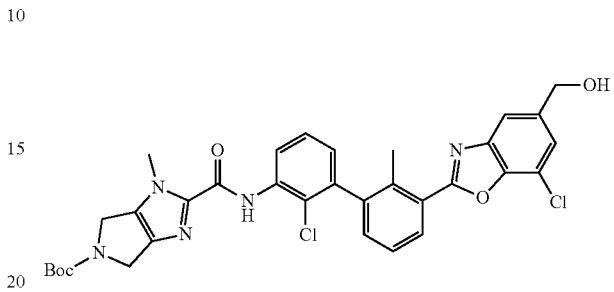

A mixture tert-butyl 2-(3-bromo-2-chlorophenylcarbamoyl)-1-methyl-4,6-dihydropyrrolo[3,4-d]imidazole-5(1H)-carboxylate (150 mg, 0.33 mmol), (7-chloro-2-(2-methyl-3-(4,4,5,5-tetramethyl-1,3,2-dioxaborolan-2-yl)phenyl)benzo[d]oxazol-5-yl)methanol (Example 1, Step 5: 158 mg, 0.39 mmol), and dichloro[1,1'-bis(dicyclohexylphosphino)ferrocene]palladium(II) (27 mg, 0.033 mmol) in 1,4-dioxane (5 ml) and water (1 mL) was added sodium carbonate (70 mg, 0.66 mmol). The reaction mixture was purged with nitrogen and then stirred at 100° C. for 12 hrs. After being cooled to room temperature, the reaction mixture was extracted with ethyl acetate. The combined organic layers were washed with brine, dried over Na$_2$SO$_4$, filtered and concentrated under reduced pressure. The residue was purified by flash chromatography on a silica gel column eluting with 0 to 100% EtOAc in hexanes to afford the desired product. LC-MS calculated for $C_{33}H_{32}Cl_2N_5O_5$ (M+H)$^+$: m/z=648.2; found 648.2.

Step 5: tert-butyl 2-(2-chloro-3'-(7-cyano-5-(hydroxymethyl)benzo[d]oxazol-2-yl)-2'-methylbiphenyl-3-ylcarbamoyl)-1-methyl-4,6-dihydropyrrolo[3,4-d]imidazole-5(1H)-carboxylate

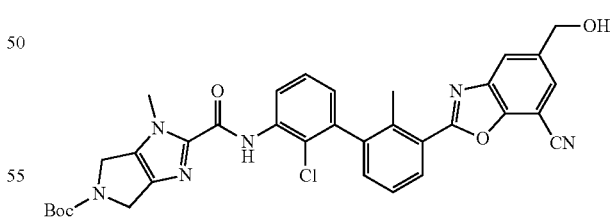

This compound was prepared using similar procedures as described for Example 12 with tert-butyl 2-(2-chloro-3'-(7-chloro-5-(hydroxymethyl)benzo[d]oxazol-2-yl)-2'-methylbiphenyl-3-ylcarbamoyl)-1-methyl-4,6-dihydropyrrolo[3,4-d]imidazole-5 (1H)-carboxylate replacing (7-chloro-2-(2,2'-dimethyl-3'-(pyrido[3,4-b]pyrazin-5-ylamino)-[1,1'-biphenyl]-3-yl)benzo[d]oxazol-5-yl)methanol in Step 1. LC-MS calculated for $C_{34}H_{32}ClN_6O_5$ (M+H)$^+$: m/z=639.2; found 639.2.

Step 6: tert-butyl 2-(2-chloro-3'-(7-cyano-5-formyl-benzo[d]oxazol-2-yl)-2'-methylbiphenyl-3-ylcarbamoyl)-1-methyl-4,6-dihydropyrrolo[3,4-d]imidazole-5(1H)-carboxylate

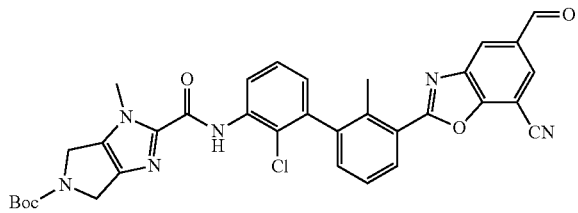 [SMILES: Cc1c(-c2nc3cc(C=O)cc(C#N)c3o2)cccc1-c1cccc(NC(=O)c2nc3c(n2C)CN(C(=O)OC(C)(C)C)C3)c1Cl]

A suspension of tert-butyl 2-(2-chloro-3'-(7-cyano-5-(hydroxymethyl)benzo[d]oxazol-2-yl)-2'-methylbiphenyl-3-ylcarbamoyl)-1-methyl-4,6-dihydropyrrolo[3,4-d]imidazole-5(1H)-carboxylate (20 mg, 0.03 mmol) and manganese dioxide (54 mg, 0.63 mmol) in DCM (6 mL) was stirred at 45° C. for 3 hrs. The reaction was filtered through a short pad of celite and then concentrated to yield a crude residue, which was used directly without further purification. LC-MS calculated for $C_{34}H_{30}ClN_6O_5(M+H)^+$: m/z=637.2; found 637.2.

Step 7: (S)-1-((2-(3'-(5-(tert-butoxycarbonyl)-1-methyl-1,4,5,6-tetrahydropyrrolo[3,4-d]imidazole-2-carboxamido)-2'-chloro-2-methylbiphenyl-3-yl)-7-cyanobenzo[d]oxazol-5-yl)methyl)pyrrolidine-3-carboxylic acid

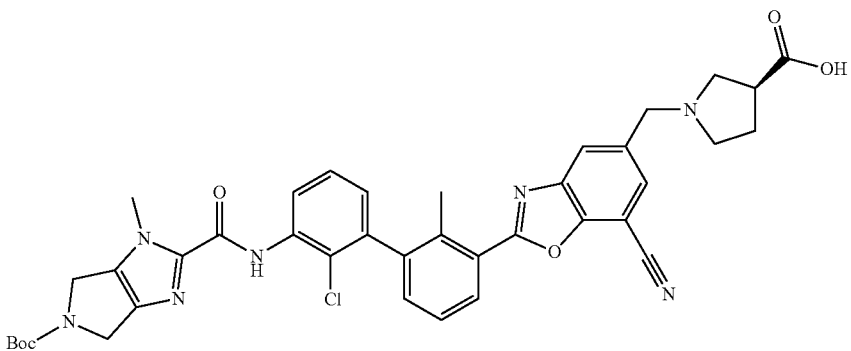 [SMILES: Cc1c(-c2nc3cc(CN4CC[C@H](C(=O)O)C4)cc(C#N)c3o2)cccc1-c1cccc(NC(=O)c2nc3c(n2C)CN(C(=O)OC(C)(C)C)C3)c1Cl]

To a solution tert-butyl 2-(2-chloro-3'-(7-cyano-5-formylbenzo[d]oxazol-2-yl)-2'-methylbiphenyl-3-ylcarbamoyl)-1-methyl-4,6-dihydropyrrolo[3,4-d]imidazole-5(1H)-carboxylate (15.0 mg, 0.024 mmol) in DCM (0.5 ml) was added (S)-pyrrolidine-3-carboxylic acid (6.5 mg, 0.047 mmol) and TEA (0.013 ml, 0.094 mmol). The mixture was stirred at r.t. for 60 min, then sodium triacetoxyborohydride (7.5 mg, 0.035 mmol) was added. The resulting mixture was stirred at r.t. overnight then concentrated. The residue was purified via prep-HPLC (pH=2, MeCN/water with TFA) to give the desired product as the TFA salt. LC-MS calculated for $C_{39}H_{39}ClN_7O_6(M+H)^+$: m/z=736.3; found 736.3.

Step 8: (S)-1-((2-(2'-chloro-3'-(1,5-dimethyl-1,4,5,6-tetrahydropyrrolo[3,4-d]imidazole-2-carboxamido)-2-methylbiphenyl-3-yl)-7-cyanobenzo[d]oxazol-5-yl)methyl)pyrrolidine-3-carboxylic acid To a solution of (S)-1-((2-(3'-(5-(tert-butoxycarbonyl)-1-methyl-1,4,5,6-tetrahydropyrrolo[3,4-d]imidazole-2-carboxamido)-2'-chloro-2-methylbiphenyl-3-yl)-7-cyanobenzo[d]oxazol-5-yl)methyl)pyrrolidine-3-carboxylic acid (10 mg, 0.014 mmol) in DCM (1 mL) was added trifluoroacetic acid (1 mL). The solution was stirred at r.t. for 1 h. then concentrate to dryness. The residue was dissolved in DCM (1.0 mL) then formaldehyde (37 wt % in water, 0.02 mL) was added. The resulting mixture was stirred at r.t. for 10 min, then sodium triacetoxyborohydride (5.8 mg, 0.027 mmol) was added. The reaction mixture was stirred at r.t. overnight then concentrated. The residue was purified via prep-HPLC (pH=2, MeCN/water with TFA) to give the desired product as the TFA salt. LC-MS calculated for $C_{35}H_{33}ClN_7O_4(M+H)^+$: m/z=650.3; found 650.3.

Example 95

(R)-1-((2-(2'-chloro-3'-(5-ethyl-1-methyl-4,5,6,7-tetrahydro-1H-imidazo[4,5-c]pyridine-2-carboxamido)-2-methylbiphenyl-3-yl)-7-cyanobenzo[d]oxazol-5-yl)methyl)-3-methylpyrrolidine-3-carboxylic acid

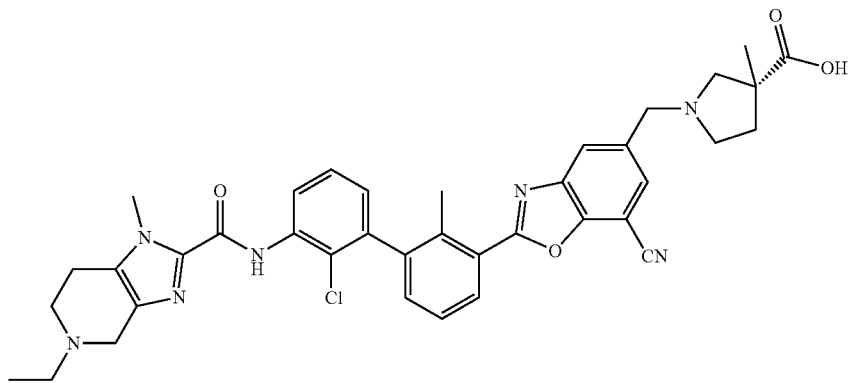 [SMILES: CCN1CCc2c(nc(C(=O)Nc3cccc(-c4cccc(-c5nc6cc(CN7CC[C@@](C)(C(=O)O)C7)cc(C#N)c6o5)c4C)c3Cl)n2C)C1]

Step 1: (R)-1-((2-(3'-(5-(tert-butoxycarbonyl)-1-methyl-4,5,6,7-tetrahydro-1H-imidazo[4,5-c]pyridine-2-carboxamido)-2'-chloro-2-methylbiphenyl-3-yl)-7-cyanobenzo[d]oxazol-5-yl)methyl)-3-methylpyrrolidine-3-carboxylic acid

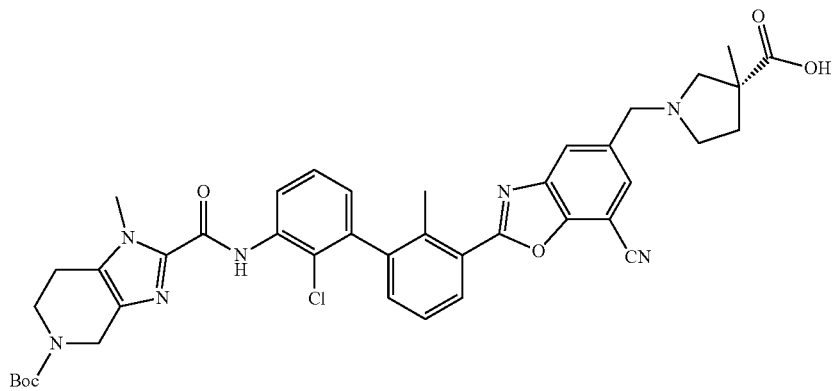 [SMILES: Cc1c(-c2nc3cc(CN4CC[C@@](C)(C(=O)O)C4)cc(C#N)c3o2)cccc1-c1cccc(NC(=O)c2nc3c(n2C)CCN(C(=O)OC(C)(C)C)C3)c1Cl]

To a solution of tert-butyl 2-(2-chloro-3'-(7-cyano-5-formylbenzo[d]oxazol-2-yl)-2'-methylbiphenyl-3-ylcarbamoyl)-1-methyl-6,7-dihydro-1H-imidazo[4,5-c]pyridine-5(4H)-carboxylate (Example 92, step 3: 25 mg, 0.043 mmol) in DCM (1 mL) was added (R)-3-methylpyrrolidine-3-carboxylic acid (7.7 mg, 0.056 mmol) and TEA (0.02 ml, 0.16 mmol). The mixture was stirred at r.t. for 60 min, then sodium triacetoxyborohydride (12.2 mg, 0.056 mmol) was added. The resulting mixture was stirred at r.t. overnight then concentrated. The residue was purified via prep-HPLC (pH=2, MeCN/water with TFA) to give the desired product as the TFA salt. LC-MS calculated for $C_{41}H_{43}ClN_7O_6$(M+H)$^+$: m/z=764.3; found 764.3.

Step 2: (R)-1-((2-(2'-chloro-3'-(5-ethyl-1-methyl-4,5,6,7-tetrahydro-1H-imidazo[4,5-c]pyridine-2-carboxamido)-2-methylbiphenyl-3-yl)-7-cyanobenzo[d]oxazol-5-yl)methyl)-3-methylpyrrolidine-3-carboxylic acid To a solution of (S)-1-((2-(3'-(5-(tert-butoxycarbonyl)-1-methyl-4,5,6,7-tetrahydro-1H-imidazo[4,5-c]pyridine-2-carboxamido)-2'-chloro-2-methylbiphenyl-3-yl)-7-cyanobenzo[d]oxazol-5-yl)methyl)pyrrolidine-3-carboxylic acid (10 mg, 0.013 mmol) in DCM (1 mL) was added trifluoroacetic acid (1 mL). The solution was stirred at r.t. for 1 h. then concentrate to dryness. The residue was dissolved in DCM (1.0 mL) then acetaldehyde (3.0 mg, 0.065 mmol) was added. The resulting mixture was stirred at r.t. for 10 min, then sodium triacetoxyborohydride (5.8 mg, 0.027 mmol) was added. The reaction mixture was stirred at r.t. overnight then concentrated. The residue was purified via prep-HPLC (pH=2, MeCN/water with TFA) to give the desired product as the TFA salt. LC-MS calculated for $C_{38}H_{39}ClN_7O_4$(M+H)$^+$: m/z=692.3; found 692.3. $^1$H NMR (600 MHz, DMSO) δ 9.95 (s, 1H), 8.39 (d, J=1.4 Hz, 1H), 8.28 (dd, J=8.2, 1.5 Hz, 1H), 8.21 (dd, J=7.9, 1.2 Hz, 1H), 8.13 (d, J=1.4 Hz, 1H), 7.59 (t, J=7.7 Hz, 1H), 7.52 (t, J=7.9 Hz, 1H), 7.48 (dd, J=7.6, 1.1 Hz, 1H), 7.20 (dd, J=7.6, 1.5 Hz, 1H), 4.59 (s, 2H), 4.52-4.14 (m, 2H), 3.95 (s, 3H), 3.88-3.24 (m, 8H), 3.03 (m, 2H), 2.46 (s, 3H), 2.39-1.79 (m, 2H), 1.38 (s, 3H), 1.30 (t, J=7.3 Hz, 3H).

Example 96

(R)-1-((7-cyano-2-(3'-(3-(1-(2-hydroxyethyl)azetidin-3-yl)-1,7-naphthyridin-8-ylamino)-2,2'-dimethylbiphenyl-3-yl)benzo[d]oxazol-5-yl)methyl)pyrrolidine-3-carboxylic acid

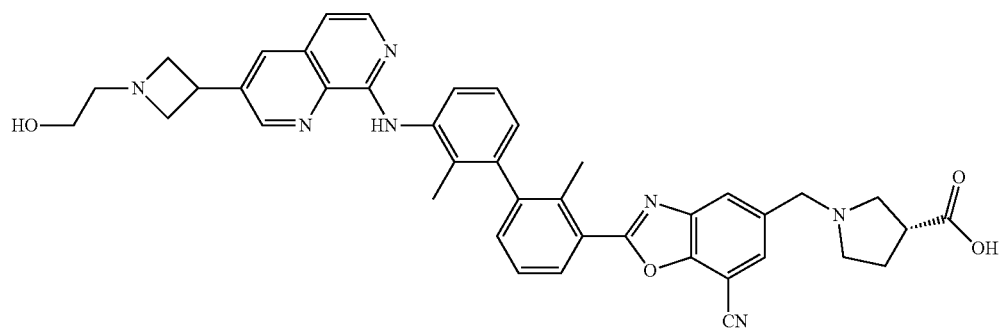 [SMILES: Cc1c(Nc2nccc3cc(C4CN(CCO)C4)cnc23)cccc1-c1cccc(-c2nc3cc(CN4CC[C@@H](C(=O)O)C4)cc(C#N)c3o2)c1C]

Step 1: tert-butyl 3-(8-chloro-1,7-naphthyridin-3-yl)azetidine-1-carboxylate

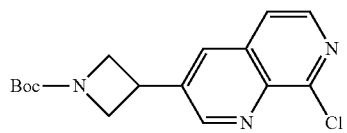 [SMILES: CC(C)(C)OC(=O)N1CC(c2cnc3c(Cl)nccc3c2)C1]

To a long, thin (~20 mL) borosilicate glass vial equipped with a Teflon-coated magnetic stir bar was added 4,7-di-tert-butyl-1,10-phenanthroline (12.01 mg, 0.041 mmol) and NiCl$_2$.glyme (9.02 mg, 0.041 mmol) and 1.0 mL THF. The vial was capped and the resulting suspension was heated briefly with a heat gun until the nickel and ligand were fully solubilized, yielding a pale green solution. The solvent was then removed under vacuum to give a fine coating of the ligated nickel complex (pale evergreen in color). Once dry, 3-bromo-8-chloro-1,7-naphthyridine (100 mg, 0.411 mmol), tert-butyl 3-(trifluoro-14-boranyl)azetidine-1-carboxylate, potassium salt (Combi-Blocks, cat # QC-6288: 108 mg, 0.411 mmol), [Ir{dFCF$_3$ppy}$_2$(bpy)]PF$_6$ (Aldrich, cat #804215: 10.37 mg, 10.27 μmol) and cesium carbonate (201 mg, 0.616 mmol) were added in succession. The vial was then capped and purged and evacuated four times. Under inert atmosphere, 1,4-dioxane (10 mL) was introduced. The vial containing all the reagents was further sealed with parafilm and stirred for 24 hrs approximately 4 cm away from two 26 W fluorescent light bulbs. The reaction mixture was then concentrated under reduced pressure. The residue was purified by flash chromatography on a silica gel column eluting with 0 to 100% EtOAc in hexanes to afford the desired product. LC-MS calculated for C$_{16}$H$_{19}$ClN$_3$O$_2$(M+H)$^+$: m/z=320.2; found 320.2.

Step 2: tert-butyl 3-(8-(3-bromo-2-methylphenylamino)-1,7-naphthyridin-3-yl)azetidine-1-carboxylate

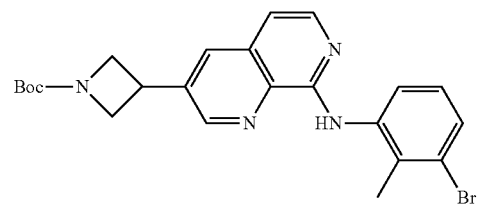 [SMILES: Cc1c(Br)cccc1Nc1nccc2cc(C3CN(C(=O)OC(C)(C)C)C3)cnc12]

A mixture of 3-bromo-2-methylaniline (31.4 mg, 0.169 mmol), tert-butyl 3-(8-chloro-1,7-naphthyridin-3-yl)azetidine-1-carboxylate (45 mg, 0.141 mmol) and sulfuric acid (7.50 μl, 0.141 mmol) in isopropanol (10 ml) was heated at 90° C. for 2 h. The reaction was then cooled to room temperature and diluted with DCM. The reaction was quenched by aqueous NaHCO$_3$ solution, extracted with DCM. The organic phase was dried over MgSO$_4$, filtered and the filtrate was concentrated. The residue was dissolved in DCM (2 mL), di-tert-butyl dicarbonate (123 mg 0.56 mmol) and TEA (57.0 mg, 0.56 mmol) were added subsequently. The resulting reactions mixture was allowed to stir for 2 hrs before quenched with sat. NaHCO$_3$. The mixture was then extracted with ethyl acetate. The combined organic layers were washed with brine, dried over Na$_2$SO$_4$, filtered and concentrated under reduced pressure. The residue was purified by flash chromatography on a silica gel column eluting with 0 to 100% EtOAc in hexanes to afford the desired product. LC-MS calculated for C$_{23}$H$_{26}$BrN$_4$O$_2$ (M+H)$^+$: m/z=469.1/471.1; found 469.2/471.2.

Step 3: tert-butyl 3-(8-(3'-(7-chloro-5-(hydroxymethyl)benzo[d]oxazol-2-yl)-2,2'-dimethylbiphenyl-3-ylamino)-1,7-naphthyridin-3-yl)azetidine-1-carboxylate

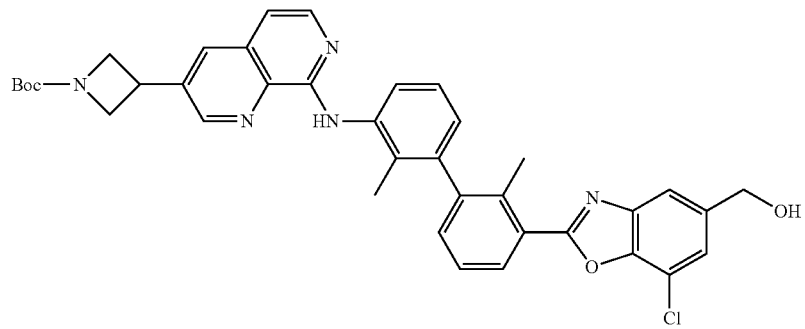

A mixture of tert-butyl 3-(8-(3-bromo-2-methylphenylamino)-1,7-naphthyridin-3-yl)azetidine-1-carboxylate (39.1 mg, 0.083 mmol), (7-chloro-2-(2-methyl-3-(4,4,5,5-tetramethyl-1,3,2-dioxaborolan-2-yl)phenyl)benzo[d]oxazol-5-yl)methanol (Example 1, Step 5: 40 mg, 0.10 mmol), sodium carbonate (24 mg, 0.22 mmol) and tetrakis(triphenylphosphine)palladium(0) (10 mg, 8.9 µmol) in a mixed water (150 µl) and 1,4-dioxane (750 µl) was purged with $N_2$ and then stirred at 100° C. for 2 h. The reaction mixture was cooled to room temperature, diluted with ethyl acetate and then washed with $H_2O$. The organic layer was dried $MgSO_4$, filtered and concentrated to give a crude residue, which was purified by flash chromatography on a silica gel column eluting with 0 to 10% MeOH/DCM to give the desired product. LC-MS calculated for $C_{38}H_{37}ClN_5O_4(M+H)^+$: m/z=662.3; found 662.3.

Step 4: tert-butyl 3-(8-(3'-(7-cyano-5-(hydroxymethyl)benzo[d]oxazol-2-yl)-2,2'-dimethylbiphenyl-3-ylamino)-1,7-naphthyridin-3-yl)azetidine-1-carboxylate

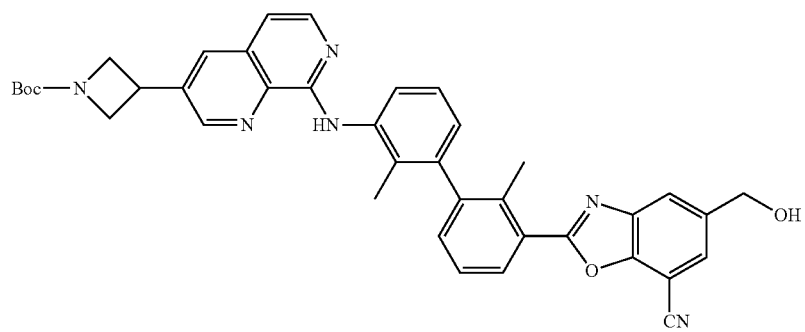 [SMILES: Cc1c(Nc2nccc3cc(C4CN(C(=O)OC(C)(C)C)C4)cnc23)cccc1-c1cccc(-c2nc3cc(CO)cc(C#N)c3o2)c1C]

This compound was prepared using similar procedures as described for Example 12 with tert-butyl 3-(8-(3'-(7-chloro-5-(hydroxymethyl)benzo[d]oxazol-2-yl)-2,2'-dimethylbiphenyl-3-ylamino)-1,7-naphthyridin-3-yl)azetidine-1-carboxylate replacing (7-chloro-2-(2,2'-dimethyl-3'-(pyrido[3,4-b]pyrazin-5-ylamino)-[1,1'-biphenyl]-3-yl)benzo[d]oxazol-5-yl)methanol in Step 1. LC-MS calculated for $C_{39}H_{37}N_6O_4$ $(M+H)^+$: m/z=653.3; found 653.3.

Step 5: tert-butyl 3-(8-(3'-(7-cyano-5-formylbenzo[d]oxazol-2-yl)-2,2'-dimethylbiphenyl-3-ylamino)-1,7-naphthyridin-3-yl)azetidine-1-carboxylate

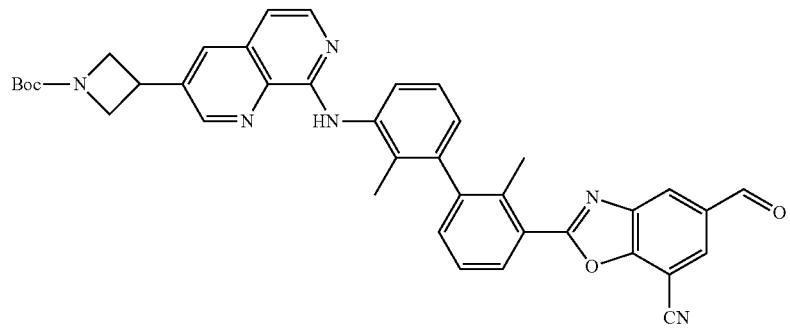 [SMILES: Cc1c(Nc2nccc3cc(C4CN(C(=O)OC(C)(C)C)C4)cnc23)cccc1-c1cccc(-c2nc3cc(C=O)cc(C#N)c3o2)c1C]

A suspension of tert-butyl 3-(8-(3'-(7-cyano-5-(hydroxymethyl)benzo[d]oxazol-2-yl)-2,2'-dimethylbiphenyl-3-ylamino)-1,7-naphthyridin-3-yl)azetidine-1-carboxylate (59 mg, 0.09 mmol) and manganese dioxide (216 mg, 2.42 mmol) in DCM (6 mL) was stirred at 45° C. for 3 hrs. The reaction was filtered through a short pad of celite and then concentrated to yield a crude residue, which was used directly without further purification. LC-MS calculated for $C_{39}H_{35}N_6O_4$ $(M+H)^+$: m/z=651.3; found 651.3.

Step 6: (R)-1-((2-(3'-(3-(1-(tert-butoxycarbonyl)azetidin-3-yl)-1,7-naphthyridin-8-ylamino)-2,2'-dimethylbiphenyl-3-yl)-7-cyanobenzo[d]oxazol-5-yl)methyl)pyrrolidine-3-carboxylic acid

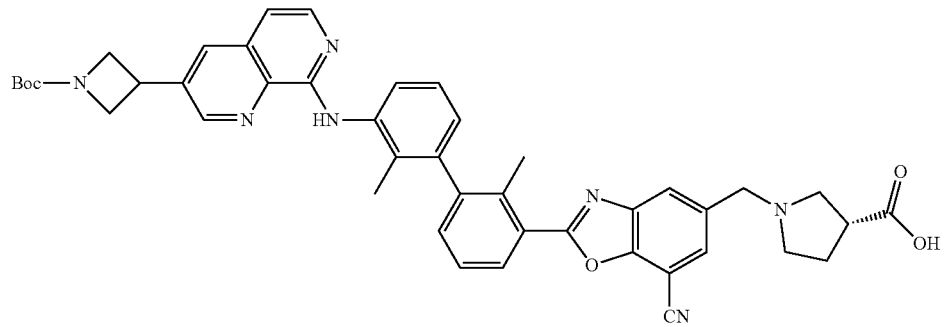 [SMILES: Cc1c(Nc2nccc3cc(C4CN(C(=O)OC(C)(C)C)C4)cnc23)cccc1-c1cccc(-c2nc3cc(CN4CC[C@@H](C(=O)O)C4)cc(C#N)c3o2)c1C]

To a solution tert-butyl 3-(8-(3'-(7-cyano-5-formylbenzo[d]oxazol-2-yl)-2,2'-dimethylbiphenyl-3-ylamino)-1,7-naphthyridin-3-yl)azetidine-1-carboxylate (20 mg, 0.03 mmol) in DCM (1 ml) was added (R)-pyrrolidine-3-carboxylic acid (5.3 mg, 0.05 mmol) and TEA (0.008 ml, 0.061 mmol). The mixture was stirred at r.t. for 60 min, then sodium triacetoxyborohydride (9.8 mg, 0.046 mmol) was added. The resulting mixture was stirred at r.t. overnight then concentrated. The residue was purified via prep-HPLC (pH=2, MeCN/water with TFA) to give the desired product as the TFA salt. LC-MS calculated for $C_{44}H_{44}N_7O_5$ $(M+H)^+$: m/z=750.3; found 750.3.

Step 7: (R)-1-((7-cyano-2-(3'-(3-(1-(2-hydroxyethyl)azetidin-3-yl)-1,7-naphthyridin-8-ylamino)-2,2'-dimethylbiphenyl-3-yl)benzo[d]oxazol-5-yl)methyl)pyrrolidine-3-carboxylic acid To a solution of (R)-1-((2-(3'-(3-(1-(tert-butoxycarbonyl)azetidin-3-yl)-1,7-naphthyridin-8-ylamino)-2,2'-dimethylbiphenyl-3-yl)-7-cyanobenzo[d]oxazol-5-yl)methyl)pyrrolidine-3-carboxylic acid (10 mg, 0.013 mmol) in DCM (1 mL) was added trifluoroacetic acid (1 mL). The solution was stirred at r.t. for 1 h. then concentrate to dryness. The residue was dissolved in DCM (1.0 mL), and 2-(tert-butyldimethylsilyloxy)acetaldehyde (9.8 mg, 0.046 mmol) was added and. The mixture was stirred at r.t. for 60 min, then sodium triacetoxyborohydride (6.4 mg, 0.037 mmol) was added. After being stirred at room temperature for 2 hrs, 2 N HCl solution in water (0.2 mL) was added, and the reaction was stirred at 50° C. for 30 min. The reaction mixture was diluted with MeOH, and purified via pH=2 preparative HPLC (MeCN/water with TFA) to give the desired product as TFA salt. LC-MS calculated for $C_{41}H_{40}N_7O_4$ $(M+H)^+$: m/z=694.3; found 694.3.

Example 97

(3R)-1-((2-(2'-chloro-2-methyl-3'-(3-(pyrrolidin-2-yl)-1,7-naphthyridin-8-ylamino)biphenyl-3-yl)-7-cyanobenzo[d]oxazol-5-yl)methyl)pyrrolidine-3-carboxylic acid

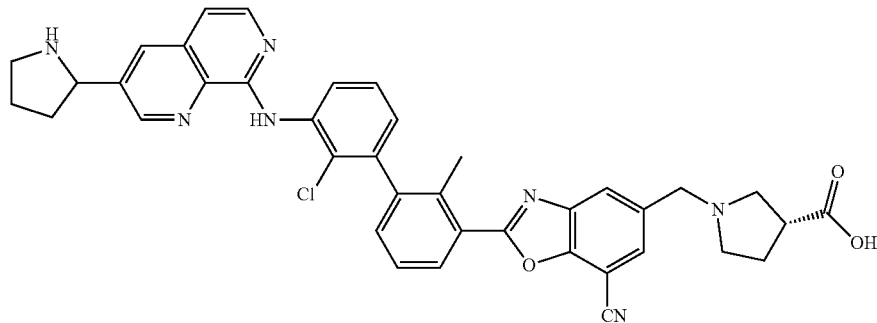 [SMILES: Cc1c(-c2nc3cc(CN4CC[C@@H](C(=O)O)C4)cc(C#N)c3o2)cccc1-c1cccc(Nc2nccc3cc(C4CCCN4)cnc23)c1Cl]

Step 1: tert-butyl 4-(8-chloro-1,7-naphthyridin-3-yl)-4-oxobutylcarbamate

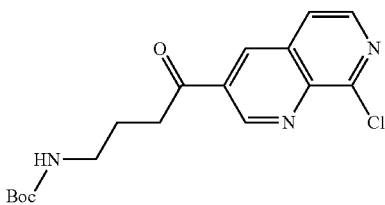 [SMILES: CC(C)(C)OC(=O)NCCCC(=O)c1cnc2c(Cl)nccc2c1]

To a solution of n-butyllithium (2.0 M in cyclohexane, 0.41 mL, 0.821 mmol) in THF (40 ml) was added 3-bromo-8-chloro-1,7-naphthyridine (100 mg, 0.411 mmol) dropwise at −78° C. After stirring at −78° C. for 1 h, tert-butyl 2-oxopyrrolidine-1-carboxylate (Aldrich, cat #464856: 0.140 ml, 0.821 mmol) was added. After stirring for 2 h, the mixture was quenched by sat. NH$_4$Cl, extracted by DCM for 3 times. The combined organic layers were washed with brine, dried over Na$_2$SO$_4$, filtered, and concentrated under reduced pressure. The residue was purified by flash chromatography on a silica gel column eluting with 0-100% ethyl acetate in hexanes to afford the desired product. LCMS calculated for C$_{17}$H$_{21}$ClN$_3$O$_3$ (M+H)$^+$: m/z=350.1; found 350.1.

Step 2: tert-butyl 2-(8-(3-bromo-2-chlorophenylamino)-1,7-naphthyridin-3-yl)pyrrolidine-1-carboxylate

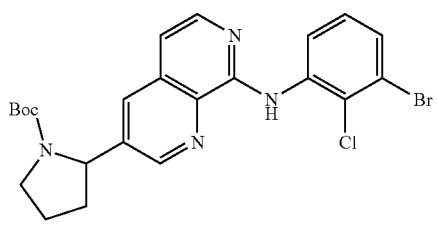 [SMILES: CC(C)(C)OC(=O)N1CCCC1c1cnc2c(Nc3cccc(Br)c3Cl)nccc2c1]

To a reaction vial, 3-bromo-2-chloroaniline (85 mg, 0.412 mmol) and tert-butyl 4-(8-chloro-1,7-naphthyridin-3-yl)-4-oxobutylcarbamate (120 mg, 0.343 mmol) were suspended in isopropanol (10 ml). Sulfuric acid (0.018 ml, 0.343 mmol) was added to the reaction mixture. The resulting mixture was heated to 100° C. for 2 hrs then concentrate to dryness.

The residue was dissolved in DCM (1.0 mL), TEA (0.1 mL, 0.68 mmol) and sodium triacetoxyborohydride (145 mg, 0.68 mmol) were added and. The mixture was stirred at r.t. for overnight before quenched with sat. NaHCO$_3$. The mixture was then extracted with DCM. The combined organic layers were washed with brine, dried over Na$_2$SO$_4$, filtered and concentrated under reduced pressure. The residue was dissolved in DCM (2 mL), di-tert-butyl dicarbonateused (123 mg 0.56 mmol) and TEA (57.0 mg, 0.56 mmol) were added subsequently. The resulting reactions mixture was allowed to stir for 2 hrs before quenched with sat. NaHCO$_3$. The mixture was then extracted with ethyl acetate. The combined organic layers were washed with brine, dried over Na$_2$SO$_4$, filtered and concentrated under reduced pressure. The residue was purified by flash chromatography on a silica gel column eluting with 0 to 100% EtOAc in hexanes to afford the desired product. LC-MS calculated for C$_{23}$H$_{25}$BrClN$_4$O$_2$(M+H)$^+$: m/z=503.1; found 503.1.

Step 3: tert-butyl 2-(8-(2-chloro-3'-(7-chloro-5-(hydroxymethyl)benzo[d]oxazol-2-yl)-2'-methylbiphenyl-3-ylamino)-1,7-naphthyridin-3-yl)pyrrolidine-1-carboxylate

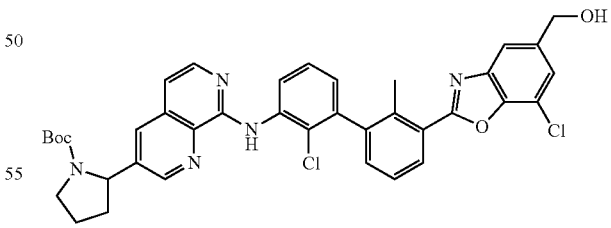

A mixture of N-(3-bromo-2-chlorophenyl)-3-(pyrrolidin-2-yl)-1,7-naphthyridin-8-amine (30 mg, 0.075 mmol), (7-chloro-2-(2-methyl-3-(4,4,5,5-tetramethyl-1,3,2-dioxaborolan-2-yl)phenyl)benzo[d]oxazol-5-yl)methanol (Example 1, Step 5: 38 mg, 0.075 mmol), sodium carbonate (16 mg, 0.15 mmol) and tetrakis(triphenylphosphine)palladium (0) (8.7 mg, 7.5 µmol) in a mixed water (150 µl) and 1,4-dioxane (750 µl) was purged with N$_2$ and then stirred at 100° C. for 2 hrs. The reaction mixture was cooled to room temperature, diluted with ethyl acetate and then washed with H₂O. The organic layer was dried over MgSO₄, filtered and concentrated to give a crude residue, which was purified by flash chromatography on a silica gel column eluting with 0 to 100% EtOAc in hexanes to give the desired product. LC-MS calculated for $C_{38}H_{36}Cl_2N_5O_4$ (M+H)⁺: m/z=696.2; found 696.2.

Step 4: tert-butyl 2-(8-(2-chloro-3'-(7-cyano-5-(hydroxymethyl)benzo[d]oxazol-2-yl)-2'-methylbiphenyl-3-ylamino)-1,7-naphthyridin-3-yl)pyrrolidine-1-carboxylate

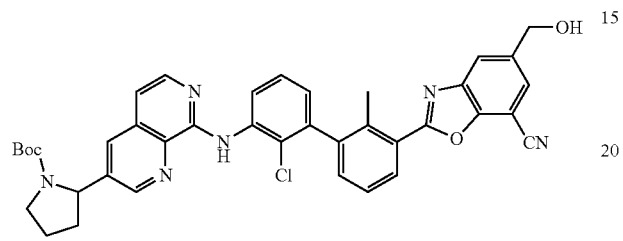

This compound was prepared using similar procedures as described for Example 12 with tert-butyl 2-(8-(2-chloro-3'-(7-chloro-5-(hydroxymethyl)benzo[d]oxazol-2-yl)-2'-methylbiphenyl-3-ylamino)-1,7-naphthyridin-3-yl)pyrrolidine-1-carboxylate replacing (7-chloro-2-(2,2'-dimethyl-3'-(pyrido[3,4-b]pyrazin-5-ylamino)-[1,1'-biphenyl]-3-yl)benzo[d]oxazol-5-yl)methanol in Step 1. LC-MS calculated for $C_{39}H_{36}ClN_6O_4$(M+H)⁺: m/z=687.2; found 687.2.

Step 5: tert-butyl 2-(8-(2-chloro-3'-(7-cyano-5-formylbenzo[d]oxazol-2-yl)-2'-methylbiphenyl-3-ylamino)-1,7-naphthyridin-3-yl)pyrrolidine-1-carboxylate

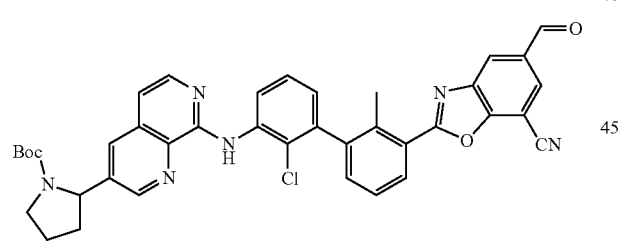

A suspension of tert-butyl 2-(8-(2-chloro-3'-(7-cyano-5-(hydroxymethyl)benzo[d]oxazol-2-yl)-2'-methylbiphenyl-3-ylamino)-1,7-naphthyridin-3-yl)pyrrolidine-1-carboxylate (40 mg, 0.06 mmol) and manganese dioxide (216 mg, 2.42 mmol) in DCM (6 mL) was stirred at 45° C. for 3 hrs. The reaction was filtered through a short pad of celite and then concentrated to yield a crude residue, which was used directly without further purification. LC-MS calculated for $C_{39}H_{34}ClN_6O_4$(M+H)⁺: m/z=685.2; found 685.2.

Step 6: (3R)-1-((2-(2'-chloro-2-methyl-3'-(3-(pyrrolidin-2-yl)-1,7-naphthyridin-8-ylamino)biphenyl-3-yl)-7-cyanobenzo[d]oxazol-5-yl)methyl)pyrrolidine-3-carboxylic acid To a solution tert-butyl 2-(8-(2-chloro-3'-(7-cyano-5-formylbenzo[d]oxazol-2-yl)-2'-methylbiphenyl-3-ylamino)-1,7-naphthyridin-3-yl)pyrrolidine-1-carboxylate (20 mg, 0.03 mmol) in DCM (1 ml) was added (R)-pyrrolidine-3-carboxylic acid (5.3 mg, 0.05 mmol) and TEA (0.008 ml, 0.061 mmol). The mixture was stirred at r.t. for 60 min, then sodium triacetoxyborohydride (9.8 mg, 0.046 mmol) was added. The resulting mixture was stirred at r.t. overnight then concentrated. The residue was dissolved in DCM (1 mL) and trifluoroacetic acid (1 mL). The solution was stirred at r.t. for 1 h. then concentrate. The residue was purified via prep-HPLC (pH=2, MeCN/water with TFA) to give the desired product as the TFA salt. LC-MS calculated for $C_{39}H_{35}ClN_7O_3$(M+H)⁺: m/z=684.2; found 684.2.

Example 98

(3R)-1-((7-cyano-2-(2,2'-dimethyl-3'-(3-(pyrrolidin-2-yl)-1,7-naphthyridin-8-ylamino)biphenyl-3-yl)benzo[d]oxazol-5-yl)methyl)pyrrolidine-3-carboxylic acid

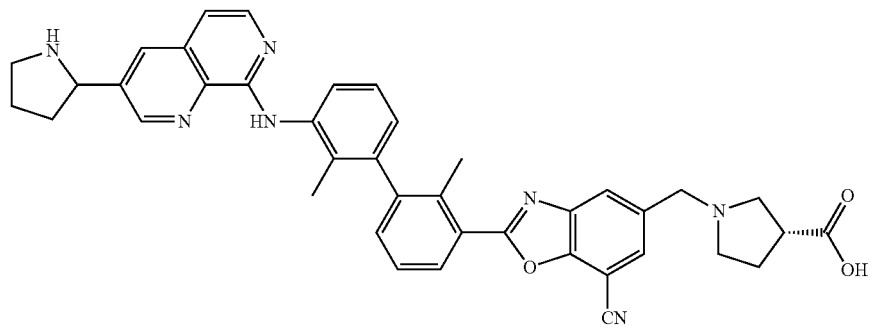 [SMILES: Cc1c(Nc2nccc3cc(C4CCCN4)cnc23)cccc1-c1cccc(-c2nc3cc(CN4CC[C@@H](C(=O)O)C4)cc(C#N)c3o2)c1C]

271

Step 1: tert-butyl 2-(8-(3-bromo-2-methylphenylamino)-1,7-naphthyridin-3-yl)pyrrolidine-1-carboxylate

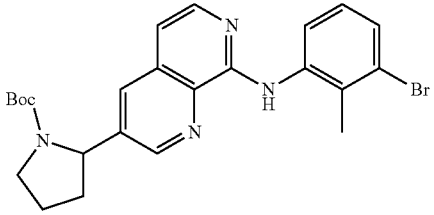 [SMILES: Cc1c(Br)cccc1Nc1nccc2cc(C3CCCN3C(=O)OC(C)(C)C)cnc12]

This compound was prepared using similar procedure as described for Example 97 with 3-bromo-2-methylaniline replacing 3-bromo-2-chloroaniline in step 2. The enantiopure compounds were obtained by chiral HPLC separation. The enantiopure compound (Peak 1 compound) that was eluted first in the chromatography was used for next reactions. LC-MS calculated for $C_{24}H_{28}BrN_4O_2(M+H)^+$: m/z=483.1, 485.1; found 483.1, 485.1.

Step 2: (3R)-1-((7-cyano-2-(2,2'-dimethyl-3'-(3-(pyrrolidin-2-yl)-1,7-naphthyridin-8-ylamino)biphenyl-3-yl)benzo[d]oxazol-5-yl)methyl)pyrrolidine-3-carboxylic acid This compound was prepared using similar procedures as described for Example 97 with tert-butyl 2-(8-(3-bromo-2-methylphenylamino)-1,7-naphthyridin-3-yl)pyrrolidine-1-carboxylate replacing tert-butyl 2-(8-(3-bromo-2-chlorophenylamino)-1,7-naphthyridin-3-yl)pyrrolidine-1-carboxylate in Step 3. The reaction mixture was diluted with MeOH and then purified by prep-HPLC (pH=2, acetonitrile/water+ TFA) to give the desired product as TFA salt. LC-MS calculated for $C_{40}H_{38}N_7O_3$ $(M+H)^+$: m/z=664.3; found 664.3. $^1$H NMR (600 MHz, DMSO) δ 9.04 (s, 1H), 8.48 (s, 1H), 8.39 (d, J=1.2 Hz, 1H), 8.19 (dd, J=7.9, 1.1 Hz, 2H), 8.12 (d, J=1.3 Hz, 1H), 8.02 (s, 1H), 7.58 (t, J=7.7 Hz, 1H), 7.47 (d, J=6.6 Hz, 1H), 7.41 (t, J=7.8 Hz, 1H), 7.23 (d, J=6.1 Hz, 1H), 7.05 (s, 1H), 4.95-4.81 (m, 1H), 4.58 (s, 2H), 3.81-3.16 (m, 7H), 2.57-2.50 (m, 1H), 2.48 (s, 3H), 2.29-2.07 (m, 5H), 2.05 (s, 3H).

Example 99

(3R)-1-((7-cyano-2-(2,2'-dimethyl-3'-(3-(pyrrolidin-2-yl)-1,7-naphthyridin-8-ylamino)biphenyl-3-yl)benzo[d]oxazol-5-yl)methyl)pyrrolidine-3-carboxylic acid

272

Step 1: tert-butyl 2-(8-(3-bromo-2-methylphenylamino)-1,7-naphthyridin-3-yl)pyrrolidine-1-carboxylate

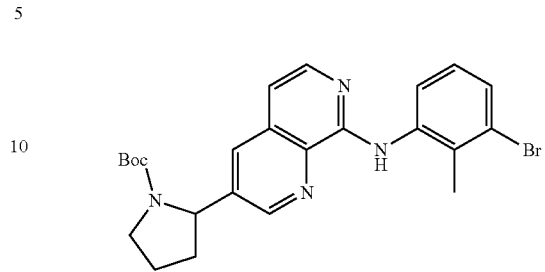

This compound was prepared using similar procedure as described for Example 97 with 3-bromo-2-methylaniline replacing 3-bromo-2-chloroaniline in step 2. The enantiopure compounds were obtained by chiral HPLC separation. The enantiopure compound (Peak 2 compound) that was eluted second in the chromatography was used for next reactions. LC-MS calculated for $C_{24}H_{28}BrN_4O_2(M+H)^+$: m/z=483.1, 485.1; found 483.1, 485.1.

Step 2: (3R)-1-((7-cyano-2-(2,2'-dimethyl-3'-(3-(pyrrolidin-2-yl)-1,7-naphthyridin-8-ylamino)biphenyl-3-yl)benzo[d]oxazol-5-yl)methyl)pyrrolidine-3-carboxylic acid This compound was prepared using similar procedures as described for Example 97 with tert-butyl 2-(8-(3-bromo-2-methylphenylamino)-1,7-naphthyridin-3-yl)pyrrolidine-1-carboxylate replacing tert-butyl 2-(8-(3-bromo-2-chlorophenylamino)-1,7-naphthyridin-3-yl)pyrrolidine-1-carboxylate in Step 3. The reaction mixture was diluted with MeOH and then purified by prep-HPLC (pH=2, acetonitrile/water+ TFA) to give the desired product as TFA salt. LC-MS calculated for $C_{40}H_{38}N_7O_3$ $(M+H)^+$: m/z=664.3; found 664.3.

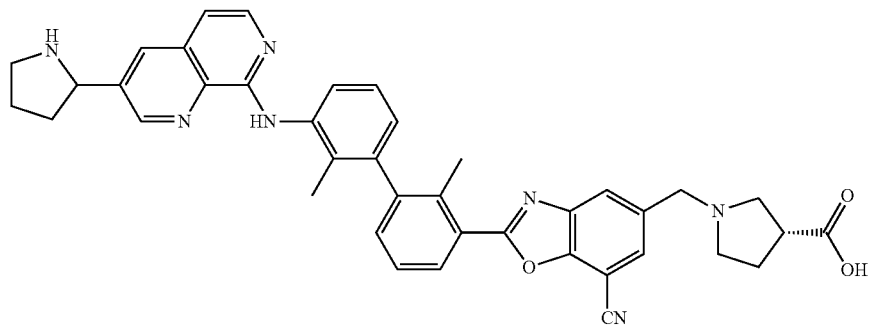 [SMILES: Cc1c(Nc2nccc3cc(C4CCCN4)cnc23)cccc1-c1cccc(-c2nc3cc(CN4CC[C@@H](C(=O)O)C4)cc(C#N)c3o2)c1C]

Example 100

(R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)-3-methylpyrrolidine-3-carboxylic acid

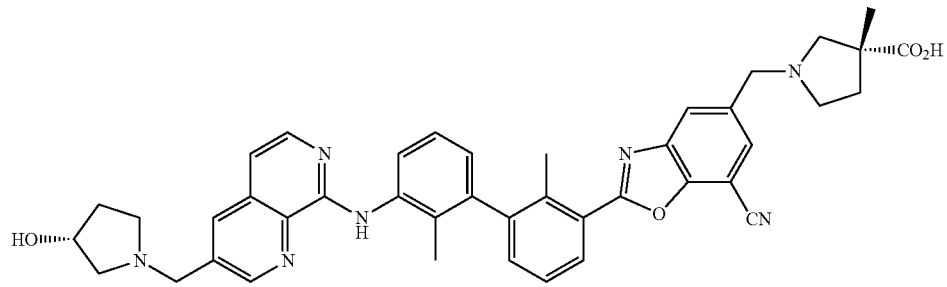 [SMILES: Cc1c(Nc2nccc3cc(CN4CC[C@@H](O)C4)cnc23)cccc1-c1cccc(-c2nc3cc(CN4CC[C@@](C)(C(=O)O)C4)cc(C#N)c3o2)c1C]

This compound was prepared using similar procedures as described for Example 24 with (R)-3-methylpyrrolidine-3-carboxylic acid replacing (R)-pyrrolidine-3-carboxylic acid in Step 5. The reaction mixture was diluted with MeOH and then purified by prep-HPLC (pH=2, acetonitrile/water+TFA) to give the desired product as TFA salt. LC-MS calculated for $C_{42}H_{42}N_7O_4$ (M+H)$^+$: m/z=708.3; found 708.3. $^1$H NMR (500 MHz, DMSO) δ 9.07 (s, 1H), 8.52 (s, 1H), 8.41 (s, 1H), 8.21 (m, 2H), 8.15 (s, 1H), 8.06 (s, 1H), 7.60 (t, J=7.7 Hz, 1H), 7.49 (d, J=7.5 Hz, 1H), 7.42 (t, J=7.7 Hz, 1H), 7.24 (d, J=5.8 Hz, 1H), 7.05 (d, J=6.3 Hz, 1H), 4.85-4.41 (m, 5H), 3.96-3.21 (m, 8H), 2.50 (s, 3H), 2.37 (m, 2H), 2.08 (s, 3H), 1.87 (m, 2H), 1.38 (s, 3H).

Example 101

(R)-3-((7-cyano-2-(3'-(3-((3-hydroxypyrrolidin-1-yl)methyl)-1,7-naphthyridin-8-ylamino)-2,2'-dimethylbiphenyl-3-yl)benzo[d]oxazol-5-yl)methylamino)propanoic acid

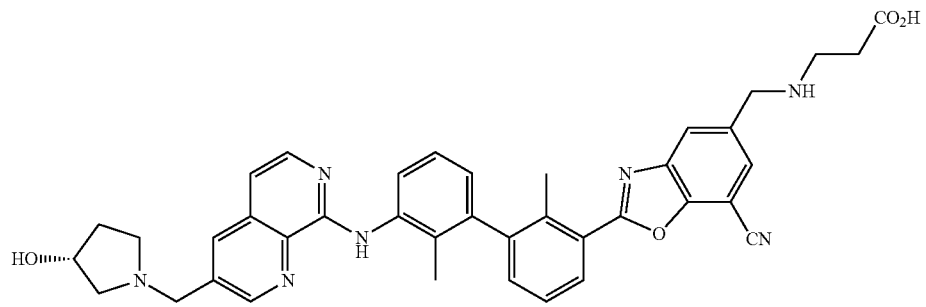 [SMILES: Cc1c(Nc2nccc3cc(CN4CC[C@@H](O)C4)cnc23)cccc1-c1cccc(-c2nc3cc(CNCCC(=O)O)cc(C#N)c3o2)c1C]

This compound was prepared using similar procedures as described for Example 24 with 3-aminopropanoic acid replacing (R)-pyrrolidine-3-carboxylic acid in Step 5. The reaction mixture was diluted with MeOH and then purified by prep-HPLC (pH=2, acetonitrile/water+TFA) to give the desired product as TFA salt. LC-MS calculated for $C_{39}H_{38}N_7O_4$ (M+H)$^+$: m/z=668.3; found 668.3.

Example 102

(R)-1-((7-cyano-2-(3'-(3-fluoro-4-(((R)-3-hydroxy-pyrrolidin-1-yl)methyl)pyridin-2-ylamino)-2,2'-dimethylbiphenyl-3-yl)benzo[d]oxazol-5-yl)methyl)pyrrolidine-3-carboxylic acid

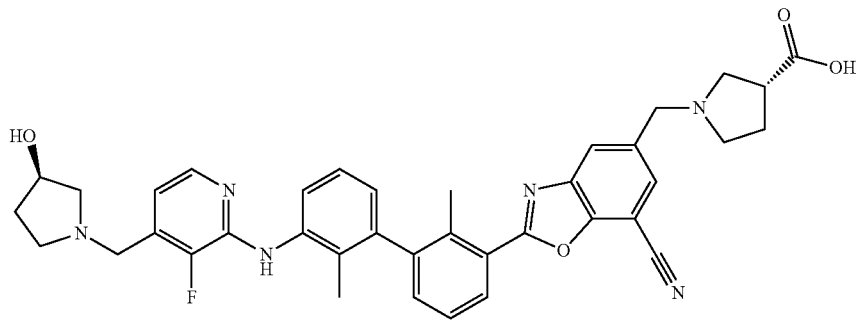 [SMILES: Cc1c(Nc2nccc(CN3CC[C@@H](O)C3)c2F)cccc1-c1cccc(-c2nc3cc(CN4CC[C@@H](C(=O)O)C4)cc(C#N)c3o2)c1C]

Step 1: (R)-1-((2-bromo-3-fluoropyridin-4-yl)methyl)pyrrolidin-3-ol

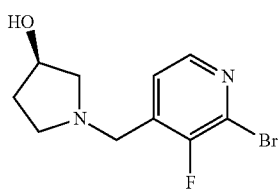 [SMILES: O[C@@H]1CCN(Cc2ccnc(Br)c2F)C1]

A mixture of 2-bromo-3-fluoroisonicotinaldehyde (70.0 mg, 0.343 mmol) and (R)-pyrrolidin-3-ol (59.8 mg, 0.686 mmol) in DCM (2.0 ml) was stirred at r.t. for 10 min. Sodium triacetoxyborohydride (218 mg, 1.029 mmol) was then added and the mixture was stirred at r.t. for 2 h. The mixture was diluted with DCM, washed with 1 N NaOH, water, brine, dried over $Na_2SO_4$, filtered and concentrated. The product was purified by chromatography eluting with DCM/MeOH (MeOH 0-10%). LC-MS calculated for $C_{10}H_{13}BrFN_2O$ $(M+H)^+$: m/z=275.0, 277.0; found 275.1, 277.1.

Step 2: (R)-1-((3-fluoro-2-(2-methyl-3-(4,4,5,5-tetramethyl-1,3,2-dioxaborolan-2-yl)phenylamino)pyridin-4-yl)methyl)pyrrolidin-3-ol

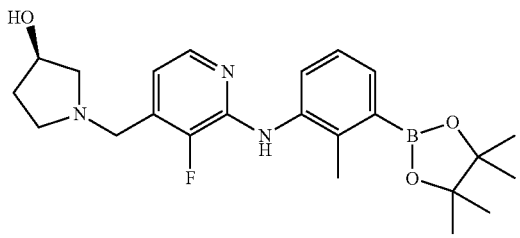 [SMILES: Cc1c(Nc2nccc(CN3CC[C@@H](O)C3)c2F)cccc1B1OC(C)(C)C(C)(C)O1]

A mixture of 2-methyl-3-(4,4,5,5-tetramethyl-1,3,2-dioxaborolan-2-yl)aniline (0.254 g, 1.090 mmol), (R)-1-((2-bromo-3-fluoropyridin-4-yl)methyl)pyrrolidin-3-ol (0.20 g, 0.727 mmol), cesium carbonate (0.592 g, 1.817 mmol) and chloro[(4,5-bis(diphenylphosphino)-9,9-dimethylxanthene)-2-(2'-amino-1,1'-biphenyl)]palladium(II) (0.019 g, 0.022 mmol) in dioxane (3.0 ml) was vacuumed and refilled with nitrogen and then stirred at 100° C. for 2 h. The mixture was filtered and concentrated and the crude was used in the next step directly. LC-MS calculated for $C_{23}H_{32}BFN_3O_3$ $(M+H)^+$: m/z=428.2; found 428.3.

Step 3: (R)-7-chloro-2-(3'-((3-fluoro-4-((3-hydroxypyrrolidin-1-yl)methyl)pyridin-2-yl)amino)-2,2'-dimethyl-[1,1'-biphenyl]-3-yl)benzo[d]oxazole-5-carbaldehyde A mixture of (R)-1-((3-fluoro-2-((2-methyl-3-(4,4,5,5-tetramethyl-1,3,2-dioxaborolan-2-yl)phenyl)amino)pyridin-4-yl)methyl)pyrrolidin-3-ol (0.10 g, 0.234 mmol), 2-(3-bromo-2-methylphenyl)-7-chlorobenzo[d]oxazole-5-carbaldehyde (Example 10, Step 1: 0.098 g, 0.281 mmol), potassium phosphate, tribasic (0.099 g, 0.468 mmol) and tetrakis(triphenylphosphine)palladium(0) (0.027 g, 0.023 mmol) in dioxane (2 ml) and water (0.5 ml) was vacuumed and refilled with nitrogen for 3 times and then the reaction was stirred at 110° C. for 3 h. The mixture was diluted with water and ethyl acetate, the organic phase was separated and washed with water, brine dried and concentrated. The product was purified by chromatograph eluting with DCM/MeOH (MeOH 0-15%). LC-MS calculated for $C_{32}H_{29}C_1FN_4O_3(M+H)^+$: m/z=571.2; found 571.1.

Step 4: (R)-2-(3'-(3-fluoro-4-((3-hydroxypyrrolidin-1-yl)methyl)pyridin-2-ylamino)-2,2'-dimethylbiphenyl-3-yl)-5-formylbenzo[d]oxazole-7-carbonitrile This compound was prepared using similar procedures as described for Example 12 with (R)-7-chloro-2-(3'-((3-fluoro-4-((3-hydroxypyrrolidin-1-yl)methyl)pyridin-2-yl)

amino)-2,2'-dimethyl-[1,1'-biphenyl]-3-yl)benzo[d]oxazole-5-carbaldehyde replacing (7-chloro-2-(2,2'-dimethyl-3'-(pyrido[3,4-b]pyrazin-5-ylamino)-[1,1'-biphenyl]-3-yl)benzo[d]oxazol-5-yl)methanol in Step 1. LC-MS calculated for $C_{33}H_{29}FN_5O_3(M+H)^+$: m/z=562.2; found 562.3.

Step 5: (R)-1-((7-cyano-2-(3'-(3-fluoro-4-(((R)-3-hydroxypyrrolidin-1-yl)methyl)pyridin-2-ylamino)-2,2'-dimethylbiphenyl-3-yl)benzo[d]oxazol-5-yl)methyl)pyrrolidine-3-carboxylic acid This compound was prepared using similar procedures as described for Example 16 with (R)-2-(3'-(3-fluoro-4-((3-hydroxypyrrolidin-1-yl)methyl)pyridin-2-ylamino)-2,2'-dimethylbiphenyl-3-yl)-5-formylbenzo[d]oxazole-7-carbonitrile replacing (S)-7-chloro-2-(3'-(3-((3-hydroxypyrrolidin-1-yl)methyl)-1,7-naphthyridin-8-ylamino)-2,2'-dimethylbiphenyl-3-yl)benzo[d]oxazole-5-carbaldehyde in Step 7. The reaction mixture was diluted with MeOH and then purified by prep-HPLC (pH=2, acetonitrile/water+TFA) to give the desired product as TFA salt. LC-MS calculated for $C_{38}H_{38}FN_6O_4(M+H)^+$: m/z=661.3; found 661.4.

Example 103

(R)-1-((2-(2'-chloro-3'-(6-isopropyl-4,5,6,7-tetrahydro-2H-pyrazolo[3,4-c]pyridin-2-yl)-2-methylbiphenyl-3-yl)-7-cyano benzo[d]oxazol-5-yl)methyl)-N-methylpyrrolidine-3-carboxamide

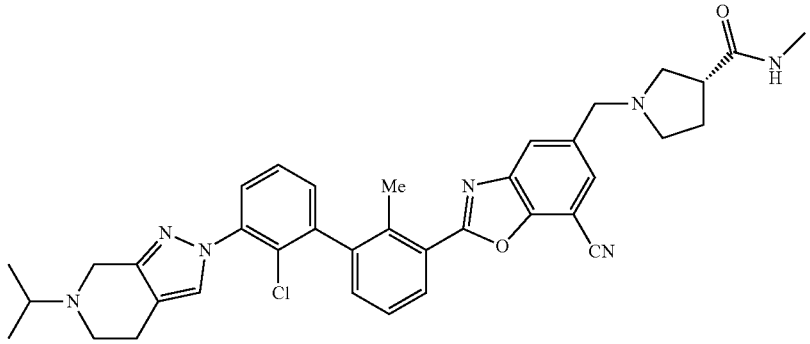 [SMILES: CNC(=O)[C@@H]1CCN(Cc2cc(C#N)c3oc(-c4cccc(-c5cccc(-n6cc7c(n6)CN(C(C)C)CC7)c5Cl)c4C)nc3c2)C1]

Hunig's base (8.2 μl, 0.047 mmol) was added to a DMF (157 μl) solution of (R)-1-((2-(2'-chloro-3'-(6-isopropyl-4,5,6,7-tetrahydro-2H-pyrazolo[3,4-c]pyridin-2-yl)-2-methyl-[1,1'-biphenyl]-3-yl)-7-cyanobenzo[d]oxazol-5-yl)methyl)pyrrolidine-3-carboxylic acid (Example 87, 20 mg, 0.031 mmol), 2M methylamine in THF (23.6 μl, 0.047 mmol), and (benzotriazol-1-yloxy)tris(dimethylamino)phosphonium hexafluorophosphate (16.7 mg, 0.038 mmol). After stirring at room temperature for 1 h, the mixture was concentrated and diluted with MeOH and then purified by prep-HPLC (pH=2, acetonitrile/water+TFA) to give the desired product as its TFA salt. LC-MS calculated for $C_{37}H_{39}ClN_7O_2(M+H)^+$: m/z=648.3; found 648.3.

Example 104

(R)-1-((2-(2'-chloro-3'-(6-isopropyl-4,5,6,7-tetrahydro-2H-pyrazolo[3,4-c]pyridin-2-yl)-2-methylbiphenyl-3-yl)-7-cyanobenzo[d]oxazol-5-yl)methyl)-N-(2-hydroxyethyl)pyrrolidine-3-carboxamide

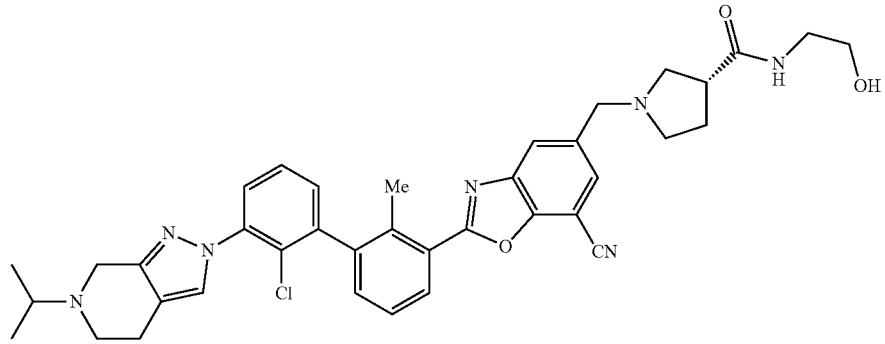 [SMILES: Cc1c(-c2nc3cc(CN4CC[C@@H](C(=O)NCCO)C4)cc(C#N)c3o2)cccc1-c1cccc(-n2cc3c(n2)CN(C(C)C)CC3)c1Cl]

Hunig's base (8.2 µl, 0.047 mmol) was added to a DMF (157 µl) solution of (R)-1-((2-(2'-chloro-3'-(6-isopropyl-4,5,6,7-tetrahydro-2H-pyrazolo[3,4-c]pyridin-2-yl)-2-methyl-[1,1'-biphenyl]-3-yl)-7-cyanobenzo[d]oxazol-5-yl)methyl) pyrrolidine-3-carboxylic acid (Example 87, 20 mg, 0.031 mmol), 2-aminoethanol (4.0 µl, 0.047 mmol), and (benzotriazol-1-yloxy)tris(dimethylamino)phosphonium hexafluorophosphate (16.7 mg, 0.038 mmol). After stirring at room temperature for 1 h, the mixture was concentrated and diluted with MeOH and then purified by prep-HPLC (pH=2, acetonitrile/water+TFA) to give the desired product as its TFA salt. LC-MS calculated for $C_{38}H_{41}ClN_7O_3(M+H)^+$: m/z=678.3; found 678.3.

Example 105

(R)-1-((7-cyano-2-(3'-(5-(2-(dimethylamino)acetyl)-5,6-dihydro-4H-pyrrolo[3,4-d]thiazol-2-yl)-2,2'-dimethylbiphenyl-3-yl)benzo[d]oxazol-5-yl)methyl) pyrrolidine-3-carboxylic acid

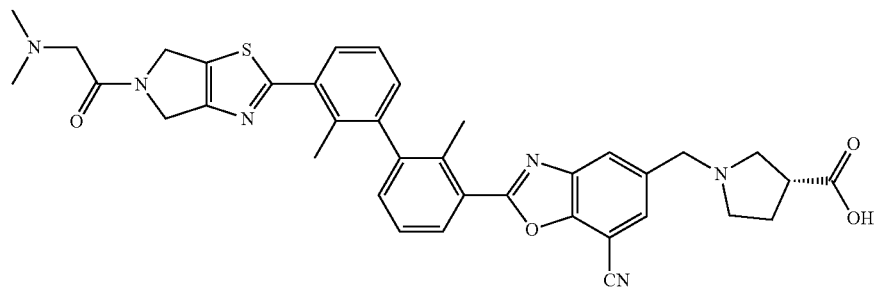 [SMILES: Cc1c(-c2nc3cc(CN4CC[C@@H](C(=O)O)C4)cc(C#N)c3o2)cccc1-c1cccc(-c2nc3c(s2)CN(C(=O)CN(C)C)C3)c1C]

Step 1: tert-butyl 2-bromo-4H-pyrrolo[3,4-d]thiazole-5(6H)-carboxylate

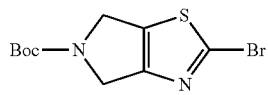

To a stirred solution of 2-bromo-5,6-dihydro-4H-pyrrolo [3,4-d]thiazole, HBr (Aurum Pharm, cat # MR22320: 220.0 mg, 0.769 mmol) and N,N-diisopropylethylamine (0.269 ml, 1.539 mmol) in DCM (5.0 ml), Boc-anhydride (201 mg, 0.923 mmol) was added at room temperature. After 1 hour, the reaction mixture was diluted with EtOAc (100 mL), and washed with water (3×15 mL). The organic layer was dried over $Na_2SO_4$, filtered and the filtrate was concentrated to afford crude tert-butyl 2-bromo-4H-pyrrolo[3,4-d]thiazole-5(6H)-carboxylate (220 mg, 0.724 mmol, 93.6% yield), which was used directly in the next step without further purification. LC-MS calculated for $C_{10}H_{14}BrN_2O_2S$ $(M+H)^+$: m/z=305.0/307.0; found 305.0/307.0.

Step 2: tert-butyl 2-(3'-(7-chloro-5-(hydroxymethyl) benzo[d]oxazol-2-yl)-2,2'-dimethylbiphenyl-3-yl)-4H-pyrrolo[3,4-d]thiazole-5(6H)-carboxylate

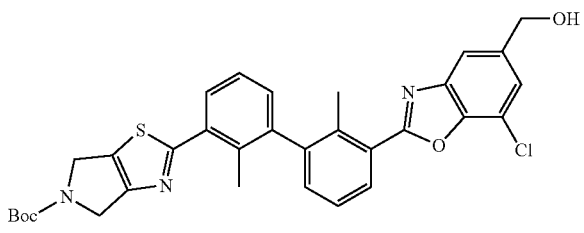 [SMILES: Cc1c(-c2nc3cc(CO)cc(Cl)c3o2)cccc1-c1cccc(-c2nc3c(s2)CN(C(=O)OC(C)(C)C)C3)c1C]

A slurry of (7-chloro-2-(2,2'-dimethyl-3'-(4,4,5,5-tetramethyl-1,3,2-dioxaborolan-2-yl)-[1,1'-biphenyl]-3-yl)benzo [d]oxazol-5-yl)methanol (Example 59, Step 2: 275 mg, 0.561 mmol), tert-butyl 2-bromo-4,6-dihydro-5H-pyrrolo[3, 4-d]thiazole-5-carboxylate (171 mg, 0.561 mmol), tetrakis (triphenylphosphine)palladium(0) (64.9 mg, 0.056 mmol) and sodium carbonate (149 mg, 1.404 mmol) in 1,4-dioxane (6 mL) and water (2 mL) was stirred at 100° C. overnight. After cooled to room temperature, the reaction mixture was diluted with EtOAc (150 mL), and washed with water (3×15 mL). The organic layer was dried over $Na_2SO_4$, filtered and the filtrate was concentrated. The crude product was purified on a silica gel column, eluting with 0-40% EtOAc/DCM to afford tert-butyl 2-(3'-(7-chloro-5-(hydroxymethyl)benzo[d] oxazol-2-yl)-2,2'-dimethylbiphenyl-3-yl)-4H-pyrrolo[3,4-d] thiazole-5(6H)-carboxylate (280 mg, 0.476 mmol, 85% yield). LC-MS calculated for $C_{32}H_{31}ClN_3O_4S$ $(M+H)^+$: m/z=588.2; found 588.3.

Step 3: tert-butyl 2-(3'-(7-cyano-5-(hydroxymethyl) benzo[d]oxazol-2-yl)-2,2'-dimethylbiphenyl-3-yl)-4H-pyrrolo[3,4-d]thiazole-5(6H)-carboxylate

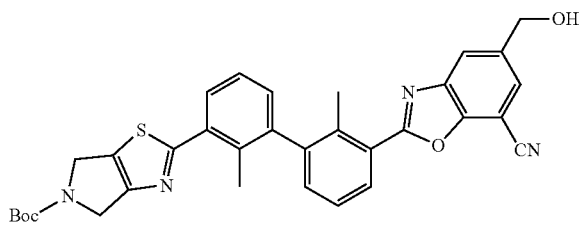 [SMILES: Cc1c(-c2nc3cc(CO)cc(C#N)c3o2)cccc1-c1cccc(-c2nc3c(s2)CN(C(=O)OC(C)(C)C)C3)c1C]

This compound was prepared using similar procedures as described for Example 12 with tert-butyl 2-(3'-(7-chloro-5-

(hydroxymethyl)benzo[d]oxazol-2-yl)-2,2'-dimethyl-[1,1'-biphenyl]-3-yl)-4,6-dihydro-5H-pyrrolo[3,4-d]thiazole-5-carboxylate replacing (7-chloro-2-(2,2'-dimethyl-3'-(pyrido[3,4-b]pyrazin-5-ylamino)-[1,1'-biphenyl]-3-yl)benzo[d]oxazol-5-yl)methanol in Step 1. LC-MS calculated for $C_{33}H_{31}N_4O_4S$ (M+H)$^+$: m/z=579.2; found 579.2.

Step 4: tert-butyl 2-(3'-(7-cyano-5-formylbenzo[d]oxazol-2-yl)-2,2'-dimethylbiphenyl-3-yl)-4H-pyrrolo[3,4-d]thiazole-5(6H)-carboxylate

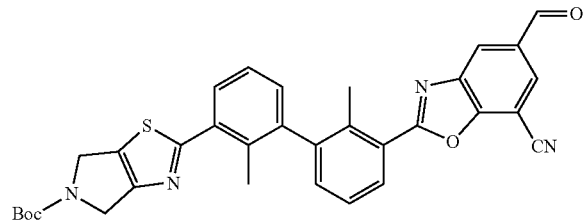 [SMILES: Cc1c(-c2nc3cc(C=O)cc(C#N)c3o2)cccc1-c1cccc(-c2nc3c(s2)CN(C(=O)OC(C)(C)C)C3)c1C]

To a stirred solution of tert-butyl 2-(3'-(7-cyano-5-(hydroxymethyl)benzo[d]oxazol-2-yl)-2,2'-dimethyl-[1,1'-biphenyl]-3-yl)-4,6-dihydro-5H-pyrrolo[3,4-dd]thiazole-5-carboxylate (0.93 g, 1.607 mmol) in DCM (10.0 mL), dess-martin periodinane (1.022 g, 2.411 mmol) was added at room temperature. After 1 hour, the reaction mixture was quenched with saturated aq. NaHCO$_3$, and extracted with DCM (4×80 mL). The organic layers were combined, dried over Na$_2$SO$_4$, filtered and the filtrate was concentrated under reduced pressure to afford crude tert-butyl 2-(3'-(7-cyano-5-formylbenzo[d]oxazol-2-yl)-2,2'-dimethylbiphenyl-3-yl)-4H-pyrrolo[3,4-d]thiazole-5(6H)-carboxylate (0.90 g, 1.56 mmol, 97% yield), which was used directly in the next step without further purification. LC-MS calculated for $C_{33}H_{29}N_4O_4S$ (M+H)$^+$: m/z=577.2; found 577.1.

Step 5: 2-(3'-(5,6-dihydro-4H-pyrrolo[3,4-d]thiazol-2-yl)-2,2'-dimethylbiphenyl-3-yl)-5-formylbenzo[d]oxazole-7-carbonitrile

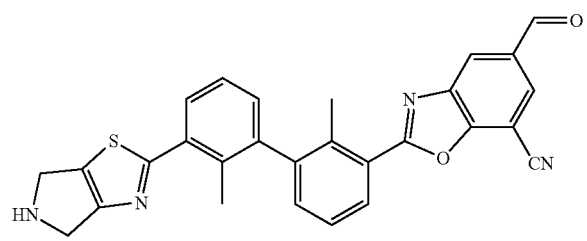 [SMILES: Cc1c(-c2nc3cc(C=O)cc(C#N)c3o2)cccc1-c1cccc(-c2nc3c(s2)CNC3)c1C]

tert-butyl 2-(3'-(7-cyano-5-formylbenzo[d]oxazol-2-yl)-2,2'-dimethylbiphenyl-3-yl)-4H-pyrrolo[3,4-d]thiazole-5(6H)-carboxylate (200 mg, 0.347 mmol) was dissolved in DCM (1 mL) and TFA (1 mL). The resulted solution was stirred at room temperature for 1 hour. The volatiles were then removed under reduced pressure to afford 2-(3'-(5,6-dihydro-4H-pyrrolo[3,4-d]thiazol-2-yl)-2,2'-dimethylbiphenyl-3-yl)-5-formylbenzo[d]oxazole-7-carbonitrile as its TFA salt, which was used directly in the next step without further purification. LC-MS calculated for $C_{28}H_{21}N_4O_2S$ (M+H)$^+$: m/z=477.1; found 477.1.

Step 6: 2-(3'-(5-(2-(dimethylamino)acetyl)-5,6-dihydro-4H-pyrrolo[3,4-d]thiazol-2-yl)-2,2'-dimethylbiphenyl-3-yl)-5-formylbenzo[d]oxazole-7-carbonitrile

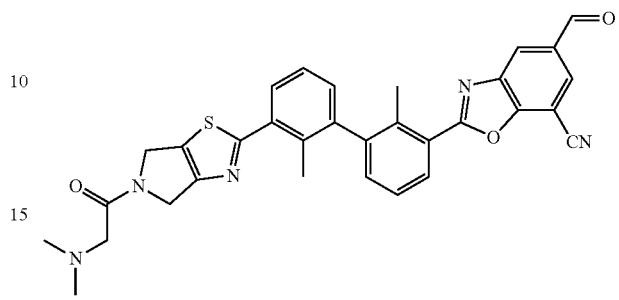

To a stirred solution of 2-(3'-(5,6-dihydro-4H-pyrrolo[3,4-d]thiazol-2-yl)-2,2'-dimethyl-[1,1'-biphenyl]-3-yl)-5-formylbenzo[d]oxazole-7-carbonitrile (100.0 mg, 0.210 mmol) and dimethylglycine (26.0 mg, 0.250 mmol) in DMF (5.0 ml), N,N,N',N'-tetramethyl-O-(7-azabenzotriazol-1-yl)uronium hexafluorophosphate (79.8 mg, 0.210 mmol), and N,N-diisopropylethylamine (146.2 µl, 0.84 mmol) were added sequentially at room temperature. After 1 hour, the reaction was diluted with EtOAc (100 mL) and washed with water (3×10 mL). The organic layer was dried over Na$_2$SO$_4$, filtered and concentrated to afford crude 2-(3'-(5-(2-(dimethylamino)acetyl)-5,6-dihydro-4H-pyrrolo[3,4-d]thiazol-2-yl)-2,2'-dimethylbiphenyl-3-yl)-5-formylbenzo[d]oxazole-7-carbonitrile (105 mg, 0.187 mmol, 89% yield). LC-MS calculated for $C_{32}H_{28}N_5O_3S$ (M+H)$^+$: m/z=562.2; found 562.2.

Step 7: (R)-1-((7-cyano-2-(3'-(5-(2-(dimethylamino)acetyl)-5,6-dihydro-4H-pyrrolo[3,4-d]thiazol-2-yl)-2,2'-dimethylbiphenyl-3-yl)benzo[d]oxazol-5-yl)methyl)pyrrolidine-3-carboxylic acid A solution of (R)-pyrrolidine-3-carboxylic acid (15.37 mg, 0.134 mmol), 2-(3'-(5-(dimethylglycyl)-5,6-dihydro-4H-pyrrolo[3,4-d]thiazol-2-yl)-2,2'-dimethyl-[1,1'-biphenyl]-3-yl)-5-formylbenzo[d]oxazole-7-carbonitrile (50.0 mg, 0.089 mmol) and N,N-diisopropylethylamine (0.019 mL, 0.107 mmol) in CH$_2$Cl$_2$ (5.0 mL) was allowed to stir for 1 hour. Then sodium triacetoxyborohydride (56.6 mg, 0.267 mmol) was added. The resulted mixture was stirred at room temperature overnight. The volatiles were removed under reduced pressure and the residue was purified by prep LCMS (pH 2, acetonitrile/water+TFA) to give the desired product as its TFA salt. LC-MS calculated for $C_{37}H_{37}N_6O_4S$ (M+H)$^+$: m/z=661.3; found 661.2. $^1$H NMR (600 MHz, DMSO) δ 8.38 (s, 1H), 8.20 (dd, J=7.9, 1.2 Hz, 1H), 8.12 (s, 1H), 7.75-7.70 (m, 1H), 7.59 (t, J=7.7 Hz, 1H), 7.50-7.45 (m, 2H), 7.33 (d, J=6.4 Hz, 1H), 4.99-4.64 (m, 4H), 4.56 (br, s, 2H), 4.29 (d, J=12.3 Hz, 2H), 3.72-3.16 (m, 5H), 2.87 (s, 3H), 2.86 (s, 3H), 2.44 (s, 3H), 2.20 (d, J=5.3 Hz, 3H), 2.25-1.99 (m, 2H).

Example 106

(R)-1-((7-cyano-2-(3'-(5-(3-(dimethylamino)propanoyl)-5,6-dihydro-4H-pyrrolo[3,4-d]thiazol-2-yl)-2,2'-dimethylbiphenyl-3-yl)benzo[d]oxazol-5-yl)methyl)pyrrolidine-3-carboxylic acid

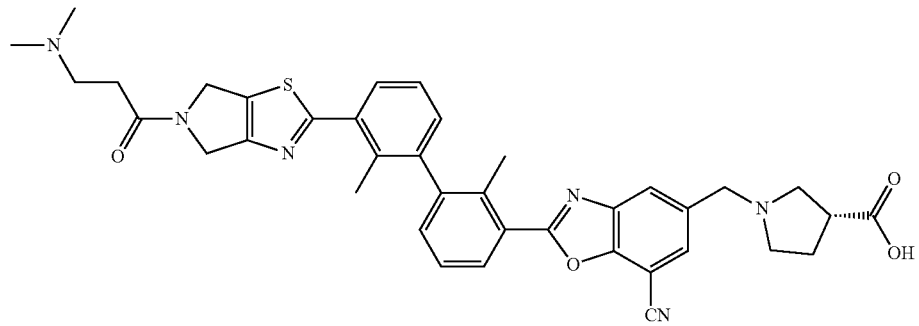 [SMILES: Cc1c(-c2nc3cc(CN4CC[C@@H](C(=O)O)C4)cc(C#N)c3o2)cccc1-c1cccc(-c2nc3c(s2)CN(C(=O)CCN(C)C)C3)c1C]

This compound was prepared using similar procedures as described for Example 105 with 3-(dimethylamino)propanoic acid replacing dimethylglycine in Step 6. The crude product was purified by prep-HPLC (pH=2, acetonitrile/water+TFA) to give the desired compound as its TFA salt. LC-MS calculated for $C_{38}H_{39}N_6O_4S$ (M+H)$^+$: m/z=675.3; found 675.3.

Example 107

(R)-1-((7-cyano-2-(2,2'-dimethyl-3'-(5-((S)-1-methylpyrrolidine-2-carbonyl)-5,6-dihydro-4H-pyrrolo[3,4-d]thiazol-2-yl)biphenyl-3-yl)benzo[d]oxazol-5-yl)methyl)pyrrolidine-3-carboxylic acid

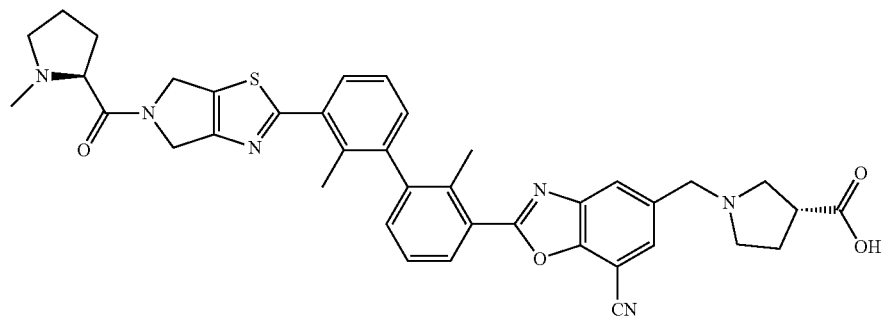 [SMILES: Cc1c(-c2nc3cc(CN4CC[C@@H](C(=O)O)C4)cc(C#N)c3o2)cccc1-c1cccc(-c2nc3c(s2)CN(C(=O)[C@@H]2CCCN2C)C3)c1C]

This compound was prepared using similar procedures as described for Example 105 with (S)-1-methylpyrrolidine-2-carboxylic acid replacing dimethylglycine in Step 6. The crude product was purified by prep-HPLC (pH=2, acetonitrile/water+TFA) to give the desired compound as its TFA salt. LC-MS calculated for $C_{39}H_{39}N_6O_4S$ (M+H)$^+$: m/z=687.3; found 687.2.

Example 108

(R)-1-((7-cyano-2-(2,2'-dimethyl-3'-(5-(2-(4-methyl-piperazin-1-yl)acetyl)-5,6-dihydro-4H-pyrrolo[3,4-d]thiazol-2-yl)biphenyl-3-yl)benzo[d]oxazol-5-yl)methyl)pyrrolidine-3-carboxylic acid

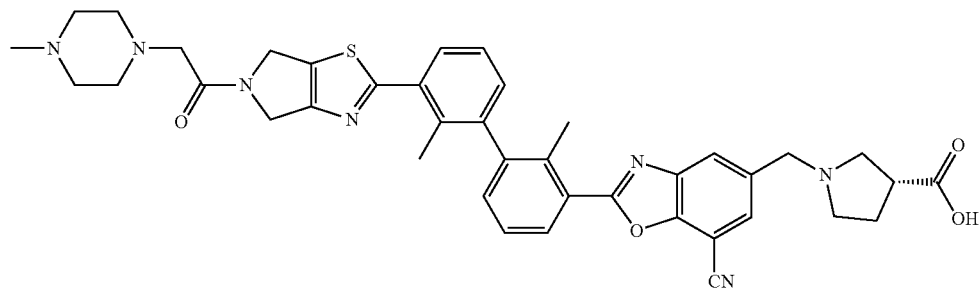 [SMILES: Cc1c(-c2nc3cc(CN4CC[C@@H](C(=O)O)C4)cc(C#N)c3o2)cccc1-c1cccc(-c2nc3c(s2)CN(C(=O)CN2CCN(C)CC2)C3)c1C]

This compound was prepared using similar procedures as described for Example 105 with 2-(4-methylpiperazin-1-yl)acetic acid replacing dimethylglycine in Step 6. The crude product was purified by prep-HPLC (pH=2, acetonitrile/water+TFA) to give the desired compound as its TFA salt. LC-MS calculated for $C_{40}H_{42}N_7O_4S$ (M+H)$^+$: m/z=716.3; found 716.2.

Example 109

(R)-1-((7-cyano-2-(3'-(5-(2-(dimethylamino)acetyl)-5,6-dihydro-4H-pyrrolo[3,4-d]thiazol-2-yl)-2,2'-dimethylbiphenyl-3-yl)benzo[d]oxazol-5-yl)methyl)-3-methylpyrrolidine-3-carboxylic acid

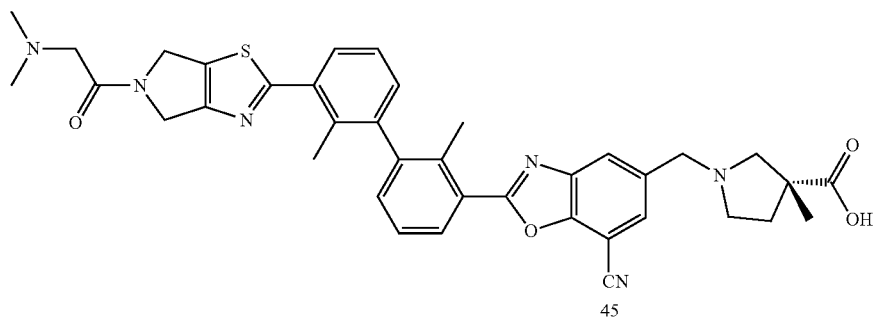

This compound was prepared using similar procedures as described for Example 105 with (R)-3-methylpyrrolidine-3-carboxylic acid replacing (R)-pyrrolidine-3-carboxylic acid in Step 7. The crude product was purified by prep-HPLC (pH=2, acetonitrile/water+TFA) to give the desired compound as its TFA salt. LC-MS calculated for $C_{38}H_{39}N_6O_4S$ (M+H)$^+$: m/z=675.3; found 675.3.

Example 110

(R)-1-((7-cyano-2-(3'-(5-(2-(isopropylamino)acetyl)-5,6-dihydro-4H-pyrrolo[3,4-d]thiazol-2-yl)-2,2'-dimethylbiphenyl-3-yl)benzo[d]oxazol-5-yl)methyl)pyrrolidine-3-carboxylic acid

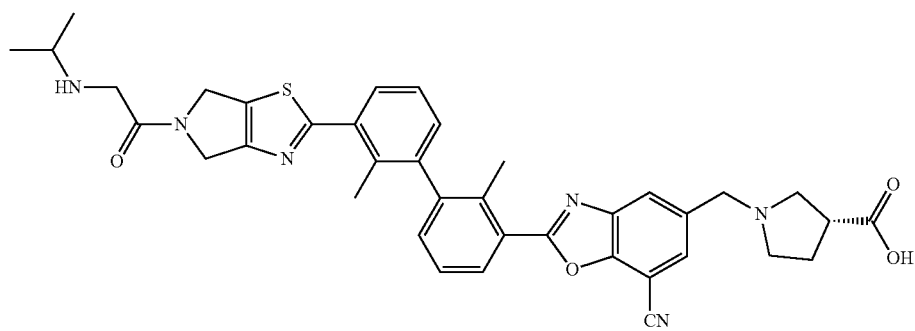

287

Step 1: (R)-1-((2-(3'-(5-(tert-butoxycarbonyl)-5,6-dihydro-4H-pyrrolo[3,4-d]thiazol-2-yl)-2,2'-dimethylbiphenyl-3-yl)-7-cyanobenzo[d]oxazol-5-yl)methyl)pyrrolidine-3-carboxylic acid

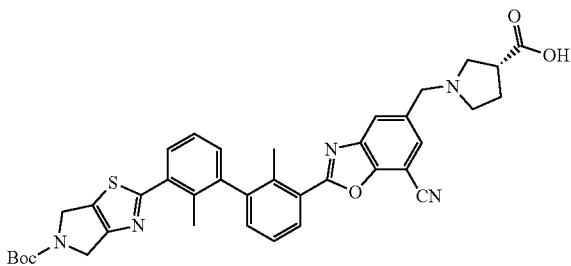 [SMILES: Cc1c(-c2nc3cc(CN4CC[C@@H](C(=O)O)C4)cc(C#N)c3o2)cccc1-c1cccc(-c2nc3c(s2)CN(C(=O)OC(C)(C)C)C3)c1C]

A slurry of (R)-pyrrolidine-3-carboxylic acid (39.9 mg, 0.347 mmol), tert-butyl 2-(3'-(7-cyano-5-formylbenzo[d]oxazol-2-yl)-2,2'-dimethyl-[1,1'-biphenyl]-3-yl)-4,6-dihydro-5H-pyrrolo[3,4-d]thiazole-5-carboxylate (Example 105, Step 4: 100.0 mg, 0.173 mmol) and N,N-diisopropylethylamine (0.045 mL, 0.260 mmol) in CH$_2$Cl$_2$ (5.0 mL) was allowed to stir for 1 hour at room temperature. Then sodium triacetoxyborohydride (110 mg, 0.520 mmol) was added. The resulted mixture was stirred at room temperature overnight. Then the mixture was diluted with DCM (100 mL) and washed with water (3×15 mL). The aqueous layers were combined and extracted with DCM/iPrOH (2:1, 3×30 mL). The organic layers were combined, dried over Na$_2$SO$_4$, filtered and the filtrate was concentrated to afford crude product, which was used in the next step without further purification. LC-MS calculated for C$_{38}$H$_{38}$N$_5$O$_5$S (M+H)$^+$: m/z=676.3; found 676.2.

Step 2: (R)-1-((7-cyano-2-(3'-(5,6-dihydro-4H-pyrrolo[3,4-d]thiazol-2-yl)-2,2'-dimethylbiphenyl-3-yl)benzo[d]oxazol-5-yl)methyl)pyrrolidine-3-carboxylic acid

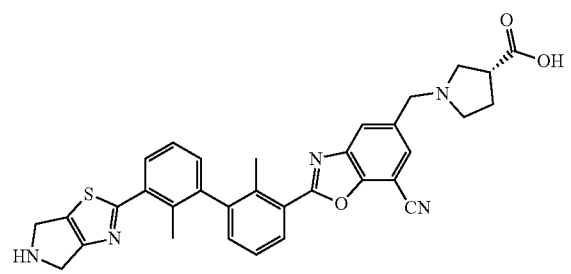 [SMILES: Cc1c(-c2nc3cc(CN4CC[C@@H](C(=O)O)C4)cc(C#N)c3o2)cccc1-c1cccc(-c2nc3c(s2)CNC3)c1C]

(R)-1-((2-(3'-(5-(tert-butoxycarbonyl)-5,6-dihydro-4H-pyrrolo[3,4-d]thiazol-2-yl)-2,2'-dimethylbiphenyl-3-yl)-7-cyanobenzo[d]oxazol-5-yl)methyl)pyrrolidine-3-carboxylic acid (105 mg, 0.155 mmol) was dissolved in DCM/TFA (1:1, 2.0 mL). The resulted solution was stirred at room temperature for 1 hour. The volatiles were removed under reduced pressure to afford the desired product as its TFA salt, which was used directly in the next step without further purification. LC-MS calculated for C$_{33}$H$_{30}$N$_5$O$_3$S (M+H)$^+$: m/z=576.2; found 576.2.

288

Step 3: (R)-1-((7-cyano-2-(2,2'-dimethyl-3'-(5-(2-oxoacetyl)-5,6-dihydro-4H-pyrrolo[3,4-d]thiazol-2-yl)biphenyl-3-yl)benzo[d]oxazol-5-ylmethyl)pyrrolidine-3-carboxylic acid

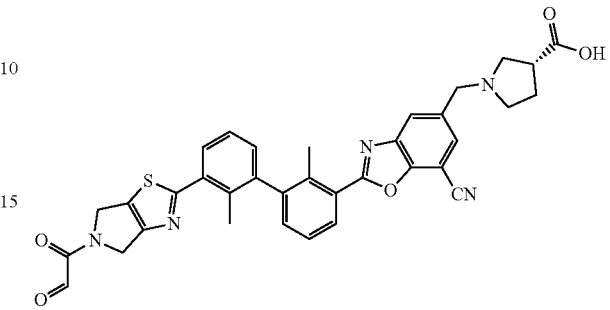

To a stirred solution of (R)-1-((7-cyano-2-(3'-(5,6-dihydro-4H-pyrrolo[3,4-d]thiazol-2-yl)-2,2'-dimethyl-[1,1'-biphenyl]-3-yl)benzo[d]oxazol-5-yl)methyl)pyrrolidine-3-carboxylic acid (700.0 mg, 1.216 mmol) and 2-oxoacetic acid (270 mg, 3.65 mmol) in DMF (8.0 ml), N,N,N',N'-Tetramethyl-O-(7-azabenzotriazol-1-yl)uronium hexafluorophosphate (462 mg, 1.216 mmol), and N,N-diisopropylethylamine (0.424 ml, 2.432 mmol) were added sequentially at rt. After 1 h, the mixture was diluted with EtOAc (200 mL) and washed with water (3×25 mL). The aqueous layers were combined and extracted with DCM/iPrOH (2:1, 3×50 mL). The organic layers were combined, dried over Na$_2$SO$_4$, filtered and the filtrate was concentrated to afford the desired aldehyde (710 mg, 1.12 mmol, 92.3% yield). LC-MS calculated for C$_{35}$H$_{30}$N$_5$O$_5$S (M+H)$^+$: m/z=632.2; found 632.2.

Step 4: (R)-1-((7-cyano-2-(3'-(5-(2-(isopropylamino)acetyl)-5,6-dihydro-4H-pyrrolo[3,4-d]thiazol-2-yl)-2,2'-dimethylbiphenyl-3-yl)benzo[d]oxazol-5-yl)methyl)pyrrolidine-3-carboxylic acid A slurry of propan-2-amine (5.61 mg, 0.095 mmol) and (R)-1-((7-cyano-2-(2,2'-dimethyl-3'-(5-(2-oxoacetyl)-5,6-dihydro-4H-pyrrolo[3,4-d]thiazol-2-yl)-[1,1'-biphenyl]-3-yl)benzo[d]oxazol-5-yl)methyl)pyrrolidine-3-carboxylic acid (30.0 mg, 0.047 mmol), N,N-diisopropylethylamine (0.025 ml, 0.142 mmol) in DMF (3.0 ml) was allowed to stir for 1 h at room temperature. Sodium cyanoborohydride (8.95 mg, 0.142 mmol) was then added. The resulted mixture was stirred at room temperature overnight. The reaction mixture was then diluted with MeOH and was purified on prep-LCMS (pH 2, acetonitrile/water+TFA) to give the desired product as its TFA salt. LC-MS calculated for C$_{38}$H$_{39}$N$_6$O$_4$S (M+H)$^+$: m/z=675.3; found 675.2. $^1$H NMR (500 MHz, DMSO) δ 8.85 (s, 1H), 8.40 (s, 1H), 8.22 (d, J=6.8 Hz, 1H), 8.14 (s, 1H), 7.74 (d, J=7.7 Hz, 1H), 7.61 (t, J=7.6 Hz, 1H), 7.49 (t, J=6.9 Hz, 2H), 7.35 (d, J=7.5 Hz, 1H), 5.09-4.66 (m, 4H), 4.57 (s, 2H), 4.09 (m, 2H), 3.70-3.15 (m, 6H), 2.46 (s, 3H), 2.23 (m, 1H), 2.22 (d, J=5.3 Hz, 3H), 2.07 (m, 1H), 1.28 (d, J=6.5 Hz, 6H).

Example 111

(R)-1-((7-cyano-2-(3'-(5-(2-((R)-3-hydroxypyrrolidin-1-yl)acetyl)-5,6-dihydro-4H-pyrrolo[3,4-d]thiazol-2-yl)-2,2'-dimethylbiphenyl-3-yl)benzo[d]oxazol-5-yl)methyl)pyrrolidine-3-carboxylic acid

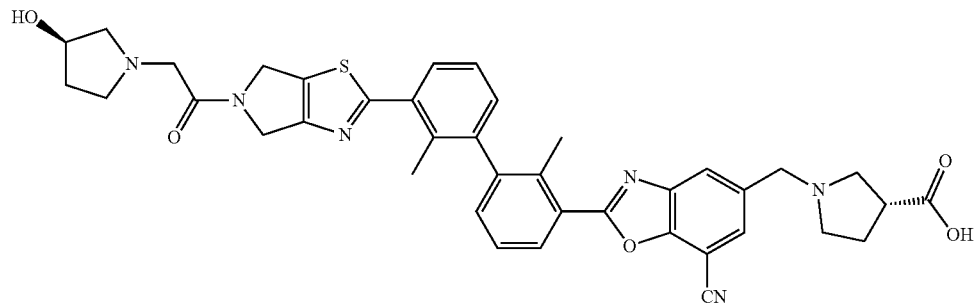 [SMILES: Cc1c(-c2nc3cc(CN4CC[C@@H](C(=O)O)C4)cc(C#N)c3o2)cccc1-c1cccc(-c2nc3c(s2)CN(C(=O)CN2CC[C@@H](O)C2)C3)c1C]

This compound was prepared using similar procedures as described for Example 110 with (R)-pyrrolidin-3-ol replacing propan-2-amine in Step 4. The crude product was purified by prep-HPLC (pH=2, acetonitrile/water+TFA) to give the desired compound as its TFA salt. LC-MS calculated for $C_{39}H_{39}N_6O_5S$ (M+H)$^+$: m/z=703.3; found 703.2.

Example 112

(R)-1-((7-cyano-2-(3'-(5-(2-((S)-3-hydroxypyrrolidin-1-yl)acetyl)-5,6-dihydro-4H-pyrrolo[3,4-d]thiazol-2-yl)-2,2'-dimethylbiphenyl-3-yl)benzo[d]oxazol-5-yl)methyl)pyrrolidine-3-carboxylic acid

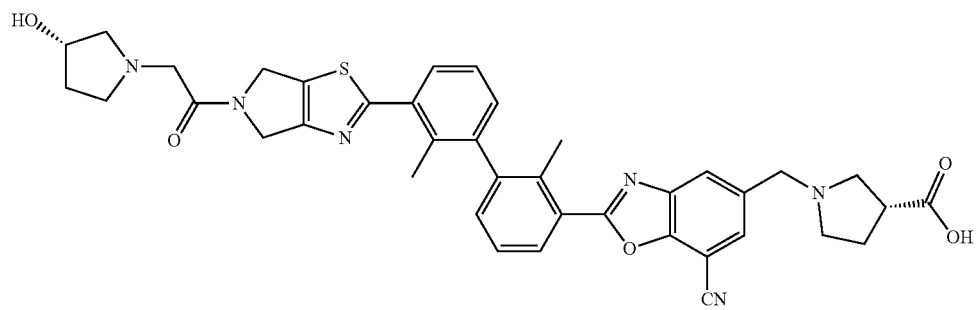 [SMILES: Cc1c(-c2nc3cc(CN4CC[C@@H](C(=O)O)C4)cc(C#N)c3o2)cccc1-c1cccc(-c2nc3c(s2)CN(C(=O)CN2CC[C@H](O)C2)C3)c1C]

This compound was prepared using similar procedures as described for Example 110 with (S)-pyrrolidin-3-ol replacing propan-2-amine in Step 4. The crude product was purified by prep-HPLC (pH=2, acetonitrile/water+TFA) to give the desired compound as its TFA salt. LC-MS calculated for $C_{39}H_{39}N_6O_5S$ (M+H)$^+$: m/z=703.3; found 703.2.

Example 113

(R)-1-((2-(3'-(5-(2-(azetidin-1-yl)acetyl)-5,6-dihydro-4H-pyrrolo[3,4-d]thiazol-2-yl)-2,2'-dimethylbiphenyl-3-yl)-7-cyano benzo[d]oxazol-5-yl)methyl)pyrrolidine-3-carboxylic acid

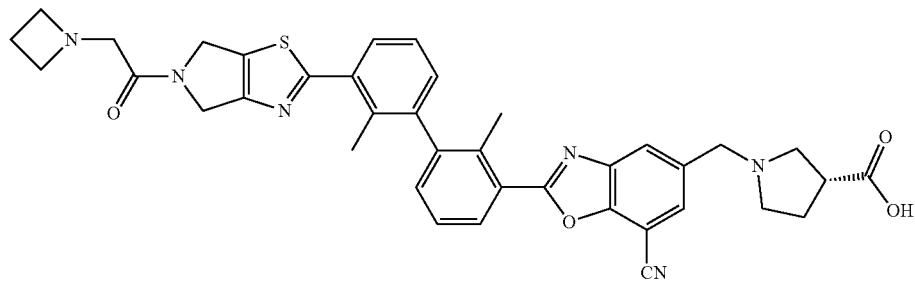 [SMILES: Cc1c(-c2nc3cc(CN4CC[C@@H](C(=O)O)C4)cc(C#N)c3o2)cccc1-c1cccc(-c2nc3c(s2)CN(C(=O)CN2CCC2)C3)c1C]

This compound was prepared using similar procedures as described for Example 110 with azetidin replacing propan-2-amine in Step 4. The crude product was purified by prep-HPLC (pH=2, acetonitrile/water+TFA) to give the desired compound as its TFA salt. LC-MS calculated for $C_{38}H_{37}N_6O_4S$ (M+H)$^+$: m/z=673.3; found 673.2.

Example 114

(R)-1-((7-cyano-2-(3'-(5-(2-(ethyl(methyl)amino)acetyl)-5,6-dihydro-4H-pyrrolo[3,4-d]thiazol-2-yl)-2,2'-dimethylbiphenyl-3-yl)benzo[d]oxazol-5-yl)methyl)pyrrolidine-3-carboxylic acid

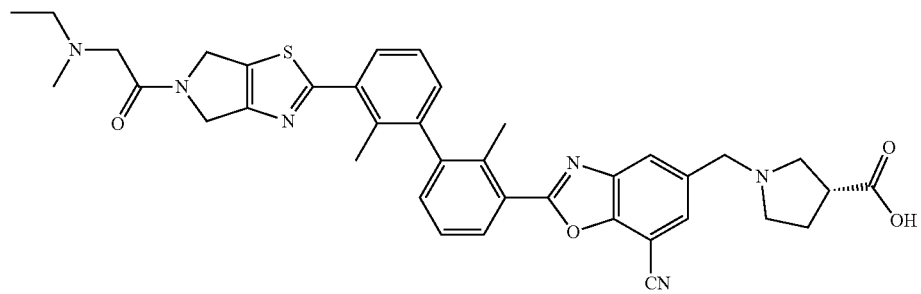 [SMILES: CCN(C)CC(=O)N1Cc2nc(-c3cccc(-c4cccc(-c5nc6cc(CN7CC[C@@H](C(=O)O)C7)cc(C#N)c6o5)c4C)c3C)sc2C1]

This compound was prepared using similar procedures as described for Example 110 with N-methylethanamine replacing propan-2-amine in Step 4. The crude product was purified by prep-HPLC (pH=2, acetonitrile/water+TFA) to give the desired compound as its TFA salt. LC-MS calculated for $C_{38}H_{39}N_6O_4S$ (M+H)$^+$: m/z=675.3; found 675.3.

Example 115

(R)-1-((7-cyano-2-(3'-(5-(2-((S)-3-hydroxy-3-methylpyrrolidin-1-yl)acetyl)-5,6-dihydro-4H-pyrrolo[3,4-d]thiazol-2-yl)-2,2'-dimethylbiphenyl-3-yl)benzo[d]oxazol-5-yl)methyl)pyrrolidine-3-carboxylic acid

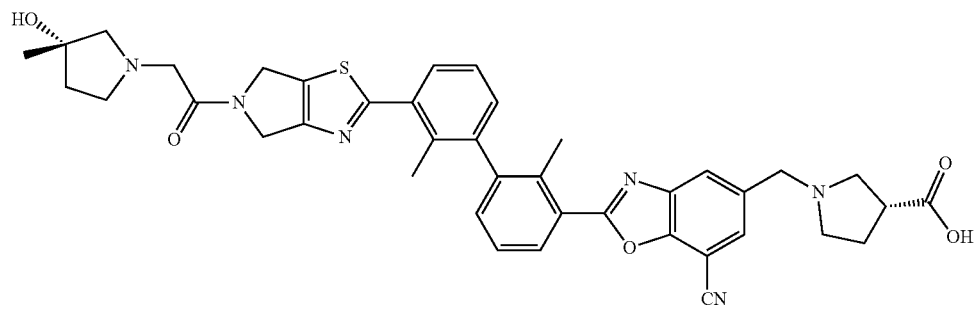 [SMILES: Cc1c(-c2nc3cc(CN4CC[C@@H](C(=O)O)C4)cc(C#N)c3o2)cccc1-c1cccc(-c2nc3c(s2)CN(C(=O)CN2CC[C@](C)(O)C2)C3)c1C]

This compound was prepared using similar procedures as described for Example 110 with (S)-3-methylpyrrolidin-3-ol replacing propan-2-amine in Step 4. The crude product was purified by prep-HPLC (pH=2, acetonitrile/water+TFA) to give the desired compound as its TFA salt. LC-MS calculated for $C_{40}H_{41}N_6O_5S$ (M+H)$^+$: m/z=717.3; found 717.2.

Example 116

(R)-1-((7-cyano-2-(3'-(5-(2-((R)-3-hydroxy-3-methylpyrrolidin-1-yl)acetyl)-5,6-dihydro-4H-pyrrolo[3,4-d]thiazol-2-yl)-2,2'-dimethylbiphenyl-3-yl)benzo[d]oxazol-5-yl)methyl)pyrrolidine-3-carboxylic acid

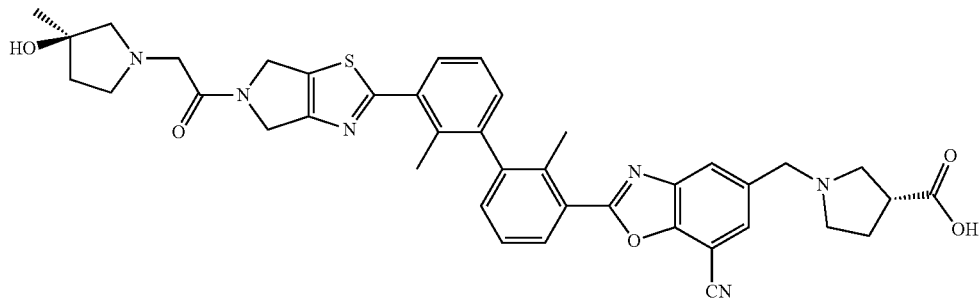 [SMILES: Cc1c(-c2nc3cc(CN4CC[C@@H](C(=O)O)C4)cc(C#N)c3o2)cccc1-c1cccc(-c2nc3c(s2)CN(C(=O)CN2CC[C@@](C)(O)C2)C3)c1C]

This compound was prepared using similar procedures as described for Example 110 with (R)-3-methylpyrrolidin-3-ol replacing propan-2-amine in Step 4. The crude product was purified by prep-HPLC (pH=2, acetonitrile/water+TFA) to give the desired compound as its TFA salt. LC-MS calculated for $C_{40}H_{41}N_6O_5S$ (M+H)$^+$: m/z=717.3; found 717.3.

Example 117

(R)-1-((7-cyano-2-(3'-(5-isopropyl-4,5,6,7-tetrahydrothiazolo[5,4-c]pyridin-2-yl)-2,2'-dimethyl-[1,1'-biphenyl]-3-yl)benzo[d]oxazol-5-yl)methyl)-N-methylpyrrolidine-3-carboxamide

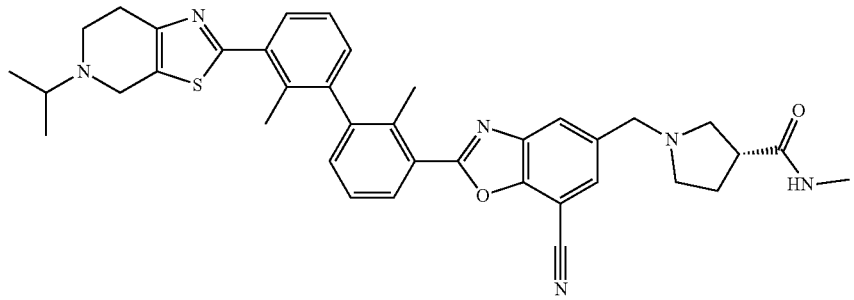 [SMILES: CNC(=O)[C@@H]1CCN(Cc2cc(C#N)c3oc(-c4cccc(-c5cccc(-c6nc7c(s6)CN(C(C)C)CC7)c5C)c4C)nc3c2)C1]

In a 1 dram vial (R)-1-((7-cyano-2-(3'-(5-isopropyl-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid (Example 63, final product: 20 mg, 0.032 mmol) and methylamine in THF (2.0 M, 100 uL) were dissolved in DMF. DIPEA (27.6 µl, 0.158 mmol) and N-[(Dimethylamino)-1H-1,2,3-triazolo-[4,5-b]pyridin-1-yl-methylene]-N-methylmethanaminium hexafluorophosphate N-oxide (36.1 mg, 0.095 mmol) were added to the reaction mixture in one portion. After 5 h, the reaction mixture was diluted with MeOH then purified by prep-HPLC (pH=2, acetonitrile/water+TFA) to give the desired product as the TFA salt. LC-MS calculated for $C_{38}H_{41}N_6O_2S$ (M+H)$^+$: m/z=645.3; found 645.2.

Example 118

N-(2-(((7-cyano-2-(3'-(5-isopropyl-4,5,6,7-tetrahydrothiazolo[5,4-c]pyridin-2-yl)-2,2'-dimethyl-[1,1'-biphenyl]-3-yl)benzo[d]oxazol-5-yl)methyl)amino)ethyl)acetamide

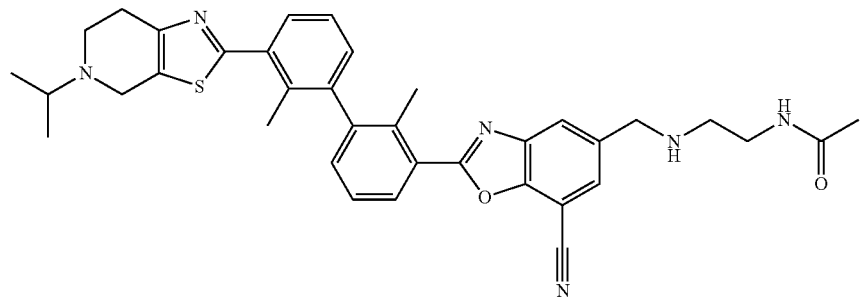 [SMILES: CC(=O)NCCNCc1cc(C#N)c2oc(-c3cccc(-c4cccc(-c5nc6c(s5)CN(C(C)C)CC6)c4C)c3C)nc2c1]

Step 1: 2-(2,2'-dimethyl-3'-(4,5,6,7-tetrahydrothiazolo[5,4-c]pyridin-2-yl)-[1,1'-biphenyl]-3-yl)-5-(hydroxymethyl)benzo[d]oxazole-7-carbonitrile

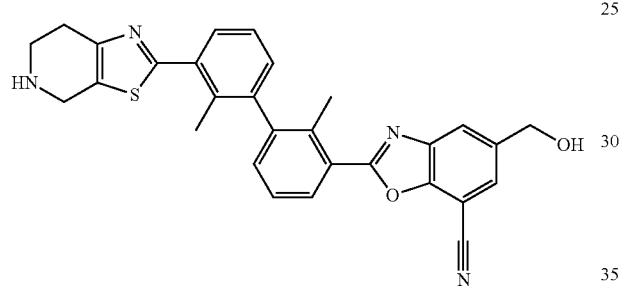

In a 4 dram vial tert-butyl 2-(3'-(7-cyano-5-(hydroxymethyl)benzo[d]oxazol-2-yl)-2,2'-dimethyl-[1,1'-biphenyl]-3-yl)-6,7-dihydrothiazolo[5,4-c]pyridine-5(4H)-carboxylate (Example 63, Step 1: 368 mg, 0.62 mmol) in methanol (3 ml) was treated with 4 N HCl in 1,4-dioxane (2 mL). The reaction mixture was heated to 40° C. After 2 h, the reaction mixture was concentrated to dryness and used as crude without further purification. LC-MS calculated for $C_{29}H_{25}N_4O_2S$ (M+H)$^+$: m/z=493.2; found 493.1.

Step 2: 5-(hydroxymethyl)-2-(3'-(5-isopropyl-4,5,6,7-tetrahydrothiazolo[5,4-c]pyridin-2-yl)-2,2'-dimethyl-[1,1'-biphenyl]-3-yl)benzo[d]oxazole-7-carbonitrile

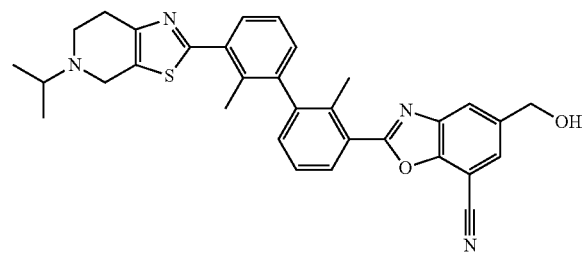 [SMILES: Cc1c(-c2nc3cc(CO)cc(C#N)c3o2)cccc1-c1cccc(-c2nc3c(s2)CN(C(C)C)CC3)c1C]

In a 1 dram vial 2-(2,2'-dimethyl-3'-(4,5,6,7-tetrahydrothiazolo[5,4-c]pyridin-2-yl)-[1,1'-biphenyl]-3-yl)-5-(hydroxymethyl)benzo[d]oxazole-7-carbonitrile (306 mg, 0.62 mmol) was dissolved in DCM (3 mL) to give a yellow solution. Acetone (306 μL, 4.17 mmol) and DIPEA (292 μL, 1.67 mmol) were added to the reaction mixture. After 1 h, sodium triacetoxyborohydride (880 mg, 4.17 mmol) was added to the reaction mixture. After 5 h, saturated NaHCO$_3$ (5 mL) was added followed by extraction with DCM (5 mL×4). The combined organic layers were dried Na$_2$SO$_4$, filtered and concentrated. The crude product was used directly in the next step. LC-MS calculated for $C_{32}H_{31}N_4O_2S$ (M+H)$^+$: m/z=535.2; found 535.3.

Step 3: 5-formyl-2-(3'-(5-isopropyl-4,5,6,7-tetrahydrothiazolo[5,4-c]pyridin-2-yl)-2,2'-dimethyl-[1,1'-biphenyl]-3-yl)benzo[d]oxazole-7-carbonitrile

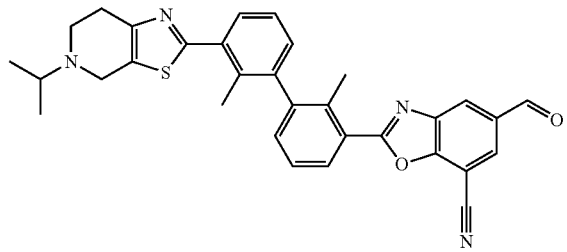 [SMILES: Cc1c(-c2nc3cc(C=O)cc(C#N)c3o2)cccc1-c1cccc(-c2nc3c(s2)CN(C(C)C)CC3)c1C]

To a solution of 5-(hydroxymethyl)-2-(3'-(5-isopropyl-4,5,6,7-tetrahydrothiazolo[5,4-c]pyridin-2-yl)-2,2'-dimethyl-[1,1'-biphenyl]-3-yl)benzo[d]oxazole-7-carbonitrile (332 mg, 0.62 mmol) in DCM (4 mL) was added Dess-Martin periodinane (395 mg, 0.93 mmol). After 1 h, saturated NaHCO$_3$ (5 mL) was added to the reaction mixture followed by extraction with DCM (5 mL×3). The combined organic layers were dried Na$_2$SO$_4$, filtered and concentrated. The crude product was used for next step without further purification. LC-MS calculated for $C_{32}H_{29}N_4O_2S$ (M+H)$^+$: m/z=533.2; found 533.3.

Step 4: N-(2-(((7-cyano-2-(3'-(5-isopropyl-4,5,6,7-tetrahydrothiazolo[5,4-c]pyridin-2-yl)-2,2'-dimethyl-[1,1'-biphenyl]-3-yl)benzo[d]oxazol-5-yl)methyl)amino)ethyl)acetamide In a 1 dram vial 5-formyl-2-(3'-(5-isopropyl-4,5,6,7-tetrahydrothiazolo[5,4-c]pyridin-2-yl)-2,2'-dimethyl-[1,1'-biphenyl]-3-yl)benzo[d]oxazole-7-carbonitrile (10 mg, 0.019 mmol), DIPEA (5 μL, 0.032 mmol) and N-acetylethylenediamine (Aldrich, cat #397261: 5 mg) were dissolved in DMF (0.5 mL). The reaction mixture was stirred at r.t. for 12 h, and then sodium cyanoborohydride (6 mg, 0.095 mmol) was added to the reaction mixture in one portion. After 2 h, the reaction mixture was diluted with MeOH then purified by prep-HPLC (pH=2, acetonitrile/water+TFA) to give the desired product as the TFA salt. LC-MS calculated for $C_{36}H_{39}N_6O_2S$ (M+H)$^+$: m/z=619.3; found 619.2.

Example 119

(R)-1-((7-cyano-2-(3'-(5-isopropyl-4,5,6,7-tetrahydrothiazolo[5,4-c]pyridin-2-yl)-2,2'-dimethyl-[1,1'-biphenyl]-3-yl)benzo[d]oxazol-5-yl)methyl)-N-(2-hydroxyethyl)pyrrolidine-3-carboxamide

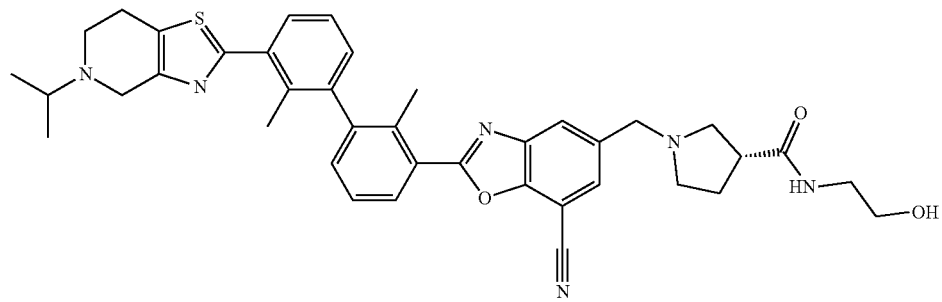

This compound was prepared using similar procedures as described for Example 117 with ethanolamine replacing methylamine. The reaction mixture was diluted with MeOH then purified by prep-HPLC (pH=2, acetonitrile/water+TFA) to give the desired product as the TFA salt. LC-MS calculated for $C_{39}H_{43}N_6O_3S$ (M+H)$^+$: m/z=675.3; found 675.3.

Example 120

5-(((2-hydroxyethyl)amino)methyl)-2-(3'-(5-isopropyl-4,5,6,7-tetrahydrothiazolo[5,4-c]pyridin-2-yl)-2,2'-dimethyl-[1,1'-biphenyl]-3-yl)benzo[d]oxazole-7-carbonitrile

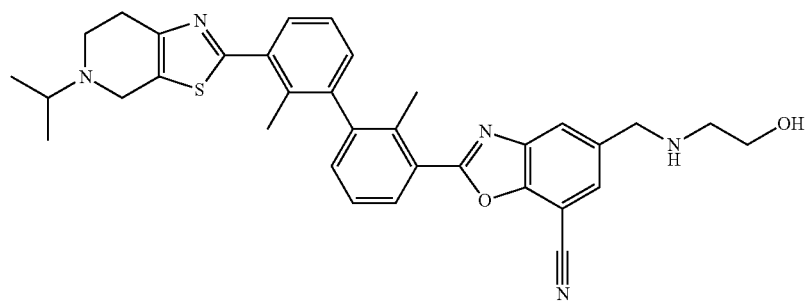 [SMILES: Cc1c(-c2nc3cc(CNCCO)cc(C#N)c3o2)cccc1-c1cccc(-c2nc3c(s2)CN(C(C)C)CC3)c1C]

This compound was prepared using similar procedures as described for Example 118 with ethanolamine replacing N-acetylethylenediamine in Step 4. The reaction mixture was diluted with MeOH then purified by prep-HPLC (pH=2, acetonitrile/water+TFA) to give the desired product as the TFA salt. LC-MS calculated for $C_{34}H_{36}N_5O_2S$ (M+H)$^+$: m/z=578.3; found 578.2.

Example 121

(R)-5-((3-hydroxypyrrolidin-1-yl)methyl)-2-(3'-(5-isopropyl-4,5,6,7-tetrahydrothiazolo[5,4-c]pyridin-2-yl)-2,2'-dimethyl-[1,1'-biphenyl]-3-yl)benzo[d]oxazole-7-carbonitrile

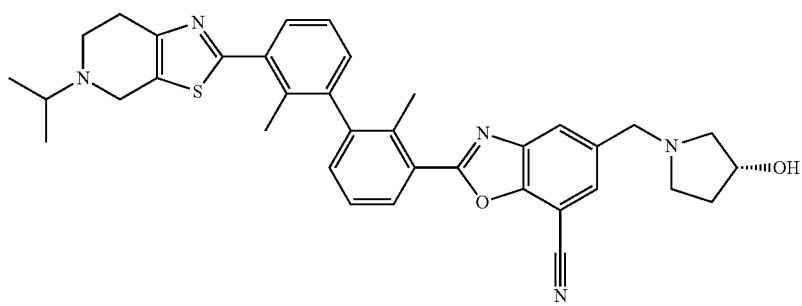 [SMILES: Cc1c(-c2nc3cc(CN4CC[C@@H](O)C4)cc(C#N)c3o2)cccc1-c1cccc(-c2nc3c(s2)CN(C(C)C)CC3)c1C]

This compound was prepared using similar procedures as described for Example 118 with (R)-3-Hydroxypyrrolidine (Aldrich, cat #382981) replacing N-acetylethylenediamine in Step 4. The reaction mixture was diluted with MeOH then purified by prep-HPLC (pH=2, acetonitrile/water+TFA) to give the desired product as the TFA salt. LC-MS calculated for $C_{36}H_{38}N_5O_2S$ (M+H)$^+$:m/z=604.3; found 604.2.

Example 122

(R)-1-((7-cyano-2-(3'-(5-(dimethylglycyl)-5,6-dihydro-4H-pyrrolo[3,4-d]oxazol-2-yl)-2,2'-dimethyl-[1,1'-biphenyl]-3-yl)benzo[d]oxazol-5-yl)methyl)pyrrolidine-3-carboxylic acid

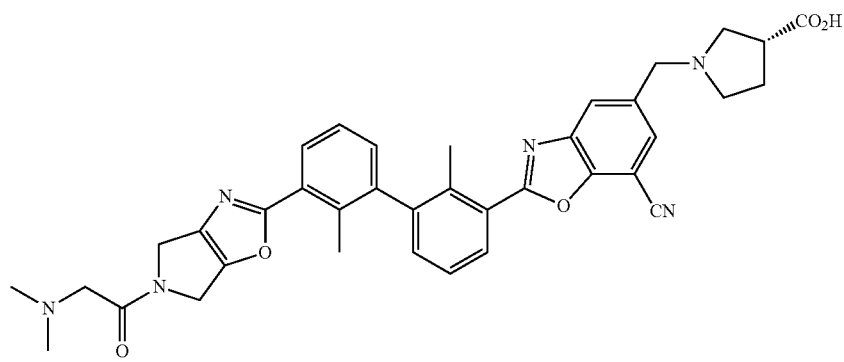 [SMILES: Cc1c(-c2nc3c(o2)CN(C(=O)CN(C)C)C3)cccc1-c1cccc(-c2nc3cc(CN4CC[C@@H](C(=O)O)C4)cc(C#N)c3o2)c1C]

Step 1: Benzyl 6-oxa-3-azabicyclo[3.1.0]hexane-3-carboxylate

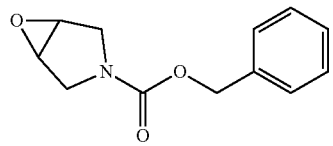 [SMILES: O=C(OCc1ccccc1)N1CC2OC2C1]

To a solution of benzyl 2,5-dihydro-1H-pyrrole-1-carboxylate (Aldrich, cat #494127: 12.4 g, 61.0 mmol) in DCM (200 ml) was added meta-chloroperoxybenzoic acid (16.20 g, 61.0 mmol). The resulting mixture was stirred at room temperature for 3 h. The reaction was quenched with saturated. NaHCO$_3$ solution, the organic layer was separated; the aqueous layer was extracted with DCM once. The combined organic layer was dried over Na$_2$SO$_4$, filtered and concentrated. The crude was purified with flash chromatography (eluting with 0-50% ethyl acetate in hexanes) to give the desired product as clear oil (13 g, 97%). LC-MS calculated for $C_{12}H_{14}NO_3$ (M+H)$^+$: m/z=220.1; found 220.1.

Step 2: Benzyl 3-amino-4-hydroxypyrrolidine-1-carboxylate

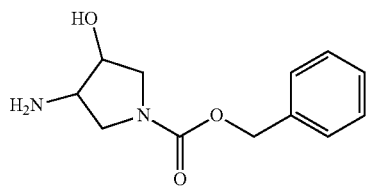 [SMILES: NC1CN(C(=O)OCc2ccccc2)CC1O]

To a flask was charged with benzyl 6-oxa-3-azabicyclo[3.1.0]hexane-3-carboxylate (13.0 g, 59.3 mmol) and ammonium hydroxide (115 ml, 2.96 mol). The reaction mixture was heated at 90° C. overnight. The solvent was removed. The residue was used in the next step without purification. LC-MS calculated for $C_{12}H_{17}N_2O_3$ (M+H)$^+$: m/z=237.1; found 237.1.

Step 3: Benzyl 3-(3-bromo-2-methylbenzamido)-4-hydroxypyrrolidine-1-carboxylate

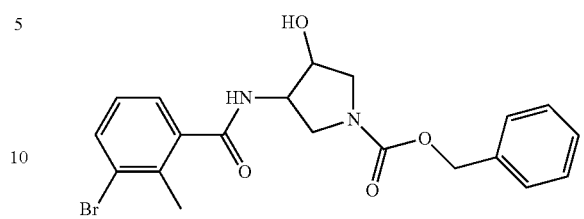

A solution of 3-bromo-2-methylbenzoic acid (9.70 g, 45.1 mmol) in DMF (226 ml) was added N,N,N',N'-tetramethyl-O-(7-azabenzotriazol-1-yl)uronium hexafluorophosphate (18.87 g, 49.6 mmol). After stirring for 5 min, benzyl 3-amino-4-hydroxypyrrolidine-1-carboxylate (10.66 g, 45.1 mmol) and N,N-diisopropylethylamine (23.57 ml, 135 mmol) was added. The reaction mixture was stirred at room temperature for 2 h. The reaction was diluted with water, the aqueous layer was extracted with DCM once. The combined organic layers were dried over Na$_2$SO$_4$, filtered and concentrated. The residue was purified with flash chromatography (eluting with 0-60% ethyl acetate in hexanes) to give the desired product (11.5 g, 59%). LC-MS calculated for $C_{20}H_{22}BrN_2O_4$ (M+H)$^+$: m/z=433.1; found 433.1.

Step 4. benzyl 3-(3-bromo-2-methylbenzamido)-4-oxopyrrolidine-1-carboxylate

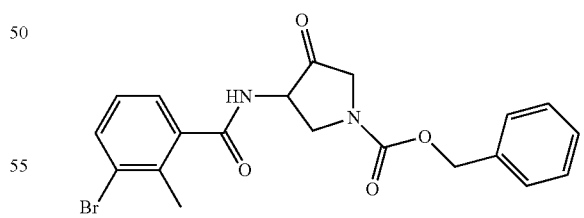

To a solution of benzyl 3-(3-bromo-2-methylbenzamido)-4-hydroxypyrrolidine-1-carboxylate (16.50 g, 38.1 mmol) in DCM (200 ml) was added Dess-Martin periodinane (19.38 g, 45.7 mmol). The resulting mixture was stirred at room temperature for 2 h. The reaction mixture was diluted with Et$_2$O and 1 M NaOH solution. After stirring for 1 h, the organic layer was separated and dried over Na$_2$SO$_4$, filtered and concentrated. The residue was purified with flash chromatography (eluting with 0-50% ethyl acetate in hexanes) to give the desired product (9.2 g, 56%). LC-MS calculated for $C_{20}H_{20}BrN_2O_4(M+H)^+$: m/z=431.1; found 431.1.

Step 5: benzyl 2-(3-bromo-2-methylphenyl)-4,6-dihydro-5H-pyrrolo[3,4-d]oxazole-5-carboxylate

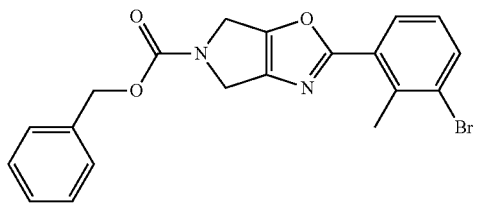 [SMILES: Cc1c(Br)cccc1-c1nc2c(o1)CN(C(=O)OCc1ccccc1)C2]

To a solution of benzyl 3-(3-bromo-2-methylbenzamido)-4-oxopyrrolidine-1-carboxylate (9.23 g, 21.40 mmol) in 1,4-dioxane (100 ml) was added $POCl_3$ (2.00 ml, 21.40 mmol). The resulting mixture was stirred at 110° C. for 3 h. After cooling to room temperature, the reaction mixture was diluted with saturated $NaHCO_3$ solution and ethyl acetate. The aqueous layer was extracted with ethyl acetate once. The combined organic layers were washed with brine, dried over $Na_2SO_4$, filtered and concentrated. The precipitate was collected via filtration and washed with ethyl acetate and hexanes to give the desired product as off white solid (4.85 g, 55%). LC-MS calculated for $C_{20}H_{18}BrN_2O_3(M+H)^+$: m/z=413.0; found 413.0.

Step 6. 2-(3-Bromo-2-methylphenyl)-5,6-dihydro-4H-pyrrolo[3,4-d]oxazole

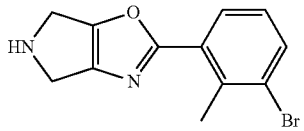 [SMILES: Cc1c(Br)cccc1-c1nc2c(o1)CNC2]

To solution of benzyl 2-(3-bromo-2-methylphenyl)-4,6-dihydro-5H-pyrrolo[3,4-d]oxazole-5-carboxylate (3.70 g, 8.95 mmol) in DCM (60 ml) was added 1 M $BBr_3$ in DCM solution (17.91 ml, 17.91 mmol) at 0° C. After stirring at same temperature for 1 h, the reaction mixture was diluted DCM and saturated $NaHCO_3$ solution. The resultant precipitate was collected vial filtration and dried under vacuum to give the desired product as white solid (2.0 g, 80%). LC-MS calculated for $C_{12}H_{12}BrN_2O$ (M+H)$^+$: m/z=279.0; found 279.0.

Step 7. 1-(2-(3-Bromo-2-methylphenyl)-4,6-dihydro-5H-pyrrolo[3,4-d]oxazol-5-yl)-2-(dimethylamino)ethan-1-one

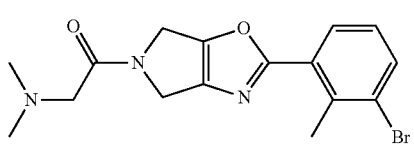 [SMILES: Cc1c(Br)cccc1-c1nc2c(o1)CN(C(=O)CN(C)C)C2]

A solution of dimethylglycine (20.5 mg, 0.199 mmol) in N,N-dimethylformamide (1 ml) was added N,N,N'N'-tetramethyl-O-(7-azabenzotriazol-1-yl)uronium hexafluorophosphate (104 mg, 0.274 mmol). After stirring for 5 min, 2-(3-bromo-2-methylphenyl)-5,6-dihydro-4H-pyrrolo[3,4-d]oxazole (55.5 mg, 0.199 mmol) and N,N-diisopropylethylamine (104 µl, 0.596 mmol). The reaction mixture was stirred at room temperature for 2 h. The reaction mixture was diluted with water, the aqueous layer was extracted with DCM once. The combined organic layers were dried over $Na_2SO_4$, filtered and concentrated. The residue was purified with silica gel column (eluting with 0-30% MeOH in DCM) to give the desired product (35 mg, 49%). LC-MS calculated for $C_{16}H_{19}BrN_3O_2$ (M+H)$^+$: m/z=364.1; found 364.1.

Step 8: 2-(3'-(5-(dimethylglycyl)-5,6-dihydro-4H-pyrrolo[3,4-d]oxazol-2-yl)-2,2'-dimethyl-[1,1'-biphenyl]-3-yl)-5-(hydroxymethyl)benzo[d]oxazole-7-carbonitrile

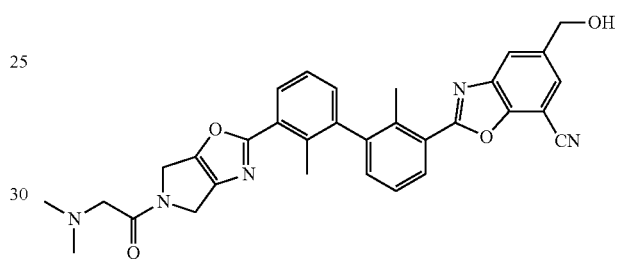

A mixture of 1-(2-(3-bromo-2-methylphenyl)-4,6-dihydro-5H-pyrrolo[3,4-d]oxazol-5-yl)-2-(dimethylamino)ethan-1-one (35.0 mg, 0.096 mmol), 5-(hydroxymethyl)-2-(2-methyl-3-(4,4,5,5-tetramethyl-1,3,2-dioxaborolan-2-yl)phenyl)benzo[d]oxazole-7-carbonitrile (Example 54, Step 2: 37.5 mg, 0.096 mmol), dicyclohexyl(2',4',6'-triisopropylbiphenyl-2-yl)phosphine-(2'-aminobiphenyl-2-yl)(chloro)palladium (1:1) (7.56 mg, 9.61 µmol) and tripotassium phosphate hydrate (48.7 mg, 0.211 mmol) in 1,4-dioxane (1.5 mL)/water (0.5 mL) was stirred at 80° C. under $N_2$ atmosphere for 1 h. The mixture was diluted with methanol and 1 N HCl solution and purified with prep-LCMS (pH 2) to give the desired product as light yellow solid (28 mg, 53%). LC-MS calculated for $C_{32}H_{30}N_5O_4$ (M+H)$^+$: m/z=548.2; found 548.3.

Step 9: 2-(3'-(5-(Dimethylglycyl)-5,6-dihydro-4H-pyrrolo[3,4-d]oxazol-2-yl)-2,2'-dimethyl-[1,1'-biphenyl]-3-yl)-5-formylbenzo[d]oxazole-7-carbonitrile

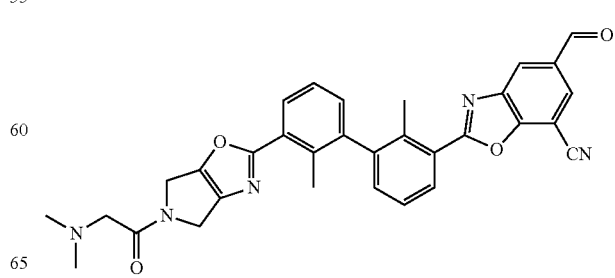

To a solution of 2-(3'-(5-(dimethylglycyl)-5,6-dihydro-4H-pyrrolo[3,4-d]oxazol-2-yl)-2,2'-dimethyl-[1,1'-biphenyl]-3-yl)-5-(hydroxymethyl)benzo[d]oxazole-7-carbonitrile (28 mg, 0.051 mmol) in DCM (2 ml) was added Dess-Martin periodinane (26.0 mg, 0.061 mmol). The resulting mixture was stirred at room temperature for 2 h. The reaction mixture was diluted with Et$_2$O and 1 M NaOH solution. After stirring for 1 h, the organic layer was separated and dried over Na$_2$SO$_4$, filtered and concentrated to give the desired product (28 mg, 100%). LC-MS calculated for C$_{32}$H$_{28}$N$_5$O$_4$ (M+H)$^+$: m/z=546.2; found 546.3.

Step 10: (R)-1-((7-Cyano-2-(3'-(5-(dimethylglycyl)-5,6-dihydro-4H-pyrrolo[3,4-d]oxazol-2-yl)-2,2'-dimethyl-[1,1'-biphenyl]-3-yl)benzo[d]oxazol-5-yl)methyl)pyrrolidine-3-carboxylic acid A mixture of (2-(3'-(5-(dimethylglycyl)-5,6-dihydro-4H-pyrrolo[3,4-d]oxazol-2-yl)-2,2'-dimethyl-[1,1'-biphenyl]-3-yl)-5-formylbenzo[d]oxazole-7-carbonitrile (10.0 mg, 0.018 mmol), (R)-pyrrolidine-3-carboxylic acid (2.1 mg, 0.018 mmol) in DCM (0.5 ml) was added DIEA (3.20 μl, 0.018 mmol). After stirring at room temperature for 2.5 h, sodium triacetoxyborohydride (7.77 mg, 0.037 mmol) was added and stirred overnight. Solvent was removed in vacuo. The residue was dissolved in methanol and water and purified with prep LCMS (pH 2, acetonitrile/water+TFA) to give the desired product as TFA salt. LC-MS calculated for C$_{37}$H$_{37}$N$_6$O$_5$ (M+H)$^+$: m/z=645.3; found 645.3. $^1$H NMR (600 MHz, DMSO) δ 8.39 (s, 1H), 8.22 (m, 1H), 8.13 (s, 1H), 8.00 (m, 1H), 7.61 (t, J=7.7 Hz, 1H), 7.55-7.46 (m, 2H), 7.37 (d, J=7.5 Hz, 1H), 4.84 (d, J=2.7 Hz, 1H), 4.73 (d, J=2.7 Hz, 1H), 4.65 (t, J=2.8 Hz, 1H), 4.55 (m, 3H), 4.30 (d, J=11.9 Hz, 2H), 3.70-3.10 (m, 5H), 2.89 (s, 6H), 2.44 (s, 3H), 2.35 (m, 5H).

Example 123

1-((7-cyano-2-(3'-(5-(dimethylglycyl)-5,6-dihydro-4H-pyrrolo[3,4-d]oxazol-2-yl)-2,2'-dimethyl-[1,1'-biphenyl]-3-yl)benzo[d]oxazol-5-yl)methyl)azetidine-3-carboxylic acid

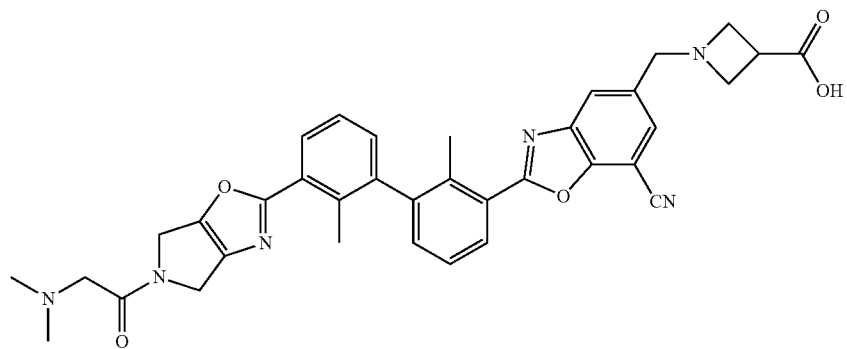 [SMILES: Cc1c(-c2nc3c(o2)CN(C(=O)CN(C)C)C3)cccc1-c1cccc(-c2nc3cc(CN4CC(C(=O)O)C4)cc(C#N)c3o2)c1C]

This compound was prepared using similar procedures as described for Example 122 with azetidine-3-carboxylic acid replacing (R)-pyrrolidine-3-carboxylic acid in Step 10. The reaction mixture was purified by prep-HPLC (pH=2, acetonitrile/water+TFA) to give the desired product as TFA salt. LC-MS calculated for C$_{36}$H$_{35}$N$_6$O$_5$ (M+H)$^+$: m/z=631.3; found 631.3.

Example 124

(R)-1-((7-cyano-2-(2,2'-dimethyl-3'-(5-(methyl-L-prolyl)-5,6-dihydro-4H-pyrrolo[3,4-d]oxazol-2-yl)-[1,1'-biphenyl]-3-yl)benzo[d]oxazol-5-yl)methyl)pyrrolidine-3-carboxylic acid

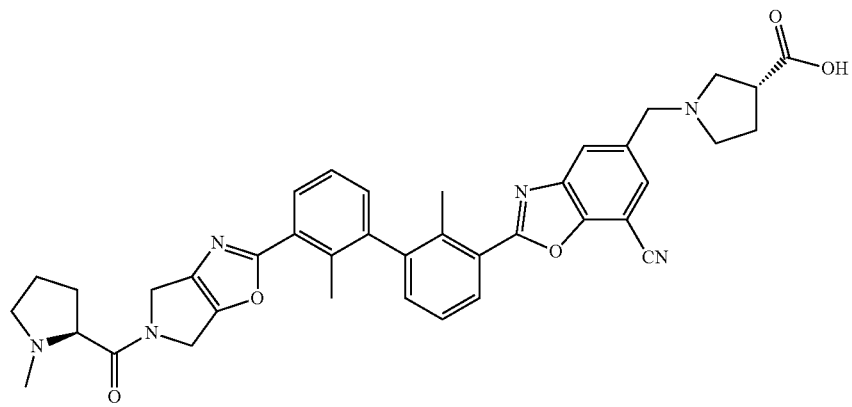 [SMILES: Cc1c(-c2nc3c(o2)CN(C(=O)[C@@H]2CCCN2C)C3)cccc1-c1cccc(-c2nc3cc(CN4CC[C@@H](C(=O)O)C4)cc(C#N)c3o2)c1C]

305

Step 1: 2-(3-bromo-2-methylphenyl)-5-(methyl-L-prolyl)-5,6-dihydro-4H-pyrrolo[3,4-d]oxazole

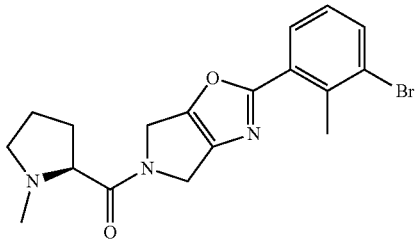 [SMILES: Cc1c(Br)cccc1-c1nc2c(o1)CN(C(=O)[C@@H]1CCCN1C)C2]

This compound was prepared using similar procedures as described for Example 122 with methyl-L-proline replacing dimethylglycine in Step 7. LC-MS calculated for $C_{18}H_{21}BrN_3O_2(M+H)^+$: m/z=390.1, 392.1; found 390.1, 392.1.

Step 2: 2-(2,2'-dimethyl-3'-(5-(methyl-L-prolyl)-5,6-dihydro-4H-pyrrolo[3,4-d]oxazol-2-yl)-[1,1'-biphenyl]-3-yl)-5-(hydroxymethyl)benzo[d]oxazole-7-carbonitrile

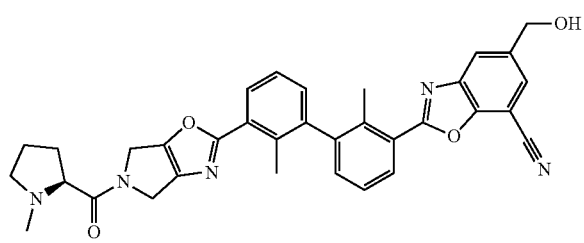 [SMILES: Cc1c(-c2nc3c(o2)CN(C(=O)[C@@H]2CCCN2C)C3)cccc1-c1cccc(-c2nc3cc(CO)cc(C#N)c3o2)c1C]

This compound was prepared using similar procedures as described for Example 122 with 2-(3-bromo-2-methylphenyl)-5-(methyl-L-prolyl)-5,6-dihydro-4H-pyrrolo[3,4-d]oxazole replacing 1-(2-(3-bromo-2-methylphenyl)-4,6-dihydro-5H-pyrrolo[3,4-d]oxazol-5-yl)-2-(dimethylamino)ethan-1-one in Step 8 LC-MS calculated for $C_{34}H_{32}N_5O_4(M+H)^+$: m/z=574.2; found 574.2.

306

Step 3: 2-(2,2'-dimethyl-3'-(5-(methyl-L-prolyl)-5,6-dihydro-4H-pyrrolo[3,4-d]oxazol-2-yl)-[1,1'-biphenyl]-3-yl)-5-formylbenzo[d]oxazole-7-carbonitrile

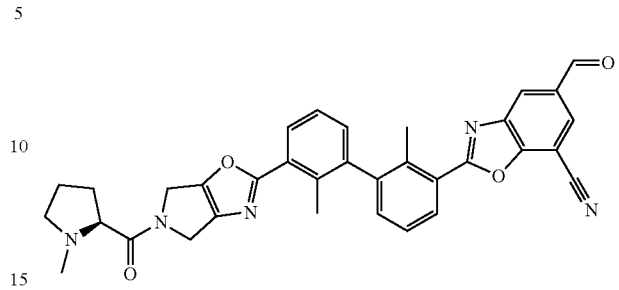

This compound was prepared using similar procedures as described for Example 122 with 2-(2,2'-dimethyl-3'-(5-(methyl-L-prolyl)-5,6-dihydro-4H-pyrrolo[3,4-d]oxazol-2-yl)-[1,1'-biphenyl]-3-yl)-5-(hydroxymethyl)benzo[d]oxazole-7-carbonitrile replacing 2-(3'-(5-(dimethylglycyl)-5,6-dihydro-4H-pyrrolo[3,4-d]oxazol-2-yl)-2,2'-dimethyl-[1,1'-biphenyl]-3-yl)-5-(hydroxymethyl)benzo[d]oxazole-7-carbonitrile in Step 9. LC-MS calculated for $C_{34}H_{30}N_5O_4(M+H)^+$: m/z=572.2; found 572.2.

Step 4: (R)-1-((7-cyano-2-(2,2'-dimethyl-3'-(5-(methyl-L-prolyl)-5,6-dihydro-4H-pyrrolo[3,4-d]oxazol-2-yl)-[1,1'-biphenyl]-3-yl)benzo[d]oxazol-5-yl)methyl)pyrrolidine-3-carboxylic acid This compound was prepared using similar procedures as described for Example 122 with (2-(2,2'-dimethyl-3'-(5-(methyl-L-prolyl)-5,6-dihydro-4H-pyrrolo[3,4-d]oxazol-2-yl)-[1,1'-biphenyl]-3-yl)-5-formylbenzo[d]oxazole-7-carbonitrile replacing (2-(3'-(5-(dimethylglycyl)-5,6-dihydro-4H-pyrrolo[3,4-d]oxazol-2-yl)-2,2'-dimethyl-[1,1'-biphenyl]-3-yl)-5-formylbenzo[d]oxazole-7-carbonitrile in Step 10. The reaction mixture was purified by prep-HPLC (pH=2, acetonitrile/water+TFA) to give the desired product as TFA salt. LC-MS calculated for $C_{39}H_{39}N_6O_5$ $(M+H)^+$: m/z=671.3; found 671.3.

Example 125

(R)-1-((7-cyano-2-(3'-(5-(3-(dimethylamino)propanoyl)-5,6-dihydro-4H-pyrrolo[3,4-d]oxazol-2-yl)-2,2'-dimethyl-[1,1'-biphenyl]-3-yl)benzo[d]oxazol-5-yl)methyl)pyrrolidine-3-carboxylic acid

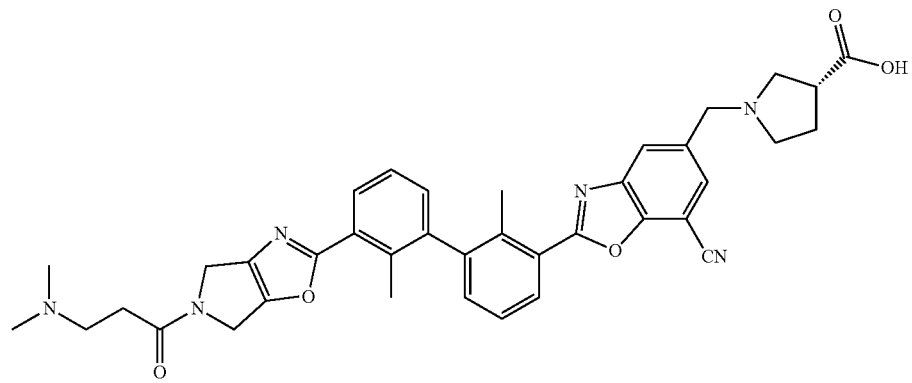 [SMILES: Cc1c(-c2nc3c(o2)CN(C(=O)CCN(C)C)C3)cccc1-c1cccc(-c2nc3cc(CN4CC[C@@H](C(=O)O)C4)cc(C#N)c3o2)c1C]

307

Step 1: 1-(2-(3-bromo-2-methylphenyl)-4,6-dihydro-5H-pyrrolo[3,4-d]oxazol-5-yl)-3-(dimethylamino)propan-1-one

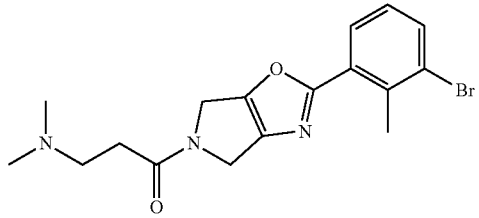 [SMILES: Cc1c(Br)cccc1-c1nc2c(o1)CN(C(=O)CCN(C)C)C2]

This compound was prepared using similar procedures as described for Example 122 with 3-(dimethylamino)propanoic acid hydrochloride replacing dimethylglycine in Step 7. LC-MS calculated for $C_{17}H_{21}BrN_3O_2(M+H)^+$: m/z= 378.1, 380.1; found 378.1, 380.1.

Step 2: 2-(3'-(5-(3-(dimethylamino)propanoyl)-5,6-dihydro-4H-pyrrolo[3,4-d]oxazol-2-yl)-2,2'-dimethyl-[1,1'-biphenyl]-3-yl)-5-(hydroxymethyl)benzo[d]oxazole-7-carbonitrile

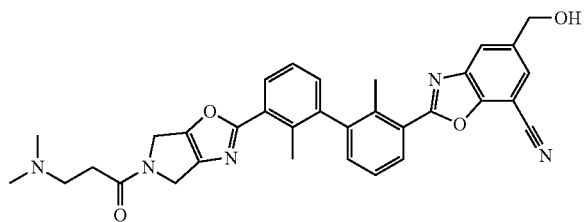 [SMILES: Cc1c(-c2nc3c(o2)CN(C(=O)CCN(C)C)C3)cccc1-c1cccc(-c2nc3cc(CO)cc(C#N)c3o2)c1C]

This compound was prepared using similar procedures as described for Example 122 with 1-(2-(3-bromo-2-methylphenyl)-4,6-dihydro-5H-pyrrolo[3,4-d]oxazol-5-yl)-3-(dimethylamino)propan-1-one replacing 1-(2-(3-bromo-2-methylphenyl)-4,6-dihydro-5H-pyrrolo[3,4-d]oxazol-5-yl)-2-(dimethylamino)ethan-1-one in Step 8. LC-MS calculated for $C_{33}H_{32}N_5O_4$ $(M+H)^+$: m/z=562.2; found 562.2.

308

Step 3: 2-(3'-(5-(3-(dimethylamino)propanoyl)-5,6-dihydro-4H-pyrrolo[3,4-d]oxazol-2-yl)-2,2'-dimethyl-[1,1'-biphenyl]-3-yl)-5-formylbenzo[d]oxazole-7-carbonitrile

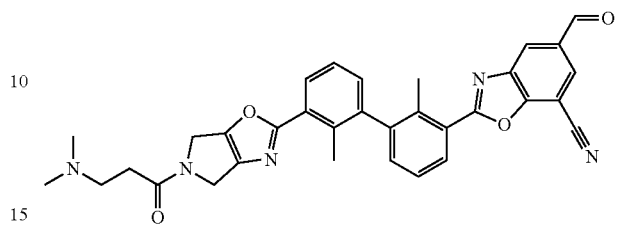

This compound was prepared using similar procedures as described for Example 122 with 2-(3'-(5-(3-(dimethylamino)propanoyl)-5,6-dihydro-4H-pyrrolo[3,4-d]oxazol-2-yl)-2,2'-dimethyl-[1,1'-biphenyl]-3-yl)-5-(hydroxymethyl)benzo[d]oxazole-7-carbonitrile replacing 2-(3'-(5-(dimethylglycyl)-5,6-dihydro-4H-pyrrolo[3,4-d]oxazol-2-yl)-2,2'-dimethyl-[1,1'-biphenyl]-3-yl)-5-(hydroxymethyl)benzo[d]oxazole-7-carbonitrile in Step 9. LC-MS calculated for $C_{33}H_{30}N_5O_4$ $(M+H)^+$: m/z=560.2; found 560.2.

Step 4: (R)-1-((7-cyano-2-(3'-(5-(3-(dimethylamino)propanoyl)-5,6-dihydro-4H-pyrrolo[3,4-d]oxazol-2-yl)-2,2'-dimethyl-[1,1'-biphenyl]-3-yl)benzo[d]oxazol-5-yl)methyl)pyrrolidine-3-carboxylic acid This compound was prepared using similar procedures as described for Example 122 with 2-(3'-(5-(3-(dimethylamino)propanoyl)-5,6-dihydro-4H-pyrrolo[3,4-d]oxazol-2-yl)-2,2'-dimethyl-[1,1'-biphenyl]-3-yl)-5-formylbenzo[d]oxazole-7-carbonitrile replacing (2-(3'-(5-(dimethylglycyl)-5,6-dihydro-4H-pyrrolo[3,4-d]oxazol-2-yl)-2,2'-dimethyl-[1,1'-biphenyl]-3-yl)-5-formylbenzo[d]oxazole-7-carbonitrile in Step 10. The reaction mixture was purified by prep-HPLC (pH=2, acetonitrile/water+TFA) to give the desired product as TFA salt. LC-MS calculated for $C_{38}H_{39}N_6O_5$ $(M+H)^+$: m/z=659.3; found 659.3.

Example 126

(R)-1-((7-cyano-2-(3'-(5-(2-((R)-3-hydroxypyrrolidin-1-yl)acetyl)-5,6-dihydro-4H-pyrrolo[3,4-d]oxazol-2-yl)-2,2'-dimethyl-[1,1'-biphenyl]-3-yl)benzo[d]oxazol-5-yl)methyl)pyrrolidine-3-carboxylic acid

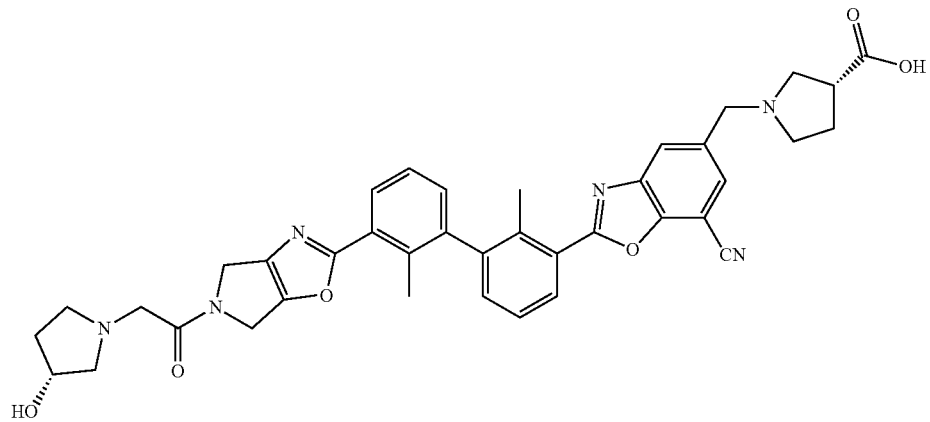 [SMILES: Cc1c(-c2nc3c(o2)CN(C(=O)CN2CC[C@@H](O)C2)C3)cccc1-c1cccc(-c2nc3cc(CN4CC[C@@H](C(=O)O)C4)cc(C#N)c3o2)c1C]

Step 1: 1-(2-(3-bromo-2-methylphenyl)-4,6-dihydro-5H-pyrrolo[3,4-d]oxazol-5-yl)-2-chloroethan-1-one

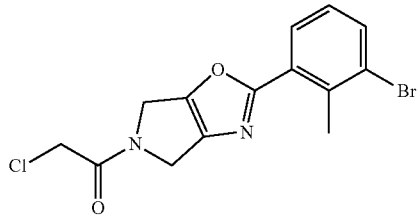 [SMILES: Cc1c(Br)cccc1-c1nc2c(o1)CN(C(=O)CCl)C2]

A solution of 2-(3-bromo-2-methylphenyl)-5,6-dihydro-4H-pyrrolo[3,4-d]oxazole (1.04 g, 3.73 mmol) in CH$_2$Cl$_2$ (18 ml) was added 2-chloroacetyl chloride (0.421 g, 3.73 mmol) and N,N-diisopropylethylamine (1.947 ml, 11.18 mmol) at 0° C. The reaction mixture was stirred at room temperature for 2 h. The reaction was diluted with water, and the aqueous layer was extracted with DCM once. The combined organic layers were dried over Na$_2$SO$_4$, filtered and concentrated. The residue was purified with flash chromatography (eluting with 0-60% ethyl acetate in hexanes) to give the desired product as white solid (0.65 g, 49%). LC-MS calculated for C$_{14}$H$_{13}$BrClN$_2$O$_2$(M+H)$^+$: m/z=355.0, 357.0; found 355.0, 357.0.

Step 2: (R)-1-(2-(3-bromo-2-methylphenyl)-4,6-dihydro-5H-pyrrolo[3,4-d]oxazol-5-yl)-2-(3-hydroxypyrrolidin-1-yl)ethan-1-one

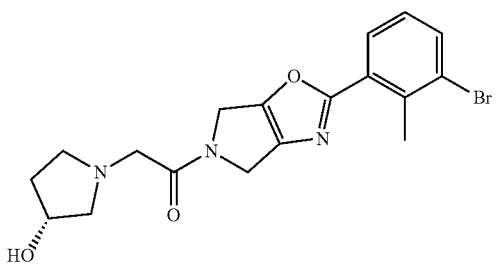 [SMILES: Cc1c(Br)cccc1-c1nc2c(o1)CN(C(=O)CN1CC[C@@H](O)C1)C2]

The mixture of 1-(2-(3-bromo-2-methylphenyl)-4,6-dihydro-5H-pyrrolo[3,4-d]oxazol-5-yl)-2-chloroethan-1-one (12 mg, 0.034 mmol), (R)-pyrrolidin-3-ol (2.94 mg, 0.034 mmol), potassium carbonate (4.66 mg, 0.034 mmol) and DMF (1.0 ml) was heated at 100° C. for 2 h. The reaction mixture was diluted with methanol and 1 N HCl, purified with prep LCMS (pH 2) to give the desired product (10 mg, 73%). LC-MS calculated for C$_{18}$H$_{21}$BrN$_3$O$_3$(M+H)$^+$: m/z=406.1, 408.1; found 406.1, 408.1.

Step 3: (R)-1-((2-(3-bromo-2-methylphenyl)-7-chlorobenzo[d]oxazol-5-yl)methyl)pyrrolidine-3-carboxylic acid

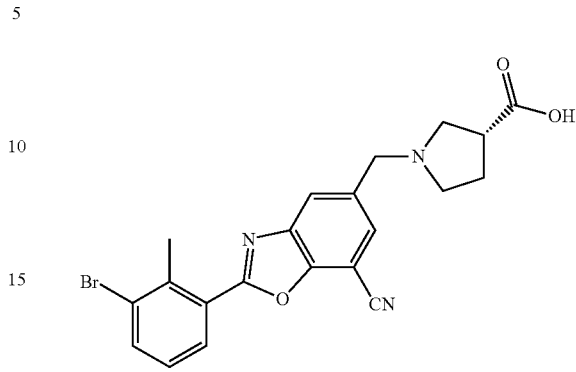

A mixture of (2-(3-bromo-2-methylphenyl)-7-chlorobenzo[d]oxazole-5-carbaldehyde (Example 10, Step 1: 3.38 g, 9.64 mmol), (R)-pyrrolidine-3-carboxylic acid hydrochloride (1.461 g, 9.64 mmol) in CH$_2$Cl$_2$ (150 ml) was added DIEA (3.87 ml, 22.17 mmol). After stirring at room temperature for 6.5 h, sodium triacetoxyborohydride (4.09 g, 19.28 mmol) was added and stirred overnight. Water was added and the mixture was stirred overnight. The precipitate was collected via filtration and washed with water and ethyl acetate. The organic layer was concentrated and purified with silica gel column (0-100% ethyl acetate in hexanes, then 0-35% methanol in DCM). LC-MS calculated for C$_{20}$H$_{19}$BrClN$_2$O$_3$(M+H)$^+$: m/z=449.0, 451.0; found 449.0, 451.0.

Step 4: (R)-1-((7-chloro-2-(2-methyl-3-(4,4,5,5-tetramethyl-1,3,2-dioxaborolan-2-yl)phenyl)benzo[d]oxazol-5-yl)methyl)pyrrolidine-3-carboxylic acid

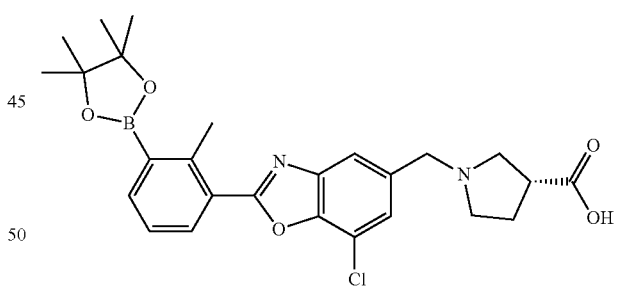

A microwave vial charged with (R)-1-((2-(3-bromo-2-methylphenyl)-7-chlorobenzo[d]oxazol-5-yl)methyl)pyrrolidine-3-carboxylic acid (1.20 g, 2.67 mmol), bis(pinacolato)diboron (0.813 g, 3.20 mmol), dichloro[1,1'-bis(diphenylphosphino)ferrocene]palladium (II) dichloromethane adduct (0.218 g, 0.267 mmol) and acetic acid, potassium salt, anhydrous (0.655 g, 6.67 mmol) was evacuated under vacuum and refilled with nitrogen and stirred at 95° C. for 2 h. The crude was diluted with DCM, and then filtered through a pad of Celite. The filtrate was concentrated. The residue was purified with flash chromatography (0-100% ethyl acetate in hexanes, then 0-35% methanol in DCM). LC-MS calculated for C$_{26}$H$_{31}$BClN$_2$O$_5$(M+H)$^+$: m/z=497.2; found 497.1.

Step 5: (R)-1-((7-cyano-2-(2-methyl-3-(4,4,5,5-tetramethyl-1,3,2-dioxaborolan-2-yl)phenyl)benzo[d]oxazol-5-yl)methyl)pyrrolidine-3-carboxylic acid

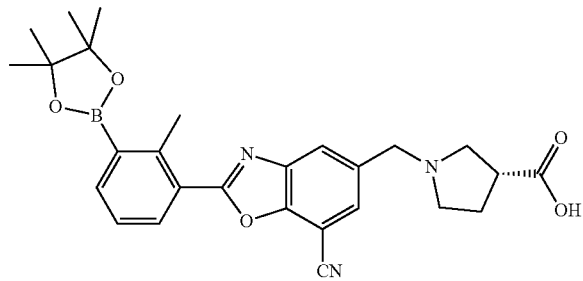 [SMILES: Cc1c(B2OC(C)(C)C(C)(C)O2)cccc1-c1nc2cc(CN3CC[C@@H](C(=O)O)C3)cc(Cl)c2o1]

Step 6: (R)-1-((7-cyano-2-(3'-(5-(2-((R)-3-hydroxypyrrolidin-1-yl)acetyl)-5,6-dihydro-4H-pyrrolo[3,4-d]oxazol-2-yl)-2,2'-dimethyl-[1,1'-biphenyl]-3-yl)benzo[d]oxazol-5-yl)methyl)pyrrolidine-3-carboxylic acid A mixture of (R)-1-(2-(3-bromo-2-methylphenyl)-4,6-dihydro-5H-pyrrolo[3,4-d]oxazol-5-yl)-2-(3-hydroxypyrrolidin-1-yl)ethan-1-one (10 mg, 0.025 mmol), (R)-1-((7-cyano-2-(2-methyl-3-(4,4,5,5-tetramethyl-1,3,2-dioxaborolan-2-yl)phenyl)benzo[d]oxazol-5-yl)methyl)pyrrolidine-3-carboxylic acid (12.00 mg, 0.025 mmol), dicyclohexyl(2',4',6'-triisopropylbiphenyl-2-yl)phosphine-(2'-aminobiphenyl-2-yl)(chloro)palladium (1:1) (1.937 mg, 2.461 μmol) and tripotassium phosphate hydrate (12.47 mg, 0.054 mmol) in 1,4-dioxane (0.6 mL) and water (0.2 mL) was stirred at 80° C. under nitrogen atmosphere for 1 h. The residue was dissolved in methanol and 1 N HCl solution and purified with prep-LCMS (pH 2) to give the desired product as the TFA salt. LC-MS calculated for $C_{39}H_{39}N_6O_6$ (M+H)$^+$: m/z=687.3; found 687.3. $^1$H NMR (600 MHz, DMSO) δ 8.40 (d, J=1.2 Hz, 1H), 8.22 (m, 1H), 8.14 (d, J=1.4 Hz, 1H), 8.00 (m, 1H), 7.65-7.58 (m, 1H), 7.54-7.46 (m, 2H), 7.37 (d, J=7.6 Hz, 1H), 4.83-4.30 (m, 9H), 3.85-3.05 (m, 9H), 2.44 (s, 3H), 2.35 (m, 3H), 2.34-1.85 (m, 4H).

Example 127

(R)-1-((7-cyano-2-(3'-(5-(2-(3-hydroxyazetidin-1-yl)acetyl)-5,6-dihydro-4H-pyrrolo[3,4-d]oxazol-2-yl)-2,2'-dimethyl-[1,1'-biphenyl]-3-yl)benzo[d]oxazol-5-yl)methyl)pyrrolidine-3-carboxylic acid

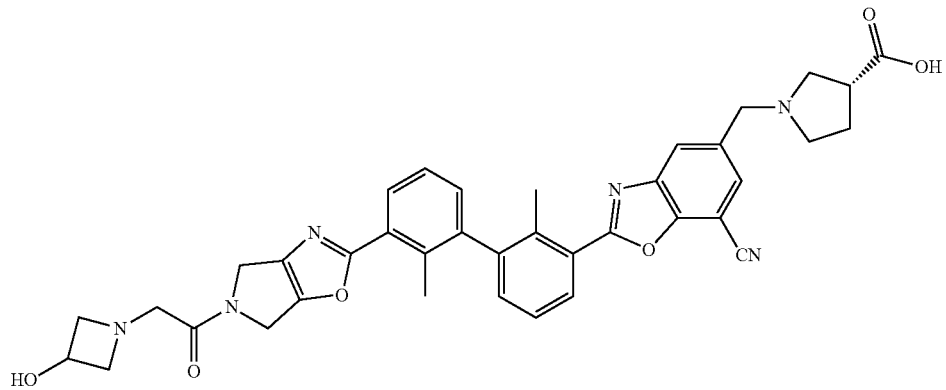 [SMILES: Cc1c(-c2nc3c(o2)CN(C(=O)CN2CC(O)C2)C3)cccc1-c1cccc(-c2nc3cc(CN4CC[C@@H](C(=O)O)C4)cc(C#N)c3o2)c1C]

Step 1: 1-(2-(3-bromo-2-methylphenyl)-4,6-dihydro-5H-pyrrolo[3,4-d]oxazol-5-yl)-2-(3-hydroxyazetidin-1-yl)ethan-1-one

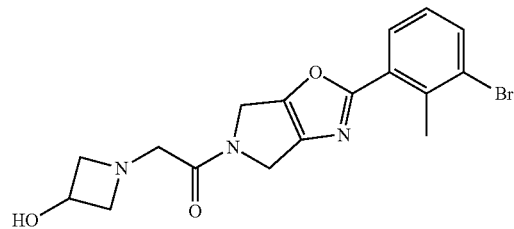 [SMILES: Cc1c(Br)cccc1-c1nc2c(o1)CN(C(=O)CN1CC(O)C1)C2]

This compound was prepared using similar procedures as described for Example 126 with azetidin-3-ol replacing (R)-pyrrolidin-3-ol in Step 2 LC-MS calculated for $C_{17}H_{19}BrN_3O_3$(M+H)$^+$: m/z=392.1, 394.1; found 392.1, 394.1.

Step 2: (R)-1-((7-cyano-2-(3'-(5-(2-(3-hydroxyazetidin-1-yl)acetyl)-5,6-dihydro-4H-pyrrolo[3,4-d]oxazol-2-yl)-2,2'-dimethyl-[1,1'-biphenyl]-3-yl)benzo[d]oxazol-5-yl)methyl)pyrrolidine-3-carboxylic acid This compound was prepared using similar procedures as described for Example 126 with 1-(2-(3-bromo-2-methylphenyl)-4,6-dihydro-5H-pyrrolo[3,4-d]oxazol-5-yl)-2-(3- hydroxyazetidin-1-yl)ethan-1-one replacing (R)-1-(2-(3-bromo-2-methylphenyl)-4,6-dihydro-5H-pyrrolo[3,4-d]oxazol-5-yl)-2-(3-hydroxypyrrolidin-1-yl)ethan-1-one in Step 6. The reaction mixture was purified by prep-HPLC (pH=2, acetonitrile/water+TFA) to give the desired product as TFA salt. LC-MS calculated for $C_{38}H_{37}N_6O_6$ (M+H)$^+$: m/z=673.3; found 673.3.

Example 128

(R)-1-((7-cyano-2-(3'-(5-(2-((S)-3-hydroxypyrrolidin-1-yl)acetyl)-5,6-dihydro-4H-pyrrolo[3,4-d]oxazol-2-yl)-2,2'-dimethyl-[1,1'-biphenyl]-3-yl)benzo[d]oxazol-5-yl)methyl)pyrrolidine-3-carboxylic acid

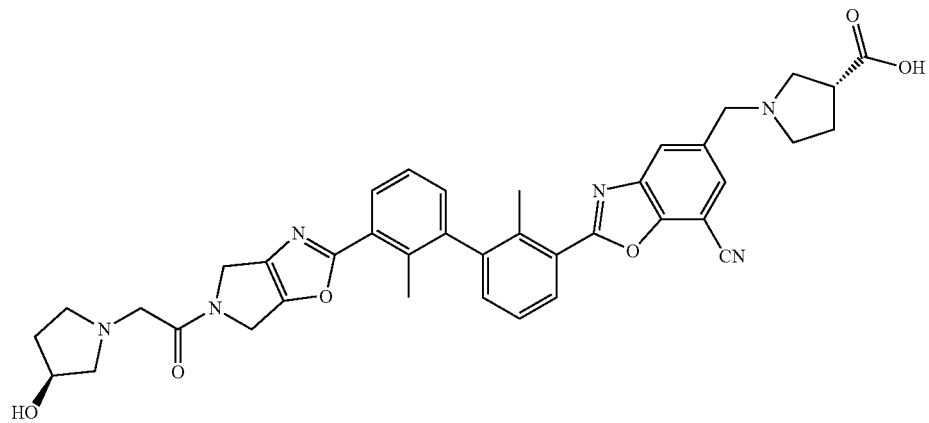 [SMILES: Cc1c(-c2nc3c(o2)CN(C(=O)CN2CC[C@H](O)C2)C3)cccc1-c1cccc(-c2nc3cc(CN4CC[C@@H](C(=O)O)C4)cc(C#N)c3o2)c1C]

Step 1: (S)-1-(2-(3-bromo-2-methylphenyl)-4,6-dihydro-5H-pyrrolo[3,4-d]oxazol-5-yl)-2-(3-hydroxypyrrolidin-1-yl) ethan-1-one

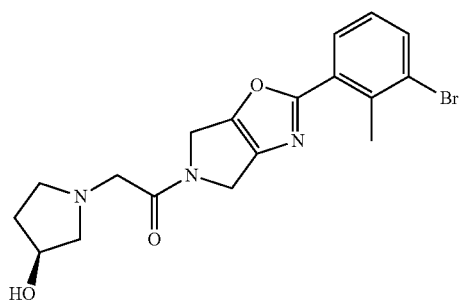 [SMILES: Cc1c(Br)cccc1-c1nc2c(o1)CN(C(=O)CN1CC[C@H](O)C1)C2]

This compound was prepared using similar procedures as described for Example 126 with (S)-pyrrolidin-3-ol replacing (R)-pyrrolidin-3-ol in Step 2. LC-MS calculated for $C_{18}H_{21}BrN_3O_3$(M+H)$^+$: m/z=406.1, 408.1; found 406.1, 408.1.

Step 2: (R)-1-((7-cyano-2-(3'-(5-(2-((S)-3-hydroxypyrrolidin-1-yl)acetyl)-5,6-dihydro-4H-pyrrolo[3,4-d]oxazol-2-yl)-2,2'-dimethyl-[1,1'-biphenyl]-3-yl)benzo[d]oxazol-5-yl)methyl)pyrrolidine-3-carboxylic acid This compound was prepared using similar procedures as described for Example 126 with (S)-1-(2-(3-bromo-2-methylphenyl)-4,6-dihydro-5H-pyrrolo[3,4-d]oxazol-5-yl)-2-(3-hydroxypyrrolidin-1-yl)ethan-1-one replacing (R)-1-(2-(3-bromo-2-methylphenyl)-4,6-dihydro-5H-pyrrolo[3,4-d]oxazol-5-yl)-2-(3-hydroxypyrrolidin-1-yl)ethan-1-one in Step 6. The reaction mixture was purified by prep-HPLC (pH=2, acetonitrile/water+TFA) to give the desired product as TFA salt. LC-MS calculated for $C_{39}H_{39}N_6O_6$ (M+H)$^+$: m/z=687.3; found 687.3.

Example 129

(R)-1-((7-cyano-2-(3'-(5-(2-(3-hydroxy-3-methylazetidin-1-yl)acetyl)-5,6-dihydro-4H-pyrrolo[3,4-d]oxazol-2-yl)-2,2'-dimethyl-[1,1'-biphenyl]-3-yl)benzo[d]oxazol-5-yl)methyl)pyrrolidine-3-carboxylic acid

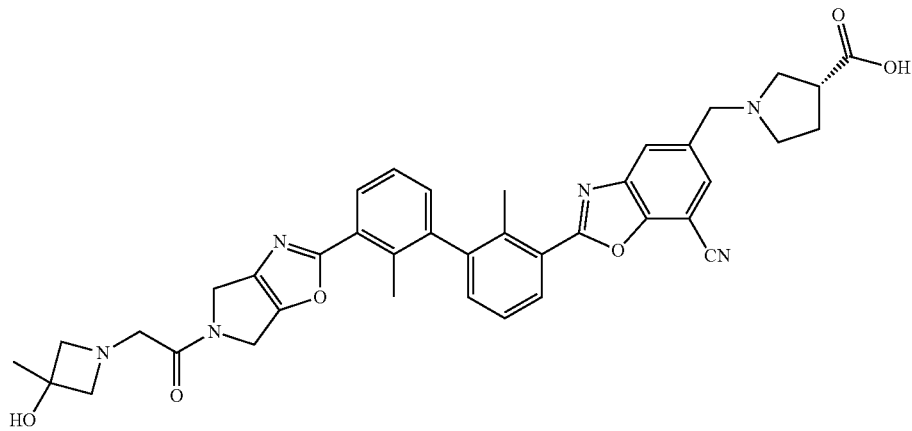 [SMILES: Cc1c(-c2nc3c(o2)CN(C(=O)CN2CC(C)(O)C2)C3)cccc1-c1cccc(-c2nc3cc(CN4CC[C@@H](C(=O)O)C4)cc(C#N)c3o2)c1C]

Step 1: 1-(2-(3-bromo-2-methylphenyl)-4,6-dihydro-5H-pyrrolo[3,4-d]oxazol-5-yl)-2-(3-hydroxy-3-methylazetidin-1-yl)ethan-1-one

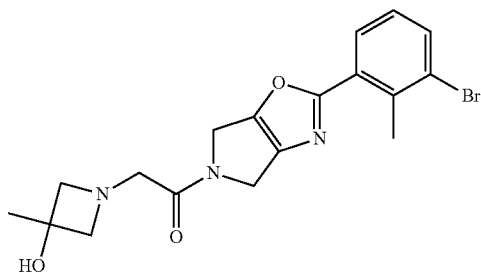 [SMILES: Cc1c(Br)cccc1-c1nc2c(o1)CN(C(=O)CN1CC(C)(O)C1)C2]

This compound was prepared using similar procedures as described for Example 126 with 3-methylazetidin-3-ol hydrochloride replacing (R)-pyrrolidin-3-ol in Step 2 LC-MS calculated for $C_{18}H_{21}BrN_3O_3$ (M+H)$^+$: m/z=406.1, 408.1; found 406.1, 408.1.

Step 2: (R)-1-((7-cyano-2-(3'-(5-(2-(3-hydroxy-3-methylazetidin-1-yl)acetyl)-5,6-dihydro-4H-pyrrolo[3,4-d]oxazol-2-yl)-2,2'-dimethyl-[1,1'-biphenyl]-3-yl)benzo[d]oxazol-5-yl)methyl)pyrrolidine-3-carboxylic acid This compound was prepared using similar procedures as described for Example 126 with 1-(2-(3-bromo-2-methylphenyl)-4,6-dihydro-5H-pyrrolo[3,4-d]oxazol-5-yl)-2-(3-hydroxy-3-methylazetidin-1-yl)ethan-1-one replacing (R)-1-(2-(3-bromo-2-methylphenyl)-4,6-dihydro-5H-pyrrolo[3,4-d]oxazol-5-yl)-2-(3-hydroxypyrrolidin-1-yl)ethan-1-one in Step 6. The reaction mixture was purified by prep-HPLC (pH=2, acetonitrile/water+TFA) to give the desired product as TFA salt. LC-MS calculated for $C_{39}H_{39}N_6O_6$ (M+H)$^+$: m/z=687.3; found 687.3.

Example 130

(R)-1-((2-(3'-(5-(2-(azetidin-1-yl)acetyl)-5,6-dihydro-4H-pyrrolo[3,4-d]oxazol-2-yl)-2,2'-dimethyl-[1,1'-biphenyl]-3-yl)-7-cyanobenzo[d]oxazol-5-yl)methyl)pyrrolidine-3-carboxylic acid

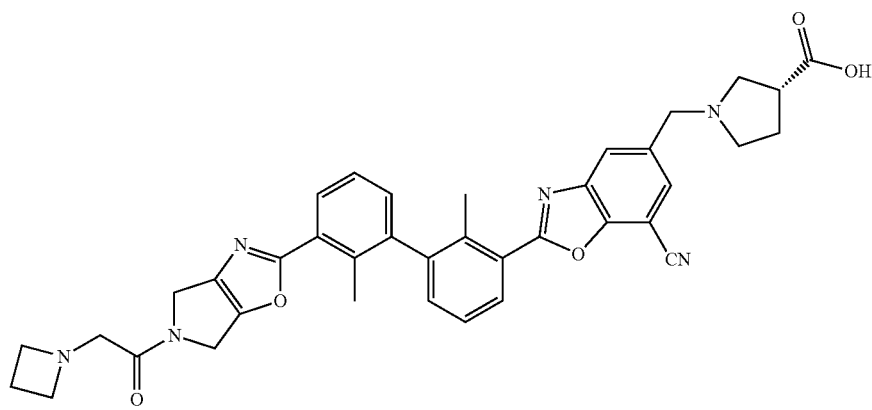 [SMILES: Cc1c(-c2nc3c(o2)CN(C(=O)CN2CCC2)C3)cccc1-c1cccc(-c2nc3cc(CN4CC[C@@H](C(=O)O)C4)cc(C#N)c3o2)c1C]

Step 1: 2-(azetidin-1-yl)-1-(2-(3-bromo-2-methylphenyl)-4,6-dihydro-5H-pyrrolo[3,4-d]oxazol-5-yl)ethan-1-one

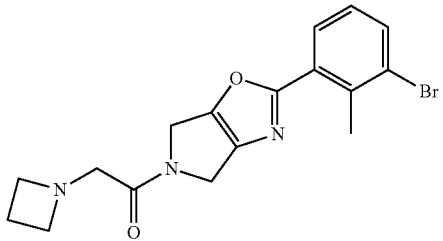 [SMILES: Cc1c(Br)cccc1-c1nc2c(o1)CN(C(=O)CN1CCC1)C2]

This compound was prepared using similar procedures as described for Example 126 with azetidine replacing (R)-pyrrolidin-3-ol in Step 2. LC-MS calculated for $C_{17}H_{19}BrN_3O_2$ (M+H)$^+$: m/z=376.1, 378.1; found 376.1, 378.1.

Step 2: (R)-1-((2-(3'-(5-(2-(azetidin-1-yl)acetyl)-5,6-dihydro-4H-pyrrolo[3,4-d]oxazol-2-yl)-2,2'-dimethyl-[1,1'-biphenyl]-3-yl)-7-cyanobenzo[d]oxazol-5-yl)methyl)pyrrolidine-3-carboxylic acid This compound was prepared using similar procedures as described for Example 126 with 2-(azetidin-1-yl)-1-(2-(3-bromo-2-methylphenyl)-4,6-dihydro-5H-pyrrolo[3,4-d]oxazol-5-yl)ethan-1-one replacing (R)-1-(2-(3-bromo-2-methylphenyl)-4,6-dihydro-5H-pyrrolo[3,4-d]oxazol-5-yl)-2-(3-hydroxypyrrolidin-1-yl)ethan-1-one in Step 6. The reaction mixture was purified by prep-HPLC (pH=2, acetonitrile/water+TFA) to give the desired product as TFA salt. LC-MS calculated for $C_{38}H_{37}N_6O_5$ (M+H)$^+$: m/z=657.3; found 657.3.

Example 131

(S)-1-(2-(2-(3'-(7-cyano-5-(((R)-3-hydroxypyrrolidin-1-yl)methyl)benzo[d]oxazol-2-yl)-2,2'-dimethyl-[1,1'-biphenyl]-3-yl)-4,6-dihydro-5H-pyrrolo[3,4-d]oxazol-5-yl)-2-oxoethyl)pyrrolidine-3-carboxylic acid

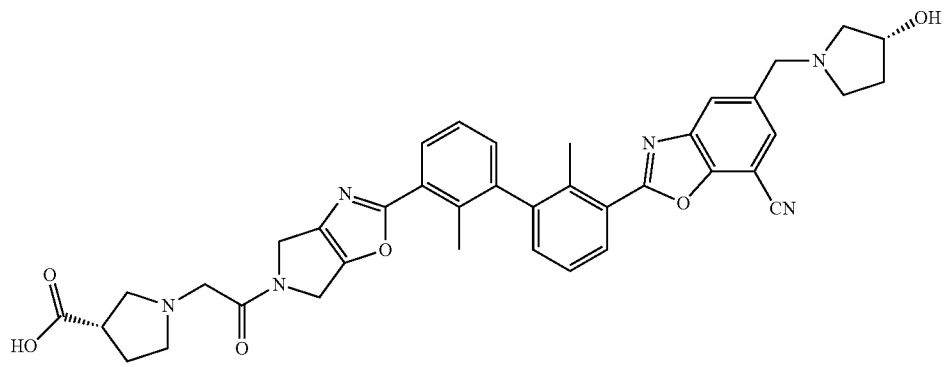 [SMILES: Cc1c(-c2nc3c(o2)CN(C(=O)CN2CC[C@H](C(=O)O)C2)C3)cccc1-c1cccc(-c2nc3cc(CN4CC[C@@H](O)C4)cc(C#N)c3o2)c1C]

Step 1: (S)-1-(2-(2-(3-bromo-2-methylphenyl)-4,6-dihydro-5H-pyrrolo[3,4-d]oxazol-5-yl)-2-oxoethyl)pyrrolidine-3-carboxylic acid

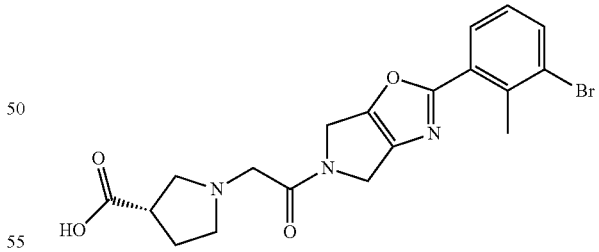

The mixture of 1-(2-(3-bromo-2-methylphenyl)-4,6-dihydro-5H-pyrrolo[3,4-d]oxazol-5-yl)-2-chloroethan-1-one (Example 126, Step 1; 15 mg, 0.042 mmol), (S)-pyrrolidine-3-carboxylic acid (4.86 mg, 0.042 mmol), TEA (0.018 ml, 0.127 mmol) and N,N-dimethylformamide (1.0 ml) was heated at 60° C. for 2 h. The reaction mixture was diluted with methanol and 1 N HCl solution, then purified with prep-LCMS (pH 2) to give the desired product (12 mg, 65%). LC-MS calculated for $C_{19}H_{21}BrN_3O_4$(M+H)$^+$: m/z=434.1, 436.1; found 434.1, 436.1.

Step 2: (R)-1-((2-(3-bromo-2-methylphenyl)-7-chlorobenzo[d]oxazol-5-yl)methyl)pyrrolidin-3-ol

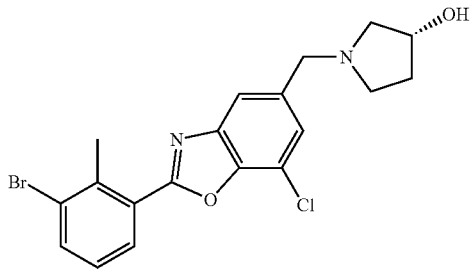 [SMILES: Cc1c(Br)cccc1-c1nc2cc(CN3CC[C@@H](O)C3)cc(Cl)c2o1]

A mixture of (2-(3-bromo-2-methylphenyl)-7-chlorobenzo[d]oxazole-5-carbaldehyde (Example 10, Step 1: 0.50 g, 1.426 mmol), (R)-pyrrolidin-3-ol (0.124 g, 1.426 mmol) in CH$_2$Cl$_2$ (20 ml) was added DIEA (0.573 ml, 3.28 mmol). After stirring at room temperature for 6.5 h, sodium triacetoxyborohydride (0.605 g, 2.85 mmol) was added and stirred overnight. Water was added and The organic layer was separated and concentrated and purified with flash chromatography (eluting with 0-100% ethyl acetate in hexanes, then 0-35% methanol in DCM) to give the desired product (0.28 g, 46%). LC-MS calculated for C$_{19}$H$_{19}$BrClN$_2$O$_2$(M+H)$^+$: m/z=421.0, 423.0; found 421.0, 423.0.

Step 3: (R)-1-((7-chloro-2-(2-methyl-3-(4,4,5,5-tetramethyl-1,3,2-dioxaborolan-2-yl)phenyl)benzo[d]oxazol-5-yl)methyl)pyrrolidin-3-ol

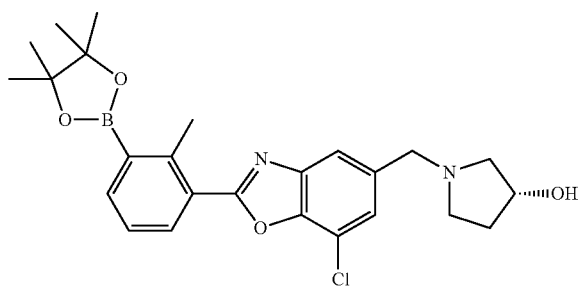 [SMILES: Cc1c(B2OC(C)(C)C(C)(C)O2)cccc1-c1nc2cc(CN3CC[C@@H](O)C3)cc(Cl)c2o1]

A mixture of (R)-1-((2-(3-bromo-2-methylphenyl)-7-chlorobenzo[d]oxazol-5-yl)methyl)pyrrolidin-3-ol (278 mg, 0.659 mmol), bis(pinacolato)diboron (201 mg, 0.791 mmol), dichloro[1,1'-bis(diphenylphosphino)ferrocene]palladium (II) dichloromethane adduct (53.8 mg, 0.066 mmol) and acetic acid, potassium salt, anhydrous (162 mg, 1.648 mmol) was stirred under nitrogen atmosphere at 95° C. for 2 h. The crude was diluted with DCM, and then filtered through a pad of Celite. The filtrate was concentrated. The residue was purified with flash chromatography (0-100% ethyl acetate in hexanes, then 0-35% methanol in DCM). LC-MS calculated for C$_{25}$H$_{31}$BClN$_2$O$_4$(M+H)$^+$: m/z=469.2; found 469.2.

Step 4: (R)-5-((3-hydroxypyrrolidin-1-yl)methyl)-2-(2-methyl-3-(4,4,5,5-tetramethyl-1,3,2-dioxaborolan-2-yl)phenyl)benzo[d]oxazole-7-carbonitrile

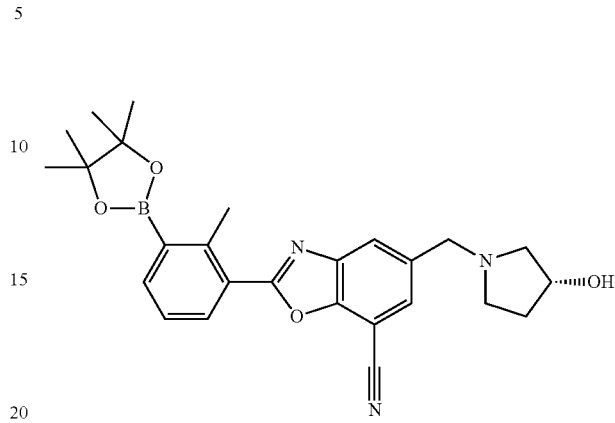

This compound was prepared using similar procedures as described for Example 126 with (R)-1-((7-chloro-2-(2-methyl-3-(4,4,5,5-tetramethyl-1,3,2-dioxaborolan-2-yl)phenyl)benzo[d]oxazol-5-yl)methyl)pyrrolidin-3-ol replacing (R)-1-((7-chloro-2-(2-methyl-3-(4,4,5,5-tetramethyl-1,3,2-dioxaborolan-2-yl)phenyl)benzo[d]oxazol-5-yl)methyl)pyrrolidine-3-carboxylic acid in Step 5. LC-MS calculated for C$_{26}$H$_{31}$BN$_3$O$_4$ (M+H)$^+$: m/z=460.2; found 460.2.

Step 5: (S)-1-(2-(2-(3'-(7-cyano-5-(((R)-3-hydroxypyrrolidin-1-yl)methyl)benzo[d]oxazol-2-yl)-2,2'-dimethyl-[1,1'-biphenyl]-3-yl)-4,6-dihydro-5H-pyrrolo[3,4-d]oxazol-5-yl)-2-oxoethyl)pyrrolidine-3-carboxylic acid A microwave vial charged with (S)-1-(2-(2-(3-bromo-2-methylphenyl)-4,6-dihydro-5H-pyrrolo[3,4-d]oxazol-5-yl)-2-oxoethyl)pyrrolidine-3-carboxylic acid (10.0 mg, 0.023 mmol), (R)-5-((3-hydroxypyrrolidin-1-yl)methyl)-2-(2-methyl-3-(4,4,5,5-tetramethyl-1,3,2-dioxaborolan-2-yl)phenyl)benzo[d]oxazole-7-carbonitrile (10.58 mg, 0.023 mmol), dicyclohexyl(2',4',6'-triisopropylbiphenyl-2-yl)phosphine-(2'-aminobiphenyl-2-yl)(chloro)palladium (1:1) (1.812 mg, 2.303 μmol) and tripotassium phosphate hydrate (11.67 mg, 0.051 mmol) was evacuated under high vacuum and refilled with nitrogen (repeated three times). 1,4-Dioxane (0.6 mL) and water (0.2 mL) was added and resulting mixture was stirred at 80° C. for 1 h. The reaction mixture was diluted with methanol and 1 N HCl solution and purified with prep-LCMS (pH 2) to give the desired product as the TFA salt. LC-MS calculated for C$_{39}$H$_{39}$N$_6$O$_6$ (M+H)$^+$: m/z=687.3; found 687.5.

Example 132

(R)-1-(2-(2-(3'-(7-cyano-5-(((R)-3-hydroxypyrrolidin-1-yl)methyl)benzo[d]oxazol-2-yl)-2,2'-dimethyl-[1,1'-biphenyl]-3-yl)-4,6-dihydro-5H-pyrrolo[3,4-d]oxazol-5-yl)-2-oxoethyl)pyrrolidine-3-carboxylic acid

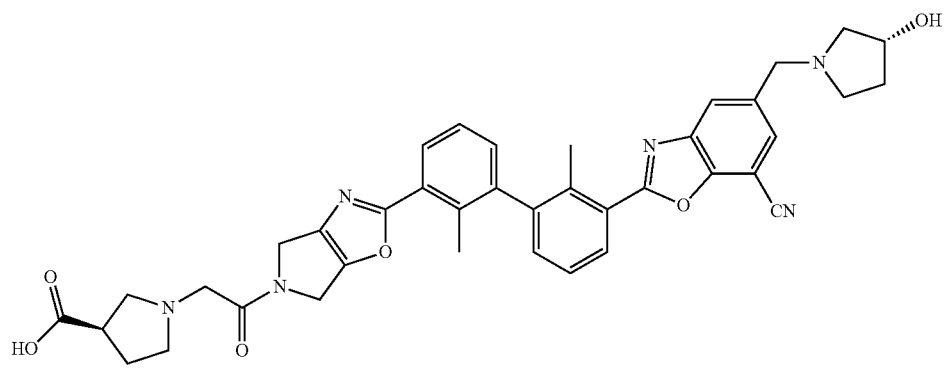 [SMILES: Cc1c(-c2nc3c(o2)CN(C(=O)CN2CC[C@@H](C(=O)O)C2)C3)cccc1-c1cccc(-c2nc3cc(CN4CC[C@@H](O)C4)cc(C#N)c3o2)c1C]

Step 1: (R)-1-(2-(2-(3-bromo-2-methylphenyl)-4,6-dihydro-5H-pyrrolo[3,4-d]oxazol-5-yl)-2-oxoethyl)pyrrolidine-3-carboxylic acid

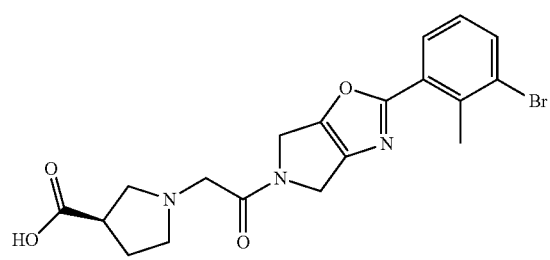 [SMILES: Cc1c(Br)cccc1-c1nc2c(o1)CN(C(=O)CN1CC[C@@H](C(=O)O)C1)C2]

This compound was prepared using similar procedures as described for Example 131 with (R)-pyrrolidine-3-carboxylic acid replacing (S)-pyrrolidine-3-carboxylic acid in Step 1. LC-MS calculated for $C_{19}H_{21}BrN_3O_4(M+H)^+$: m/z=434.1, 436.1; found 434.1, 436.1.

Step 2: (R)-1-(2-(2-(3'-(7-cyano-5-(((R)-3-hydroxypyrrolidin-1-yl)methyl)benzo[d]oxazol-2-yl)-2,2'-dimethyl-[1,1'-biphenyl]-3-yl)-4,6-dihydro-5H-pyrrolo[3,4-d]oxazol-5-yl)-2-oxoethyl)pyrrolidine-3-carboxylic acid This compound was prepared using similar procedures as described for Example 131 with (R)-1-(2-(2-(3-bromo-2-methylphenyl)-4,6-dihydro-5H-pyrrolo[3,4-d]oxazol-5-yl)-2-oxoethyl)pyrrolidine-3-carboxylic acid replacing (S)-1-(2-(2-(3-bromo-2-methylphenyl)-4,6-dihydro-5H-pyrrolo[3,4-d]oxazol-5-yl)-2-oxoethyl)pyrrolidine-3-carboxylic acid in Step 5. The reaction mixture was purified by prep-HPLC (pH=2, acetonitrile/water+TFA) to give the desired product as TFA salt. LC-MS calculated for $C_{39}H_{39}N_6O_6$ $(M+H)^+$: m/z=687.3; found 687.5.

Example 133

(S)-1-(2-(2-(3'-(7-cyano-5-(((R)-3-hydroxypyrrolidin-1-yl)methyl)benzo[d]oxazol-2-yl)-2,2'-dimethyl-[1,1"-biphenyl]-3-yl)-4,6-dihydro-5H-pyrrolo[3,4-d]oxazol-5-yl)-2-oxoethyl)piperidine-2-carboxylic acid

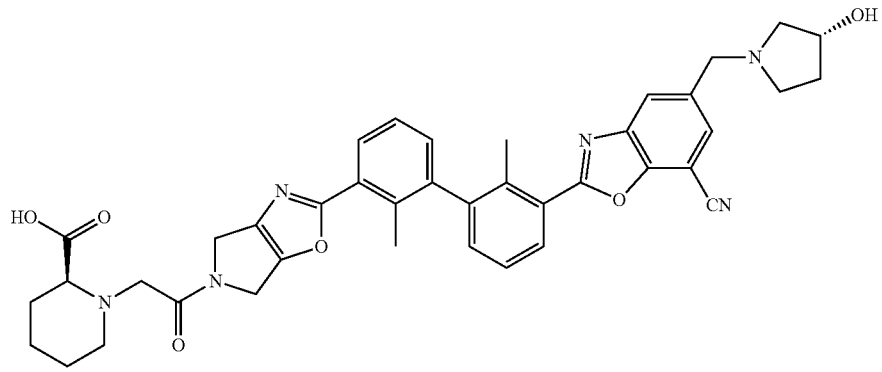 [SMILES: Cc1c(-c2nc3c(o2)CN(C(=O)CN2CCCC[C@H]2C(=O)O)C3)cccc1-c1cccc(-c2nc3cc(CN4CC[C@@H](O)C4)cc(C#N)c3o2)c1C]

Step 1: (S)-1-(2-(2-(3-bromo-2-methylphenyl)-4,6-dihydro-5H-pyrrolo[3,4-d]oxazol-5-yl)-2-oxoethyl)piperidine-2-carboxylic acid

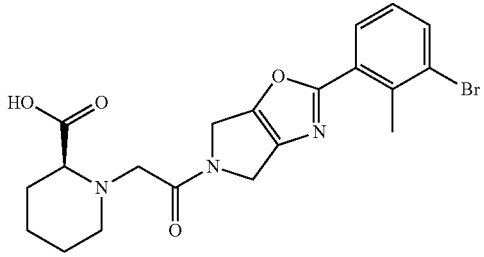 [SMILES: Cc1c(Br)cccc1-c1nc2c(o1)CN(C(=O)CN1CCCC[C@H]1C(=O)O)C2]

This compound was prepared using similar procedures as described for Example 131 with (S)-piperidine-2-carboxylic acid replacing (S)-pyrrolidine-3-carboxylic acid in Step 1 LC-MS calculated for $C_{20}H_{23}BrN_3O_4(M+H)^+$: m/z=448.1, 450.1; found 448.1, 450.1.

Step 2: (S)-1-(2-(2-(3'-(7-cyano-5-(((R)-3-hydroxypyrrolidin-1-yl)methyl)benzo[d]oxazol-2-yl)-2,2'-dimethyl-[1,1'-biphenyl]-3-yl)-4,6-dihydro-5H-pyrrolo[3,4-d]oxazol-5-yl)-2-oxoethyl)piperidine-2-carboxylic acid This compound was prepared using similar procedures as described for Example 131 with (S)-1-(2-(2-(3-bromo-2-methylphenyl)-4,6-dihydro-5H-pyrrolo[3,4-d]oxazol-5-yl)-2-oxoethyl)piperidine-2-carboxylic acid replacing (S)-1-(2-(2-(3-bromo-2-methylphenyl)-4,6-dihydro-5H-pyrrolo[3,4-d]oxazol-5-yl)-2-oxoethyl)pyrrolidine-3-carboxylic acid in Step 5. The reaction mixture was purified by prep-HPLC (pH=2, acetonitrile/water+TFA) to give the desired product as TFA salt. LC-MS calculated for $C_{40}H_{41}N_6O_6$ $(M+H)^+$: m/z=701.3; found 701.3.

Example 134

(R)-1-((7-cyano-2-(2,2'-dimethyl-3'-(3-(pyrrolidin-1-ylmethyl)-1,7-naphthyridin-8-ylamino)biphenyl-3-yl)benzo[d]oxazol-5-yl)methyl)pyrrolidine-3-carboxylic acid

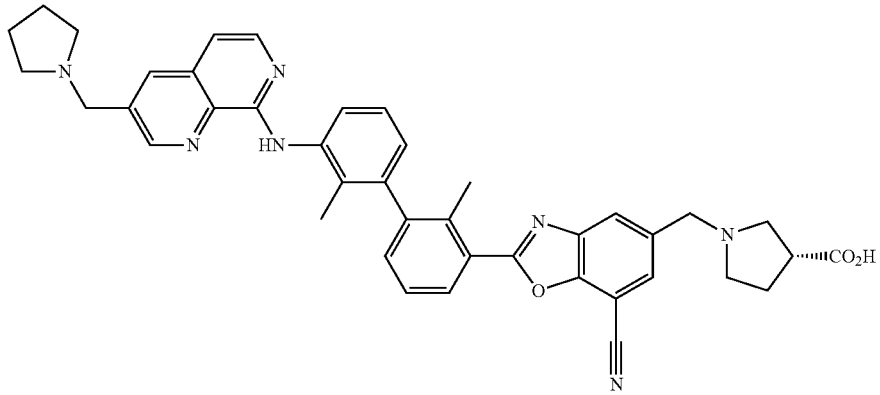 [SMILES: Cc1c(Nc2nccc3cc(CN4CCCC4)cnc23)cccc1-c1cccc(-c2nc3cc(CN4CC[C@@H](C(=O)O)C4)cc(C#N)c3o2)c1C]

This compound was prepared using similar procedures as described for Example 24 with pyrrolidine replacing (R)-pyrrolidin-3-ol in Step 1. The reaction mixture was diluted with MeOH and then purified by prep-HPLC (pH=2, acetonitrile/water+TFA) to give the desired product as TFA salt. LC-MS calculated for $C_{41}H_{40}N_7O_3$ $(M+H)^+$: m/z=678.3; found 678.3.

Example 135

(R)-1-((2-(3'-(3-(azetidin-1-ylmethyl)-1,7-naphthyridin-8-ylamino)-2,2'-dimethyl biphenyl-3-yl)-7-cyanobenzo[d]oxazol-5-yl)methyl)pyrrolidine-3-carboxylic acid

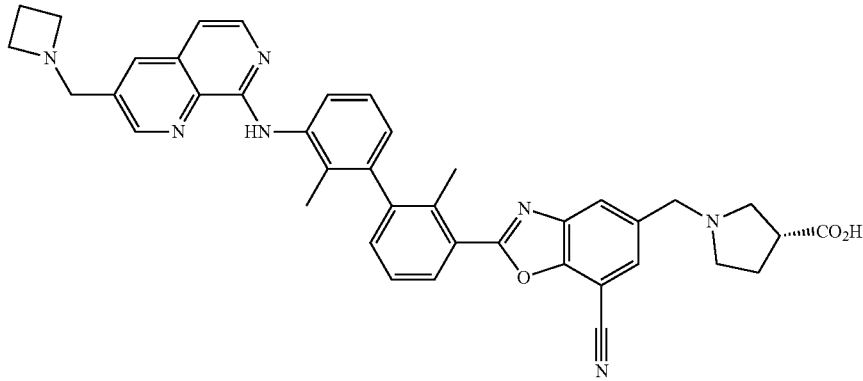 [SMILES: Cc1c(Nc2nccc3cc(CN4CCC4)cnc23)cccc1-c1cccc(-c2nc3cc(CN4CC[C@@H](C(=O)O)C4)cc(C#N)c3o2)c1C]

This compound was prepared using similar procedures as described for Example 24 with azetidine replacing (R)-pyrrolidin-3-ol in Step 1. The reaction mixture was diluted with MeOH and then purified by prep-HPLC (pH=2, acetonitrile/water+TFA) to give the desired product as TFA salt. LC-MS calculated for $C_{40}H_{38}N_7O_3$ $(M+H)^+$: m/z=664.3; found 664.3.

Example 136

(R)-1-((7-cyano-2-(3'-(3-((3-hydroxyazetidin-1-yl)methyl)-1,7-naphthyridin-8-ylamino)-2,2'-dimethyl-biphenyl-3-yl)benzo[d]oxazol-5-yl)methyl)pyrrolidine-3-carboxylic acid

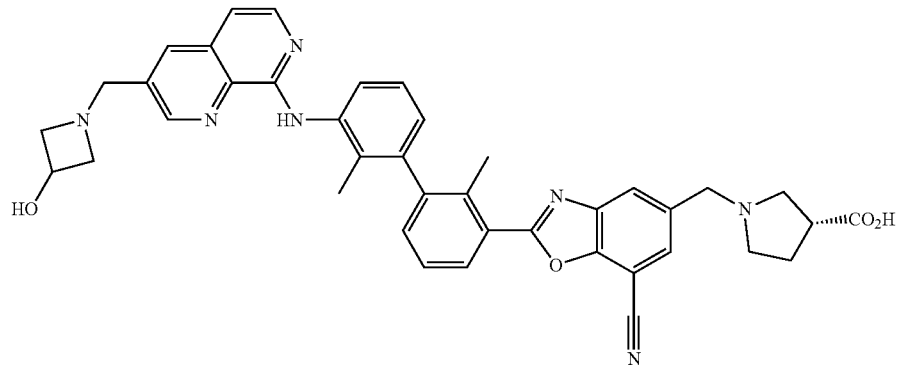 [SMILES: Cc1c(Nc2nccc3cc(CN4CC(O)C4)cnc23)cccc1-c1cccc(-c2nc3cc(CN4CC[C@@H](C(=O)O)C4)cc(C#N)c3o2)c1C]

This compound was prepared using similar procedures as described for Example 24 with 3-hydroxyazetidine replacing (R)-pyrrolidin-3-ol in Step 1. The reaction mixture was diluted with MeOH and then purified by prep-HPLC (pH=2, acetonitrile/water+TFA) to give the desired product as TFA salt. LC-MS calculated for $C_{40}H_{38}N_7O_4$ $(M+H)^+$: m/z=680.3; found 680.2.

Example 137

(R)-1-((7-cyano-2-(3'-(3-(((R)-3-hydroxy-3-methyl-pyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid

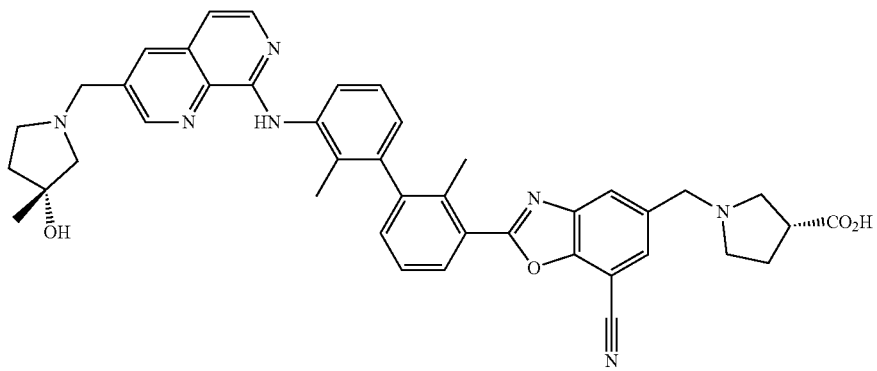 [SMILES: Cc1c(Nc2nccc3cc(CN4CC[C@@](C)(O)C4)cnc23)cccc1-c1cccc(-c2nc3cc(CN4CC[C@@H](C(=O)O)C4)cc(C#N)c3o2)c1C]

This compound was prepared using similar procedures as described for Example 24 with (R)-3-methylpyrrolin-3-ol replacing (R)-pyrrolidin-3-ol in Step 1. The reaction mixture was diluted with MeOH and then purified by prep-HPLC (pH=2, acetonitrile/water+TFA) to give the desired product as TFA salt. LC-MS calculated for $C_{42}H_{42}N_7O_4$ $(M+H)^+$: m/z=708.3; found 708.3.

Example 138

(R)-1-((7-cyano-2-(3'-(3-(((S)-3-hydroxy-3-methyl-pyrrolidin-1-yl)methyl)-1,7-naphthyridin-8-ylamino)-2,2'-dimethylbiphenyl-3-yl)benzo[d]ox-azol-5-yl)methyl)pyrrolidine-3-carboxylic acid

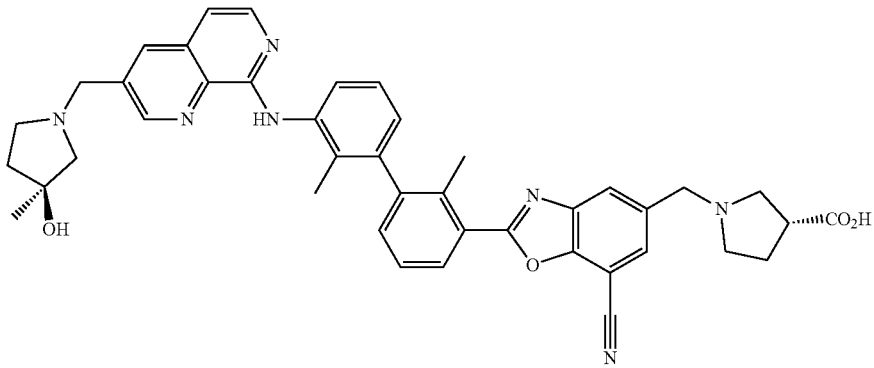 [SMILES: Cc1c(Nc2nccc3cc(CN4CC[C@](C)(O)C4)cnc23)cccc1-c1cccc(-c2nc3cc(CN4CC[C@@H](C(=O)O)C4)cc(C#N)c3o2)c1C]

Step 1: 5-formyl-2-(2-methyl-3-(4,4,5,5-tetram-ethyl-1,3,2-dioxaborolan-2-yl)phenyl)benzo[d]ox-azole-7-carbonitrile

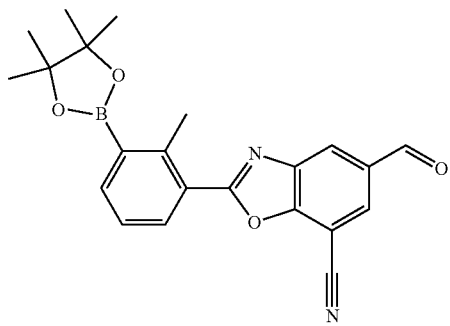 [SMILES: Cc1c(B2OC(C)(C)C(C)(C)O2)cccc1-c1nc2cc(C=O)cc(C#N)c2o1]

To a solution of 5-(hydroxymethyl)-2-(2-methyl-3-(4,4,5,5-tetramethyl-1,3,2-dioxaborolan-2-yl)phenyl)benzo[d]ox-azole-7-carbonitrile (Example 54, Step 2: 1.00 g, 2.56 mmol) in DCM (17.0 mL) was added sodium bicarbonate (1.08 g, 12.81 mmol) followed by Dess-Martin periodinane (1.30 g, 3.07 mmol). The mixture was stirred at r.t. for 1 h. Then the mixture was loaded directly on silica gel. Purification of the mixture using EtOAc in DCM (0-30%) with 5% TEA by flash chromatography was performed. LCMS calculated for $C_{22}H_{22}BN_2O_4(M+H)^+$: m/z=389.2; found 389.2.

Step 2: (R)-1-((7-cyano-2-(2-methyl-3-(4,4,5,5-te-tramethyl-1,3,2-dioxaborolan-2-yl)phenyl)benzo[d]oxazol-5-yl)methyl)pyrrolidine-3-carboxylic acid

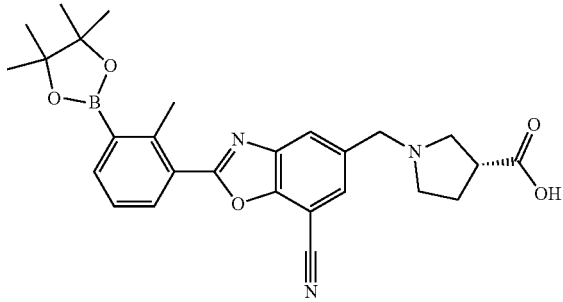 [SMILES: Cc1c(B2OC(C)(C)C(C)(C)O2)cccc1-c1nc2cc(CN3CC[C@@H](C(=O)O)C3)cc(C#N)c2o1]

A mixture of 5-formyl-2-(2-methyl-3-(4,4,5,5-tetram-ethyl-1,3,2-dioxaborolan-2-yl)phenyl)benzo[d]oxazole-7-carbonitrile (901 mg, 2.321 mmol), (R)-pyrrolidine-3-car-boxylic acid (534 mg, 4.64 mmol) and triethylamine (647 µl, 4.64 mmol) in DCM (15.5 mL) was stirred at r.t. for 2 h. Then sodium triacetoxyborohydride (984 mg, 4.64 mmol) was added. The mixture was further stirred at r.t. for 1 h. The reaction was diluted in DCM, washed with water. The aqueous solution was back extracted with DCM for six times. The combined organic phase was concentrated and used directly. LCMS calculated for $C_{27}H_{31}BN_3O_5(M+H)^+$: m/z=488.2; found 488.2.

Step 3: (S)-1-((8-(3-bromo-2-methylphenylamino)-1,7-naphthyridin-3-yl)methyl)-3-methylpyrrolidin-3-ol

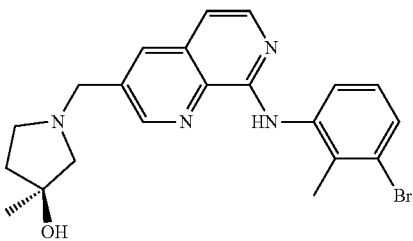 [SMILES: Cc1c(Br)cccc1Nc1nccc2cc(CN3CC[C@](C)(O)C3)cnc12]

This compound was prepared using similar procedure as described in Step 1, Example 24 with (S)-3-methylpyrrolin-3-ol replacing (R)-pyrrolidin-3-ol. LC-MS calculated for $C_{21}H_{24}BrN_4O$ (M+H)$^+$: m/z=427.1, 429.1; found 427.1, 429.1.

Step 4: (R)-1-((7-cyano-2-(3'-(3-(((S)-3-hydroxy-3-methylpyrrolidin-1-yl)methyl)-1,7-naphthyridin-8-ylamino)-2,2'-dimethylbiphenyl-3-yl)benzo[d]ox-azol-5-yl)methyl)pyrrolidine-3-carboxylic acid A mixture of (S)-1-((8-((3-bromo-2-methylphenyl)amino)-1,7-naphthyridin-3-yl)methyl)-3-methylpyrrolidin-3-ol (12 mg, 0.028 mmol), (R)-1-((7-cyano-2-(2-methyl-3-(4,4,5,5-tetramethyl-1,3,2-dioxaborolan-2-yl)phenyl)benzo[d]oxazol-5-yl)methyl) pyrrolidine-3-carboxylic acid (15 mg, 0.031 mmol), sodium carbonate (7.4 mg, 0.070 mmol) and tetrakis(triphenylphosphine)palladium(0) (3.2 mg, 2.8 mmol) in water (50 µl) and 1,4-dioxane (250 µl) was purged with $N_2$ and then stirred at 100° C. for 3 h. The reaction was cooled to room temperature and concentrated. The reaction mixture was diluted with MeOH and then purified by prep-HPLC (pH=10, acetonitrile/water+$NH_4OH$) to give the desired product. LC-MS calculated for $C_{42}H_{42}N_7O_4$ $(M+H)^+$: m/z=708.3; found 708.3.

Example 139

(R)-1-((7-cyano-2-(3'-(7-(((R)-3-hydroxypyrrolidin-1-yl)methyl)pyrido[3,2-d]pyrimidin-4-ylamino)-2,2'-dimethylbiphenyl-3-yl)benzo[d]oxazol-5-yl)methyl) pyrrolidine-3-carboxylic acid

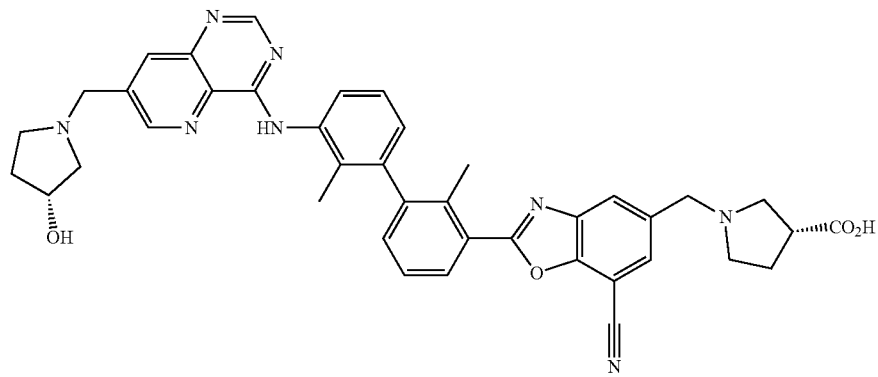 [SMILES: Cc1c(Nc2ncnc3cc(CN4CC[C@@H](O)C4)cnc23)cccc1-c1cccc(-c2nc3cc(CN4CC[C@@H](C(=O)O)C4)cc(C#N)c3o2)c1C]

Step 1: 7-bromo-N-(3-chloro-2-methylphenyl) pyrido[3,2-d]pyrimidin-4-amine

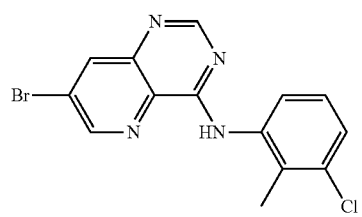 [SMILES: Cc1c(Cl)cccc1Nc1ncnc2cc(Br)cnc12]

In a vial, 3-chloro-2-methylaniline (92 mg, 0.65 mmol) and 7-bromo-4-chloropyrido[3,2-d]pyrimidine (160 mg, 0.65 mmol) were suspended in 2-propanol (3.25 mL). Sulfuric acid (0.035 ml, 0.65 mmol) was added to the reaction mixture. The resulting mixture was heated to 100° C. for 1 h. The mixture was cooled, quenched with aqueous saturated sodium bicarbonate, and diluted with DCM. The layers were separated and the water layer was further extracted with DCM/2-propanol (3:1). The combined organic layers were dried over magnesium sulfate, filtered and concentrated in vacuo. The crude solid was used directly. LC-MS calculated for $C_{14}H_{11}BrClN_4$ $(M+H)^+$: m/z=349.0, 351.0; found 349.0, 351.0.

Step 2: N-(3-chloro-2-methylphenyl)-7-vinylpyrido [3,2-d]pyrimidin-4-amine

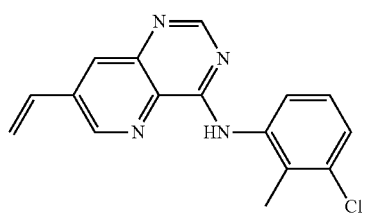 [SMILES: C=Cc1cnc2c(Nc3cccc(Cl)c3C)ncnc2c1]

A mixture of 7-bromo-N-(3-chloro-2-methylphenyl) pyrido[3,2-d]pyrimidin-4-amine (149 mg, 0.427 mmol), 4,4,5,5-tetramethyl-2-vinyl-1,3,2-dioxaborolane (79 mg, 0.51 mmol), sodium carbonate (113 mg, 1.069 mmol) and tetrakis (triphenylphosphine) palladium(0) (49 mg, 0.043 mmol) in tert-butanol (855 µl) and water (855 µl) was degassed with $N_2$ and sealed. It was stirred at 80° C. for 2 h. The reaction mixture was cooled then extracted with ethyl acetate. The combined organic layers were washed with brine, dried over $MgSO_4$, filtered and concentrated under reduced pressure. The crude residue was used directly in the next step without further purification. LC-MS calculated for $C_{16}H_{14}ClN_4$ $(M+H)^+$: m/z=297.1; found 297.1.

Step 3: 4-(3-chloro-2-methylphenylamino)pyrido[3,2-d]pyrimidine-7-carbaldehyde

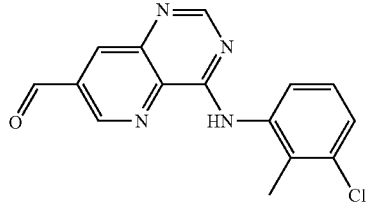 [SMILES: Cc1c(Cl)cccc1Nc1ncnc2cc(C=O)cnc12]

A vial was charged with N-(3-chloro-2-methylphenyl)-7-vinylpyrido[3,2-d]pyrimidin-4-amine (0.121 g, 0.408 mmol), a stir bar, THF (3.26 mL) and water (0.815 ml). To this suspension was added osmium tetraoxide in water (4% w/w, 0.89 mL, 0.14 mmol) followed by sodium periodate (0.436 g, 2.039 mmol) was added. After stirring at r.t. for 1 h, the reaction was quenched with a saturated aqueous solution of sodium thiosulfate. The mixture was then extracted with ethyl acetate, and the combined organic layers were separated, washed with brine, dried over $Na_2SO_4$, filtered, and concentrated in vacuo. The crude residue was used directly. LC-MS calculated for $C_{15}H_{12}ClN_4O$ $(M+H)^+$: m/z=299.1; found 299.0.

Step 4: (R)-1-((4-(3-chloro-2-methylphenylamino)pyrido[3,2-d]pyrimidin-7-yl)methyl)pyrrolidin-3-ol

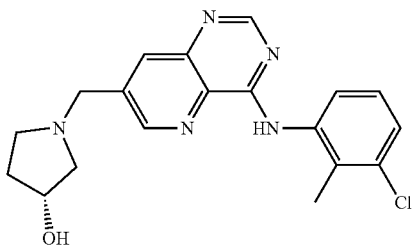 [SMILES: Cc1c(Cl)cccc1Nc1ncnc2cc(CN3CC[C@@H](O)C3)cnc12]

A mixture of 4-((3-chloro-2-methylphenyl)amino)pyrido[3,2-d]pyrimidine-7-carbaldehyde (0.120 g, 0.402 mmol) and (R)-pyrrolidin-3-ol (0.070 g, 0.803 mmol) in DCM (2.68 ml) was stirred at r.t. for 2 h. Then sodium triacetoxyborohydride (0.170 g, 0.803 mmol) was added. The mixture was further stirred at r.t. for 1 h. The reaction was diluted in DCM, washed with water. The aqueous solution was extracted with DCM for three times. The combined organic phase was concentrated and purified by column chromatography on silica gel (0-8% MeOH in DCM) to provide the desired product as white foam. LC-MS calculated for $C_{19}H_{21}ClN_5O$ $(M+H)^+$: m/z=370.1; found 370.2.

Step 5: (R)-1-((7-cyano-2-(3'-(7-(((R)-3-hydroxypyrrolidin-1-yl)methyl)pyrido[3,2-d]pyrimidin-4-ylamino)-2,2'-dimethylbiphenyl-3-yl)benzo[d]oxazol-5-yl)methyl)pyrrolidine-3-carboxylic acid This compound was prepared using similar procedures as described for Example 138 with (R)-1-((4-(3-chloro-2-methylphenylamino)pyrido[3,2-d]pyrimidin-7-yl)methyl)pyrrolidin-3-ol replacing (S)-1-((8-((3-bromo-2-methylphenyl)amino)-1,7-naphthyridin-3-yl)methyl)-3-methylpyrrolidin-3-ol and dichloro[1,1'-bis(dicyclohexylphosphino)ferrocene]palladium(II) replacing tetrakis(triphenylphosphine)palladium(0) in Step 4. The reaction was concentrated, then diluted in MeOH, filtered then purified by prep-HPLC (pH=2, acetonitrile/water+TFA) to give the desired product as TFA salt. LC-MS calculated for $C_{40}H_{39}N_8O_4$ $(M+H)^+$: m/z=695.3; found 695.3. $^1$H NMR (500 MHz, DMSO) δ 10.31 (s, 1H), 9.05 (s, 1H), 8.62 (s, 1H), 8.43 (d, J=1.9 Hz, 1H), 8.38 (d, J=1.3 Hz, 1H), 8.24-8.15 (m, 1H), 8.12 (d, J=1.4 Hz, 1H), 7.69 (d, J=7.4 Hz, 1H), 7.58 (t, J=7.7 Hz, 1H), 7.47 (d, J=6.5 Hz, 1H), 7.40 (t, J=7.8 Hz, 1H), 7.13 (d, J=6.8 Hz, 1H), 4.87-4.35 (m, 5H), 3.74-3.02 (m, 9H), 2.47 (s, 3H), 2.39-1.87 (m, 4H), 1.98 (s, 3H).

Example 140

(3R)-1-((7-cyano-2-(3'-(3-(1-((R)-3-hydroxypyrrolidin-1-yl)ethyl)-1,7-naphthyridin-8-ylamino)-2,2'-dimethylbiphenyl-3-yl)benzo[d]oxazol-5-yl)methyl)pyrrolidine-3-carboxylic acid

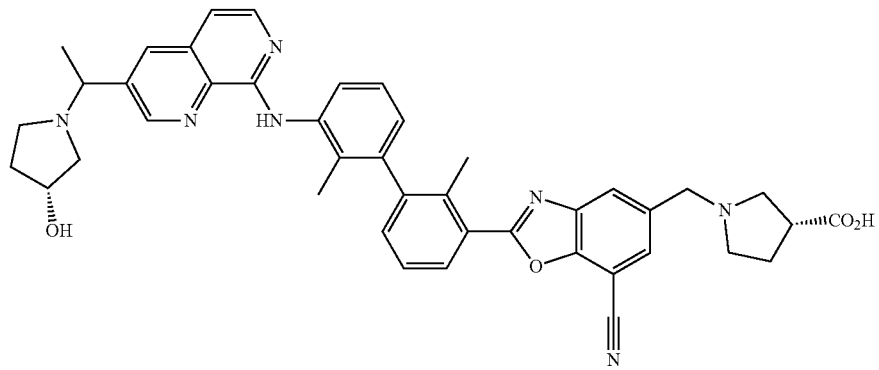 [SMILES: Cc1c(Nc2nccc3cc(C(C)N4CC[C@@H](O)C4)cnc23)cccc1-c1cccc(-c2nc3cc(CN4CC[C@@H](C(=O)O)C4)cc(C#N)c3o2)c1C]

Step 1: N-(3-chloro-2-methylphenyl)-3-vinyl-1,7-naphthyridin-8-amine

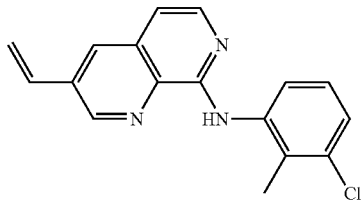 [SMILES: C=Cc1cnc2c(Nc3cccc(Cl)c3C)nccc2c1]

This compound was prepared using similar procedures as described for Example 16 with 3-chloro-2-methylaniline replacing 3-bromo-2-methylaniline in Step 2. LC-MS calculated for $C_{17}H_{15}ClN_3$ (M+H)$^+$: m/z=296.1; found 296.1.

Step 2: 8-(3-chloro-2-methylphenylamino)-1,7-naphthyridine-3-carbaldehyde

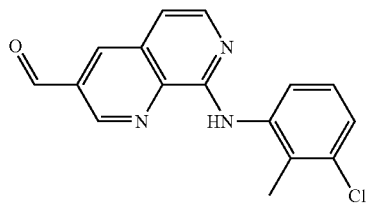 [SMILES: Cc1c(Cl)cccc1Nc1nccc2cc(C=O)cnc12]

A vial was charged with N-(3-chloro-2-methylphenyl)-3-vinyl-1,7-naphthyridin-8-amine (391 mg, 1.322 mmol), a stir bar, 1,4-dioxane (10 mL) and water (3.3 mL). To this suspension was added osmium tetroxide, 4% w/w in water (519 µl, 0.066 mmol). The reaction was stirred for 5 min then sodium periodate (1414 mg, 6.61 mmol) was added. After stirring at r.t. for 1 h, the reaction was quenched with a saturated aqueous solution of sodium thiosulfate. The mixture was then extracted with ethyl acetate, and the combined organic layers were separated, washed with brine, dried over $Na_2SO_4$, filtered, and concentrated in vacuo. The crude residue was used directly. LC-MS calculated for $C_{16}H_{13}ClN_3O$ (M+H)$^+$: m/z=298.1; found 298.1.

Step 3: 1-(8-(3-chloro-2-methylphenylamino)-1,7-naphthyridin-3-yl)ethanone

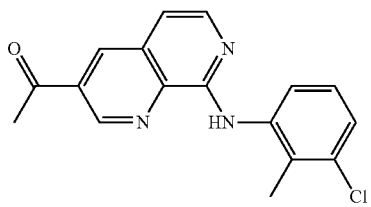 [SMILES: CC(=O)c1cnc2c(Nc3cccc(Cl)c3C)nccc2c1]

To a solution of 8-((3-chloro-2-methylphenyl)amino)-1,7-naphthyridine-3-carbaldehyde (76 mg, 0.26 mmol) in THF (2.5 mL) was added methylmagnesium bromide (3.0 M in THF, 85 µl, 0.26 mmol) at 0° C. The mixture was stirred at this temperature for 20 min. Then the reaction was quenched by EtOAc, washed with water. The aqueous phase was extracted by EtOAc. The organic phase was combined, dried over $MgSO_4$, and filtered. The filtrate was concentrated and used directly. LC-MS calculated for $C_{17}H_{17}ClN_3O$ (M+H)$^+$: m/z=314.1; found 314.1. To the above residue in DCM (2 mL) was added dess-martin periodinane (141 mg, 0.332 mmol). The mixture was stirred at rt for 30 min. Then the reaction was quenched by $NaHCO_3$ sat. solution and $Na_2S_2O_3$ solution, and extracted with DCM. The organic phase was dried over $MgSO_4$ and filtered. The filtrate was concentrated and used directly. LC-MS calculated for $C_{17}H_{15}ClN_3O$ (M+H)$^+$: m/z=312.1; found 312.1.

Step 4: (3R)-1-(1-(8-(3-chloro-2-methylphenylamino)-1,7-naphthyridin-3-yl)ethyl)pyrrolidin-3-ol

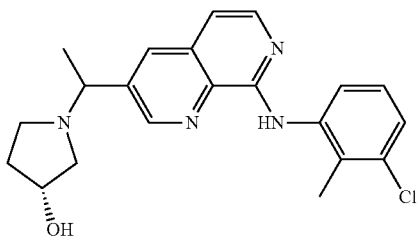 [SMILES: Cc1c(Cl)cccc1Nc1nccc2cc(C(C)N3CC[C@@H](O)C3)cnc12]

This compound was prepared using similar procedures as described for Example 16 with 1-(8-(3-chloro-2-methylphenylamino)-1,7-naphthyridin-3-yl)ethanone replacing 8-(3-bromo-2-methylphenylamino)-1,7-naphthyridine-3-carbaldehyde in Step 4. LC-MS calculated for $C_{21}H_{24}ClN_4O$ (M+H)$^+$: m/z=383.2; found 383.1.

Step 5: (3R)-1-((7-cyano-2-(3'-(3-(1-((R)-3-hydroxypyrrolidin-1-yl)ethyl)-1,7-naphthyridin-8-ylamino)-2,2'-dimethylbiphenyl-3-yl)benzo[d]oxazol-5-yl)methyl)pyrrolidine-3-carboxylic acid This compound was prepared using similar procedures as described for Example 138 with (3R)-1-(1-(8-(3-chloro-2-methylphenylamino)-1,7-naphthyridin-3-yl)ethyl)pyrrolidin-3-ol replacing (S)-1-((8-((3-bromo-2-methylphenyl)amino)-1,7-naphthyridin-3-yl)methyl)-3-methylpyrrolidin-3-ol and chloro(2-dicyclohexylphosphino-2',4',6'-triisopropyl-1,1'-biphenyl)[2-(2'-amino-1,1'-biphenyl)]palladium(II) replacing tetrakis(triphenylphosphine)palladium(0) in Step 4. The reaction mixture was diluted with MeOH and then purified by prep-HPLC (pH=10, acetonitrile/water+$NH_4OH$) to give the desired product. LC-MS calculated for $C_{42}H_{42}N_7O_4$ (M+H)$^+$: m/z=708.3; found 708.3.

Example 141

(R)-1-((8-(3'-(7-cyano-5-(((R)-3-hydroxypyrrolidin-1-yl)methyl)benzo[d]oxazol-2-yl)-2,2'-dimethylbiphenyl-3-ylamino)-1,7-naphthyridin-3-yl)methyl)pyrrolidine-3-carboxylic acid

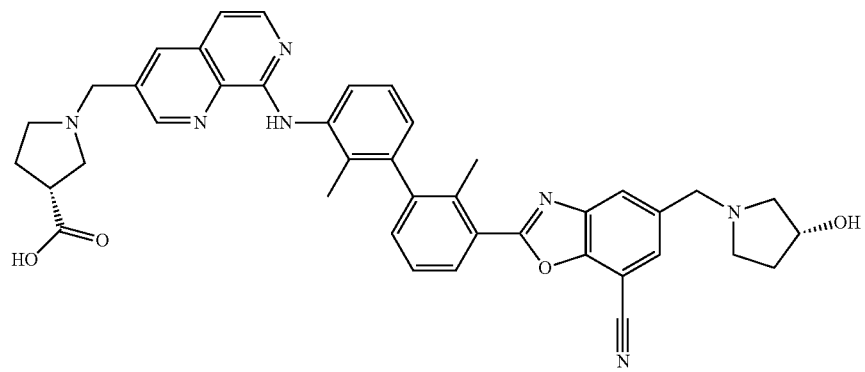 [SMILES: Cc1c(Nc2nccc3cc(CN4CC[C@@H](C(=O)O)C4)cnc23)cccc1-c1cccc(-c2nc3cc(CN4CC[C@@H](O)C4)cc(C#N)c3o2)c1C]

Step 1: (R)-1-((8-(3-bromo-2-methylphenylamino)-1,7-naphthyridin-3-yl)methyl) pyrrolidine-3-carboxylic acid

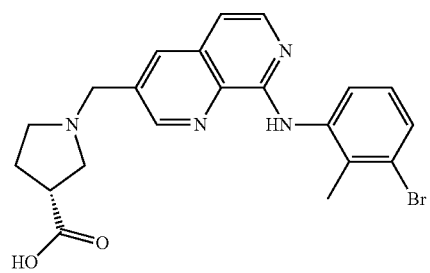 [SMILES: Cc1c(Br)cccc1Nc1nccc2cc(CN3CC[C@@H](C(=O)O)C3)cnc12]

A mixture of 8-((3-bromo-2-methylphenyl)amino)-1,7-naphthyridine-3-carbaldehyde (Example 16, Step 3: 31 mg, 0.091 mmol) and (R)-pyrrolidine-3-carboxylic acid (20.9 mg, 0.181 mmol) in DCM (450 μl) was stirred at rt for 0.5 h. Then sodium triacetoxyborohydride (28.8 mg, 0.136 mmol) and acetic acid (8.0 μl, 0.14 mmol) was added. The mixture was further stirred at room temperature for 1 h. The reaction was quenched by water, and extracted with DCM. The organic phased was dried over MgSO$_4$, filtered, concentrated and purified by column chromatography (0-10% MeOH in DCM). LC-MS calculated for $C_{21}H_{22}BrN_4O_2(M+H)^+$: m/z=441.1, 443.1; found 441.2, 443.2.

Step 2: (R)-1-((8-(3'-(7-chloro-5-(hydroxymethyl)benzo[d]oxazol-2-yl)-2,2'-dimethylbiphenyl-3-ylamino)-1,7-naphthyridin-3-yl)methyl)pyrrolidine-3-carboxylic acid

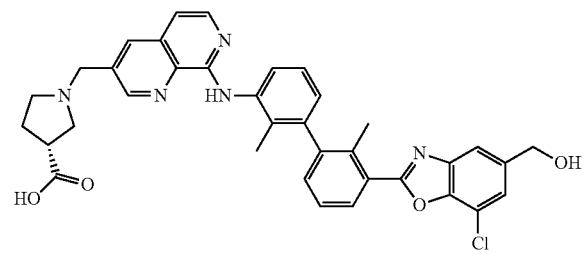 [SMILES: Cc1c(Nc2nccc3cc(CN4CC[C@@H](C(=O)O)C4)cnc23)cccc1-c1cccc(-c2nc3cc(CO)cc(Cl)c3o2)c1C]

A mixture of (R)-1-((8-((3-bromo-2-methylphenyl)amino)-1,7-naphthyridin-3-yl)methyl)pyrrolidine-3-carboxylic acid (28 mg, 0.063 mmol), (7-chloro-2-(2-methyl-3-(4,4,5,5-tetramethyl-1,3,2-dioxaborolan-2-yl)phenyl)benzo[d]oxazol-5-yl)methanol (Example 1, Step 5; 28 mg, 0.070 mmol), sodium carbonate (16.8 mg, 0.159 mmol) and tetrakis(triphenylphosphine)palladium(0) (5.1 mg, 4.4 μmol) in water (106 μl) and 1,4-dioxane (529 μl) was purged with N$_2$ and then stirred at 100° C. for 4 h. The reaction was cooled to room temperature. The reaction mixture was diluted with DCM and H$_2$O. The layers were separated. The aqueous layer was extracted with DCM three times. The organic layer was dried MgSO$_4$, filtered and concentrated to give a crude residue, which was purified by flash chromatography on a silica gel column eluting with 0 to 14% MeOH/DCM to give the desired product. LC-MS calculated for $C_{36}H_{33}ClN_5O_4(M+H)^+$: m/z=634.2; found 634.3.

Step 3: (R)-1-((8-(3'-(7-chloro-5-formylbenzo[d]oxazol-2-yl)-2,2'-dimethylbiphenyl-3-ylamino)-1,7-naphthyridin-3-yl)methyl)pyrrolidine-3-carboxylic acid

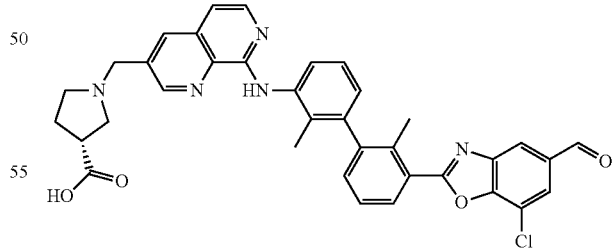

To a solution of (R)-1-((8-((3'-(7-chloro-5-(hydroxymethyl)benzo[d]oxazol-2-yl)-2,2'-dimethyl-[1,1'-biphenyl]-3-yl)amino)-1,7-naphthyridin-3-yl)methyl)pyrrolidine-3-carboxylic acid (9 mg, 0.014 mmol) in DCM (142 μl) was added dess-martin periodinane (7.2 mg, 0.017 mmol). The mixture was stirred at r.t. for 20 min. The reaction was used directly for next step. LC-MS calculated for $C_{36}H_{31}ClN_5O_4$ $(M+H)^+$: m/z=632.2; found 632.2.

Step 4: (R)-1-((8-(3'-(7-chloro-5-(((R)-3-hydroxy-pyrrolidin-1-yl)methyl)benzo[d]oxazol-2-yl)-2,2'-dimethylbiphenyl-3-ylamino)-1,7-naphthyridin-3-yl)methyl)pyrrolidine-3-carboxylic acid

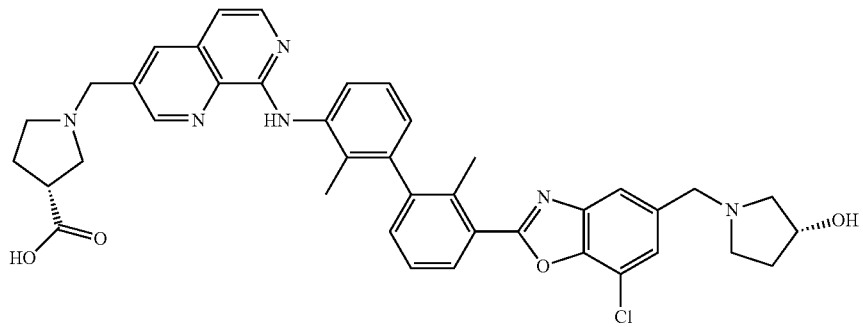 [SMILES: Cc1c(Nc2nccc3cc(CN4CC[C@@H](C(=O)O)C4)cnc23)cccc1-c1cccc(-c2nc3cc(CN4CC[C@@H](O)C4)cc(Cl)c3o2)c1C]

A mixture of (R)-1-((8-((3'-(7-chloro-5-formylbenzo[d]oxazol-2-yl)-2,2'-dimethyl-[1,1'-biphenyl]-3-yl)amino)-1,7-naphthyridin-3-yl)methyl)pyrrolidine-3-carboxylic acid (8.3 mg, 0.013 mmol) and (R)-pyrrolidin-3-ol (2.3 mg, 0.026 mmol) in DCM (66.0 µl) was stirred at r.t. for 0.5 h. Then sodium triacetoxyborohydride (4.20 mg, 0.020 mmol) was added. The mixture was further stirred at r.t. for 1 h. The reaction was quenched by water, and extracted with DCM five times. The organic layer was dried over MgSO$_4$, then filtered, concentrated to provide a crude product, which was used directly. LC-MS calculated for $C_{40}H_{40}ClN_6O_4$ (M+H)$^+$: m/z=703.3; found 703.3.

Step 5: (R)-1-((8-(3'-(7-cyano-5-(((R)-3-hydroxy-pyrrolidin-1-yl)methyl)benzo[d]oxazol-2-yl)-2,2'-dimethylbiphenyl-3-ylamino)-1,7-naphthyridin-3-yl)methyl)pyrrolidine-3-carboxylic acid A mixture of (R)-1-((8-((3'-(7-chloro-5-(((R)-3-hydroxy-pyrrolidin-1-yl)methyl)benzo[d]oxazol-2-yl)-2,2'-dimethyl-[1,1'-biphenyl]-3-yl)amino)-1,7-naphthyridin-3-yl)methyl)pyrrolidine-3-carboxylic acid (5.8 mg, 8.2 µmol), potassium ferrocyanide(II) hydrate (3.5 mg, 8.2 µmol), potassium acetate (0.40 mg, 4.1 µmol) and methanesulfonato (2-di-t-butylphosphino-2',4',6'-tri-1-propyl-1,1'-biphenyl)(2'-amino-1,1'-biphenyl-2-yl)palladium(II) (1.310 mg, 1.650 µmol) in 1,4-dioxane (41 µl) and water (41 µl) was stirred and heated at 80° C. for 4 h. After cooling to r.t., the reaction was concentrated, then diluted in MeOH, filtered then purified by prep-HPLC (pH=10, acetonitrile/water+NH$_4$OH) to give the desired product. LC-MS calculated for $C_{41}H_{40}N_7O_4$ (M+H)$^+$: m/z=694.3; found 694.3.

Example 142

(S)-1-((2-(2'-chloro-3'-(5-ethyl-1-methyl-4,5,6,7-tetrahydro-1H-imidazo[4,5-c]pyridine-2-carboxamido)-2-methyl-[1,1'-biphenyl]-3-yl)-7-cyanobenzo[d]oxazol-5-yl)methyl)pyrrolidine-3-carboxylic acid

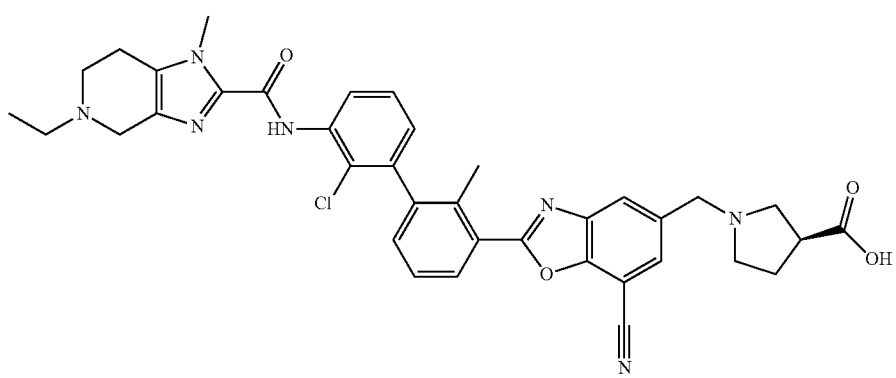 [SMILES: CCN1CCc2c(nc(C(=O)Nc3cccc(-c4cccc(-c5nc6cc(CN7CC[C@H](C(=O)O)C7)cc(C#N)c6o5)c4C)c3Cl)n2C)C1]

Step 1: N-(2-chloro-3'-(7-chloro-5-(hydroxymethyl)benzo[d]oxazol-2-yl)-2'-methyl-[1,1'-biphenyl]-3-yl)-5-ethyl-1-methyl-4,5,6,7-tetrahydro-1H-imidazo[4,5-c]pyridine-2-carboxamide

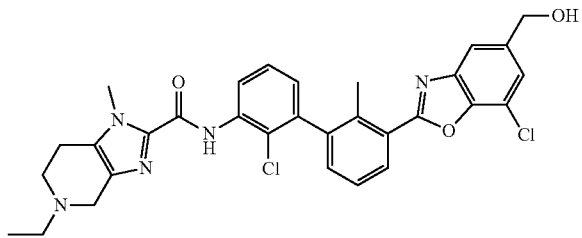 [SMILES: CCN1CCc2c(nc(C(=O)Nc3cccc(-c4cccc(-c5nc6cc(CO)cc(Cl)c6o5)c4C)c3Cl)n2C)C1]

To a solution of tert-butyl 2-(2-chloro-3'-(7-chloro-5-(hydroxymethyl)benzo[d]oxazol-2-yl)-2'-methylbiphenyl-3-ylcarbamoyl)-1-methyl-6,7-dihydro-1H-imidazo[4,5-c]pyridine-5(4H)-carboxylate (Example 92, Step 1: 140 mg, 0.211 mmol) in DCM (3 mL) was added trifluoroacetic acid (1.0 mL). The solution was stirred at r.t. for 1 hour, then concentrate to dryness. To a solution of above residue in DCM (5.00 mL) was added TEA (0.059 mL, 0.423 mmol), then acetaldehyde (0.060 mL, 1.056 mmol). After the reaction mixture was stirred at r.t. 30 min, sodium triacetoxyborohydride (134 mg, 0.634 mmol) was added. The mixture was stirred at r.t. 2 hours, quenched with sat. NH$_4$Cl solution, and extracted with DCM. The combined extracts were washed with water and brine, dried over MgSO$_4$, filtered and concentrated under reduced pressure. The residue was purified by flash chromatography on a silica gel column eluting with 10% MeOH in DCM to afford the desired product. LC-MS calculated for C$_{31}$H$_{30}$Cl$_2$N$_5$O$_3$ (M+H)$^+$: m/z=590.2; found 590.1.

Step 2: N-(2-chloro-3'-(7-cyano-5-(hydroxymethyl)benzo[d]oxazol-2-yl)-2'-methyl-[1,1'-biphenyl]-3-yl)-5-ethyl-1-methyl-4,5,6,7-tetrahydro-1H-imidazo[4,5-c]pyridine-2-carboxamide

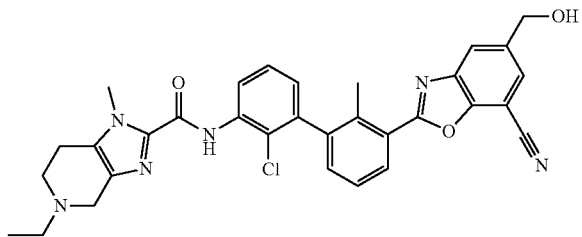 [SMILES: CCN1CCc2c(nc(C(=O)Nc3cccc(-c4cccc(-c5nc6cc(CO)cc(C#N)c6o5)c4C)c3Cl)n2C)C1]

This compound was prepared using similar procedures as described for Example 12 with N-(2-chloro-3'-(7-chloro-5-(hydroxymethyl)benzo[d]oxazol-2-yl)-2'-methyl-[1,1'-biphenyl]-3-yl)-5-ethyl-1-methyl-4,5,6,7-tetrahydro-1H-imidazo[4,5-c]pyridine-2-carboxamide replacing (7-chloro-2-(2,2'-dimethyl-3'-(pyrido[3,4-b]pyrazin-5-ylamino)-[1,1'-biphenyl]-3-yl)benzo[d]oxazol-5-yl)methanol in Step 1. LC-MS calculated for C$_{32}$H$_{30}$ClN$_6$O$_3$(M+H)$^+$: m/z=581.2; found 581.2.

Step 3: N-(2-chloro-3'-(7-cyano-5-formylbenzo[d]oxazol-2-yl)-2'-methyl-[1,1'-biphenyl]-3-yl)-5-ethyl-1-methyl-4,5,6,7-tetrahydro-1H-imidazo[4,5-c]pyridine-2-carboxamide

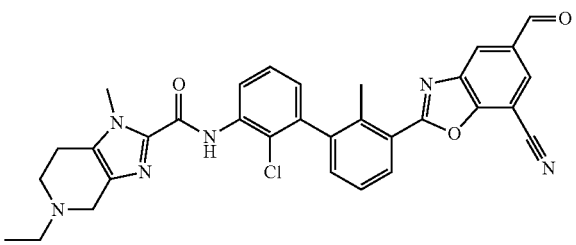 [SMILES: CCN1CCc2c(nc(C(=O)Nc3cccc(-c4cccc(-c5nc6cc(C=O)cc(C#N)c6o5)c4C)c3Cl)n2C)C1]

To a stirred solution of N-(2-chloro-3'-(7-cyano-5-(hydroxymethyl)benzo[d]oxazol-2-yl)-2'-methyl-[1,1'-biphenyl]-3-yl)-5-ethyl-1-methyl-4,5,6,7-tetrahydro-1H-imidazo[4,5-c]pyridine-2-carboxamide (60.0 mg, 0.103 mmol) in DCM (3.0 ml) was added sodium bicarbonate (87 mg, 1.033 mmol) and dess-martin periodinane (65.7 mg, 0.155 mmol). The resulted mixture was stirred at r.t. for 2 h. The reaction mixture was diluted with water then extracted with DCM. The combined extracts were washed with water and brine, dried over MgSO$_4$, filtered and concentrated under reduced pressure. The residue was used in the next step directly. LC-MS calculated for: C$_{32}$H$_{28}$ClN$_6$O$_3$: m/z=579.2; found 579.2.

Step 4: (S)-1-((2-(2'-chloro-3'-(5-ethyl-1-methyl-4,5,6,7-tetrahydro-1H-imidazo[4,5-c]pyridine-2-carboxamido)-2-methyl-[1,1'-biphenyl]-3-yl)-7-cyanobenzo[d]oxazol-5-yl)methyl)pyrrolidine-3-carboxylic acid To a solution of N-(2-chloro-3'-(7-cyano-5-formylbenzo[d]oxazol-2-yl)-2'-methyl-[1,1'-biphenyl]-3-yl)-5-ethyl-1-methyl-4,5,6,7-tetrahydro-1H-imidazo[4,5-c]pyridine-2-carboxamide (10 mg, 0.017 mmol) in DCM (1 ml) was added (S)-pyrrolidine-3-carboxylic acid (9.94 mg, 0.086 mmol) and DIEA (0.024 ml, 0.138 mmol), the mixture was stirred at r.t. 60 min, then sodium triacetoxyborohydride (10.98 mg, 0.052 mmol) was added, and continue to stirred at r.t. over night. The reaction mixture was concentrated, and the residue was dissolved in MeOH and then purified by prep-HPLC (pH=2, acetonitrile/water+TFA) to give the desired product as TFA salt. LC-MS calculated for C$_{37}$H$_{37}$ClN$_7$O$_4$(M+H)$^+$: m/z=678.3; found 678.3.

Example 143

(R)-1-((2-(2'-chloro-3'-(5-ethyl-1-methyl-4,5,6,7-tetrahydro-1H-imidazo[4,5-c]pyridine-2-carboxamido)-2-methyl-[1,1'-biphenyl]-3-yl)-7-cyanobenzo[d]oxazol-5-yl)methyl)pyrrolidine-3-carboxylic acid

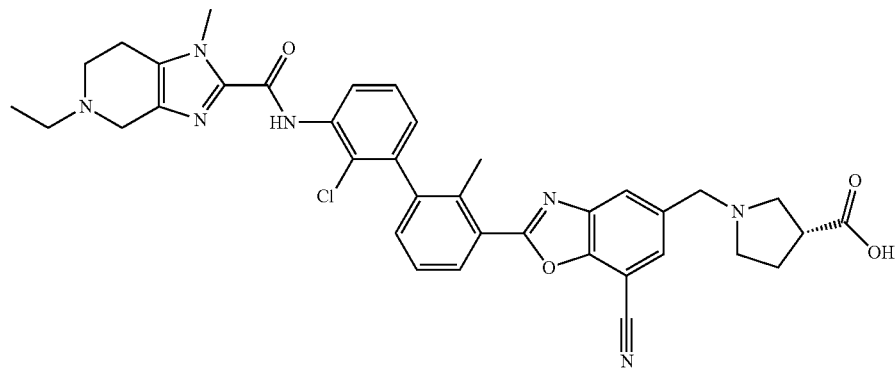 [SMILES: CCN1CCc2c(nc(C(=O)Nc3cccc(-c4cccc(-c5nc6cc(CN7CC[C@@H](C(=O)O)C7)cc(C#N)c6o5)c4C)c3Cl)n2C)C1]

This compound was prepared using similar procedures as described for Example 147 with (R)-pyrrolidine-3-carboxylic acid replacing (S)-pyrrolidine-3-carboxylic acid in Step 4. The reaction mixture was concentrated, the residue was dissolved in MeOH and then purified by prep-HPLC (pH=2, acetonitrile/water+TFA) to give the desired product as TFA salt. LC-MS calculated for $C_{37}H_{37}ClN_7O_4(M+H)^+$: m/z=678.3; found 678.3.

Example 144

(S)-1-((7-cyano-2-(3'-((4-(((S)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid

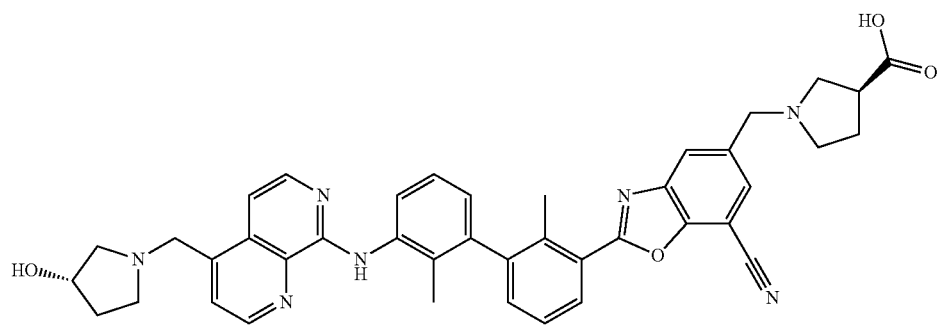 [SMILES: Cc1c(Nc2nccc3c(CN4CC[C@H](O)C4)ccnc23)cccc1-c1cccc(-c2nc3cc(CN4CC[C@H](C(=O)O)C4)cc(C#N)c3o2)c1C]

Step 1: 8-((3-bromo-2-methylphenyl)amino)-1,7-naphthyridin-4(1H)-one

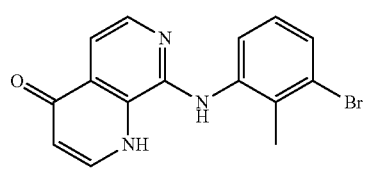 [SMILES: Cc1c(Br)cccc1Nc1nccc2c(=O)cc[nH]c12]

A mixture of 3-bromo-2-methylaniline (280.0 mg, 1.505 mmol), 8-chloro-1,7-naphthyridin-4(1H)-one (272 mg, 1.505 mmol) and 4M HCl in dioxane (376 µL) was heated in tert-butanol (7.5 mL) at 120° C. for 2 hours. After the reaction mixture was cooled to r.t., it was concentrated to dryness and used in the next step directly without further purification. LC-MS calculated for $C_{15}H_{13}BrN_3O$ $(M+H)^+$: m/z=330.0, 332.0; found 330.0, 332.0.

Step 2: N-(3-bromo-2-methylphenyl)-4-chloro-1,7-naphthyridin-8-amine

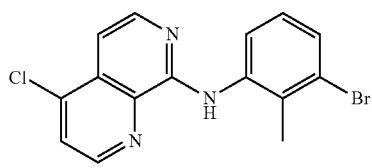 [SMILES: Cc1c(Br)cccc1Nc1nccc2c(Cl)ccnc12]

Phosphoryl chloride (0.494 mL, 5.30 mmol) was added to a mixture of 8-((3-bromo-2-methylphenyl)amino)-1,7-naphthyridin-4(1H)-one (350 mg, 1.060 mmol), benzyltriethylammonium chloride (483 mg, 2.120 mmol) and N,N-diethylaniline (0.253 mL, 1.590 mmol) in acetonitrile (10 mL) and then the reaction was stirred at 80° C. for 1 h. The solvent was then removed, and the residue was diluted with DCM, washed with sat'd NaHCO$_3$ aqueous solution, water, brine, dried over Na$_2$SO$_4$, filtered and concentrated. The residue was purified by flash chromatography on a silica gel column eluting with 2% ethyl acetate in DCM to afford the desired product. LCMS calculated for $C_{15}H_{12}BrClN_3$ (M+H)$^+$: m/z=348.0, 350.0, found 348.0, 350.0.

Step 3: (7-chloro-2-(2,2'-dimethyl-3'-((4-vinyl-1,7-naphthyridin-8-yl)amino)-[1,1'-biphenyl]-3-yl)benzo[d]oxazol-5-yl)methanol

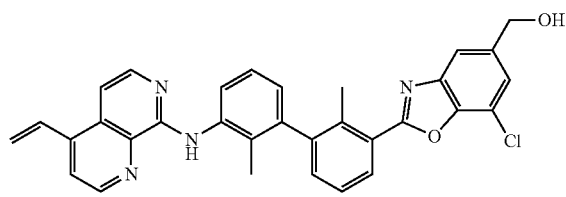 [SMILES: C=Cc1ccnc2c(Nc3cccc(-c4cccc(-c5nc6cc(CO)cc(Cl)c6o5)c4C)c3C)nccc12]

The mixture of N-(3-bromo-2-methylphenyl)-4-chloro-1,7-naphthyridin-8-amine (130 mg, 0.373 mmol), (7-chloro-2-(2-methyl-3-(4,4,5,5-tetramethyl-1,3,2-dioxaborolan-2-yl)phenyl)benzo[d]oxazol-5-yl)methanol (Example 1, Step 5; 149 mg, 0.373 mmol), 1,1'-bis(diphenylphosphino)ferrocene-palladium(II)dichloride dichloromethane complex (18.27 mg, 0.022 mmol) and sodium carbonate (119 mg, 1.119 mmol) in dioxane (5.0 mL) and water (1.0 mL) was vacuumed and refilled with N$_2$. Then the mixture was stirred at 90° C. for 2 hs. After the reaction mixture was cooled to r.t., to this reaction mixture was added 4,4,5,5-tetramethyl-2-vinyl-1,3,2-dioxaborolane (115 mg, 0.746 mmol) and another portion of catalyst. The reaction mixture was degassed with N$_2$ and heated at 100° C. for another 5 hours. After being cooled to room temperature, the reaction mixture was concentrated under reduced pressure. The residue was purified by flash chromatography on a silica gel column eluting with 20% AcOEt in DCM to afford the desired product. LC-MS calculated for $C_{32}H_{26}ClN_4O_2$(M+H)$^+$: m/z=533.2; found 533.2.

Step 4: 8-((3'-(7-chloro-5-(hydroxymethyl)benzo[d]oxazol-2-yl)-2,2'-dimethyl-[1,1'-biphenyl]-3-yl)amino)-1,7-naphthyridine-4-carbaldehyde

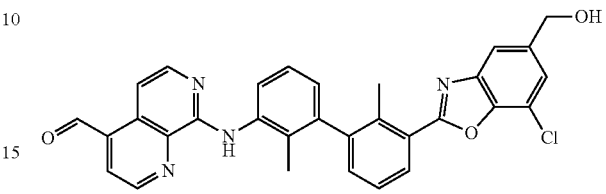

To a solution of (7-chloro-2-(2,2'-dimethyl-3'-((4-vinyl-1,7-naphthyridin-8-yl)amino)-[1,1'-biphenyl]-3-yl)benzo[d]oxazol-5-yl)methanol (200 mg, 0.375 mmol) in 1,4-dioxane (10 mL) and water (2 mL) was added osmium tetraoxide (4% w/w in water, 0.014 ml) at room temperature. The mixture was stirred for 10 min and then sodium periodate (241 mg, 1.126 mmol) was added. The reaction mixture was stirred at r.t. for 2 hours. The reaction mixture was diluted with water then extracted with DCM. The combined extracts were washed with water and brine, dried over MgSO$_4$, filtered and concentrated under reduced pressure. The residue was purified by flash chromatography on a silica gel column eluting with 25% AcOEt in DCM to afford the desired product. LC-MS calculated for $C_{31}H_{24}ClN_4O_3$ (M+H)$^+$: m/z=535.1; found 535.1.

Step 5: (S)-1-((8-((3'-(7-chloro-5-(hydroxymethyl)benzo[d]oxazol-2-yl)-2,2'-dimethyl-[1,1'-biphenyl]-3-yl)amino)-1,7-naphthyridin-4-yl)methyl)pyrrolidin-3-ol

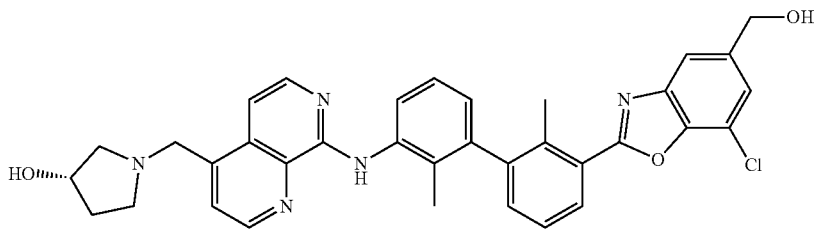 [SMILES: Cc1c(Nc2nccc3c(CN4CC[C@H](O)C4)ccnc23)cccc1-c1cccc(-c2nc3cc(CO)cc(Cl)c3o2)c1C]

To a solution of 8-((3'-(7-chloro-5-(hydroxymethyl)benzo[d]oxazol-2-yl)-2,2'-dimethyl-[1,1'-biphenyl]-3-yl)amino)-1,7-naphthyridine-4-carbaldehyde (100 mg, 0.187 mmol) in DCM (4 mL) was added (S)-pyrrolidin-3-ol (32.6 mg, 0.374 mmol), the mixture was stirred at r.t. 10 min, then sodium triacetoxyborohydride (119 mg, 0.561 mmol) was added, continue to stir at r.t. over night. The reaction mixture was diluted with water then extracted with DCM. The combined extracts were washed with water and brine, dried over MgSO$_4$, filtered and concentrated under reduced pressure to afford the desired compound, which was used for next step without further purification. LC-MS calculated for $C_{35}H_{33}ClN_5O_3$(M+H)$^+$: m/z=606.2; found 606.2.

Step 6: (S)-7-chloro-2-(3'-((4-((3-hydroxypyrrolidin-1-yl)methyl)-1,7-naphthyridin-8-yl)amino)-2,2'-dimethyl-[1,1'-biphenyl]-3-yl)benzo[d]oxazole-5-carbaldehyde

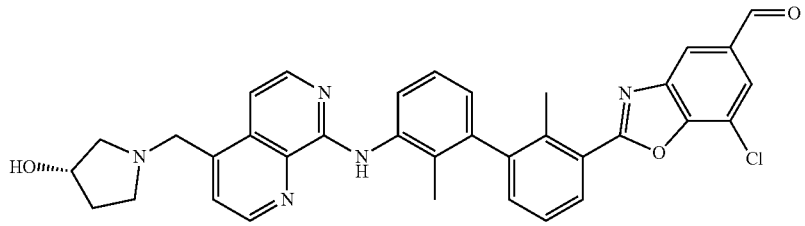 [SMILES: Cc1c(Nc2nccc3c(CN4CC[C@H](O)C4)ccnc23)cccc1-c1cccc(-c2nc3cc(C=O)cc(Cl)c3o2)c1C]

A suspension of (S)-1-((8-((3'-(7-chloro-5-(hydroxymethyl)benzo[d]oxazol-2-yl)-2,2'-dimethyl-[1,1'-biphenyl]-3-yl)amino)-1,7-naphthyridin-4-yl)methyl)pyrrolidin-3-ol (80 mg, 0.132 mmol) and manganese(IV) oxide (229 mg, 2.64 mmol) in DCM (10 ml) was stirred at 45° C. for 3 hours. After cooling, the solid was filtered off and washed with DCM thoroughly.

The filtrate was concentrated under reduced pressure. The residue was purified by flash chromatography on a silica gel column eluting with 10% MeOH in DCM to afford the desired product. LC-MS calculated for $C_{35}H_{31}ClN_5O_3$(M+H)$^+$: m/z=604.2; found 604.2.

Step 7: (S)-5-formyl-2-(3'-((4-((3-hydroxypyrrolidin-1-yl)methyl)-1,7-naphthyridin-8-yl)amino)-2,2'-dimethyl-[1,1'-biphenyl]-3-yl)benzo[d]oxazole-7-carbonitrile

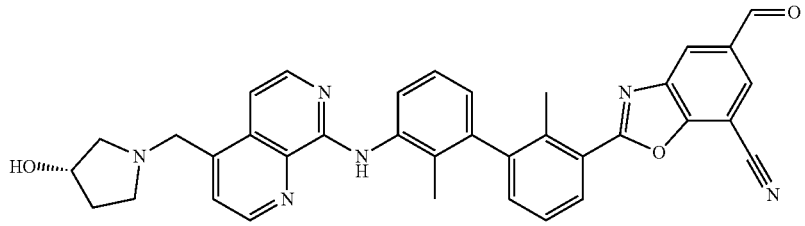 [SMILES: Cc1c(Nc2nccc3c(CN4CC[C@H](O)C4)ccnc23)cccc1-c1cccc(-c2nc3cc(C=O)cc(C#N)c3o2)c1C]

This compound was prepared using similar procedures as described for Example 12 with (S)-7-chloro-2-(3'-((4-((3-hydroxypyrrolidin-1-yl)methyl)-1,7-naphthyridin-8-yl)amino)-2,2'-dimethyl-[1,1'-biphenyl]-3-yl)benzo[d]oxazole-5-carbaldehyde replacing (7-chloro-2-(2,2'-dimethyl-3'-(pyrido[3,4-b]pyrazin-5-ylamino)-[1,1'-biphenyl]-3-yl)benzo[d]oxazol-5-yl)methanol in Step 1. LC-MS calculated for: $C_{36}H_{31}N_6O_3$: m/z=595.2; found 595.2.

Step 8: (S)-1-((7-cyano-2-(3'-((4-(((S)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid To a solution of (S)-5-formyl-2-(3'-((4-((3-hydroxypyrrolidin-1-yl)methyl)-1,7-naphthyridin-8-yl)amino)-2,2'-dimethyl-[1,1'-biphenyl]-3-yl)benzo[d]oxazole-7-carbonitrile (10 mg, 0.017 mmol) in DCM (1 ml) was added (S)-pyrrolidine-3-carboxylic acid (9.68 mg, 0.084 mmol) and DIEA (0.023 ml, 0.135 mmol), the mixture was stir at r.t. 60 min, then sodium triacetoxyborohydride (10.69 mg, 0.050 mmol) was added, and continued to stir at r.t. overnight. The reaction was concentrated, then diluted in MeOH, filtered, and then purified by prep-HPLC (pH=2, acetonitrile/water+TFA) to give the desired product as TFA salt. LC-MS calculated for $C_{41}H_{40}N_7O_4$ (M+H): m/z=694.3; found 694.3.

Example 145

(R)-1-((7-cyano-2-(3'-((4-(((S)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid

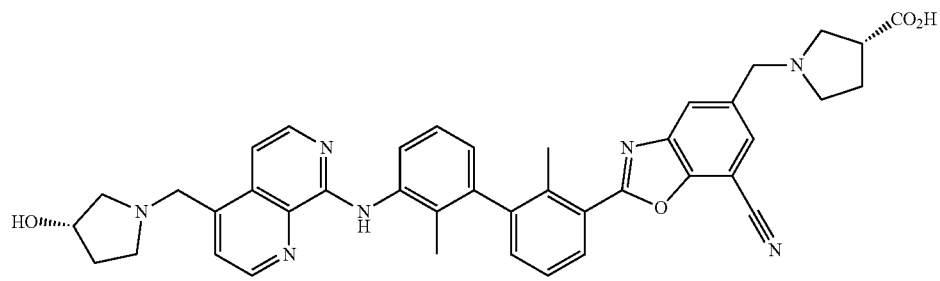 [SMILES: Cc1c(Nc2nccc3c(CN4CC[C@H](O)C4)ccnc23)cccc1-c1cccc(-c2nc3cc(CN4CC[C@@H](C(=O)O)C4)cc(C#N)c3o2)c1C]

This compound was prepared using similar procedures as described for Example 144 with (R)-pyrrolidine-3-carboxylic acid replacing (S)-pyrrolidine-3-carboxylic acid in Step 8. The reaction was concentrated, then diluted in MeOH, filtered then purified by prep-HPLC (pH=2, acetonitrile/water+TFA) to give the desired product as TFA salt. LC-MS calculated for $C_{41}H_{40}N_7O_4$ (M+H): m/z=694.3; found 694.3.

Example 146

(R)-1-((7-cyano-2-(3'-((3-((((S)-2-hydroxypropyl)amino)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid

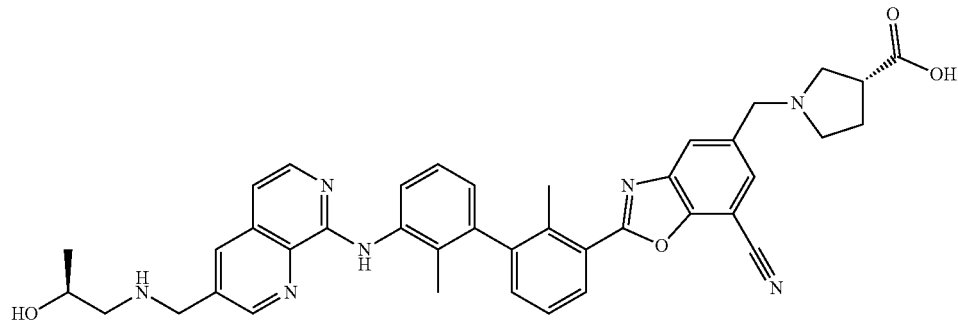 [SMILES: Cc1c(Nc2nccc3cc(CNC[C@H](C)O)cnc23)cccc1-c1cccc(-c2nc3cc(CN4CC[C@@H](C(=O)O)C4)cc(C#N)c3o2)c1C]

Step 1: N-(3-bromo-2-methylphenyl)-3-(chloromethyl)-1,7-naphthyridin-8-amine

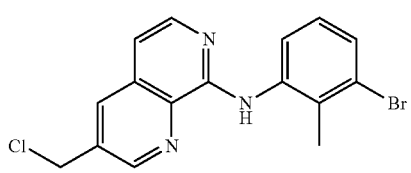 [SMILES: Cc1c(Br)cccc1Nc1nccc2cc(CCl)cnc12]

To a solution of (8-((3-bromo-2-methylphenyl)amino)-1,7-naphthyridin-3-yl)methanol (Affinity Research Chemicals, cat # ARI-0169: 200 mg, 0.581 mmol) in DCM (5 ml) was added thionyl chloride (51 μl, 0.699 mmol) dropwise. The reaction mixture was stirred at r.t. 30 minutes. LC/MS check reaction completed. The reaction mixture was concentrated to dryness under reduced pressure. The residue was washed with hexanes, filtered to afford the desired compound and used in the next step directly. LC-MS calculated for $C_{16}H_{14}BrClN_3$ (M+H)$^+$: m/z=362.0, 364.0; found 362.0, 364.0.

Step 2: (S)-1-(((8-((3-bromo-2-methylphenyl)amino)-1,7-naphthyridin-3-yl)methyl)amino)propan-2-ol

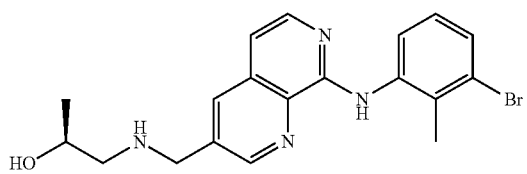 [SMILES: Cc1c(Br)cccc1Nc1nccc2cc(CNC[C@H](C)O)cnc12]

To a solution of N-(3-bromo-2-methylphenyl)-3-(chloromethyl)-1,7-naphthyridin-8-amine (15 mg, 0.041 mmol) in ACN (1 ml) was added DIEA (0.022 ml, 0.124 mmol) and(S)-1-aminopropan-2-ol (3.11 mg, 0.041 mmol), the mixture was stir at 60° C. overnight.

The reaction mixture was diluted with water and then extracted with DCM. The combined extracts were washed with NaHCO$_3$ aqueous solution and brine, dried over MgSO$_4$, filtered and concentrated under reduced pressure to afford the desired product, which was used in the next step without further purification. LC-MS calculated for $C_{19}H_{22}BrN_4O$ (M+H)$^+$: m/z=401.1, 403.1; found 401.1, 403.1.

Step 3: (R)-1-((7-cyano-2-(3'-((3-((((S)-2-hydroxypropyl)amino)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid This compound was prepared using similar procedures as described for Example 138 with (S)-1-(((8-((3-bromo-2-methylphenyl)amino)-1,7-naphthyridin-3-yl)methyl)amino) propan-2-ol replacing (S)-1-((8-((3-bromo-2-methylphenyl)amino)-1,7-naphthyridin-3-yl)methyl)-3-methylpyrrolidin-3-ol in Step 4. The reaction was concentrated, then diluted in MeOH, filtered, and then purified by prep-HPLC (pH=2, acetonitrile/water+TFA) to give the desired product as TFA salt. LC-MS calculated for $C_{40}H_{40}N_7O_4$ (M+H)$^+$: m/z=682.2; found 682.2.

Example 147

(R)-1-((7-cyano-2-(3'-((3-((((R)-2-hydroxypropyl)amino)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid

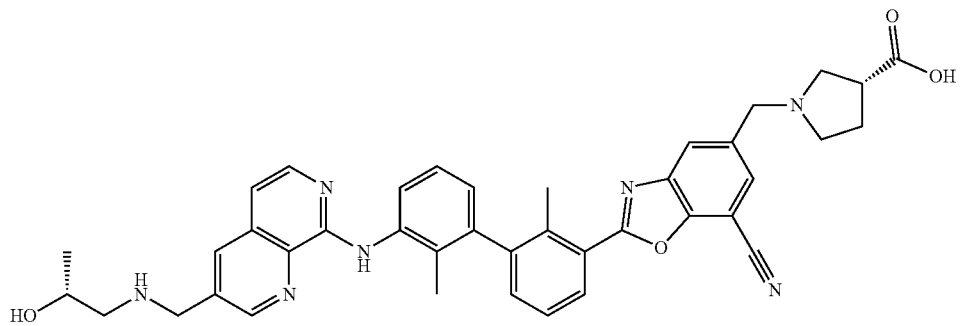 [SMILES: Cc1c(Nc2nccc3cc(CNC[C@@H](C)O)cnc23)cccc1-c1cccc(-c2nc3cc(CN4CC[C@@H](C(=O)O)C4)cc(C#N)c3o2)c1C]

This compound was prepared using similar procedures as described for Example 146 with (R)-1-(((8-((3-bromo-2-methylphenyl)amino)-1,7-naphthyridin-3-yl)methyl)amino) propan-2-ol replacing (S)-1-((8-((3-bromo-2-methylphenyl)amino)-1,7-naphthyridin-3-yl)methyl)-3-methylpyrrolidin-3-ol in Step 3. The reaction was concentrated, then diluted in MeOH, filtered then purified by prep-HPLC (pH=2, acetonitrile/water+TFA) to give the desired product as TFA salt. LC-MS calculated for $C_{40}H_{40}N_7O_4$ (M+H)$^+$: m/z=682.2; found 682.2.

Example 148

(R)-1-((7-chloro-2-(3'-((2-chloro-5-((5-cyanopyridin-3-yl)methoxy)-4-(((R)-3-hydroxypyrrolidin-1-yl)methyl)phenoxy)methyl)-2,2'-dimethyl-[1,1'-biphenyl]-3-yl)benzo[d]oxazol-5-yl)methyl)pyrrolidine-3-carboxylic acid

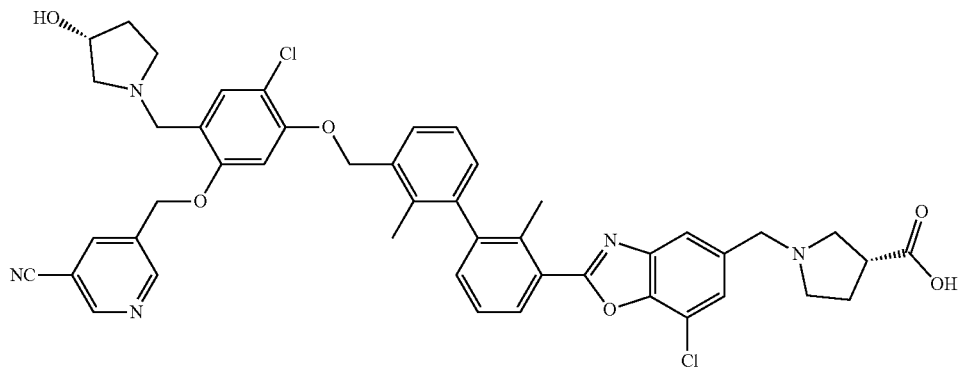 [SMILES: Cc1c(COc2cc(OCc3cncc(C#N)c3)c(CN3CC[C@@H](O)C3)cc2Cl)cccc1-c1cccc(-c2nc3cc(CN4CC[C@@H](C(=O)O)C4)cc(Cl)c3o2)c1C]

Step 1: 4-((3-bromo-2-methylbenzyl)oxy)-5-chloro-2-hydroxybenzaldehyde

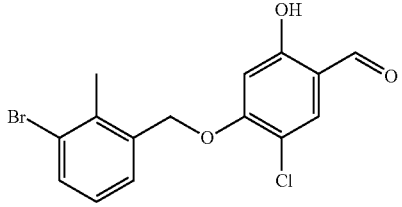 [SMILES: Cc1c(Br)cccc1COc1cc(O)c(C=O)cc1Cl]

To a mixture of (3-bromo-2-methylphenyl)methanol (2.330 g, 11.59 mmol), 5-chloro-2,4-dihydroxybenzaldehyde (2.0 g, 11.59 mmol) and triphenylphosphine (3.65 g, 13.91 mmol) in THF (10 ml) at 0° C. was added diisopropyl azodicarboxylate (2.93 ml, 15.07 mmol). The mixture was stirred at room temperature overnight. The mixture was concentrated and diluted with EtOAc. The solid was collected by filtration to give the desired ether (2.0 g, 5.62 mmol, 48.5% yield). LCMS calculated for $C_{15}H_{13}BrClO_3$ $(M+H)^+$: m/z=357.2; found 357.2.

Step 2: 5-((5-((3-bromo-2-methylbenzyl)oxy)-4-chloro-2-formylphenoxy)methyl)nicotinonitrile

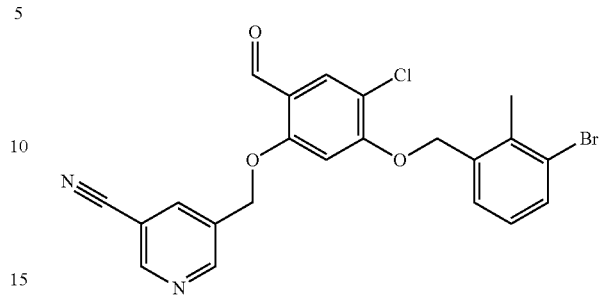

A mixture of 4-((3-bromo-2-methylbenzyl)oxy)-5-chloro-2-hydroxybenzaldehyde (2.0 g, 5.62 mmol), 5-(chloromethyl)nicotinonitrile (0.927 g, 6.07 mmol) and cesium carbonate (2.75 g, 8.44 mmol) in DMF (12 ml) was stirred at 70° C. for 3 hours. The mixture was poured into water. The solid was collected by filtration and air dried to give the desired aldehyde (2.2 g, 4.66 mmol, 83% yield). LCMS calculated for $C_{22}H_{17}BrClN_2O_3$ $(M+H)^+$: m/z=473.0; found 473.0.

Step 3: (R)-1-((7-chloro-2-(3'-((2-chloro-5-((5-cyanopyridin-3-yl)methoxy)-4-formylphenoxy)methyl)-2,2'-dimethyl-[1,1'-biphenyl]-3-yl)benzo[d]oxazol-5-yl)methyl)pyrrolidine-3-carboxylic acid

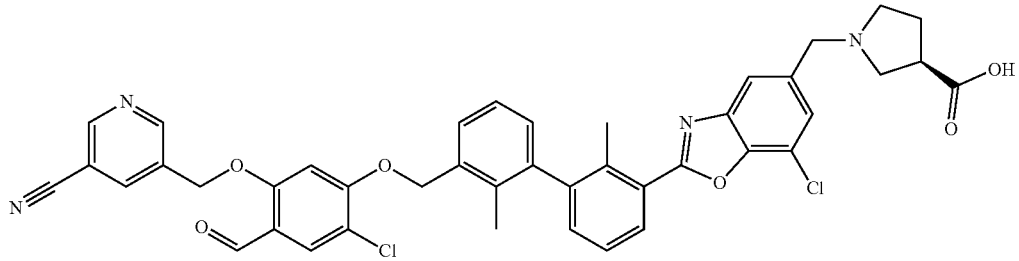 [SMILES: Cc1c(COc2cc(OCc3cncc(C#N)c3)c(C=O)cc2Cl)cccc1-c1cccc(-c2nc3cc(CN4CC[C@@H](C(=O)O)C4)cc(Cl)c3o2)c1C]

A mixture of 5-((5-((3-bromo-2-methylbenzyl)oxy)-4-chloro-2-formylphenoxy)methyl)nicotinonitrile (30 mg, 0.064 mmol), (R)-1-((7-chloro-2-(2-methyl-3-(4,4,5,5-tetramethyl-1,3,2-dioxaborolan-2-yl)phenyl)benzo[d]oxazol-5-yl)methyl)pyrrolidine-3-carboxylic acid (Example 126, Step 4; 37.9 mg, 0.076 mmol), potassium carbonate (17.58 mg, 0.127 mmol) and (1,1'-bis(diphenylphosphino)ferrocene)-dichloropalladium(II) (4.65 mg, 6.36 µmol) in 1,4-dioxane (3 ml) and water (0.60 ml) was purged with nitrogen, and heated at 95° C. for 2 hours. The mixture was purified on prep-HPLC (pH=2, acetonitrile/water+TFA) to give the desired acid (11 mg, 0.014 mmol, 22.71% yield). LCMS calculated for $C_{42}H_{35}Cl_2N_4O_6$ $(M+H)^+$: m/z=761.2; found 761.2.

Step 4: (R)-1-((7-chloro-2-(3'-((2-chloro-5-((5-cyanopyridin-3-yl)methoxy)-4-(((R)-3-hydroxypyrrolidin-1-yl)methyl)phenoxy)methyl)-2,2'-dimethyl-[1,1'-biphenyl]-3-yl)benzo[d]oxazol-5-yl)methyl)pyrrolidine-3-carboxylic acid Sodium triacetoxyborohydride (1.252 mg, 5.91 µmol) was added to a mixture of (R)-1-((7-chloro-2-(3'-((2-chloro-5-((5-cyanopyridin-3-yl)methoxy)-4-formylphenoxy)methyl)-

((5-cyanopyridin-3-yl)methoxy)-4-formylphenoxy)methyl)-2,2'-dimethyl-[1,1'-biphenyl]-3-yl)benzo[d]oxazol-5-yl)methyl)pyrrolidine-3-carboxylic acid (3.0 mg, 3.9 μmol), (R)pyrrolidin-3-ol (0.34 mg, 3.9 μmol) and triethylamine (1.1 μl, 7.9 μmol) in DCM (1.0 ml). After stirring at room temperature for 2 hours, mixture was purified on prep-HPLC (pH=2, acetonitrile/water+TFA) to give the desired product as TFA salt. LC-MS calculated for $C_{46}H_{44}Cl_2N_5O_6$ (M+H)$^+$: m/z=832.2; found 832.2.

Example 149

(S)-1-(4-(((3'-(5-(((R)-3-carboxypyrrolidin-1-yl)methyl)-7-cholorbenzo[d]oxazol-2-yl)-2,2'-dimethyl-[1,1'-biphenyl]-3-yl)methoxy)-5-chloro-2-((5-cyanopyridin-3-yl)methoxy)benzyl)piperidine-2-carboxylic acid

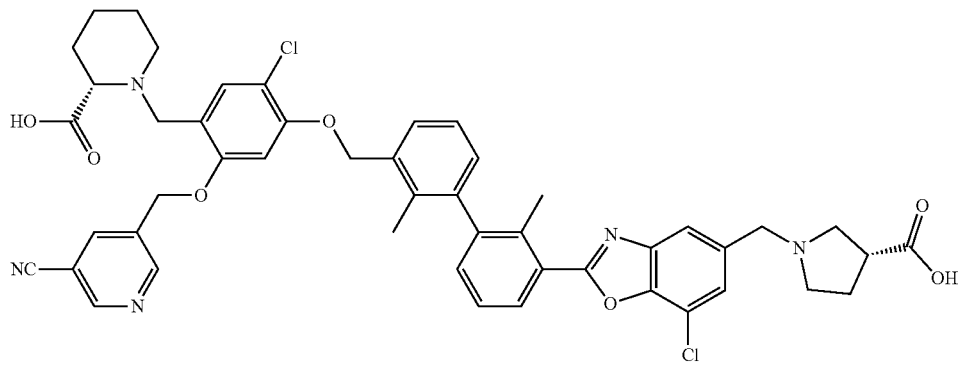 [SMILES: Cc1c(COc2cc(OCc3cncc(C#N)c3)c(CN3CCCC[C@H]3C(=O)O)cc2Cl)cccc1-c1cccc(-c2nc3cc(CN4CC[C@@H](C(=O)O)C4)cc(Cl)c3o2)c1C]

Sodium triacetoxyborohydride (1.25 mg, 5.91 μmol) was added to a mixture of (R)-1-((7-chloro-2-(3'-((2-chloro-5-((5-cyanopyridin-3-yl)methoxy)-4-formylphenoxy)methyl)-2,2'-dimethyl-[1,1'-biphenyl]-3-yl)benzo[d]oxazol-5-yl)methyl)pyrrolidine-3-carboxylic acid (Example 148, Step 3: 3.0 mg, 3.9 μmol), (S)-piperidine-2-carboxylic acid (0.76 mg, 5.9 μmol) and triethylamine (1.1 μl, 7.9 μmol) in DCM (1.0 ml). After stirring at room temperature for 2 hours, the mixture was purified on prep-HPLC (pH=2, acetonitrile/water+TFA) to give the desired product as TFA salt. LC-MS calculated for $C_{48}H_{46}Cl_2N_5O_7$ (M+H)$^+$: m/z=874.2; found 874.2.

Example 150

(R)-1-((7-chloro-2-(3'-((2-chloro-5-((5-cyanopyridin-3-yl)methoxy)-4-(((2-hydroxyethyl)amino)methyl)phenoxy)methyl)-2,2'-dimethyl-[1,1'-biphenyl]-3-yl)benzo[d]oxazol-5-yl)methyl)pyrrolidine-3-carboxylic acid

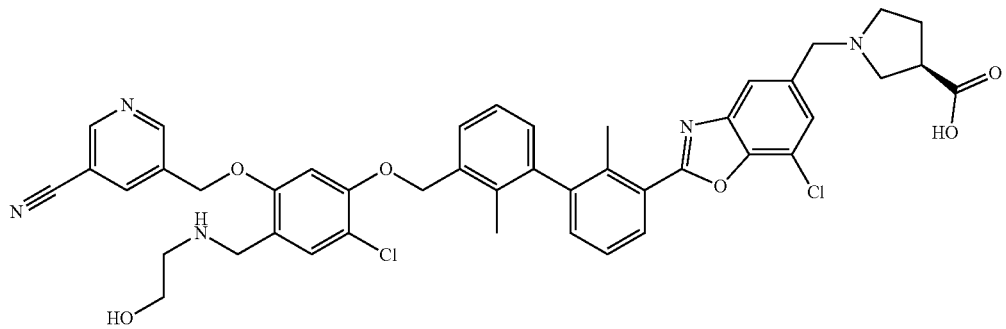 [SMILES: Cc1c(COc2cc(OCc3cncc(C#N)c3)c(CNCCO)cc2Cl)cccc1-c1cccc(-c2nc3cc(CN4CC[C@@H](C(=O)O)C4)cc(Cl)c3o2)c1C]

This compound was prepared using similar procedures as described for Example 148 with 2-aminoethan-1-ol replacing (R)-pyrrolidin-3-ol in Step 4. The reaction was concentrated, then diluted in MeOH, filtered then purified by prep-HPLC (pH=2, acetonitrile/water+TFA) to give the desired product as TFA salt. LC-MS calculated for $C_{44}H_{42}Cl_2N_5O_6$ (M+H)$^+$: m/z=806.2; found 806.2.

Example 151

(R)-1-((5-(2-chloro-3'-(7-chloro-5-(((R)-3-hydroxy-pyrrolidin-1-yl)methyl)benzo[d]oxazol-2-yl)-2'-methylbiphenyl-3-ylcarbamoyl)-1-methyl-6-oxo-1,6-dihydropyridin-3-yl)methyl)pyrrolidine-3-carboxylic acid

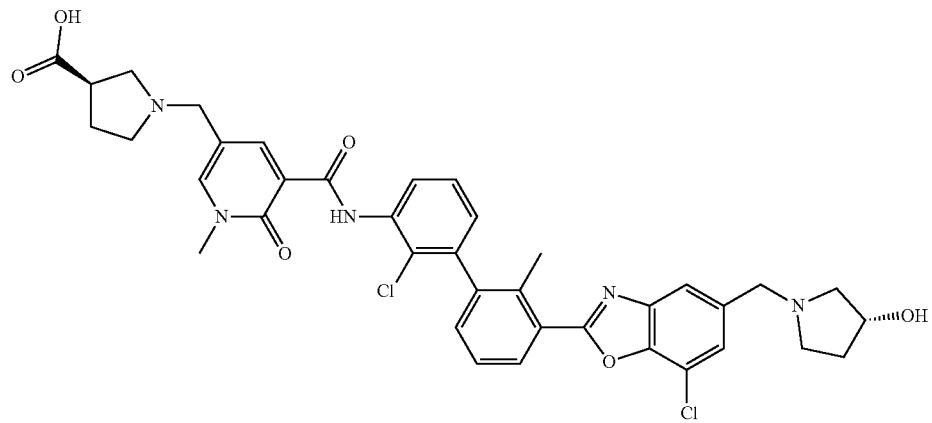 [SMILES: Cc1c(-c2nc3cc(CN4CC[C@@H](O)C4)cc(Cl)c3o2)cccc1-c1cccc(NC(=O)c2cc(CN3CC[C@@H](C(=O)O)C3)cn(C)c2=O)c1Cl]

Step 1: 5-bromo-1-methyl-2-oxo-1,2-dihydropyridine-3-carboxylic acid

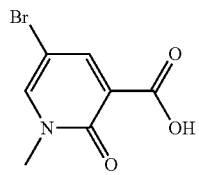

Methyl iodide (1.71 ml, 27.5 mmol) was added to a mixture of 5-bromo-2-hydroxynicotinic acid (5.00 g, 22.94 mmol) and potassium carbonate (4.75 g, 34.4 mmol) in MeOH (76.0 mL). The reaction mixture was stir at 80° C. for 10 hrs. The reaction was cooled to room temperature and the solvent was concentrated under reduced pressure. Water was added, and the mixture was washed with DCM twice. To the aqueous phase was added 1 M aqueous solution of HCl until the pH=2. Then, the acidic aqueous layer was extracted with DCM twice. The organic phase was dried over MgSO$_4$, filtered and the filtrate was concentrated. The crude residue was used directly in the next step without further purification. LC-MS calculated for C$_7$H$_7$BrNO$_3$ (M+H)$^+$: m/z=232.0, 234.0; found 232.0, 234.0.

Step 2: 1-methyl-2-oxo-5-vinyl-1,2-dihydropyridine-3-carboxylic acid

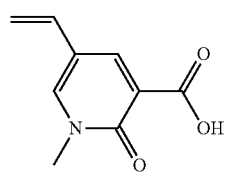

A mixture of 5-bromo-1-methyl-2-oxo-1,2-dihydropyridine-3-carboxylic acid (321 mg, 1.385 mmol), 4,4,5,5-tetramethyl-2-vinyl-1,3,2-dioxaborolane (213 mg, 1.385 mmol), sodium carbonate (440 mg, 4.15 mmol) and tetrakis(triphenylphosphine)palladium(0) (80 mg, 0.069 mmol) in t-butanol (1.4 ml) and water (1.4 ml) was degassed and sealed. It was stirred at 80° C. for 2 h. The reaction was cooled to room temperature and the solvent was concentrated under reduced pressure. Water was added, and the mixture was washed with DCM twice. To the aqueous phase was added 1 M aqueous solution of HCl until the pH=2. Then, the acidic aqueous layer was extracted with DCM twice. The organic phase was dried over MgSO$_4$, filtered and the filtrate was concentrated. The crude residue was used directly in the next step without further purification. LC-MS calculated for C$_9$H$_{10}$NO$_3$ (M+H)$^+$: m/z=180.1; found 180.1.

Step 3: N-(2-chloro-3'-(7-chloro-5-(hydroxymethyl)benzo[d]oxazol-2-yl)-2'-methylbiphenyl-3-yl)-1-methyl-2-oxo-5-vinyl-1,2-dihydropyridine-3-carboxamide

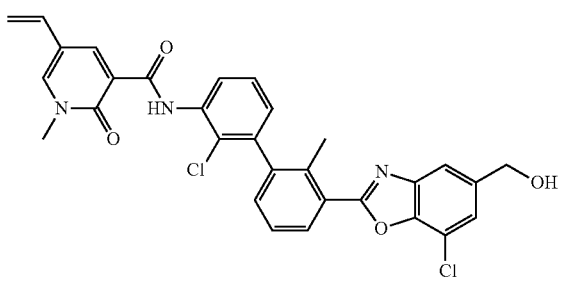 [SMILES: C=Cc1cc(C(=O)Nc2cccc(-c3cccc(-c4nc5cc(CO)cc(Cl)c5o4)c3C)c2Cl)c(=O)n(C)c1]

To a solution of 1-methyl-2-oxo-5-vinyl-1,2-dihydropyridine-3-carboxylic acid (30.0 mg, 0.170 mmol), (2-(3'-amino-2'-chloro-2-methyl-[1,1'-biphenyl]-3-yl)-7-chlorobenzo[d]oxazol-5-yl)methanol (Example 15, Step 1: 68.0 mg, 0.17 mmol), and 2-(3H-[1,2,3]triazolo[4,5-b]pyridin-3-yl)-1,1,3,3-tetramethylisouronium hexafluorophosphate(V) (78.0 mg, 0.204 mmol) in 1,2-dichloroethane (2.2 ml) was added N,N-diisopropylethylamine (60 μl, 0.34 mmol). The mixture was stirred at room temperature for 2 hrs. Then, the mixture was diluted with DCM, and washed with water and brine. The organic phase was dried over MgSO$_4$ before filtering. The filtrate was concentrated and purified by flash chromatography to afford the desired product. LC-MS calculated for $C_{30}H_{24}Cl_2N_3O_4$ (M+H)$^+$: m/z=560.1; found 560.1.

Step 4: N-(2-chloro-3'-(7-chloro-5-formylbenzo[d]oxazol-2-yl)-2'-methylbiphenyl-3-yl)-1-methyl-2-oxo-5-vinyl-1,2-dihydropyridine-3-carboxamide

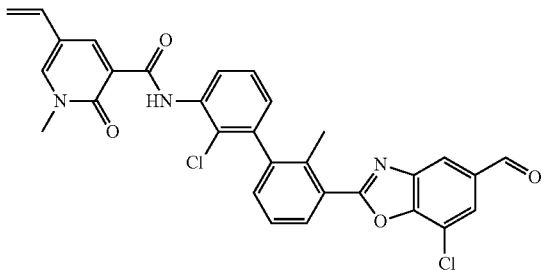 [SMILES: C=Cc1cc(C(=O)Nc2cccc(-c3cccc(-c4nc5cc(C=O)cc(Cl)c5o4)c3C)c2Cl)c(=O)n(C)c1]

To a stirred solution of N-(2-chloro-3'-(7-chloro-5-(hydroxymethyl)benzo[d]oxazol-2-yl)-2'-methylbiphenyl-3-yl)-1-methyl-2-oxo-5-vinyl-1,2-dihydropyridine-3-carboxamide (86.0 mg, 0.153 mmol) in DCM (3.0 ml) was added Dess-Martin Periodinane (65.0 mg, 0.153 mmol). The resulted mixture was stirred at r.t. for 2 hrs, and then filtered. The filtrate was concentrated under reduced pressure. The residue was used in the next step directly without further purification. LC-MS calculated for $C_{30}H_{22}Cl_2N_3O_4$ (M+H)$^+$: m/z=558.1; found 558.1.

Step 5: (R)—N-(2-chloro-3'-(7-chloro-5-((3-hydroxypyrrolidin-1-yl)methyl)benzo[d]oxazol-2-yl)-2'-methylbiphenyl-3-yl)-1-methyl-2-oxo-5-vinyl-1,2-dihydropyridine-3-carboxamide

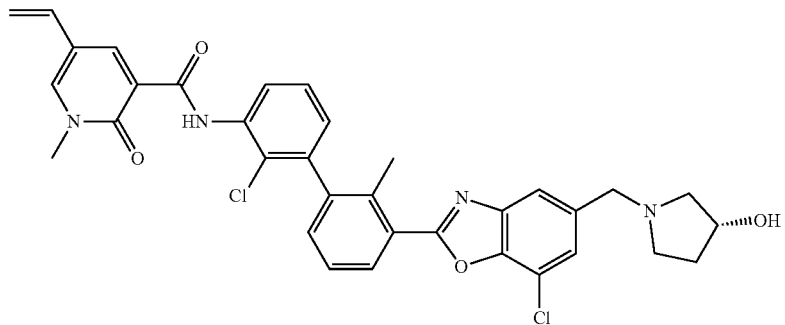 [SMILES: C=Cc1cc(C(=O)Nc2cccc(-c3cccc(-c4nc5cc(CN6CC[C@@H](O)C6)cc(Cl)c5o4)c3C)c2Cl)c(=O)n(C)c1]

A mixture of N-(2-chloro-3'-(7-chloro-5-formylbenzo[d]oxazol-2-yl)-2'-methylbiphenyl-3-yl)-1-methyl-2-oxo-5-vinyl-1,2-dihydropyridine-3-carboxamide (47 mg, 0.085 mmol) and (R)-pyrrolidin-3-ol (22.0 mg, 0.255 mmol) in THF (0.85 mL) was stirred at room temperature for 0.5 h. Then sodium triacetoxyborohydride (54 mg, 0.255 mmol) was added. The mixture was further stirred at room temperature for 1 h. The reaction mixture was quenched by NH$_4$OH aqueous solution then extracted with DCM. The organic phases were combined and dried over MgSO$_4$, then filtered. The filtrate was concentrated and used directly in the next step without further purification. LC-MS calculated for $C_{34}H_{31}Cl_2N_4O_4$ (M+H)$^+$: m/z=629.2; found 629.2.

Step 6: (R)—N-(2-chloro-3'-(7-chloro-5-((3-hydroxypyrrolidin-1-yl)methyl)benzo[d]oxazol-2-yl)-2'-methylbiphenyl-3-yl)-5-formyl-1-methyl-2-oxo-1,2-dihydropyridine-3-carboxamide

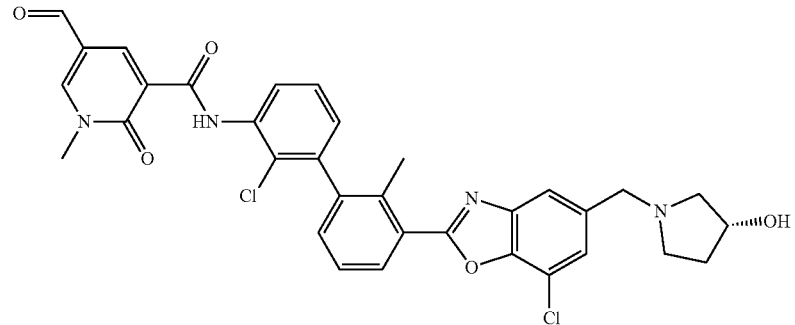 [SMILES: Cc1c(-c2nc3cc(CN4CC[C@@H](O)C4)cc(Cl)c3o2)cccc1-c1cccc(NC(=O)c2cc(C=O)cn(C)c2=O)c1Cl]

A vial was charged with (R)—N-(2-chloro-3'-(7-chloro-5-((3-hydroxypyrrolidin-1-yl)methyl)benzo[d]oxazol-2-yl)-2'-methylbiphenyl-3-yl)-1-methyl-2-oxo-5-vinyl-1,2-dihydropyridine-3-carboxamide (50 mg, 0.08 mmol), a stir bar, 1,4-dioxane (0.6 ml) and water (0.2 ml). To this suspension was added potassium osmate dihydrate (1.5 mg, 0.004 mmol). The reaction was stirred for 5 min, and then sodium periodate (86 mg, 0.4 mmol) was added. After stirring at room temperature for 1 h, the reaction mixture was quenched with a saturated aqueous solution of sodium thiosulfate. The mixture was then extracted with ethyl acetate, and the combined organic layers were separated, washed with brine, dried over $Na_2SO_4$, filtered, and concentrated in vacuo. The crude residue was purified by flash chromatography on a silica gel column eluting with 0 to 6% MeOH in DCM to afford the desired product. LC-MS calculated for $C_{33}H_{29}Cl_2N_4O_5$ $(M+H)^+$: m/z=631.1; found 631.1.

Step 7: (R)-1-((5-(2-chloro-3'-(7-chloro-5-(((R)-3-hydroxypyrrolidin-1-yl)methyl)benzo[d]oxazol-2-yl)-2'-methylbiphenyl-3-ylcarbamoyl)-1-methyl-6-oxo-1,6-dihydropyridin-3-yl)methyl)pyrrolidine-3-carboxylic acid

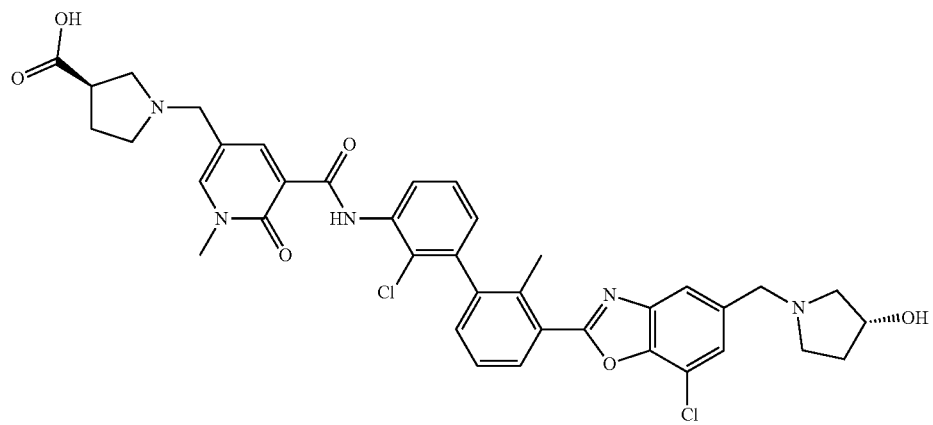 [SMILES: Cc1c(-c2nc3cc(CN4CC[C@@H](O)C4)cc(Cl)c3o2)cccc1-c1cccc(NC(=O)c2cc(CN3CC[C@@H](C(=O)O)C3)cn(C)c2=O)c1Cl]

A mixture of (R)—N-(2-chloro-3'-(7-chloro-5-((3-hydroxypyrrolidin-1-yl)methyl)benzo[d]oxazol-2-yl)-2'-methylbiphenyl-3-yl)-5-formyl-1-methyl-2-oxo-1,2-dihydropyridine-3-carboxamide (51 mg, 0.08 mmol) and (R)-pyrrolidine-3-carboxylic acid (9.21 mg, 0.08 mmol) in THF (0.5 mL) was stirred at room temperature for 0.5 h. Then sodium triacetoxyborohydride (51 mg, 0.24 mmol) was added. The mixture was further stirred at room temperature for 1 h. The mixture was concentrated and diluted with MeOH and then purified by prep-HPLC (pH=2, acetonitrile/water+TFA) to give the desired product as its TFA salt. LC-MS calculated for $C_{38}H_{38}Cl_2N_5O_6$ $(M+H)^+$: m/z=730.2; found 730.2.

Example 152

(S)-1-((7-cyano-2-(3'-(3-(((S)-3-hydroxypyrrolidin-1-yl)methyl)imidazo[1,2-a]pyrazin-8-ylamino)-2,2'-dimethylbiphenyl-3-yl)benzo[d]oxazol-5-yl)methyl)pyrrolidine-3-carboxylic acid

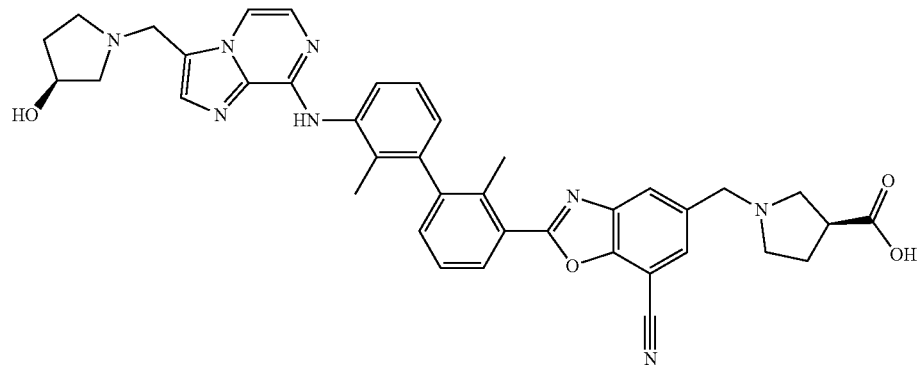 [SMILES: Cc1c(Nc2nccn3c(CN4CC[C@H](O)C4)cnc23)cccc1-c1cccc(-c2nc3cc(CN4CC[C@H](C(=O)O)C4)cc(C#N)c3o2)c1C]

Step 1: 8-chloro-3-vinylimidazol[1,2-a]pyrazine

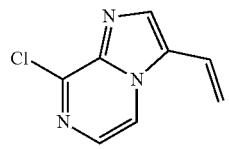

A mixture of 3-bromo-8-chloroimidazo[1,2-a]pyrazine (400 mg, 1.721 mmol) (Ark Pharm, cat # AK-24131), 4,4,5,5-tetramethyl-2-vinyl-1,3,2-dioxaborolane (350 µL, 2.065 mmol), sodium carbonate (456 mg, 4.30 mmol) and tetrakis(triphenylphosphine)palladium(0) (99 mg, 0.086 mmol) in tert-butanol (4.0 mL) and water (4.0 mL) was purged with nitrogen and then stirred at 100° C. for 2 h. The reaction mixture was cooled then extracted with ethyl acetate. The combined organic layers were washed with brine, dried over Na$_2$SO$_4$, filtered and concentrated under reduced pressure. The residue was purified by flash chromatography on a silica gel column eluting with 50% ethyl acetate in hexanes to afford the desired product. LC-MS calculated for C$_8$H$_7$ClN$_3$ (M+H)$^+$: m/z=180.0; found 180.1.

Step 2: N-(3-bromo-2-methylphenyl)-3-vinylimidazo[1,2-a]pyrazin-8-amine

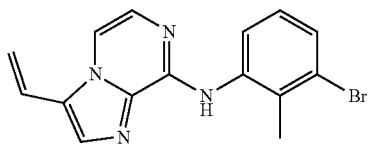 [SMILES: C=Cc1cnc2c(Nc3cccc(Br)c3C)nccn12]

A mixture of 3-bromo-2-methylaniline (120 mg, 0.645 mmol), 8-chloro-3-vinylimidazo[1,2-a]pyrazine (Step 1: 139 mg, 0.774 mmol) and HCl in dioxane (4.0 M, 161 µL, 0.645 mmol) in tert-butanol (3.2 mL) was heated at 100° C. for 1 h. The reaction was then cooled to room temperature and diluted with dichloromethane. The reaction was quenched by aqueous NaHCO$_3$ solution and extracted with dichloromethane. The organic phase was dried over Na$_2$SO$_4$, filtered and the filtrate was concentrated. The residue was used directly for next step. LC-MS calculated for C$_{15}$H$_{1-4}$BrN$_4$ (M+H)$^+$: m/z=329.0/331.0; found 329.1/331.1.

Step 3: 8-((3-bromo-2-methylphenyl)amino) imidazo[1,2-a]pyrazine-3-carbaldehyde

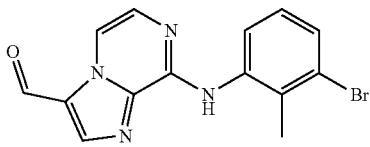 [SMILES: Cc1c(Br)cccc1Nc1nccn2c(C=O)cnc12]

Osmium tetroxide (4% w/w in water, 0.253 ml, 0.032 mmol) was added to a mixture of N-(3-bromo-2-methylphenyl)-3-vinylimidazo[1,2-a]pyrazin-8-amine (Step 2: 0.212 g, 0.645 mmol) in 1,4-dioxane (4.8 mL) and water (1.6 mL). The reaction was stirred for 5 min then sodium periodate (0.690 g, 3.23 mmol) was added. After being stirred at room temperature for 1 h, the reaction was quenched with a saturated aqueous solution of sodium thiosulfate. The mixture was then extracted with ethyl acetate, and the combined organic layers were separated, washed with brine, dried over Na$_2$SO$_4$, filtered, and concentrated under reduced pressure. The crude residue was used directly for next step. LC-MS calculated for C$_{14}$H$_{12}$BrN$_4$O (M+H)$^+$: m/z=331.0/333.0; found 331.0/333.0.

Step 4: (S)-1-((8-((3-bromo-2-methylphenyl)amino)imidazo[1,2-a]pyrazin-3-yl)methyl)pyrrolidin-3-ol

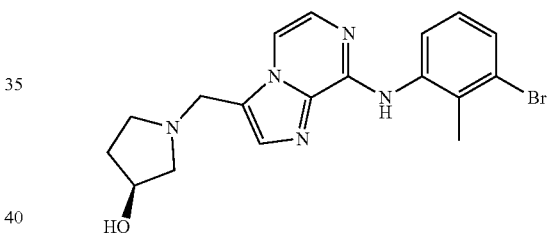

A mixture of 8-((3-bromo-2-methylphenyl)amino)imidazo[1,2-a]pyrazine-3-carbaldehyde (Step 3: 166 mg, 0.5 mmol) and (S)-pyrrolidin-3-ol (131 mg, 1.500 mmol) in dichloromethane (5.0 mL) was stirred at room temperature for 2 h. Then sodium triacetoxyborohydride (318 mg, 1.500 mmol) and acetic acid (86 µL, 1.500 mmol) were added. The mixture was further stirred at room temperature for 1 h. The reaction was quenched by NH$_4$OH aqueous solution and extracted with dichloromethane. The combined organic layers were washed with brine, dried over Na$_2$SO$_4$, filtered and concentrated under reduced pressure. The residue was purified by flash chromatography on a silica gel column eluting with 10% methanol in dichloromethane to afford the desired product. LCMS calculated for C$_{18}$H$_{21}$BrN$_5$O (M+H)$^+$: m/z=402.1/404.1; found 402.1/404.1.

Step 5: (S)-1-((8-((3'-(7-chloro-5-(hydroxymethyl)benzo[d]oxazol-2-yl)-2,2'-dimethyl-[1,1'-biphenyl]-3-yl)amino)imidazo[1,2-a]pyrazin-3-yl)methyl)pyrrolidin-3-ol

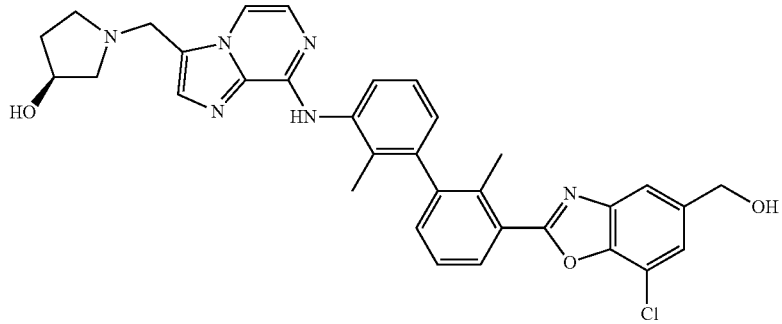 [SMILES: Cc1c(Nc2nccn3c(CN4CC[C@H](O)C4)cnc23)cccc1-c1cccc(-c2nc3cc(CO)cc(Cl)c3o2)c1C]

A mixture of(S)-1-((8-((3-bromo-2-methylphenyl)amino)imidazo[1,2-a]pyrazin-3-yl)methyl)pyrrolidin-3-ol (Step 4: 50 mg, 0.124 mmol), (7-chloro-2-(2-methyl-3-(4,4,5,5-tetramethyl-1,3,2-dioxaborolan-2-yl)phenyl)benzo[d]oxazol-5-yl)methanol (Example 1, Step 5: 49.7 mg, 0.124 mmol), sodium carbonate (32.9 mg, 0.311 mmol) and tetrakis(triphenylphosphine)palladium(0) (14.36 mg, 0.012 mmol) in water (0.2 mL) and 1,4-dioxane (1.0 mL) was purged with nitrogen and then stirred at 100° C. for 4 h. After being cooled to room temperature, the reaction mixture was extracted with ethyl acetate. The combined organic layers were washed with brine, dried over $Na_2SO_4$, filtered and concentrated under reduced pressure. The residue was purified by flash chromatography on a silica gel column eluting with 10% methanol in dichloromethane to afford the desired product. LC-MS calculated for $C_{33}H_{32}ClN_6O_3(M+H)^+$: m/z=595.2; found 595.1.

Step 6: (S)-5-(hydroxymethyl)-2-(3'-((3-((3-hydroxypyrrolidin-1-yl)methyl)imidazo[1,2-a]pyrazin-8-yl)amino)-2,2'-dimethyl-[1,1'-biphenyl]-3-yl)benzo[d]oxazole-7-carbonitrile

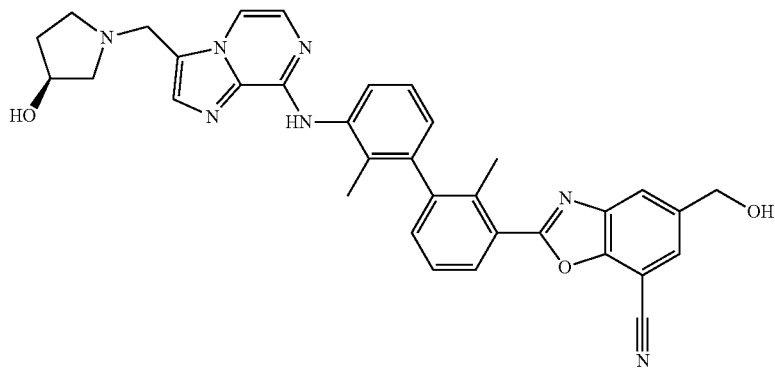 [SMILES: Cc1c(Nc2nccn3c(CN4CC[C@H](O)C4)cnc23)cccc1-c1cccc(-c2nc3cc(CO)cc(C#N)c3o2)c1C]

This compound was prepared using similar procedures as described for Example 12 with (S)-1-((8-((3'-(7-chloro-5-(hydroxymethyl)benzo[d]oxazol-2-yl)-2,2'-dimethyl-[1,1'-biphenyl]-3-yl)amino)imidazo[1,2-a]pyrazin-3-yl)methyl)pyrrolidin-3-ol replacing (7-chloro-2-(2,2'-dimethyl-3'-(pyrido[3,4-b]pyrazin-5-ylamino)-[1,1'-biphenyl]-3-yl)benzo[d]oxazol-5-yl)methanol in Step 1. LC-MS calculated for $C_{34}H_{32}N_7O_3$ $(M+H)^+$: m/z=586.3; found 586.5.

Step 7: (S)-5-formyl-2-(3'-(3-((3-hydroxypyrrolidin-1-yl)methyl)imidazo[1,2-a]pyrazin-8-ylamino)-2,2'-dimethylbiphenyl-3-yl)benzo[d]oxazole-7-carbonitrile

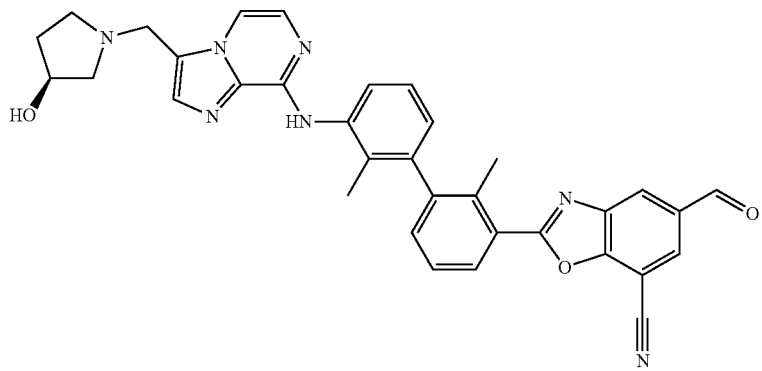 [SMILES: Cc1c(Nc2nccn3c(CN4CC[C@H](O)C4)cnc23)cccc1-c1cccc(-c2nc3cc(C=O)cc(C#N)c3o2)c1C]

A suspension of (S)-5-(hydroxymethyl)-2-(3'-(3-((3-hydroxypyrrolidin-1-yl)methyl)imidazo[1,2-a]pyrazin-8-yl)amino)-2,2'-dimethyl-[1,1'-biphenyl]-3-yl)benzo[d]oxazole-7-carbonitrile (Step 6: 20 mg, 0.034 mmol) and manganese dioxide (44.5 mg, 0.512 mmol) in dichloromethane (0.25 mL) was stirred at 45° C. for 30 min. The reaction was filtered through a short pad of celite and then concentrated to yield a crude residue, which was used directly without further purification. LC-MS calculated for $C_{34}H_{30}N_7O_3$ (M+H)$^+$: m/z=584.2; found 584.3.

Step 8: (S)-1-((7-cyano-2-(3'-(3-(((S)-3-hydroxypyrrolidin-1-yl)methyl)imidazo[1,2-a]pyrazin-8-ylamino)-2,2'-dimethylbiphenyl-3-yl)benzo[d]oxazol-5-yl)methyl)pyrrolidine-3-carboxylic acid A mixture of (S)-5-formyl-2-(3'-(3-((3-hydroxypyrrolidin-1-yl)methyl)imidazo[1,2-a]pyrazin-8-ylamino)-2,2'-dimethylbiphenyl-3-yl)benzo[d]oxazole-7-carbonitrile (Step 7: 20.00 mg, 0.034 mmol) and (S)-pyrrolidine-3-carboxylic acid (3.93 mg, 0.034 mmol) in dichloromethane (0.25 mL) was stirred at room temperature for 1 h. Then sodium triacetoxyborohydride (7.24 mg, 0.034 mmol) and acetic acid (1.955 µL, 0.034 mmol) was added. After being stirred at room temperature for 1 h, the reaction mixture was diluted with MeOH, and purified via pH 2 preparative HPLC (MeCN/water with TFA) to give the desired product as TFA salt. LC-MS calculated for $C_{39}H_{39}N_8O_4$ (M+H)$^+$: m/z=683.3; found 683.5.

Example 153

1-((7-chloro-2-(2'-chloro-3'-((5-(((S)-3-hydroxypyrrolidin-1-yl)methyl)-3-methylpyrazin-2-yloxy)methyl)-2-methylbiphenyl-3-yl)benzo[d]oxazol-5-yl)methyl)pyrrolidine-3-carboxylic acid

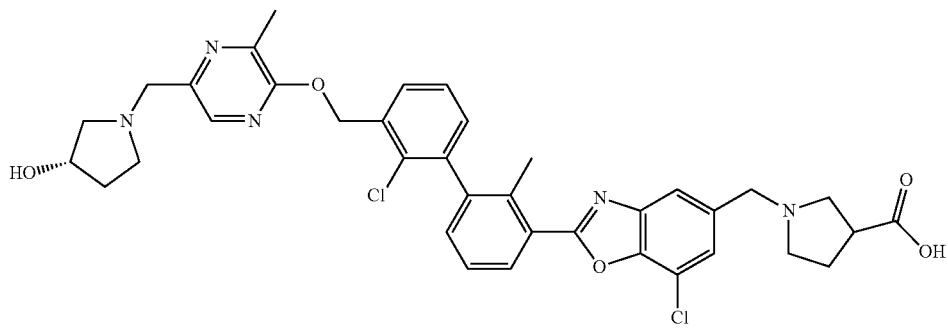 [SMILES: Cc1nc(CN2CC[C@H](O)C2)cnc1OCc1cccc(-c2cccc(-c3nc4cc(CN5CCC(C(=O)O)C5)cc(Cl)c4o3)c2C)c1Cl]

Step 1: (2-(3-bromo-2-methylphenyl)-7-chlorobenzo[d]oxazol-5-yl)methyl methanesulfonate

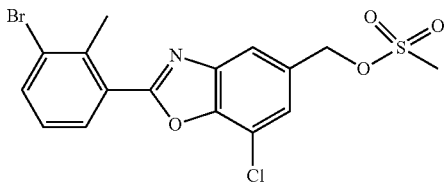 [SMILES: Cc1c(Br)cccc1-c1nc2cc(COS(C)(=O)=O)cc(Cl)c2o1]

To a solution of (2-(3-bromo-2-methylphenyl)-7-chlorobenzo[d]oxazol-5-yl)methanol (Example 1, Step 4: 2.0 g, 5.67 mmol) in DCM (30.0 ml) was added triethylamine (1.186 ml, 8.51 mmol) with stirring at r.t., followed by addition of methanesulfonyl chloride (0.530 ml, 6.81 mmol). The solution was vigorously stirred at r.t. for 2 hours. It was diluted with DCM, washed with water (×2), brine; dried over $Na_2SO_4$. After filtration, the filtrate was concentrated and the residue was used directly. LC-MS calculated for $C_{16}H_{14}BrClNO_4S$ (M+H)$^+$: m/z=432.0; found 431.9.

Step 2: tert-butyl 1-((2-(3-bromo-2-methylphenyl)-7-chlorobenzo[d]oxazol-5-yl)methyl)pyrrolidine-3-carboxylate

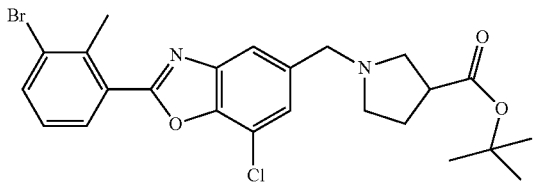 [SMILES: Cc1c(Br)cccc1-c1nc2cc(CN3CCC(C(=O)OC(C)(C)C)C3)cc(Cl)c2o1]

To a solution of (2-(3-bromo-2-methylphenyl)-7-chlorobenzo[d]oxazol-5-yl)methyl methanesulfonate (400 mg, 0.929 mmol) and tert-butylpyrrolidine-3-carboxylate (184 mg, 1.022 mmol) in DCM (15.00 ml) was added sodium carbonate (295 mg, 2.79 mmol) with stirring at r.t. The suspension was vigorously stirred at r.t. for 2 hours. After filtration, the filtrate was concentrated. The crude material was purified by flash column. LC-MS calculated for $C_{24}H_{27}BrClN_2O_3$(M+H)$^+$: m/z=507.1; found 507.0.

Step 3: tert-butyl 1-((7-chloro-2-(2-methyl-3-(4,4,5,5-tetramethyl-1,3,2-dioxaborolan-2-yl)phenyl)benzo[d]oxazol-5-yl)methyl)pyrrolidine-3-carboxylate

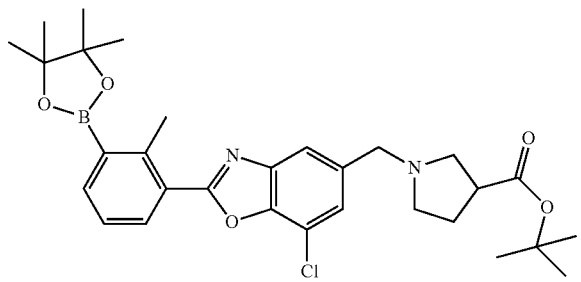 [SMILES: Cc1c(B2OC(C)(C)C(C)(C)O2)cccc1-c1nc2cc(CN3CCC(C(=O)OC(C)(C)C)C3)cc(Cl)c2o1]

A mixture of tert-butyl 1-((2-(3-bromo-2-methylphenyl)-7-chlorobenzo[d]oxazol-5-yl)methyl)pyrrolidine-3-carboxylate (300 mg, 0.593 mmol), bis(pinacolato)diboron (181 mg, 0.712 mmol) and potassium acetate (87 mg, 0.890 mmol) in dioxane (3 ml) in a glass vial was degassed for 5 min. Then to the mixture was added tricyclohexylphosphine (11.64 mg, 0.042 mmol), followed by tris(dibenzylideneacetone)dipalladium(0) (32.6 mg, 0.036 mmol). The mixture was degassed for another 2 min. It was sealed and stirred at 120° C. for 1.5 hours. LCMS showed product formed. After cooling, the reaction mixture was concentrated. The crude material was purified by flash column eluting with EA/hexanes 0-100%. LC-MS calculated for $C_{30}H_{39}BClN_2O_5$(M+H)$^+$: m/z=553.3; found 553.3.

Step 4: methyl 5-(3-bromo-2-chlorobenzyloxy)-6-methylpyrazine-2-carboxylate

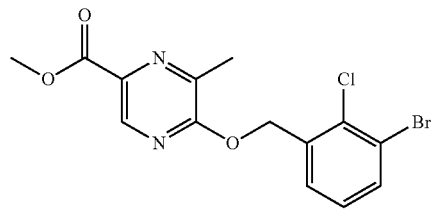 [SMILES: COC(=O)c1cnc(OCc2cccc(Br)c2Cl)c(C)n1]

A mixture of (3-bromo-2-chlorophenyl)methanol (534 mg, 2.412 mmol) and sodium hydride (90 mg, 60% dispersion in mineral oil, 2.251 mmol) in N,N-dimethylformamide (5 ml) was stirred at r.t. for 30 min. Then to the mixture was added methyl 5-chloro-6-methylpyrazine-2-carboxylate (300 mg, 1.608 mmol). The mixture was stirred at r.t. for 1 hr. LCMS showed product formed. It was quenched with water, extracted with EA. After separation, the organic solution was washed with water (×2), brine; dried over $Na_2SO_4$. After filtration, the filtrate was concentrated to yield crude material, which was purified by flash column. LC-MS calculated for $C_{14}H_{13}BrClN_2O_3$(M+H)$^+$: m/z=373.0; found 373.0.

Step 5: (5-(3-bromo-2-chlorobenzyloxy)-6-methylpyrazin-2-yl)methanol

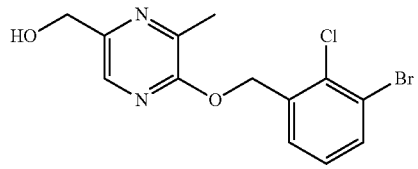 [SMILES: Cc1nc(CO)cnc1OCc1cccc(Br)c1Cl]

To a solution of methyl 5-((3-bromo-2-chlorobenzyl)oxy)-6-methylpyrazine-2-carboxylate (0.58 g, 1.561 mmol) in THF (10 ml) was added dropwisely lithium aluminum hydride in THF (1N, 1.093 ml, 1.093 mmol) with stirring at 0° C. The reaction was stirred at this temperature for 1 hr. Then it was diluted with EA, washed with water (×2), brine; and dried over $Na_2SO_4$. After filtration, the filtrate was concentrated and the residue was used directly. LC-MS calculated for $C_{13}H_{13}BrClN_2O_2$ (M+H)$^+$: m/z=345.0; found 345.0.

Step 6: 5-(3-bromo-2-chlorobenzyloxy)-6-methyl-pyrazine-2-carbaldehyde

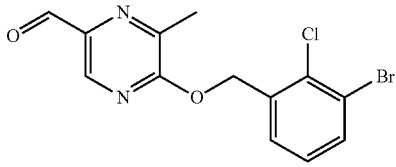 [SMILES: Cc1nc(C=O)cnc1OCc1cccc(Br)c1Cl]

To a solution of (5-((3-bromo-2-chlorobenzyl)oxy)-6-methylpyrazin-2-yl)methanol (0.50 g, 1.46 mmol) in DCM (20 ml) was added Dess-Martin periodinane (0.541 ml, 1.746 mmol). The mixture was stirred at r.t. for 2 hrs. Then it was diluted with DCM, and quenched with sat'd NaHCO$_3$ solution. After separation, the organic solution was washed with water, brine, and dried over Na$_2$SO$_4$. After filtration, the filtrate was concentrated. The crude material was purified by flash column to yield the title compound. LC-MS calculated for $C_{13}H_{11}BrClN_2O_2(M+H)^+$: m/z=343.0; found 342.9.

Step 7: tert-butyl 1-((7-chloro-2-(2'-chloro-3'-((5-formyl-3-methylpyrazin-2-yloxy)methyl)-2-methyl-biphenyl-3-yl)benzo[d]oxazol-5-yl)methyl)pyrrolidine-3-carboxylate

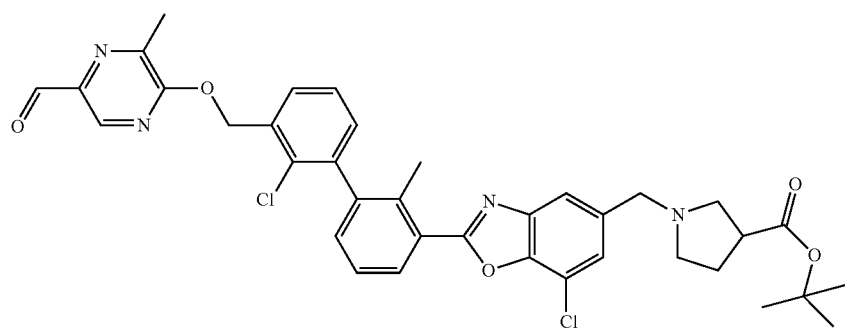 [SMILES: Cc1nc(C=O)cnc1OCc1cccc(-c2cccc(-c3nc4cc(CN5CCC(C(=O)OC(C)(C)C)C5)cc(Cl)c4o3)c2C)c1Cl]

A mixture of tert-butyl 1-((7-chloro-2-(2-methyl-3-(4,4,5,5-tetramethyl-1,3,2-dioxaborolan-2-yl)phenyl)benzo[d]oxazol-5-yl)methyl)pyrrolidine-3-carboxylate (220 mg, 0.398 mmol), 5-((3-bromo-2-chlorobenzyl)oxy)-6-methyl-pyrazine-2-carbaldehyde (150 mg, 0.438 mmol) and cesium carbonate (324 mg, 0.995 mmol) in t-BuOH (0.8 ml) and water (0.200 ml) was degassed with N$_2$ for 3 min, and then to the mixture was added 1,1'-bis(di-cyclohexylphosphino) ferrocene palladium dichloride (30.1 mg, 0.040 mmol). The resulting mixture was degassed with N$_2$ for another 2 min. Then it was sealed and stirred at 68° C. for 2 hours. LCMS showed product formed. After cooling, the mixture was diluted with EA, washed with brine, and dried over Na$_2$SO$_4$. After filtration, the filtrate was concentrated. The crude material was purified by flash column to yield the title compound. LC-MS calculated for $C_{37}H_{37}Cl_2N_4O_5$ $(M+H)^+$: m/z=687.2; found 687.2.

Step 8: 1-((7-chloro-2-(2'-chloro-3'-((5-(((S)-3-hydroxypyrrolidin-1-yl)methyl)-3-methylpyrazin-2-yloxy)methyl)-2-methylbiphenyl-3-yl)benzo[d]oxazol-5-yl)methyl)pyrrolidine-3-carboxylic acid A mixture of tert-butyl 1-((7-chloro-2-(2'-chloro-3'-(((5-formyl-3-methylpyrazin-2-yl)oxy)methyl)-2-methyl-[1,1'-biphenyl]-3-yl)benzo[d]oxazol-5-yl)methyl)pyrrolidine-3-carboxylate (10 mg, 0.015 mmol) and (S)-(-)-3-pyrrolidinol (3.80 mg, 0.044 mmol) in DCM (1 ml) was stirred at r.t. for 1 h. Then to the mixture was added sodium triacetoxyborohydride (9.25 mg, 0.044 mmol). It was then stirred at r.t. for 2 hours. After quenching with water, the reaction was extracted with DCM. The combined extracts were concentrated. The residue was redissolved in DCM (1 ml). To the solution was added trifluoroacetic acid (0.7 ml, 9.09 mmol). The mixture was stirred at r.t. for 1 h. After concentration, the reaction was diluted with MeOH and then purified by prep-HPLC (pH=2, acetonitrile/water+TFA) to give the desired product as TFA salt. LC-MS calculated for $C_{37}H_{38}Cl_2N_5O_5$ $(M+H)^+$: m/z=702.2; found 702.2.

Example 154

1-((2-(2'-chloro-2-methyl-3'-(1-methyl-4,5,6,7-tetra-hydro-1H-imidazo[4,5-c]pyridine-2-carboxamido)biphenyl-3-yl)-7-cyanobenzo[d]oxazol-5-yl)methyl)piperidine-4-carboxylic acid

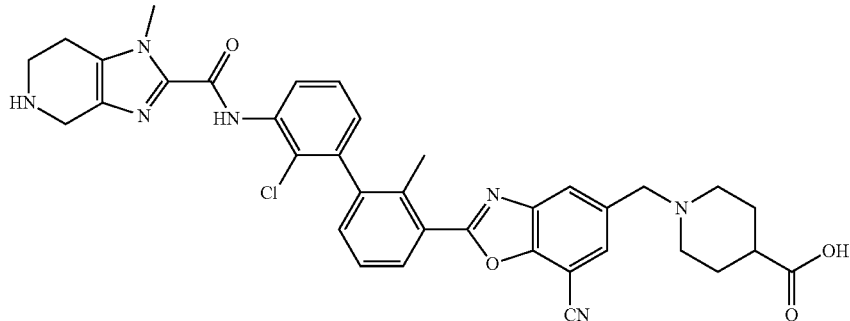 [SMILES: Cc1c(-c2nc3cc(CN4CCC(C(=O)O)CC4)cc(C#N)c3o2)cccc1-c1cccc(NC(=O)c2nc3c(n2C)CCNC3)c1Cl]

To a solution of tert-butyl 2-(2-chloro-3'-(7-cyano-5-formylbenzo[d]oxazol-2-yl)-2'-methylbiphenyl-3-ylcarbamoyl)-1-methyl-6,7-dihydro-1H-imidazo[4,5-c]pyridine-5 (4H)-carboxylate (Example 92, Step 3: 40 mg, 0.061 mmol) in DCM (2 mL) was added piperidine-4-carboxylic acid (11.9 mg, 0.092 mmol) and TEA (17.1 µl, 0.123 mmol). The mixture was stirred at r.t. for 60 min. Then sodium triacetoxyborohydride (19.5 mg, 0.092 mmol) was added. The resulting mixture was stirred at r.t. overnight before 1 mL of TFA was added. The reaction mixture was further stirred for 1 h. The reaction mixture was then concentrated and purified via prep-HPLC (pH=2, MeCN/water with TFA) to give the desired product as the TFA salt. LC-MS calculated for $C_{36}H_{35}ClN_7O_4(M+H)^+$: m/z=664.2; found 664.2.

Example 155

(R)-1-((2-(2'-chloro-3'-(5-(2-hydroxypropyl)-1-methyl-4,5,6,7-tetrahydro-1H-imidazo[4,5-c]pyridine-2-carboxamido)-2-methylbiphenyl-3-yl)-7-cyanobenzo[d]oxazol-5-yl)methyl)piperidine-4-carboxylic acid

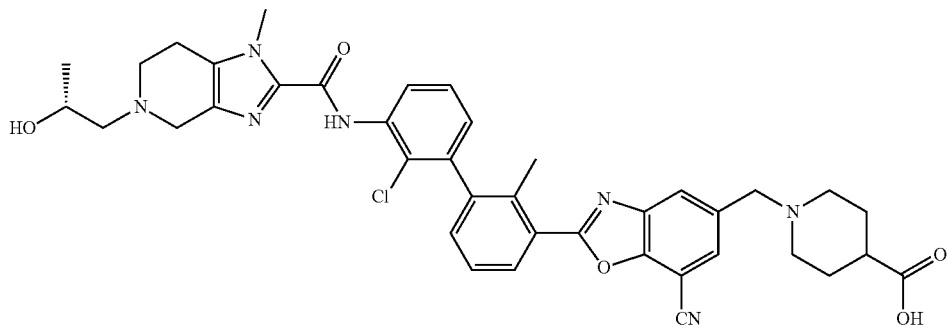 [SMILES: Cc1c(-c2nc3cc(CN4CCC(C(=O)O)CC4)cc(C#N)c3o2)cccc1-c1cccc(NC(=O)c2nc3c(n2C)CCN(C[C@@H](C)O)C3)c1Cl]

A solution of 1-((2-(2'-chloro-2-methyl-3'-(1-methyl-4,5,6,7-tetrahydro-1H-imidazo[4,5-c]pyridine-2-carboxamido)biphenyl-3-yl)-7-cyanobenzo[d]oxazol-5-yl)methyl)piperidine-4-carboxylic acid, 3TFA (Example 154: 20 mg, 20 mmol), (R)-2-((tert-butyldimethylsilyl)oxy)propanal (11.6 mg, 0.062 mmol) and Hünig's base (10.8 µL, 0.062 mmol) in THF (0.5 mL) was stirred at room temperature for 1 h. Sodium triacetoxyborohydride (13.0 mg, 0.062 mmol) was added. After being stirred at room temperature for 2 h, 2 N HCl aqueous solution (0.2 mL) was added, and the reaction was stirred at 50° C. for 30 min. The reaction mixture was diluted with acetonitrile, and purified via pH 2 preparative HPLC (MeCN/water with TFA) to give the desired product as TFA salt. LC-MS calculated for $C_{39}H_{41}ClN_7O_5(M+H)^+$: m/z=722.3; found 722.3.

TABLE 1

| Ex. No. | Name/¹HNMR | Structure | LCMS [M + H] |
|---|---|---|---|
| 156 | 1-((2-(2'-chloro-3'-(5-(2-hydroxyethyl)-1-methyl-4,5,6,7-tetrahydro-1H-imidazo[4,5-c]pyridine-2-carboxamido)-2-methylbiphenyl-3-yl)-7-cyanobenzo[d]oxazol-5-yl)methyl)piperidine-4-carboxylic acid | 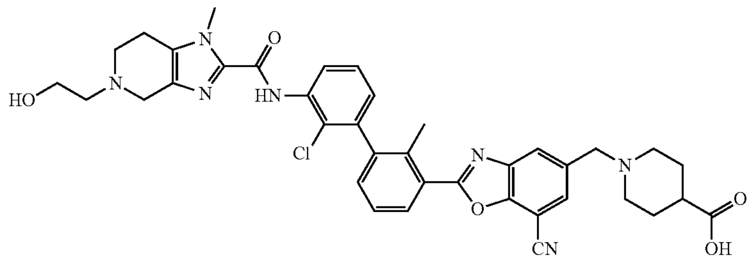 [SMILES: Cc1c(-c2nc3cc(CN4CCC(C(=O)O)CC4)cc(C#N)c3o2)cccc1-c1cccc(NC(=O)c2nc3c(n2C)CCN(CCO)C3)c1Cl] | 708.3 |
| 157 | (R)-1-((2-(2'-chloro-3'-(5-((R)-2-hydroxypropyl)-1-methyl-4,5,6,7-tetrahydro-1H-imidazo[4,5-c]pyridine-2-carboxamido)-2-methylbiphenyl-3-yl)-7-cyanobenzo[d]oxazol-5-yl)methyl)-3-methylpyrrolidine-3-carboxylic acid ¹H NMR (600 MHz, DMSO) δ 9.97 (s, 1H), 8.41 (s, 1H), 8.29 (s, 1H), 8.23 (d, J = 9.1 Hz, 1H), 8.15 (s, 1H), 7.61 (t, J = 1.8 Hz, 1H), 7.55 (t, J = 1.8 Hz, 1H), 7.50 (dd, J = 6.6, 1.2 Hz, 1H), 7.22 (dd, J = 7.2, 1.8 Hz, 1H), 5.53 (br, s, 1H), 4.59 (br, 2H), 4.52-4.26 (m, 2H), 4.18 (br, s, 1H), 3.96 (s, 3H), 3.94-2.96 (m, 10H), 2.54-2.48 (s, 3H), 2.03-1.86 (m, 2H), 1.41-1.34 (m, 3H), 1.15 (d, J = 6 Hz, 3H). | 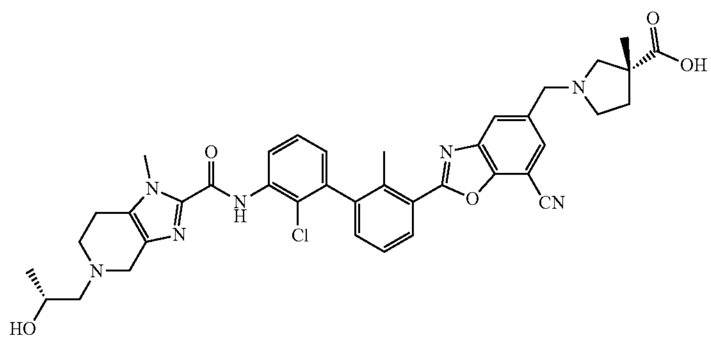 [SMILES: Cc1c(-c2nc3cc(CN4CC[C@@](C)(C(=O)O)C4)cc(C#N)c3o2)cccc1-c1cccc(NC(=O)c2nc3c(n2C)CCN(C[C@@H](C)O)C3)c1Cl] | 722.3 |

The compounds in Table 1 were prepared in accordance with the synthetic protocols set forth in Example 154 and 155, using the appropriate starting materials.

Example 158

(R)-1-((2-(2'-chloro-3'-(1,5-dimethyl-1,4,5,6-tetrahydropyrrolo[3,4-d]imidazole-2-carboxamido)-2-methylbiphenyl-3-yl)-7-cyanobenzo[d]oxazol-5-yl)methyl)-3-methyl pyrrolidine-3-carboxylic acid

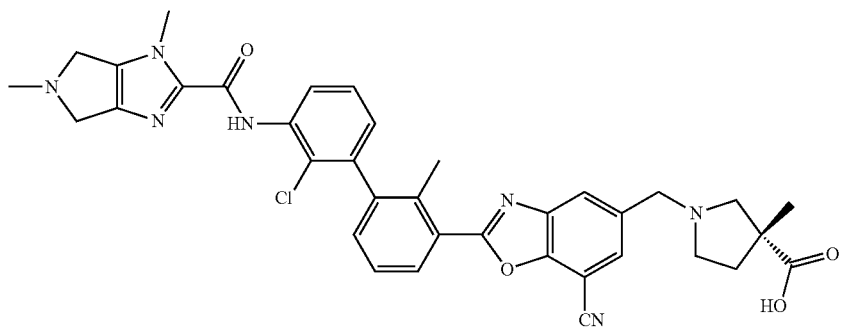 [SMILES: Cc1c(-c2nc3cc(CN4CC[C@@](C)(C(=O)O)C4)cc(C#N)c3o2)cccc1-c1cccc(NC(=O)c2nc3c(n2C)CN(C)C3)c1Cl]

Step 1: (R)-1-((2-(2'-chloro-2-methyl-3'-(1-methyl-1,4,5,6-tetrahydropyrrolo[3,4-d]imidazole-2-carboxamido)biphenyl-3-yl)-7-cyanobenzo[d]oxazol-5-yl)methyl)-3-methylpyrrolidine-3-carboxylic acid

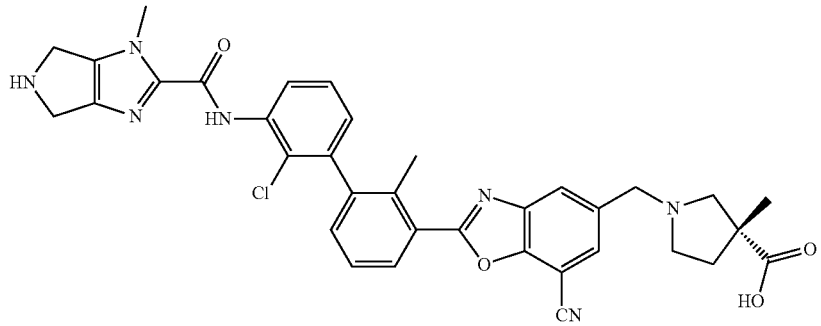 [SMILES: Cc1c(-c2nc3cc(CN4CC[C@@](C)(C(=O)O)C4)cc(C#N)c3o2)cccc1-c1cccc(NC(=O)c2nc3c(n2C)CNC3)c1Cl]

To a solution of tert-butyl 2-(2-chloro-3'-(7-cyano-5-formylbenzo[d]oxazol-2-yl)-2'-methylbiphenyl-3-ylcarbamoyl)-1-methyl-4,6-dihydropyrrolo[3,4-d]imidazole-5(1H)-carboxylate (Example 94, Step 6: 20 mg, 0.031 mmol) in DCM (1 mL) was added (R)-3-methyl pyrrolidine-3-carboxylic acid (8.0 mg, 0.062 mmol) and TEA (17.13 μl, 0.123 mmol). The mixture was stirred at r.t. for 60 min, then sodium triacetoxyborohydride (19.5 mg, 0.092 mmol) was added. The resulting mixture was stirred at r.t. overnight before 1 mL of TFA was added. The reaction mixture was further stirred for 1 h. The reaction mixture was then quenched with sat. NaHCO₃ and extracted with chloroform/isopropanol (3/1 volume ratio). The combined organic layers were washed with brine, dried over Na₂SO₄, filtered and concentrated then used in next step without further purification. LC-MS calculated for $C_{35}H_{33}ClN_7O_4(M+H)^+$: m/z=650.2; found 650.2.

Step 2: (R)-1-((2-(2'-chloro-3'-(1,5-dimethyl-1,4,5,6-tetrahydropyrrolo[3,4-d]imidazole-2-carboxamido)-2-methylbiphenyl-3-yl)-7-cyanobenzo[d]oxazol-5-yl)methyl)-3-methylpyrrolidine-3-carboxylic acid Sodium triacetoxyborohydride (12.7 mg, 0.06 mmol) was added to a solution of (R)-1-((2-(2'-chloro-2-methyl-3'-(1-methyl-1,4,5,6-tetrahydropyrrolo[3,4-d]imidazole-2-carboxamido) biphenyl-3-yl)-7-cyanobenzo[d]oxazol-5-yl) methyl)-3-methylpyrrolidine-3-carboxylic acid (10 mg, 0.015 mmol) and 37 wt. % formaldehyde in water (4.5 μL, 0.06 mmol) in DCM (0.5 mL). The reaction mixture was stirred at room temperature for 1 h, then concentrated and purified via pH 2 preparative HPLC (MeCN/water with TFA) to give the desired product as TFA salt. LC-MS calculated for $C_{36}H_{35}ClN_7O_4(M+H)^+$: m/z=664.2; found 664.2.

Example 159

(3R)-1-((2-(2'-chloro-3'-(1,6-dimethyl-4,5,6,7-tetrahydro-H-imidazo[4,5-c]pyridine-2-carboxamido)-2-methylbiphenyl-3-yl)-7-cyanobenzo[d]oxazol-5-yl)methyl)pyrrolidine-3-carboxylic acid

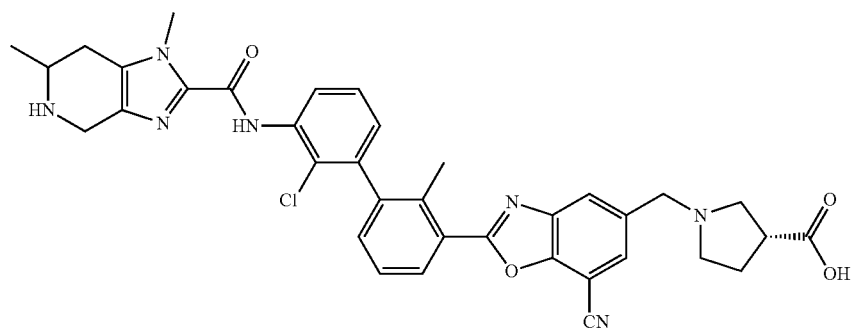 [SMILES: Cc1c(-c2nc3cc(CN4CC[C@@H](C(=O)O)C4)cc(C#N)c3o2)cccc1-c1cccc(NC(=O)c2nc3c(n2C)CC(C)NC3)c1Cl]

Step 1: tert-butyl 6-methyl-6,7-dihydro-1H-imidazo[4,5-c]pyridine-5(4H)-carboxylate

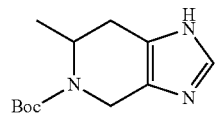

To a stirred solution of (R)-1-(1H-imidazol-5-yl)propan-2-amine HCl salt (J&W PharmLab, Cat #40R0144: 500 mg, 2.94 mmol) in ethanol (5.0 ml) and water (5.0 mL) was added formaldehyde (37 wt. % in water, 0.36 mL). The resulted mixture was heated to reflux for 4 hrs. The reaction was concentrated under reduced pressure. The residue was dissolved in DCM (10 mL) and MeOH (10 mL). Di-tert-butyl dicarbonate (2.2 g, 10.21 mmol) and triethylamine (1.56 mL, 11.23 mmol) were added, and the resulting solution was stirred at rt. for 1 hr before concentrated under reduced pressure. The residue was then dissolved in 7N NH$_3$ in MeOH and heated at 70° C. for 6 hrs. The reaction was finally concentrated under reduced pressure and purified by flash chromatography on a silica gel column eluting with 0 to 20% MeOH in DCM to afford the racemic product. LC-MS calculated for $C_{12}H_{20}N_3O_2$ (M+H)$^+$: m/z=238.2; found 238.2.

Step 2: tert-butyl 1,6-dimethyl-6,7-dihydro-1H-imidazo[4,5-c]pyridine-5(4H)-carboxylate

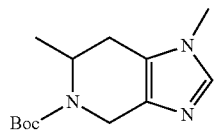 [SMILES: CC1Cc2c(ncn2C)CN1C(=O)OC(C)(C)C]

Potassium bis(trimethylsilyl)amide (1.0 M in THF, 1.01 mL) was added to a solution of tert-butyl 6-methyl-1,4,6,7-tetrahydro-5H-imidazo[4,5-c]pyridine-5-carboxylate (200 mg, 0.843 mmol) in THF (4.2 mL) at −20° C. After stirring for 30 min, methyl iodide (63.2 µl, 1.011 mmol) was added and the mixture was allowed to warm slowly to r.t. The mixture was continued to stir at this temperature for 1 h. The reaction mixture was then quenched with sat. NaHCO$_3$ solution and extracted with DCM. The combined organic layers were washed with brine, dried over Na$_2$SO$_4$, filtered and concentrated and used in next step without further purification. LC-MS calculated for $C_{13}H_{22}N_3O_2$ (M+H)$^+$: m/z=252.2; found 252.2.

Step 3: 5-tert-butyl 2-methyl 1,6-dimethyl-6,7-dihydro-1H-imidazo[4,5-c]pyridine-2,5(4H)-dicarboxylate

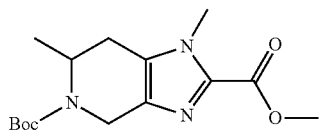

n-Butyl lithium (2.5 M in hexanes, 522 µl) was added to a cold (−78° C.) solution of tert-butyl-1,6-dimethyl-1,4,6,7-tetrahydro-5H-imidazo[4,5-c]pyridine-5-carboxylate (210 mg, 0.836 mmol) in THF (6 mL). The reaction mixture was stirred at −78° C. for 10 min prior to the addition of methyl chloroformate (162 µL, 2.09 mmol). After being stirred at −78° C. for 30 min, the reaction was then quenched with saturated aqueous NaHCO$_3$ solution, and extracted with ethyl acetate, dried over Na$_2$SO$_4$, filtered, and concentrated under reduced pressure. The residue was purified by flash chromatography on a silica gel column eluting with 100% ethyl acetate in hexanes to afford the desired product. LC-MS calculated for $C_{15}H_{24}N_3O_4$ (M+H)$^+$: m/z=310.2; found 310.2.

Step 4: tert-butyl 2-(3-bromo-2-chlorophenylcarbamoyl)-1,6-dimethyl-6,7-dihydro-1H-imidazo[4,5-c]pyridine-5(4H)-carboxylate

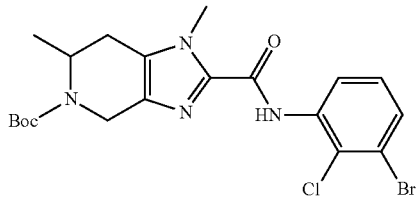 [SMILES: CC1Cc2c(nc(C(=O)Nc3cccc(Br)c3Cl)n2C)CN1C(=O)OC(C)(C)C]

Potassium tert-butoxide (1.0 M in THF, 0.36 mL) was added to a solution of 5-(tert-butyl) 2-methyl-1,6-dimethyl-1,4,6,7-tetrahydro-5H-imidazo[4,5-c]pyridine-2,5-dicarboxylate (56.0 mg, 0.181 mmol) and 3-bromo-2-chloroaniline (44.8 mg, 0.217 mmol) in tetrahydrofuran (6.0 mL). After being stirred at room temperature for 1 hr, the reaction mixture was quenched with water, and extracted with ethyl acetate. The combined organic layers were washed with brine, dried over Na$_2$SO$_4$, filtered, and concentrated under reduced pressure. The residue was purified by flash chromatography on a silica gel column eluting with 50% ethyl acetate in hexanes to afford the desired product. LCMS calculated for $C_{20}H_{25}BrClN_4O_3$(M+H)$^+$: m/z=483.1; found 483.1.

Step 5: tert-butyl 2-(2-chloro-3'-(7-cyano-5-(hydroxymethyl)benzo[d]oxazol-2-yl)-2'-methylbiphenyl-3-ylcarbamoyl)-1,6-dimethyl-6,7-dihydro-1H-imidazo[4,5-c]pyridine-5(4H)-carboxylate

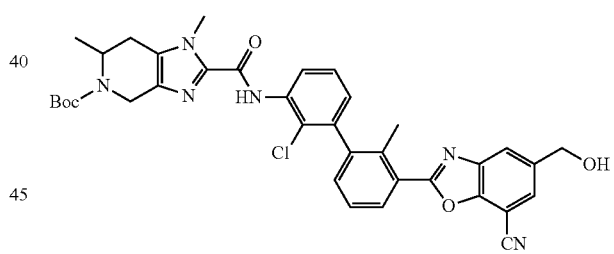

A mixture of tert-butyl-2-((3-bromo-2-chlorophenyl)carbamoyl)-1,6-dimethyl-1,4,6,7-tetrahydro-5H-imidazo[4,5-c]pyridine-5-carboxylate (78 mg, 0.161 mmol), 5-(hydroxymethyl)-2-(2-methyl-3-(4,4,5,5-tetramethyl-1,3,2-dioxaborolan-2-yl)phenyl)benzo[d]oxazole-7-carbonitrile (Example 54, Step 2: 70.0 mg, 0.18 mmol), and dichloro[1,1'-bis(dicyclohexyl phosphino)ferrocene]palladium(II) (13 mg, 0.002 mmol) in 1,4-dioxane (2 mL) and water (0.4 mL) was added cesium carbonate (38 mg, 0.36 mmol). The reaction mixture was purged with nitrogen and then stirred at 100° C. for 12 hrs. After being cooled to room temperature, the reaction mixture was extracted with ethyl acetate. The combined organic layers were washed with brine, dried over Na$_2$SO$_4$, filtered and concentrated under reduced pressure. The residue was purified by flash chromatography on a silica gel column eluting with 0 to 100% EtOAc in hexanes to afford the desired product. LC-MS calculated for $C_{36}H_{36}ClN_6O_5$(M+H)$^+$: m/z=667.2; found 667.2.

Step 6: tert-butyl 2-(2-chloro-3'-(7-cyano-5-formyl-benzo[d]oxazol-2-yl)-2'-methylbiphenyl-3-ylcarbamoyl)-1,6-dimethyl-6,7-dihydro-1H-imidazo[4,5-c]pyridine-5(4H)-carboxylate

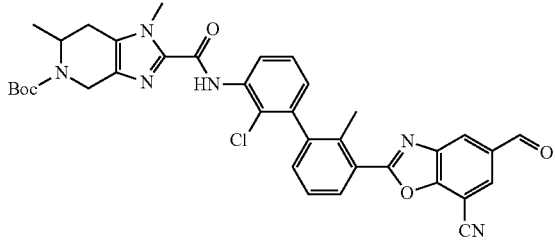 [SMILES: Cc1c(-c2nc3cc(C=O)cc(C#N)c3o2)cccc1-c1cccc(NC(=O)c2nc3c(n2C)CC(C)N(C(=O)OC(C)(C)C)C3)c1Cl]

To a stirred solution of tert-butyl 2-(2-chloro-3'-(7-cyano-5-(hydroxymethyl)benzo[d]oxazol-2-yl)-2'-methylbiphenyl-3-ylcarbamoyl)-1,6-dimethyl-6,7-dihydro-1H-imidazo[4,5-c]pyridine-5(4H)-carboxylate (50 mg, 0.11 mmol) in DCM (5.0 ml) was added $MnO_2$ (215 mg, 2.5 mmol). The resulted mixture was stirred at 45° C. for 2 hrs, then filtered. The filtrate was concentrated under reduced pressure. The residue was used in the next step directly without further purification. LC-MS calculated for $C_{36}H_{34}ClN_6O_5$ $(M+H)^+$: m/z=665.2; found 665.2.

Step 7: (3R)-1-((2-(2'-chloro-3'-(1,6-dimethyl-4,5,6,7-tetrahydro-1H-imidazo[4,5-c]pyridine-2-carboxamido)-2-methylbiphenyl-3-yl)-7-cyanobenzo[d]oxazol-5-yl)methyl)pyrrolidine-3-carboxylic acid To a solution of tert-butyl 2-(2-chloro-3'-(7-cyano-5-formylbenzo[d]oxazol-2-yl)-2'-methylbiphenyl-3-ylcarbamoyl)-1,6-dimethyl-6,7-dihydro-1H-imidazo[4,5-c]pyridine-5 (4H)-carboxylate (12 mg, 0.015 mmol) in DCM (0.5 mL) was added (R)-pyrrolidine-3-carboxylic acid (4.0 mg, 0.032 mmol) and TEA (8.6 µl, 0.07 mmol). The mixture was stirred at r.t. for 60 min. Sodium triacetoxyborohydride (9.8 mg, 0.046 mmol) was then added. The resulting mixture was stirred at r.t. overnight before 1 mL of TFA was added. The reaction mixture was further stirred for 1 hr and concentrated under reduced pressure. The residue was dissolved in MeOH, and purified via pH 2 preparative HPLC (MeCN/water with TFA) to give the desired product as TFA salt. LC-MS calculated for $C_{36}H_{35}ClN_7O_4(M+H)^+$: m/z=664.2; found 664.2.

Example 160

(3R)-1-((2-(2'-chloro-2-methyl-3'-(1,5,6-trimethyl-4,5,6,7-tetrahydro-1H-imidazo[4,5-c]pyridine-2-carboxamido)biphenyl-3-yl)-7-cyanobenzo[d]oxazol-5-yl)methyl)pyrrolidine-3-carboxylic acid

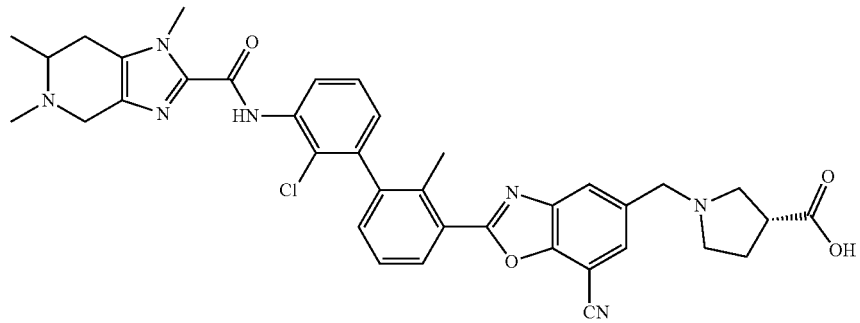 [SMILES: Cc1c(-c2nc3cc(CN4CC[C@@H](C(=O)O)C4)cc(C#N)c3o2)cccc1-c1cccc(NC(=O)c2nc3c(n2C)CC(C)N(C)C3)c1Cl]

Sodium triacetoxyborohydride (11.2 mg, 0.05 mmol) was added to a solution of (3R)-1-((2-(2'-chloro-3'-(1,6-dimethyl-4,5,6,7-tetrahydro-1H-imidazo[4,5-c]pyridine-2-carboxamido)-2-methylbiphenyl-3-yl)-7-cyanobenzo[d]oxazol-5-yl)methyl)pyrrolidine-3-carboxylic acid (Example 159, Step 7: 10 mg, 0.015 mmol) and 37 wt. % formaldehyde in water (4.5 µL, 0.06 mmol) in DCM (0.5 mL). The reaction mixture was stirred at room temperature for 1 h, then concentrated and purified via pH 2 preparative HPLC (MeCN/water with TFA) to give the desired product as TFA salt. LC-MS calculated for $C_{37}H_{37}ClN_7O_4$ $(M+H)^+$: m/z=678.2; found 678.2.

TABLE 2

| Ex. No. | Name | Structure | LCMS [M + H] |
|---|---|---|---|
| 161 | (3R)-1-((2-(2'-chloro-2-methyl-3'-(1,5,6-trimethyl-4,5,6,7-tetrahydro-1H-imidazo[4,5-c]pyridine-2-carboxamido)biphenyl-3-yl)-7-cyanobenzo[d]oxazol-5-yl)methyl)-3-methylpyrrolidine-3-carboxylic acid | 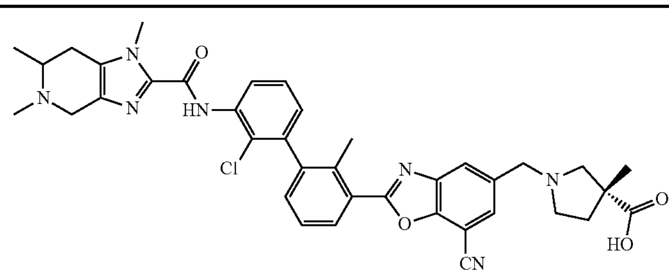 | 692.2 |

TABLE 2-continued

| Ex. No. | Name | Structure | LCMS [M + H] |
|---|---|---|---|
| 162 | 1-((2-(2'-chloro-2-methyl-3'-(1,5,6-trimethyl-4,5,6,7-tetrahydro-1H-imidazo[4,5-c]pyridine-2-carboxamido)biphenyl-3-yl)-7-cyanobenzo[d]oxazol-5-yl)methyl)piperidine-4-carboxylic acid | 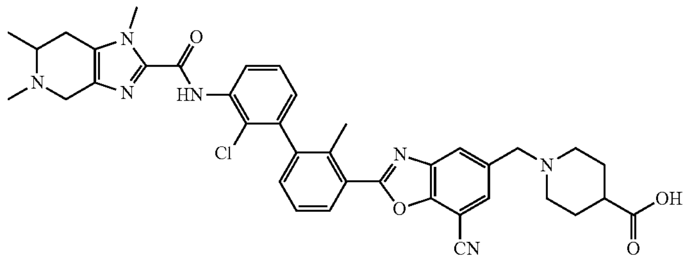 [SMILES: Cc1c(-c2nc3cc(CN4CCC(C(=O)O)CC4)cc(C#N)c3o2)cccc1-c1cccc(NC(=O)c2nc3c(n2C)CC(C)N(C)C3)c1Cl] | 692.2 |
| 163 | (3R)-1-((2-(2'-chloro-3'-(1,6-dimethyl-4,5,6,7-tetrahydro-1H-imidazo[4,5-c]pyridine-2-carboxamido)-2-methyl biphenyl-3-yl)-7-cyanobenzo[d]oxazol-5-yl)methyl)-3-methylpyrrolidine-3-carboxylic acid | 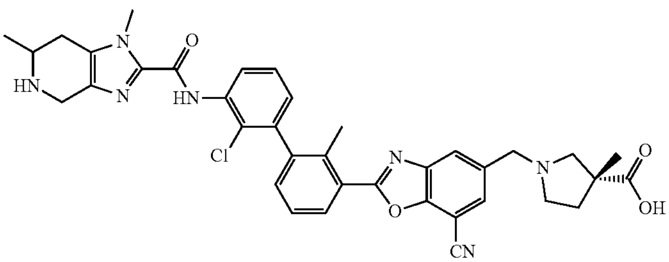 [SMILES: Cc1c(-c2nc3cc(CN4CC[C@@](C)(C(=O)O)C4)cc(C#N)c3o2)cccc1-c1cccc(NC(=O)c2nc3c(n2C)CC(C)NC3)c1Cl] | 678.3 |
| 164 | 1-((2-(2'-chloro-3'-(1,6-dimethyl-4,5,6,7-tetrahydro-1H-imidazo[4,5-c]pyridine-2-carboxamido)-2-methylbiphenyl-3-yl)-7-cyanobenzo[d]oxazol-5-yl)methyl)piperidine-4-carboxylic acid | 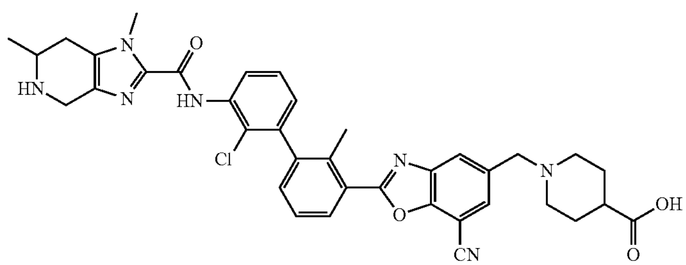 | 678.3 |

The compounds in Table 2 were prepared in accordance with the synthetic protocols set forth in Example 159 and 160, using the appropriate starting materials.

Example 165

2-(2-chloro-3'-(7-cyano-5-(((R)-3-hydroxypyrrolidin-1-yl)methyl)benzo[d]oxazol-2-yl)-2'-methylbiphenyl-3-ylcarbamoyl)-1,5,6-trimethyl-4,5,6,7-tetrahydro-1H-imidazo[4,5-c]pyridine-6-carboxylic acid

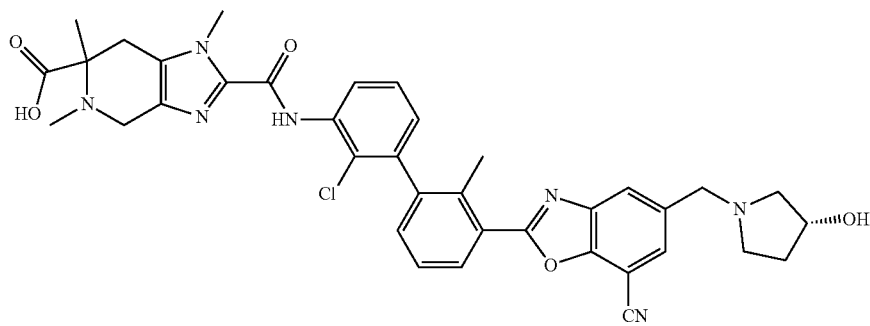 [SMILES: Cc1c(-c2nc3cc(CN4CC[C@@H](O)C4)cc(C#N)c3o2)cccc1-c1cccc(NC(=O)c2nc3c(n2C)CC(C)(C(=O)O)N(C)C3)c1Cl]

Step 1: 5-tert-butyl 6-methyl 1-methyl-6,7-dihydro-1H-imidazo[4,5-c]pyridine-5,6(4H)-dicarboxylate

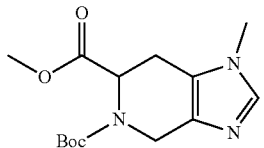 [SMILES: COC(=O)C1Cc2c(ncn2C)CN1C(=O)OC(C)(C)C]

To a stirred solution of (S)-2-amino-3-(1-methyl-1H-imidazol-5-yl)propanoic acid (500 mg, 2.06 mmol) in ethanol (5.0 ml) and water (5.0 mL) was added formaldehyde (37 wt. % in water, 0.36 ml). The resulted mixture was heated to reflux for 4 h. The reaction was concentrated under reduced pressure. The residue was dissolved MeOH (10 mL), and $SOCl_2$ (0.40 ml, 5.5 mmol) was slowly added to the above solution at 0° C. After addition, the resulting mixture was heated to reflux for 12 hrs before quenched with sat. $NaHCO_3$ solution. The mixture was then extracted with extracted with chloroform/isopropanol (3:1 volume ratio). The combined organic layers were washed with brine, dried over $Na_2SO_4$, filtered and concentrated under reduced pressure. The residue was then dissolved in DCM (10 mL), followed by adding di-tert-butyl dicarbonate (1.2 g, 5.52 mmol) and triethylamine (0.77 mL, 5.52 mmol). The resulting solution was stirred at rt. for 1 hr before concentrated and purified by flash chromatography on a silica gel column eluting with 0 to 100% EtOAc in hexanes to afford the racemic product. LC-MS calculated for $C_{14}H_{22}N_3O_4$ $(M+H)^+$: m/z=296.2; found 296.2.

Step 2: 5-tert-butyl 6-methyl 1,6-dimethyl-6,7-dihydro-1H-imidazo[4,5-c]pyridine-5,6(4H)-dicarboxylate

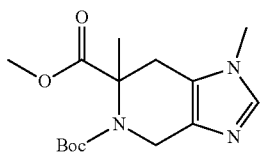 [SMILES: COC(=O)C1(C)Cc2c(ncn2C)CN1C(=O)OC(C)(C)C]

Potassium bis(trimethylsilyl)amide (1.0 M in THF, 0.37 mL, 0.37 mmol) was added to a solution of 5-tert-butyl 6-methyl 1-methyl-6,7-dihydro-1H-imidazo[4,5-c]pyridine-5,6(4H)-dicarboxylate (110 mg, 0.37 mmol) in THF (4 mL) at −20° C. After stirring for 30 min, methyl iodide (35 μl, 0.56 mmol) was added and the mixture was allowed to warm slowly to r.t. The reaction was continued to stir at this temperature for 1 h. The reaction mixture was then quenched with sat. $NaHCO_3$ aqueous solution and extracted with DCM. The combined organic layers were washed with brine, dried over $Na_2SO_4$, filtered and concentrated and used in next step without further purification. LC-MS calculated for $C_{15}H_{24}N_3O_4$ $(M+H)^+$: m/z=310.2; found 310.2.

Step 3: 5-tert-butyl 2,6-dimethyl 1,6-dimethyl-6,7-dihydro-1H-imidazo[4,5-c]pyridine-2,5,6(4H)-tricarboxylate

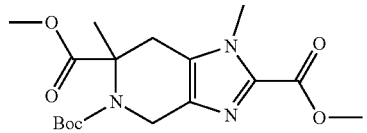

LDA (1.0 M in THF, 550 μl) was added to a cold (−78° C.) solution of 5-tert-butyl 6-methyl 1,6-dimethyl-6,7-dihydro-1H-imidazo[4,5-c]pyridine-5,6(4H)-dicarboxylate (170 mg, 0.55 mmol) in tetrahydrofuran (4 mL). The reaction mixture was stirred at −78° C. for 20 min prior to the addition of methyl chloroformate (106 μL, 1.37 mmol). After being stirred at −78° C. for 30 min, the reaction was then quenched with saturated aqueous $NaHCO_3$ solution, and extracted with ethyl acetate, dried over $Na_2SO_4$, filtered, and concentrated under reduced pressure. The residue was purified by flash chromatography on a silica gel column eluting with 100% ethyl acetate in hexanes to afford the desired product. LC-MS calculated for $C_{17}H_{26}N_3O_6$ $(M+H)^+$: m/z=368.2; found 368.2.

Step 4: 5-tert-butyl 6-methyl 2-(3-bromo-2-chlorophenylcarbamoyl)-1,6-dimethyl-6,7-dihydro-1H-imidazo[4,5-c]pyridine-5,6(4H)-dicarboxylate

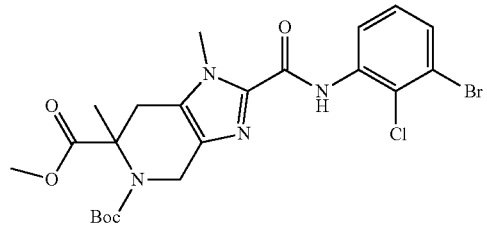 [SMILES: COC(=O)C1(C)Cc2c(nc(C(=O)Nc3cccc(Br)c3Cl)n2C)CN1C(=O)OC(C)(C)C]

Potassium tert-butoxide (1.0 M in THF, 0.653 ml) was added to a solution of 5-tert-butyl 2,6-dimethyl 1,6-dimethyl-6,7-dihydro-1H-imidazo[4,5-c]pyridine-2,5,6(4H)-tricarboxylate (120 mg, 0.327 mmol) and 3-bromo-2-chloroaniline (101 mg, 0.490 mmol) in tetrahydrofuran (6.0 mL). After being stirred at room temperature for 1 h, the reaction mixture was quenched with water, and extracted with ethyl acetate. The combined organic layers were washed with brine, dried over $Na_2SO_4$, filtered, and concentrated under reduced pressure. The residue was purified by flash chromatography on a silica gel column eluting with 0 to 100% ethyl acetate in hexanes to afford the desired product. LCMS calculated for $C_{22}H_{27}BrClN_4O_5$ $(M+H)^+$: m/z=541.1; found 541.1.

Step 5: 2-(3-bromo-2-chlorophenylcarbamoyl)-1,5,6-trimethyl-4,5,6,7-tetrahydro-1H-imidazo[4,5-c]pyridine-6-carboxylic acid

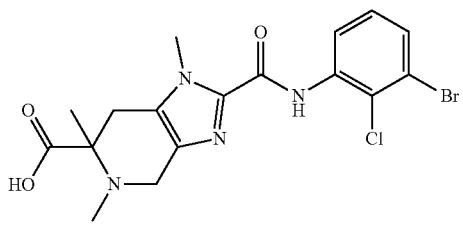 [SMILES: CN1Cc2nc(C(=O)Nc3cccc(Br)c3Cl)n(C)c2CC1(C)C(=O)O]

A DCM (1 mL) solution of 5-tert-butyl 6-methyl 2-(3-bromo-2-chlorophenylcarbamoyl)-1,6-dimethyl-6,7-dihydro-1H-imidazo[4,5-c]pyridine-5,6(4H)-dicarboxylate (40 mg, 0.074 mmol) was added TFA (1 mL). The resulting mixture was stirred at r.t. for 1 h before concentrated under reduced pressure. The residue was then dissolved in dry DCM, triethylamine (20.6 μl, 0.148 mmol), 37 wt. % formaldehyde in water (11.0 μl, 0.148 mmol) and sodium triacetoxyborohydride (31.3 mg, 0.148 mmol) were added subsequently. The resulting mixture was stirred for another 1 hr before quenched with sat. NaHCO₃ solution. The mixture was then extracted with extracted with chloroform/isopropanol (3:1 volume ratio). The combined organic layers were washed with brine, dried over Na₂SO₄, filtered and concentrated under reduced pressure. The residue was then dissolved in THF/MeOH/water (1:1:1 volume ratio), LiOH (8.8 mg, 0.37 mmol) was added and the reaction was stirred at 70° C. for 5 hrs. After completion, the reaction was neutralized with 1N HCl solution and extracted with chloroform/isopropanol (3:1 volume ratio). The combined organic layers were washed with brine, dried over Na₂SO₄, filtered and concentrated under reduced pressure. The crude product was used in the next reaction without further purification. LCMS calculated for $C_{17}H_{19}BrClN_4O_3$ (M+H)⁺: m/z=441.1; found 441.1.

Step 6: 2-(2-chloro-3'-(7-cyano-5-(((R)-3-hydroxypyrrolidin-1-yl)methyl)benzo[d]oxazol-2-yl)-2'-methylbiphenyl-3-ylcarbamoyl)-1,5,6-trimethyl-4,5,6,7-tetrahydro-1H-imidazo[4,5-c]pyridine-6-carboxylic acid To a mixture of (R)-5-((3-hydroxypyrrolidin-1-yl)methyl)-2-(2-methyl-3-(4,4,5,5-tetramethyl-1,3,2-dioxaborolan-2-yl)phenyl)benzo[d]oxazole-7-carbonitrile (Example 131, Step 4: 15.0 mg, 0.033 mmol), 2-((3-bromo-2-chlorophenyl)carbamoyl)-1,5,6-trimethyl-4,5,6,7-tetrahydro-1H-imidazo[4,5-c]pyridine-6-carboxylic acid (12.0 mg, 0.027 mmol), and dichloro[1,1'-bis(dicyclohexylphosphino)ferrocene]palladium(II) (2.1 mg, 0.003 mmol) in 1,4-dioxane (1 mL) and water (0.2 mL) was added sodium carbonate (6 mg, 0.054 mmol). The reaction mixture was purged with nitrogen and then stirred at 100° C. for 12 hrs. After being cooled to room temperature, the reaction mixture was extracted with ethyl acetate. The combined organic layers were washed with brine, dried over Na₂SO₄, filtered and concentrated under reduced pressure. The residue was dissolved in MeOH, and purified via pH 2 preparative HPLC (MeCN/water with TFA) to give the desired product as TFA salt. LC-MS calculated for $C_{37}H_{37}ClN_7O_5$(M+H)⁺: m/z=694.2; found 694.2.

Example 166

(R)-1-((7-cyano-2-(3'-(3-(4,5-dihydro-1H-imidazol-2-yl)-1,7-naphthyridin-8-ylamino)-2,2'-dimethylbiphenyl-3-yl)benzo[d]oxazol-5-yl)methyl)pyrrolidine-3-carboxylic acid

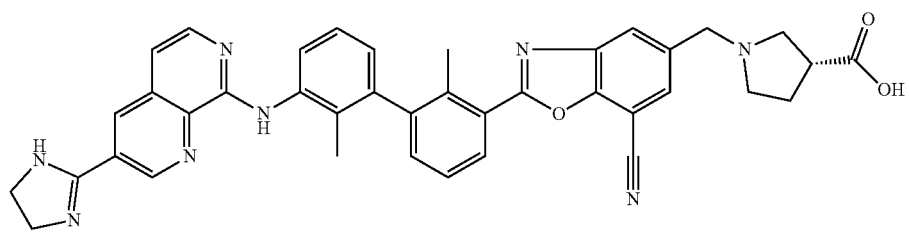 [SMILES: Cc1c(Nc2nccc3cc(C4=NCCN4)cnc23)cccc1-c1cccc(-c2nc3cc(CN4CC[C@@H](C(=O)O)C4)cc(C#N)c3o2)c1C]

Step 1: N-(3-bromo-2-methylphenyl)-3-(4,5-dihydro-1H-imidazol-2-yl)-1,7-naphthyridin-8-amine

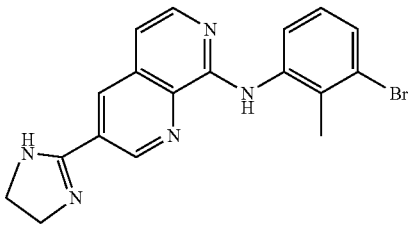 [SMILES: Cc1c(Br)cccc1Nc1nccc2cc(C3=NCCN3)cnc12]

To a suspension of 8-((3-bromo-2-methylphenyl)amino)-1,7-naphthyridine-3-carbaldehyde (Example 16, Step 3: 146 mg, 0.427 mmol) in tert-butanol (4.3 ml) was added ethane-1,2-diamine (28.2 mg, 0.469 mmol). The mixture was stirred at r.t. under N₂ atmosphere for 30 min, and then hypochlorous acid tert-butyl ester (57.7 μl, 0.512 mmol) was added, and the mixture was stirred at 50° C. After 2 h, the mixture was quenched with sat. aq Na₂SO₃ (10 mL) and was extracted with DCM (3×10 mL). The organic layer was washed with sat. aq Na₂CO₃ and brine, and dried over Na₂SO₄. After filtration, the mixture was evaporated. The product was purified by flash column chromatography. LCMS calculated for $C_{18}H_{17}BrN_5$ (M+H)⁺: m/z=382.1, 384.1; found 382.1, 384.1.

Step 2: 2-(3'-(3-(4,5-dihydro-1H-imidazol-2-yl)-1,7-naphthyridin-8-ylamino)-2,2'-dimethylbiphenyl-3-yl)-5-formylbenzo[d]oxazole-7-carbonitrile

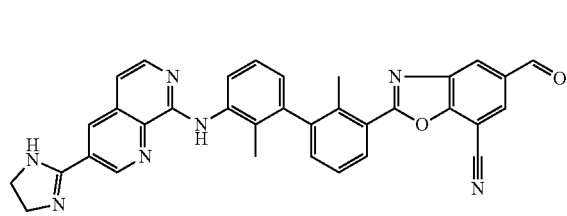 [SMILES: Cc1c(Nc2nccc3cc(C4=NCCN4)cnc23)cccc1-c1cccc(-c2nc3cc(C=O)cc(C#N)c3o2)c1C]

A mixture of N-(3-bromo-2-methylphenyl)-3-(4,5-dihydro-1H-imidazol-2-yl)-1,7-naphthyridin-8-amine (26 mg, 0.068 mmol), 5-formyl-2-(2-methyl-3-(4,4,5,5-tetramethyl-1,3,2-dioxaborolan-2-yl)phenyl)benzo[d]oxazole-7-carbonitrile (Example 138, Step 1: 34 mg, 0.088 mmol), tetrakis(triphenylphosphine)palladium(0) (7.86 mg, 6.80 μmol) and sodium carbonate (18.0 mg, 0.170 mmol) in water (76 μl) and dioxane (378 μl) was purged with $N_2$ and then stirred at 100° C. for 5 h. The reaction was cooled to room temperature. The reaction mixture was diluted with DCM and $H_2O$. The layers were separated. The aqueous layer was extracted with DCM three times. The organic layer was dried over $MgSO_4$, filtered and concentrated to give a crude residue, which was purified by flash chromatography on a silica gel column eluting with 0 to 14% MeOH/DCM to give the desired product. LC-MS calculated for $C_{34}H_{26}N_7O_2$ (M+H)$^+$: m/z=564.2; found 564.2.

Step 3: (R)-1-((7-cyano-2-(3'-(3-(4,5-dihydro-1H-imidazol-2-yl)-1,7-naphthyridin-8-ylamino)-2,2'-dimethylbiphenyl-3-yl)benzo[d]oxazol-5-yl)methyl)pyrrolidine-3-carboxylic acid This compound was prepared using similar procedure as described in Step 5, Example 24 with 2-(3'-(3-(4,5-dihydro-1H-imidazol-2-yl)-1,7-naphthyridin-8-ylamino)-2,2'-dimethylbiphenyl-3-yl)-5-formylbenzo[d]oxazole-7-carbonitrile replacing (R)-5-formyl-2-(3'-(3-((3-hydroxypyrrolidin-1-yl)methyl)-1,7-naphthyridin-8-ylamino)-2,2'-dimethylbiphenyl-3-yl)benzo[d]oxazole-7-carbonitrile. The reaction was diluted with MeOH and then purified by prep-HPLC (pH=2, acetonitrile/water+TFA) to give the desired product as the TFA salt. LC-MS calculated for $C_{39}H_{35}N_8O_3$ (M+H)$^+$: m/z=663.3; found 663.3.

Example 167

(R)-1-((7-cyano-2-(3'-(3-(2-((R)-3-hydroxypyrrolidin-1-yl)ethyl)-1,7-naphthyridin-8-ylamino)-2,2'-dimethylbiphenyl-3-yl)benzo[d]oxazol-5-yl)methyl)pyrrolidine-3-carboxylic acid

Step 1: 2-(8-(3-bromo-2-methylphenylamino)-1,7-naphthyridin-3-yl)acetaldehyde

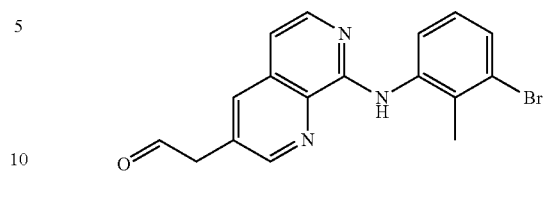

(methoxymethyl)triphenylphosphonium chloride (Aldrich #309567: 145 mg, 0.422 mmol) was dissolved in dry THF (1622 μl) under nitrogen. This solution was cooled at 0° C. and potassium tert-butoxide (1.0 M in THF, 389 μl) was added. The reaction mixture was stirred at 0° C. for 30 min. A solution of 8-((3-bromo-2-methylphenyl)amino)-1,7-naphthyridine-3-carbaldehyde (111 mg, 0.324 mmol) in dry THF was added, then the reaction mixture was warmed up to r.t. and stirred for 1 hour. The solvent was removed under reduced pressure, the residue was taken with ethyl acetate, stirred, filtered and the solid cake washed with ethyl acetate (2 times). The filtrate was evaporated under reduced pressure. To the above residue and sodium iodide (72.9 mg, 0.487 mmol) in acetonitrile (1.6 ml) was added chlorotrimethylsilane (52.9 mg, 0.487 mmol). The mixture was stirred at r.t. for 2 h.

The mixture was then filtered to remove the insoluble. The filtrate was concentrated and the residue was used directly in next step without further purification. LC-MS calculated for $C_{17}H_{15}BrN_3O$ (M+H)$^+$: m/z=356.0, 358.0; found 356.2, 358.1.

Step 2: (R)-1-(2-(8-(3-bromo-2-methylphenylamino)-1,7-naphthyridin-3-yl)ethyl)pyrrolidin-3-ol

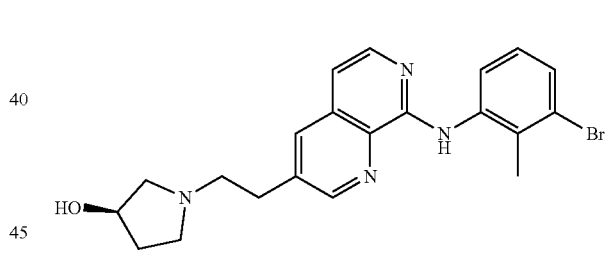

This compound was prepared using similar procedure as described in Step 1, Example 24 with 2-(8-(3-bromo-2-methylphenylamino)-1,7-naphthyridin-3-yl)acetaldehyde replacing 8-((3-bromo-2-methylphenyl)amino)-1,7-naphthyridine-3-carbaldehyde. The crude material was purified by column chromatography. LC-MS calculated for $C_{21}H_{24}BrN_4O$ (M+H)$^+$: m/z=427.1, 429.1; found 427.3, 429.3.

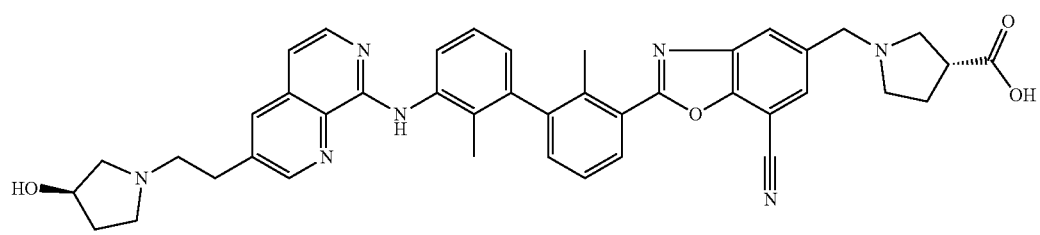 [SMILES: Cc1c(Nc2nccc3cc(CCN4CC[C@@H](O)C4)cnc23)cccc1-c1cccc(-c2nc3cc(CN4CC[C@@H](C(=O)O)C4)cc(C#N)c3o2)c1C]

Step 3: (R)-1-((7-cyano-2-(3'-(3-(2-((R)-3-hydroxy-pyrrolidin-1-yl)ethyl)-1,7-naphthyridin-8-ylamino)-2,2'-dimethylbiphenyl-3-yl)benzo[d]oxazol-5-yl)methyl)pyrrolidine-3-carboxylic acid A mixture of (R)-1-(2-(8-((3-bromo-2-methylphenyl)amino)-1,7-naphthyridin-3-yl)ethyl)pyrrolidin-3-ol (15 mg, 0.035 mmol), (R)-1-((7-cyano-2-(2-methyl-3-(4,4,5,5-tetramethyl-1,3,2-dioxaborolan-2-yl)phenyl)benzo[d]oxazol-5-yl)methyl)pyrrolidine-3-carboxylic acid (Example 126, Step 5: 18.82 mg, 0.039 mmol), sodium carbonate (9.30 mg, 0.088 mmol) and 1,1'-bis(di-cyclohexylphosphino)ferrocene palladium dichloride (2.6 mg, 3.5 µmol) in water (58 µl) and 1,4-dioxane (293 µl) was purged with $N_2$ and then stirred at 100° C. for 1 h. The reaction was cooled to room temperature. The reaction was concentrated, then diluted in MeOH, filtered then purified by prep-HPLC (pH=2, acetonitrile/water+TFA) to give the desired product as the TFA salt. LC-MS calculated for $C_{42}H_{42}N_7O_4$ $(M+H)^+$: m/z=708.3; found 708.3.

Example 168

(R)-1-((2-(2-chloro-3'-(3-(((R)-3-hydroxypyrrolidin-1-yl)methyl)-1,7-naphthyridin-8-ylamino)-2'-methylbiphenyl-3-yl)-7-cyanobenzo[d]oxazol-5-yl)methyl)pyrrolidine-3-carboxylic acid

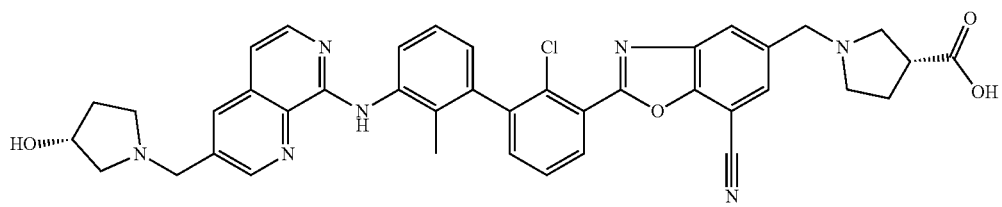 [SMILES: Cc1c(Nc2nccc3cc(CN4CC[C@@H](O)C4)cnc23)cccc1-c1cccc(-c2nc3cc(CN4CC[C@@H](C(=O)O)C4)cc(C#N)c3o2)c1Cl]

Step 1: 2-chloro-3-(7-chloro-5-(hydroxymethyl)benzo[d]oxazol-2-yl)phenylboronic acid

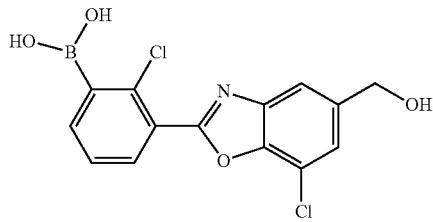 [SMILES: OCc1cc(Cl)c2oc(-c3cccc(B(O)O)c3Cl)nc2c1]

A mixture of 4,4,4',4',5,5,5',5'-octamethyl-2,2'-bi(1,3,2-dioxaborolane) (178 mg, 0.702 mmol), (2-(3-bromo-2-chlorophenyl)-7-chlorobenzo[d]oxazol-5-yl)methanol (Example 69, Step 3: 238 mg, 0.638 mmol), potassium acetate (157 mg, 1.595 mmol) and 1,1'-bis(diphenylphosphino)ferrocene-palladium(II)dichloride dichloromethane complex (52 mg, 0.064 mmol) in dioxane (4.2 ml) was purged with $N_2$ and then stirred at 90° C. for 3 h. The reaction was then cooled to r.t. The mixture was diluted with DCM, filtered through a short pad of Celite. The filtrate was concentrated and purified by column chromatography. LC-MS calculated for $C_{14}H_{11}BCl_2NO_4$ $(M+H)^+$: m/z=338.0; found 338.0.

Step 2: (R)-1-((2-(2-chloro-3'-(3-(((R)-3-hydroxy-pyrrolidin-1-yl)methyl)-1,7-naphthyridin-8-ylamino)-2'-methylbiphenyl-3-yl)-7-cyanobenzo[d]oxazol-5-yl)methyl)pyrrolidine-3-carboxylic acid This compound was prepared using similar procedure as described in Step 2-5, Example 24 with 2-chloro-3-(7-chloro-5-(hydroxymethyl)benzo[d]oxazol-2-yl)phenylboronic acid replacing (7-chloro-2-(2-methyl-3-(4,4,5,5-tetramethyl-1,3,2-dioxaborolan-2-yl)phenyl)benzo[d]oxazol-5-yl)methanol in Step 2. The reaction mixture was purified by prep-HPLC (pH=2, acetonitrile/water+TFA) to give the desired product as TFA salt. LC-MS calculated for $C_{40}H_{37}ClN_7O_4(M+H)^+$: m/z=714.3; found 714.3.

TABLE 3

| Ex. No. | Name | Structure | LCMS [M + H] |
|---|---|---|---|
| 169 | (1R,3S)-3-((7-cyano-2-(3'-(3-(((R)-3-hydroxypyrrolidin-1-yl)methyl)-1,7-naphthyridin-8-ylamino)-2,2'-dimethyl biphenyl-3-yl)benzo[d]oxazol-5-yl)methylamino) cyclopentanecarboxylic acid | 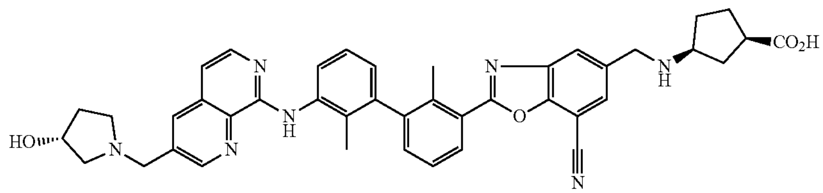 [SMILES: Cc1c(Nc2nccc3cc(CN4CC[C@@H](O)C4)cnc23)cccc1-c1cccc(-c2nc3cc(CN[C@H]4CC[C@@H](C(=O)O)C4)cc(C#N)c3o2)c1C] | 708.3 |
| 170 | (1S,3R)-3-((7-cyano-2-(3'-(3-(((R)-3-hydroxypyrrolidin-1-yl)methyl)-1,7-naphthyridin-8-ylamino)-2,2'-dimethyl biphenyl-3-yl)benzo[d]oxazol-5-yl)methylamino) cyclopentanecarboxylic acid | 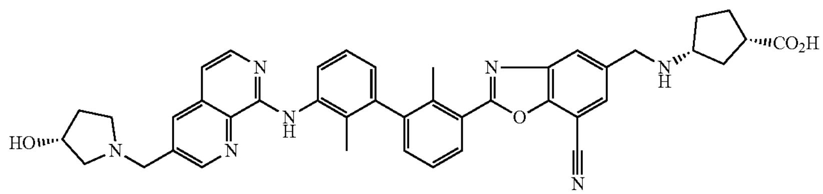 [SMILES: Cc1c(Nc2nccc3cc(CN4CC[C@@H](O)C4)cnc23)cccc1-c1cccc(-c2nc3cc(CN[C@@H]4CC[C@H](C(=O)O)C4)cc(C#N)c3o2)c1C] | 708.3 |
| 171 | (R)-4-(2-((7-cyano-2-(3'-3-((3-hydroxy pyrrolidin-1-yl)methyl)-1,7-naphthyridin-8-ylamino)-2,2'-dimethylbiphenyl-3-yl)benzo[d]oxazol-5-yl)methylamino)ethyl)benzoic acid | 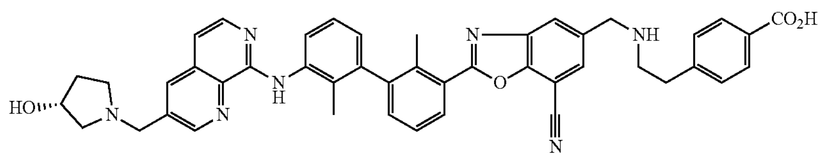 [SMILES: Cc1c(Nc2nccc3cc(CN4CC[C@@H](O)C4)cnc23)cccc1-c1cccc(-c2nc3cc(CNCCc4ccc(C(=O)O)cc4)cc(C#N)c3o2)c1C] | 744.3 |
| 172 | cis-4-((7-cyano-2-(3'-(3-(((R)-3-hydroxy pyrrolidin-1-yl)methyl)-1,7-naphthyridin-8-ylamino)-2,2'-dimethylbiphenyl-3-yl)benzo[d]oxazol-5-yl)methylamino) cyclohexanecarboxylic acid | 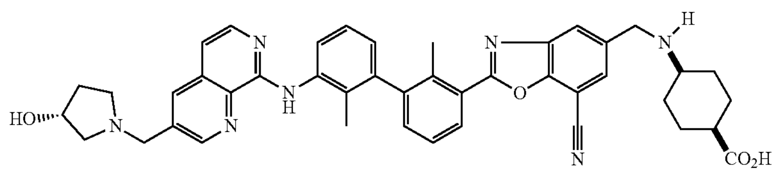 | 722.6 |
| 173 | 2-((R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidin-3-yl)acetic acid | 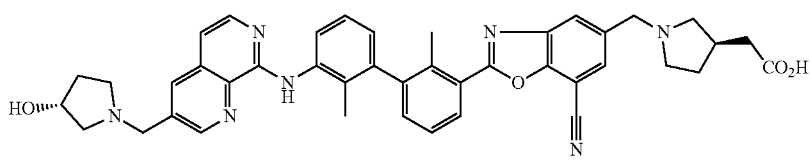 [SMILES: Cc1c(Nc2nccc3cc(CN4CC[C@@H](O)C4)cnc23)cccc1-c1cccc(-c2nc3cc(CN4CC[C@H](CC(=O)O)C4)cc(C#N)c3o2)c1C] | 708.5 |
| 174 | 2-((S)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidin-3-yl)acetic acid | 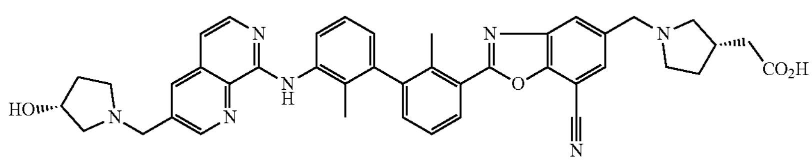 [SMILES: Cc1c(Nc2nccc3cc(CN4CC[C@@H](O)C4)cnc23)cccc1-c1cccc(-c2nc3cc(CN4CC[C@@H](CC(=O)O)C4)cc(C#N)c3o2)c1C] | 708.5 |
| 175 | (1R,2S)-2-((7-cyano-2-(3'-(3-(((R)-3-hydroxypyrrolidin-1-yl)methyl)-1,7-naphthyridin-8-ylamino)-2,2'-dimethyl biphenyl-3-yl)benzo[d]oxazol-5-yl)methylamino) cyclopentanecarboxylic acid | 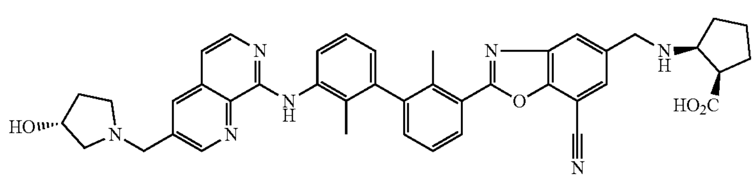 [SMILES: Cc1c(Nc2nccc3cc(CN4CC[C@@H](O)C4)cnc23)cccc1-c1cccc(-c2nc3cc(CN[C@H]4CCC[C@H]4C(=O)O)cc(C#N)c3o2)c1C] | 708.3 |
| 176 | 2-((7-cyano-2-(3'-(3-(((R)-3-hydroxy pyrrolidin-1-yl)methyl)-1,7-naphthyridin-8-ylamino)-2,2'-dimethylbiphenyl-3-yl)benzo[d]oxazol-5-yl)methyl)-2-aza bicyclo[2.2.1]heptane-5-carboxylic acid | 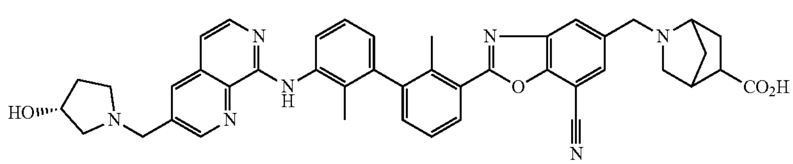 [SMILES: Cc1c(Nc2nccc3cc(CN4CC[C@@H](O)C4)cnc23)cccc1-c1cccc(-c2nc3cc(CN4CC5CC4CC5C(=O)O)cc(C#N)c3o2)c1C] | 720.3 |

TABLE 3-continued

| Ex. No. | Name | Structure | LCMS [M + H] |
|---|---|---|---|
| 177 | 2-((7-cyano-2-(3'-(3-(((R)-3-hydroxy pyrrolidin-1-yl)methyl)-1,7-naphthyridin-8-ylamino)-2,2'-dimethylbiphenyl-3-yl)benzo[d]oxazol-5-yl)methyl)-2-azaspiro[3.3]heptane-6-carboxylic acid | 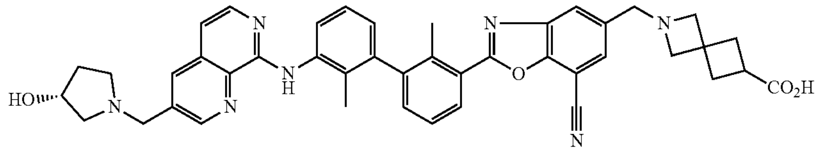 [SMILES: Cc1c(Nc2nccc3cc(CN4CC[C@@H](O)C4)cnc23)cccc1-c1cccc(-c2nc3cc(CN4CC5(CC(C(=O)O)C5)C4)cc(C#N)c3o2)c1C] | 720.3 |
| 178 | (R)-2-((7-cyano-2-(3'-(3-((3-hydroxy pyrrolidin-1-yl)methyl)-1,7-naphthyridin-8-ylamino)-2,2'-dimethylbiphenyl-3-yl)benzo[d]oxazol-5-yl)methyl)-2-aza bicyclo[2.1.1]hexane-4-carboxylic acid | 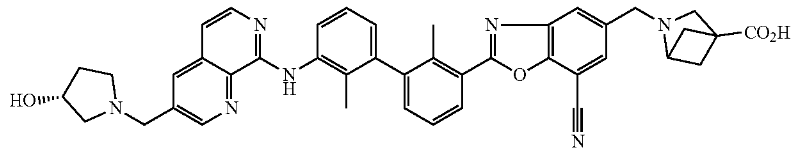 [SMILES: Cc1c(Nc2nccc3cc(CN4CC[C@@H](O)C4)cnc23)cccc1-c1cccc(-c2nc3cc(CN4CC5(C(=O)O)CC4C5)cc(C#N)c3o2)c1C] | 706.3 |
| 179 | (1S,2S)-2-((7-cyano-2-(3'-(3-(((R)-3-hydroxypyrrolidin-1-yl)methyl)-1,7-naphthyridin-8-ylamino)-2,2'-dimethyl biphenyl-3-yl)benzo[d]oxazol-5-yl)methylamino)cyclopentanecarboxylic acid | 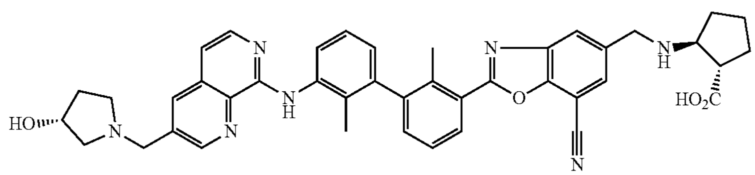 [SMILES: Cc1c(Nc2nccc3cc(CN4CC[C@@H](O)C4)cnc23)cccc1-c1cccc(-c2nc3cc(CN[C@H]4CCC[C@@H]4C(=O)O)cc(C#N)c3o2)c1C] | 708.6 |

The compounds in Table 3 were prepared in accordance with the synthetic protocols set forth in Example 24, using the appropriate amines for reductive amination in last step.

TABLE 4

| Ex. No. | Name | Structure | LCMS [M + H] |
|---|---|---|---|
| 180 | cis-3-((7-cyano-2-(3'-(3-(((R)-3-hydroxy pyrrolidin-1-yl)methyl)-1,7-naphthyridin-8-ylamino)-2,2'-dimethylbiphenyl-3-yl)benzo[d]oxazol-5-yl)methylamino)cyclobutane carboxylic acid | 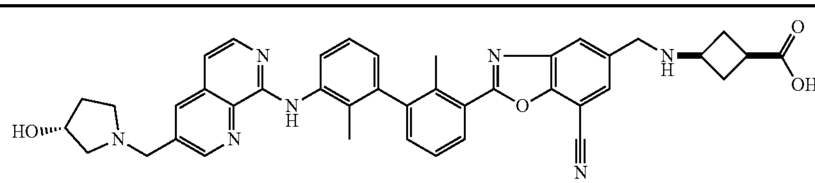 | 694.5 |
| 181 | trans-3-((7-cyano-2-(3'-(3-(((R)-3-hydroxy pyrrolidin-1-yl)methyl)-1,7-naphthyridin-8-ylamino)-2,2'-dimethylbiphenyl-3-yl)benzo[d]oxazol-5-yl)methylamino)cyclobutane carboxylic acid | 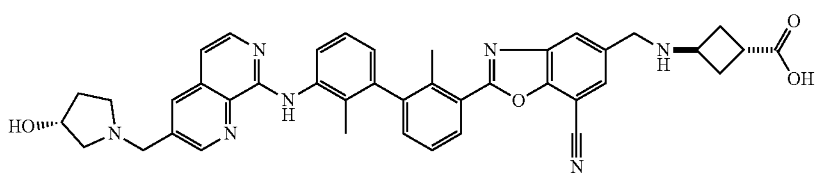 | 694.5 |
| 182 | (1S,3S)-3-((7-cyano-2-(3'-(3-(((R)-3-hydroxy pyrrolidin-1-yl)methyl)-1,7-naphthyridin-8-ylamino)-2,2'-dimethylbiphenyl-3-yl)benzo[d]oxazol-5-yl)methylamino)cyclopentane carboxylic acid | 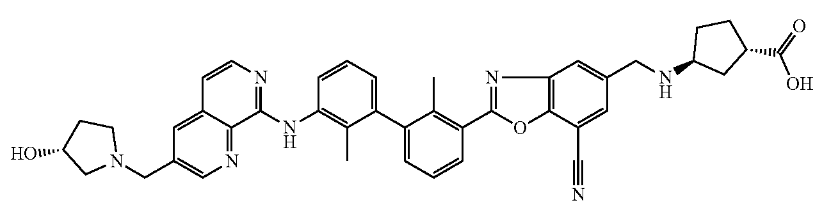 [SMILES: Cc1c(Nc2nccc3cc(CN4CC[C@@H](O)C4)cnc23)cccc1-c1cccc(-c2nc3cc(CN[C@H]4CC[C@H](C(=O)O)C4)cc(C#N)c3o2)c1C] | 708.5 |
| 183 | (R)-4-((7-cyano-2-(3'-(3-((3-hydroxy pyrrolidin-1-yl)methyl)-1,7-naphthyridin-8-ylamino)-2,2'-dimethylbiphenyl-3-yl)benzo[d]oxazol-5-yl)methylamino)bicyclo[2.2.1]heptane-1-carboxylic acid | 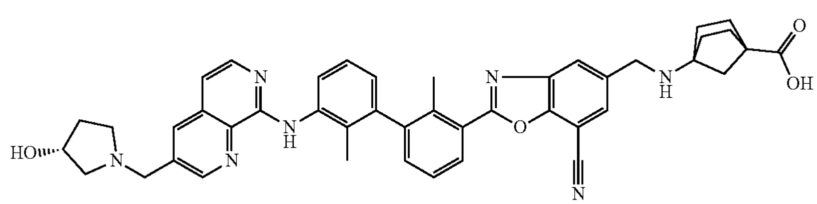 [SMILES: Cc1c(Nc2nccc3cc(CN4CC[C@@H](O)C4)cnc23)cccc1-c1cccc(-c2nc3cc(CNC45CCC(C(=O)O)(CC4)C5)cc(C#N)c3o2)c1C] | 734.5 |

TABLE 4-continued

| Ex. No. | Name | Structure | LCMS [M + H] |
|---|---|---|---|
| 184 | 2-(trans-4-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methylamino)cyclohexyl)acetic acid | 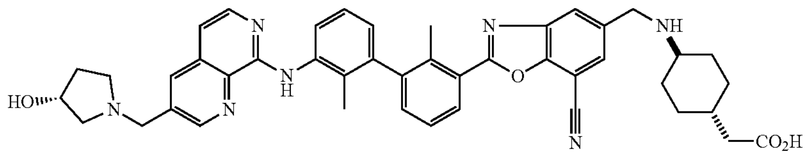 | 736.5 |

The compounds in Table 4 were prepared in accordance with the synthetic protocols set forth in Example 24, using the appropriate amino esters for reductive amination followed by saponification.

TABLE 5

| Ex. No. | Name | Structure | LCMS [M + H] |
|---|---|---|---|
| 185 | 1-((7-cyano-2-(3'-(3-(((R)-3-hydroxy pyrrolidin-1-yl)methyl)-1,7-naphthyridin-8-ylamino)-2,2'-dimethylbiphenyl-3-yl)benzo[d]oxazol-5-yl)methyl-3-(methoxy methyl)pyrrolidine-3-carboxylic acid | 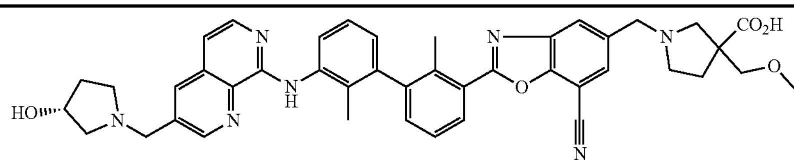 | 738.5 |
| 186 | (R)-1-((7-cyano-2-(3'-(3-((3-hydroxy pyrrolidin-1-yl)methyl)-1,7-naphthyridin-8-ylamino)-2,2'-dimethylbiphenyl-3-yl)benzo[d]oxazol-5-yl)methyl)piperidine-4-carboxylic acid | 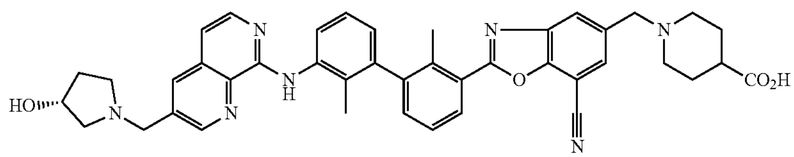 [SMILES: Cc1c(Nc2nccc3cc(CN4CC[C@@H](O)C4)cnc23)cccc1-c1cccc(-c2nc3cc(CN4CCC(C(=O)O)CC4)cc(C#N)c3o2)c1C] | 708.3 |

The compounds in Table 5 were prepared in accordance with the synthetic protocols set forth in Example 24, using the appropriate amino tert-butyl esters for reductive amination followed by treatment of TFA in DCM to remove the tert-butyl groups.

TABLE 6

| Ex. No. | Name | Structure | LCMS [M + H] |
|---|---|---|---|
| 187 | (R)-1-((2-(2'-chloro-3'-(3-(((R)-3-hydroxy pyrrolidin-1-yl)methyl)-1,7-naphthyridin-8-ylamino)-2-methylbiphenyl-3-yl)-7-cyanobenzo[d]oxazol-5-yl)methyl)-3-methylpyrrolidine-3-carboxylic acid | 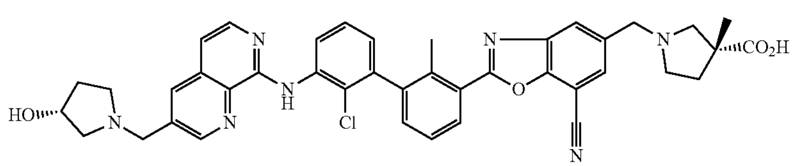 | 728.2 |
| 188 | (R)-1-((2-(2'-chloro-3'-(3-((3-hydroxy pyrrolidin-1-yl)methyl)-1,7-naphthyridin-8-ylamino)-2-methylbiphenyl-3-yl)-7-cyanobenzo[d]oxazol-5-yl)methyl)piperidine-4-carboxylic acid | 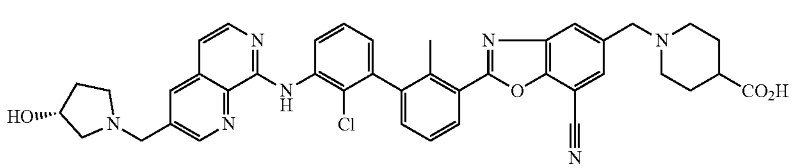 [SMILES: Cc1c(-c2nc3cc(CN4CCC(C(=O)O)CC4)cc(C#N)c3o2)cccc1-c1cccc(Nc2nccc3cc(CN4CC[C@@H](O)C4)cnc23)c1Cl] | 728.2 |

The compounds in Table 6 were prepared in accordance with the synthetic protocols set forth in Example 30, using the appropriate starting material (R)-pyrrolidin-3-ol and different amino acids.

Example 189

(R)-1-((7-cyano-2-(3'-(3-((2-hydroxyethylamino)methyl)-1,7-naphthyridin-8-ylamino)-2,2'-dimethylbiphenyl-3-yl)benzo[d]oxazol-5-yl)methyl)-3-methylpyrrolidine-3-carboxylic acid

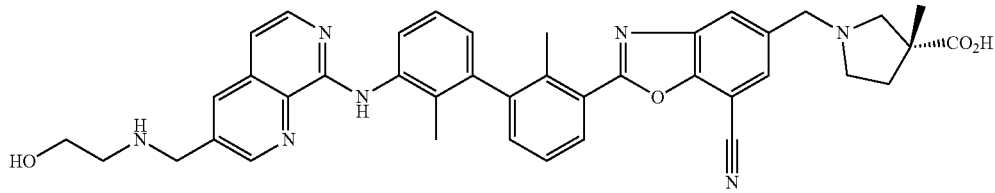 [SMILES: Cc1c(Nc2nccc3cc(CNCCO)cnc23)cccc1-c1cccc(-c2nc3cc(CN4CC[C@@](C)(C(=O)O)C4)cc(C#N)c3o2)c1C]

Step 1: (R)-1-((7-cyano-2-(2-methyl-3-(4,4,5,5-tetramethyl-1,3,2-dioxaborolan-2-yl)phenyl)benzo[d]oxazol-5-yl)methyl)-3-methylpyrrolidine-3-carboxylic acid

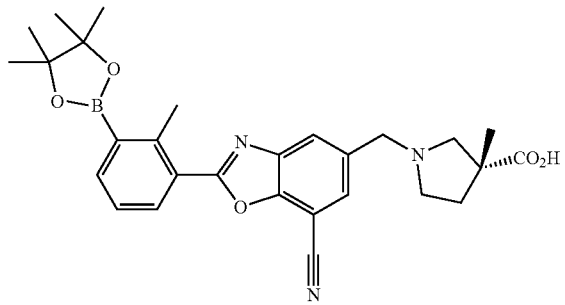 [SMILES: Cc1c(B2OC(C)(C)C(C)(C)O2)cccc1-c1nc2cc(CN3CC[C@@](C)(C(=O)O)C3)cc(C#N)c2o1]

This compound was prepared using similar procedure as described in Example 138, Step 2 with (R)-3-methylpyrrolidine-3-carboxylic acid replacing (R)-pyrrolidine-3-carboxylic acid. LC-MS calculated for $C_{28}H_{33}BN_3O_5$ (M+H)$^+$: m/z=502.2; found 502.2.

Step 2: (R)-1-((7-cyano-2-(3'-(3-formyl-1,7-naphthyridin-8-ylamino)-2,2'-dimethylbiphenyl-3-yl)benzo[d]oxazol-5-yl)methyl)-3-methylpyrrolidine-3-carboxylic acid A mixture of 8-((3-bromo-2-methylphenyl)amino)-1,7-naphthyridine-3-carbaldehyde (Example 16, Step 3: 278 mg, 0.812 mmol), (R)-1-((7-cyano-2-(2-methyl-3-(4,4,5,5-tetramethyl-1,3,2-dioxaborolan-2-yl)phenyl)benzo[d]oxazol-5-yl)methyl)-3-methylpyrrolidine-3-carboxylic acid (370 mg, 0.738 mmol), tetrakis(triphenylphosphine)palladium(0) (85 mg, 0.074 mmol) and potassium phosphate (392 mg, 1.845 mmol) in water (820 µl) and dioxane (4100 µl) was purged with $N_2$ and then stirred at 100° C. for 3 h. The reaction was cooled to room temperature. The reaction mixture was diluted with DCM and $H_2O$. The layers were separated. The aqueous layer was extracted with DCM three times. The organic layer was dried over $MgSO_4$, filtered and concentrated to give a crude residue, which was purified by flash chromatography on a silica gel column eluting with 0 to 14% MeOH/DCM to give the desired product. LC-MS calculated for $C_{38}H_{33}N_6O_4$ (M+H)$^+$: m/z=637.3; found 637.3.

Step 3: (R)-1-((7-cyano-2-(3'-(3-((2-hydroxyethylamino)methyl)-1,7-naphthyridin-8-ylamino)-2,2'-dimethylbiphenyl-3-yl)benzo[d]oxazol-5-yl)methyl)-3-methylpyrrolidine-3-carboxylic acid A mixture of (R)-1-((7-cyano-2-(3'-((3-formyl-1,7-naphthyridin-8-yl)amino)-2,2'-dimethyl-[1,1'-biphenyl]-3-yl)benzo[d]oxazol-5-yl)methyl)-3-methylpyrrolidine-3-carboxylic acid (9.5 mg, 0.015 mmol) and 2-aminoethan-1-ol (1.367 mg, 0.022 mmol) in DCM (0.15 ml) was stirred at rt for 2 h. Then sodium triacetoxyborohydride (6.32 mg, 0.030 mmol) were added. The mixture was further stirred at r.t. for 1 h. The reaction was concentrated, then diluted in MeOH, filtered then purified by prep-HPLC (pH=10, acetonitrile/water+$NH_4OH$) to give the desired product. LC-MS calculated for $C_{40}H_{40}N_7O_4$ (M+H)$^+$: m/z=682.3; found 682.2.

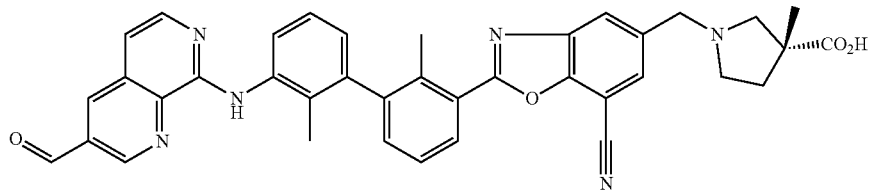 [SMILES: Cc1c(Nc2nccc3cc(C=O)cnc23)cccc1-c1cccc(-c2nc3cc(CN4CC[C@@](C)(C(=O)O)C4)cc(C#N)c3o2)c1C]

TABLE 7

| Ex. No. | Name | Structure | LCMS [M + H] |
|---|---|---|---|
| 190 | (R)-1-((7-cyano-2-(3'-(3-(((2-hydroxyethyl)(methyl)amino)methyl)-1,7-naphthyridin-8-ylamino)-2,2'-dimethylbiphenyl-3-yl)benzo[d]oxazol-5-yl)methyl)-3-methylpyrrolidine-3-carboxylic acid | 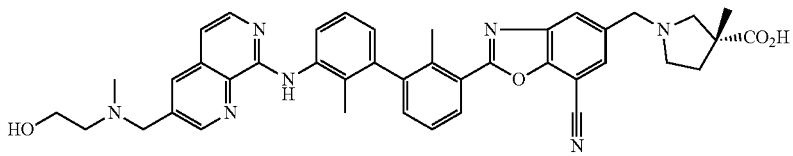 [SMILES: Cc1c(Nc2nccc3cc(CN(C)CCO)cnc23)cccc1-c1cccc(-c2nc3cc(CN4CC[C@@](C)(C(=O)O)C4)cc(C#N)c3o2)c1C] | 696.3 |
| 191 | (R)-1-((7-cyano-2-(3'-(3-(((S)-2-hydroxypropylamino)methyl)-1,7-naphthyridin-8-ylamino)-2,2'-dimethylbiphenyl-3-yl)benzo[d]oxazol-5-yl)methyl)-3-methylpyrrolidine-3-carboxylic acid | 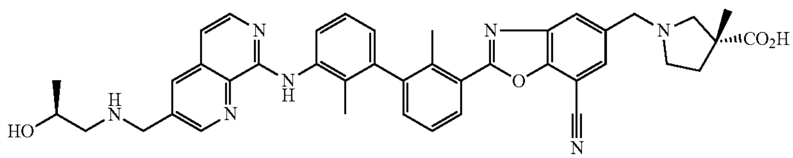 | 696.3 |
| 192 | (R)-1-((7-cyano-2-(3'-(3-(((R)-2-hydroxypropylamino)methyl)-1,7-naphthyridin-8-ylamino)-2,2'-dimethylbiphenyl-3-yl)benzo[d]oxazol-5-yl)methyl)-3-methylpyrrolidine-3-carboxylic acid | 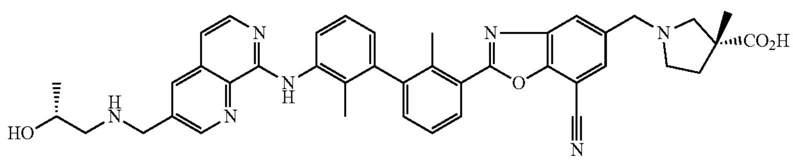 [SMILES: Cc1c(Nc2nccc3cc(CNC[C@@H](C)O)cnc23)cccc1-c1cccc(-c2nc3cc(CN4CC[C@@](C)(C(=O)O)C4)cc(C#N)c3o2)c1C] | 696.3 |
| 193 | (R)-1-((7-cyano-2-(2,2'-dimethyl-3'-(3-(pyrrolidin-1-ylmethyl)-1,7-naphthyridin-8-ylamino)biphenyl)-3-yl)benzo[d]oxazol-5-yl)methyl)-3-methylpyrrolidine-3-carboxylic acid | 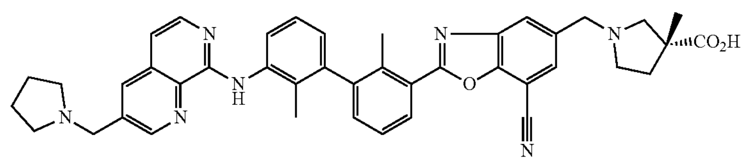 [SMILES: Cc1c(Nc2nccc3cc(CN4CCCC4)cnc23)cccc1-c1cccc(-c2nc3cc(CN4CC[C@@](C)(C(=O)O)C4)cc(C#N)c3o2)c1C] | 692.3 |
| 194 | (R)-1-((7-cyano-2-(3'-(3-(((S)-1-hydroxybutan-2-ylamino)methyl)-1,7-naphthyridin-8-ylamino)-2,2'-dimethylbiphenyl-3-yl)benzo[d]oxazol-5-yl)methyl)-3-methylpyrrolidine-3-carboxylic acid | 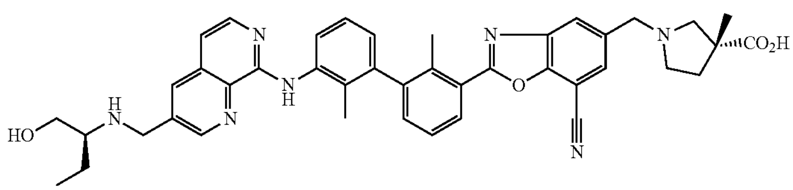 [SMILES: CC[C@@H](CO)NCc1cnc2c(Nc3cccc(-c4cccc(-c5nc6cc(CN7CC[C@@](C)(C(=O)O)C7)cc(C#N)c6o5)c4C)c3C)nccc2c1] | 710.3 |
| 195 | (R)-1-((7-cyano-2-(3'-(3-(((S)-1-hydroxypropan-2-ylamino)methyl)-1,7-naphthyridin-8-ylamino)-2,2'-dimethylbiphenyl-3-yl)benzo[d]oxazol-5-yl)methyl)-3-methylpyrrolidine-3-carboxylic acid | 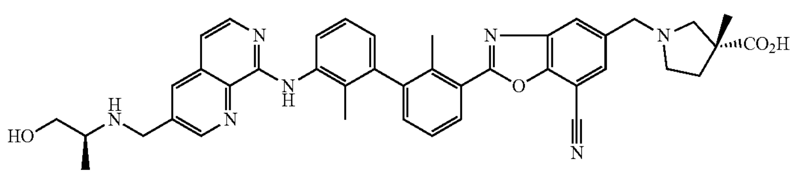 [SMILES: Cc1c(Nc2nccc3cc(CN[C@@H](C)CO)cnc23)cccc1-c1cccc(-c2nc3cc(CN4CC[C@@](C)(C(=O)O)C4)cc(C#N)c3o2)c1C] | 696.3 |
| 196 | (R)-1-((7-cyano-2-(3'-(3-(((R)-1-hydroxy propan-2-ylamino)methyl)-1,7-naphthyridin-8-ylamino)-2,2'-dimethyl biphenyl-3-yl)benzo[d]oxazol-5-yl)methyl)-3-methylpyrrolidine-3-carboxylic acid | 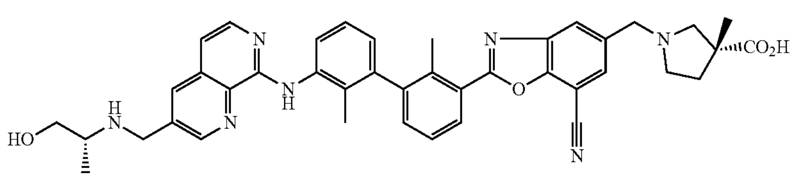 [SMILES: Cc1c(Nc2nccc3cc(CN[C@H](C)CO)cnc23)cccc1-c1cccc(-c2nc3cc(CN4CC[C@@](C)(C(=O)O)C4)cc(C#N)c3o2)c1C] | 696.3 |
| 197 | (R)-1-((7-cyano-2-(2,2'-dimethyl-3'-(3-((methylamino)methyl)-1,7-naphthyridin-8-ylamino)biphenyl-3-yl)benzo[d]oxazol-5-yl)methyl)-3-methylpyrrolidine-3-carboxylic acid | 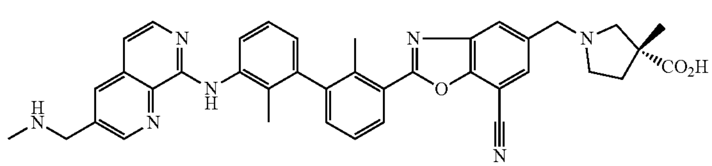 [SMILES: CNCc1cnc2c(Nc3cccc(-c4cccc(-c5nc6cc(CN7CC[C@@](C)(C(=O)O)C7)cc(C#N)c6o5)c4C)c3C)nccc2c1] | 652.2 |
| 198 | (R)-1-((7-cyano-2-(3'-(3-((1-hydroxy-2-methylpropan-2-ylamino)methyl)-1,7-naphthyridin-8-ylamino)-2,2'-dimethyl biphenyl-3-yl)benzo[d]oxazol-5-yl)methyl)-3-methylpyrrolidine-3-carboxylic acid | 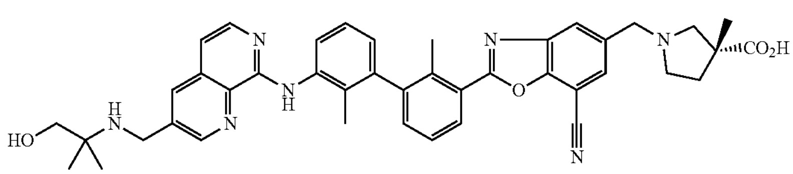 [SMILES: Cc1c(Nc2nccc3cc(CNC(C)(C)CO)cnc23)cccc1-c1cccc(-c2nc3cc(CN4CC[C@@](C)(C(=O)O)C4)cc(C#N)c3o2)c1C] | 710.3 |

TABLE 7-continued

| Ex. No. Name | Structure | LCMS [M + H] |
|---|---|---|
| 199 (R)-1-((7-cyano-2-(3'-(3-(((1-hydroxycyclopropyl)methylamino)methyl)-1,7-naphthyridin-8-ylamino)-2,2'-dimethylbiphenyl-3-yl)benzo[d]oxazol-5-yl)methyl)-3-methylpyrrolidine-3-carboxylic acid | | 708.3 |
| 200 (R)-1-((7-cyano-2-(3'-(3-(((S)-3-hydroxy-3-methylpyrrolidin-1-yl)methyl)-1,7-naphthyridin-8-ylamino)2,2'-dimethyl biphenyl-3-yl)benzo[d]oxazol-5-yl)methyl)-3-methylpyrrolidine-3-carboxylic acid | | 722.3 |

The compounds in Table 7 were prepared in accordance with the synthetic protocols set forth in Example 189, using the appropriate starting materials.

Example 201

(S)-1-((7-cyano-2-(3'-(3-((1-hydroxypropan-2-ylamino)methyl)-1,7-naphthyridin-8-ylamino)-2,2'-dimethylbiphenyl-3-yl)benzo[d]oxazol-5-yl)methyl)piperidine-4-carboxylic acid

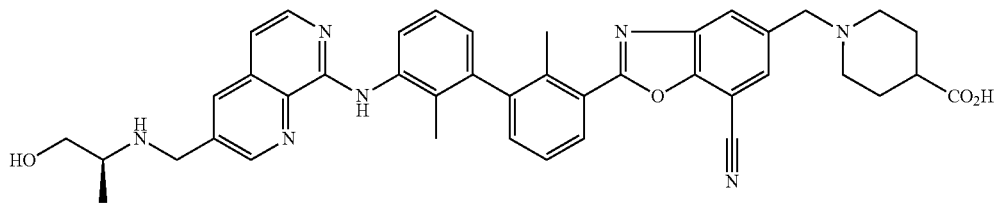 [SMILES: Cc1c(Nc2nccc3cc(CN[C@@H](C)CO)cnc23)cccc1-c1cccc(-c2nc3cc(CN4CCC(C(=O)O)CC4)cc(C#N)c3o2)c1C]

Step 1: tert-butyl 1-((7-cyano-2-(2-methyl-3-(4,4,5,5-tetramethyl-1,3,2-dioxaborolan-2-yl)phenyl)benzo[d]oxazol-5-yl)piperidine-4-carboxylate

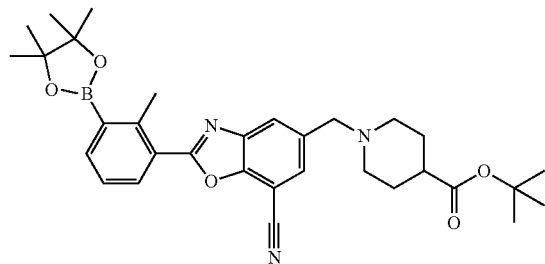 [SMILES: Cc1c(B2OC(C)(C)C(C)(C)O2)cccc1-c1nc2cc(CN3CCC(C(=O)OC(C)(C)C)CC3)cc(C#N)c2o1]

This compound was prepared using similar procedure as described in Example 138, Step 2 with tert-butyl piperidine-4-carboxylate replacing (R)-pyrrolidine-3-carboxylic acid. LC-MS calculated for $C_{32}H_{41}BN_3O_5(M+H)^+$: m/z=558.3; found 558.3.

Step 2: tert-butyl 1-((7-cyano-2-(3'-(3-formyl-1,7-naphthyridin-8-ylamino)-2,2'-dimethyl biphenyl-3-yl)benzo[d]oxazol-5-yl)methyl)piperidine-4-carboxylate

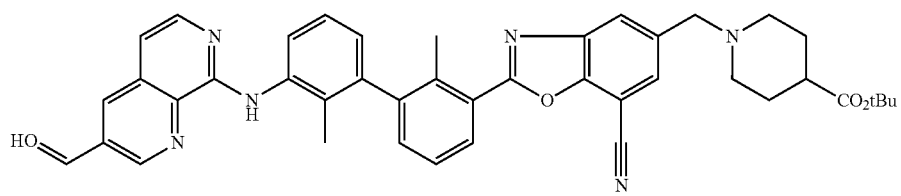 [SMILES: Cc1c(Nc2nccc3cc(C=O)cnc23)cccc1-c1cccc(-c2nc3cc(CN4CCC(C(=O)OC(C)(C)C)CC4)cc(C#N)c3o2)c1C]

This compound was prepared using similar procedure as described in Example 189, Step 2 with tert-butyl 1-((7-cyano-2-(2-methyl-3-(4,4,5,5-tetramethyl-1,3,2-dioxaborolan-2-yl)phenyl)benzo[d]oxazol-5-yl)methyl)piperidine-4-carboxylate replacing (R)-1-((7-cyano-2-(2-methyl-3-(4,4,5,5-tetramethyl-1,3,2-dioxaborolan-2-yl)phenyl)benzo[d]oxazol-5-yl)methyl)-3-methylpyrrolidine-3-carboxylic acid. LC-MS calculated for $C_{42}H_{41}N_6O_4$ (M+H)$^+$: m/z=693.3; found 693.3.

Step 3: (S)-1-((7-cyano-2-(3'-(3-((1-hydroxypropan-2-ylamino)methyl)-1,7-naphthyridin-8-ylamino)-2,2'-dimethylbiphenyl-3-yl)benzo[d]oxazol-5-yl)methyl)piperidine-4-carboxylic acid A mixture of tert-butyl 1-((7-cyano-2-(3'-(3-formyl-1,7-naphthyridin-8-ylamino)-2,2'-dimethyl biphenyl-3-yl)benzo[d]oxazol-5-yl)methyl)piperidine-4-carboxylate (10.5 mg, 0.015 mmol) and (S)-2-aminopropan-1-ol (1.7 mg, 0.023 mmol) in DCM (0.15 ml) was stirred at r.t. for 2 h. Then sodium triacetoxyborohydride (6.42 mg, 0.030 mmol) were added. The mixture was further stirred at r.t. for 1 h. Then trifluoroacetic acid (140 µl, 1.82 mmol) was added. The mixture was stirred at r.t. for 30 min. The reaction was concentrated, then diluted in MeOH, filtered then purified by prep-HPLC (pH=2, acetonitrile/water+TFA) to give the desired product as TFA salt. LC-MS calculated for $C_{41}H_{42}N_7O_4$ (M+H)$^+$: m/z=696.3; found 696.3.

TABLE 8

| Ex. No. | Name | Structure | LCMS [M + H] |
|---|---|---|---|
| 202 | (R)-1-((7-cyano-2-(3'-(3-((1-hydroxypropan-2-ylamino)methyl)-1,7-naphthyridin-8-ylamino)-2,2'-dimethyl biphenyl-3-yl)benzo[d]oxazol-5-yl)methyl)piperidine-4-carboxylic acid | 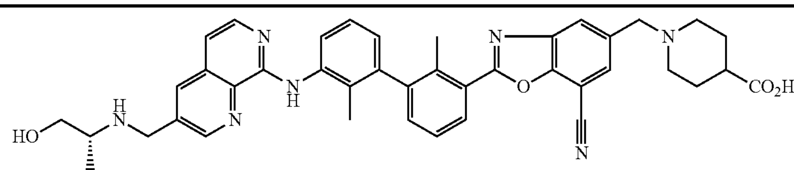 | 696.3 |
| 203 | (R)-1-((7-cyano-2-(3'-(3-((2-hydroxypropyl amino)methyl)-1,7-naphthyridin-8-ylamino)-2,2'-dimethyl biphenyl-3-yl)benzo[d]oxazol-5-yl)methyl)piperidine-4-carboxylic acid | 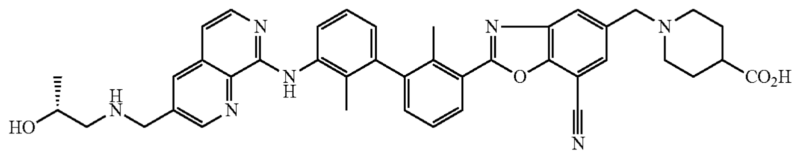 [SMILES: Cc1c(Nc2nccc3cc(CNC[C@@H](C)O)cnc23)cccc1-c1cccc(-c2nc3cc(CN4CCC(C(=O)O)CC4)cc(C#N)c3o2)c1C] | 696.3 |
| 204 | (S)-1-((7-cyano-2-(3'-(3-((2-hydroxypropylamino)methyl)-1,7-naphthyridin-8-ylamino)-2,2'-dimethylbiphenyl-3-yl)benzo[d]oxazol-5-yl)methyl)piperidine-4-carboxylic acid | 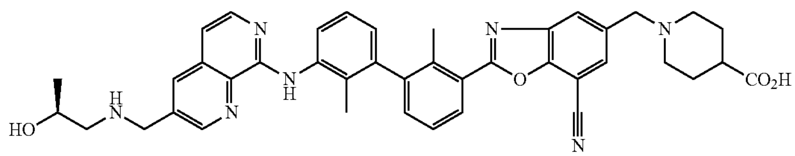 [SMILES: Cc1c(Nc2nccc3cc(CNC[C@H](C)O)cnc23)cccc1-c1cccc(-c2nc3cc(CN4CCC(C(=O)O)CC4)cc(C#N)c3o2)c1C] | 696.3 |

The compounds in Table 8 were prepared in accordance with the synthetic protocols set forth in Example 201, using the appropriate starting materials.

TABLE 9

| Ex. No. | Name/$^1$HNMR | Structure | LCMS [M + H] |
|---|---|---|---|
| 205 | (R)-1-((7-cyano-2-(3'-(7-(((R)-3-hydroxypyrrolidin-1-yl)methyl)pyrido[3,2-d]pyrimidin-4-ylamino)-2,2'-dimethylbiphenyl-3-yl)benzo[d]oxazol-5-yl)methyl)-3-methylpyrrolidine-3-carboxylic acid | 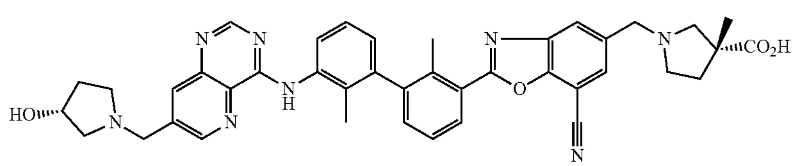 [SMILES: Cc1c(Nc2ncnc3cc(CN4CC[C@@H](O)C4)cnc23)cccc1-c1cccc(-c2nc3cc(CN4CC[C@@](C)(C(=O)O)C4)cc(C#N)c3o2)c1C] | 709.3 |
| 206 | (S)-1-((7-cyano-2-(3'-(7-(((R)-3-hydroxypyrrolidin-1-yl)methyl)pyrido[3,2-d]pyrimidin-4-ylamino)-2,2'-dimethylbiphenyl-3-yl)benzo[d]oxazol-5-yl)methyl)piperidine-3-carboxylic acid | 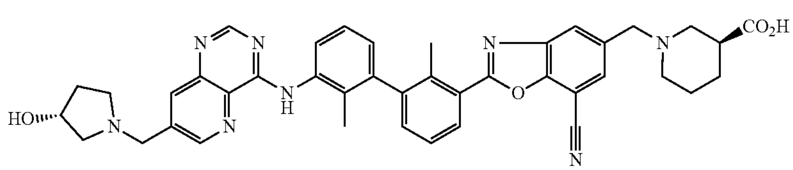 [SMILES: Cc1c(Nc2ncnc3cc(CN4CC[C@@H](O)C4)cnc23)cccc1-c1cccc(-c2nc3cc(CN4CCC[C@H](C(=O)O)C4)cc(C#N)c3o2)c1C] | 709.3 |

TABLE 9-continued

| Ex. No. | Name/¹HNMR | Structure | LCMS [M + H] |
|---|---|---|---|
| 207 | (R)-1-((7-cyano-2-(3'-(7-((3-hydroxypyrrolidin-1-yl)methyl)pyrido[3,2-d]pyrimidin-4-ylamino)-2,2'-dimethylbiphenyl-3-yl)benzo[d]oxazol-5-yl)methyl)piperidine-4-carboxylic acid<br>¹H NMR (500 MHz, DMSO) δ 9.09 (s, 1H), 8.69 (s, 1H), 8.45 (d, J = 1.5 Hz, 1H), 8.36 (s, 1H), 8.19 (d, J = 7.7 Hz, 1H), 8.10 (s, 1H), 7.65 (d, J = 7.8 Hz, 1H), 7.59 (t, J = 7.7 Hz, 1H), 7.47 (d, J = 7.4 Hz, 1H), 7.41 (t, J = 7.7 Hz, 1H), 7.16 (d, J = 7.3 Hz, 1H), 4.69 (br, s, 2H), 4.57-4.41 (m, 3H), 3.84-2.91 (m, 8H), 2.57-2.51 (m, 1H), 2.47 (s, 3H), 2.36-1.66 (m, 6H), 1.98 (s, 3H). | 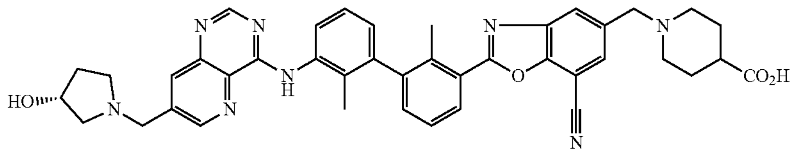 [SMILES: Cc1c(Nc2ncnc3cc(CN4CC[C@@H](O)C4)cnc23)cccc1-c1cccc(-c2nc3cc(CN4CCC(C(=O)O)CC4)cc(C#N)c3o2)c1C] | 709.3 |
| 208 | (R)-1-((7-cyano-2-(3'-(7-(((S)-2-hydroxypropylamino)methyl)pyrido[3,2-d]pyrimidin-4-ylamino)-2,2'-dimethyl biphenyl-3-yl)benzo[d]oxazol-5-yl)methyl)-3-methylpyrrolidine-3-carboxylic acid | 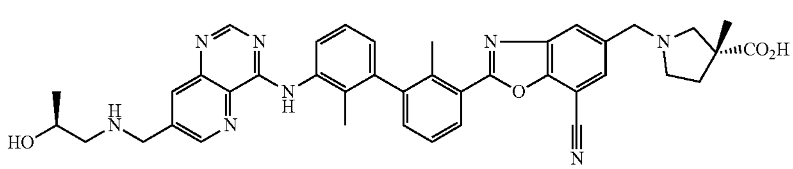 [SMILES: Cc1c(Nc2ncnc3cc(CNC[C@H](C)O)cnc23)cccc1-c1cccc(-c2nc3cc(CN4CC[C@@](C)(C(=O)O)C4)cc(C#N)c3o2)c1C] | 697.3 |
| 209 | (R)-1-((7-cyano-2-(2,2'-dimethyl-3'-(7-(pyrrolidin-1-ylmethyl)pyrido[3,2-d]pyrimidin-4-ylamino)biphenyl-3-yl)benzo[d]oxazol-5-yl)methyl)pyrrolidine-3-carboxylic acid | 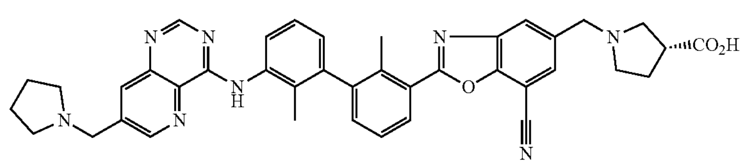 [SMILES: Cc1c(Nc2ncnc3cc(CN4CCCC4)cnc23)cccc1-c1cccc(-c2nc3cc(CN4CC[C@@H](C(=O)O)C4)cc(C#N)c3o2)c1C] | 679.3 |

The compounds in Table 9 were prepared in accordance with the synthetic protocols set forth in Example 139, using the appropriate starting materials.

Example 210

(R)-1-((8-(3'-(7-cyano-5-(((S)-2-hydroxypropylamino)methyl)benzo[d]oxazol-2-yl)-2,2'-dimethylbiphenyl-3-ylamino)-1,7-naphthyridin-3-yl)methyl)pyrrolidine-3-carboxylic acid

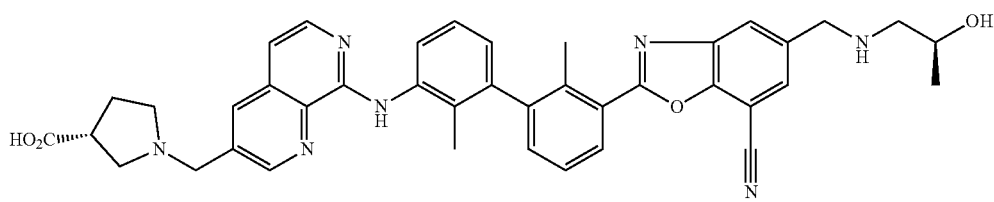 [SMILES: Cc1c(Nc2nccc3cc(CN4CC[C@@H](C(=O)O)C4)cnc23)cccc1-c1cccc(-c2nc3cc(CNC[C@H](C)O)cc(C#N)c3o2)c1C]

Step 1: (R)-1-((8-(3'-(7-cyano-5-formylbenzo[d]oxazol-2-yl)-2,2'-dimethylbiphenyl-3-ylamino)-1,7-naphthyridin-3-yl)methyl)pyrrolidine-3-carboxylic acid

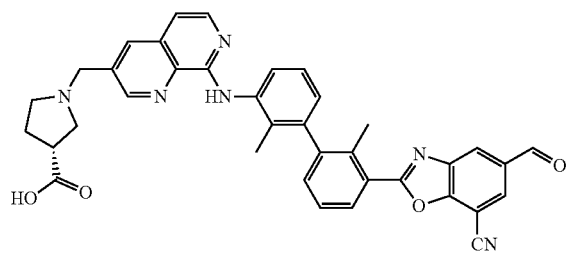 [SMILES: Cc1c(Nc2nccc3cc(CN4CC[C@@H](C(=O)O)C4)cnc23)cccc1-c1cccc(-c2nc3cc(C=O)cc(C#N)c3o2)c1C]

A mixture of (R)-1-((8-(3-bromo-2-methylphenylamino)-1,7-naphthyridin-3-yl)methyl)pyrrolidine-3-carboxylic acid (Example 141, Step 1: 333 mg, 0.755 mmol), 5-formyl-2-(2-methyl-3-(4,4,5,5-tetramethyl-1,3,2-dioxaborolan-2-yl)phenyl)benzo[d]oxazole-7-carbonitrile (Example 138, Step 1: 293 mg, 0.755 mmol), potassium phosphate (400 mg, 1.886 mmol) and tetrakis(triphenylphosphine) palladium(0) (87 mg, 0.075 mmol) in water (838 μl) and dioxane (4192 μl) was purged with $N_2$ and then stirred at 100° C. for 4 h. The reaction was cooled to room temperature. The reaction mixture was diluted with DCM/isopropanol (4:1) and $H_2O$. The layers were separated. The aqueous layer was extracted with DCM/isopropanol (4:1) three times. The organic layer was dried over $MgSO_4$, filtered and concentrated to give a crude residue, which was purified by flash chromatography on a silica gel column eluting with 0 to 15% MeOH/DCM to give the desired product. LC-MS calculated for $C_{37}H_{31}N_6O_4$ $(M+H)^+$: m/z=623.2; found 623.2.

Step 2: (R)-1-((8-(3'-(7-cyano-5-(((S)-2-hydroxypropylamino)methyl)benzo[d]oxazol-2-yl)-2,2'-dimethylbiphenyl-3-ylamino)-1,7-naphthyridin-3-yl)methyl)pyrrolidine-3-carboxylic acid A mixture of (R)-1-((8-(3'-(7-cyano-5-formylbenzo[d]oxazol-2-yl)-2,2'-dimethyl biphenyl-3-ylamino)-1,7-naphthyridin-3-yl)methyl)pyrrolidine-3-carboxylic acid (11 mg, 0.018 mmol) and (S)-2-aminopropan-1-ol (2.0 mg, 0.026 mmol) in DCM (0.12 ml) was stirred at r.t. for 1 h. Then sodium triacetoxyborohydride (7.5 mg, 0.035 mmol) was added. The mixture was further stirred at r.t. for 1 h. The reaction was concentrated, then diluted in MeOH, filtered then purified by prep-HPLC (pH=2, acetonitrile/water+TFA) to give the desired TFA salt. LC-MS calculated for $C_{40}H_{40}N_7O_4$ $(M+H)^+$: m/z=682.3; found 682.3.

TABLE 10

| Ex. No. | Name | Structure | LCMS [M + H] |
|---|---|---|---|
| 211 | (R)-1-((8-(3'-(7-cyano-5-(((S)-1-hydroxypropan-2-ylamino)methyl)benzo[d]oxazol-2-yl)-2,2'-dimethyl biphenyl-3-ylamino)-1,7-naphthyridin-3-yl)methyl)pyrrolidine-3-carboxylic acid | 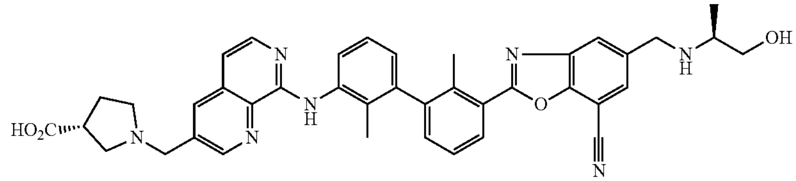 [SMILES: Cc1c(Nc2nccc3cc(CN4CC[C@@H](C(=O)O)C4)cnc23)cccc1-c1cccc(-c2nc3cc(CN[C@@H](C)CO)cc(C#N)c3o2)c1C] | 682.3 |
| 212 | (S)-1-((8-(3'-(7-cyano-5-((2-hydroxypropyl amino)methyl)benzo[d]oxazol-2-yl)-2,2'-dimethylbiphenyl-3-ylamino)-1,7-naphthyridin-3-yl)methyl)piperidine-4-carboxylic acid | 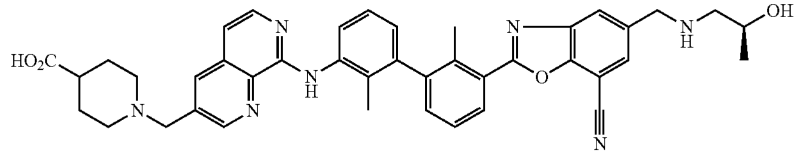 [SMILES: Cc1c(Nc2nccc3cc(CN4CCC(C(=O)O)CC4)cnc23)cccc1-c1cccc(-c2nc3cc(CNC[C@H](C)O)cc(C#N)c3o2)c1C] | 696.3 |
| 213 | (S)-1-((8-(3'-(7-cyano-5-((1-hydroxypropan-2-ylamino)methyl)benzo[d]oxazol-2-yl)-2,2'-dimethyl biphenyl-3-ylamino)-1,7-naphthyridin-3-yl)methyl)piperidine-4-carboxylic acid | 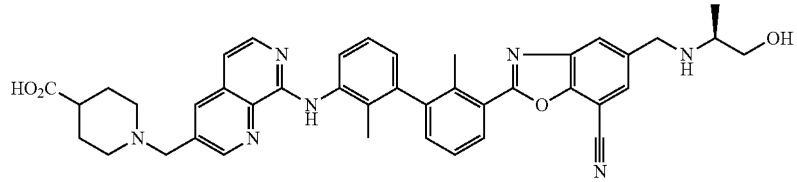 [SMILES: Cc1c(Nc2nccc3cc(CN4CCC(C(=O)O)CC4)cnc23)cccc1-c1cccc(-c2nc3cc(CN[C@@H](C)CO)cc(C#N)c3o2)c1C] | 696.3 |
| 214 | (R)-1-((8-(3'-(7-cyano-5-((3-hydroxypyrrolidin-1-yl)methyl)benzo[d]oxazol-2-yl)-2,2'-dimethyl biphenyl-3-ylamino)-1,7-naphthyridin-3-yl)methyl)piperidine-4-carboxylic acid | 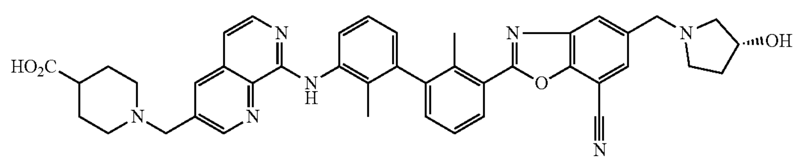 [SMILES: Cc1c(Nc2nccc3cc(CN4CCC(C(=O)O)CC4)cnc23)cccc1-c1cccc(-c2nc3cc(CN4CC[C@@H](O)C4)cc(C#N)c3o2)c1C] | 708.3 |

TABLE 10-continued

| Ex. No. | Name | Structure | LCMS [M + H] |
|---|---|---|---|
| 215 | (R)-1-((8-(3'-(7-cyano-5-(((S)-1-hydroxypropan-2-ylamino)methyl)benzo[d]oxazol-2-yl)-2,2'-dimethyl biphenyl-3-ylamino)-1,7-naphthyridin-3-yl)methyl)-3-methylpyrrolidine-3-carboxylic acid | 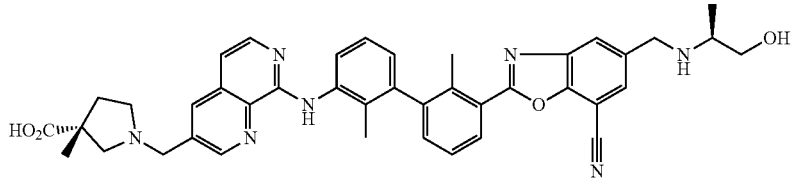 [SMILES: Cc1c(Nc2nccc3cc(CN4CC[C@@](C)(C(=O)O)C4)cnc23)cccc1-c1cccc(-c2nc3cc(CN[C@@H](C)CO)cc(C#N)c3o2)c1C] | 696.3 |
| 216 | (R)-1-((8-(3'-(7-cyano-5-(((R)-3-hydroxypyrrolidin-1-yl)methyl)benzo[d]oxazol-2-yl)-2,2'-dimethylbiphenyl-3-ylamino)-1,7-naphthyridin-3-yl)methyl)-3-methylpyrrolidine-3-carboxylic acid | 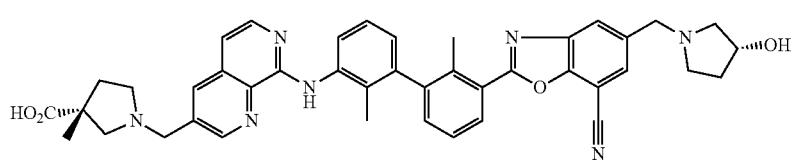 [SMILES: Cc1c(Nc2nccc3cc(CN4CC[C@@](C)(C(=O)O)C4)cnc23)cccc1-c1cccc(-c2nc3cc(CN4CC[C@@H](O)C4)cc(C#N)c3o2)c1C] | 708.3 |

The compounds in Table 10 were prepared in accordance with the synthetic protocols set forth in Example 210, using the appropriate starting materials.

Example 217

(R)-1-((7-cyano-2-(3'-(5-(2-(isopropyl(methyl)amino)acetyl)-5,6-dihydro-4H-pyrrolo[3,4-d]thiazol-2-yl)-2,2'-dimethylbiphenyl-3-yl)benzo[d]oxazol-5-yl)methyl)-3-methylpyrrolidine-3-carboxylic acid

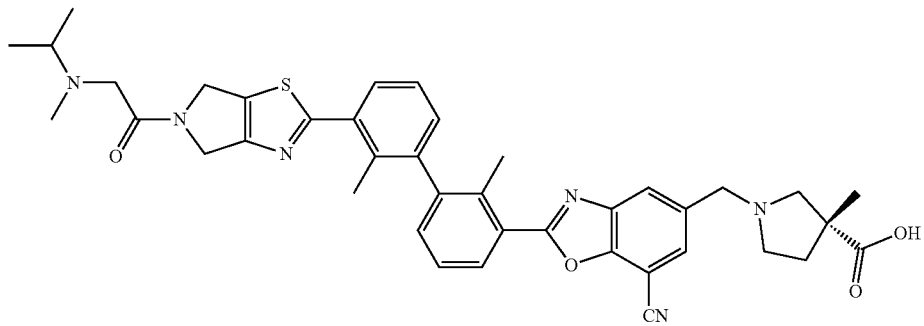 [SMILES: Cc1c(-c2nc3cc(CN4CC[C@@](C)(C(=O)O)C4)cc(C#N)c3o2)cccc1-c1cccc(-c2nc3c(s2)CN(C(=O)CN(C)C(C)C)C3)c1C]

Step 1: 2-(3'-(5-(2-chloroacetyl)-5,6-dihydro-4H-pyrrolo[3,4-d]thiazol-2-yl)-2,2'-dimethylbiphenyl-3-yl)-5-formylbenzo[d]oxazole-7-carbonitrile

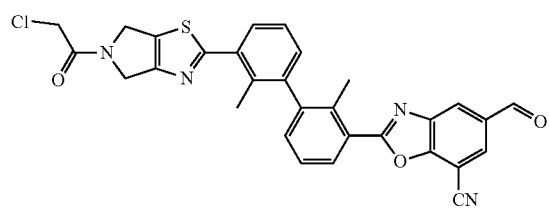 [SMILES: Cc1c(-c2nc3cc(C=O)cc(C#N)c3o2)cccc1-c1cccc(-c2nc3c(s2)CN(C(=O)CCl)C3)c1C]

To a stirred solution of 2-(3'-(5,6-dihydro-4H-pyrrolo[3,4-d]thiazol-2-yl)-2,2'-dimethyl-[1,1'-biphenyl]-3-yl)-5-formylbenzo[d]oxazole-7-carbonitrile (Example 105, Step 5: 100 mg, 0.210 mmol) in DCM (5.0 ml), Hunig's base (0.073 ml, 0.420 mmol) and 2-chloroacetyl chloride (28.4 mg, 0.252 mmol) were added sequentially at room temperature. After 1 hour, the reaction mixture was quenched with saturated aq. NaHCO$_3$, extracted with DCM (3×20 mL). The organic layers were combined, dried over Na$_2$SO$_4$, filtered and the filtrate was concentrated under reduced pressure. The residue was purified by chromatography on silica gel, eluting with 0-60% EtOAc/hexanes, to give the desired product (102 mg). LC-MS calculated for C$_{30}$H$_{22}$ClN$_4$O$_3$S (M+H)$^+$: m/z=553.1; found 553.1.

Step 2: 5-formyl-2-(3'-(5-(2-(isopropyl(methyl)amino)acetyl)-5,6-dihydro-4H-pyrrolo[3,4-d]thiazol-2-yl)-2,2'-dimethylbiphenyl-3-yl)benzo[d]oxazole-7-carbonitrile

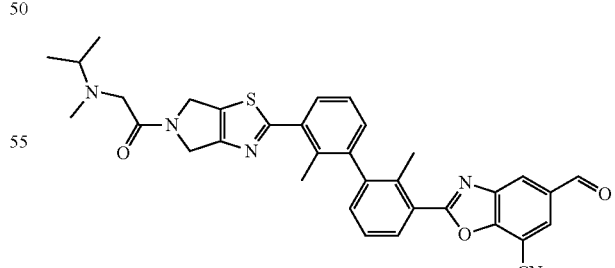

To a stirred solution of 2-(3'-(5-(2-chloroacetyl)-5,6-dihydro-4H-pyrrolo[3,4-d]thiazol-2-yl)-2,2'-dimethyl-[1,1'-biphenyl]-3-yl)-5-formylbenzo[d]oxazole-7-carbonitrile (40 mg, 0.072 mmol) in acetonitrile (1.0 ml), Hunig's base (0.025 ml, 0.145 mmol) and N-methylpropan-2-amine (7.94 mg, 0.108 mmol) were added sequentially at room temperature. After 6 h, the volatiles were removed and the residue was purified by chromatography on silica gel, eluting with 0-15% MeOH/DCM, to give the desired product (36 mg). LC-MS calculated for $C_{34}H_{32}N_5O_3S$ (M+H)$^+$: m/z=590.2; found 590.2.

Step 3: (R)-1-((7-cyano-2-(3'-(5-(2-(isopropyl (methyl)amino)acetyl)-5,6-dihydro-4H-pyrrolo[3,4-d]thiazol-2-yl)-2,2'-dimethylbiphenyl-3-yl)benzo[d]oxazol-5-yl)methyl)-3-methylpyrrolidine-3-carboxylic acid To a stirred solution of 5-formyl-2-(3'-(5-(2-(isopropyl (methyl)amino)acetyl)-5,6-dihydro-4H-pyrrolo[3,4-d]thiazol-2-yl)-2,2'-dimethylbiphenyl-3-yl)benzo[d]oxazole-7-carbonitrile (5.0 mg, 8.90 μmol) and (R)-3-methylpyrrolidine-3-carboxylic acid (2.3 mg, 0.018 mmol) in DMF (0.5 ml)/Water (0.2 ml), Hunig's base (4.7 μl, 0.027 mmol) was added at room temperature. After 0.5 h, sodium cyanoborohydride (1.7 mg, 0.027 mmol) was added and the resulted mixture was stirred at room temperature overnight. The reaction mixture was then diluted with MeOH, purified on prep LCMS (pH 2, acetonitrile/water+TFA) to give the desired product as its TFA salt. LC-MS calculated for $C_{40}H_{43}N_6O_4S$ (M+H)$^+$: m/z=703.3; found 703.3.

TABLE 11

| Ex. No. | Name | Structure | LCMS [M + H] |
|---|---|---|---|
| 218 | (R)-1-((7-cyano-2-(3'-(5-(2-(ethyl(methyl)amino)acetyl)-5,6-dihydro-4H-pyrrolo[3,4-d]thiazol-2-yl)-2,2'-dimethylbiphenyl-3-yl)benzo[d]oxazol-5-yl)methyl)-3-meethylpyrrolidine-3-carboxylic acid | 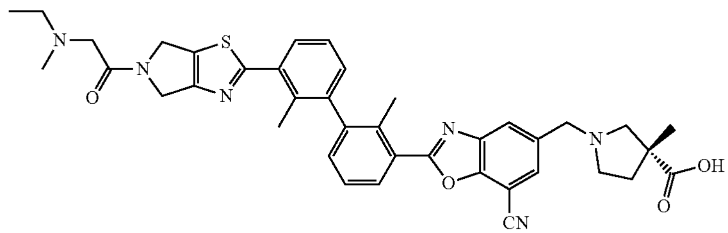 [SMILES: CCN(C)CC(=O)N1Cc2nc(-c3cccc(-c4cccc(-c5nc6cc(CN7CC[C@@](C)(C(=O)O)C7)cc(C#N)c6o5)c4C)c3C)sc2C1] | 689.3 |
| 219 | (R)-1-((7-cyano-2-(3'-(5-(2-((cyclopropylmethyl)(methyl)amino)acetyl)-5,6-dihydro-4H-pyrrolo[3,4-d]thiazol-2-yl)-2,2'-dimethylbiphenyl-3-yl)benzo[d]oxazol-5-yl)methyl)-3-methylpyrrolidine-3-carboxylic acid | 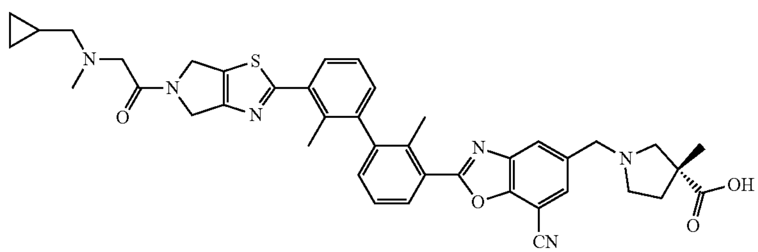 [SMILES: Cc1c(-c2nc3cc(CN4CC[C@@](C)(C(=O)O)C4)cc(C#N)c3o2)cccc1-c1cccc(-c2nc3c(s2)CN(C(=O)CN(C)CC2CC2)C3)c1C] | 715.3 |
| 220 | 2-((7-cyano-2-(3'-(5-(2-(ethyl(methyl)amino)acetyl)-5,6-dihydro-4H-pyrrolo[3,4-d]thiazol-2-yl)-2,2'-dimethylbiphenyl-3-yl)benzo[d]oxazol-5-yl)methyl)-2-azabicyclo[2.1.1]hexane-4-carboxylic acid | 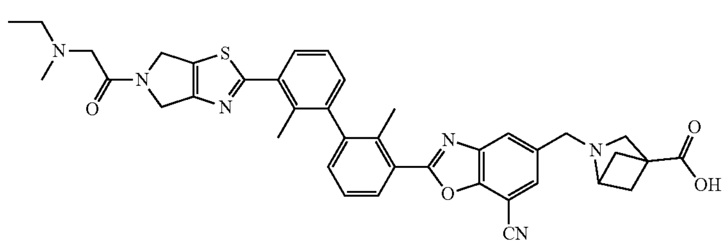 [SMILES: CCN(C)CC(=O)N1Cc2nc(-c3cccc(-c4cccc(-c5nc6cc(CN7CC8(C(=O)O)CC7C8)cc(C#N)c6o5)c4C)c3C)sc2C1] | 687.3 |

The compounds in Table 11 were prepared in accordance with the synthetic protocols set forth in Example 217, using the appropriate starting materials.

Example 221

(R)-1-((7-cyano-2-(3'-(5-(2-((S)-3-hydroxypyrrolidin-1-yl)acetyl)-5,6-dihydro-4H-pyrrolo[3,4-d]thiazol-2-yl)-2,2'-dimethylbiphenyl-3-yl)benzo[d]oxazol-5-yl)methyl)-3-methylpyrrolidine-3-carboxylic acid

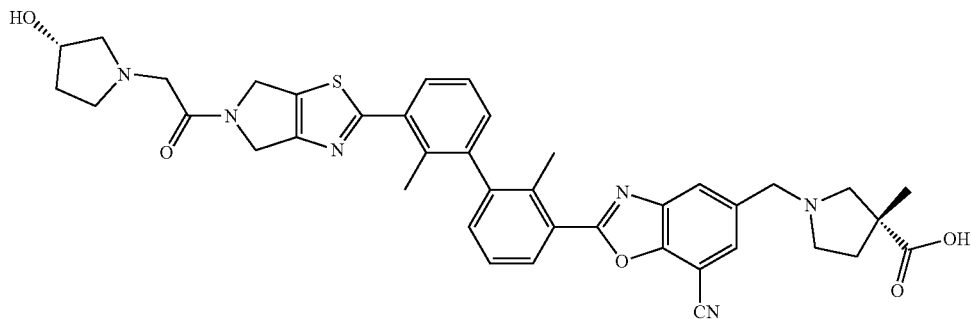 [SMILES: Cc1c(-c2nc3cc(CN4CC[C@@](C)(C(=O)O)C4)cc(C#N)c3o2)cccc1-c1cccc(-c2nc3c(s2)CN(C(=O)CN2CC[C@H](O)C2)C3)c1C]

Step 1: (R)-1-((2-(3'-(5-(2-chloroacetyl)-5,6-dihydro-4H-pyrrolo[3,4-d]thiazol-2-yl)-2,2'-dimethylbiphenyl-3-yl)-7-cyanobenzo[d]oxazol-5-yl)methyl)-3-methylpyrrolidine-3-carboxylic acid

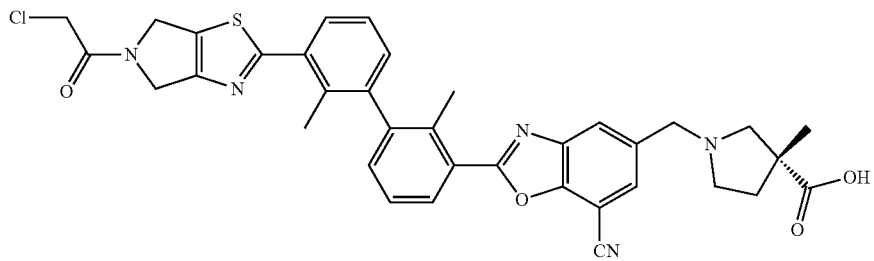 [SMILES: Cc1c(-c2nc3cc(CN4CC[C@@](C)(C(=O)O)C4)cc(C#N)c3o2)cccc1-c1cccc(-c2nc3c(s2)CN(C(=O)CCl)C3)c1C]

A solution of 2-(3'-(5-(2-chloroacetyl)-5,6-dihydro-4H-pyrrolo[3,4-d]thiazol-2-yl)-2,2'-dimethyl-[1,1'-biphenyl]-3-yl)-5-formylbenzo[d]oxazole-7-carbonitrile (Example 217, Step 1: 100.0 mg, 0.181 mmol) and (R)-3-methylpyrrolidine-3-carboxylic acid (35.0 mg, 0.271 mmol) in DMF (3.0 ml) was stirred at room temperature for 30 min. Sodium cyanoborohydride (22.7 mg, 0.262 mmol) was then added and the resulted mixture was stirred at room temperature overnight. The volatiles were removed under reduced pressure and the residue was purified by chromatography on silica gel, eluting with 0-15% MeOH/DCM, to give the desired product (66 mg). LC-MS calculated for $C_{36}H_{33}ClN_5O_4S$ (M+H)$^+$: m/z=666.2; found 666.2.

Step 2: (R)-1-((7-cyano-2-(3'-(5-(2-((S)-3-hydroxypyrrolidin-1-yl)acetyl)-5,6-dihydro-4H-pyrrolo[3,4-d]thiazol-2-yl)-2,2'-dimethylbiphenyl-3-yl)benzo[d]oxazol-5-yl)methyl)-3-methylpyrrolidine-3-carboxylic acid To a stirred solution of (R)-1-((2-(3'-(5-(2-chloroacetyl)-5,6-dihydro-4H-pyrrolo[3,4-d]thiazol-2-yl)-2,2'-dimethyl-[1,1'-biphenyl]-3-yl)-7-cyanobenzo[d]oxazol-5-yl)methyl)-3-methylpyrrolidine-3-carboxylic acid (10.0 mg, 0.015 mmol) in acetonitrile (1.0 mL), (S)-pyrrolidin-3-ol (1.962 mg, 0.023 mmol) and Hunig's base (7.87 µl, 0.045 mmol) were added at room temperature. The resulted mixture was heated at 60° C. After 2 h, the volatiles were removed under reduced pressure and the residue was purified by purified on prep LCMS (pH 2, acetonitrile/water+TFA) to give the desired product as its TFA salt. LC-MS calculated for $C_{40}H_{41}N_6O_5S$ (M+H)$^+$: m/z=717.3; found 717.3.

TABLE 12

| Ex. No. | Name | Structure | LCMS [M + H] |
|---|---|---|---|
| 222 | (R)-1-((7-cyano-2-(3'-(5-(2-((R)-3-hydroxypyrrolidin-1-yl)acetyl)-5,6-dihydro-4H-pyrrolo[3,4-d]thiazol-2-yl)-2,2'-dimethylbiphenyl-3-yl)benzo[d]oxazol-5-yl)methyl)-3-methylpyrrolidine-3-carboxylic acid | 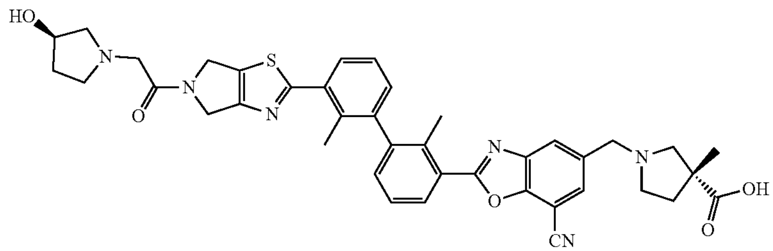 [SMILES: Cc1c(-c2nc3cc(CN4CC[C@@](C)(C(=O)O)C4)cc(C#N)c3o2)cccc1-c1cccc(-c2nc3c(s2)CN(C(=O)CN2CC[C@@H](O)C2)C3)c1C] | 717.3 |
| 223 | (R)-1-((7-cyano-2-(3'-(5-(2-(4-ethylpiperazin-1-yl)acetyl)-5,6-dihydro-4H-pyrrolo[3,4-d]thiazol-2-yl)-2,2'-dimethylbiphenyl-3-yl)benzo[d]oxazol-5-yl)methyl)-3-methylpyrrolidine-3-carboxylic acid | 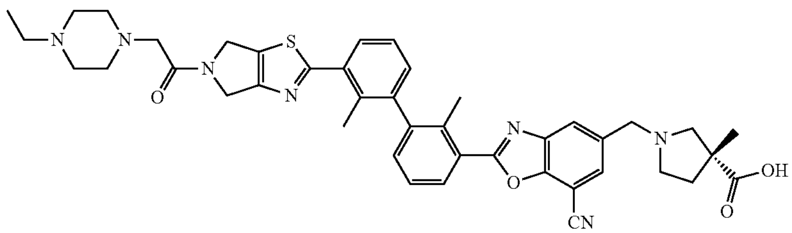 [SMILES: CCN1CCN(CC(=O)N2Cc3nc(-c4cccc(-c5cccc(-c6nc7cc(CN8CC[C@@](C)(C(=O)O)C8)cc(C#N)c7o6)c5C)c4C)sc3C2)CC1] | 744.3 |
| 224 | (R)-1-((7-cyano-2-(3'-(5-(2-((2-hydroxyethyl)(methyl)amino)acetyl)-5,6-dihydro-4H-pyrrolo[3,4-d]thiazol-2-yl)-2,2'-dimethylbiphenyl-3-yl)benzo[d]oxazol-5-yl)methyl)-3-methylpyrrolidine-3-carboxylic acid | 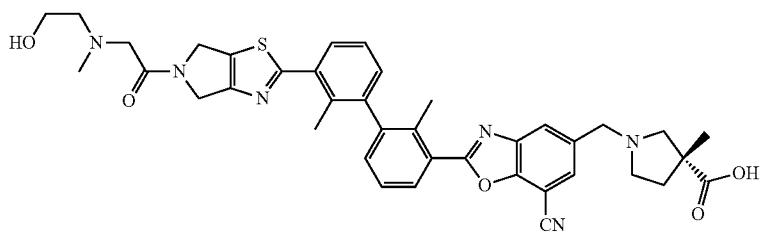 [SMILES: Cc1c(-c2nc3cc(CN4CC[C@@](C)(C(=O)O)C4)cc(C#N)c3o2)cccc1-c1cccc(-c2nc3c(s2)CN(C(=O)CN(C)CCO)C3)c1C] | 705.3 |
| 225 | (R)-1-((7-cyano-2-(3'-(5-(2-(((R)-1-hydroxypropan-2-yl)(methyl)amino)acetyl)-5,6-dihydro-4H-pyrrolo[3,4-d]thiazol-2-yl)-2,2'-dimethylbiphenyl-3-yl)benzo[d]oxazol-5-yl)methyl)-3-methylpyrrolidine-3-carboxylic acid | 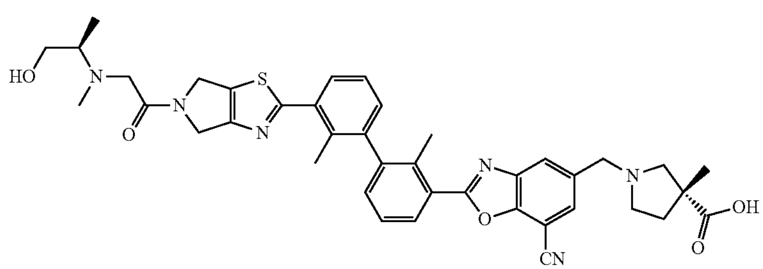 [SMILES: Cc1c(-c2nc3cc(CN4CC[C@@](C)(C(=O)O)C4)cc(C#N)c3o2)cccc1-c1cccc(-c2nc3c(s2)CN(C(=O)CN(C)[C@H](C)CO)C3)c1C] | 719.3 |
| 226 | (R)-1-((7-cyano-2-(3'-(5-(2-(((S)-1-hydroxypropan-2-yl)(methyl)amino)acetyl)-5,6-dihydro-4H-pyrrolo[3,4-d]thiazol-2-yl)-2,2'-dimethylbiphenyl-3-yl)benzo[d]oxazol-5-yl)methyl)-3-methylpyrrolidine-3-carboxylic acid | 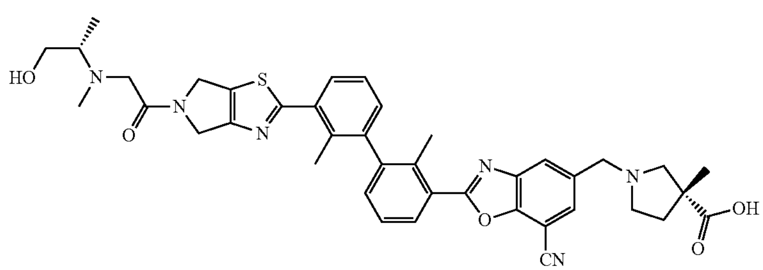 [SMILES: Cc1c(-c2nc3cc(CN4CC[C@@](C)(C(=O)O)C4)cc(C#N)c3o2)cccc1-c1cccc(-c2nc3c(s2)CN(C(=O)CN(C)[C@@H](C)CO)C3)c1C] | 719.3 |
| 227 | (R)-1-((7-cyano-2-(3'-(5-(2-(3-hydroxyazetidin-1-yl)acetyl)-5,6-dihydro-4H-pyrrolo[3,4-d]thiazol-2-yl)-2,2'-dimethylbiphenyl-3-yl)benzo[d]oxazol-5-yl)methyl)-3-methylpyrrolidine-3-carboxylic acid | 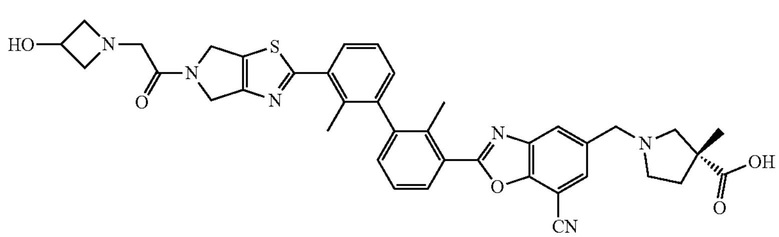 [SMILES: Cc1c(-c2nc3cc(CN4CC[C@@](C)(C(=O)O)C4)cc(C#N)c3o2)cccc1-c1cccc(-c2nc3c(s2)CN(C(=O)CN2CC(O)C2)C3)c1C] | 703.4 |

TABLE 12-continued

| Ex. No. | Name | Structure | LCMS [M + H] |
|---|---|---|---|
| 228 | (R)-1-((7-cyano-2-(3'-(5-(2-(cis-3-hydroxycyclobutylamino)acetyl)-5,6-dihydro-4H-pyrrolo[3,4-d]thiazol-2-yl)-2,2'-dimethylbiphenyl-3-yl)benzo[d]oxazol-5-yl)methyl)-3-methylpyrrolidine-3-carboxylic acid | 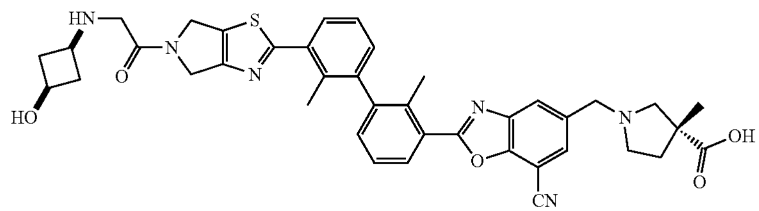 | 717.4 |
| 229 | (R)-1-((7-cyano-2-(3'-(5-(2-(trans-3-hydroxycyclobutylamino)acetyl)-5,6-dihydro-4H-pyrrolo[3,4-d]thiazol-2-yl)-2,2'-dimethylbiphenyl-3-yl)benzo[d]oxazol-5-yl)methyl)-3-methylpyrrolidine-3-carboxylic acid | 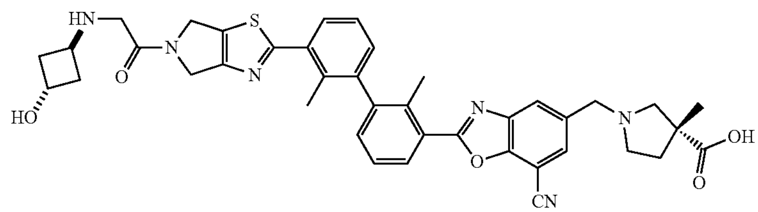 | 717.4 |
| 230 | 2-((7-cyano-2-(3'-(5-(2-((2-hydroxyethyl)(methyl)amino)acetyl)-5,6-dihydro-4H-pyrrolo[3,4-d]thiazol-2-yl)-2,2'-dimethylbiphenyl-3-yl)benzo[d]oxazol-5-yl)methyl)-2-azaspiro[3.3]heptane-6-carboxylic acid | 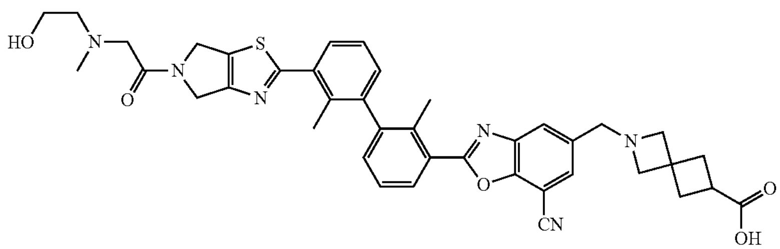 [SMILES: Cc1c(-c2nc3cc(CN4CC5(CC(C(=O)O)C5)C4)cc(C#N)c3o2)cccc1-c1cccc(-c2nc3c(s2)CN(C(=O)CN(C)CCO)C3)c1C] | 717.3 |
| 231 | 2-((7-cyano-2-(3'-(5-(2-(((R)-1-hydroxypropan-2-yl)(methyl)amino)acetyl)-5,6-dihydro-4H-pyrrolo[3,4-d]thiazol-2-yl)-2,2'-dimethylbiphenyl-3-yl)benzo[d]oxazol-5-yl)methyl)-2-azaspiro[3.3]heptane-6-carboxylic acid | 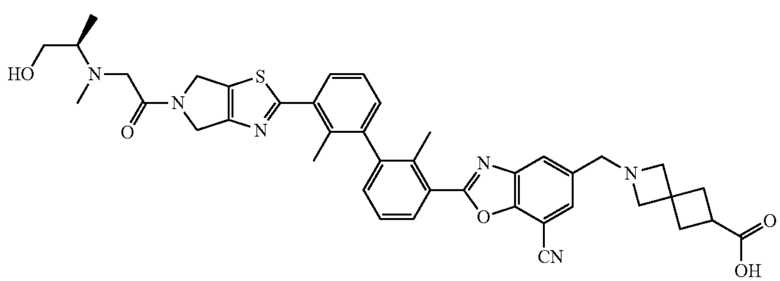 [SMILES: Cc1c(-c2nc3cc(CN4CC5(CC(C(=O)O)C5)C4)cc(C#N)c3o2)cccc1-c1cccc(-c2nc3c(s2)CN(C(=O)CN(C)[C@H](C)CO)C3)c1C] | 731.3 |
| 232 | 2-((7-cyano-2-(3'-(5-(2-(((S)-1-hydroxypropan-2-yl)(methyl)amino)acetyl)-5,6-dihydro-4H-pyrrolo[3,4-d]thiazol-2-yl)-2,2'-dimethylbiphenyl-3-yl)benzo[d]oxazol-5-yl)methyl)-2-azaspiro[3.3]heptane-6-carboxylic acid | 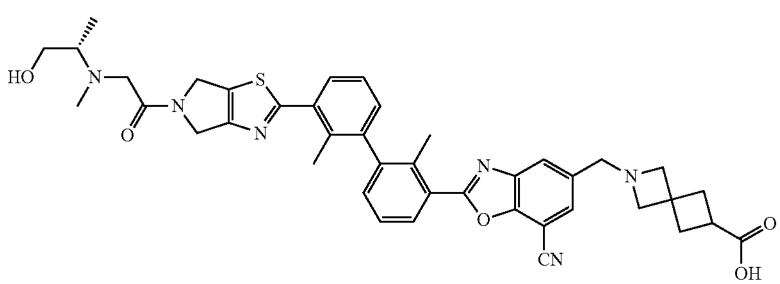 [SMILES: Cc1c(-c2nc3cc(CN4CC5(CC(C(=O)O)C5)C4)cc(C#N)c3o2)cccc1-c1cccc(-c2nc3c(s2)CN(C(=O)CN(C)[C@@H](C)CO)C3)c1C] | 731.3 |
| 233 | 2-((7-cyano-2-(3'-(5-(2-((S)-3-hydroxypyrrolidin-1-yl)acetyl)-5,6-dihydro-4H-pyrrolo[3,4-d]thiazol-2-yl)-2,2'-dimethylbiphenyl-3-yl)benzo[d]oxazol-5-yl)methyl)-2-azaspiro[3.3]heptane-6-carboxylic acid | 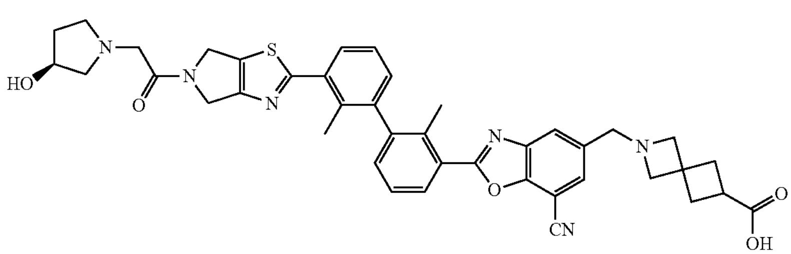 [SMILES: Cc1c(-c2nc3cc(CN4CC5(CC(C(=O)O)C5)C4)cc(C#N)c3o2)cccc1-c1cccc(-c2nc3c(s2)CN(C(=O)CN2CC[C@H](O)C2)C3)c1C] | 729.4 |

TABLE 12-continued

| Ex. No. | Name | Structure | LCMS [M + H] |
|---|---|---|---|
| 234 | 2-((7-cyano-2-(3'-(5-(2-((R)-3-hydroxypyrrolidin-1-yl)acetyl)-5,6-dihydro-4H-pyrrolo[3,4-d]thiazol-2-yl)-2,2'-dimethylbiphneyl-3-yl)benzo[d]oxazol-5-yl)methyl)-2-azaspiro[3.3]heptane-6-carboxylic acid | 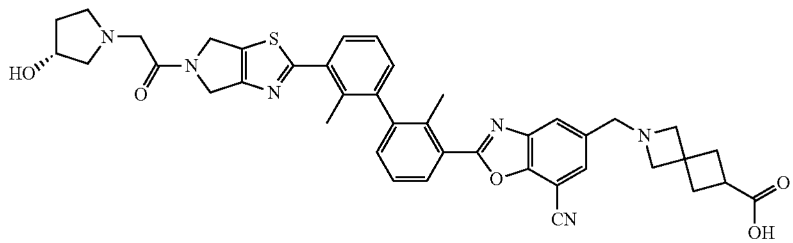 [SMILES: Cc1c(-c2nc3cc(CN4CC5(CC(C(=O)O)C5)C4)cc(C#N)c3o2)cccc1-c1cccc(-c2nc3c(s2)CN(C(=O)CN2CC[C@@H](O)C2)C3)c1C] | 729.4 |

The compounds in Table 12 were prepared in accordance with the synthetic protocols set forth in Example 221, using the appropriate starting materials.

TABLE 13

| Ex. No | Name | Structure | LCMS [M + H] |
|---|---|---|---|
| 235 | 2-((7-cyano-2-(3'-(5-(2-(dimethylamino)acetyl)-5,6-dihydro-4H-pyrrolo[3,4-d]thiazol-2-yl)-2,2'-dimethylbiphenyl-3-yl)benzo[d]oxazol-5-yl)methyl)-2-azabicyclo[2.1.1]hexane-4-carboxylic acid | 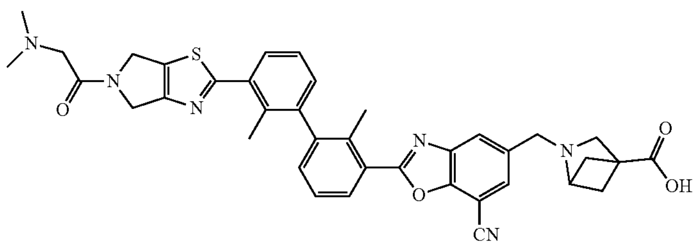 [SMILES: Cc1c(-c2nc3cc(CN4CC5(C(=O)O)CC4C5)cc(C#N)c3o2)cccc1-c1cccc(-c2nc3c(s2)CN(C(=O)CN(C)C)C3)c1C] | 673.3 |
| 236 | 1-((7-cyano-2-(3'-(5-(2-(dimethylamino)acetyl)-5,6-dihydro-4H-pyrrolo[3,4-d]thiazol-2-yl)-2,2'-dimethylbiphenyl-3-yl)benzo[d]oxazol-5-yl)methyl)piperidine-4-carboxylic acid | 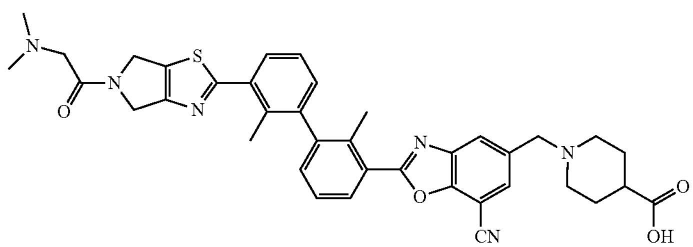 [SMILES: Cc1c(-c2nc3cc(CN4CCC(C(=O)O)CC4)cc(C#N)c3o2)cccc1-c1cccc(-c2nc3c(s2)CN(C(=O)CN(C)C)C3)c1C] | 675.4 |
| 237 | 2-((7-cyano-2-(3'-(5-(2-(dimethylamino)acetyl)-5,6-dihydro-4H-pyrrolo[3,4-d]thiazol-2-yl)-2,2'-dimethylbiphenyl-3-yl)benzo[d]oxazol-5-yl)methyl)-2-azabicyclo[2.2.1]heptane-5-carboxylic acid | 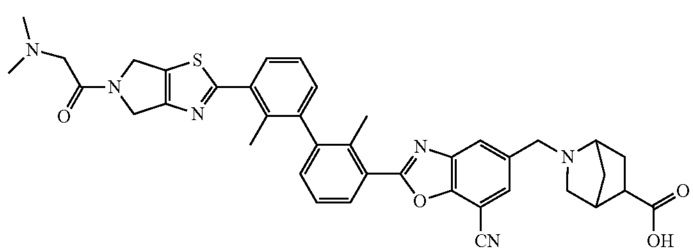 [SMILES: Cc1c(-c2nc3cc(CN4CC5CC4CC5C(=O)O)cc(C#N)c3o2)cccc1-c1cccc(-c2nc3c(s2)CN(C(=O)CN(C)C)C3)c1C] | 687.2 |

The compounds in Table 13 were prepared in accordance with the synthetic protocols set forth in Example 105, using the appropriate starting materials.

Example 238

(R)-1-((7-cyano-2-(3'-(5-isopropyl-4,5,6,7-tetrahy-drothiazolo[5,4-c]pyridin-2-yl)-2,2'-dimethyl-[1,1'-biphenyl]-3-yl)benzo[d]oxazol-5-yl)methyl)-N-(methylsulfonyl)pyrrolidine-3-carboxamide

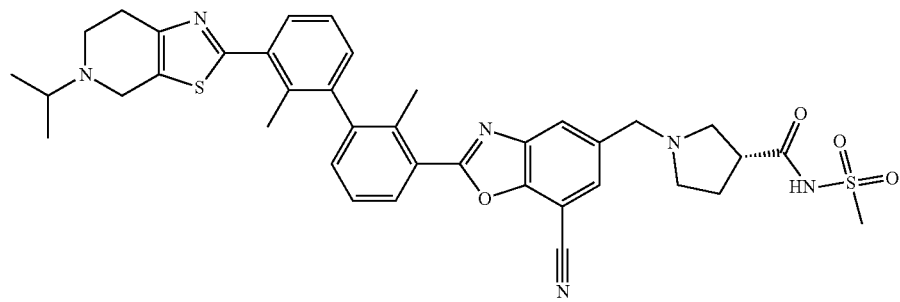 [SMILES: Cc1c(-c2nc3cc(CN4CC[C@@H](C(=O)NS(C)(=O)=O)C4)cc(C#N)c3o2)cccc1-c1cccc(-c2nc3c(s2)CN(C(C)C)CC3)c1C]

In a dram vial, (R)-1-((7-cyano-2-(3'-(5-isopropyl-4,5,6,7-tetrahydrothiazolo[5,4-c]pyridin-2-yl)-2,2'-dimethyl-[1,1'-biphenyl]-3-yl)benzo[d]oxazol-5-yl)methyl)pyrrolidine-3-carboxylic acid (Example 63, final product: 3 mg, 0.0048 mmol) and methanesulfonamide (2.2 mg, 0.024 mmol) were dissolved in DMF (0.3 mL). DMAP (2.9 mg, 0.024 mmol) and N,N'-dicyclohexylcarbodiimide (4.9 mg, 0.024 mmol) were added to the reaction mixture in one portion. After 16 h, the reaction mixture was diluted with MeOH then purified by prep-HPLC (pH=2, acetonitrile/water+TFA) to give the desired product as the TFA salt. LC-MS calculated for $C_{38}H_{41}N_6O_4S_2(M+H)^+$: m/z=709.3; found 709.2.

Example 239

1-((2-(2'-chloro-3'-(6-isopropyl-4,5,6,7-tetrahydro-2H-pyrazolo[3,4-c]pyridin-2-yl)-2-methylbiphenyl-3-yl)-7-cyanobenzo[d]oxazol-5-yl)methyl)azetidine-3-carboxylic acid

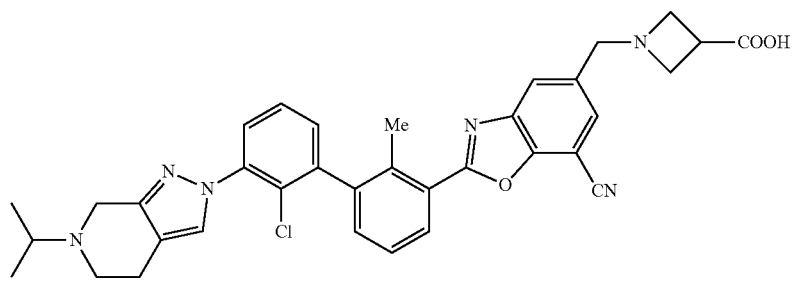 [SMILES: Cc1c(-c2nc3cc(CN4CC(C(=O)O)C4)cc(C#N)c3o2)cccc1-c1cccc(-n2cc3c(n2)CN(C(C)C)CC3)c1Cl]

423

Step 1: 1-((2-(2'-chloro-2-methyl-3'-(4,5,6,7-tetra-hydro-2H-pyrazolo[3,4-c]pyridin-2-yl)biphenyl-3-yl)-7-cyanobenzo[d]oxazol-5-yl)methyl)azetidine-3-carboxylic acid

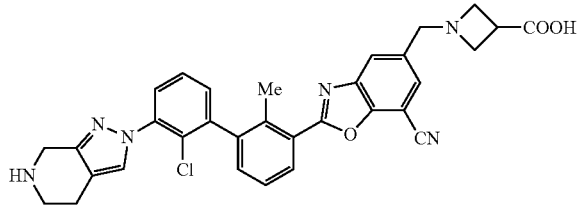 [SMILES: Cc1c(-c2nc3cc(CN4CC(C(=O)O)C4)cc(C#N)c3o2)cccc1-c1cccc(-n2cc3c(n2)CNCC3)c1Cl]

This compound was prepared using similar method in Example 54, Step 1-6 with tert-butyl 1,4,5,7-tetrahydro-6H-pyrazolo[3,4-c]pyridine-6-carboxylate (Astatech, cat #792-48) replacing tert-butyl 1,4,6,7-tetrahydro-5H-pyrazolo[4,3-c]pyridine-5-carboxylate in Step 1, and with azetidine-3-carboxylic acid replacing (R)-pyrrolidine-3-carboxylic acid in Step 5. The reaction mixture was concentrated and used in next step without further purification. LC-MS calculated for $C_{32}H_{28}ClN_6O_3(M+H)^+$: m/z=579.2; found 579.2.

424

Step 2: 1-((2-(2'-chloro-3'-(6-isopropyl-4,5,6,7-tetra-hydro-2H-pyrazolo[3,4-c]pyridin-2-yl)-2-methylbi-phenyl-3-yl)-7-cyanobenzo[d]oxazol-5-yl)methyl)azetidine-3-carboxylic acid A mixture of 1-((2-(2'-chloro-2-methyl-3'-(4,5,6,7-tetrahydro-2H-pyrazolo[3,4-c]pyridin-2-yl)biphenyl-3-yl)-7-cyanobenzo[d]oxazol-5-yl)methyl)azetidine-3-carboxylic acid (10 mg, 0.017 mmol) and acetone (2.4 µL, 0.034 mmol) in DCM (169 µl) was allowed to stir for 2 h. Then sodium triacetoxyborohydride (7.0 mg, 0.034 mmol) was added to the mixture. After 2 h, the mixture was concentrated and diluted with MeOH and then purified by prep-HPLC (pH=2, acetonitrile/water+TFA) to give the desired product as its TFA salt. LC-MS calculated for $C_{35}H_{34}ClN_6O_3(M+H)^+$: m/z=621.2; found 621.2.

Example 240

(R)-4-((2-(2-chloro-3'-(7-cyano-5-((3-hydroxypyrro-lidin-1-yl)methyl)benzo[d]oxazol-2-yl)-2'-methylbi-phenyl-3-ylcarbamoyl)-1-methyl-6,7-dihydro-1H-imidazo[4,5-c]pyridin-5(4H)-yl)methyl)phenylboronic acid

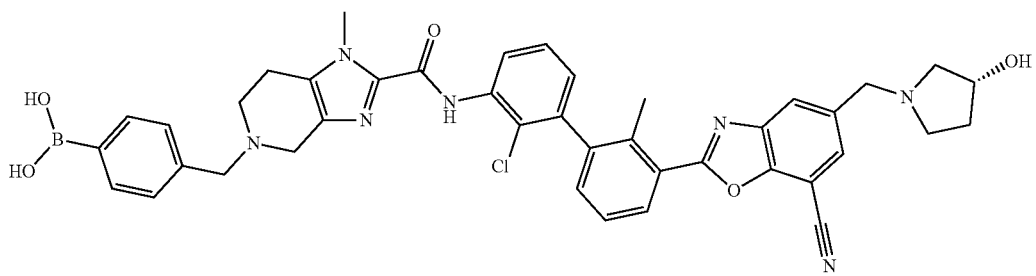 [SMILES: Cc1c(-c2nc3cc(CN4CC[C@@H](O)C4)cc(C#N)c3o2)cccc1-c1cccc(NC(=O)c2nc3c(n2C)CCN(Cc2ccc(B(O)O)cc2)C3)c1Cl]

Step 1: (R)—N-(2-chloro-3'-(7-cyano-5-((3-hy-droxypyrrolidin-1-yl)methyl)benzo[dd]oxazol-2-yl)-2'-methylbiphenyl-3-yl)-1-methyl-4,5,6,7-tetra-hydro-1H-imidazo[4,5-c]pyridine-2-carboxamide

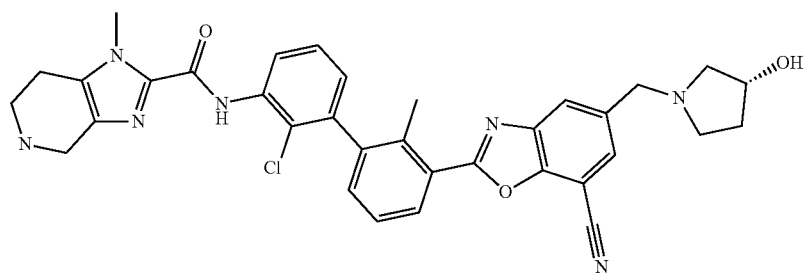 [SMILES: Cc1c(-c2nc3cc(CN4CC[C@@H](O)C4)cc(C#N)c3o2)cccc1-c1cccc(NC(=O)c2nc3c(n2C)CCNC3)c1Cl]

This compound was prepared using similar method in Example 92, Step 1-5 with (R)-pyrrolidin-3-ol replacing (S)-pyrrolidine-3-carboxylic acid in Step 5. The reaction mixture was concentrated and used in next step without further purification. LC-MS calculated for $C_{34}H_{33}ClN_7O_3$ $(M+H)^+$: m/z=622.2; found 622.3.

Step 2: (R)-4-((2-(2-chloro-3'-(7-cyano-5-((3-hydroxypyrrolidin-1-yl)methyl)benzo[d]oxazol-2-yl)-2'-methylbiphenyl-3-ylcarbamoyl)-1-methyl-6,7-dihydro-1H-imidazo[4,5-c]pyridin-5(4H)-yl)methyl)phenylboronic acid A mixture of (R)—N-(2-chloro-3'-(7-cyano-5-((3-hydroxypyrrolidin-1-yl)methyl)benzo[d]oxazol-2-yl)-2'-methylbiphenyl-3-yl)-1-methyl-4,5,6,7-tetrahydro-1H-imidazo[4,5-c]pyridine-2-carboxamide (10 mg, 0.017 mmol) and 4-formylphenylboronic acid (5.1 mg, 0.034 mmol) in DCM (169 µl) was allowed to stir for 2 h. Then sodium triacetoxyborohydride (7.0 mg, 0.034 mmol) was added to the mixture. After 2 h, the mixture was concentrated and diluted with MeOH and then purified by prep-HPLC (pH=2, acetonitrile/water+TFA) to give the desired product as its TFA salt. LC-MS calculated for $C_{41}H_{40}BClN_7O_5(M+H)^+$: m/z=756.3; found 756.3.

Example 241

(R)-1-((7-cyano-2-(3'-(5-(N-ethyl-N-methylglycyl)-5,6-dihydro-4H-pyrrolo[3,4-d]oxazol-2-yl)-2,2'-dimethyl-[1,1'-biphenyl]-3-yl)benzo[d]oxazol-5-yl)methyl)pyrrolidine-3-carboxylic acid

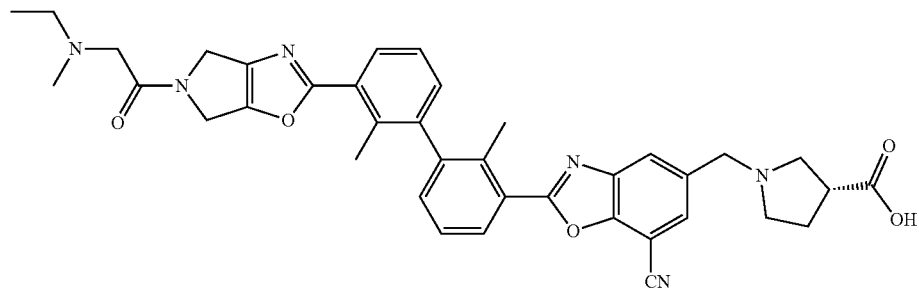 [SMILES: CCN(C)CC(=O)N1Cc2nc(-c3cccc(-c4cccc(-c5nc6cc(CN7CC[C@@H](C(=O)O)C7)cc(C#N)c6o5)c4C)c3C)oc2C1]

Step 1: 1-(2-(3-bromo-2-methylphenyl)-4,6-dihydro-5H-pyrrolo[3,4-d]oxazol-5-yl)-2-(ethyl(methyl)amino)ethan-1-one

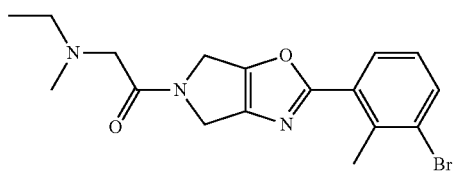 [SMILES: CCN(C)CC(=O)N1Cc2nc(-c3cccc(Br)c3C)oc2C1]

This compound was prepared using similar procedures as described for Example 126, Step 2 with N-methylethanamine replacing (R)-pyrrolidin-3-ol. LC-MS calculated for $C_{17}H_{21}BrN_3O_2(M+H)^+$: m/z=378.1, 380.1; found 378.1, 380.1.

Step 2: (R)-1-((7-cyano-2-(3'-(5-(N-ethyl-N-methylglycyl)-5,6-dihydro-4H-pyrrolo[3,4-d]oxazol-2-yl)-2,2'-dimethyl-[1,1'-biphenyl]-3-yl)benzo[d]oxazol-5-yl)methyl)pyrrolidine-3-carboxylic acid This compound was prepared using similar procedures as described for Example 126, Step 6 with 1-(2-(3-bromo-2-methylphenyl)-4,6-dihydro-5H-pyrrolo[3,4-d]oxazol-5-yl)-2-(ethyl(methyl)amino)ethan-1-one replacing (R)-1-(2-(3-bromo-2-methylphenyl)-4,6-dihydro-5H-pyrrolo[3,4-d]oxazol-5-yl)-2-(3-hydroxypyrrolidin-1-yl)ethan-1-one. The reaction mixture was purified by prep-HPLC (pH=2, acetonitrile/water+TFA) to give the desired product as TFA salt. LC-MS calculated for $C_{38}H_{39}N_6O_5$ $(M+H)^+$: m/z=659.3; found 659.3. $^1$H NMR (600 MHz, DMSO) δ 8.38 (s, 1H), 8.21 (dd, J=7.9, 1.2 Hz, 1H), 8.13 (d, J=1.2 Hz, 1H), 8.02-7.95 (m, 1H), 7.59 (t, J=7.7 Hz, 1H), 7.50 (t, J=7.7 Hz, 1H), 7.48-7.46 (m, 1H), 7.36 (d, J=7.6 Hz, 1H), 4.85 (s, 1H), 4.77-4.62 (m, 3H), 4.61-4.48 (m, 3H), 4.38-4.16 (m, 2H), 3.90-3.08 (m, 6H), 2.83 (s, 3H), 2.42 (s, 3H), 2.33 (d, J=3.3 Hz, 3H), 2.26-2.01 (m, 2H), 1.26 (t, J=7.3 Hz, 3H).

Example 242

2-((7-cyano-2-(3'-(5-(N-ethyl-N-methylglycyl)-5,6-dihydro-4H-pyrrolo[3,4-d]oxazol-2-yl)-2,2'-dimethyl-[1,1'-biphenyl]-3-yl)benzo[d]oxazol-5-yl)methyl)-2-azabicyclo[2.1.1]hexane-4-carboxylic acid

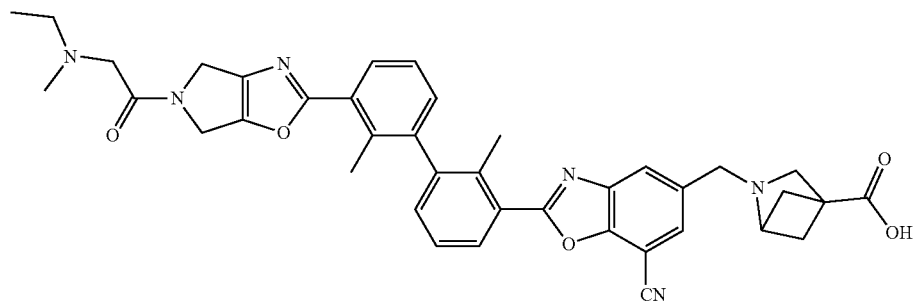 [SMILES: CCN(C)CC(=O)N1Cc2nc(-c3cccc(-c4cccc(-c5nc6cc(CN7CC8(C(=O)O)CC7C8)cc(C#N)c6o5)c4C)c3C)oc2C1]

Step 1: 2-(3'-(5-(N-ethyl-N-methylglycyl)-5,6-dihydro-4H-pyrrolo[3,4-d]oxazol-2-yl)-2,2'-dimethyl-[1,1'-biphenyl]-3-yl)-5-(hydroxymethyl)benzo[d]oxazole-7-carbonitrile

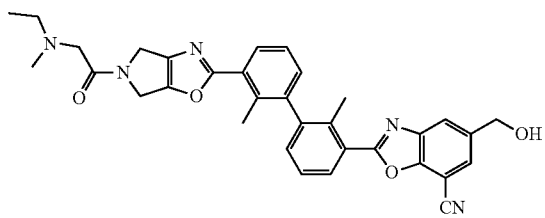 [SMILES: CCN(C)CC(=O)N1Cc2nc(-c3cccc(-c4cccc(-c5nc6cc(CO)cc(C#N)c6o5)c4C)c3C)oc2C1]

This compound was prepared using similar procedures as described for Example 122, Step 8 with 1-(2-(3-bromo-2-methylphenyl)-4,6-dihydro-5H-pyrrolo[3,4-d]oxazol-5-yl)-2-(ethyl(methyl)amino)ethan-1-one (Example 241, Step 1) replacing 1-(2-(3-bromo-2-methylphenyl)-4,6-dihydro-5H-pyrrolo[3,4-d]oxazol-5-yl)-2-(dimethylamino)ethan-1-one. LC-MS calculated for $C_{33}H_{32}N_5O_4$ $(M+H)^+$: m/z=562.2; found 562.2.

Step 2: 2-(3'-(5-(N-ethyl-N-methylglycyl)-5,6-dihydro-4H-pyrrolo[3,4-d]oxazol-2-yl)-2,2'-dimethyl-[1,1'-biphenyl]-3-yl)-5-formylbenzo[d]oxazole-7-carbonitrile

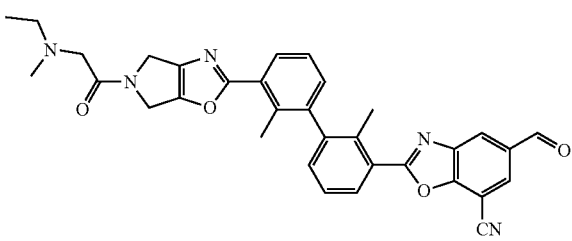 [SMILES: CCN(C)CC(=O)N1Cc2nc(-c3cccc(-c4cccc(-c5nc6cc(C=O)cc(C#N)c6o5)c4C)c3C)oc2C1]

This compound was prepared using similar procedures as described for Example 122, Step 9 with 2-(3'-(5-(N-ethyl-N-methylglycyl)-5,6-dihydro-4H-pyrrolo[3,4-d]oxazol-2-yl)-2,2'-dimethyl-[1,1'-biphenyl]-3-yl)-5-(hydroxymethyl)benzo[d]oxazole-7-carbonitrile replacing 2-(3'-(5-(dimethylglycyl)-5,6-dihydro-4H-pyrrolo[3,4-d]oxazol-2-yl)-2,2'-dimethyl-[1,1'-biphenyl]-3-yl)-5-(hydroxymethyl)benzo[d]oxazole-7-carbonitrile. LC-MS calculated for $C_{33}H_{30}N_5O_4$ $(M+H)^+$: m/z=560.2; found 560.2.

Step 3: 2-((7-cyano-2-(3'-(5-(N-ethyl-N-methylglycyl)-5,6-dihydro-4H-pyrrolo[3,4-d]oxazol-2-yl)-2,2'-dimethyl-[1,1'-biphenyl]-3-yl)benzo[d]oxazol-5-yl)methyl)-2-azabicyclo[2.1.1]hexane-4-carboxylic acid To a mixture of 2-(3'-(5-(N-ethyl-N-methylglycyl)-5,6-dihydro-4H-pyrrolo[3,4-d]oxazol-2-yl)-2,2'-dimethyl-[1,1'-biphenyl]-3-yl)-5-formylbenzo[d]oxazole-7-carbonitrile (10.0 mg, 0.018 mmol), 2-(tert-butoxycarbonyl)-2-azabicyclo[2.1.1]hexane-4-carboxylic acid (4.1 mg, 0.018 mmol) in DCM (0.5 ml) was added DIEA (3.2 µl, 0.018 mmol). After stirring at room temperature for 2.5 h, sodium triacetoxyborohydride (7.6 mg, 0.036 mmol) was added and the reaction mixture was stirred overnight. After removal of solvent, the residue was dissolved in methanol and water and purified by prep-HPLC (pH=2, acetonitrile/water+TFA) to give the desired product as TFA salt. LC-MS calculated for $C_{39}H_{39}N_6O_5$ $(M+H)^+$: m/z=671.3; found 671.3.

TABLE 14

| Ex. No. | Name/¹HNMR | Structure | LCMS [M + H] |
|---|---|---|---|
| 243 | (R)-1-((7-cyano-2-(3'-(5-(N-ethyl-N-methylglycyl)-5,6-dihydro-4H-pyrrolo[3,4-d]oxazol-2-yl)-2,2'-dimethyl-[1,1'-biphenyl]-3-yl)benzo[d]oxazol-5-yl)methyl)-3-methylpyrrolidine-3-carboxylic acid ¹H NMR (500 MHz, DMSO) δ 8.39 (s, 1H), 8.21 (d, J = 6.9 Hz, 1H), 8.13 (s, 1H), 7.98 (t, J = 7.2 Hz, 1H), 7.59 (t, J = 7.7 Hz, 1H), 7.50 (t, J = 7.8 Hz, 1H), 7.47 (d, J = 6.9 Hz, 1H), 7.36 (d, J = 7.6 Hz, 1H), 4.85 (s, 1H), 4.72 (s, 1H), 4.66 (s, 1H), 4.58 (s, 2H), 4.54 (s, 1H), 4.38-4.15 (m, 2H), 3.87-3.36 (m, 4H), 3.30-3.07 (m, 2H), 2.83 (s, 3H), 2.49-2.31 (m, 1H), 2.42 (s, 3H), 2.33 (s, 3H), 2.12-1.76 (m, 1H), 1.44-1.30 (m, 3H), 1.26 (t, J = 7.3 Hz, 3H). | 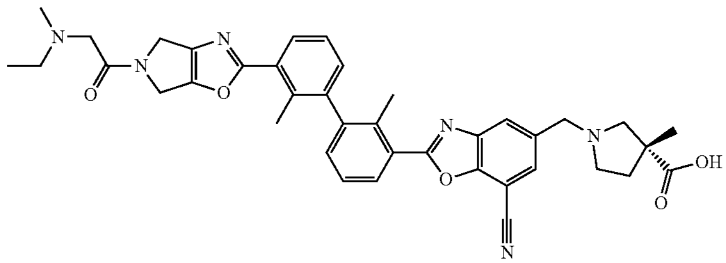 [SMILES: CCN(C)CC(=O)N1Cc2nc(-c3cccc(-c4cccc(-c5nc6cc(CN7CC[C@@](C)(C(=O)O)C7)cc(C#N)c6o5)c4C)c3C)oc2C1] | 673.3 |
| 244 | 1-((7-cyano-2-(3'-(5-(N-ethyl-N-methylglycyl)-5,6-dihydro-4H-pyrrolo[3,4-d]oxazol-2-yl)-2,2'-dimethyl-[1,1'-biphenyl]-3-yl)benzo[d]oxazol-5-yl)methyl)piperidine-4-carboxylic acid | 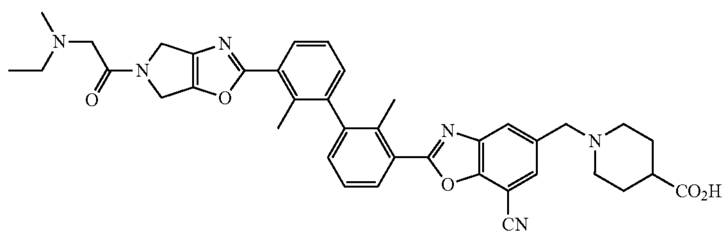 [SMILES: CCN(C)CC(=O)N1Cc2nc(-c3cccc(-c4cccc(-c5nc6cc(CN7CCC(C(=O)O)CC7)cc(C#N)c6o5)c4C)c3C)oc2C1] | 673.3 |
| 245 | (R)-1-((7-cyano-2-(3'-(5-(dimethylglycyl)-5,6-dihydro-4H-pyrrolo[3,4-d]oxazol-2-yl)-2,2'-dimethyl-[1,1'-biphenyl]-3-yl)benzo[d]oxazol-5-yl)methyl)-3-methylpyrrolidine-3-carboxylic acid | 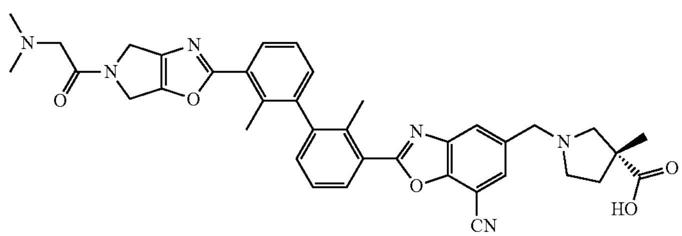 [SMILES: Cc1c(-c2nc3c(o2)CN(C(=O)CN(C)C)C3)cccc1-c1cccc(-c2nc3cc(CN4CC[C@@](C)(C(=O)O)C4)cc(C#N)c3o2)c1C] | 659.3 |
| 246 | 1-((7-cyano-2-(3'-(5-(dimethylglycyl)-5,6-dihydro-4H-pyrrolo[3,4-d]oxazol-2-yl)-2,2'-dimethyl-[1,1'-biphenyl]-3-yl)benzo[d]oxazol-5-yl)methyl)piperidine-4-carboxylic acid | 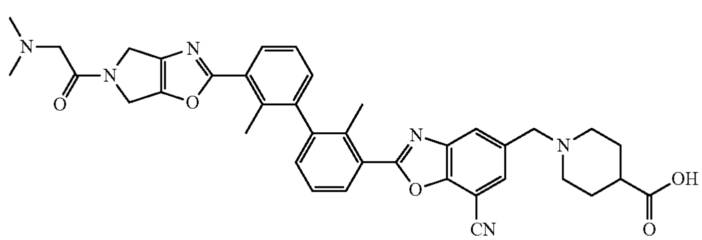 [SMILES: Cc1c(-c2nc3c(o2)CN(C(=O)CN(C)C)C3)cccc1-c1cccc(-c2nc3cc(CN4CCC(C(=O)O)CC4)cc(C#N)c3o2)c1C] | 659.3 |
| 247 | (R)-1-((7-cyano-2-(3'-(5-(2-((R)-3-hydroxypyrrolidin-1-yl)acetyl)-5,6-dihydro-4H-pyrrolo[3,4-d]oxazol-2-yl)-2,2'-dimethyl-[1,1'-biphenyl]-3-yl)benzo[d]oxazol-5-yl)methyl)-3-methylpyrrolidine-3-carboxylic acid | 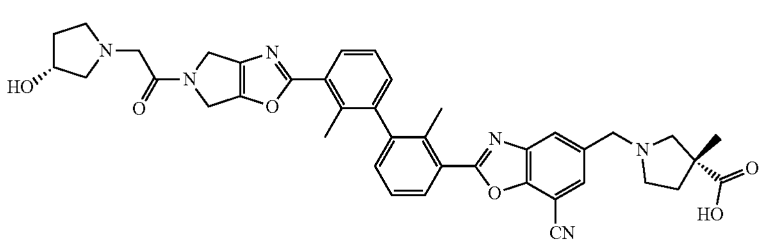 [SMILES: Cc1c(-c2nc3c(o2)CN(C(=O)CN2CC[C@@H](O)C2)C3)cccc1-c1cccc(-c2nc3cc(CN4CC[C@@](C)(C(=O)O)C4)cc(C#N)c3o2)c1C] | 701.3 |

TABLE 14-continued

| Ex. No. | Name/¹HNMR | Structure | LCMS [M + H] |
|---|---|---|---|
| 248 | (R)-1-((7-cyano-2-(3'-(5-(N-isopropyl-N-methylglycyl)-5,6-dihydro-4H-pyrrolo[3,4-d]oxazol-2-yl)-2,2'-dimethyl-[1,1'-biphenyl]-3-yl)benzo[d]oxazol-5-yl)methyl)-3-methylpyrrolidine-3-carboxylic acid | 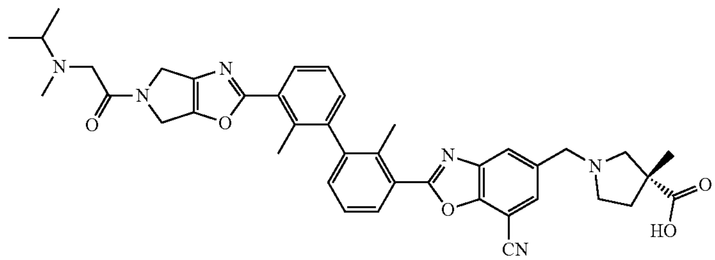 [SMILES: Cc1c(-c2nc3c(o2)CN(C(=O)CN(C)C(C)C)C3)cccc1-c1cccc(-c2nc3cc(CN4CC[C@@](C)(C(=O)O)C4)cc(C#N)c3o2)c1C] | 687.3 |
| 249 | (R)-1-((7-cyano-2-(3'-(5-(2-(4-hydroxypiperidin-1-yl)acetyl)-5,6-dihydro-4H-pyrrolo[3,4-d]oxazol-2-yl)-2,2'-dimethyl-[1,1'-biphenyl]-3-yl)benzo[d]oxazol-5-yl)methyl)-3-methylpyrrolidine-3-carboxylic acid | 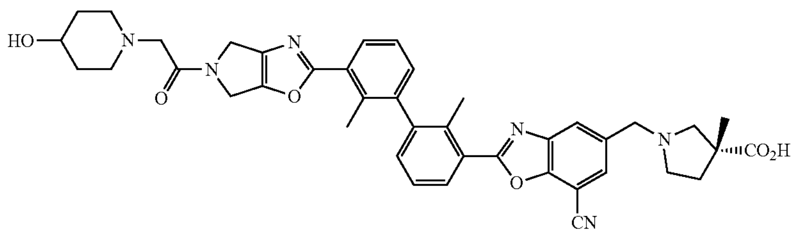 [SMILES: Cc1c(-c2nc3c(o2)CN(C(=O)CN2CCC(O)CC2)C3)cccc1-c1cccc(-c2nc3cc(CN4CC[C@@](C)(C(=O)O)C4)cc(C#N)c3o2)c1C] | 715.3 |
| 250 | (R)-1-((7-cyano-2-(3'-(5-(2-(4-hydroxypiperidin-1-yl)acetyl)-5,6-dihydro-4H-pyrrolo[3,4-d]oxazol-2-yl)-2,2'-dimethyl-[1,1'-biphenyl]-3-yl)benzo[d]oxazol-5-yl)methyl)pyrrolidine-3-carboxylic acid | 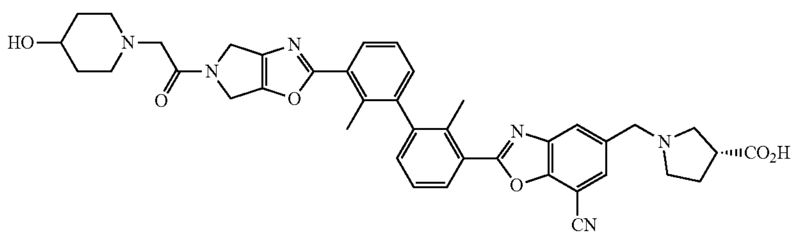 [SMILES: Cc1c(-c2nc3c(o2)CN(C(=O)CN2CCC(O)CC2)C3)cccc1-c1cccc(-c2nc3cc(CN4CC[C@@H](C(=O)O)C4)cc(C#N)c3o2)c1C] | 701.3 |
| 251 | 2-((7-cyano-2-(3'-(5-(2-(4-hydroxypiperidin-1-yl)acetyl)-5,6-dihydro-4H-pyrrolo[3,4-d]oxazol-2-yl)-2,2'-dimethyl-[1,1'-biphenyl]-3-yl)benzo[d]oxazol-5-yl)methyl)-2-azabicyclo[2.2.1]heptane-5-carboxylic acid | 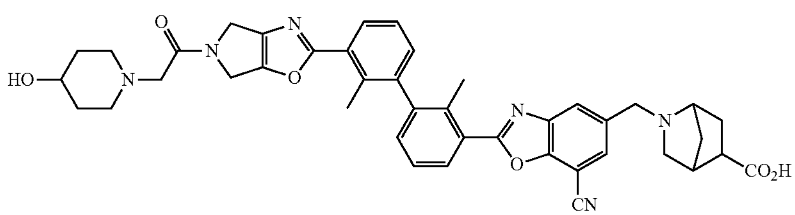 [SMILES: Cc1c(-c2nc3c(o2)CN(C(=O)CN2CCC(O)CC2)C3)cccc1-c1cccc(-c2nc3cc(CN4CC5CC4CC5C(=O)O)cc(C#N)c3o2)c1C] | 727.3 |
| 252 | (R)-1-((7-cyano-2-(3'-(5-(N-(2-hydroxyethyl)-N-methylglycyl)-5,6-dihydro-4H-pyrrolo[3,4-d]oxazol-2-yl)-2,2'-dimethyl-[1,1'-biphenyl]-3-yl)benzo[d]oxazol-5-yl)methyl)-3-methylpyrrolidine-3-carboxylic acid | 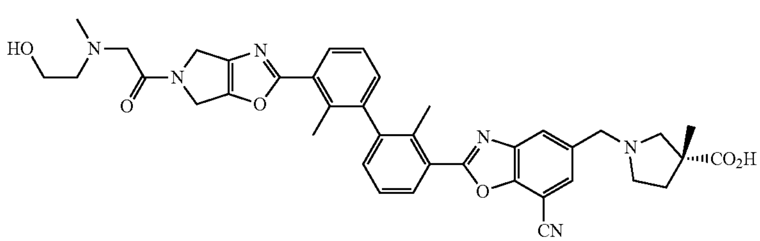 [SMILES: Cc1c(-c2nc3c(o2)CN(C(=O)CN(C)CCO)C3)cccc1-c1cccc(-c2nc3cc(CN4CC[C@@](C)(C(=O)O)C4)cc(C#N)c3o2)c1C] | 689.3 |
| 253 | 2-((7-cyano-2-(2,2'-dimethyl-3'-(5-(2-(4-methylpiperazin-1-yl)acetyl)-5,6-dihydro-4H-pyrrolo[3,4-d]oxazol-2-yl)-[1,1'-biphenyl]-3-yl)benzo[d]oxazol-5-yl)methyl)-2-azabicyclo[2.2.1]heptane-5-carboxylic acid | 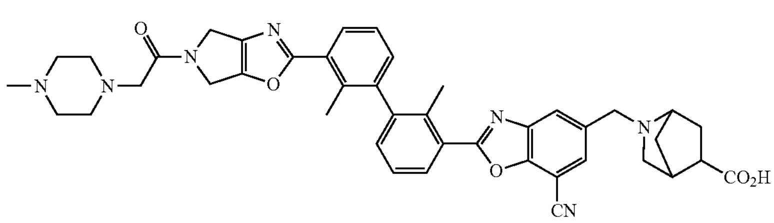 [SMILES: Cc1c(-c2nc3c(o2)CN(C(=O)CN2CCN(C)CC2)C3)cccc1-c1cccc(-c2nc3cc(CN4CC5CC4CC5C(=O)O)cc(C#N)c3o2)c1C] | 726.3 |

TABLE 14-continued

| Ex. No. | Name/¹HNMR | Structure | LCMS [M + H] |
|---|---|---|---|
| 254 | (R)-1-((7-cyano-2-(2,2'-dimethyl-3'-(5-(2-(4-methylpiperazin-1-yl)acetyl)-5,6-dihydro-4H-pyrrolo[3,4-d]oxazol-2-yl)-[1,1'-biphenyl]-3-yl)benzo[d]oxazol-5-yl)methyl)-3-methylpyrrolidine-3-carboxylic acid | 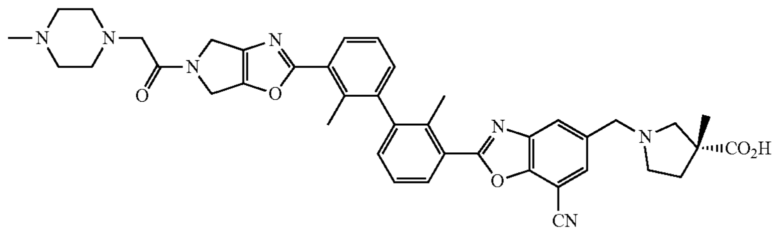 [SMILES: Cc1c(-c2nc3c(o2)CN(C(=O)CN2CCN(C)CC2)C3)cccc1-c1cccc(-c2nc3cc(CN4CC[C@@](C)(C(=O)O)C4)cc(C#N)c3o2)c1C] | 714.3 |
| 255 | (3R)-1-((7-cyano-2-(2,2'-dimethyl-3'-(5-(2-(5-methyl-2,5-diazabicyclo[2.2.1]heptan-2-yl)acetyl)-5,6-dihydro-4H-pyrrolo[3,4-d]oxazol-2-yl)biphenyl-3-yl)benzo[d]oxazol-5-yl)methyl)pyrrolidine-3-carboxylic acid | 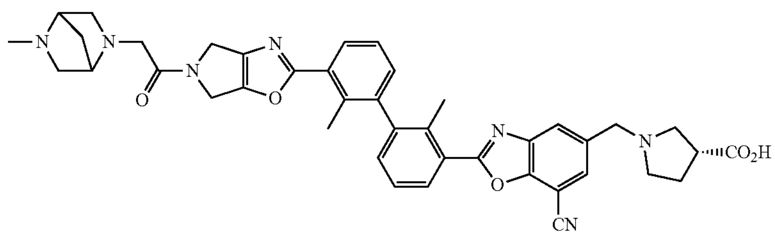 [SMILES: Cc1c(-c2nc3c(o2)CN(C(=O)CN2CC4CC2CN4C)C3)cccc1-c1cccc(-c2nc3cc(CN4CC[C@@H](C(=O)O)C4)cc(C#N)c3o2)c1C] | 712.3 |

The compounds in Table 14 were prepared in accordance with the synthetic protocols set forth in Example 242, using the appropriate starting materials.

Example 256

(R)-1-((2-(2'-chloro-3'-(5-(2-((R)-3-hydroxypyrrolidin-1-yl)acetyl)-5,6-dihydro-4H-pyrrolo[3,4-d]oxazol-2-yl)-2-methyl-[1,1'-biphenyl]-3-yl)-7-cyanobenzo[d]oxazol-5-yl)methyl)pyrrolidine-3-carboxylic acid

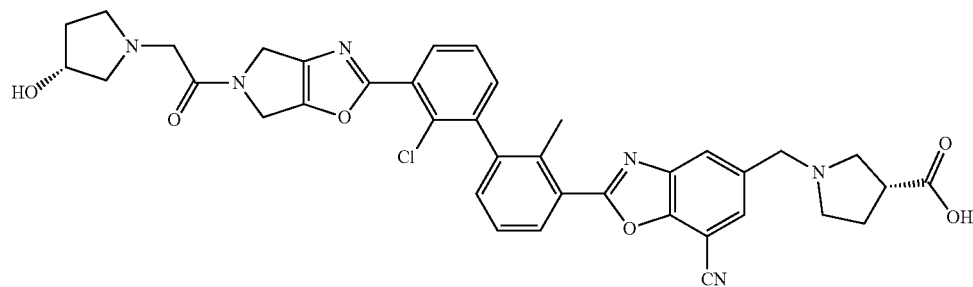 [SMILES: Cc1c(-c2nc3cc(CN4CC[C@@H](C(=O)O)C4)cc(C#N)c3o2)cccc1-c1cccc(-c2nc3c(o2)CN(C(=O)CN2CC[C@@H](O)C2)C3)c1Cl]

Step 1: 2-(3-bromo-2-chlorophenyl)-5,6-dihydro-4H-pyrrolo[3,4-d]oxazole

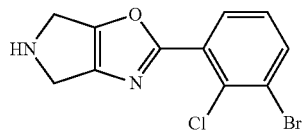

This compound was prepared using similar procedures as described for Example 122, Step 1-6, with 3-bromo-2-chlorobenzoic acid replacing 3-bromo-2-methylbenzoic acid in Step 3. LC-MS calculated for $C_{11}H_9BrClN_2O$ (M+H)⁺: m/z=299.0, 301.0; found 299.0, 301.0.

Step 2: 1-(2-(3-bromo-2-chlorophenyl)-4,6-dihydro-5H-pyrrolo[3,4-d]oxazol-5-yl)-2-chloroethan-1-one

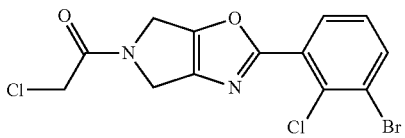 [SMILES: O=C(CCl)N1Cc2nc(-c3cccc(Br)c3Cl)oc2C1]

This compound was prepared using similar procedures as described for Example 126, Step 1 with 2-(3-bromo-2-chlorophenyl)-5,6-dihydro-4H-pyrrolo[3,4-d]oxazole replacing 2-(3-bromo-2-methylphenyl)-5,6-dihydro-4H-pyrrolo[3,4-d]oxazole. LC-MS calculated for $C_{13}H_{10}BrCl_2N_2O_2$ (M+H)⁺: m/z=374.9, 376.9; found 374.9, 376.9.

Step 3: (R)-1-(2-(3-bromo-2-chlorophenyl)-4,6-dihydro-5H-pyrrolo[3,4-d]oxazol-5-yl)-2-(3-hydroxypyrrolidin-1-yl)ethan-1-one

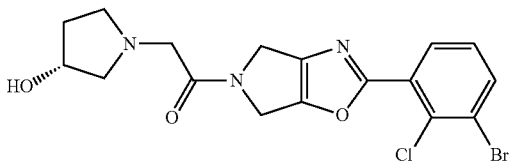 [SMILES: O=C(CN1CC[C@@H](O)C1)N1Cc2nc(-c3cccc(Br)c3Cl)oc2C1]

The mixture of 1-(2-(3-bromo-2-chlorophenyl)-4,6-dihydro-5H-pyrrolo[3,4-d]oxazol-5-yl)-2-chloroethan-1-one (154 mg, 0.410 mmol), (R)-pyrrolidin-3-ol (35.7 mg, 0.410 mmol), TEA (0.171 ml, 1.229 mmol) and DMF (1.0 ml) was heated at 60° C. for 2 h. The reaction mixture was diluted with methanol and 1 N HCl and purified with prep-LCMS (pH=2, acetonitrile/water+TFA) to give the desired product (165 mg, 94%). LC-MS calculated for $C_{17}H_{18}BrClN_3O_3$ (M+H)$^+$: m/z=426.0, 428.0; found 426.0, 428.0.

Step 4: (R)-1-((2-(2'-chloro-3'-(5-(2-((R)-3-hydroxypyrrolidin-1l-yl)acetyl)-5,6-dihydro-4H-pyrrolo[3,4-d]oxazol-2-yl)-2-methyl-[1,1'-biphenyl]-3-yl)-7-cyanobenzo[d]oxazol-5-yl)methyl)pyrrolidine-3-carboxylic acid This compound was prepared using similar procedures as described for Example 126, Step 6 with (R)-1-(2-(3-bromo-2-chlorophenyl)-4,6-dihydro-5H-pyrrolo[3,4-d]oxazol-5-yl)-2-(3-hydroxypyrrolidin-1-yl)ethan-1-one replacing (R)-1-(2-(3-bromo-2-methylphenyl)-4,6-dihydro-5H-pyrrolo[3,4-d]oxazol-5-yl)-2-(3-hydroxypyrrolidin-1-yl)ethan-1-one. The reaction mixture was purified by prep-HPLC (pH=2, acetonitrile/water+TFA) to give the desired product as TFA salt. LC-MS calculated for $C_{38}H_{36}ClN_6O_6$ (M+H)$^+$: m/z=707.2; found 707.2.

TABLE 15

| Ex. No. | Name | Structure | LCMS [M + H] |
|---|---|---|---|
| 257 | (R)-1-((7-cyano-2-(3'-(3-(((S)-1-hydroxypropan-2-ylamino)methyl)-1,7-naphthyridin-8-ylamino)-2,2'-dimethylbiphenyl-3-yl)benzo[d]oxazol-5-yl)methyl)pyrrolidine-3-carboxylic acid | 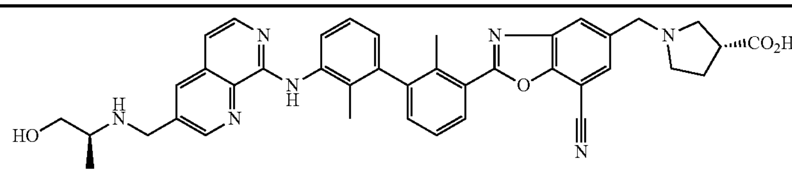 | 682.2 |
| 258 | (R)-1-((7-cyano-2-(3'-(3-(((R)-1-hydroxypropan-2-ylamino)methyl)-1,7-naphthyridin-8-ylamino)-2,2'-dimethylbiphenyl-3-yl)benzo[d]oxazol-5-yl)methyl)pyrrolidine-3-carboxylic acid | 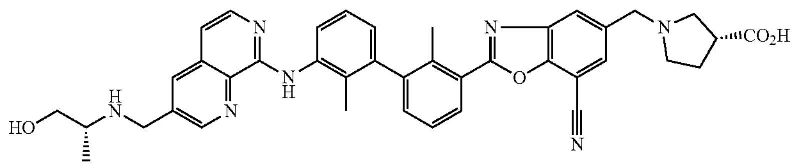 [SMILES: Cc1c(Nc2nccc3cc(CN[C@H](C)CO)cnc23)cccc1-c1cccc(-c2nc3cc(CN4CC[C@@H](C(=O)O)C4)cc(C#N)c3o2)c1C] | 682.2 |

The compounds in Table 15 were prepared in accordance with the syntheticprotocols set forth in Example 146, using the appropriate amino alcohols.

TABLE 16

| Ex. No. | Name | Structure | LCMS [M + H] |
|---|---|---|---|
| 259 | 1-((7-cyano-2-(3'-(1,5-dimethyl-4,5,6,7-tetrahydro-1H-imidazo[4,5-c]pyridine-2-carboxamido)-2,2'-dimethylbiphenyl-3-yl)benzo[d]oxazol-5-yl)methyl)piperidine-4-carboxylic acid | 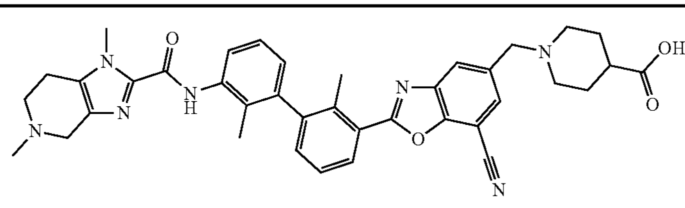 | 658.3 |
| 260 | (R)-1-((7-cyano-2-(3'-(1,5-dimethyl-4,5,6,7-tetrahydro-1H-imidazo[4,5-c]pyridine-2-carboxamido)-2,2'-dimethylbiphenyl-3-yl)benzo[d]oxazol-5-yl)methyl)-3-methylpyrrolidine-3-carboxylic acid | 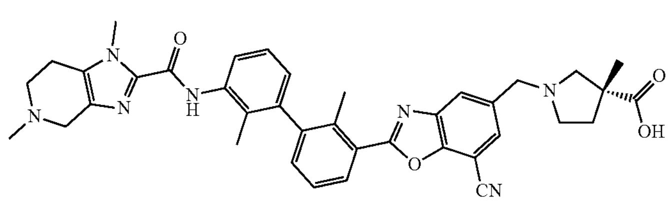 [SMILES: Cc1c(NC(=O)c2nc3c(n2C)CCN(C)C3)cccc1-c1cccc(-c2nc3cc(CN4CC[C@@](C)(C(=O)O)C4)cc(C#N)c3o2)c1C] | 658.3 |

The compounds in Table 16 were prepared in accordance with the synthetic protocols set forth in Example 36, using the appropriate starting materials.

Example 261 trans-4-((2-(2-chloro-3'-(7-cyano-5-(((R)-3-hydroxy-pyrrolidin-1-yl)methyl)benzo[d]oxazol-2-yl)-2'-methylbiphenyl-3-ylcarbamoyl)-1-methyl-6,7-dihydro-1H-imidazo[4,5-c]pyridin-5(4H)-yl)methyl)cyclohexanecarboxylic acid

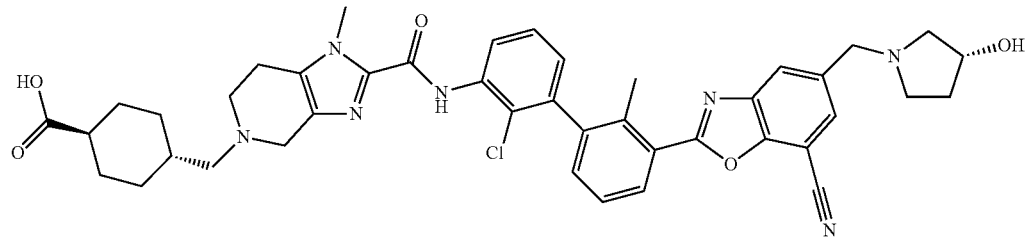 [SMILES: Cc1c(-c2nc3cc(CN4CC[C@@H](O)C4)cc(C#N)c3o2)cccc1-c1cccc(NC(=O)c2nc3c(n2C)CCN(C[C@H]2CC[C@H](C(=O)O)CC2)C3)c1Cl]

Step 1: (R)—N-(2-chloro-3'-(7-cyano-5-((3-hydroxypyrrolidin-1-yl)methyl)benzo([d]oxazol-2-yl)-2'-methylbiphenyl-3-yl)-1-methyl-4,5,6,7-tetrahydro-1H-imidazo[4,5-c]pyridine-2-carboxamide

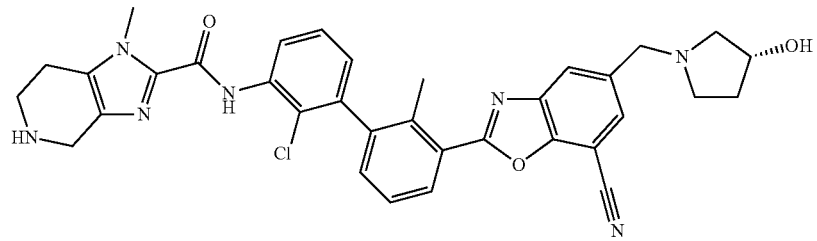 [SMILES: Cc1c(-c2nc3cc(CN4CC[C@@H](O)C4)cc(C#N)c3o2)cccc1-c1cccc(NC(=O)c2nc3c(n2C)CCNC3)c1Cl]

This compound was prepared using similar procedures as described for Example 92 with (R)-pyrrolidin-3-ol replacing (S)-pyrrolidine-3-carboxylic acid in Step 4. LC-MS calculated for $C_{34}H_{33}ClN_7O_3(M+H)^+$: m/z=622.1; found 622.2.

Step 2: trans-4-((2-(2-chloro-3'-(7-cyano-5-(((R)-3-hydroxypyrrolidin-1-yl)methyl)benzo[d]oxazol-2-yl)-2'-methylbiphenyl-3-ylcarbamoyl)-1-methyl-6,7-dihydro-1H-imidazo[4,5-c]pyridin-5(4H)-yl)methyl)cyclohexanecarboxylic acid To a solution of (R)—N-(2-chloro-3'-(7-cyano-5-((3-hydroxypyrrolidin-1-yl)methyl)benzo[d]oxazol-2-yl)-2'-methylbiphenyl-3-yl)-1-methyl-4,5,6,7-tetrahydro-1H-imidazo[4,5-c]pyridine-2-carboxamide (40 mg, 0.064 mmol) in DCM (5 ml) was added methyl trans-4-formylcyclohexane-1-carboxylate (22 mg, 0.13 mmol) and DIEA (0.034 mL, 0.193 mmol). The mixture was stirred at r.t. for 60 min. Then sodium triacetoxyborohydride (41 mg, 0.19 mmol) was added. The reaction mixture was continued to stir at r.t. overnight. The reaction mixture was diluted with DCM, washed by NaHCO$_3$ aqueous solution, water, and brine. The organic phase was dried over Na$_2$SO$_4$, filtered and concentrated under reduced pressure. To a solution of above residue in THF (2 mL) was added lithium hydroxide (6.2 mg, 0.26 mmol) and a few drops of water. The reaction mixture was stirred at 40° C. for two days. The reaction mixture was diluted with MeCN/water, and purified via prep-HPLC (pH=2, MeCN/water with TFA) to give the desired product as the TFA salt. LC-MS calculated for $C_{42}H_{45}ClN_7O_5(M+H)^+$: m/z=762.3; found 762.2. $^1$H NMR (500 MHz, DMSO) δ 9.94 (s, 1H), 8.40 (s, 1H), 8.30 (d, J=8.3 Hz, 1H), 8.21 (d, J=7.9 Hz, 1H), 8.14 (s, 1H), 7.59 (t, J=7.8 Hz, 1H), 7.52 (t, J=7.9 Hz, 1H), 7.48 (d, J=6.8 Hz, 1H), 7.20 (dd, J=7.6, 1.4 Hz, 1H), 4.67-4.15 (m, 5H), 3.95 (s, 3H), 3.87-2.95 (m, 10H), 2.46 (s, 3H), 2.33-2.22 (m, 1H), 2.15 (t, J=12.2 Hz, 1H), 2.03-1.94 (m, 1H), 1.94-1.74 (m, 5H), 1.47-1.24 (m, 2H), 1.09-0.90 (m, 2H).

TABLE 17

| Ex. No. | Name | Structure | LCMS [M + H] |
|---|---|---|---|
| 262 | (R)-3-((2-(2-chloro-3'-(7-cyano-5-((3-hydroxypyrrolidin-1-yl)methyl)benzo[d]oxazol-2-yl)-2'-methylbiphenyl-3-ylcarbamoyl)-1-methyl-6,7-dihydro-1H-imidazo[4,5-c]pyridin-5(4H)-yl)methyl)bicyclo[1.1.1]pentane-1-carboxylic acid | 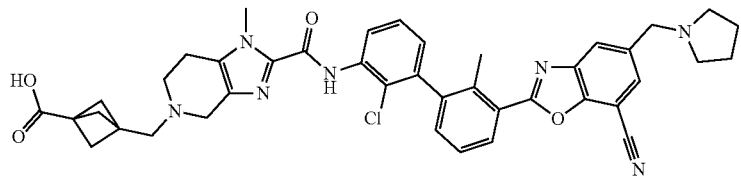 | 746.2 |

TABLE 17-continued

| Ex. No. | Name | Structure | LCMS [M + H] |
|---|---|---|---|
| 263 | (R)-3-(2-(2-chloro-3'-(7-cyano-5-((3-hydroxypyrrolidin-1-yl)methyl)benzo[d]oxazol-2-yl)-2'-methylbiphenyl-3-ylcarbamoyl)-1-methyl-6,7-dihydro-1H-imidazo[4,5-c]pyridin-5(4H)-yl)-1-methylcyclobutanecarboxylic acid | 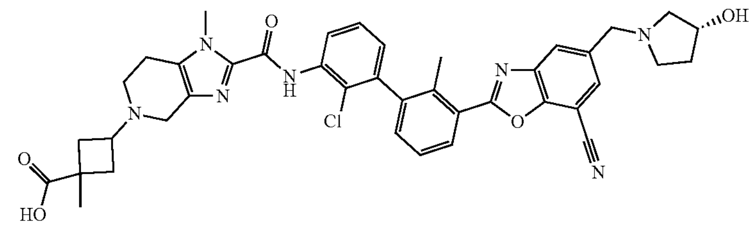 [SMILES: Cc1c(-c2nc3cc(CN4CC[C@@H](O)C4)cc(C#N)c3o2)cccc1-c1cccc(NC(=O)c2nc3c(n2C)CCN(C2CC(C)(C(=O)O)C2)C3)c1Cl] | 734.2 |
| 264 | 4-(2-(2-chloro-3'-(7-cyano-5-(((R)-3-hydroxypyrrolidin-1-yl)methyl)benzo[d]oxazol-2-yl)-2'-methylbiphenyl-3-ylcarbamoyl)-1-methyl-6,7-dihydro-1H-imidazo[4,5-c]pyridin-5(4H)-yl)-1-methylcyclobutanecarboxylic acid | 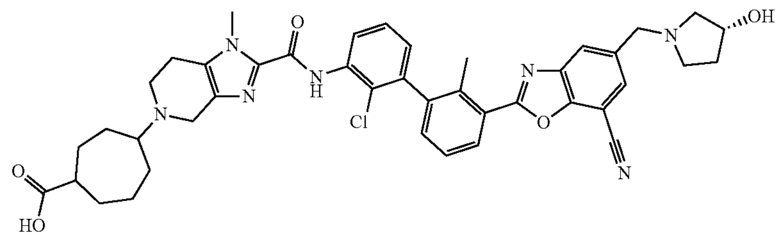 [SMILES: Cc1c(-c2nc3cc(CN4CC[C@@H](O)C4)cc(C#N)c3o2)cccc1-c1cccc(NC(=O)c2nc3c(n2C)CCN(C2CCCC(C(=O)O)CC2)C3)c1Cl] | 762.3 |
| 265 | (R)-4-(2-(2-(2-chloro-3'-(7-cyano-5-((3-hydroxypyrrolidin-1-yl)methyl)benzo[d]oxazol-2-yl)-2'-methylbiphenyl-3-ylcarbamoyl)-1-methyl-6,7-dihydro-1H-imidazo[4,5-c]pyridin-5(4H)-yl)ethyl)cyclohexane carboxylic acid | 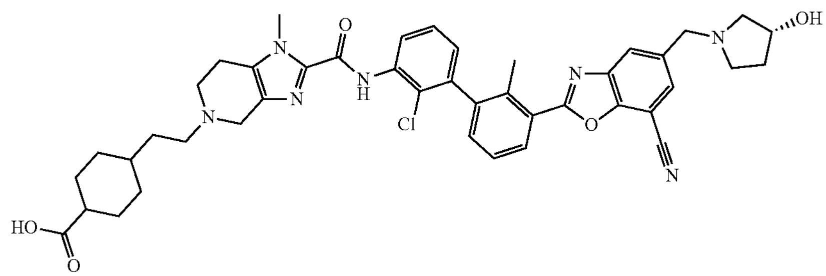 [SMILES: Cc1c(-c2nc3cc(CN4CC[C@@H](O)C4)cc(C#N)c3o2)cccc1-c1cccc(NC(=O)c2nc3c(n2C)CCN(CCC2CCC(C(=O)O)CC2)C3)c1Cl] | 776.2 |
| 266 | cis-4-((2-(2-chloro-3'-(7-cyano-5-(((R)-3-hydroxypyrrolidin-1-yl)methyl)benzo[d]oxazol-2-yl)-2'-methylbiphenyl-3-ylcarbamoyl)-1-methyl-6,7-dihydro-1H-imidazo[4,5-c]pyridin-5(4H)-yl)methyl)cyclohexane carboxylic acid | 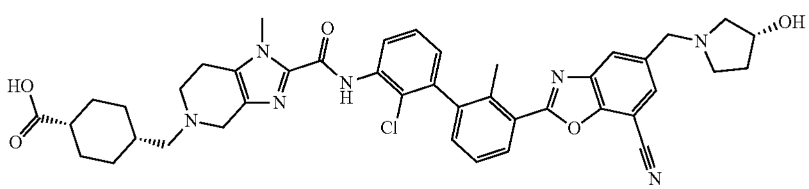 [SMILES: Cc1c(-c2nc3cc(CN4CC[C@@H](O)C4)cc(C#N)c3o2)cccc1-c1cccc(NC(=O)c2nc3c(n2C)CCN(C[C@H]2CC[C@@H](C(=O)O)CC2)C3)c1Cl] | 762.3 |

The compounds in Table 17 were prepared in accordance with the synthetic protocols set forth in Example 261, using the appropriate starting materials.

Example 267

(R)-4-((2-(2-chloro-3'-(7-cyano-5-((3-hydroxypyrrolidin-1-yl)methyl)benzo[d]oxazol-2-yl)-2'-methylbiphenyl-3-ylcarbamoyl)-1-methyl-6,7-dihydro-1H-imidazo[4,5-c]pyridin-5(4H)-yl)methyl)bicyclo[2.2.1]heptane-1-carboxylic acid

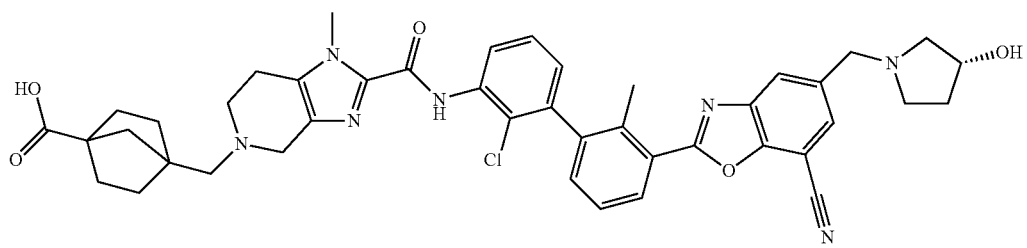 [SMILES: Cc1c(-c2nc3cc(CN4CC[C@@H](O)C4)cc(C#N)c3o2)cccc1-c1cccc(NC(=O)c2nc3c(n2C)CCN(CC24CCC(C(=O)O)(CC2)C4)C3)c1Cl]

Step 1: methyl 4-formylbicyclo[2.2.1]heptane-1-carboxylate

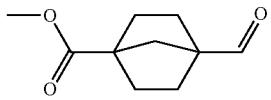

Example 268

(R)-4-((2-(2-chloro-3'-(7-cyano-5-((3-hydroxypyrrolidin-1-yl)methyl)benzo[d]oxazol-2-yl)-2'-methylbiphenyl-3-ylcarbamoyl)-1-methyl-6,7-dihydro-1H-imidazo[4,5-c]pyridin-5(4H)-yl)methyl)-1-methylcyclohexanecarboxylic acid (peak 1)

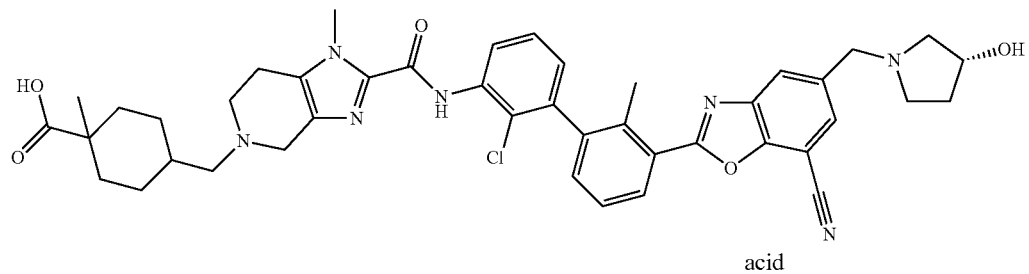

A mixture of methyl 4-(hydroxymethyl)bicyclo[2.2.1]heptane-1-carboxylate (400 mg, 2.171 mmol) and Dess-Martin periodinane (1381 mg, 3.26 mmol) in DCM (12.0 mL) was stirred at room temperature for 3 h. The reaction mixture was quenched with 20% aqueous $Na_2S_2O_3$ solution and saturated $NaHCO_3$ solution, and extracted with ethyl acetate. The combined organic layers were washed with brine, dried over $Na_2SO_4$, filtered, and concentrated under reduced pressure. The crude product was used directly in the next step without further purification.

Step 2: (R)-4-((2-(2-chloro-3'-(7-cyano-5-((3-hydroxypyrrolidin-1-yl)methyl)benzo[d]oxazol-2-yl)-2'-methylbiphenyl-3-ylcarbamoyl)-1-methyl-6,7-dihydro-1H-imidazo[4,5-c]pyridin-5(4H)-yl)methyl) bicyclo[2.2.1]heptane-1-carboxylic acid To a solution of (R)—N-(2-chloro-3'-(7-cyano-5-((3-hydroxypyrrolidin-1-yl)methyl)benzo[d]oxazol-2-yl)-2'-methylbiphenyl-3-yl)-1-methyl-4,5,6,7-tetrahydro-1H-imidazo[4,5-c]pyridine-2-carboxamide (Example 261, Step 1: 10 mg, 0.016 mmol) in DCM (5 ml) was added methyl 4-formylbicyclo[2.2.1]heptane-1-carboxylate (8.8 mg, 0.048 mmol) and DIEA (0.008 ml, 0.048 mmol). The mixture was stirred at r.t. for 60 min. Then sodium triace-toxyborohydride (10.2 mg, 0.048 mmol) was added. The reaction mixture was continued to stir at r.t. overnight. The reaction mixture was diluted with DCM, washed by $NaHCO_3$ aqueous solution, water, and brine. The organic phase was dried over $MgSO_4$, filtered and concentrated under reduced pressure. To a solution of above residue in THF (2 mL) was added lithium hydroxide (3.8 mg, 0.16 mmol) and a few drops of water. The reaction mixture was stirred at 40° C. for two days. The reaction mixture was diluted with MeCN/water, and purified via prep-HPLC (pH=2, MeCN/water with TFA) to give the desired product as the TFA salt. LC-MS calculated for $C_{43}H_{45}ClN_7O_5(M+H)^+$: m/z=774.3; found 774.3. $^1$H NMR (600 MHz, DMSO) δ 9.95 (s, 1H), 8.40 (d, J=12.6 Hz, 1H), 8.28 (d, J=7.0 Hz, 1H), 8.21 (d, J=7.8 Hz, 1H), 8.14 (d, J=8.9 Hz, 1H), 7.60 (t, J=7.6 Hz, 1H), 7.52 (t, J=7.8 Hz, 1H), 7.48 (d, J=7.5 Hz, 1H), 7.20 (d, J=7.2 Hz, 1H), 4.69-4.20 (m, 5H), 3.96 (s, 3H), 3.82-3.16 (m, 8H), 3.07 (s, 2H), 2.46 (s, 3H), 2.28 (d, J=6.4 Hz, 1H), 2.05-1.49 (n, 11H).

Step 1: 4-formyl-1-methylcyclohexanecarboxylic acid

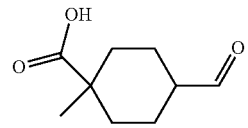

To a solution of methyl 4-formyl-1-methylcyclohexane-1-carboxylate (J&W PharmLab, cat #10R0682: 14.8 mg, 0.080 mmol) in THF/MeOH (2/1 v/v, 3 mL) was added lithium hydroxide (3.8 mg, 0.16 mmol) and water (1 mL). The reaction mixture was stirred at 40° C. overnight. Then the mixture was concentrated and the residue was dissolved in DCM.

After acidification with 1N HCl aqueous solution to pH=4, the mixture was extracted with DCM and the combined organic layers were washed with brine, dried over $Na_2SO_4$, filtered, and concentrated under reduced pressure. The crude product was used directly in the next step without further purification.

Step 2: (R)-4-((2-(2-chloro-3'-(7-cyano-5-((3-hydroxypyrrolidin-1-yl)methyl)benzo[d]oxazol-2-yl)-2'-methylbiphenyl-3-ylcarbamoyl)-1-methyl-6,7-dihydro-1H-imidazo[4,5-c]pyridin-5(4H)-yl) methyl)-1-methylcyclohexanecarboxylic acid To a solution of (R)—N-(2-chloro-3'-(7-cyano-5-((3-hydroxypyrrolidin-1-yl)methyl)benzo[d]oxazol-2-yl)-2'-methylbiphenyl-3-yl)-1-methyl-4,5,6,7-tetrahydro-1H-imidazo[4,5-c]pyridine-2-carboxamide (Example 261, Step 1: 10 mg, 0.016 mmol) in DCM (1 ml) was added 4-formyl-1-methylcyclohexanecarboxylic acid (13.6 mg, 0.080 mmol) and DIEA (0.008 ml, 0.048 mmol). The mixture was stirred at r.t. for 60 min. Then sodium triacetoxy-borohydride (10.2 mg, 0.048 mmol) was added. The reaction mixture was continued to stir at r.t. for 2 hrs. The reaction mixture was concentrated, then diluted with MeCN/water, and purified via prep-HPLC (pH=2, MeCN/water with TFA) to give two desired products (cis/trans isomers) as the TFA salt.

Peak 1:

retention time on analytical LC-MS (pH=2, acetonitrile/water+TFA) $t_r$=1.98 min, LC-MS calculated for $C_{43}H_{47}ClN_7O_5(M+H)^+$: m/z=776.3; found 776.3.

Example 269

(R)-4-((2-(2-chloro-3'-(7-cyano-5-((3-hydroxypyrrolidin-1-yl)methyl)benzo[d]oxazol-2-yl)-2'-methylbiphenyl-3-ylcarbamoyl)-1-methyl-6,7-dihydro-1H-imidazo[4,5-c]pyridin-5(4H)-yl)methyl)-1-methylcyclohexanecarboxylic acid (peak 2)

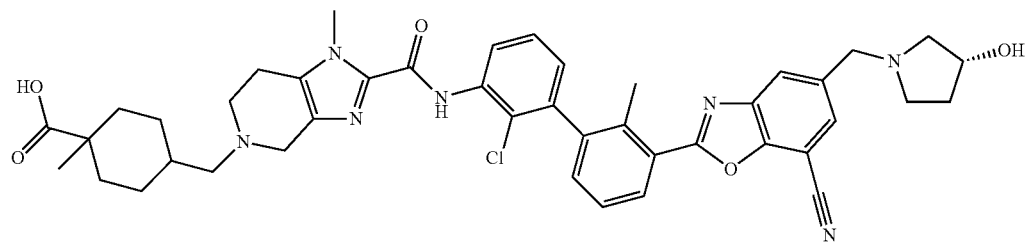 [SMILES: Cc1c(-c2nc3cc(CN4CC[C@@H](O)C4)cc(C#N)c3o2)cccc1-c1cccc(NC(=O)c2nc3c(n2C)CCN(CC2CCC(C)(C(=O)O)CC2)C3)c1Cl]

This compound was prepared using the same procedures as described for Example 268. In the prep-HPLC (pH=2, acetonitrile/water+TFA), the second desired peak was collected to give the desired product as TFA salt. Peak 2: retention time on analytical LC-MS (pH=2, acetonitrile/water+TFA) $t_r$=2.00 min, LC-MS calculated for $C_{43}H_{47}ClN_7O_5$ (M+H)$^+$: m/z=776.3; found 776.3.

Example 270 trans-4-((2-(2-chloro-3'-(7-cyano-5-((5-hydroxy-2-azabicyclo[2.2.1]heptan-2-yl)methyl)benzo[d]oxazol-2-yl)-2'-methylbiphenyl-3-ylcarbamoyl)-1-methyl-6,7-dihydro-1H-imidazo[4,5-c]pyridin-5(4H)-yl)methyl)cyclohexanecarboxylic acid

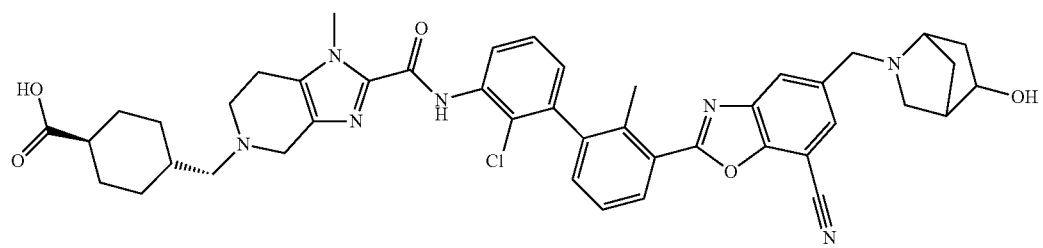

Step 1: trans-methyl 4-((2-(2-chloro-3'-(7-cyano-5-(hydroxymethyl)benzo[d]oxazol-2-yl)-2'-methylbiphenyl-3-ylcarbamoyl)-1-methyl-6,7-dihydro-1H-imidazo[4,5-c]pyridin-5(4H)-yl)methyl)cyclohexanecarboxylate

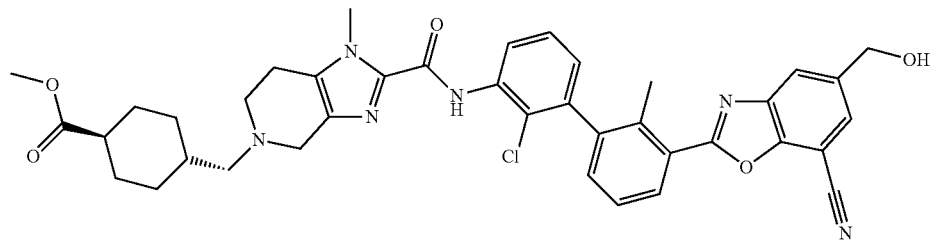

To a solution of tert-butyl 2-(2-chloro-3'-(7-cyano-5-(hydroxymethyl)benzo[d]oxazol-2-yl)-2'-methylbiphenyl-3-ylcarbamoyl)-1-methyl-6,7-dihydro-1H-imidazo[4,5-c]pyridine-5(4H)-carboxylate (Example 92, Step 2: 200.0 mg, 0.306 mmol) in DCM (5 mL) was added HCl (4M in dioxane, 0.383 ml). The solution was stirred at r.t. for 2 hours, then concentrated to dryness. To a solution of the above residue in DCM (5 ml) was added methyl trans-4-formylcyclohexane-1-carboxylate (104 mg, 0.612 mmol) and DIEA (0.160 ml, 0.919 mmol). The mixture was stir at r.t. for 60 min. Then sodium triacetoxyborohydride (195 mg, 0.919 mmol) was added, the reaction mixture was stirred at r.t. overnight. The reaction solution was diluted with DCM, then washed with aqueous NaHCO$_3$ solution, water and brine. The organic layer was dried over Na$_2$SO$_4$, filtered, and concentrated under reduced pressure. The residue was purified by silica gel chromatography eluting with 5% MeOH in DCM to give desired product. LC-MS calculated for C$_{39}$H$_{40}$ClN$_6$O$_5$(M+H)$^+$: m/z=707.3; found: 707.3.

Step 2: trans-methyl 4-((2-(2-chloro-3'-(7-cyano-5-formylbenzo[d]oxazol-2-yl)-2'-methyl biphenyl-3-ylcarbamoyl)-1-methyl-6,7-dihydro-1H-imidazo[4,5-c]pyridin-5(4H)-yl)methyl)cyclohexanecarboxylate Step 3: trans-4-((2-(2-chloro-3'-(7-cyano-5-((5-hydroxy-2-azabicyclo[2.2.1]heptan-2-yl)methyl)benzo[d]oxazol-2-yl)-2'-methylbiphenyl-3-ylcarbamoyl)-1-methyl-6,7-dihydro-1H-imidazo[4,5-c]pyridin-5(4H)-yl)methyl)cyclohexanecarboxylic acid To a solution of trans-methyl 4-((2-(2-chloro-3'-(7-cyano-5-formylbenzo[d]oxazol-2-yl)-2'-methyl biphenyl-3-ylcarbamoyl)-1-methyl-6,7-dihydro-1H-imidazo[4,5-c]pyridin-5(4H)-yl)methyl)cyclohexanecarboxylate (20 mg, 0.028 mmol) in DCM (2 mL) was added 2-azabicyclo[2.2.1]heptan-5-ol HCl salt (8.5 mg, 0.057 mmol) and DIEA (0.015 mL, 0.085 mmol). The mixture was stirred at r.t. for 30 min. Then sodium triacetoxyborohydride (18.0 mg, 0.085 mmol) was added. The reaction mixture was continued to stir at r.t. overnight. The reaction mixture was diluted with DCM, washed by NaHCO$_3$ aqueous solution, water and brine. The organic layer was dried over MgSO$_4$, filtered and concentrated under reduced pressure. To a solution of the above residue in THF (2 mL) was added lithium hydroxide (6.2 mg, 0.26 mmol) and a few drops of water. The reaction mixture was stirred at 40° C. for two days. The reaction mixture was diluted with MeCN/Water, and purified via

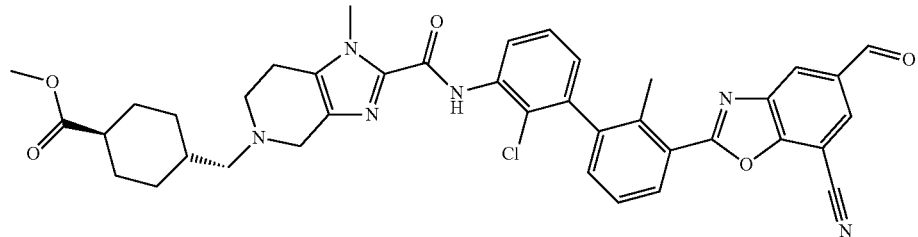

To a stirred solution of trans-methyl 4-((2-(2-chloro-3'-(7-cyano-5-(hydroxymethyl)benzo[d]oxazol-2-yl)-2'-methylbiphenyl-3-ylcarbamoyl)-1-methyl-6,7-dihydro-1H-imidazo[4,5-c]pyridin-5(4H)-yl)methyl)cyclohexanecarboxylate (175 mg, 0.247 mmol) in DCM (5.0 ml) was added sodium bicarbonate (208 mg, 2.474 mmol) and dess-martin periodinane (126 mg, 0.297 mmol). The resulted mixture was stirred at r.t. for 1 hour. The reaction solution was diluted with DCM, then washed with aqueous NaHCO$_3$ solution, water, and brine. The organic layer was dried over Na$_2$SO$_4$, filtered, and concentrated under reduce pressure. The residue was purified by silica gel chromatography eluting with 5% MeOH in DCM to give the desired product. LC-MS calculated for C$_{39}$H$_{38}$ClN$_6$O$_5$ (M+H)$^+$: m/z=705.2; found: 705.2.

prep-HPLC (pH=2, MeCN/water with TFA) to give the desired product as the TFA salt. LC-MS calculated for C$_{44}$H$_{47}$ClN$_7$O$_5$(M+H)$^+$: m/z=788.3; found 788.3.

Example 271 trans-4-((2-(2-chloro-3'-(7-cyano-5-(pyrrolidin-1-ylmethyl)benzo[d]oxazol-2-yl)-2'-methylbiphenyl-3-ylcarbamoyl)-1-methyl-6,7-dihydro-1H-imidazo[4,5-c]pyridin-5(4H)-yl)methyl)cyclohexanecarboxylic acid

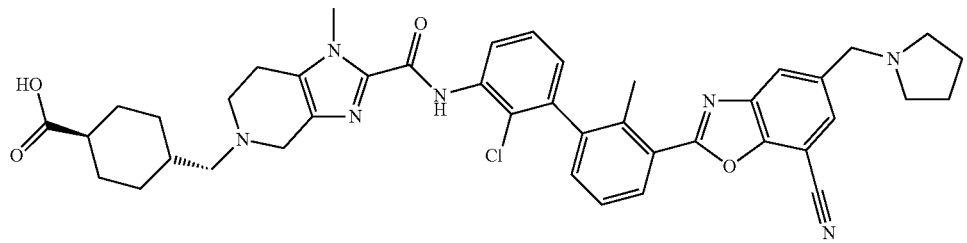

This compound was prepared using similar procedures as described for Example 270 with pyrrolidine replacing 2-azabicyclo[2.2.1]heptan-5-ol in Step 3. The reaction mixture was concentrated, then diluted in MeCN/Water, filtered then purified by prep-HPLC (pH=2, acetonitrile/water+

TFA) to give the desired product as TFA salt. LC-MS calculated for $C_{42}H_{45}ClN_7O_4(M+H)^+$: m/z=746.3; found 746.3.

Example A. PD-1/PD-L1 Homogeneous Time-Resolved Fluorescence (HTRF) Binding Assay The assays were conducted in a standard black 384-well polystyrene plate with a final volume of 20 µL. Inhibitors were first serially diluted in DMSO and then added to the plate wells before the addition of other reaction components. The final concentration of DMSO in the assay was 1%. The assays were carried out at 25° C. in the PBS buffer (pH 7.4) with 0.05% Tween-20 and 0.1% BSA. Recombinant human PD-L1 protein (19-238) with a His-tag at the C-terminus was purchased from AcroBiosystems (PD1-H5229). Recombinant human PD-1 protein (25-167) with Fc tag at the C-terminus was also purchased from AcroBiosystems (PD1-H5257). PD-L1 and PD-1 proteins were diluted in the assay buffer and 10 µL was added to the plate well. Plates were centrifuged and proteins were preincubated with inhibitors for 40 minutes. The incubation was followed by the addition of 10 µL of HTRF detection buffer supplemented with Europium cryptate-labeled anti-human IgG (PerkinElmer-AD0212) specific for Fc and anti-His antibody conjugated to SureLight®-Allophycocyanin (APC, PerkinElmer-AD0059H). After centrifugation, the plate was incubated at 25° C. for 60 min. before reading on a PHERAstar FS plate reader (665 nm/620 nm ratio). Final concentrations in the assay were ~3 nM PD1, 10 nM PD-L1, 1 nM europium anti-human IgG and 20 nM anti-His-Allophycocyanin. $IC_{50}$ determination was performed by fitting the curve of percent control activity versus the log of the inhibitor concentration using the GraphPad Prism 5.0 software.

Compounds of the present disclosure, as exemplified in Examples 1-9, showed $IC_{50}$ values in the following ranges: +=$IC_{50}$≤10 nM; ++=10 nM≤$IC_{50}$<100 nM; +++=100 nM<$IC_{50}$≤1000 nM Data obtained for the Example compounds using the PD-1/PD-L1 homogenous time-resolved fluorescence (HTRF) binding assay described in Example A is provided in Table 1A.

TABLE 1A

| Example | PD-1/PD-L1 HTRF $IC_{50}$ (nM) |
| --- | --- |
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | + |
| 29 | + |
| 30 | + |
| 31 | + |
| 32 | + |
| 33 | + |
| 34 | + |
| 35 | + |
| 36 | + |
| 37 | + |
| 38 | + |
| 39 | + |
| 40 | ++ |
| 41 | + |
| 42 | + |
| 43 | + |
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |
| 59 | + |
| 60 | + |
| 61 | + |
| 62 | + |
| 63 | + |
| 64 | + |
| 65 | + |
| 66 | + |
| 67 | + |
| 68 | + |
| 69 | + |
| 70 | + |
| 71 | + |
| 72 | + |
| 73 | + |
| 74 | + |
| 75 | + |
| 76 | + |
| 77 | + |
| 78 | + |
| 79 | + |
| 80 | + |
| 81 | + |
| 82 | + |
| 83 | + |
| 84 | + |
| 85 | + |
| 86 | + |
| 87 | + |
| 88 | + |
| 89 | + |
| 90 | + |
| 91 | + |
| 92 | + |
| 93 | + |
| 94 | + |
| 95 | + |
| 96 | + |
| 97 | + |
| 98 | + |

TABLE 1A-continued

| Example | PD-1/PD-L1 HTRF IC$_{50}$ (nM) |
|---|---|
| 99 | + |
| 100 | + |
| 101 | + |
| 102 | + |
| 103 | + |
| 104 | + |
| 105 | + |
| 106 | + |
| 107 | + |
| 108 | + |
| 109 | + |
| 110 | + |
| 111 | + |
| 112 | + |
| 113 | + |
| 114 | + |
| 115 | + |
| 116 | + |
| 117 | + |
| 118 | + |
| 119 | + |
| 120 | + |
| 121 | + |
| 122 | + |
| 123 | + |
| 124 | + |
| 125 | + |
| 126 | + |
| 127 | + |
| 128 | + |
| 129 | + |
| 130 | + |
| 131 | + |
| 132 | + |
| 133 | + |
| 134 | + |
| 135 | + |
| 136 | + |
| 137 | + |
| 138 | + |
| 139 | + |
| 140 | + |
| 141 | + |
| 142 | + |
| 143 | + |
| 144 | + |
| 145 | + |
| 146 | + |
| 147 | + |
| 148 | + |
| 149 | ++ |
| 150 | ++ |
| 151 | + |
| 152 | + |
| 153 | + |
| 154 | + |
| 155 | + |
| 156 | + |
| 157 | + |
| 158 | + |
| 159 | + |
| 160 | + |
| 161 | + |
| 162 | + |
| 163 | + |
| 164 | + |
| 165 | + |
| 166 | + |
| 167 | + |
| 168 | + |
| 169 | + |
| 170 | + |
| 171 | + |
| 172 | + |
| 173 | + |
| 174 | + |
| 175 | + |
| 176 | + |
| 177 | + |
| 178 | + |
| 179 | + |
| 180 | + |
| 181 | + |
| 182 | + |
| 183 | + |
| 184 | + |
| 185 | + |
| 186 | + |
| 187 | + |
| 188 | + |
| 189 | + |
| 190 | + |
| 191 | + |
| 192 | + |
| 193 | + |
| 194 | + |
| 195 | + |
| 196 | + |
| 197 | + |
| 198 | + |
| 199 | + |
| 200 | + |
| 201 | + |
| 202 | + |
| 203 | + |
| 204 | + |
| 205 | + |
| 206 | + |
| 207 | + |
| 208 | + |
| 209 | + |
| 210 | + |
| 211 | + |
| 212 | + |
| 213 | + |
| 214 | + |
| 215 | + |
| 216 | + |
| 217 | + |
| 218 | + |
| 219 | + |
| 220 | + |
| 221 | + |
| 222 | + |
| 223 | + |
| 224 | + |
| 225 | + |
| 226 | + |
| 227 | + |
| 228 | + |
| 229 | + |
| 230 | + |
| 231 | + |
| 232 | + |
| 233 | + |
| 234 | + |
| 235 | + |
| 236 | + |
| 237 | + |
| 238 | + |
| 239 | + |
| 240 | + |
| 241 | + |
| 242 | + |
| 243 | + |
| 244 | + |
| 245 | + |
| 246 | + |
| 247 | + |
| 248 | + |
| 249 | + |
| 250 | + |
| 251 | + |
| 252 | + |

TABLE 1A-continued

| Example | PD-1/PD-L1 HTRF IC$_{50}$ (nM) |
|---|---|
| 253 | + |
| 254 | + |
| 255 | + |
| 256 | + |
| 257 | + |
| 258 | + |
| 259 | + |
| 260 | + |
| 261 | + |
| 262 | + |
| 263 | + |
| 264 | + |
| 265 | + |
| 266 | + |
| 267 | + |
| 268 | + |
| 269 | + |
| 270 | + |
| 271 | + |

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A compound of Formula (IIc-4):

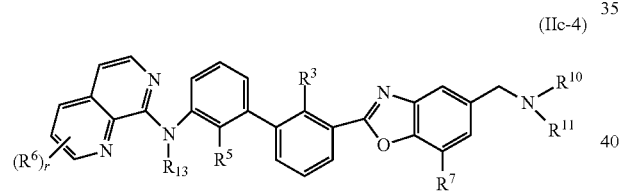

(IIc-4)

or a pharmaceutically acceptable salt or a stereoisomer thereof, wherein:

the subscript r is an integer of 1, 2 or 3;

$R^3$ is methyl or halo;

$R^5$ is $C_{1-4}$ alkyl, $C_{1-4}$ alkoxy, $C_{1-4}$ haloalkyl, $C_{1-4}$ haloalkoxy, CN, halo, or OH;

each $R^6$ is independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, CN, $OR^a$, $C(O)R^a$, $C(O)NR^aR^a$, $C(O)OR^a$, $NHR^a$, $NR^aR^a$, and $NR^aC(O)R^a$, wherein the $C_{1-6}$ alkyl, $C_{2-6}$ alkenyl, and $C_{2-6}$ alkynyl of $R^6$ are each optionally substituted with 1 or 2 $R^b$ substituents;

$R^7$ is H, $C_{1-4}$ alkyl, $C_{1-4}$ alkoxy, $C_{1-4}$ haloalkyl, $C_{1-4}$ haloalkoxy, CN, halo, or OH;

$R^{10}$ and $R^{11}$ are each independently selected from H, $C_{1-6}$ alkyl, $C_{1-6}$ haloalkyl, —C(O)R$^g$, —C(O)OR$^g$, and —C(O)NR$^g$R$^g$, wherein the $C_{1-6}$ alkyl and $C_{1-6}$ haloalkyl of $R^{10}$ or $R^{11}$ are each optionally substituted with 1, 2 or 3 independently selected $R^f$ substituents;

or $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1 or 2 $R^h$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, or OH;

each $R^a$ is independently selected from H, CN, $C_{1-6}$ alkyl, $C_{1-4}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^a$ are each optionally substituted with 1 or 2 $R^d$ substituents;

each $R^d$ is independently selected from $C_{1-6}$ alkyl, $C_{1-6}$ haloalkyl, halo, CN, NH$_2$, OR$^e$, C(O)R$^e$, C(O)NR$^e$R$^e$, C(O)OR$^e$, NHR$^e$, NR$^e$R$^e$, and NR$^e$C(O)R$^e$;

each $R^e$ is independently selected from H, $C_{1-6}$ alkyl, $C_{1-6}$ haloalkyl, $C_{2-6}$ alkenyl, and $C_{2-6}$ alkynyl;

each $R^b$ substituent is independently selected from halo, $C_{1-6}$ alkyl, $C_{1-6}$ haloalkyl, $C_{1-6}$ haloalkoxy, 5-10 membered heteroaryl, 4-10 membered heterocycloalkyl, (5-10 membered heteroaryl)-$C_{1-4}$ alkyl-, (4-10 membered heterocycloalkyl)-$C_{1-4}$ alkyl-, CN, OH, NH$_2$, OR$^c$, C(O)R$^c$, C(O)NR$^c$R$^c$, C(O)OR$^c$, NHR$^c$, NR$^c$R$^c$, and NR$^c$C(O)R$^c$; wherein the $C_{1-4}$ alkyl, $C_{1-4}$ haloalkyl, $C_{1-4}$ haloalkoxy, 5-10 membered heteroaryl, 4-10 membered heterocycloalkyl, (5-10 membered heteroaryl)-$C_{1-4}$ alkyl- and (4-10 membered heterocycloalkyl)-$C_{1-4}$ alkyl- of $R^b$ are each further optionally substituted with 1 or 2 independently selected $R^d$ substituents;

each $R^c$ is independently selected from H, $C_{1-6}$ alkyl, $C_{1-4}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^c$ are each optionally substituted with 1, 2, or 3 $R^f$ substituents;

each $R^f$ is independently selected from $C_{1-4}$ alkyl, $C_{1-4}$ haloalkyl, $C_{2-6}$ alkenyl, $C_{2-6}$ alkynyl, halo, CN, OR$^g$, C(O)R$^g$, C(O)NR$^g$R$^g$, C(O)OR$^g$, NHR$^g$, NR$^g$R$^g$, and NR$^g$C(O)R$^g$;

each $R^g$ is independently selected from H, $C_{1-6}$ alkyl, $C_{1-4}$ haloalkyl, $C_{2-6}$ alkenyl, and $C_{2-6}$ alkynyl;

each $R^h$ is independently selected from $C_{1-6}$ alkyl, $C_{1-6}$ haloalkyl, $C_{1-6}$ haloalkoxy, $C_{2-6}$ alkenyl, $C_{2-6}$ alkynyl, halo, CN, OR$^i$, C(O)R$^i$, C(O)NR$^i$R$^i$, C(O)OR$^i$, NR$^i$R$^i$, and NR$^i$C(O)R$^i$; and each $R^i$ is independently selected from H, $C_{1-4}$ alkyl, $C_{1-6}$ haloalkyl, $C_{1-6}$ haloalkoxy, $C_{2-4}$ alkenyl, and $C_{2-4}$ alkynyl.

2. The compound of claim 1, or a pharmaceutically acceptable salt or a stereoisomer thereof, wherein $R^{13}$ is H.

3. The compound of claim 1, or a pharmaceutically acceptable salt or a stereoisomer thereof, wherein $R^6$ is (3-hydroxypyrrolidin-1-yl)methyl, (R)-(3-hydroxypyrrolidin-1-yl)methyl, or (S)-(3-hydroxypyrrolidin-1-yl).

4. The compound of claim 1, or a pharmaceutically acceptable salt or a stereoisomer thereof, wherein $R^5$ is halo or $C_{1-4}$ alkyl.

5. The compound of claim 1, or a pharmaceutically acceptable salt or a stereoisomer thereof, wherein $R^5$ is halo, methyl or CN.

6. The compound of claim 1, or a pharmaceutically acceptable salt or a stereoisomer thereof, wherein $R^3$ is methyl or Cl.

7. The compound of claim 1, or a pharmaceutically acceptable salt or a stereoisomer thereof, wherein $NR^{10}R^{11}$ is 3-carboxypyrrolidin-1-yl, (R)-3-carboxypyrrolidin-1-yl, or (S)-3-carboxypyrrolidin-1-yl.

8. The compound of claim 1, or a pharmaceutically acceptable salt thereof, wherein each $R^6$ is independently selected from $C_{1-6}$ alkyl, which is optionally substituted with 1 or 2 $R^b$ substituents.

9. The compound of claim 1, or a pharmaceutically acceptable salt thereof, wherein the subscript r is an integer of 1.

10. The compound of claim 5, or a pharmaceutically acceptable salt thereof, wherein $R^3$ is methyl.

11. The compound of claim 1, or a pharmaceutically acceptable salt thereof, wherein $R^7$ is CN.

12. The compound of claim 10, or a pharmaceutically acceptable salt or a stereoisomer thereof, wherein $R^{13}$ is H.

13. The compound of claim 12, or a pharmaceutically acceptable salt thereof, wherein the subscript r is an integer of 1.

14. The compound of claim 13, or a pharmaceutically acceptable salt thereof, wherein $R^7$ is CN.

15. The compound of claim 14, or a pharmaceutically acceptable salt thereof, wherein each $R^6$ is independently selected from $C_{1-6}$ alkyl, which is optionally substituted with 1 or 2 $R^b$ substituents.

16. The compound of claim 14, or a pharmaceutically acceptable salt thereof, wherein each $R^6$ is (3-hydroxypyrrolidin-1-yl)methyl, (R)-(3-hydroxypyrrolidin-1-yl)methyl, or (S)-(3-hydroxypyrrolidin-1-yl).

17. The compound of claim 14, or a pharmaceutically acceptable salt thereof, wherein —$NR^{10}R^{11}$ is 3-carboxypyrrolidin-1-yl, (R)-3-carboxypyrrolidin-1-yl, or (S)-3-carboxypyrrolidin-1-yl.

18. A pharmaceutical composition comprising a compound of claim 1, or a pharmaceutically acceptable salt or a stereoisomer thereof, and one or more pharmaceutically acceptable excipient or carrier.

* * * * *

UNITED STATES PATENT AND TRADEMARK OFFICE
CERTIFICATE OF CORRECTION

PATENT NO. : 10,800,768 B2
APPLICATION NO. : 16/373150
DATED : October 13, 2020
INVENTOR(S) : Liangxing Wu et al.

Page 1 of 1

It is certified that error appears in the above-identified patent and that said Letters Patent is hereby corrected as shown below:

On the Title Page

Column 2, Line 2 (of OTHER PUBLICATIONS), delete "acylation" and insert -- arylation --.

In the Claims

Column 451, Lines 35-42, Claim 1, delete

"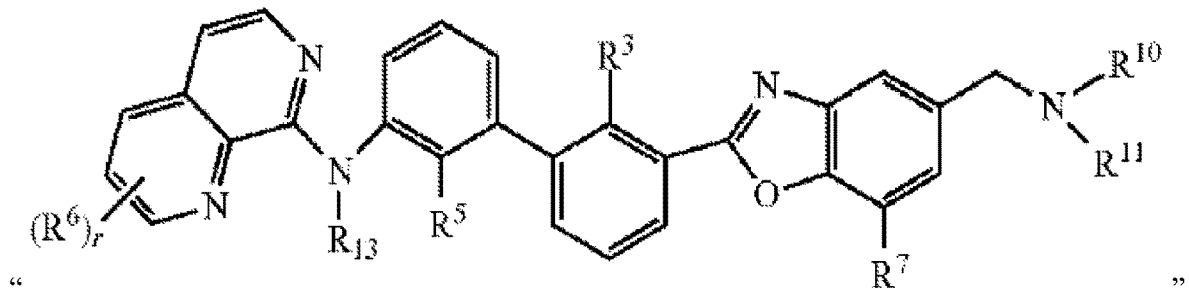"

and insert

--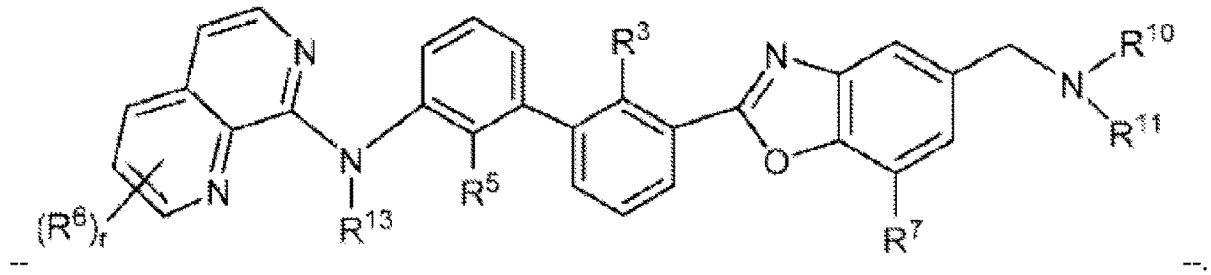--.

Column 452, Line 40, Claim 1, before "$NR^iR^i$," insert -- $NHR^i$, --.
Column 452, Line 50, Claim 3, delete "(3-hydroxypyrrolidin-1-yl)." and insert
-- (3-hydroxypyrrolidin-1-yl)methyl. --.
Column 452, Line 61, Claim 7, delete "$NR^{10}R^{11}$" and insert -- —$NR^{10}R^{11}$ --.

Signed and Sealed this
Thirty-first Day of August, 2021

Drew Hirshfeld
*Performing the Functions and Duties of the
Under Secretary of Commerce for Intellectual Property and
Director of the United States Patent and Trademark Office*